United States Patent
Nielsen et al.

(10) Patent No.: US 9,346,809 B2
(45) Date of Patent: May 24, 2016

(54) HETEROCYCLIC COMPOUNDS AS JAK RECEPTOR AND PROTEIN TYROSINE KINASE INHIBITORS

(75) Inventors: Simon Feldbæk Nielsen, Herlev (DK); Daniel Rodriguez Greve, Stenløse (DK); Carsten Ryttersgaard, Roskilde (DK); Gunnar Grue-Sørensen, Roskilde (DK); Erik Rytter Ottosen, Ølstykke (DK); Tina Dahlerup Poulsen, Brønshøj (DK); Søren Christian Schou, Roskilde (DK); Anthony Murray, Charlottenlund (DK)

(73) Assignee: LEO PHARMA A/S, Ballerup (DK)

( * ) Notice: Subject to any disclaimer, the term of this patent is extended or adjusted under 35 U.S.C. 154(b) by 798 days.

(21) Appl. No.: 13/382,665

(22) PCT Filed: Jul. 8, 2010

(86) PCT No.: PCT/DK2010/000105
§ 371 (c)(1),
(2), (4) Date: Mar. 27, 2012

(87) PCT Pub. No.: WO2011/003418
PCT Pub. Date: Jan. 13, 2011

(65) Prior Publication Data
US 2012/0178740 A1    Jul. 12, 2012

Related U.S. Application Data

(60) Provisional application No. 61/223,943, filed on Jul. 8, 2009.

(51) Int. Cl.
| | | |
|---|---|---|
| C07D 487/04 | (2006.01) | |
| C07D 519/00 | (2006.01) | |
| A61K 31/519 | (2006.01) | |
| C07D 471/04 | (2006.01) | |
| A61P 37/00 | (2006.01) | |
| A61P 19/02 | (2006.01) | |
| A61P 25/28 | (2006.01) | |
| A61P 35/00 | (2006.01) | |
| A61P 11/06 | (2006.01) | |
| A61P 3/10 | (2006.01) | |
| A61P 17/06 | (2006.01) | |
| A61P 17/14 | (2006.01) | |
| A61P 17/10 | (2006.01) | |
| A61P 17/00 | (2006.01) | |

(Continued)

(52) U.S. Cl.
CPC ............ *C07D 487/04* (2013.01); *C07D 471/04* (2013.01); *C07D 519/00* (2013.01)

(58) Field of Classification Search
CPC ... C07D 487/04; C07D 519/00; A61K 31/519
USPC ...................... 544/280; 514/265.1
See application file for complete search history.

(56) References Cited

U.S. PATENT DOCUMENTS

| 2004/0058922 A1 | 3/2004 | Blumenkopf et al. |
| 2005/0130954 A1 | 6/2005 | Mitchell et al. |

(Continued)

FOREIGN PATENT DOCUMENTS

| WO | WO 99/65908 A1 | 12/1999 |
| WO | WO 99/65909 A1 | 12/1999 |

(Continued)

OTHER PUBLICATIONS

Harrison et al., "Novel Class of LIM-Kinase 2 Inhibitors for the Treatment of Ocular Hypertension and Associated Glaucoma." Journal of Medicinal Chemistry, 2009, vol. 52, No. 21, pp. 6515-6518.

(Continued)

*Primary Examiner* — Susanna Moore
(74) *Attorney, Agent, or Firm* — Birch, Stewart, Kolasch & Birch, LLP

(57) ABSTRACT

The invention relates to compounds of general formula (I) wherein A, $R_1$, $R_2$, $R_3$, $R_4$, $R_5$, $R_9$, m and n are defined as defined herein, and pharmaceutically acceptable salts, hydrates, or solvates thereof, for use—alone or in combination with one or more other pharmaceutically active compounds—in therapy, as JAK kinase and protein tyrosine kinase inhibitors for preventing, treating or ameliorating diseases and complications thereof, including, for example, psoriasis, atopic dermatitis, rosacea, lupus, multiple sclerosis, rheumatoid arthritis, Type I diabetes, asthma, cancer, autoimmune thyroid disorders, ulcerative colitis, Crohn's disease, Alzheimer's disease, leukaemia, eye diseases such as diabetic retinopathy and macular degeneration as well as other autoimmune diseases and indications where immunosuppression would be desirable for example in organ transplantation.

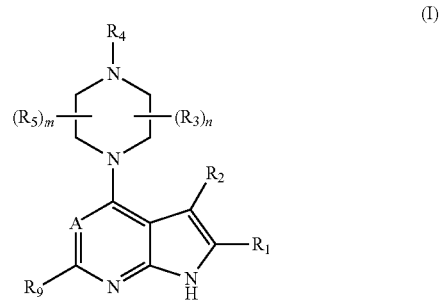

(I)

31 Claims, No Drawings

(51) Int. Cl.
 *A61P 17/08* (2006.01)
 *A61P 17/04* (2006.01)
 *A61P 19/06* (2006.01)
 *A61P 11/00* (2006.01)

(56) References Cited

U.S. PATENT DOCUMENTS

2006/0189638 A1 8/2006 Rawlins et al.
2009/0042893 A1* 2/2009 Harrison et al. .............. 514/249

FOREIGN PATENT DOCUMENTS

| WO | WO 01/42246 A2 | 6/2001 |
| WO | WO 03/022214 A2 | 3/2003 |
| WO | WO 2004/035740 A2 | 4/2004 |
| WO | WO 2004/099205 A1 | 11/2004 |
| WO | WO 2005/051393 A1 | 6/2005 |
| WO | WO 2005/060972 A2 | 7/2005 |
| WO | WO 2005/112938 A2 | 12/2005 |
| WO | WO 2006/069080 A2 | 6/2006 |
| WO | WO 2006/096270 A1 | 9/2006 |
| WO | WO 2006/127587 A1 | 11/2006 |
| WO | WO 2006/077949 A1 | 7/2007 |
| WO | WO 2007/104944 A1 | 9/2007 |
| WO | WO 2007/117494 A1 | 10/2007 |
| WO | WO 2008005368 * | 1/2008 |
| WO | WO 2008/128072 A2 | 10/2008 |
| WO | WO 2009/021169 A2 | 2/2009 |

OTHER PUBLICATIONS

Written Opinion of the International Searching Authority issued in PCT/DK2010/000105, dated Aug. 26, 2010.

* cited by examiner

HETEROCYCLIC COMPOUNDS AS JAK RECEPTOR AND PROTEIN TYROSINE KINASE INHIBITORS

CROSS REFERENCE

This application is the National Phase of PCT International Application No. PCT/DK2010/000105, filed on Jul. 8, 2010, which claims priority under 35 U.S.C. 119(e) to U.S. Provisional Application No. 61/223,943, filed on Jul. 8, 2009, all of which are hereby expressly incorporated by reference into the present application.

FIELD OF THE INVENTION

This invention relates to compounds which are inhibitors of protein tyrosine kinases, such as the Janus kinases, and to said compounds for use in therapy, to pharmaceutical compositions comprising said compounds, to methods of treating diseases comprising administering to a patient in need thereof an effective amount of said compound, and to the use of said compounds in the manufacture of medicaments.

BACKGROUND OF THE INVENTION

This invention relates to novel compounds which are inhibitors of protein tyrosine kinases such as the Janus kinases, also referred to as JAK1, JAK2, JAK3 and TYK2. Said compounds are useful in the treatment of diseases related to activity of Janus kinases, including, for example, psoriasis, atopic dermatitis, rosacea, lupus, multiple sclerosis, rheumatoid arthritis, Type I diabetes and complications from diabetes, asthma, cancer, autoimmune thyroid disorders, ulcerative colitis, Crohn's disease, Alzheimer's disease, leukaemia, eye diseases such as diabetic retinopathy and macular degeneration as well as other autoimmune diseases and indications where immunosuppression would be desirable for example in organ transplantation.

Protein tyrosine kinases are a family of enzymes catalysing the transfer of the terminal phosphate of adenosine triphosphate to tyrosine residues in protein substrates. Phosphorylation of tyrosine residues on protein substrates leads to transduction of intracellular signals which regulate a wide variety of intracellular processes such as growth, differentiation and activation of cells of the immune system. As activation of T-cells and B-cells as well as other cells of the immune system such as monocytes and macrophages is implicated in a number of inflammatory conditions and other disorders of the immune system (e.g. autoimmune diseases), modulation of the activity of protein tyrosine kinases appears to be an attractive route to the management of inflammatory diseases. A large number of protein tyrosine kinases have been identified which may be receptor protein tyrosine kinases, e.g. the insulin receptor, or non-receptor protein tyrosine kinases.

The protein tyrosine kinases JAK1, JAK2, JAK3 and TYK2 have essential roles in cytokine-dependent regulation of proliferation and function of cells involved in immune response. They are critical in signal transduction in response to their activation via tyrosine phosphorylation by stimulation of interleukin receptors.

While JAK1, JAK2 and TYK2 are ubiquitously expressed JAK3 is predominantly expressed in hematopoietic cells.

JAK1 plays a critical role in mediation of biological responses and JAK1 is widely expressed and associated with several major cytokine receptor families. It is involved in signalling by members of the IL-2 receptor family (IL-2, IL-4, IL-7R, IL-9R, IL-15R and IL-21R), the IL-4 receptor family (IL-4R, IL-13R), the gp130 receptor family and class II cytokine receptors.

JAK2 is implicated in signalling by several single chain receptors (including Epo-R, GHR, PRL-R), the IL-3 receptor family, the gp130 receptor family and Class II receptor cytokine family. Thus, JAK2 plays a critical role in transducing signals for Epo, IL-3, GM-CSF, IL-5 and IFNγ. JAK2 knock-out mice exhibit an embryonic lethal phenotype.

JAK3 is involved in signal transduction by receptors that employ the common gamma chain of the type I cytokine receptor family (e.g. IL-2, IL-4, IL-7, IL-9, IL-15 and IL-21). XSCID patient populations have been identified with reduced levels of JAK3 protein or with genetic defects to the common gamma chain, suggesting that immune suppression should result from blocking signalling through the JAK3 pathway. Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as immune system diseases, in particular autoimmune diseases.

TYK2 is implicated in type I interferons, IL-6, IL-10, IL-12 and IL-23 signalling. A human patient with a TYK2 deficiency has been described and this patient had a primary immunodeficiency disorder characterized as a hyper-IgE-like syndrome with many opportunistic infections by virus, bacteria and fungi. Because Il-23 has been found to play an important role in many chronic inflammatory conditions, a TYK2 inhibitor could conceivably be very effective in treating diseased influenced by IL-23.

Inhibitors of the Janus kinases are accordingly expected to show utility in the treatment of inflammatory and non-infectious autoimmune diseases wherein these kinases are involved.

It is further envisaged that compounds of the present invention may be useful as inhibitors of other kinases, such as Src family kinases (Src, Yes, Fyn, Lyn, Fgr, Blk, Lck and/or Hck) responsible for receptor mediated signalling in T, B and other immune cells; Raf-1/Ras, MAP kinase signalling pathway; Syk and ZAP70 kinases responsible of activation of immune cells.

WO1999065908A1, WO1999065909A1, and WO2001042246A2 disclose pyrrolo[2,3-d]pyrimidine compounds as inhibitors of the enzyme protein tyrosine kinases such as Janus kinase 3 and as useful therapy as immunosuppressive agents.

WO2003022214A3 discloses piperazine and homopiperazine compounds for use in the treatment of thrombosis.

WO2004035740A3 discloses aromatic bicyclic heterocycles to modulate IL-12 production.

WO2004099205A1 discloses azaindole compounds as kinase inhibitors.

WO 2005112938A3 discloses disalt nitrogen-heteroaryl inhibitors of IL-12 production.

WO2005051393A1 discloses a method of treatment of atherosclerosis by administering a pyrrolo[2,3-d]pyrimidine compound.

WO2005060972A2 discloses a method of treating or preventing chronic, acute or hyperacute organ transplant rejection using pyrrolo[2,3-d]pyrimidine compounds.

WO2006096270A1 discloses pyrrolopyrimidines useful as inhibitors of protein kinase.

WO2006069080A2 discloses pyrrolo[2,3-d]pyridine-4-yl amines and pyrrolo[2,3b]pyrimidine-4-yl amines useful in the treatment of diseases related to activity of Janus kinases.

WO2006127587A1 discloses pyrrolopyrimidines useful as inhibitors of protein kinase.

WO2007077949A1 discloses heterocyclic Janus kinase 3 inhibitors being useful for the treatment or prevention of various immune diseases.

WO2007117494A1 discloses deazapurines useful as inhibitors of Janus kinases.

WO2007104944A1 discloses pyrrolopyrimidine derivatives having HSP90 inhibitory activity and useful in the treatment of inter alia cancer.

WO2008128072A3 discloses heterocyclic compounds as AXL kinase inhibitors useful for the treatment of cancer or hyperproliferative disorders.

WO2009021169A2 discloses heterocyclic compounds useful as kinase inhibitors.

US2004/0058922 A1 discloses pyrrolo[2,3-d]pyrimidine compounds as inhibitors of protein tyrosine kinases, such as the enzyme Janus Kinase 3 and as useful therapy as immunosuppressive agents.

US2005/0130954 A1 discloses AKT protein kinase inhibitors for the treatment of hyperproliferative diseases such as cancer.

US2006/0189638 A1 discloses 4-piperidin-1-yl-7H-pyrrolo[2,3-d]pyrimidine compounds and their use for e.g. treatment of hyperproliferative disorders.

SUMMARY OF THE INVENTION

The present inventors have surprisingly found that a novel class of compounds exhibit a high inhibitory activity on one or more of the Janus kinase receptors JAK1, JAK2, JAK3 and TYK2.

It is further envisaged that compounds of the present invention may be useful as inhibitors of other kinases, such as Src family kinases (Src, Yes, Fyn, Lyn, Fgr, Blk, Lck and/or Hck) responsible for receptor mediated signalling in T, B and other immune cells; Raf-1/Ras, MAP kinase signalling pathway; Syk and ZAP70 kinases responsible of activation of immune cells and as such show utility in the treatment of inflammatory and non-infectious autoimmune diseases wherein these kinases are involved.

Compounds of the present invention may have improved pharmacokinetic properties such as improved solubility and absorption, reduced adverse side effects and decreased metabolic stability in comparison to known structurally related compounds. A particular advantage of some of the compounds of the present invention is that they show high systemic clearance.

Accordingly, the invention relates to compounds of general formula I:

I and pharmaceutically acceptable salts, prodrugs, hydrates, or solvates thereof wherein m is 0-3;
n is 2, 4, 6, or 8;
A is N or C—$R_6$;
$R_6$ is selected from the group consisting of hydrogen, halogen, hydroxy, cyano, —$NH_2$, —$SO_2NH_2$, —$SONH_2$, —$CONH_2$, $R_{6a}O$—, $(R_{6a})_2N$—, and $R_{6a}S$—;
or $R_6$ is selected from the group consisting of alkyl-, cycloalkyl-, heterocyclyl-, aryl- and heteroaryl-, either of which may be optionally substituted with one or more $R_{6b}$;
$R_{6a}$ is hydrogen;
or $R_{6a}$ is selected from the group consisting of alkyl-, cycloalkyl-, heterocyclyl-, aryl- and heteroaryl-, either of which may be optionally substituted with one or more $R_{6b}$; or in the case where two $R_{6a}$s are attached to the same N, they may together with the N atom to which they are attached form a heterocycle which may be optionally substituted with one or more $R_{6b}$;
$R_{6b}$ is selected from the group consisting of halogen, cyano, hydroxy, oxo, —$NH_2$, —$SO_2NH_2$, —$SONH_2$, —$CONH_2$, alkyl-, alkenyl-, alkynyl-, cycloalkyl-, cycloalkenyl-, heterocyclyl-, $R_{6b1}O$—, $R_{6b1}S$—, $(R_{6b1})_2N$—, $R_{6b1}$—C(=O)—, $(R_{6b1})_2N$—C(=O)—, $R_{6b1}$—C(=O)N($R_{6b1}$)—, $R_{6b1}O$—C(=O)N($R_{6b1}$)—, $(R_{6b1})_2N$—C(=O)N($R_{6b1}$)—, $R_{6b1}$—C(=O)O—, $R_{6b1}O$—C(=O)O—, $(R_{6b1})_2N$—C(=O)O—, $R_{6b1}O$—S(=O)$_2$—, $(R_{6b1})_2N$—S(=O)$_2$—, $R_{6b1}$—S(=O)$_2N(R_{6b1})$—, $R_{6b1}O$—S(=O)$_2N(R_{6b1})$—, $(R_{6b1})_2N$—S(=O)$_2N(R_{6b1})$—, $R_{6b1}$—S(=O)$_2$O—, $R_{6b1}O$—S(=O)$_2$O—, $(R_{6b1})_2N$—S(=O)$_2$O—, aryl-, aryloxy-, heteroaryl-, and heteroaryloxy-;
$R_{6b1}$ independently at each occurrence is selected from the group consisting of alkyl-, cycloalkyl-, heterocyclyl-, aryl- and heteroaryl-;
or in the case where two $R_{61b}$s are attached to the same N, they may together with the N atom to which they are attached form a heterocycle;
$R_1$, $R_2$ and $R_9$ independently are selected from the group consisting of hydrogen, halogen, cyano, —$NH_2$, —$SO_2NH_2$, —$SONH_2$, and —$CONH_2$;
or $R_1$, $R_2$ and $R_9$ independently are selected from the group consisting of alkyl-, alkenyl-, alkynyl-, alkenylalkyl-, alkynylalkyl-, cycloalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, $R_{1a}O$-L-, $R_{1a}S$-L-, $(R_{1a})_2N$-L-, $R_{1b}$—C(=O)-L-, $R_{1b}O$—C(=O)-L-, $(R_{1b})_2N$—C(=O)-L-, $R_{1b}$—C(=O)N($R_{1c}$)-L-, $R_{1b}O$—C(=O)N($R_{1c}$)-L-, $(R_{1b})_2N$—C(=O)N($R_{1c}$)-L-, $R_{1b}O$—C(=O)O-L-, $R_{1b}O$—C(=O)O-L-, $(R_{1b})_2N$—C(=O)O-L-, $R_{1b}$—S(=O)-L-, $R_{1b}$—S(=O)$_2$-L-, $R_{1b}O$—S(=O)-L-, $R_{1b}O$—S(=O)$_2$-L-, $(R_{1b})_2N$—S(=O)-L-, $(R_{1b})_2N$—S(=O)$_2$-L-, $R_{1b}$—S(=O)N($R_{1c}$)-L-, $R_{1b}$—S(=O)$_2N(R_{1c}$)-L-, $R_{1b}O$—S(=O)N($R_{1c}$)-L-, $R_{1b}O$—S(=O)$_2$ N($R_{1c}$)-L-, $R_{1b}N$—S(=O)N($R_{1c}$)-L-, $(R_{1b})_2N$—S(=O)$_2N(R_{1c})$-L-, $R_{1b}$—S(=O)$_2$O-L-, $R_{1b}O$—S(=O)O-L-, $R_{1b}O$—, S(=O)$_2$O-L-, $(R_{1b})_2N$—S(=O)O-L-, $(R_{1b})_2N$—S(=O)$_2$O-L-, aryl-, arylalkyl-, arylalkenyl-, arylalkynyl-, arylcycloalkyl-, aryloxy-, aryloxyalkyl-, aryloxycycloalkyl-, heteroaryl-, heteroarylalkyl-, heteroarylalkenyl-, heteroarylalkynyl-, heteroarylcycloalkyl, heteroaryloxy-, heteroaryloxyalkyl-, and heteroaryloxycycloalkyl-, either of which may be optionally substituted with one or more $R_{1d}$;
L is a covalent bond or L is independently at each occurrence selected from the group consisting of alkyl-, cycloalkyl-, alkylcycloalkyl- and cycloalkylalkyl-;
$R_{1a}$ is hydrogen;
or $R_{1a}$ independently at each occurrence is selected from the group consisting of alkyl-, alkenyl-, alkynyl-, cycloalkyl -heterocyclyl-, aryl- and heteroaryl-, either of which may be optionally substituted with one or more $R_{1e}$;

or in the case where two $R_{1a}$s are attached to the same N, they may together with the N atom to which they are attached form a heterocycle which may be optionally substituted with one or more $R_{1e}$;

$R_{1b}$ and $R_{1c}$ independently at each occurrence are selected from the group consisting of alkyl-, alkenyl-, alkynyl-, cycloalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, aryl-, arylalkyl-, arylalkenyl-, arylalkynyl-, arylcycloalkyl-, aryloxyalkyl-, aryloxycycloalkyl-, heteroaryl-, heteroarylalkyl-, heteroarylalkenyl-, heteroarylalkynyl-, heteroarylcycloalkyl, heteroaryloxyalkyl-, and heteroaryloxycycloalkyl-, either of which may be optionally substituted with one or more $R_{1e}$;

or in the case where two $R_{1b}$s or two $R_{1c}$s are attached to the same N, they may together with the N atom to which they are attached form a heterocycle which may be optionally substituted with one or more $R_{1e}$;

$R_{1d}$ and $R_{1e}$ independently at each occurrence are selected from the group consisting of halogen, cyano, hydroxy, oxo, —$NH_2$, —$SO_2NH_2$, —$SONH_2$, —$CONH_2$, alkyl-, alkenyl-, alkynyl-, cycloalkyl-, cycloalkenyl-, heterocyclyl-, $(R_{1f})_2$N-L-, $R_{1f}$—C(=O)-L-, $R_{1f}$O—C(=O)-L-, $(R_{1f})_2$N—C(=O)-L-, $R_{1f}$—C(=O)N($R_{1f}$)-L-, $R_{1f}$—O—C(=O)N($R_{1f}$)-L-, $(R_{1f})_2$N—C(=O)N($R_{1f}$)-L-, $R_{1f}$—C(=O)O-L-, $R_{1f}$O—C(=O)O-L-, $(R_{1f})_2$N—C(=O)O-L-, $R_{1f}$—S(=O)$_2$-L-, $(R_{1f})_2$N—S(=O)$_2$-L-, $R_{1f}$—S(=O)$_2$N($R_{1f}$)-L-, $R_{1f}$O—S(=O)$_2$N($R_{1f}$)-L-, $(R_{1f})_2$N—S(=O)$_2$N($R_{1f}$)-L-, $R_{1f}$—S(=O)$_2$O-L-, $R_{1f}$O—S(=O)$_2$O-L-, $(R_{1f})_2$N—S(=O)$_2$O-L-, aryl-, aryloxy-, heteroaryl-, and heteroaryloxy-;

$R_{1f}$ independently at each occurrence is selected from the group consisting of alkyl-, alkenyl-, alkynyl-, cycloalkyl-, heterocyclyl-, aryl- and heteroaryl-;

$R_3$ is independently at each occurrence a covalent bond or alkyl- or heteroalkyl-, which may be optionally substituted with one or more $R_{3a}$, wherein any two $R_3$s form, together with the ring atom(s) to which they are attached, a cycloalkyl or heterocycle, with the proviso that said two $R_3$s are either attached to the same C atom or to two non-adjacent C atoms;

$R_{3a}$ independently at each occurrence is selected from the group consisting of halogen, cyano, hydroxy, oxo, —$NH_2$, —$SO_2NH_2$, —$SONH_2$, —$CONH_2$, alkyl-, alkenyl-, alkynyl-, alkenylalkyl-, alkynylalkyl-, cycloalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, $R_{3b}$O-L-, $R_{3b}$S-L-, $(R_{3b})_2$N-L-, $R_{3b}$—C(=O)-L-, $R_{3b}$O—C(=O)-L-, $(R_{3b})_2$N—C(=O)-L-, $R_{3b}$—C(=O)N($R_{3c}$)-L-, $R_{3b}$O—C(=O)N($R_{3c}$)-L-, $(R_{3b})_2$N—C(=O)N($R_{3c}$)-L-, $R_{3b}$—C(=O)O-L-, $R_{3b}$O—C(=O)O-L-, $(R_{3b})_2$N—C(=O)O-L-, $R_{3b}$—S(=O)-L-, $R_{3b}$—S(=O)$_2$-L-, $R_{3b}$O—S(=O)-L-, $R_{3b}$O—S(=O)$_2$-L-, $(R_{3b})_2$N—S(=O)-L-, $(R_{3b})_2$N—S(=O)$_2$-L-, $R_{3b}$—S(=O)N($R_{3c}$)-L-, $R_{3b}$—S(=O)$_2$N($R_{3c}$)-L-, $R_{3b}$O—S(=O)N($R_{3c}$)-L-, $R_{3b}$O—S(=O)$_2$N($R_{3c}$)-L-, $R_{3b}$N—S(=O)N($R_{3c}$)-L-, $(R_{3b})_2$N—S(=O)$_2$N($R_{3c}$)-L-, $R_{3b}$—S(=O)O-L-, $R_{3b}$—S(=O)$_2$O-L-, $R_{3b}$O—S(=O)O-L-, $R_{3b}$O—S(=O)$_2$O-L-, $(R_{3b})_2$N—S(=O)O-L-, $(R_{3b})_2$N—S(=O)$_2$O-L-, aryl-, arylalkyl-, arylalkenyl-, arylalkynyl-, arylcycloalkyl-, aryloxy-, aryloxyalkyl-, aryloxycycloalkyl-, heteroaryl-, heteroarylalkyl-, heteroarylalkenyl-, heteroarylalkynyl-, heteroarylcycloalkyl, heteroaryloxy-, heteroaryloxyalkyl-, and heteroaryloxycycloalkyl-;

wherein L is a covalent bond or L is independently at each occurrence selected from the group consisting of alkyl-, cycloalkyl-, alkylcycloalkyl- and cycloalkylalkyl-;

$R_{3b}$ and $R_{3c}$ independently at each occurrence are selected from the group consisting of hydrogen, alkyl-, alkenyl-, alkynyl-, cycloalkyl-, heterocyclyl-, aryl- and heteroaryl-;

$R_5$ independently at each occurrence is selected from the group consisting of halogen, cyano, hydroxy, oxo, —$NH_2$, —$SO_2NH_2$, —$SONH_2$, —$CONH_2$, alkyl-, alkenyl-, alkynyl-, alkenylalkyl-, alkynylalkyl-, cycloalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, $R_{5a}$O-L-, $R_{5a}$S-L-, $(R_{5a})_2$N-L-, $R_{5a}$—C(=O)-L-, $R_{5a}$O—C(=O)-L-, $(R_{5a})_2$N—C(=O)-L-, $R_{5a}$—C(=O)N($R_{5b}$)-L-, $R_{5a}$O—C(=O)N($R_{5b}$)-L-, $(R_{5a})_2$N—C(=O)N($R_{5b}$)-L-, $R_{5a}$—C(=O)O-L-, $R_{5a}$O—C(=O)O-L-, $(R_{5a})_2$N—C(=O)O-L-, $R_{5a}$—S(=O)-L-, $R_{5a}$—S(=O)$_2$-L-, $R_{5a}$O—S(=O)-L-, $R_{5a}$O—S(=O)$_2$-L-, $(R_{5a})_2$N—S(=O)-L-, $(R_{5a})_2$N—S(=O)$_2$-L-, $R_{5a}$—S(=O)N($R_{5b}$)-L-, $R_{5a}$—S(=O)$_2$N($R_{5b}$)-L-, $R_{5a}$O—S(=O)N($R_{5b}$)-L-, $R_{5a}$O—S(=O)$_2$N($R_{5b}$)-L-, $R_{5a}$N—S(=O)N($R_{5b}$)-L-, $(R_{5a})_2$N—S(=O)$_2$N($R_{5b}$)-L-, $R_{5a}$—S(=O)O-L-, $R_{5a}$—S(=O)$_2$O-L-, $R_{5a}$O—S(=O)O-L-, $R_{5a}$O—S(=O)$_2$O-L-, $(R_{5a})_2$N—S(=O)O-L-, $(R_{5a})_2$N—S(=O)$_2$O-L-, aryl-, arylalkyl-, arylalkenyl-, arylalkynyl-, arylcycloalkyl-, aryloxy-, aryloxyalkyl-, aryloxycycloalkyl-, heteroaryl-, heteroarylalkyl-, heteroarylalkenyl-, heteroarylalkynyl-, heteroarylcycloalkyl, heteroaryloxy-, heteroaryloxyalkyl-, and heteroaryloxycycloalkyl-;

wherein L is a covalent bond or L is independently at each occurrence selected from the group consisting of alkyl-, cycloalkyl-, alkylcycloalkyl- and cycloalkylalkyl-;

$R_{5a}$ and $R_{5b}$ independently at each occurrence are selected from the group consisting of hydrogen, alkyl-, alkenyl-, alkynyl-, cycloalkyl-, heterocyclyl-, aryl- and heteroaryl-;

$R_4$ is selected from the group consisting of

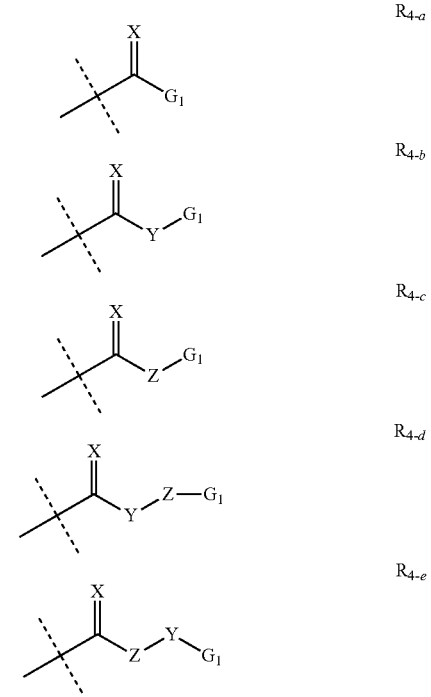

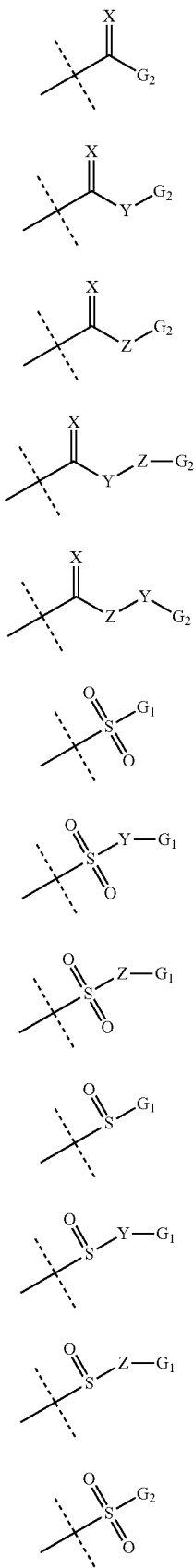

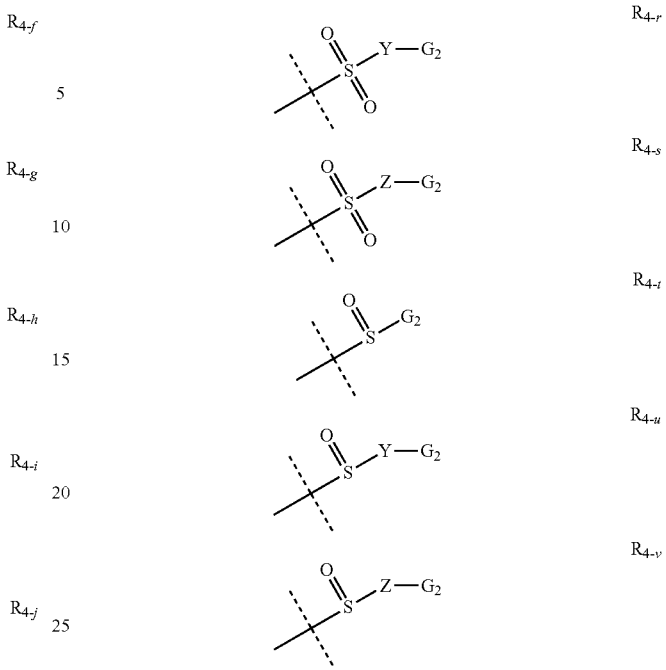

wherein
X is O or S;
Y is O or N—R$_7$;
Z is C$_{1-5}$-alkylene, C$_{2-5}$-alkenylene, or C$_{2-5}$-alkynylene, either of which may be optionally substituted with one or more R$_8$;
G$_1$ is selected from the group consisting of cycloalkyl-, cycloalkenyl-, heterocyclyl-, aryl- and heteroaryl-, either of which may be optionally substituted with one or more R$_G$;
G$_2$ is selected from the group consisting of alkyl-, alkenyl-, alkynyl-, R$_{G2a}$O-L-, R$_{G2a}$S-L-, (R$_{G2a}$)$_2$N-L-, R$_{G2a}$—C(=O)-L-, R$_{G2a}$O—C(=O)-L-, (R$_{G2a}$)$_2$N—C(=O)-L-, R$_{G2a}$—C(=O)N(R$_{G2b}$)-L-, R$_{G2a}$O—C(=O)N(R$_{G2}$)-L-, (R$_{G2a}$)$_2$N—C(=O)N(R$_{G2b}$)-L-, R$_{G2a}$—C(=O)O-L-, R$_{G2a}$O—C(=O)O-L-, (R$_{G2a}$)$_2$N—C(=O)O-L-, R$_{G2a}$—S(=O)-L-, R$_{G2a}$—S(=O)$_2$-L-, R$_{G2a}$O—S(=O)-L-, R$_{G2a}$O—S(=O)$_2$-L-, (R$_{G2a}$)$_2$N—S(=O)-L-, (R$_{G2a}$)$_2$N—S(=O)$_2$-L-, R$_{G2a}$—S(=O)N(R$_{G2}$)-L-, R$_{G2a}$—S(=O)$_2$N(R$_{G2}$)-L-, R$_{G2a}$O—S(=O)N(R$_{G2}$)-L-, R$_{G2a}$O—S(=O)$_2$N(R$_{G2}$)-L-, R$_{G2a}$N—S(=O)N(R$_{G2}$)-L-, (R$_{G2a}$)$_2$N—S(=O)$_2$N(R$_{G2b}$)-L-, R$_{G2a}$—S(=O)O-L-, R$_{G2a}$—S(=O)$_2$O-L-, R$_{G2a}$O—S(=O)O-L-, R$_{G2a}$O—S(=O)$_2$O-L-, (R$_{G2a}$)$_2$N—S(=O)O-L-, and (R$_{G2a}$)$_2$N—S(=O)$_2$O-L-; either of which may be optionally substituted with one or more R$_G$;
wherein L is a covalent bond or L is independently at each occurrence selected from the group consisting of alkyl-, cycloalkyl-, alkylcycloalkyl- and cycloalkylalkyl-;
R$_{G2a}$ and R$_{G2b}$ independently at each occurrence are selected from the group consisting of hydrogen, alkyl-, alkenyl-, alkynyl-, cycloalkyl-, heterocyclyl-, aryl- and heteroaryl-;
R$_G$ is selected from the group consisting of halogen, cyano, hydroxy, oxo, —NH$_2$, —SO$_2$NH$_2$, —SONH$_2$, —CONH$_2$, alkyl- and cycloalkyl-, wherein said alkyl- or cycloalkyl- is optionally substituted by one or more substituents selected from the group consisting of halogen, cyano, hydroxy, trifluoromethyl and —NH$_2$; or R$_G$ is selected from the group consisting of alkenyl-, alkynyl-, alkenylalkyl-, alkynylalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, $R_{Ga}$O-L-, $R_{Ga}$S-L-, $(R_{Ga})_2$N-L-, $R_{Ga}$—C(=O)-L-, $R_{Ga}$O—C(=O)-L-, $(R_{Ga})_2$N—C(=O)-L-, $R_{Ga}$—C(=O)N($R_{Gb}$)-L-, $R_{Ga}$O—C(=O)N($R_{Gb}$)-L-, $(R_{Ga})_2$N—C(=O)N($R_{Gb}$)-L-, $R_{Ga}$—C(=O)O-L-, $R_{Ga}$O—C(=O)O-L-, $(R_{Ga})_2$N—C(=O)O-L-, $R_{Ga}$—S(=O)-L-, $R_{Ga}$—S(=O)$_2$-L-, $R_{Ga}$O—S(=O)-L-, $R_{Ga}$O—S(=O)$_2$-L-, $(R_{Ga})_2$N—S(=O)-L-, $(R_{Ga})_2$N—S(=O)$_2$-L-, $R_{Ga}$—S(=O)N($R_{Gb}$)-L-, $R_{Ga}$—S(=O)$_2$N($R_{Gb}$)-L-, $R_{Ga}$O—S(=O)N($R_{Gb}$)-L-, $R_{Ga}$O—S(=O)$_2$N($R_{Gb}$)-L-, $R_{Ga}$N—S(=O)N($R_{Gb}$)-L-, $(R_{Ga})_2$N—S(=O)$_2$N($R_{Gb}$)-L-, $R_{Ga}$—S(=O)O-L-, $R_{Ga}$—S(=O)$_2$O-L-, $R_{Ga}$O—S(=O)O-L-, $R_{Ga}$O—S(=O)$_2$O-L-, $(R_{Ga})_2$N—S(=O)O-L-, $(R_{Ga})_2$N—S(=O)$_2$O-L-, aryl-, arylalkyl-, arylalkenyl-, arylalkynyl-, arylcycloalkyl-, aryloxy-, aryloxyalkyl-, aryloxycycloalkyl-, heteroaryl-, heteroarylalkyl-, heteroarylalkenyl-, heteroarylalkynyl-, heteroarylcycloalkyl, heteroaryloxy-, heteroaryloxyalkyl-, and heteroaryloxycycloalkyl-;

wherein L is a covalent bond or L is independently at each occurrence selected from the group consisting of alkyl-, cycloalkyl-, alkylcycloalkyl- and cycloalkylalkyl-;

$R_{Ga}$ and $R_{Gb}$ independently at each occurrence are selected from the group consisting of hydrogen, alkyl-, alkenyl-, alkynyl-, cycloalkyl-, heterocyclyl-, heterocyclylalkyl, aryl-, heteroaryl- and heteroarylalkyl; wherein said alkyl-, alkenyl-, alkynyl-, cycloalkyl-, heterocyclyl-, heterocyclylalkyl, aryl-, heteroaryl- or heteroarylalkyl group is optionally substituted one or more times by a substituent selected from the group consisting of halogen, cyano, hydroxy, methyl, trifluoromethyl, methoxy and —$NH_2$;

$R_7$ is hydrogen or is independently at each occurrence selected from the group consisting of alkyl-, alkenyl-, alkynyl-, cycloalkyl-, heterocyclyl-, aryl- and heteroaryl-, either of which may be optionally substituted with one or more $R_{7a}$;

$R_{7a}$ independently at each occurrence is selected from the group consisting of halogen, cyano, hydroxy, oxo, —$NH_2$, —$SO_2NH_2$, —$SONH_2$, —$CONH_2$, alkyl-, alkenyl-, alkynyl-, cycloalkyl-, heterocyclyl-, aryl- and heteroaryl-;

$R_8$ independently at each occurrence is selected from the group consisting of hydrogen, halogen, cyano, hydroxy, oxo, —$NH_2$, —$SO_2NH_2$, —$SONH_2$, —$CONH_2$, alkyl- and cycloalkyl, wherein said alkyl- or cycloalkyl- is optionally substituted by one or more substituents selected from the group consisting of halogen, cyano, hydroxy, trifluoromethyl and —$NH_2$;

or two $R_8$s may, together with the C atom(s) to which they are attached, form an optionally substituted cycloalkyl or heterocycle;

with the proviso that the compound of the formula I is not 3-(5-methyl-7H-pyrrolo[2,3-d]pyrimidin-4-yl)-3,8-diazabicyclo[3.2.1]octane-8-carboxylic acid (3-bromo-phenyl)-amide, N-(3-bromophenyl)-N'-cyano-5-(5-methyl-7H-pyrrolo[2,3-d]pyrimidin-4-yl)-2,5-diazabicyclo[2.2.1]heptane-2-carboximidamide or tert-butyl-3-(5-methyl-7H-pyrrolo[2,3-d]pyrimidin-4-yl)-3,8-diazzbicyclo[3.2.1]octane-8-carboxylate.

In another aspect, the invention relates to pharmaceutical compositions comprising a compound of formula I or a pharmaceutically acceptable salt, hydrate, or solvate thereof together with a pharmaceutically acceptable vehicle or excipient.

In another aspect, the invention relates to pharmaceutical compositions comprising a compound of formula I or a pharmaceutically acceptable salt, hydrate, or solvate thereof further comprising another therapeutically active compound.

In one aspect, the invention relates to the compounds of general formula I for use—alone or in combination with one or more other pharmaceutically active compounds—in therapy.

In another aspect, the invention relates to the compounds of general formula I for use—alone or in combination with one or more other pharmaceutically active compounds—for treating diseases associated with the immune system, such as autoimmune diseases.

In another aspect, the invention relates to the compounds of general formula I for use—alone or in combination with one or more other pharmaceutically active compounds—in the prophylaxis, treatment or amelioration of skin diseases, such as psoriasis, rosacea, lupus, and other autoimmune diseases such as multiple sclerosis, rheumatoid arthritis, Type I diabetes and complications from diabetes, asthma, atopic dermatitis, cancer, autoimmune thyroid disorders, ulcerative colitis, Crohn's disease, Alzheimer's disease, leukaemia, eye diseases such as diabetic retinopathy and macular degeneration as well as other autoimmune diseases.

In another aspect, the invention relates to a use of a compound of general formula I—alone or in combination with one or more other pharmaceutically active compounds—for the manufacture of a medicament for the prophylaxis, treatment and/or amelioration of diseases of the immune system, such as autoimmune diseases.

In another aspect, the invention relates to compounds according to formula I for use as an anti-inflammatory agent capable of modulating the activity of a protein tyrosin kinase of the Janus kinase family.

In another aspect, the invention relates to compounds according to formula I for use as an anti-inflammatory agent capable of modulating the activity of JAK1, JAK2, JAK3 or TYK2 protein tyrosine kinases.

In another aspect, the invention relates to compounds according to formula I for use in the treatment, amelioration or prophylaxis of non-infectious anti-inflammatory or autoimmune diseases or conditions wherein the non-infectious inflammatory diseases or conditions are selected from the group consisting of acute inflammatory diseases such as acute lung injury, acute respiratory distress syndrome, allergy, anaphylaxis, sepsis or graft-vs-host disease, or chronic inflammatory diseases such as osteoarthritis, gout, psoriatic arthritis, hepatic cirrhosis, multiple sclerosis, or ocular diseases or conditions such as non-infectious (e.g. allergic) conjunctivitis, uveitis, iritis, keratitis, scleritis, episcleritis, sympathitic ophthalmitis, blepharitis, keratoconjunctivitis sicca, or immunological cornea graft rejection, and the autoimmune diseases or conditions are selected from the group consisting of autoimmune gastritis, Addison's disease, autoimmune hemolytic anemia, autoimmune thyroiditis, chronic idiopathic urticaria, chronic immune polynephropathy, diabetes, diabetic nephropathy, myasthenia gravis, pemphigus vulgaris, pernicious anemia, primary biliary cirrhosis, systemic lupus erythematosus and thyroid eye disease.

In another aspect, the invention relates to method of preventing, treating or ameliorating diseases of the immune system, such as autoimmune diseases, the method comprising administering an effective amount of a compound according to formula I to a patient in need thereof.

DETAILED DESCRIPTION OF THE INVENTION

Definitions

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-20 carbon atoms, and preferably comprises 1-12 or 1-10 e.g. 1-6, e.g. 1-4, e.g. 1-3, e.g. 1-2 carbon atoms. The term includes alkyl, alkenyl, cycloalkyl, cycloalkenyl, alkynyl and aryl, as indicated below.

In the present context, the term "alkyl" is intended to indicate the radical obtained when one hydrogen atom is removed from a hydrocarbon. Said alkyl may be branched or straight-chained and comprises 1-20, preferably 1-10, such as 2-6, such as 3-4 carbon atoms. The term includes the subclasses normal alkyl (n-alkyl), secondary and tertiary alkyl, such as methyl, ethyl, n-propyl, isopropyl, n-butyl, isobutyl, sec-butyl, tert-butyl, pentyl, isopentyl, hexyl and isohexyl.

The term "alkylene" is intended to indicate a divalent saturated aliphatic hydrocarbyl group preferably having from 1 to 6 and more preferably 1 to 3 carbon atoms that are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) or (—CH(CH$_3$)CH$_2$—), and the like.

The term "cycloalkyl" is intended to indicate a saturated cycloalkane radical, including polycyclic radicals, such as bicyclic or tricyclic radicals, comprising 3-20 carbon atoms, preferably 3-10 carbon atoms, in particular 3-8 carbon atoms, such as 3-6 carbon atoms, such as 4-5 carbon atoms, e.g. cyclopropyl, cyclobutyl, cyclopentyl, cyclohexyl, cycloheptyl and cyclooctyl.

The term "cycloalkylene" is intended to indicate a divalent cycloalkyl group as defined herein.

The term "alkenyl" is intended to indicate a hydrocarbon radical comprising 2-20 carbon atoms, preferably 2-10, in particular 2-6 carbon atoms, such as 2-4 carbon atoms, and having at least 1 and preferably from 1 to 2 sites of double bond unsaturation, e.g. ethenyl, allyl, propenyl, butenyl, pentenyl, nonenyl, or hexenyl. Included within this term are the cis and trans isomers or mixtures of these isomers.

The term "alkenylene" is intended to indicate a divalent aliphatic hydrocarbyl group preferably having from 2 to 6 and more preferably 2 to 4 carbon atoms that are either straight-chained or branched and having at least 1 and preferably from 1 to 2 sites of double bond unsaturation. This term is exemplified by groups such as ethenylene (—CH=CH—), propenylene (—CH=CHCH$_2$—), 1-butenylene (—CH=CHCH$_2$CH$_2$—) or 2-butenylene (—CH$_2$CH=CHCH$_2$—), and the like.

The term "cycloalkenyl" is intended to indicate mono-, di-tri- or tetraunsaturated non-aromatic cyclic hydrocarbon radicals, including polycyclic radicals, comprising 3-20 carbon atoms, typically comprising 3-10 carbon atoms, such as 3-8 carbon atoms, such as 4-6 carbon atoms, e.g. cyclopropenyl, cyclobutenyl, cyclopentenyl or cyclohexenyl.

The term "cycloalkenylene" is intended to indicate a divalent cycloalkenyl group as defined herein.

The term "alkynyl" is intended to indicate an hydrocarbon radical comprising 1-5 C—C triple bonds and 2-20 carbon atoms, the alkane chain typically comprising 2-10 carbon atoms, in particular 2-6 carbon atoms, such as 2-4 carbon atoms, e.g. ethynyl, propynyl, butynyl, pentynyl or hexynyl.

The term "alkynylene" is intended to indicate a divalent aliphatic hydrocarbyl group preferably having from 2 to 6 and more preferably 2 to 4 carbon atoms that are either straight-chained or branched and having at least 1 and preferably from 1 to 2 sites of triple bond unsaturation. This term is exemplified by groups such as ethynylene (—CC—), propynylene (—CCCH$_2$—), 1-butynylene (—CCCH$_2$CH$_2$—) or 2-butynylene (—CH$_2$CCCH$_2$—), and the like.

The term "cycloalkynyl" is intended to indicate mono-, di-, tri- or tetra-unsaturated non-aromatic cyclic hydrocarbon radicals, including polycyclic radicals, comprising 3-20 carbon atoms, typically comprising 3-10 carbon atoms, such as 3-8 carbon atoms, such as 4-6 carbon atoms, and at least 1 and preferably from 1 to 2 sites of triple bond unsaturation, e.g. cyclopropynyl, cyclobutynyl, cyclopentynyl or cyclohexynyl.

The term "cycloalkynylene" is intended to indicate a divalent cycloalkynyl group as defined herein.

The term "heterocyclic" and "heterocyclyl" is intended to indicate a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulphur and oxygen, wherein, in fused ring systems, one or more of the rings can be cycloalkyl, aryl, or heteroaryl, provided that the point of attachment is through the non-aromatic ring. In one embodiment, the nitrogen and/or sulphur atom(s) of the heterocyclic group are optionally oxidized to provide for the N-oxide, —S(O)—, or —SO2- moieties. Examples include tetrahydrofuranyl, pyrrolidinyl, dioxolanyl, morpholinyl, or piperidinyl.

The term "heterocycloalkenyl" is intended to indicate a cycloalkenyl radical as defined above, including polycyclic radicals, optionally fused with carbocyclic rings, comprising 1-6 heteroatoms, preferably 1-3 heteroatoms, selected from O, N, or S, e.g. tetrahydropyranol.

The term "heterocyclylalkyl" is intended to indicate a heterocyclyl group as defined herein connected via an alkyl group as defined herein.

The term "aryl" is intended to indicate a radical of aromatic carbocyclic rings comprising 6-20 carbon atoms, such as 6-14 carbon atoms, preferably 6-12, such as 6-10 carbon atoms, in particular 5- or 6-membered rings, optionally fused carbocyclic rings with at least one aromatic ring, such as phenyl, naphthyl, biphenyl, anthracenyl, indenyl or indanyl.

The terms "arylalkyl" and "arylcycloalkyl" are intended to indicate an aryl group as defined herein connected via an alkyl or a cycloalkyl group as defined herein, respectively.

The term "heteroaryl" is intended to include radicals of heterocyclic aromatic rings, optionally fused with carbocyclic rings or heterocyclic rings, comprising 1-6 heteroatoms (selected from O, S and N) and 1-20 carbon atoms, such as 1-5 heteroatoms and 1-10 carbon atoms, such as 1-5 heteroatoms and 1-6 carbon atoms, such as 1-5 heteroatoms and 1-3 carbon atoms, in particular 5- or 6-membered rings with 1-4 heteroatoms or 1-2 heteroatoms selected from O, S and N, or optionally fused bicyclic rings with 1-4 heteroatoms, and wherein at least one ring is aromatic. Examples of heteroaryl include, but are not limited to, pyridyl, quinolyl, isoquinolyl, indolyl, tetrazolyl, furyl, thiazolyl, imidazolyl, imidazo[1,2-a]pyrimidinyl, pyrazolyl, oxazolyl, oxadiazolyl, thiophenyl, 1,2,4-triazolyl, isoxazolyl, thienyl, pyrazinyl, pyrimidinyl, [1,2,3]triazolyl, isothiazolyl, imidazo[2,1-b]thiazolyl, benzimidazolyl, benzothiophenyl or benzofuranyl.

The term "aryloxy" is intended to indicate groups —O-aryl, wherein aryl is as defined herein, including, by way of example, phenoxy, napthoxy, and the like.

The term "alkyloxy" is intended to indicate the groups —O-alkyl, —O-alkenyl-, and —O-alkynyl-, wherein alkyl, alkenyl and alkynyl are as defined herein.

The term "halogen" is intended to indicate a substituent from the 7$^{th}$ main group of the periodic table, preferably fluoro, chloro and bromo.

The term "amino" refers to the group —NH$_2$.

The term "aminoalkyl" is intended to indicate a radical of the formula -alkyl-NH$_2$, wherein alkyl represents alkylene, cycloalkylene as indicated above, e.g. aminoalkylene, aminocycloethylene etc.

The term "arylamino" is intended to indicate a radical of the formula —NR$_2$, wherein R is aryl as indicated above e.g. phenylamino.

The term "arylaminoalkyl" is intended to indicate an arylamino group as defined herein connected via an alkyl group as defined herein.

The term "alkylthio" is intended to indicate a radical of the formula —S—R, wherein R is alkyl as indicated above.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, silver hydroxide, ammonia or the like.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

Unless indicated otherwise, the nomenclature of substituents that are not explicitly defined herein are arrived at by naming the terminal portion of the functionality followed by the adjacent functionality towards the point of attachment. For example, the group "arylalkyloxycarbonyl" refers to the group (aryl)-(alkyl)-O—C(O)—.

The term "JAK1" is used to indicate a protein tyrosine kinase of the JAK (Janus protein tyrosine kinase) family highly expressed in immune cells where it is essential for signalling by members of the IL-2 receptor family (IL-2, IL-4, IL-7R, IL-9R, IL-15R and IL-21R), the IL-4 receptor family (IL-4R, IL-13R), the gp130 receptor family and class II cytokine receptors.

The term "JAK2" is used to indicate a protein tyrosine kinase of the JAK (Janus protein tyrosine kinase) family highly expressed in immune cells where it is essential for signalling downstream of many cytokines and growth factors including the proinflammatory cytokines Epo, IFN-γ, IL-3, IL-5, and GM-CSF.

The term "JAK3" is used to indicate a protein tyrosine kinase of the JAK (Janus protein tyrosine kinase) family highly expressed in immune cells where it is essential for signalling downstream of many cytokines and growth factors including the proinflammatory cytokines IL-2, IL-4, IL-7, IL-9, IL-15 and IL-21.

The term "TYK2" is used to indicate a protein tyrosine kinase of the JAK (Janus protein tyrosine kinase) family, and TYK2 is implicated in type I interferons, IL-6, IL-10, IL-12 and IL-23 signaling.

Embodiments of Compounds of Formula I

In an embodiment of the invention $R_{Ga}$ and $R_{Gb}$ independently at each occurrence are selected from the group consisting of hydrogen, alkyl-, alkenyl-, alkynyl-, cycloalkyl-, heterocyclyl-, aryl- and heteroaryl-; wherein said alkyl-, alkenyl-, alkynyl-, cycloalkyl-, heterocyclyl-, aryl- or heteroaryl-group is optionally substituted one or more times by a substituent selected from the group consisting of halogen, cyano, hydroxy, trifluoromethyl and —NH$_2$;

In another embodiment of the invention A is N.

In another embodiment of the invention A is C—R$_6$ wherein R$_6$ is H, cyano, —CONH$_2$, C$_{1-6}$-alkyl, C$_{3-6}$-cycloalkyl, C$_{2-6}$-heterocyclyl and R$_{6a}$—O;

wherein R$_{6a}$ is hydrogen;

or R$_{6a}$ is selected from the group consisting of C$_{1-6}$-alkyl, C$_{3-6}$-cycloalkyl, C$_{2-6}$-heterocyclyl, C$_{6-10}$-aryl- and C$_{2-8}$-heteroaryl-, either of which may be optionally substituted with one or more R$_{6b}$;

R$_{6b}$ is selected from the group consisting of cyano, hydroxy, oxo, —SO$_2$NH$_2$, —CONH$_2$, C$_{1-6}$-alkyl, C$_{3-6}$-cycloalkyl, C$_{2-6}$-heterocyclyl, R$_{6b1}$O—, (R$_{6b1}$)$_2$N—, R$_{6b1}$—C(=O)—, (R$_{6b1}$)$_2$N—C(=O)—, R$_{6b1}$—C(=O)N(R$_{6b1}$)—, R$_{6b1}$O—C(=O)N(R$_{6b1}$)—, (R$_{6b1}$)$_2$N—C(=O)N(R$_{6b1}$)—, (R$_{6b1}$)$_2$N—C(=O)O—, (R$_{6b1}$)$_2$N—S(=O)$_2$—, R$_{6b1}$—S(=O)$_2$N(R$_{6b1}$)—, aryl-, aryloxy-, heteroaryl-, and heteroaryloxy-;

R$_{6b1}$ independently at each occurrence is selected from the group consisting of C$_{1-6}$-alkyl, C$_{3-6}$-cycloalkyl, C$_{2-6}$-heterocyclyl, C$_{6-10}$-aryl- and C$_{2-8}$-heteroaryl-; or in the case where two R$_{61b}$s are attached to the same N, they may together with the N atom to which they are attached form a heterocycle.

In another embodiment A is C—R$_6$ wherein R$_6$ is H, cyano, hydroxy, —CONH$_2$, C$_{1-6}$-alkyl, C$_{3-6}$-cycloalkyl, C$_{3-6}$-heterocyclyl or R$_{6a}$—O, wherein R$_{6a}$ is C$_{1-6}$-alkyl or C$_{3-6}$-cycloalkyl.

In another embodiment A is C—R$_6$ wherein R$_6$ is H, cyano, hydroxy, —CONH$_2$, C$_{1-6}$-alkyl, C$_{3-6}$-cycloalkyl, C$_{3-6}$-heterocyclyl or R$_{6a}$—O, wherein R$_{6a}$ is C$_{1-6}$-alkyl or C$_{3-6}$-cycloalkyl.

In another embodiment R$_6$ is H or R$_{6a}$—O, wherein R$_{6a}$ is C$_{1-6}$-alkyl.

In another embodiment m is 0.

In another embodiment n is 2 or 4.

In another embodiment n is 2.

In yet another embodiment R$_1$, R$_2$ and R$_9$ independently are selected from the group consisting of hydrogen, cyano, —SO$_2$NH$_2$, —SONH$_2$, and —CONH$_2$;

or R$_1$, R$_2$ and R$_9$ independently are selected from the group consisting of C$_{1-6}$-alkyl-, C$_{3-6}$-cycloalkyl-, C$_{3-6}$-cycloalkyl-C$_{1-6}$-alkyl-, C$_{2-6}$-heterocyclyl-, C$_{2-6}$-heterocyclyl-C$_{1-6}$-alkyl-, R$_{1a}$O-L-, (R$_{1a}$)$_2$N-L-, R$_{1b}$O—C(=O)-L-, (R$_{1b}$)$_2$N—C(=O)-L-, R$_{1b}$—C(=O)N(R$_{1c}$)-L-, R$_{1b}$O—C(=O)N(R$_{1c}$)-L-, (R$_{1b}$)$_2$N—C(=O)N(R$_{1c}$)-L-, R$_{1b}$—C(=O)O-L-, (R$_{1b}$)$_2$N—C(=O)O-L-, (R$_{1b}$)$_2$N—S(=O)$_2$-L-, R$_{1b}$—S(=O)$_2$N(R$_{1c}$)-L-, R$_{1b}$O—S(=O)$_2$N(R$_{1c}$)-L-, (R$_{1b}$)$_2$N—S(=O)$_2$N(R$_{1c}$)-L-, (R$_{1b}$)$_2$N—S(=O)$_2$O-L-, aryl-, arylalkyl-, arylcycloalkyl-, aryloxy-, aryloxyalkyl-, aryloxycycloalkyl-, heteroaryl-, heteroarylalkyl-, heteroarylcycloalkyl, heteroaryloxy-, heteroaryloxyalkyl-, and heteroaryloxycycloalkyl-, either of which may be optionally substituted with one or more R$_{1d}$;

wherein R$_{1a}$ is hydrogen or C$_{1-6}$-alkyl-, C$_{3-6}$-cycloalkyl-, C$_{2-6}$-heterocyclyl-, or C$_{6-10}$-aryl;

R$_{1b}$ and R$_{1c}$ independently at each occurrence are selected from the group consisting of C$_{1-6}$-alkyl-, C$_{3-6}$-cycloalkyl-, C$_{3-6}$-cycloalkyl-C$_{1-6}$-alkyl-, C$_{2-6}$-heterocyclyl-, C$_{2-6}$-heterocyclyl-C$_{1-6}$-alkyl-, C$_{6-10}$-aryl-, and C$_{2-8}$-heteroaryl-, either of which may be optionally substituted with one or more R$_{1e}$;

or in the case where two $R_{1b}$s or two $R_{1c}$s are attached to the same N, they may together with the N atom to which they are attached form a heterocycle which may be optionally substituted with one or more $R_{1e}$;

$R_{1d}$ and $R_{1e}$ independently at each occurrence are selected from the group consisting of cyano, hydroxy, oxo, —SO$_2$NH$_2$, —CONH$_2$, C$_{1-6}$-alkyl-, C$_{3-6}$-cycloalkyl-, C$_{2-6}$-heterocyclyl-, R$_{1f}$S-L-, R$_{1f}$S-L-, (R$_{1f}$)$_2$N-L-, (R$_{1f}$)$_2$N—C(=O)-L-, R$_{1f}$—C(=O)N(R$_{1f}$)-L-, R$_{1f}$O—C(=O)N(R$_{1f}$)-L-, (R$_{1f}$)$_2$N—C(=O)N(R$_{1f}$)-L-, (R$_{1f}$)$_2$N—C(=O)O-L-, (R$_{1f}$)$_2$N—S(=O)$_2$-L-, R$_{1f}$—S(=O)$_2$N(R$_{1f}$)-L-, R$_{1f}$O—S(=O)$_2$N(R$_{1f}$)-L-, (R$_{1f}$)$_2$N—S(=O)$_2$N(R$_{1f}$)-L-;

and R$_{1f}$ independently at each occurrence is selected from the group consisting of C$_{1-6}$-alkyl-, C$_{3-6}$-cycloalkyl-, C$_{2-6}$-heterocyclyl-.

In yet another embodiment R$_1$, R$_2$ and R$_9$ independently are selected from the group consisting of hydrogen, cyano, —SO$_2$NH$_2$, —SONH$_2$, and —CONH$_2$;

or R$_1$, R$_2$ and R$_9$ independently are selected from the group consisting of C$_{1-6}$-alkyl-, C$_{3-6}$-cycloalkyl-, C$_{2-6}$-heterocyclyl-, R$_{1a}$O-L-, (R$_{1a}$)$_2$N-L-, (R$_{1b}$)$_2$N—C(=O)-L-, C(=O)N(R$_{1c}$)-L-, R$_{1b}$O—C(=O)N(R$_{1c}$)-L-, (R$_{1b}$)$_2$N—C(=O)N(R$_{1c}$)-L-, (R$_{1b}$)$_2$N—C(=O)O-L-, (R$_{1b}$)$_2$N—S(=O)$_2$-L-, R$_{1b}$—S(=O)$_2$N(R$_{1c}$)-L-, R$_{1b}$O—S(=O)$_2$N(R$_{1c}$)-L-, (R$_{1b}$)$_2$N—S(=O)$_2$N(R$_{1c}$)-L-, (R$_{1b}$)$_2$N—S(=O)$_2$O-L- either of which may be optionally substituted with one or more $R_{1d}$;

wherein $R_{1a}$ is hydrogen or C$_{1-6}$-alkyl-, C$_{3-6}$-cycloalkyl-, C$_{2-6}$-heterocyclyl-, or C$_{6-10}$-aryl;

$R_{1b}$ and $R_{1c}$ independently at each occurrence are selected from the group consisting of C$_{1-6}$-alkyl-, C$_{3-6}$-cycloalkyl-, C$_{3-6}$-cycloalkyl-C$_{1-6}$-alkyl-, C$_{2-6}$-heterocyclyl-, C$_{2-6}$-heterocyclyl-C$_{1-6}$-alkyl-, C$_{6-10}$-aryl-, C$_{2-8}$-heteroaryl-, which may be optionally substituted with one or more $R_{1e}$;

or in the case where two $R_{1b}$s or two $R_{1c}$s are attached to the same N, they may together with the N atom to which they are attached form a heterocycle which may be optionally substituted with one or more $R_{1e}$;

$R_{1d}$ and $R_{1e}$ independently at each occurrence are selected from the group consisting of cyano, hydroxy, oxo, —SO$_2$NH$_2$, —CONH$_2$, C$_{1-6}$-alkyl-, C$_{3-6}$-cycloalkyl-, C$_{2-6}$-heterocyclyl-, R$_{1f}$O-L-, R$_{1f}$S-L-, (R$_{1f}$)$_2$N-L-, (R$_{1f}$)$_2$N—C(=O)-L-, R$_{1f}$—C(=O)N(R$_{1f}$)-L-, R$_{1f}$O—C(=O)N(R$_{1f}$)-L-, (R$_{1f}$)$_2$N—C(=O)N(R$_{1f}$)-L-, (R$_{1f}$)$_2$N—C(=O)O-L-, (R$_{1f}$)$_2$N—S(=O)$_2$-L-, R$_{1f}$—S(=O)$_2$N(R$_{1f}$)-L-, R$_{1f}$O—S(=O)$_2$N(R$_{1f}$)-L-, (R$_{1f}$)$_2$N—S(=O)$_2$N(R$_{1f}$)-L-;

and R$_{1f}$ independently at each occurrence is selected from the group consisting of C$_{1-6}$-alkyl-, C$_{3-6}$-cycloalkyl-, and C$_{2-6}$-heterocyclyl-.

In yet another embodiment R$_1$, R$_2$ and R$_9$ independently are selected from the group consisting of hydrogen, halogen, cyano, —SO$_2$NH$_2$, —SONH$_2$, and —CONH$_2$;

or R$_1$, R$_2$ and R$_9$ independently are selected from the group consisting of C$_{1-6}$-alkyl-, C$_{3-6}$-cycloalkyl-, C$_{3-6}$-cycloalkyl-C$_{1-6}$-alkyl-, C$_{2-6}$-heterocyclyl-, C$_{2-6}$-heterocyclyl-C$_{1-6}$-alkyl-, R$_{1b}$O—C(=O)-L-, (R$_{1b}$)$_2$N—C(=O)-L-, R$_{1b}$—C(=O)N(R$_{1c}$)-L-, R$_{1b}$O—C(=O)N(R$_{1c}$)-L-, (R$_{1b}$)$_2$N—C(=O)N(R$_{1c}$)-L-, R$_{1b}$—C(=O)O-L-, (R$_{1b}$)$_2$N—C(=O)O-L-, (R$_{1b}$)$_2$N—S(=O)$_2$-L-, R$_{1b}$—S(=O)$_2$N(R$_{1c}$)-L-, R$_{1b}$O—S(=O)$_2$N(R$_{1c}$)-L-, (R$_{1b}$)$_2$N—S(=O)$_2$N(R$_{1c}$)-L-, (R$_{1b}$)$_2$N—S(=O)$_2$O-L-, aryl-, arylalkyl-, arylcycloalkyl-, aryloxy-, aryloxyalkyl-, aryloxycycloalkyl-, heteroaryl-, heteroarylalkyl-, heteroarylcycloalkyl, heteroaryloxy-, heteroaryloxyalkyl-, and heteroaryloxycycloalkyl-, either of which may be optionally substituted with one or more $R_{1d}$;

wherein $R_{1a}$ is hydrogen or C$_{1-6}$-alkyl-, C$_{3-6}$-cycloalkyl-, C$_{2-6}$-heterocyclyl-, or C$_{6-10}$-aryl;

$R_{1b}$ and $R_{1c}$ independently at each occurrence are selected from the group consisting of C$_{1-6}$-alkyl-, C$_{3-6}$-cycloalkyl-, C$_{3-6}$-cycloalkyl-C$_{1-6}$-alkyl-, C$_{2-6}$-heterocyclyl-, C$_{2-6}$-heterocyclyl-C$_{1-6}$-alkyl-, C$_{6-10}$-aryl-, and C$_{2-8}$-heteroaryl-, either of which may be optionally substituted with one or more $R_{1e}$;

or in the case where two $R_{1b}$s or two $R_{1c}$s are attached to the same N, they may together with the N atom to which they are attached form a heterocycle which may be optionally substituted with one or more $R_{1e}$;

$R_{1d}$ and $R_{1e}$ independently at each occurrence are selected from the group consisting of cyano, hydroxy, oxo, —SO$_2$NH$_2$, —CONH$_2$, C$_{3-6}$-cycloalkyl-, C$_{2-6}$-heterocyclyl-, R$_{1f}$O-L-, R$_{1f}$S-L-, (R$_{1f}$)$_2$N-L-, (R$_{1f}$)$_2$N—C(=O)-L-, R$_{1f}$—C(=O)N(R$_{1f}$)-L-, R$_{1f}$O—C(=O)N(R$_{1f}$)-L-, (R$_{1f}$)$_2$N—C(=O)N(R$_{1f}$)-L-, (R$_{1f}$)$_2$N—C(=O)O-L-, (R$_{1f}$)$_2$N—S(=O)$_2$-L-, R$_{1f}$—S(=O)$_2$N(R$_{1f}$)-L-, R$_{1f}$O—S(=O)$_2$N(R$_{1f}$)-L-, (R$_{1f}$)$_2$N—S(=O)$_2$N(R$_{1f}$)-L-;

and R$_{1f}$ independently at each occurrence is selected from the group consisting of C$_{1-6}$-alkyl-, C$_{3-6}$-cycloalkyl-, C$_{2-6}$-heterocyclyl-.

In yet another embodiment R$_1$, R$_2$ and R$_9$ independently are selected from the group consisting of hydrogen, halogen, cyano, —SO$_2$NH$_2$, —SONH$_2$, and —CONH$_2$;

or R$_1$, R$_2$ and R$_9$ independently are selected from the group consisting of C$_{1-6}$-alkyl-, C$_{3-6}$-cycloalkyl-, C$_{2-6}$-heterocyclyl-, R$_{1a}$O-L-, (R$_{1a}$)$_2$N-L-, R$_{1b}$O—C(=O)-L, (R$_{1b}$)$_2$N—C(=O)-L-, R$_{1b}$—C(=O)N(R$_{1c}$)-L-, R$_{1b}$O—C(=O)N(R$_{1c}$)-L-, (R$_{1b}$)$_2$N—C(=O)N(R$_{1c}$)-L-, (R$_{1b}$)$_2$N—C(=O)O-L-, (R$_{1b}$)$_2$N—S(=O)$_2$-L-, R$_{1b}$—S(=O)$_2$N(R$_{1c}$)-L-, R$_{1b}$O—S(=O)$_2$N(R$_{1c}$)-L-, (R$_{1b}$)$_2$N—S(=O)$_2$N(R$_{1c}$)-L-, (R$_{1b}$)$_2$N—S(=O)$_2$O-L- either of which may be optionally substituted with one or more $R_{1d}$;

wherein $R_{1a}$ is hydrogen or C$_{1-6}$-alkyl-, C$_{3-6}$-cycloalkyl-, C$_{2-6}$-heterocyclyl-, or C$_{6-10}$-aryl;

$R_{1b}$ and $R_{1c}$ independently at each occurrence are selected from the group consisting of C$_{1-6}$-alkyl-, C$_{3-6}$-cycloalkyl-, C$_{2-6}$-heterocyclyl-, C$_{2-6}$-heterocyclyl-C$_{1-6}$-alkyl-, C$_{6-10}$-aryl-, C$_{2-8}$-heteroaryl-, which may be optionally substituted with one or more $R_{1e}$;

or in the case where two $R_{1b}$s or two $R_{1c}$s are attached to the same N, they may together with the N atom to which they are attached form a heterocycle which may be optionally substituted with one or more $R_{1e}$;

$R_{1d}$ and $R_{1e}$ independently at each occurrence are selected from the group consisting of cyano, hydroxy, oxo, —SO$_2$NH$_2$, —CONH$_2$, C$_{3-6}$-cycloalkyl-, C$_{2-6}$-heterocyclyl-, (R$_{1f}$)$_2$N—C(=O)-L-, R$_{1f}$C(=O)N(R$_{1f}$)-L-, R$_{1f}$O—C(=O)N(R$_{1f}$)-L-, (R$_{1f}$)$_2$N—C(=O)N(R$_{1f}$)-L-, (R$_{1f}$)$_2$N—C(=O)O-L-, (R$_{1f}$)$_2$N—S(=O)$_2$-L-, R$_{1f}$S(=O)$_2$N(R$_{1f}$)-L-, R$_{1f}$O—S(=O)$_2$N(R$_{1f}$)-L-, (R$_{1f}$)$_2$N—S(=O)$_2$N(R$_{1f}$)-L-;

and R$_{1f}$ independently at each occurrence is selected from the group consisting of C$_{1-6}$-alkyl-, C$_{3-6}$-cycloalkyl-, and C$_{2-6}$-heterocyclyl-.

In yet another embodiment R$_1$ is hydrogen or R$_{1b}$O—C(=O)-L, wherein $R_{1b}$ is C$_{1-6}$-alkyl-.

In another embodiment R$_1$ is hydrogen.

In another embodiment R$_2$ is selected from the group consisting of hydrogen, halogen and In another embodiment R$_2$ is hydrogen.

In another embodiment R$_9$ is selected from the group consisting of hydrogen, (R$_{1a}$)$_2$N-L-, (R$_{1b}$)$_2$N—C(=O)-L-, and R$_{1b}$—C(=O)N(R$_{1c}$)-L-, wherein $R_{1a}$ is hydrogen, and $R_{1b}$ and $R_{1c}$ are selected from the group consisting of C$_{1-6}$-alkyl-, C$_{6-10}$-aryl-, and C$_{2-8}$-heteroaryl-.

In another embodiment R$_9$ is hydrogen.

In a further embodiment R$_3$ is a covalent bond or C$_{1-3}$-alkyl or C$_{1-3}$-heteroalkyl, which may be optionally substituted by one or more $R_{3a}$, wherein $R_{3a}$ independently at each occurrence is selected from the group consisting of cyano, hydroxy, oxo, —$NH_2$, —$SO_2NH_2$, —$CONH_2$, alkyl-, cycloalkyl-, heterocyclyl-, $R_{3b}$O-L-, $R_{3b}$S-L-, $(R_{3b})_2$N-L-, $R_{3b}$—C(=O)-L-, $R_{3b}$O—C(=O)-L-, $(R_{3b})_2$N—C(=O)-L-, $R_{3b}$—C(=O)N($R_{3c}$)-L-, $R_{3b}$O—C(=O)N($R_{3c}$)-L-, $(R_{3b})_2$N—C(=O)N($R_{3c}$)-L-, $(R_{3b})_2$N—C(=O)O-L-, $R_{3b}$—S(=O)$_2$-L-, $R_{3b}$O—S(=O)$_2$-L-, $(R_{3b})_2$N—S(=O)$_2$-L-, $R_{3b}$—S(=O)$_2$N($R_{3c}$)-L-, $R_{3b}$O—S(=O)$_2$N($R_{3b}$)-L-, $(R_{3b})_2$N—S(=O)$_2$N($R_{3b}$)-L-, $R_{3b}$—S(=O)$_2$O-L-, $R_{3b}$O—S(=O)$_2$O-L-, $(R_{3b})_2$N—S(=O)$_2$O-L-; wherein $R_{3b}$ independently at each occurrence is selected from the group consisting of $C_{1-5}$-alkyl-, $C_{3-5}$-cycloalkyl-, and $C_{2-6}$-heterocyclyl-.

In a still further embodiment the n $R_3$ together with the piperazine ring and the ring atom(s) to which they are attached, form a structure selected from the group consisting of:

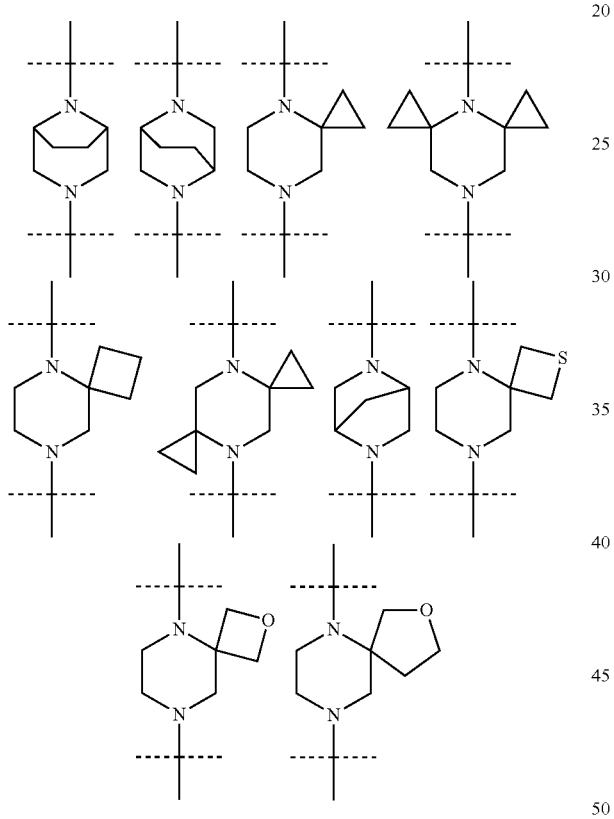

In particular the n $R_3$ together with the piperazine ring and the ring atom(s) to which they are attached, form a structure selected from the group consisting of:

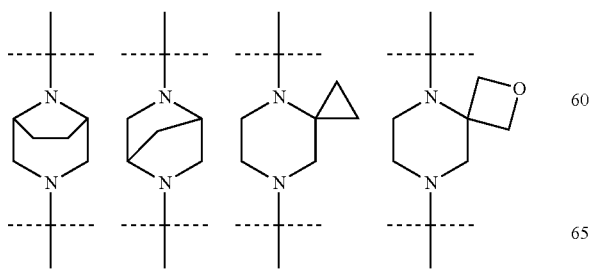

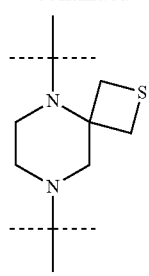

In another embodiment $R_5$ is hydrogen or $C_{1-6}$-alkyl-.

In another embodiment of the present invention $R_4$ is selected from the group consisting of:

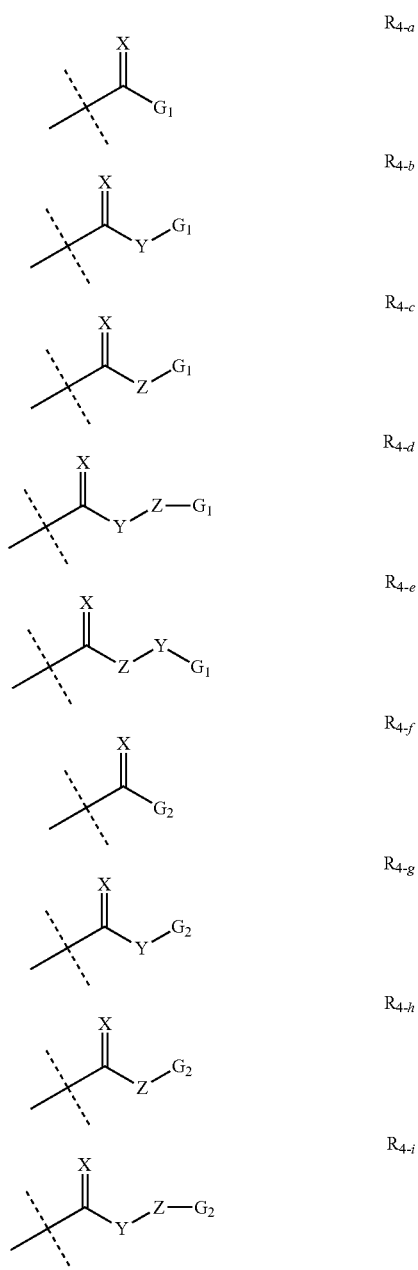

R4-j 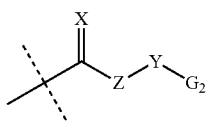

R4-k 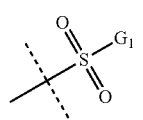

R4-l 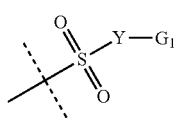

R4-m 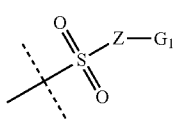

R4-n 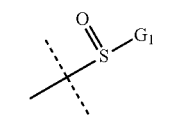

R4-o 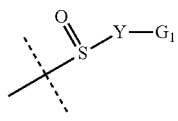

R4-p 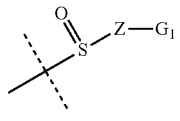

R4-q 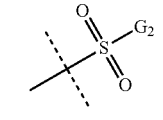

R4-r 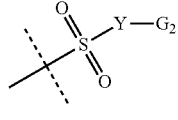

R4-s 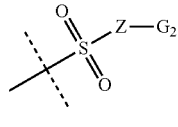

R4-t 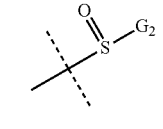

R4-u 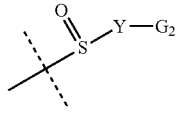

R4-v 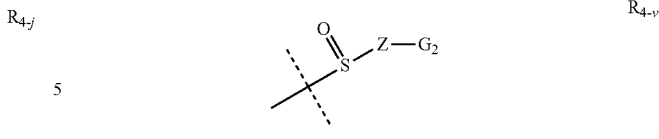

wherein
X is O or S;
Y is O or N—$R_7$;
Z is $C_{1-6}$-alkylene which may be optionally substituted with one or more $R_8$;
$G_1$ is selected from the group consisting of $C_{3-8}$-cycloalkyl-, $C_{3-8}$-cycloalkenyl-, $C_{2-8}$-heterocyclyl-, $C_{6-10}$-aryl- and $C_{2-10}$-heteroaryl-, either of which may be optionally substituted with one or more $R_G$;
$G_2$ is selected from the group consisting of $C_{1-6}$-alkyl-, $C_{2-6}$-alkenyl-, $C_{2-6}$-alkynyl-, $R_{G2a}$O-L-, $R_{G2a}$S-L-, $(R_{G2a})_2$N-L-, $R_{G2a}$—C(=O)-L-, $R_{G2a}$O—C(=O)-L-, $(R_{G2a})_2$N—C(=O)-L-, $R_{G2a}$—C(=O)N($R_{G2b}$)-L-, $R_{G2a}$O—C(=O)N($R_{G2b}$)-L-, $(R_{G2a})_2$N—C(=O)N($R_{G2b}$)-L-, $R_{G2a}$—C(=O)O-L-, $(R_{G2a})_2$N—C(=O)O-L-, $R_{G2a}$—S(=O)-L-, $R_{G2a}$—S(=O)$_2$-L-, $R_{G2a}$O—S(=O)$_2$-L-, $(R_{G2a})_2$N—S(=O)-L-, $(R_{G2a})_2$N—S(=O)$_2$-L-, $R_{G2a}$—S(=O)N($R_{G2b}$)-L-, $R_{G2a}$—S(=O)$_2$N($R_{G2b}$)-L-, $R_{G2a}$O—S(=O)$_2$N($R_{G2b}$)-L-, $R_{G2a}$N—S(=O)N($R_{G2b}$)-L-, $(R_{G2a})_2$N—S(=O)$_2$N($R_{G2b}$)-L-, $R_{G2a}$—S(=O)$_2$O-L-, $R_{G2a}$O—S(=O)$_2$O-L- either of which may be optionally substituted with one or more $R_G$;
wherein L is a covalent bond or L is independently at each occurrence selected from the group consisting of $C_{1-6}$-alkyl- or $C_{3-6}$-cycloalkyl-;
$R_{G2a}$ and $R_{G2b}$ independently at each occurrence are selected from the group consisting of hydrogen, $C_{1-6}$-alkyl-, $C_{3-6}$-cycloalkyl-, and $C_{2-6}$-heterocyclyl-;
$R_G$ is selected from the group consisting of halogen, cyano, hydroxy, oxo, —$NH_2$, —$SO_2NH_2$, —$SONH_2$, —$CONH_2$, $C_{1-6}$-alkyl- and $C_{3-6}$-cycloalkyl-, wherein said $C_{1-6}$-alkyl- or $C_{3-6}$-cycloalkyl- is optionally substituted by one or more substituents selected from the group consisting of halogen, cyano, hydroxy, trifluoromethyl and —$NH_2$; or $R_G$ is selected from the group consisting of $C_{2-6}$-heterocyclyl-, $C_{2-6}$-heterocyclyl-$C_{1-6}$-alkyl, $R_{Ga}$O-L-, $R_{Ga}$S-L-, $(R_{Ga})_2$N-L-, $R_{Ga}$—C(=O)-L-, $R_{Ga}$O—C(=O)-L-, $(R_{Ga})_2$N—C(=O)-L-, $R_{Ga}$—C(=O)N($R_{Gb}$)-L-, $R_{Ga}$O—C(=O)N($R_{Gb}$)-L-, $(R_{Ga})_2$N—C(=O)N($R_{Gb}$)-L-, $R_{Ga}$—C(=O)O-L-, $R_{Ga}$O—C(=O)O-L-, $(R_{Ga})_2$N—C(=O)O-L-, $R_{Ga}$-S(=O)$_2$N($R_{Gb}$)-L-, $(R_{Ga})_2$N—S(=O)$_2$N($R_{Gb}$)-L-, $R_{Ga}$—S(=O)$_2$O-L-, S(=O)$_2$N($R_{Gb}$)-L-, $R_{Ga}$O—S(=O)$_2$N($R_{Gb}$)-L-, $(R_{Ga})_2$N—S(=O)$_2$N($R_{Gb}$)-L-, $R_{Ga}$—S(=O)$_2$O-L-, $R_{Ga}$O—S(=O)$_2$O-L-, $(R_{Ga})_2$N—S(=O)$_2$O-L-, aryl-, arylalkyl-, aryloxy-, aryloxyalkyl-, heteroaryl-, heteroarylalkyl-, heteroaryloxy- and heteroaryloxyalkyl-;
wherein L is a covalent bond or L is independently at each occurrence selected from the group consisting of $C_{1-6}$-alkyl- and $C_{3-6}$-cycloalkyl-;
$R_{Ga}$ and $R_{Gb}$ independently at each occurrence are selected from the group consisting of hydrogen, $C_{1-6}$-alkyl-, $C_{3-6}$-cycloalkyl-, $C_{2-6}$-heterocyclyl-, $C_{6-10}$-aryl- and $C_{3-8}$-heteroaryl-; wherein said $C_{1-6}$-alkyl-, $C_{3-6}$-cycloalkyl-, $C_{2-6}$-heterocyclyl-, $C_{6-10}$-aryl- and $C_{3-8}$-heteroaryl-group is optionally substituted one or more times by a substituent selected from the group consisting of halogen, cyano, hydroxy, trifluoromethyl and —$NH_2$;
$R_7$ is hydrogen or is independently at each occurrence selected from the group consisting of $C_{1-6}$-alkyl-, $C_{3-6}$-cycloalkyl-, $C_{2-6}$-heterocyclyl-, $C_{6-10}$-aryl- and $C_{3-8}$-heteroaryl-, either of which may be optionally substituted with one or more $R_{7a}$;

wherein $R_{7a}$ independently at each occurrence is selected from the group consisting of cyano, hydroxy, oxo, —$SO_2NH_2$, —$CONH_2$, $C_{1-6}$-alkyl-, $C_{3-6}$-cycloalkyl-, $C_{2-6}$-heterocyclyl-, $C_{6-10}$-aryl- and $C_{3-8}$-heteroaryl-.

In yet another embodiment $R_4$ is selected from the group consisting of:

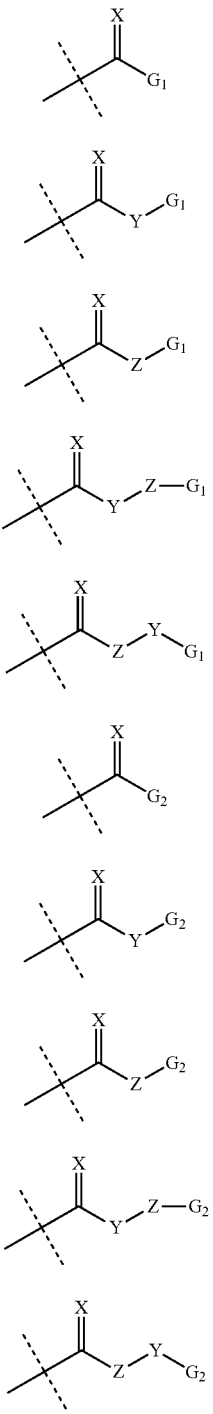

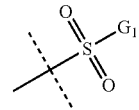

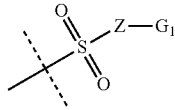

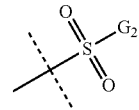

X is O or S;
Y is O or N—$R_7$;
Z is $C_{1-6}$-alkylene;
$G_1$ is selected from the group consisting of $C_{3-6}$-cycloalkyl-, $C_{3-6}$-heterocyclyl-, $C_{6-10}$-aryl- and $C_{3-8}$-heteroaryl-, either of which may be optionally substituted with one or more $R_G$;
$G_2$ is selected from the group consisting of $C_{1-6}$-alkyl-, $C_{2-6}$-alkynyl-, $R_{G2a}$O-L-, $R_{G2a}$S-L-, $(R_{G2a})_2$N-L-, $R_{G2a}$—C(=O)-L-, $R_{G2a}$O—C(=O)-L-, $(R_{G2a})_2$N—C(=O)-L-, $R_{G2a}$—C(=O)N($R_{G2b}$)-L-, $R_{G2a}$O—C(=O)N($R_{G2b}$)-L-, $(R_{G2a})_2$N—C(=O)N($R_{G2b}$)-L-, $R_{G2a}$—C(=O)O-L-, $(R_{G2a})_2$N—C(=O)O-L-, $R_{G2a}$—S(=O)$_2$-L-, $(R_{G2a})_2$N—S(=O)$_2$-L-, $R_{G2a}$—S(=O)$_2$N($R_{G2b}$)-L-, and $(R_{G2a})_2$N—S(=O)$_2$N($R_{G2b}$)-L-; either of which may be optionally substituted with one or more $R_G$;
wherein L is a covalent bond or $C_{1-6}$-alkylene-;
$R_{G2a}$ and $R_{G2b}$ independently at each occurrence are hydrogen or $C_{1-6}$-alkyl-;
$R_G$ is selected from the group consisting of halogen, cyano, hydroxy, oxo, —$NH_2$, —$SO_2NH_2$, —$SONH_2$, —$CONH_2$, $C_{1-6}$-alkyl- and $C_{3-6}$-cycloalkyl-, wherein said $C_{1-6}$-alkyl- or $C_{3-6}$-cycloalkyl- is optionally substituted by one or more substituents selected from the group consisting of halogen, cyano, hydroxy, trifluoromethyl and —$NH_2$; or $R_G$ is selected from the group consisting of $R_{Ga}$O-L-, $(R_{Ga})_2$N-L-, $R_{Ga}$—C(=O)-L-, $R_{Ga}$O—C(=O)-L-, $(R_{Ga})_2$N—C(=O)-L-, $R_{Ga}$—C(=O)N($R_{Gb}$)-L-, $R_{Ga}$O—C(=O)N($R_{Gb}$)-L-, $(R_{Ga})_2$N—C(=O)N($R_{Gb}$)-L-, $R_{Ga}$—C(=O)O-L-, $(R_{Ga})_2$N—C(=O)O-L-, $R_{Ga}$—S(=O)$_2$-L-, $(R_{Ga})_2$N—S(=O)$_2$-L-, $R_{Ga}$—S(=O)$_2$ N($R_{Gb}$)-L-, aryl-, arylalkyl-, heteroaryl-, and heteroarylalkyl-;
wherein L is a covalent bond or $C_{1-6}$-alkylene-;
$R_{Ga}$ and $R_{Gb}$ are hydrogen, $C_{1-6}$-alkyl- or aryl, each of which may be substituted one or more times by a substituent selected from the group consisting of halogen, cyano, hydroxy, trifluoromethyl and —$NH_2$; and
$R_7$ is hydrogen.

In another embodiment X is O or X is S.
In another embodiment Y is O or Y is $NR_7$. In particular $R_7$ is hydrogen.
In yet another embodiment $G_2$ is selected from the group consisting of $C_{1-6}$-alkyl, $C_{2-6}$-alkenyl, $C_{2-6}$-alkynyl, $R_{G2a}$O-

L-, R$_{G2a}$—C(═O)-L-, R$_{G2a}$O—C(═O)-L-, (R$_{G2a}$)$_2$N—C(═O)-L-, and R$_{G2a}$—S(═O)$_2$-L-; either of which may be optionally substituted with one or more R$_G$.

In yet another embodiment G$_1$ is selected from the group consisting of cyclopentyl, cyclohexyl, phenyl, biphenyl, indolyl, piperidinyl, pyridinyl, pyrimidinyl, pyrrolidinyl, sulfindolyl, tetrahydrofuranyl, and tetrahydrothiopyranyl; either of which may be optionally substituted with one or more R$_G$.

In yet another embodiment R$_G$ is selected from the group consisting of fluoro, chloro, bromo, iodo, cyano, oxo, —SO$_2$NH$_2$, —CONH$_2$, C$_{1-6}$-haloalkyl, C$_{1-6}$-cyanoalkyl, R$_{Ga}$O-L-, R$_{Ga}$O—C(═O)-L-, R$_{Ga}$—C(═O)-L-, (R$_{Ga}$)$_2$N—C(═O)-L-, phenyl- or pyridinyl.

In yet another embodiment R$_{Ga}$ is hydrogen or is selected from the group consisting of C$_{1-6}$-alkyl and phenyl-, which may be substituted one or more times by halogen or trifluoromethyl.

In another embodiment L is a covalent bond or L is C$_{1-6}$-alkyl.

In another embodiment, compounds of formula I may be selected from the group consisting of
[3-(7H-Pyrrolo[2,3-d]pyrimidin-4-yl)-3,8-diazabicyclo[3.2.1]oct-8-yl]-(4-trifluoromethylphenyl)-methanone,
Pyridin-2-yl-[7-(7H-pyrrolo[2,3-d]pyrimidin-4-yl)-4,7-diazaspiro[2.5]oct-4-yl]-methanone,
Pyridin-4-yl-[7-(7H-pyrrolo[2,3-d]pyrimidin-4-yl)-4,7-diazaspiro[2.5]oct-4-yl]-methanone,
2-Pyridin-3-yl-1-[7-(7H-pyrrolo[2,3-d]pyrimidin-4-yl)-4,7-diazaspiro[2.5]oct-4-yl]-ethanone,
Biphenyl-4-yl-[7-(7H-pyrrolo[2,3-d]pyrimidin-4-yl)-4,7-diazaspiro[2.5]oct-4-yl]-methanone,
Biphenyl-3-yl-[7-(7H-pyrrolo[2,3-d]pyrimidin-4-yl)-4,7-diazaspiro[2.5]oct-4-yl]-methanone,
[7-(7H-Pyrrolo[2,3-d]pyrimidin-4-yl)-4,7-diazaspiro[2.5]oct-4-yl]-(tetrahydro-furan-3-yl)-methanone,
2-{3-[7-(7H-Pyrrolo[2,3-d]pyrimidin-4-yl)-4,7-diazaspiro[2.5]octane-4-carbonyl]-phenyl}-propionitrile,
3-(7H-Pyrrolo[2,3-d]pyrimidin-4-yl)-3,8-diazabicyclo[3.2.1]octane-8-carboxylic acid tert-butyl ester,
3-(7H-Pyrrolo[2,3-d]pyrimidin-4-yl)-3,8-diazabicyclo[3.2.1]octane-8-carbothioic acid isobutyl-amide,
3-(7H-Pyrrolo[2,3-d]pyrimidin-4-yl)-3,8-diazabicyclo[3.2.1]octane-8-carbothioic acid benzylamide,
3-(7H-Pyrrolo[2,3-d]pyrimidin-4-yl)-3,8-diazabicyclo[3.2.1]octane-8-carboxylic acid 2-methoxy-ethyl ester,
(1,1-Dioxo-hexahydro-1lambda*6*-thiopyran-4-yl)-[7-(7H-pyrrolo[2,3-d]pyrimidin-4-yl)-4,7-diazaspiro[2.5]oct-4-yl]-methanone,
2-(1H-Indol-3-yl)-1-[7-(7H-pyrrolo[2,3-d]pyrimidin-4-yl)-4,7-diazaspiro[2.5]oct-4-yl]-ethanone,
4-[7-(7H-Pyrrolo[2,3-d]pyrimidin-4-yl)-4,7-diazaspiro[2.5]octane-4-carbonyl]-benzonitrile,
(1H-Indol-3-yl)[7-(7H-pyrrolo[2,3-d]pyrimidin-4-yl)-4,7-diazaspiro[2.5]oct-4-yl]-methanone,
3-Oxo-3-[7-(7H-pyrrolo[2,3-d]pyrimidin-4-yl)-4,7-diazaspiro[2.5]oct-4-yl]-propane-1-sulfonic acid amide,
{4-[7-(7H-Pyrrolo[2,3-d]pyrimidin-4-yl)-4,7-diazaspiro[2.5]octane-4-carbonyl]-phenyl}-acetonitrile,
Pyrazin-2-yl-[7-(7H-pyrrolo[2,3-d]pyrimidin-4-yl)-4,7-diazaspiro[2.5]oct-4-yl]-methanone,
[7-(7H-Pyrrolo[2,3-d]pyrimidin-4-yl)-4,7-diazaspiro[2.5]oct-4-yl]-(3-trifluoromethylphenyl)-methanone,
2-Pyridin-4-yl-1-[7-(7H-pyrrolo[2,3-d]pyrimidin-4-yl)-4,7-diazaspiro[2.5]oct-4-yl]-ethanone,
[7-(7H-Pyrrolo[2,3-d]pyrimidin-4-yl)-4,7-diazaspiro[2.5]oct-4-yl]-(tetrahydrofuran-2-yl)-methanone,
4-[7-(7H-Pyrrolo[2,3-d]pyrimidin-4-yl)-4,7-diazaspiro[2.5]octane-4-carbonyl]-cyclohexanone,
3,3,3-Trifluoro-1-[7-(7H-pyrrolo[2,3-d]pyrimidin-4-yl)-4,7-diazaspiro[2.5]oct-4-yl]-propan-1-one,
3-{2-Oxo-2-[7-(7H-pyrrolo[2,3-d]pyrimidin-4-yl)-4,7-diazaspiro[2.5]oct-4-yl]-ethyl}-benzonitrile,
Benzo[b]thiophen-2-yl-[7-(7H-pyrrolo[2,3-d]pyrimidin-4-yl)-4,7-diazaspiro[2.5]oct-4-yl]-methanone,
Phenyl-[7-(7H-pyrrolo[2,3-d]pyrimidin-4-yl)-4,7-diazaspiro[2.5]oct-4-yl]-methanone,
4,4,4-Trifluoro-1-[7-(7H-pyrrolo[2,3-d]pyrimidin-4-yl)-4,7-diazaspiro[2.5]oct-4-yl]-butan-1-one,
[3-(7H-Pyrrolo[2,3-d]pyrimidin-4-yl)-3,8-diazabicyclo[3.2.1]octane-8-carbothioyl]-carbamic acid ethyl ester,
1-[3-(7H-Pyrrolo[2,3-d]pyrimidin-4-yl)-3,8-diazabicyclo[3.2.1]oct-8-yl]-propan-1-one,
4-[3-(7H-Pyrrolo[2,3-d]pyrimidin-4-yl)-3,8-diazabicyclo[3.2.1]octane-8-carbonyl]-benzonitrile,
2-Phenyl-1-[3-(7H-pyrrolo[2,3-d]pyrimidin-4-yl)-3,8-diazabicyclo[3.2.1]oct-8-yl]-ethanone,
Phenyl-[3-(7H-pyrrolo[2,3-d]pyrimidin-4-yl)-3,8-diazabicyclo[3.2.1]oct-8-yl]-methanone,
N-{2-Oxo-2-[3-(7H-pyrrolo[2,3-d]pyrimidin-4-yl)-3,8-diazabicyclo[3.2.1]oct-8-yl]-ethyl}-acetamide,
4-{2-Oxo-2-[7-(7H-pyrrolo[2,3-d]pyrimidin-4-yl)-4,7-diazaspiro[2.5]oct-4-yl]-ethyl}-benzonitrile,
(1H-Indol-6-yl)-[7-(7H-pyrrolo[2,3-d]pyrimidin-4-yl)-4,7-diazaspiro[2.5]oct-4-yl]-methanone,
3-Methanesulfonyl-1-[7-(7H-pyrrolo[2,3-d]pyrimidin-4-yl)-4,7-diazaspiro[2.5]oct-4-yl]-propan-1-one,
2-Cyclopentyl-1-[3-(7H-pyrrolo[2,3-d]pyrimidin-4-yl)-3,8-diazabicyclo[3.2.1]oct-8-yl]-ethanone,
3-(7H-Pyrrolo[2,3-d]pyrimidin-4-yl)-3,8-diazabicyclo[3.2.1]octane-8-carbothioic acid (3-methoxypropyl)-amide,
3,3,3-Trifluoro-1-[3-(7H-pyrrolo[2,3-d]pyrimidin-4-yl)-3,8-diazabicyclo[3.2.1]oct-8-yl]-propan-1-one,
2-Methyl-5-[7-(7H-pyrrolo[2,3-d]pyrimidin-4-yl)-4,7-diazaspiro[2.5]octane-4-carbonyl]-N-(3-trifluoromethylphenyl)-benzamide,
Pyridin-3-yl-[7-(7H-pyrrolo[2,3-d]pyrimidin-4-yl)-4,7-diazaspiro[2.5]oct-4-yl]-methanone,
1-{4-[7-(7H-Pyrrolo[2,3-d]pyrimidin-4-yl)-4,7-diazaspiro[2.5]octane-4-carbonyl]-piperidin-1-yl}-ethanone,
3-[7-(7H-Pyrrolo[2,3-d]pyrimidin-4-yl)-4,7-diazaspiro[2.5]octane-4-carbonyl]-benzonitrile,
7-(7H-Pyrrolo[2,3-d]pyrimidin-4-yl)-4,7-diazaspiro[2.5]octane-4-carboxylic acid tert-butyl ester,
3-(7H-Pyrrolo[2,3-d]pyrimidin-4-yl)-3,8-diazabicyclo[3.2.1]octane-8-carboxylic acid cyclohexylamide,
3-(7H-Pyrrolo[2,3-d]pyrimidin-4-yl)-3,8-diazabicyclo[3.2.1]octane-8-carbothioic acid (2-oxotetrahydrofuran-3-yl)-amide,
[7-(7H-Pyrrolo[2,3-d]pyrimidin-4-yl)-4,7-diazaspiro[2.5]oct-4-yl]-(4-trifluoromethylphenyl)-methanone,
4-[7-(7H-Pyrrolo[2,3-d]pyrimidin-4-yl)-4,7-diazaspiro[2.5]octane-4-carbonyl]-benzamide,
1-{2-[7-(7H-Pyrrolo[2,3-d]pyrimidin-4-yl)-4,7-diazaspiro[2.5]octane-4-carbonyl]-pyrrolidin-1-yl}-ethanone,
4-[8-(Propane-1-sulfonyl)-3,8-diazabicyclo[3.2.1]oct-3-yl]-7H-pyrrolo[2,3-d]pyrimidine,
3-(7H-Pyrrolo[2,3-d]pyrimidin-4-yl)-3,8-diazabicyclo[3.2.1]octane-8-carboxylic acid ethyl ester,
3-Oxo-3-[3-(7H-pyrrolo[2,3-d]pyrimidin-4-yl)-3,8-diazabicyclo[3.2.1]oct-8-yl]-propionitrile,
3-Oxo-3-[7-(7H-pyrrolo[2,3-d]pyrimidin-4-yl)-4,7-diazaspiro[2.5]oct-4-yl]-propionitrile, (1H-Indol-2-yl)-[7-(7H-pyrrolo[2,3-d]pyrimidin-4-yl)-4,7-diazaspiro[2.5]oct-4-yl]-methanone,
5-[7-(7H-Pyrrolo[2,3-d]pyrimidin-4-yl)-4,7-diazaspiro[2.5]octane-4-carbonyl]-1H-pyridin-2-one,
Pyridin-3-yl-[3-(7H-pyrrolo[2,3-d]pyrimidin-4-yl)-3,8-diazabicyclo[3.2.1]oct-8-yl]-methanone,
3-(7H-Pyrrolo[2,3-d]pyrimidin-4-yl)-3,8-diazabicyclo[3.2.1]octane-8-carboxylic acid benzyl ester,
3-(7H-Pyrrolo[2,3-d]pyrimidin-4-yl)-3,8-diazabicyclo[3.2.1]octane-8-carboxylic acid prop-2-ynyl ester,
5-[7-(7H-Pyrrolo[2,3-d]pyrimidin-4-yl)-4,7-diaza-spiro[2.5]octane-4-carbonyl]-thiophene-3-carbonitrile
(5,6-Dihydro-4H-cyclopenta[b]thiophen-2-yl)-[7-(7H-pyrrolo[2,3-d]pyrimidin-4-yl)-4,7-diaza-spiro[2.5]oct-4-yl]-methanone
(4-Methyl-thiophen-2-yl)-[7-(7H-pyrrolo[2,3-d]pyrimidin-4-yl)-4,7-diaza-spiro[2.5]oct-4-yl]-methanone
4-{2-Oxo-2-[7-(7H-pyrrolo[2,3-d]pyrimidin-4-yl)-4,7-diaza-spiro[2.5]oct-4-yl]-acetyl}-benzenesulfonamide
4-{1,1-Difluoro-2-oxo-2-[7-(7H-pyrrolo[2,3-d]pyrimidin-4-yl)-4,7-diaza-spiro[2.5]oct-4-yl]-ethyl}-benzonitrile
4-{1,1-Difluoro-2-oxo-2-[3-(7H-pyrrolo[2,3-d]pyrimidin-4-yl)-3,8-diaza-bicyclo[3.2.1]oct-8-yl]-ethyl}-benzonitrile
2-Fluoro-5-{2-oxo-2-[7-(7H-pyrrolo[2,3-d]pyrimidin-4-yl)-4,7-diaza-spiro[2.5]oct-4-yl]-ethyl}-benzonitrile
{3-[7-(7H-Pyrrolo[2,3-d]pyrimidin-4-yl)-4,7-diaza-spiro[2.5]octane-4-carbonyl]-phenoxy}-acetonitrile
{4-[7-(7H-Pyrrolo[2,3-d]pyrimidin-4-yl)-4,7-diaza-spiro[2.5]octane-4-carbonyl]-phenoxy}-acetonitrile
(4-{2-Oxo-2-[7-(7H-pyrrolo[2,3-d]pyrimidin-4-yl)-4,7-diaza-spiro[2.5]oct-4-yl]-ethyl}-phenoxy)-acetonitrile
(3-{2-Oxo-2-[7-(7H-pyrrolo[2,3-d]pyrimidin-4-yl)-4,7-diaza-spiro[2.5]oct-4-yl]-ethyl}-phenoxy)-acetonitrile
5-[3-(7H-Pyrrolo[2,3-d]pyrimidin-4-yl)-3,8-diaza-bicyclo[3.2.1]octane-8-carbonyl]-thiophene-2-carbonitrile
(3-Methyl-pyrazin-2-yl)-[3-(7H-pyrrolo[2,3-d]pyrimidin-4-yl)-3,8-diaza-bicyclo[3.2.1]oct-8-yl]-methanone
(6-Methyl-pyrazin-2-yl)-[3-(7H-pyrrolo[2,3-d]pyrimidin-4-yl)-3,8-diaza-bicyclo[3.2.1]oct-8-yl]-methanone
(5-Methyl-pyrazin-2-yl)-[3-(7H-pyrrolo[2,3-d]pyrimidin-4-yl)-3,8-diaza-bicyclo[3.2.1]oct-8-yl]-methanone
Benzo[b]thiophen-2-yl-[9-(7H-pyrrolo[2,3-d]pyrimidin-4-yl)-6,9-diaza-spiro[4.5]dec-6-yl]-methanone
3-[7-(7H-Pyrrolo[2,3-d]pyrimidin-4-yl)-4,7-diaza-spiro[2.5]octane-4-sulfonylmethyl]-benzonitrile
3-[3-(7H-Pyrrolo[2,3-d]pyrimidin-4-yl)-3,8-diaza-bicyclo[3.2.1]octane-8-sulfonylmethyl]-benzonitrile
4-[3-(7H-Pyrrolo[2,3-d]pyrimidin-4-yl)-3,8-diaza-bicyclo[3.2.1]octane-8-sulfonylmethyl]-benzonitrile
4-[7-(7H-Pyrrolo[2,3-d]pyrimidin-4-yl)-4,7-diaza-spiro[2.5]octane-4-sulfonylmethyl]-benzonitrile
Benzo[b]thiophen-2-yl-[4-(1H-pyrrolo[2,3-b]pyridin-4-yl)-piperazin-1-yl]-methanone
1-[4-(7H-Pyrrolo[2,3-d]pyrimidin-4-yl)-piperazine-1-carbonyl]-cyclopropanecarbonitrile
Benzo[b]thiophen-2-yl-[7-(1H-pyrrolo[2,3-b]pyridin-4-yl)-4,7-diaza-spiro[2.5]oct-4-yl]-methanone
Benzo[b]thiophen-2-yl-[4-(7H-pyrrolo[2,3-d]pyrimidin-4-yl)-piperazin-1-yl]-methanone
1-[4-(1H-Pyrrolo[2,3-b]pyridin-4-yl)-piperazine-1-carbonyl]-cyclopropanecarbonitrile
1-[7-(7H-Pyrrolo[2,3-d]pyrimidin-4-yl)-4,7-diaza-spiro[2.5]octane-4-carbonyl]-cyclopropanecarboxylic acid
1-[7-(7H-Pyrrolo[2,3-d]pyrimidin-4-yl)-4,7-diaza-spiro[2.5]octane-4-carbonyl]-cyclopropanecarboxylic acid cyanomethyl-methyl-amide
1-[7-(7H-Pyrrolo[2,3-d]pyrimidin-4-yl)-4,7-diaza-spiro[2.5]octane-4-carbonyl]-cyclopropanecarboxylic acid (2-cyano-ethyl)-methyl-amide
1-{1-[7-(7H-Pyrrolo[2,3-d]pyrimidin-4-yl)-4,7-diaza-spiro[2.5]octane-4-carbonyl]-cyclopropanecarbonyl}-pyrrolidine-3-carbonitrile
7-(7H-Pyrrolo[2,3-d]pyrimidin-4-yl)-4,7-diaza-spiro[2.5]octane-4-carboxylic acid but-2-ynyl ester
(3-Methyl-thiophen-2-yl)-[7-(7H-pyrrolo[2,3-d]pyrimidin-4-yl)-4,7-diaza-spiro[2.5]oct-4-yl]-methanone
(5-Methyl-thiophen-2-yl)[7-(7H-pyrrolo[2,3-d]pyrimidin-4-yl)-4,7-diaza-spiro[2.5]oct-4-yl]-methanone
3-Fluoro-4-[7-(7H-pyrrolo[2,3-d]pyrimidin-4-yl)-4,7-diaza-spiro[2.5]octane-4-carbonyl]-benzonitrile
N-(4-{4-[2-(4-Cyano-phenyl)-acetyl]-4,7-diaza-spiro[2.5]oct-7-yl}-7H-pyrrolo[2,3-d]pyrimidin-2-yl)-acetamide
{3-[7-(7H-Pyrrolo[2,3-d]pyrimidin-4-yl)-4,7-diaza-spiro[2.5]octane-4-carbonyl]-piperidin-1-yl}-acetonitrile
3-{3-[7-(7H-Pyrrolo[2,3-d]pyrimidin-4-yl)-4,7-diaza-spiro[2.5]octane-4-carbonyl]-piperidin-1-yl}-propionitrile
N-(4-{4-[2-(4-Cyano-phenyl)-acetyl]-4,7-diaza-spiro[2.5]oct-7-yl}-7H-pyrrolo[2,3-d]pyrimidin-2-yl)-2-(2-methoxy-ethoxy)-acetamide
3-{4-[7-(7H-Pyrrolo[2,3-d]pyrimidin-4-yl)-4,7-diaza-spiro[2.5]octane-4-carbonyl]-piperidin-1-yl}-propionitrile
N-(4-{4-[2-(4-Cyano-phenyl)-acetyl]-4,7-diaza-spiro[2.5]oct-7-yl}-7H-pyrrolo[2,3-d]pyrimidin-2-yl)-benzamide
Isoxazole-5-carboxylic acid (4-{4-[2-(4-cyano-phenyl)-acetyl]-4,7-diaza-spiro[2.5]oct-7-yl}-7H-pyrrolo[2,3-d]pyrimidin-2-yl)-amide
Acetic acid (4-{4-[2-(4-cyano-phenyl)-acetyl]-4,7-diaza-spiro[2.5]oct-7-yl}-7H-pyrrolo[2,3-d]pyrimidin-2-ylcarbamoyl)-methyl ester
2-(3-Methanesulfonyl-phenyl)-1-[7-(7H-pyrrolo[2,3-d]pyrimidin-4-yl)-4,7-diaza-spiro[2.5]oct-4-yl]-ethanone
2-Chloro-5-{2-oxo-2-[7-(7H-pyrrolo[2,3-d]pyrimidin-4-yl)-4,7-diaza-spiro[2.5]oct-4-yl]-ethoxy}-benzenesulfonamide
2-Chloro-4-[7-(7H-pyrrolo[2,3-d]pyrimidin-4-yl)-4,7-diaza-spiro[2.5]octane-4-carbonyl]-benzenesulfonamide
N-Methyl-4-[7-(7H-pyrrolo[2,3-d]pyrimidin-4-yl)-4,7-diaza-spiro[2.5]octane-4-carbonyl]-benzenesulfonamide
Indan-1-yl-[7-(7H-pyrrolo[2,3-d]pyrimidin-4-yl)-4,7-diaza-spiro[2.5]oct-4-yl]-methanone
Benzo[b]thiophen-5-yl-[7-(7H-pyrrolo[2,3-d]pyrimidin-4-yl)-4,7-diaza-spiro[2.5]oct-4-yl]-methanone
2-(4-Methanesulfonyl-phenyl)-1-[7-(7H-pyrrolo[2,3-d]pyrimidin-4-yl)-4,7-diaza-spiro[2.5]oct-4-yl]-ethanone
(5-Methoxy-thiophen-3-yl)-[3-(7H-pyrrolo[2,3-d]pyrimidin-4-yl)-3,8-diaza-bicyclo[3.2.1]oct-8-yl]-methanone
1-[3-(7H-Pyrrolo[2,3-d]pyrimidin-4-yl)-3,8-diaza-bicyclo[3.2.1]oct-8-yl]-2-thiophen-2-yl-ethanone
(5-Fluoro-6-methyl-1H-indol-2-yl)-[3-(7H-pyrrolo[2,3-d]pyrimidin-4-yl)-3,8-diaza-bicyclo[3.2.1]oct-8-yl]-methanone
(4-Hydroxymethyl-thiophen-2-yl)-[3-(7H-pyrrolo[2,3-d]pyrimidin-4-yl)-3,8-diaza-bicyclo[3.2.1]oct-8-yl]-methanone
1-{4-[3-(7H-Pyrrolo[2,3-d]pyrimidin-4-yl)-3,8-diaza-bicyclo[3.2.1]octane-8-carbonyl]-thiophen-2-yl}-ethanone
2-{2-Oxo-2-[7-(7H-pyrrolo[2,3-d]pyrimidin-4-yl)-4,7-diaza-spiro[2.5]oct-4-yl]-ethyl}-benzonitrile
1-[7-(7H-Pyrrolo[2,3-d]pyrimidin-4-yl)-4,7-diaza-spiro[2.5]octane-4-carbonyl]-cyclopentanecarbonitrile
4-{2-Oxo-2-[7-(1H-pyrrolo[2,3-b]pyridin-4-yl)-4,7-diaza-spiro[2.5]oct-4-yl]-ethyl}-benzonitrile 4-Oxo-4-[7-(1H-pyrrolo[2,3-b]pyridin-4-yl)-4,7-diaza-spiro[2.5]oct-4-yl]-butyronitrile
1-[7-(1H-Pyrrolo[2,3-b]pyridin-4-yl)-4,7-diaza-spiro[2.5]octane-4-carbonyl]-cyclopropanecarbonitrile
4-[7-(5-Methyl-7H-pyrrolo[2,3-d]pyrimidin-4-yl)-4,7-diaza-spiro[2.5]octane-4-carbonyl]-benzonitrile
3-[7-(5-Methyl-7H-pyrrolo[2,3-d]pyrimidin-4-yl)-4,7-diaza-spiro[2.5]octane-4-carbonyl]-benzonitrile
[7-(5-Methyl-7H-pyrrolo[2,3-d]pyrimidin-4-yl)-4,7-diaza-spiro[2.5]oct-4-yl]-quinoxalin-2-yl-methanone
4-{4-[2-(3-Cyanomethyl-phenyl)-acetyl]-4,7-diaza-spiro[2.5]oct-7-yl}-7H-pyrrolo[2,3-d]pyrimidine-6-carboxylic acid methyl ester
4-{4-[2-(4-Cyanomethyl-phenyl)-acetyl]-4,7-diaza-spiro[2.5]oct-7-yl}-7H-pyrrolo[2,3-d]pyrimidine-6-carboxylic acid methyl ester
4-{4-[2-(3-Cyano-phenyl)-acetyl]-4,7-diaza-spiro[2.5]oct-7-yl}-7H-pyrrolo[2,3-d]pyrimidine-6-carboxylic acid methyl ester
4-{4-[2-(4-Cyano-phenyl)-acetyl]-4,7-diaza-spiro[2.5]oct-7-yl}-7H-pyrrolo[2,3-d]pyrimidine-6-carboxylic acid methyl ester
Bicyclo[4.2.0]octa-1(6),2,4-trien-7-yl-[7-(7H-pyrrolo[2,3-d]pyrimidin-4-yl)-4,7-diaza-spiro[2.5]oct-4-yl]-methanone
3-[7-(7H-Pyrrolo[2,3-d]pyrimidin-4-yl)-4,7-diaza-spiro[2.5]octane-4-carbonyl]-indan-1-one
2-Chloro-5-{2-oxo-2-[3-(7H-pyrrolo[2,3-d]pyrimidin-4-yl)-3,8-diaza-bicyclo[3.2.1]oct-8-yl]-ethoxy}-benzenesulfonamide
4-{2-Oxo-2-[3-(7H-pyrrolo[2,3-d]pyrimidin-4-yl)-3,8-diaza-bicyclo[3.2.1]oct-8-yl]-acetyl}-benzonitrile
2-[3-(7H-Pyrrolo[2,3-d]pyrimidin-4-yl)-3,8-diaza-bicyclo[3.2.1]octane-8-carbonyl]-1H-indole-5-carbonitrile
(5-Methanesulfonyl-1H-indol-2-yl)-[3-(7H-pyrrolo[2,3-d]pyrimidin-4-yl)-3,8-diaza-bicyclo[3.2.1]oct-8-yl]-methanone
(3-Fluoro-4-methanesulfonyl-phenyl)-[3-(7H-pyrrolo[2,3-d]pyrimidin-4-yl)-3,8-diaza-bicyclo[3.2.1]oct-8-yl]-methanone
Bicyclo[4.2.0]octa-1(6),2,4-trien-7-yl-[3-(7H-pyrrolo[2,3-d]pyrimidin-4-yl)-3,8-diaza-bicyclo[3.2.1]oct-8-yl]-methanone
2-[3-(7H-Pyrrolo[2,3-d]pyrimidin-4-yl)-3,8-diaza-bicyclo[3.2.1]octane-8-carbonyl]-indan-1-one
2-(4-Methanesulfonyl-phenyl)-1-[3-(7H-pyrrolo[2,3-d]pyrimidin-4-yl)-3,8-diaza-bicyclo[3.2.1]oct-8-yl]-ethanone
(3-Methanesulfonyl-phenyl)-[3-(7H-pyrrolo[2,3-d]pyrimidin-4-yl)-3,8-diaza-bicyclo[3.2.1]oct-8-yl]-methanone
(5-Fluoro-1H-indol-2-yl)-[3-(7H-pyrrolo[2,3-d]pyrimidin-4-yl)-3,8-diaza-bicyclo[3.2.1]oct-8-yl]-methanone
[3-(7H-Pyrrolo[2,3-d]pyrimidin-4-yl)-3,8-diaza-bicyclo[3.2.1]oct-8-yl]-(1,2,3,4-tetrahydro-naphthalen-1-yl)-methanone
2-Methyl-5-[3-(7H-pyrrolo[2,3-d]pyrimidin-4-yl)-3,8-diaza-bicyclo[3.2.1]octane-8-carbonyl]-benzenesulfonamide
(5,6-Dihydro-4H-cyclopenta[b]thiophen-2-yl)-[3-(7H-pyrrolo[2,3-d]pyrimidin-4-yl)-3,8-diaza-bicyclo[3.2.1]oct-8-yl]-methanone
(5,7-Difluoro-1H-indol-2-yl)-[3-(7H-pyrrolo[2,3-d]pyrimidin-4-yl)-3,8-diaza-bicyclo[3.2.1]oct-8-yl]-methanone
1-Methyl-5-[3-(7H-pyrrolo[2,3-d]pyrimidin-4-yl)-3,8-diaza-bicyclo[3.2.1]octane-8-carbonyl]-1H-pyrrole-2-sulfonic acid amide
1-Methyl-5-[3-(7H-pyrrolo[2,3-d]pyrimidin-4-yl)-3,8-diaza-bicyclo[3.2.1]octane-8-carbonyl]-1H-pyrrole-3-sulfonic acid amide
4-Oxo-4-[7-(7H-pyrrolo[2,3-d]pyrimidin-4-yl)-4,7-diaza-spiro[2.5]oct-4-yl]-butane-1-sulfonic acid amide
[3-(7H-Pyrrolo[2,3-d]pyrimidin-4-yl)-3,8-diaza-bicyclo[3.2.1]oct-8-yl]-(tetrahydro-furan-3-yl)-methanone
3-[6-Methyl-7-(7H-pyrrolo[2,3-d]pyrimidin-4-yl)-4,7-diaza-spiro[2.5]octane-4-carbonyl]-benzonitrile
3-{2-[6-Methyl-7-(7H-pyrrolo[2,3-d]pyrimidin-4-yl)-4,7-diaza-spiro[2.5]oct-4-yl]-2-oxo-ethyl}-benzonitrile
4-{2-[6-Methyl-7-(7H-pyrrolo[2,3-d]pyrimidin-4-yl)-4,7-diaza-spiro[2.5]oct-4-yl]-2-oxo-ethyl}-benzonitrile
4-[6-Methyl-7-(7H-pyrrolo[2,3-d]pyrimidin-4-yl)-4,7-diaza-spiro[2.5]octane-4-carbonyl]-benzonitrile
1-[6-Methyl-7-(7H-pyrrolo[2,3-d]pyrimidin-4-yl)-4,7-diaza-spiro[2.5]octane-4-carbonyl]-cyclopropanecarbonitrile
4-[6-Methyl-7-(7H-pyrrolo[2,3-d]pyrimidin-4-yl)-4,7-diaza-spiro[2.5]oct-4-yl]-4-oxo-butyronitrile
N-{2-Oxo-2-[7-(7H-pyrrolo[2,3-d]pyrimidin-4-yl)-4,7-diaza-spiro[2.5]oct-4-yl]-ethyl}-acetamide
2-Phenyl-1-[7-(7H-pyrrolo[2,3-d]pyrimidin-4-yl)-4,7-diaza-spiro[2.5]oct-4-yl]-ethanone
3-Phenyl-1-[7-(7H-pyrrolo[2,3-d]pyrimidin-4-yl)-4,7-diaza-spiro[2.5]oct-4-yl]-propan-1-one
(1-Phenyl-cyclopropyl)-[7-(7H-pyrrolo[2,3-d]pyrimidin-4-yl)-4,7-diaza-spiro[2.5]oct-4-yl]-methanone
(4-Hydroxymethyl-phenyl)-[7-(7H-pyrrolo[2,3-d]pyrimidin-4-yl)-4,7-diaza-spiro[2.5]oct-4-yl]-methanone
4-Oxo-4-[7-(7H-pyrrolo[2,3-d]pyrimidin-4-yl)-4,7-diaza-spiro[2.5]oct-4-yl]-butyramide
(1H-Indol-5-yl)[7-(7H-pyrrolo[2,3-d]pyrimidin-4-yl)-4,7-diaza-spiro[2.5]oct-4-yl]-methanone
(4-Hydroxy-cyclohexyl)-[7-(7H-pyrrolo[2,3-d]pyrimidin-4-yl)-4,7-diaza-spiro[2.5]oct-4-yl]-methanone
(1H-Indol-4-yl)-[7-(7H-pyrrolo[2,3-d]pyrimidin-4-yl)-4,7-diaza-spiro[2.5]oct-4-yl]-methanone
[7-(7H-Pyrrolo[2,3-d]pyrimidin-4-yl)-4,7-diaza-spiro[2.5]oct-4-yl]-(3-trifluoromethoxy-phenyl)-methanone
[7-(7H-Pyrrolo[2,3-d]pyrimidin-4-yl)-4,7-diaza-spiro[2.5]oct-4-yl]-quinoxalin-2-yl-methanone
(1H-Benzoimidazol-5-yl)[7-(7H-pyrrolo[2,3-d]pyrimidin-4-yl)-4,7-diaza-spiro[2.5]oct-4-yl]-methanone
[7-(7H-Pyrrolo[2,3-d]pyrimidin-4-yl)-4,7-diaza-spiro[2.5]oct-4-yl]-quinolin-3-yl-methanone
[7-(7H-Pyrrolo[2,3-d]pyrimidin-4-yl)-4,7-diaza-spiro[2.5]oct-4-yl]-quinolin-8-yl-methanone
1-[7-(7H-Pyrrolo[2,3-d]pyrimidin-4-yl)-4,7-diaza-spiro[2.5]octane-4-carbonyl]-cyclopropanecarbonitrile
(6-Hydroxy-pyridin-2-yl)-[7-(7H-pyrrolo[2,3-d]pyrimidin-4-yl)-4,7-diaza-spiro[2.5]oct-4-yl]-methanone
4-Oxo-4-[7-(7H-pyrrolo[2,3-d]pyrimidin-4-yl)-4,7-diaza-spiro[2.5]oct-4-yl]-butyronitrile
3-Phenyl-1-[3-(7H-pyrrolo[2,3-d]pyrimidin-4-yl)-3,8-diaza-bicyclo[3.2.1]oct-8-yl]-propan-1-one
Benzo[b]thiophen-2-yl-[3-(7H-pyrrolo[2,3-d]pyrimidin-4-yl)-3,8-diaza-bicyclo[3.2.1]oct-8-yl]-methanone
2-(1H-Indol-3-yl)-1-[3-(7H-pyrrolo[2,3-d]pyrimidin-4-yl)-3,8-diaza-bicyclo[3.2.1]oct-8-yl]-ethanone
2-Pyridin-4-yl-1-[3-(7H-pyrrolo[2,3-d]pyrimidin-4-yl)-3,8-diaza-bicyclo[3.2.1]oct-8-yl]-ethanone
2-Pyridin-3-yl-1-[3-(7H-pyrrolo[2,3-d]pyrimidin-4-yl)-3,8-diaza-bicyclo[3.2.1]oct-8-yl]-ethanone
3-[3-(7H-Pyrrolo[2,3-d]pyrimidin-4-yl)-3,8-diaza-bicyclo[3.2.1]octane-8-carbonyl]-benzonitrile 4-Oxo-4-[3-(7H-pyrrolo[2,3-d]pyrimidin-4-yl)-3,8-diaza-bicyclo[3.2.1]oct-8-yl]-butyramide
{4-[3-(7H-Pyrrolo[2,3-d]pyrimidin-4-yl)-3,8-diaza-bicyclo[3.2.1]octane-8-carbonyl]-phenyl}-acetonitrile
N-{3-Oxo-3-[3-(7H-pyrrolo[2,3-d]pyrimidin-4-yl)-3,8-diaza-bicyclo[3.2.1]oct-8-yl]-propyl}-methanesulfonamide
Oxazol-2-yl-[3-(7H-pyrrolo[2,3-d]pyrimidin-4-yl)-3,8-diaza-bicyclo[3.2.1]oct-8-yl]-methanone
Biphenyl-3-yl-[3-(7H-pyrrolo[2,3-d]pyrimidin-4-yl)-3,8-diaza-bicyclo[3.2.1]oct-8-yl]-methanone
3-{2-Oxo-2-[3-(7H-pyrrolo[2,3-d]pyrimidin-4-yl)-3,8-diaza-bicyclo[3.2.1]oct-8-yl]-ethyl}-benzonitrile
4-{2-Oxo-2-[3-(7H-pyrrolo[2,3-d]pyrimidin-4-yl)-3,8-diaza-bicyclo[3.2.1]oct-8-yl]-ethyl}-benzonitrile
4,4,4-Trifluoro-1-[3-(7H-pyrrolo[2,3-d]pyrimidin-4-yl)-3,8-diaza-bicyclo[3.2.1]oct-8-yl]-butan-1-one
4-Oxo-4-[3-(7H-pyrrolo[2,3-d]pyrimidin-4-yl)-3,8-diaza-bicyclo[3.2.1]oct-8-yl]-butyronitrile
(2-Fluoro-4-methanesulfonyl-phenyl)-[7-(7H-pyrrolo[2,3-d]pyrimidin-4-yl)-4,7-diaza-spiro[2.5]oct-4-yl]-methanone
(5-Methyl-1H-indol-2-yl)-[7-(7H-pyrrolo[2,3-d]pyrimidin-4-yl)-4,7-diaza-spiro[2.5]oct-4-yl]-methanone
(5-Fluoro-3-methyl-1H-indol-2-yl)-[7-(7H-pyrrolo[2,3-d]pyrimidin-4-yl)-4,7-diaza-spiro[2.5]oct-4-yl]-methanone
2-[7-(7H-Pyrrolo[2,3-d]pyrimidin-4-yl)-4,7-diaza-spiro[2.5]octane-4-carbonyl]-1H-indole-5-sulfonic acid amide
1-Methyl-5-[7-(7H-pyrrolo[2,3-d]pyrimidin-4-yl)-4,7-diaza-spiro[2.5]octane-4-carbonyl]-1H-pyrrole-2-sulfonic acid amide
1-Methyl-5-[7-(7H-pyrrolo[2,3-d]pyrimidin-4-yl)-4,7-diaza-spiro[2.5]octane-4-carbonyl]-1H-pyrrole-3-sulfonic acid amide
N,N-Dimethyl-4-[7-(7H-pyrrolo[2,3-d]pyrimidin-4-yl)-4,7-diaza-spiro[2.5]octane-4-carbonyl]-benzenesulfonamide
1-[7-(7H-Pyrrolo[2,3-d]pyrimidin-4-yl)-4,7-diaza-spiro[2.5]oct-4-yl]-2-thiophen-2-yl-ethanone
4-{2-Oxo-2-[7-(7H-pyrrolo[2,3-d]pyrimidin-4-yl)-4,7-diaza-spiro[2.5]oct-4-yl]-ethyl}-benzenesulfonamide
(5,7-Difluoro-1H-indol-2-yl)-[7-(7H-pyrrolo[2,3-d]pyrimidin-4-yl)-4,7-diaza-spiro[2.5]oct-4-yl]-methanone
5-[7-(7H-Pyrrolo[2,3-d]pyrimidin-4-yl)-4,7-diaza-spiro[2.5]octane-4-carbonyl]-thiophene-2-carbonitrile
(4-Methanesulfonyl-3-pyrrolidin-1-yl-phenyl)-[7-(7H-pyrrolo[2,3-d]pyrimidin-4-yl)-4,7-diaza-spiro[2.5]oct-4-yl]-methanone
5-{2-Oxo-2-[7-(7H-pyrrolo[2,3-d]pyrimidin-4-yl)-4,7-diaza-spiro[2.5]oct-4-yl]-ethyl}-thiophene-2-sulfonic acid amide
[4-(Propane-2-sulfonyl)-phenyl]-[7-(7H-pyrrolo[2,3-d]pyrimidin-4-yl)-4,7-diaza-spiro[2.5]oct-4-yl]-methanone
4-{3-Oxo-3-[7-(7H-pyrrolo[2,3-d]pyrimidin-4-yl)-4,7-diaza-spiro[2.5]oct-4-yl]-propenyl}-benzenesulfonamide
5-[7-(7H-Pyrrolo[2,3-d]pyrimidin-4-yl)-4,7-diaza-spiro[2.5]octane-4-carbonyl]-furan-2-sulfonic acid amide
5-[3-(7H-Pyrrolo[2,3-d]pyrimidin-4-yl)-3,8-diaza-bicyclo[3.2.1]octane-8-carbonyl]-thiophene-3-carbonitrile
(5-Methyl-1H-indol-2-yl)-[3-(7H-pyrrolo[2,3-d]pyrimidin-4-yl)-3,8-diaza-bicyclo[3.2.1]oct-8-yl]-methanone
(5-Fluoro-3-methyl-1H-indol-2-yl)-[3-(7H-pyrrolo[2,3-d]pyrimidin-4-yl)-3,8-diaza-bicyclo[3.2.1]oct-8-yl]-methanone
[4-(Propane-2-sulfonyl)-phenyl]-[3-(7H-pyrrolo[2,3-d]pyrimidin-4-yl)-3,8-diaza-bicyclo[3.2.1]oct-8-yl]-methanone
[4-(Propane-2-sulfonyl)-phenyl]-[3-(7H-pyrrolo[2,3-d]pyrimidin-4-yl)-3,8-diaza-bicyclo[3.2.1]oct-8-yl]-methanone
4-[7-(7H-Pyrrolo[2,3-d]pyrimidin-4-yl)-4,7-diaza-spiro[2.5]oct-4-yl]-N-thiophen-2-ylmethyl-benzenesulfonamide
1-[7-(7H-Pyrrolo[2,3-d]pyrimidin-4-yl)-4,7-diaza-spiro[2.5]oct-4-yl]-2-thiophen-2-yl-ethane-1,2-dione
(5-Methoxy-thiophen-2-yl)-[7-(7H-pyrrolo[2,3-d]pyrimidin-4-yl)-4,7-diaza-spiro[2.5]oct-4-yl]-methanone
(5-Propyl-thiophen-3-yl)-[7-(7H-pyrrolo[2,3-d]pyrimidin-4-yl)-4,7-diaza-spiro[2.5]oct-4-yl]-methanone
(4-Bromo-5-methyl-thiophen-2-yl)[7-(7H-pyrrolo[2,3-d]pyrimidin-4-yl)-4,7-diaza-spiro[2.5]oct-4-yl]-methanone
(4-Bromo-5-ethyl-thiophen-2-yl)-[7-(7H-pyrrolo[2,3-d]pyrimidin-4-yl)-4,7-diaza-spiro[2.5]oct-4-yl]-methanone
Ethanesulfonic acid {4-[7-(7H-pyrrolo[2,3-d]pyrimidin-4-yl)-4,7-diaza-spiro[2.5]octane-4-carbonyl]-phenyl}-amide
[7-(7H-Pyrrolo[2,3-d]pyrimidin-4-yl)-4,7-diaza-spiro[2.5]oct-4-yl]-thiophen-2-yl-methanone
(2,3-Dimethoxy-phenyl)-[7-(7H-pyrrolo[2,3-d]pyrimidin-4-yl)-4,7-diaza-spiro[2.5]oct-4-yl]-methanone
(3,5-Dimethoxy-phenyl)-[7-(7H-pyrrolo[2,3-d]pyrimidin-4-yl)-4,7-diaza-spiro[2.5]oct-4-yl]-methanone
Benzo[b]thiophen-3-yl-[7-(7H-pyrrolo[2,3-d]pyrimidin-4-yl)-4,7-diaza-spiro[2.5]oct-4-yl]-methanone
(5-Phenyl-thiophen-2-yl)-[7-(7H-pyrrolo[2,3-d]pyrimidin-4-yl)-4,7-diaza-spiro[2.5]oct-4-yl]-methanone
(2-Methoxy-pyridin-3-yl)-[7-(7H-pyrrolo[2,3-d]pyrimidin-4-yl)-4,7-diaza-spiro[2.5]oct-4-yl]-methanone
2-[7-(7H-Pyrrolo[2,3-d]pyrimidin-4-yl)-4,7-diaza-spiro[2.5]octane-4-carbonyl]-1H-indole-5-carbonitrile
[7-(7H-Pyrrolo[2,3-d]pyrimidin-4-yl)-4,7-diaza-spiro[2.5]oct-4-yl]-(5,6,7,8-tetrahydro-naphthalen-2-yl)-methanone
2-Fluoro-4-[7-(7H-pyrrolo[2,3-d]pyrimidin-4-yl)-4,7-diaza-spiro[2.5]octane-4-carbonyl]-benzonitrile
3-Oxo-3-[7-(1H-pyrrolo[2,3-b]pyridin-4-yl)-4,7-diaza-spiro[2.5]oct-4-yl]-propionitrile
Phenyl-[7-(1H-pyrrolo[2,3-b]pyridin-4-yl)-4,7-diaza-spiro[2.5]oct-4-yl]-methanone
Pyridin-2-yl-[7-(1H-pyrrolo[2,3-b]pyridin-4-yl)-4,7-diaza-spiro[2.5]oct-4-yl]-methanone
Pyridin-3-yl-[7-(1H-pyrrolo[2,3-b]pyridin-4-yl)-4,7-diaza-spiro[2.5]oct-4-yl]-methanone
Pyridin-4-yl-[7-(1H-pyrrolo[2,3-b]pyridin-4-yl)-4,7-diaza-spiro[2.5]oct-4-yl]-methanone
Pyrazin-2-yl-[7-(1H-pyrrolo[2,3-b]pyridin-4-yl)-4,7-diaza-spiro[2.5]oct-4-yl]-methanone
4-[7-(1H-Pyrrolo[2,3-b]pyridin-4-yl)-4,7-diaza-spiro[2.5]octane-4-carbonyl]-benzonitrile
3-[7-(1H-Pyrrolo[2,3-b]pyridin-4-yl)-4,7-diaza-spiro[2.5]octane-4-carbonyl]-benzonitrile
(3-Methyl-thiophen-2-yl)-[7-(1H-pyrrolo[2,3-b]pyridin-4-yl)-4,7-diaza-spiro[2.5]oct-4-yl]-methanone
[7-(1H-Pyrrolo[2,3-b]pyridin-4-yl)-4,7-diaza-spiro[2.5]oct-4-yl]-(3-trifluoromethoxy-phenyl)-methanone
{4-[7-(1H-Pyrrolo[2,3-b]pyridin-4-yl)-4,7-diaza-spiro[2.5]octane-4-carbonyl]-phenyl}-acetonitrile
(5-Methyl-thiophen-2-yl)-[7-(1H-pyrrolo[2,3-b]pyridin-4-yl)-4,7-diaza-spiro[2.5]oct-4-yl]-methanone
(3-Methyl-benzo[b]thiophen-2-yl)[7-(1H-pyrrolo[2,3-b]pyridin-4-yl)-4,7-diaza-spiro[2.5]oct-4-yl]-methanone
Benzo[b]thiophen-3-yl-[7-(1H-pyrrolo[2,3-b]pyridin-4-yl)-4,7-diaza-spiro[2.5]oct-4-yl]-methanone
(5-Methyl-benzo[b]thiophen-2-yl)[7-(1H-pyrrolo[2,3-b]pyridin-4-yl)-4,7-diaza-spiro[2.5]oct-4-yl]-methanone
2-[7-(1H-Pyrrolo[2,3-b]pyridin-4-yl)-4,7-diaza-spiro[2.5]octane-4-carbonyl]-benzonitrile 3-{2-Oxo-2-[7-(1H-pyrrolo[2,3-b]pyridin-4-yl)-4,7-diaza-spiro[2.5]oct-4-yl]-ethyl}-benzonitrile
2-{2-Oxo-2-[7-(1H-pyrrolo[2,3-b]pyridin-4-yl)-4,7-diaza-spiro[2.5]oct-4-yl]-ethyl}-benzonitrile
[7-(1H-Pyrrolo[2,3-b]pyridin-4-yl)-4,7-diaza-spiro[2.5]oct-4-yl]-(4-trifluoromethoxy-phenyl)-methanone
2,2-Dimethyl-3-oxo-3-[3-(7H-pyrrolo[2,3-d]pyrimidin-4-yl)-3,8-diaza-bicyclo[3.2.1]oct-8-yl]-propionitrile
Phenyl-[3-(7H-pyrrolo[2,3-d]pyrimidin-4-yl)-3,8-diaza-bicyclo[3.2.1]oct-8-yl]-methanone
Pyridin-2-yl-[3-(7H-pyrrolo[2,3-d]pyrimidin-4-yl)-3,8-diaza-bicyclo[3.2.1]oct-8-yl]-methanone
Pyridin-4-yl-[3-(7H-pyrrolo[2,3-d]pyrimidin-4-yl)-3,8-diaza-bicyclo[3.2.1]oct-8-yl]-methanone
(3-Methyl-thiophen-2-yl)-[3-(7H-pyrrolo[2,3-d]pyrimidin-4-yl)-3,8-diaza-bicyclo[3.2.1]oct-8-yl]-methanone
[3-(7H-Pyrrolo[2,3-d]pyrimidin-4-yl)-3,8-diaza-bicyclo[3.2.1]oct-8-yl]-(3-trifluoromethoxy-phenyl)-methanone
(3-Methyl-benzo[b]thiophen-2-yl)-[3-(7H-pyrrolo[2,3-d]pyrimidin-4-yl)-3,8-diaza-bicyclo[3.2.1]oct-8-yl]-methanone
Benzo[b]thiophen-3-yl-[3-(7H-pyrrolo[2,3-d]pyrimidin-4-yl)-3,8-diaza-bicyclo[3.2.1]oct-8-yl]-methanone
(5-Methyl-benzo[b]thiophen-2-yl)-[3-(7H-pyrrolo[2,3-d]pyrimidin-4-yl)-3,8-diaza-bicyclo[3.2.1]oct-8-yl]-methanone
4-[3-(7H-Pyrrolo[2,3-d]pyrimidin-4-yl)-3,8-diaza-bicyclo[3.2.1]octane-8-carbonyl]-tetrahydro-pyran-4-carbonitrile
2-[3-(7H-Pyrrolo[2,3-d]pyrimidin-4-yl)-3,8-diaza-bicyclo[3.2.1]octane-8-carbonyl]-benzonitrile
2-{2-Oxo-2-[3-(7H-pyrrolo[2,3-d]pyrimidin-4-yl)-3,8-diaza-bicyclo[3.2.1]oct-8-yl]-ethyl}-benzonitrile
[3-(7H-Pyrrolo[2,3-d]pyrimidin-4-yl)-3,8-diaza-bicyclo[3.2.1]oct-8-yl]-(4-trifluoromethoxy-phenyl)-methanone
{2-[5-(7H-Pyrrolo[2,3-d]pyrimidin-4-yl)-2,5-diaza-bicyclo[2.2.1]heptane-2-carbonyl]-phenyl}-acetonitrile
Phenyl-[5-(7H-pyrrolo[2,3-d]pyrimidin-4-yl)-2,5-diaza-bicyclo[2.2.1]hept-2-yl]-methanone
Pyridin-2-yl-[5-(7H-pyrrolo[2,3-d]pyrimidin-4-yl)-2,5-diaza-bicyclo[2.2.1]hept-2-yl]-methanone
Pyridin-3-yl-[5-(7H-pyrrolo[2,3-d]pyrimidin-4-yl)-2,5-diaza-bicyclo[2.2.1]hept-2-yl]-methanone
Pyridin-4-yl-[5-(7H-pyrrolo[2,3-d]pyrimidin-4-yl)-2,5-diaza-bicyclo[2.2.1]hept-2-yl]-methanone
Pyrazin-2-yl-[5-(7H-pyrrolo[2,3-d]pyrimidin-4-yl)-2,5-diaza-bicyclo[2.2.1]hept-2-yl]-methanone
4-[5-(7H-Pyrrolo[2,3-d]pyrimidin-4-yl)-2,5-diaza-bicyclo[2.2.1]heptane-2-carbonyl]-benzonitrile
3-[5-(7H-Pyrrolo[2,3-d]pyrimidin-4-yl)-2,5-diaza-bicyclo[2.2.1]heptane-2-carbonyl]-benzonitrile
(3-Methyl-thiophen-2-yl)-[5-(7H-pyrrolo[2,3-d]pyrimidin-4-yl)-2,5-diaza-bicyclo[2.2.1]hept-2-yl]-methanone
1-[5-(7H-Pyrrolo[2,3-d]pyrimidin-4-yl)-2,5-diaza-bicyclo[2.2.1]heptane-2-carbonyl]-cyclopentanecarbonitrile
(1H-Indol-4-yl)-[5-(7H-pyrrolo[2,3-d]pyrimidin-4-yl)-2,5-diaza-bicyclo[2.2.1]hept-2-yl]-methanone
{4-[5-(7H-Pyrrolo[2,3-d]pyrimidin-4-yl)-2,5-diaza-bicyclo[2.2.1]heptane-2-carbonyl]-phenyl}-acetonitrile
(1H-Indol-2-yl)-[5-(7H-pyrrolo[2,3-d]pyrimidin-4-yl)-2,5-diaza-bicyclo[2.2.1]hept-2-yl]-methanone
(5-Methyl-thiophen-2-yl)-[5-(7H-pyrrolo[2,3-d]pyrimidin-4-yl)-2,5-diaza-bicyclo[2.2.1]hept-2-yl]-methanone
(3-Methyl-benzo[b]thiophen-2-yl)-[5-(7H-pyrrolo[2,3-d]pyrimidin-4-yl)-2,5-diaza-bicyclo[2.2.1]hept-2-yl]-methanone
Benzo[b]thiophen-3-yl-[5-(7H-pyrrolo[2,3-d]pyrimidin-4-yl)-2,5-diaza-bicyclo[2.2.1]hept-2-yl]-methanone
(5-Methyl-benzo[b]thiophen-2-yl)-[5-(7H-pyrrolo[2,3-d]pyrimidin-4-yl)-2,5-diaza-bicyclo[2.2.1]hept-2-yl]-methanone
(5-Phenyl-thiophen-2-yl)-[5-(7H-pyrrolo[2,3-d]pyrimidin-4-yl)-2,5-diaza-bicyclo[2.2.1]hept-2-yl]-methanone
1-[5-(7H-Pyrrolo[2,3-d]pyrimidin-4-yl)-2,5-diaza-bicyclo[2.2.1]heptane-2-carbonyl]-cyclopropanecarbonitrile
2-[5-(7H-Pyrrolo[2,3-d]pyrimidin-4-yl)-2,5-diaza-bicyclo[2.2.1]heptane-2-carbonyl]-1H-indole-5-carbonitrile
2-Fluoro-4-[5-(7H-pyrrolo[2,3-d]pyrimidin-4-yl)-2,5-diaza-bicyclo[2.2.1]heptane-2-carbonyl]-benzonitrile
3-Fluoro-4-[5-(7H-pyrrolo[2,3-d]pyrimidin-4-yl)-2,5-diaza-bicyclo[2.2.1]heptane-2-carbonyl]-benzonitrile
4-[5-(7H-Pyrrolo[2,3-d]pyrimidin-4-yl)-2,5-diaza-bicyclo[2.2.1]heptane-2-carbonyl]-tetrahydro-pyran-4-carbonitrile
5-Oxo-5-[5-(7H-pyrrolo[2,3-d]pyrimidin-4-yl)-2,5-diaza-bicyclo[2.2.1]hept-2-yl]-pentanenitrile
2-[5-(7H-Pyrrolo[2,3-d]pyrimidin-4-yl)-2,5-diaza-bicyclo[2.2.1]heptane-2-carbonyl]-benzonitrile
3-{2-Oxo-2-[5-(7H-pyrrolo[2,3-d]pyrimidin-4-yl)-2,5-diaza-bicyclo[2.2.1]hept-2-yl]-ethyl}-benzonitrile
4-{2-Oxo-2-[5-(7H-pyrrolo[2,3-d]pyrimidin-4-yl)-2,5-diaza-bicyclo[2.2.1]hept-2-yl]-ethyl}-benzonitrile
2-{2-Oxo-2-[5-(7H-pyrrolo[2,3-d]pyrimidin-4-yl)-2,5-diaza-bicyclo[2.2.1]hept-2-yl]-ethyl}-benzonitrile
4-Oxo-4-[5-(7H-pyrrolo[2,3-d]pyrimidin-4-yl)-2,5-diaza-bicyclo[2.2.1]hept-2-yl]-butyronitrile
{2-[5-(7H-Pyrrolo[2,3-d]pyrimidin-4-yl)-2,5-diaza-bicyclo[2.2.1]heptane-2-carbonyl]-phenyl}-acetonitrile
[5-(7H-Pyrrolo[2,3-d]pyrimidin-4-yl)-2,5-diaza-bicyclo[2.2.1]hept-2-yl]-(4-trifluoromethoxy-phenyl)-methanone
[7-(5-Methoxy-1H-pyrrolo[2,3-b]pyridin-4-yl)-4,7-diaza-spiro[2.5]oct-4-yl]-phenyl-methanone
Benzo[b]thiophen-2-yl-[7-(5-methoxy-1H-pyrrolo[2,3-b]pyridin-4-yl)-4,7-diaza-spiro[2.5]oct-4-yl]-methanone
[7-(5-Methoxy-1H-pyrrolo[2,3-b]pyridin-4-yl)-4,7-diaza-spiro[2.5]oct-4-yl]-pyrazin-2-yl-methanone
4-[7-(5-Methoxy-1H-pyrrolo[2,3-b]pyridin-4-yl)-4,7-diaza-spiro[2.5]octane-4-carbonyl]-benzonitrile
3-[7-(5-Methoxy-1H-pyrrolo[2,3-b]pyridin-4-yl)-4,7-diaza-spiro[2.5]octane-4-carbonyl]-benzonitrile
(1H-Indol-2-yl)-[7-(5-methoxy-1H-pyrrolo[2,3-b]pyridin-4-yl)-4,7-diaza-spiro[2.5]oct-4-yl]-methanone
Benzo[b]thiophen-3-yl-[7-(5-methoxy-1H-pyrrolo[2,3-b]pyridin-4-yl)-4,7-diaza-spiro[2.5]oct-4-yl]-methanone
[7-(5-Methoxy-1H-pyrrolo[2,3-b]pyridin-4-yl)-4,7-diaza-spiro[2.5]oct-4-yl]-(5-phenyl-thiophen-2-yl)-methanone
2-[7-(5-Methoxy-1H-pyrrolo[2,3-b]pyridin-4-yl)-4,7-diaza-spiro[2.5]octane-4-carbonyl]-1H-indole-5-carbonitrile
2-Fluoro-4-[7-(5-methoxy-1H-pyrrolo[2,3-b]pyridin-4-yl)-4,7-diaza-spiro[2.5]octane-4-carbonyl]-benzonitrile
5-[7-(5-Methoxy-1H-pyrrolo[2,3-b]pyridin-4-yl)-4,7-diaza-spiro[2.5]oct-4-yl]-5-oxo-pentanenitrile
3-{2-[7-(5-Methoxy-1H-pyrrolo[2,3-b]pyridin-4-yl)-4,7-diaza-spiro[2.5]oct-4-yl]-2-oxo-ethyl}-benzonitrile
4-{2-[7-(5-Methoxy-1H-pyrrolo[2,3-b]pyridin-4-yl)-4,7-diaza-spiro[2.5]oct-4-yl]-2-oxo-ethyl}-benzonitrile
(3-Methyl-benzo[b]thiophen-2-yl)-[7-(7H-pyrrolo[2,3-d]pyrimidin-4-yl)-4,7-diaza-spiro[2.5]oct-4-yl]-methanone
(5-Methyl-benzo[b]thiophen-2-yl)-[7-(7H-pyrrolo[2,3-d]pyrimidin-4-yl)-4,7-diaza-spiro[2.5]oct-4-yl]-methanone
5-Oxo-5-[7-(7H-pyrrolo[2,3-d]pyrimidin-4-yl)-4,7-diaza-spiro[2.5]oct-4-yl]-pentanenitrile 2-[7-(7H-Pyrrolo[2,3-d]pyrimidin-4-yl)-4,7-diaza-spiro [2.5]octane-4-carbonyl]-benzonitrile
{2-[7-(7H-Pyrrolo[2,3-d]pyrimidin-4-yl)-4,7-diaza-spiro [2.5]octane-4-carbonyl]-phenyl}-acetonitrile
3-[7-(7H-Pyrrolo[2,3-d]pyrimidin-4-yl)-4,7-diaza-spiro [2.5]octane-4-carbonyl]-1H-indazole-6-carbonitrile
[7-(2-Amino-7H-pyrrolo[2,3-d]pyrimidin-4-yl)-4,7-diaza-spiro[2.5]oct-4-yl]-pyrazin-2-yl-methanone
4-[7-(2-Amino-7H-pyrrolo[2,3-d]pyrimidin-4-yl)-4,7-diaza-spiro[2.5]octane-4-carbonyl]-benzonitrile
3-[7-(2-Amino-7H-pyrrolo[2,3-d]pyrimidin-4-yl)-4,7-diaza-spiro[2.5]octane-4-carbonyl]-benzonitrile
[7-(2-Amino-7H-pyrrolo[2,3-d]pyrimidin-4-yl)-4,7-diaza-spiro[2.5]oct-4-yl]-quinoxalin-2-yl-methanone
(3-{2-[7-(2-Amino-7H-pyrrolo[2,3-d]pyrimidin-4-yl)-4,7-diaza-spiro[2.5]oct-4-yl]-2-oxo-ethyl}-phenyl)-acetonitrile
(4-{2-[7-(2-Amino-7H-pyrrolo[2,3-d]pyrimidin-4-yl)-4,7-diaza-spiro[2.5]oct-4-yl]-2-oxo-ethyl}-phenyl)-acetonitrile
1-[7-(2-Amino-7H-pyrrolo[2,3-d]pyrimidin-4-yl)-4,7-diaza-spiro[2.5]octane-4-carbonyl]-cyclopropanecarbonitrile
1-[7-(2-Amino-7H-pyrrolo[2,3-d]pyrimidin-4-yl)-4,7-diaza-spiro[2.5]oct-4-yl]-2-(4-trifluoromethyl-phenyl)-ethanone
5-[7-(2-Amino-7H-pyrrolo[2,3-d]pyrimidin-4-yl)-4,7-diaza-spiro[2.5]oct-4-yl]-5-oxo-pentanenitrile
3-{2-[7-(2-Amino-7H-pyrrolo[2,3-d]pyrimidin-4-yl)-4,7-diaza-spiro[2.5]oct-4-yl]-2-oxo-ethyl}-benzonitrile
4-{2-[7-(2-Amino-7H-pyrrolo[2,3-d]pyrimidin-4-yl)-4,7-diaza-spiro[2.5]oct-4-yl]-2-oxo-ethyl}-benzonitrile
4-[7-(2-Amino-7H-pyrrolo[2,3-d]pyrimidin-4-yl)-4,7-diaza-spiro[2.5]oct-4-yl]-4-oxo-butyronitrile
[7-(5-Chloro-7H-pyrrolo[2,3-d]pyrimidin-4-yl)-4,7-diaza-spiro[2.5]oct-4-yl]-pyrazin-2-yl-methanone
4-[7-(5-Chloro-7H-pyrrolo[2,3-d]pyrimidin-4-yl)-4,7-diaza-spiro[2.5]octane-4-carbonyl]-benzonitrile
3-[7-(5-Chloro-7H-pyrrolo[2,3-d]pyrimidin-4-yl)-4,7-diaza-spiro[2.5]octane-4-carbonyl]-benzonitrile
[7-(5-Chloro-7H-pyrrolo[2,3-d]pyrimidin-4-yl)-4,7-diaza-spiro[2.5]oct-4-yl]-quinoxalin-2-yl-methanone
(3-{2-[7-(5-Chloro-7H-pyrrolo[2,3-d]pyrimidin-4-yl)-4,7-diaza-spiro[2.5]oct-4-yl]-2-oxo-ethyl}-phenyl)-acetonitrile
(4-{2-[7-(5-Chloro-7H-pyrrolo[2,3-d]pyrimidin-4-yl)-4,7-diaza-spiro[2.5]oct-4-yl]-2-oxo-ethyl}-phenyl)-acetonitrile
1-[7-(5-Chloro-7H-pyrrolo[2,3-d]pyrimidin-4-yl)-4,7-diaza-spiro[2.5]oct-4-yl]-2-(4-fluoro-phenyl)-ethanone
1-[7-(5-Chloro-7H-pyrrolo[2,3-d]pyrimidin-4-yl)-4,7-diaza-spiro[2.5]oct-4-yl]-2-(4-trifluoromethyl-phenyl)-ethanone
5-[7-(5-Chloro-7H-pyrrolo[2,3-d]pyrimidin-4-yl)-4,7-diaza-spiro[2.5]oct-4-yl]-5-oxo-pentanenitrile
3-{2-[7-(5-Chloro-7H-pyrrolo[2,3-d]pyrimidin-4-yl)-4,7-diaza-spiro[2.5]oct-4-yl]-2-oxo-ethyl}-benzonitrile
4-{2-[7-(5-Chloro-7H-pyrrolo[2,3-d]pyrimidin-4-yl)-4,7-diaza-spiro[2.5]oct-4-yl]-2-oxo-ethyl}-benzonitrile
4-[7-(5-Chloro-7H-pyrrolo[2,3-d]pyrimidin-4-yl)-4,7-diaza-spiro[2.5]oct-4-yl]-4-oxo-butyronitrile
[7-(5-Methyl-7H-pyrrolo[2,3-d]pyrimidin-4-yl)-4,7-diaza-spiro[2.5]oct-4-yl]-pyrazin-2-yl-methanone
(3-{2-[7-(5-Methyl-7H-pyrrolo[2,3-d]pyrimidin-4-yl)-4,7-diaza-spiro[2.5]oct-4-yl]-2-oxo-ethyl}-phenyl)-acetonitrile
(4-{2-[7-(5-Methyl-7H-pyrrolo[2,3-d]pyrimidin-4-yl)-4,7-diaza-spiro[2.5]oct-4-yl]-2-oxo-ethyl}-phenyl)-acetonitrile
1-[7-(5-Methyl-7H-pyrrolo[2,3-d]pyrimidin-4-yl)-4,7-diaza-spiro[2.5]octane-4-carbonyl]-cyclopropanecarbonitrile
2-(4-Fluoro-phenyl)-1-[7-(5-methyl-7H-pyrrolo[2,3-d]pyrimidin-4-yl)-4,7-diaza-spiro[2.5]oct-4-yl]-ethanone
1-[7-(5-Methyl-7H-pyrrolo[2,3-d]pyrimidin-4-yl)-4,7-diaza-spiro[2.5]oct-4-yl]-2-(4-trifluoromethyl-phenyl)-ethanone
5-[7-(5-Methyl-7H-pyrrolo[2,3-d]pyrimidin-4-yl)-4,7-diaza-spiro[2.5]oct-4-yl]-5-oxo-pentanenitrile
3-{2-[7-(5-Methyl-7H-pyrrolo[2,3-d]pyrimidin-4-yl)-4,7-diaza-spiro[2.5]oct-4-yl]-2-oxo-ethyl}-benzonitrile
4-{2-[7-(5-Methyl-7H-pyrrolo[2,3-d]pyrimidin-4-yl)-4,7-diaza-spiro[2.5]oct-4-yl]-2-oxo-ethyl}-benzonitrile
4-[7-(5-Methyl-7H-pyrrolo[2,3-d]pyrimidin-4-yl)-4,7-diaza-spiro[2.5]oct-4-yl]-4-oxo-butyronitrile
4-[4-(1-Cyano-cyclopropanecarbonyl)-4,7-diaza-spiro[2.5]oct-7-yl]-7H-pyrrolo[2,3-d]pyrimidine-6-carboxylic acid methyl ester
4-{4-[2-(4-Fluoro-phenyl)-acetyl]-4,7-diaza-spiro[2.5]oct-7-yl}-7H-pyrrolo[2,3-d]pyrimidine-6-carboxylic acid methyl ester
4-{4-[2-(4-Trifluoromethyl-phenyl)-acetyl]-4,7-diaza-spiro[2.5]oct-7-yl}-7H-pyrrolo[2,3-d]pyrimidine-6-carboxylic acid methyl ester
4-[4-(4-Cyano-butyryl)-4,7-diaza-spiro[2.5]oct-7-yl]-7H-pyrrolo[2,3-d]pyrimidine-6-carboxylic acid methyl ester
4-[4-(4-Cyano-butyryl)-4,7-diaza-spiro[2.5]oct-7-yl]-7H-pyrrolo[2,3-d]pyrimidine-6-carboxylic acid methyl ester
(1H-Indol-5-yl)-[3-(7H-pyrrolo[2,3-d]pyrimidin-4-yl)-3,8-diaza-bicyclo[3.2.1]oct-8-yl]-methanone
{4-[3-(7H-Pyrrolo[2,3-d]pyrimidin-4-yl)-3,8-diaza-bicyclo[3.2.1]octane-8-carbonyl]-phenoxy}-acetonitrile
{3-[3-(7H-Pyrrolo[2,3-d]pyrimidin-4-yl)-3,8-diaza-bicyclo[3.2.1]octane-8-carbonyl]-phenoxy}-acetonitrile
(1H-Indol-4-yl)-[3-(7H-pyrrolo[2,3-d]pyrimidin-4-yl)-3,8-diaza-bicyclo[3.2.1]oct-8-yl]-methanone
[3-(7H-Pyrrolo[2,3-d]pyrimidin-4-yl)-3,8-diaza-bicyclo[3.2.1]oct-8-yl]-quinoxalin-2-yl-methanone
(3-{2-Oxo-2-[3-(7H-pyrrolo[2,3-d]pyrimidin-4-yl)-3,8-diaza-bicyclo[3.2.1]oct-8-yl]-ethyl}-phenyl)-acetonitrile
(4-{2-Oxo-2-[3-(7H-pyrrolo[2,3-d]pyrimidin-4-yl)-3,8-diaza-bicyclo[3.2.1]oct-8-yl]-ethyl}-phenyl)-acetonitrile
(1H-Indol-2-yl)[3-(7H-pyrrolo[2,3-d]pyrimidin-4-yl)-3,8-diaza-bicyclo[3.2.1]oct-8-yl]-methanone
1-[3-(7H-Pyrrolo[2,3-d]pyrimidin-4-yl)-3,8-diaza-bicyclo[3.2.1]oct-8-yl]-2-(4-trifluoromethyl-phenyl)-ethanone
2-Fluoro-4-[3-(7H-pyrrolo[2,3-d]pyrimidin-4-yl)-3,8-diaza-bicyclo[3.2.1]octane-8-carbonyl]-benzonitrile
3-Fluoro-4-[3-(7H-pyrrolo[2,3-d]pyrimidin-4-yl)-3,8-diaza-bicyclo[3.2.1]octane-8-carbonyl]-benzonitrile
5-Oxo-5-[3-(7H-pyrrolo[2,3-d]pyrimidin-4-yl)-3,8-diaza-bicyclo[3.2.1]oct-8-yl]-pentanenitrile
4-[3-(7H-Pyrrolo[2,3-d]pyrimidin-4-yl)-3,8-diaza-bicyclo[3.2.1]octane-8-carbonyl]-benzenesulfonamide
N-{4-[3-(7H-Pyrrolo[2,3-d]pyrimidin-4-yl)-3,8-diaza-bicyclo[3.2.1]octane-8-carbonyl]-phenyl}-acetamide
6-[3-(7H-Pyrrolo[2,3-d]pyrimidin-4-yl)-3,8-diaza-bicyclo[3.2.1]octane-8-carbonyl]-1H-quinolin-2-one
(4-Methanesulfonyl-phenyl)-[3-(7H-pyrrolo[2,3-d]pyrimidin-4-yl)-3,8-diaza-bicyclo[3.2.1]oct-8-yl]-methanone
(1H-Indol-6-yl)-[3-(7H-pyrrolo[2,3-d]pyrimidin-4-yl)-3,8-diaza-bicyclo[3.2.1]oct-8-yl]-methanone 4-[3-(7H-Pyrrolo[2,3-d]pyrimidin-4-yl)-3,8-diaza-bicyclo
   [3.2.1]octane-8-carbonyl]-benzamide
(6-Hydroxy-naphthalen-1-yl)-[3-(7H-pyrrolo[2,3-d]pyrimi-
   din-4-yl)-3,8-diaza-bicyclo[3.2.1]oct-8-yl]-methanone
(6-Bromo-benzo[d]isothiazol-3-yl)-[3-(7H-pyrrolo[2,3-d]
   pyrimidin-4-yl)-3,8-diaza-bicyclo[3.2.1]oct-8-yl]-metha-
   none
(5-Fluoro-1H-indol-2-yl)-[7-(7H-pyrrolo[2,3-d]pyrimidin-
   4-yl)-4,7-diaza-spiro[2.5]oct-4-yl]-methanone
(7-Fluoro-1H-indol-2-yl)-[7-(7H-pyrrolo[2,3-d]pyrimidin-
   4-yl)-4,7-diaza-spiro[2.5]oct-4-yl]-methanone
(6-Fluoro-1H-indol-2-yl)-[7-(7H-pyrrolo[2,3-d]pyrimidin-
   4-yl)-4,7-diaza-spiro[2.5]oct-4-yl]-methanone
(4-Methanesulfonyl-phenyl)-[7-(7H-pyrrolo[2,3-d]pyrimi-
   din-4-yl)-4,7-diaza-spiro[2.5]oct-4-yl]-methanone
(5-Methanesulfonyl-1H-indol-2-yl)-[7-(7H-pyrrolo[2,3-d]
   pyrimidin-4-yl)-4,7-diaza-spiro[2.5]oct-4-yl]-methanone
(4-Fluoro-3-methanesulfonyl-phenyl)-[7-(7H-pyrrolo[2,3-
   d]pyrimidin-4-yl)-4,7-diaza-spiro[2.5]oct-4-yl]-metha-
   none
(3-Methanesulfonyl-phenyl)-[7-(7H-pyrrolo[2,3-d]pyrimi-
   din-4-yl)-4,7-diaza-spiro[2.5]oct-4-yl]-methanone
(4-Fluoro-1H-indol-2-yl)-[7-(7H-pyrrolo[2,3-d]pyrimidin-
   4-yl)-4,7-diaza-spiro[2.5]oct-4-yl]-methanone
4-[7-(7H-Pyrrolo[2,3-d]pyrimidin-4-yl)-4,7-diaza-spiro
   [2.5]octane-4-carbonyl]-benzenesulfonamide
(3-Fluoro-4-methanesulfonyl-phenyl)-[7-(7H-pyrrolo[2,3-
   d]pyrimidin-4-yl)-4,7-diaza-spiro[2.5]oct-4-yl]-metha-
   none
3-[7-(7H-Pyrrolo[2,3-d]pyrimidin-4-yl)-4,7-diaza-spiro
   [2.5]octane-4-carbonyl]-benzenesulfonamide
5-[7-(7H-Pyrrolo[2,3-d]pyrimidin-4-yl)-4,7-diaza-spiro
   [2.5]octane-4-carbonyl]-thiophene-3-sulfonic acid amide
5-[7-(7H-Pyrrolo[2,3-d]pyrimidin-4-yl)-4,7-diaza-spiro
   [2.5]octane-4-carbonyl]-thiophene-3-sulfonic acid methy-
   lamide
2-Methyl-5-[7-(7H-pyrrolo[2,3-d]pyrimidin-4-yl)-4,7-
   diaza-spiro[2.5]octane-4-carbonyl]-thiophene-3-sulfonic
   acid amide
2-Methyl-5-[7-(7H-pyrrolo[2,3-d]pyrimidin-4-yl)-4,7-
   diaza-spiro[2.5]octane-4-carbonyl]-thiophene-3-sulfonic
   acid methylamide
4-Methyl-5-[7-(7H-pyrrolo[2,3-d]pyrimidin-4-yl)-4,7-
   diaza-spiro[2.5]octane-4-carbonyl]-thiophene-3-sulfonic
   acid methylamide
N-Propyl-4-[7-(7H-pyrrolo[2,3-d]pyrimidin-4-yl)-4,7-
   diaza-spiro[2.5]octane-4-carbonyl]-benzenesulfonamide
2-Methoxy-4-[7-(7H-pyrrolo[2,3-d]pyrimidin-4-yl)-4,7-
   diaza-spiro[2.5]octane-4-carbonyl]-benzenesulfonamide
3-Methyl-4-[7-(7H-pyrrolo[2,3-d]pyrimidin-4-yl)-4,7-
   diaza-spiro[2.5]octane-4-carbonyl]-benzenesulfonamide
2-Methyl-4-[7-(7H-pyrrolo[2,3-d]pyrimidin-4-yl)-4,7-
   diaza-spiro[2.5]octane-4-carbonyl]-benzenesulfonamide
4-{2-Oxo-2-[7-(7H-pyrrolo[2,3-d]pyrimidin-4-yl)-4,7-
   diaza-spiro[2.5]oct-4-yl]-acetyl}-benzonitrile
(2-Chloro-4-methanesulfonyl-phenyl)-[7-(7H-pyrrolo[2,3-
   d]pyrimidin-4-yl)-4,7-diaza-spiro[2.5]oct-4-yl]-metha-
   none
4-{3-Oxo-3-[7-(7H-pyrrolo[2,3-d]pyrimidin-4-yl)-4,7-
   diaza-spiro[2.5]oct-4-yl]-propyl}-benzenesulfonamide
(5-Methoxy-thiophen-3-yl)-[7-(7H-pyrrolo[2,3-d]pyrimi-
   din-4-yl)-4,7-diaza-spiro[2.5]oct-4-yl]-methanone
(4-Hydroxy-thiophen-2-yl)-[7-(7H-pyrrolo[2,3-d]pyrimi-
   din-4-yl)-4,7-diaza-spiro[2.5]oct-4-yl]-methanone
(4-Methoxy-thiophen-2-yl)-[7-(7H-pyrrolo[2,3-d]pyrimi-
   din-4-yl)-4,7-diaza-spiro[2.5]oct-4-yl]-methanone
2-(4-Bromo-thiophen-2-yl)-1-[7-(7H-pyrrolo[2,3-d]pyrimi-
   din-4-yl)-4,7-diaza-spiro[2.5]oct-4-yl]-ethanone
4-Methyl-3-[7-(7H-pyrrolo[2,3-d]pyrimidin-4-yl)-4,7-
   diaza-spiro[2.5]octane-4-carbonyl]-benzenesulfonamide
3-Methoxy-4-[7-(7H-pyrrolo[2,3-d]pyrimidin-4-yl)-4,7-
   diaza-spiro[2.5]octane-4-carbonyl]-benzenesulfonamide
2-Methoxy-4-[3-(7H-pyrrolo[2,3-d]pyrimidin-4-yl)-3,8-
   diaza-bicyclo[3.2.1]octane-8-carbonyl]-benzenesulfona-
   mide
3-Methyl-4-[3-(7H-pyrrolo[2,3-d]pyrimidin-4-yl)-3,8-
   diaza-bicyclo[3.2.1]octane-8-carbonyl]-benzenesulfona-
   mide
2-Methyl-4-[3-(7H-pyrrolo[2,3-d]pyrimidin-4-yl)-3,8-
   diaza-bicyclo[3.2.1]octane-8-carbonyl]-benzenesulfona-
   mide
3-Methoxy-4-[3-(7H-pyrrolo[2,3-d]pyrimidin-4-yl)-3,8-
   diaza-bicyclo[3.2.1]octane-8-carbonyl]-benzenesulfona-
   mide
4-[7-(7H-Pyrrolo[2,3-d]pyrimidin-4-yl)-4,7-diaza-spiro
   [2.5]octane-4-carbonyl]-N-(tetrahydro-furan-2-ylm-
   ethyl)-benzenesulfonamide
N-(2-Cyano-ethyl)-4-[7-(7H-pyrrolo[2,3-d]pyrimidin-4-yl)-
   4,7-diaza-spiro[2.5]octane-4-carbonyl]-benzenesulfona-
   mide
N-(2-Methoxy-ethyl)-4-[7-(7H-pyrrolo[2,3-d]pyrimidin-4-
   yl)-4,7-diaza-spiro[2.5]octane-4-carbonyl]-benzene-
   sulfonamide
4-[7-(7H-Pyrrolo[2,3-d]pyrimidin-4-yl)-4,7-diaza-spiro
   [2.5]octane-4-carbonyl]-N-(2-thiophen-2-yl-ethyl)-ben-
   zenesulfonamide
3-{2-Oxo-2-[7-(7H-pyrrolo[2,3-d]pyrimidin-4-yl)-4,7-
   diaza-spiro[2.5]oct-4-yl]-ethyl}-benzenesulfonamide
4-{2-Oxo-2-[7-(7H-pyrrolo[2,3-d]pyrimidin-4-yl)-4,7-
   diaza-spiro[2.5]oct-4-yl]-ethoxy}-benzenesulfonamide
4-{5-[7-(7H-Pyrrolo[2,3-d]pyrimidin-4-yl)-4,7-diaza-spiro
   [2.5]octane-4-carbonyl]-furan-2-yl}-benzenesulfonamide
2-Oxo-2-[7-(7H-pyrrolo[2,3-d]pyrimidin-4-yl)-4,7-diaza-
   spiro[2.5]oct-4-yl]-N-(4-sulfamoyl-phenyl)-acetamide
5-[7-(7H-Pyrrolo[2,3-d]pyrimidin-4-yl)-4,7-diaza-spiro
   [2.5]octane-4-carbonyl]-1H-pyrrole-3-sulfonic acid
   amide
(4-Methanesulfonyl-3-methyl-phenyl)-[7-(7H-pyrrolo[2,3-
   d]pyrimidin-4-yl)-4,7-diaza-spiro[2.5]oct-4-yl]-metha-
   none
4-{2-Oxo-2-[7-(7H-pyrrolo[2,3-d]pyrimidin-4-yl)-4,7-
   diaza-spiro[2.5]oct-4-yl]-ethylsulfanyl}-benzenesulfona-
   mide
5-[7-(7H-Pyrrolo[2,3-d]pyrimidin-4-yl)-4,7-diaza-spiro
   [2.5]octane-4-carbonyl]-thiophene-2-sulfonic acid amide
[4-(2-Hydroxy-ethanesulfonyl)-phenyl]-[7-(7H-pyrrolo[2,
   3-d]pyrimidin-4-yl)-4,7-diaza-spiro[2.5]oct-4-yl]-metha-
   none
(4-Cyclopentanesulfonyl-phenyl)-[7-(7H-pyrrolo[2,3-d]py-
   rimidin-4-yl)-4,7-diaza-spiro[2.5]oct-4-yl]-methanone
4-{4-[7-(7H-Pyrrolo[2,3-d]pyrimidin-4-yl)-4,7-diaza-spiro
   [2.5]octane-4-carbonyl]-benzenesulfonyl}-butyronitrile
{4-[7-(7H-Pyrrolo[2,3-d]pyrimidin-4-yl)-4,7-diaza-spiro
   [2.5]octane-4-carbonyl]-phenyl}-methanesulfonamide
N-{2-Oxo-2-[7-(7H-pyrrolo[2,3-d]pyrimidin-4-yl)-4,7-
   diaza-spiro[2.5]oct-4-yl]-ethyl}-4-sulfamoyl-benzamide
3-Methyl-4-{2-oxo-2-[7-(7H-pyrrolo[2,3-d]pyrimidin-4-
   yl)-4,7-diaza-spiro[2.5]oct-4-yl]-ethoxy}-benzene-
   sulfonamide
1-{2-Oxo-2-[7-(7H-pyrrolo[2,3-d]pyrimidin-4-yl)-4,7-
   diaza-spiro[2.5]oct-4-yl]-ethyl}-1H-pyrazole-4-sulfonic
   acid amide Indan-1-yl-[7-(7H-pyrrolo[2,3-d]pyrimidin-4-yl)-4,7-diaza-spiro[2.5]oct-4-yl]-methanone
(5-Methyl-pyrazin-2-yl)[7-(7H-pyrrolo[2,3-d]pyrimidin-4-yl)-4,7-diaza-spiro[2.5]oct-4-yl]-methanone
[7-(7H-Pyrrolo[2,3-d]pyrimidin-4-yl)-4,7-diaza-spiro[2.5]oct-4-yl]-(1,2,3,4-tetrahydro-naphthalen-1-yl)-methanone
[7-(7H-Pyrrolo[2,3-d]pyrimidin-4-yl)-4,7-diaza-spiro[2.5]oct-4-yl]-(1,2,3,4-tetrahydro-naphthalen-1-yl)-methanone
(3-Methyl-pyrazin-2-yl)-[7-(7H-pyrrolo[2,3-d]pyrimidin-4-yl)-4,7-diaza-spiro[2.5]oct-4-yl]-methanone
(6-Methyl-pyrazin-2-yl)[7-(7H-pyrrolo[2,3-d]pyrimidin-4-yl)-4,7-diaza-spiro[2.5]oct-4-yl]-methanone
(3-Methyl-quinoxalin-2-yl)-[7-(7H-pyrrolo[2,3-d]pyrimidin-4-yl)-4,7-diaza-spiro[2.5]oct-4-yl]-methanone
2-(4-Methanesulfonyl-phenyl)-1-[7-(7H-pyrrolo[2,3-d]pyrimidin-4-yl)-4,7-diaza-spiro[2.5]oct-4-yl]-ethanone
Pyrazin-2-yl-[3-(7H-pyrrolo[2,3-d]pyrimidin-4-yl)-3,8-diaza-bicyclo[3.2.1]oct-8-yl]-methanone
5-[7-(7H-Pyrrolo[2,3-d]pyrimidin-4-yl)-4,7-diaza-spiro[2.5]octane-4-carbonyl]-thiophene-3-sulfonic acid isobutyl-amide
5-[7-(7H-Pyrrolo[2,3-d]pyrimidin-4-yl)-4,7-diaza-spiro[2.5]octane-4-carbonyl]-thiophene-3-sulfonic acid isobutyl-amide
N-(3-{4-[7-(7H-Pyrrolo[2,3-d]pyrimidin-4-yl)-4,7-diaza-spiro[2.5]octane-4-carbonyl]-benzenesulfonylamino}-propyl)-acetamide
N-(2-{4-[7-(7H-Pyrrolo[2,3-d]pyrimidin-4-yl)-4,7-diaza-spiro[2.5]octane-4-carbonyl]-benzenesulfonylamino}-ethyl)-acetamide
N-Furan-2-ylmethyl-4-[7-(7H-pyrrolo[2,3-d]pyrimidin-4-yl)-4,7-diaza-spiro[2.5]octane-4-carbonyl]-benzenesulfonamide
N-(5-Methyl-furan-2-ylmethyl)-4-[7-(7H-pyrrolo[2,3-d]pyrimidin-4-yl)-4,7-diaza-spiro[2.5]octane-4-carbonyl]-benzenesulfonamide
(2-{4-[7-(7H-Pyrrolo[2,3-d]pyrimidin-4-yl)-4,7-diaza-spiro[2.5]octane-4-carbonyl]-benzenesulfonylamino}-ethyl)-carbamic acid tert-butyl ester
4-{1-[7-(7H-Pyrrolo[2,3-d]pyrimidin-4-yl)-4,7-diaza-spiro[2.5]octane-4-carbonyl]-cyclopropyl}-benzonitrile
N-{4-[7-(7H-Pyrrolo[2,3-d]pyrimidin-4-yl)-4,7-diaza-spiro[2.5]octane-4-carbonyl]-phenyl}-methanesulfonamide
Propane-1-sulfonic acid {4-[7-(7H-pyrrolo[2,3-d]pyrimidin-4-yl)-4,7-diaza-spiro[2.5]octane-4-carbonyl]-phenyl}-amide
Propane-2-sulfonic acid {4-[7-(7H-pyrrolo[2,3-d]pyrimidin-4-yl)-4,7-diaza-spiro[2.5]octane-4-carbonyl]-phenyl}-amide
[4-(2-Methoxy-ethanesulfonyl)-phenyl]-[7-(7H-pyrrolo[2,3-d]pyrimidin-4-yl)-4,7-diaza-spiro[2.5]oct-4-yl]-methanone
3-Fluoro-4-{2-oxo-2-[7-(7H-pyrrolo[2,3-d]pyrimidin-4-yl)-4,7-diaza-spiro[2.5]oct-4-yl]-ethoxy}-benzenesulfonamide
1-{3-Oxo-3-[7-(7H-pyrrolo[2,3-d]pyrimidin-4-yl)-4,7-diaza-spiro[2.5]oct-4-yl]-propyl}-1H-pyrazole-4-sulfonic acid amide
7-(7H-Pyrrolo[2,3-d]pyrimidin-4-yl)-4,7-diaza-spiro[2.5]octane-4-carboxylic acid cyclohexylamide
7-(7H-Pyrrolo[2,3-d]pyrimidin-4-yl)-4,7-diaza-spiro[2.5]octane-4-carbothioic acid cyclohexylamide
7-(7H-Pyrrolo[2,3-d]pyrimidin-4-yl)-4,7-diaza-spiro[2.5]octane-4-carbothioic acid benzylamide
(5,6-Dihydro-4H-cyclopenta[b]thiophen-2-yl)-[7-(7H-pyrrolo[2,3-d]pyrimidin-4-yl)-4,7-diaza-spiro[2.5]oct-4-yl]-methanethione
(5,6-Dihydro-4H-cyclopenta[b]thiophen-2-yl)-[7-(7H-pyrrolo[2,3-d]pyrimidin-4-yl)-4,7-diaza-spiro[2.5]oct-4-yl]-methanethione
4-{2-[7-(7H-Pyrrolo[2,3-d]pyrimidin-4-yl)-4,7-diaza-spiro[2.5]oct-4-yl]-2-thioxo-ethyl}-benzonitrile
2-Phenoxy-1-[7-(7H-pyrrolo[2,3-d]pyrimidin-4-yl)-4,7-diaza-spiro[2.5]oct-4-yl]-ethanone
2-Methoxy-1-[7-(7H-pyrrolo[2,3-d]pyrimidin-4-yl)-4,7-diaza-spiro[2.5]oct-4-yl]-ethanone
7-(7H-Pyrrolo[2,3-d]pyrimidin-4-yl)-4,7-diaza-spiro[2.5]octane-4-carboxylic acid butylamide
7-(7H-Pyrrolo[2,3-d]pyrimidin-4-yl)-4,7-diaza-spiro[2.5]octane-4-carboxylic acid phenethyl-amide
7-(7H-Pyrrolo[2,3-d]pyrimidin-4-yl)-4,7-diaza-spiro[2.5]octane-4-carboxylic acid 4-chloro-phenyl ester
2-Methoxy-1-[7-(7H-pyrrolo[2,3-d]pyrimidin-4-yl)-4,7-diaza-spiro[2.5]oct-4-yl]-ethanethione
2-Phenoxy-1-[7-(7H-pyrrolo[2,3-d]pyrimidin-4-yl)-4,7-diaza-spiro[2.5]oct-4-yl]-ethanethione
4-[4-(2-Methyl-propane-2-sulfinyl)-4,7-diaza-spiro[2.5]oct-7-yl]-7H-pyrrolo[2,3-d]pyrimidine
7-(7H-Pyrrolo[2,3-d]pyrimidin-4-yl)-4,7-diaza-spiro[2.5]octane-4-carboxylic acid cyclopentyl ester
2-Phenylamino-1-[7-(7H-pyrrolo[2,3-d]pyrimidin-4-yl)-4,7-diaza-spiro[2.5]oct-4-yl]-ethanone
4-{3-Oxo-3-[7-(7H-pyrrolo[2,3-d]pyrimidin-4-yl)-4,7-diaza-spiro[2.5]oct-4-yl]-propoxy}-benzenesulfonamide
4-{3-Oxo-3-[7-(7H-pyrrolo[2,3-d]pyrimidin-4-yl)-4,7-diaza-spiro[2.5]oct-4-yl]-propylamino}-benzenesulfonamide
4-{2-Oxo-2-[7-(7H-pyrrolo[2,3-d]pyrimidin-4-yl)-4,7-diaza-spiro[2.5]oct-4-yl]-ethylamino}-benzenesulfonamide
3-Methylsulfanyl-1-[7-(7H-pyrrolo[2,3-d]pyrimidin-4-yl)-4,7-diaza-spiro[2.5]oct-4-yl]-propan-1-one
3-Methoxy-1-[7-(7H-pyrrolo[2,3-d]pyrimidin-4-yl)-4,7-diaza-spiro[2.5]oct-4-yl]-propan-1-one
3-Dimethylamino-1-[7-(7H-pyrrolo[2,3-d]pyrimidin-4-yl)-4,7-diaza-spiro[2.5]oct-4-yl]-propan-1-one
7-(7H-Pyrrolo[2,3-d]pyrimidin-4-yl)-4,7-diaza-spiro[2.5]octane-4-sulfonic acid (2-cyano-ethyl)-methyl-amide
7-(7H-Pyrrolo[2,3-d]pyrimidin-4-yl)-4,7-diaza-spiro[2.5]octane-4-sulfonic acid diethylamide, and
7-(7H-Pyrrolo[2,3-d]pyrimidin-4-yl)-4,7-diaza-spiro[2.5]octane-4-sulfonic acid cyclohexyl-methyl-amide.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Compounds of formula I may comprise asymmetrically substituted (chiral) carbon atoms and carbon-carbon double bonds which may give rise to the existence of isomeric forms, e.g. enantiomers, diastereomers and geometric isomers. The present invention relates to all such isomers, either in pure form or as mixtures thereof. The invention also relates to all possible tautomers of the compounds of formula I.

In an embodiment of the invention the compounds of formula I according to the invention may be used in therapy.

In an embodiment of the invention the compounds of formula I according to the invention may be useful in therapy, such as for the use in the treatment of dermal diseases or conditions or acute or chronic cutaneous wound disorders.

In an embodiment of the invention the dermal disease or condition is selected from the group consisting of proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

In an embodiment of the invention the compounds of formula I according to the invention may be used in the prophylaxis, treatment and/or amelioration of diseases of the immune system, in particular autoimmune diseases.

In an embodiment of the invention the compounds of formula I according to the invention may be used in the prophylaxis, treatment and/or amelioration of diseases, such as psoriasis, rosacea, lupus, multiple sclerosis, rheumatoid arthritis, Type I diabetes and complications from diabetes, asthma, atopic dermatitis, cancer, autoimmune thyroid disorders, ulcerative colitis, Crohn's disease, Alzheimer's disease, leukaemia, eye diseases such as diabetic retinopathy and macular degeneration as well as other autoimmune diseases In an embodiment of the invention the compounds of formula I according to the invention may be used as an anti-inflammatory agent capable of modulating the activity of a protein tyrosin kinase of the JAK family of protein tyrosine kinases.

In an embodiment of the invention the compounds of formula I according to the invention may be used as an anti-inflammatory agent capable of modulating the activity of JAK1, JAK2, JAK3 or TYK2 protein tyrosine kinases.

In an embodiment of the invention the compounds of formula I according to the invention may be used in the treatment, amelioration or prophylaxis of non-infectious anti-inflammatory or autoimmune diseases or conditions wherein the non-infectious inflammatory diseases or conditions are selected from the group consisting of acute inflammatory diseases such as acute lung injury, acute respiratory distress syndrome, allergy, anaphylaxis, sepsis or graft-versus-host disease, or chronic inflammatory diseases such as osteoarthritis, gout, psoriatic arthritis, hepatic cirrhosis, multiple sclerosis, or ocular diseases or conditions such as non-infectious (e.g. allergic) conjunctivitis, uveitis, iritis, keratitis, scleritis, episcleritis, sympathitic ophthalmitis, blepharitis, keratoconjunctivitis sicca, or immunological cornea graft rejection, and the autoimmune diseases or conditions are selected from the group consisting of autoimmune gastritis, Addison's disease, autoimmune hemolytic anemia, autoimmune thyroiditis, chronic idiopathic urticaria, chronic immune polynephropathy, diabetes, diabetic nephropathy, myasthenia gravis, pemphigus vulgaris, pernicious anemia, primary biliary cirrhosis, systemic lupus erythematosus and thyroid eye disease.

Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition or pharmaceutical formulation. The invention therefore relates to a pharmaceutical composition comprising a compound of formula I, optionally together with one or more other therapeutically active compounds, such as differentiating agents such as vitamin D derivatives and all-trans retinoid acid; corticosteroids, such as dexamethasone and prednisone, chemotherapeutic agents, anticancer agents, cytotoxic agents, together with a pharmaceutically acceptable excipient or vehicle. The excipient must be "acceptable" in the sense of being compatible with the other ingredients of the composition and not deleterious to the recipient thereof.

If the treatment involves administration of another therapeutically active compound it is recommended to consult *Goodman & Gilman's The Pharmacological Basis of Therapeutics*, 9$^{th}$ Ed., J. G. Hardman and L. E. Limbird (Eds.), McGraw-Hill 1995, for useful dosages of said compounds.

Conveniently, the active ingredient comprises from 0.1-99.9% by weight of the composition.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers. In the form of a dosage unit, the compound may be administered one or more times a day at appropriate intervals, always depending, however, on the condition of the patient, and in accordance with the prescription made by the medical practitioner. It is also envisaged that in certain treatment regimes, administration with longer intervals e.g. every other day, every week, or even with longer intervals may be beneficial.

Conveniently, dosage unit of a formulation contains between 0.01 mg and 1000 mg, preferably between 1 mg and 500 mg, such as between 5 mg and 100 mg of a compound of formula I.

The formulations include e.g. those in a form suitable for ophthalmic (including sustained or time-released), oral (including sustained or timed release), rectal, parenteral (including subcutaneous, intraperitoneal, intramuscular, intraarticular and intravenous), transdermal, topical, nasal or buccal administration.

The formulations may conveniently be presented in dosage unit form and may be prepared by any of the methods well known in the art of pharmacy, e.g. as disclosed in Remington, *The Science and Practice of Pharmacy*, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops, intravitreal injection and time-released drug systems.

For topical administration, the compound of formula I may typically be present in an amount of from 0.01 to 20% by weight of the composition, such as 0.1% to about 10%, but may also be present in an amount of up to about 50% of the composition.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution.

The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compound of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable for nasal or buccal administration include powder, self-propelling and spray formulations, such as aerosols and atomisers. Such formulations are disclosed in greater detail in e.g. *Modern Pharmaceutics*, 2$^{nd}$ ed., G. S. Banker and C. T. Rhodes (Eds.), page 427-432, Marcel Dekker, New York; *Modern Pharmaceutics*, 3$^{th}$ ed., G. S. Banker and C. T. Rhodes (Eds.), page 618-619 and 718-721, Marcel Dekker, New York and *Encyclopedia of Pharmaceutical Technology vol.* 10, J Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

EXAMPLES

Methods of Preparation

The compounds of the present invention can be prepared in a number of ways well known to those skilled in the art of synthesis. The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art of organic synthesis. Not all compounds falling into a given class may be compatible with some of the reaction conditions required in some of the methods described. Such restrictions to the substituents which are compatible with the reaction conditions will be readily apparent to one skilled in the art and alternative methods can be used.

Starting materials are either known or commercially available compounds or can be prepared by routine synthetic methods well known to a person skilled in the art.

GENERAL PROCEDURES, PREPARATIONS AND EXAMPLES $^1$H nuclear magnetic resonance (NMR) spectra were recorded at 300 MHz or 600 MHz. Chemical shift values (δ, in ppm) are quoted in the specified solvent relative to internal tetramethylsilane (δ=0.00) or chloroform (δ=7.25) standards. DMSO-d$_6$ is simply referred to as DMSO in the lists containing the NMR data. The value of a multiplet, either defined (doublet (d), triplet (t), quartet (q)) or not (m) at the approximate mid point is given unless a range is quoted. (br) indicates a broad peak. The organic solvents used were usually anhydrous. Chromatography was performed on Merck silica gel 60 (0.040-0-063 mm). The solvent ratios indicated refer to v:v unless otherwise noted.

The following abbreviations have been used throughout:
BOC tert-butoxycarbonyl
CBT 1,1'-carbonylbisbenzotriazole
CDI N,N-carbonyldiimidazole
COMU (1-Cyano-2-ethoxy-2-oxoethylidenaminooxy)-dimethylamino-morpholino-carbenium hexafluorophosphate
DCC dicyclohexylcarbodiimide
DCM dichloromethane
DMF N,N'-Dimethylformamide
DMSO dimethyl sulfoxide
EDC 1-ethyl-3-(3-dimethylaminopropyl)carbodiimide
Et ethyl
EtOAc ethylacetate
EtOH ethanole HATU O-(7-azabenzotriazol-1-yl)-1,1,3,3-tetramethyluronium hexafluorophosphate
L liter
LG leaving group
m milli
Me methyl
NMR nuclear magnetic resonance
Ms mesylate
PG protecting group
Ph phenyl
PyBroP bromotri(pyrrolidino)phosphonium hexafluorophosphate
SEM 2-(trimethylsilyl)ethoxymethyl
THF tetrahydrofuran
TIPS triisopropylsilyl
Ts tosylate
v volume
Preparative HPLC/MS Preparative HPLC/MS was performed on a Dionex APS-system with two Shimadzu PP150 prep. pumps and a Thermo MSQ Plus mass spectrometer. Column: Waters XTerra C-18, 150 mm×19 mm, 5 μm; solvent system: A=water (0.1% formic acid) and B=acetonitrile (0.1% formic acid); flow rate=18 mL/min; method (10 min): Linear gradient method going from 10% B to 100% B in 6 minutes and staying at 100% B for another 2 minutes. The fractions were collected based on ion traces of relevant ions and PDA signal (240-400 nm).

Analytical HPLC/MS

Analytical HPLC/MS was performed on a system consisting of a Waters 2795 HPLC, Micromass ZQ mass spectrometer, Waters 996 PDA. Column: Waters XTerra C-18, 50 mm×3.0 mm, 5 μm; solvent system: A=water:acetonitrile 95:5 (0.05% formic acid) and B=acetonitrile (0.05% formic acid); flow rate=1.0 mL/min; method (8 min): Linear gradient method going from 10% B to 100% B in 6.0 minutes and staying at 100% B for 1 minute.

General Procedure of Preparation:

The compounds of the invention can for example be prepared by the general methods outlined in Scheme 1:

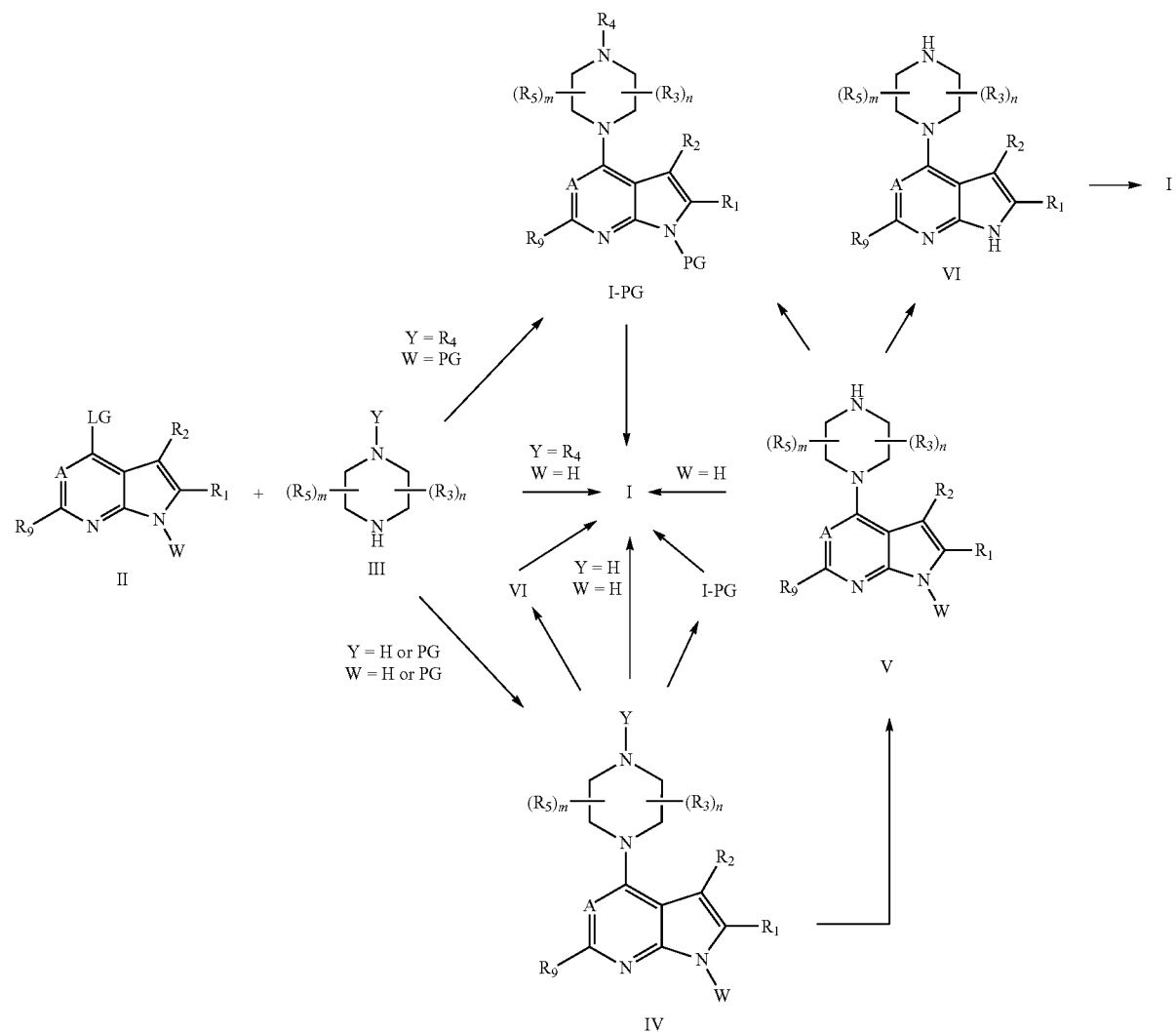

wherein A, $R_1$, $R_2$, $R_3$, $R_4$, $R_5$, $R_9$, m and n are defined as described herein, and W and Y represents either hydrogen or a suitable protecting group ("Protective Groups in Organic Synthesis", 3$^{rd}$ ed., Greene T. W. and Wuts P. G. M., John Wiley & Sons Inc.), such as, but not restricted to, BOC, SEM and Ts, and LG represents a suitable leaving group, such as, but not restricted to: fluorine, chlorine, bromide, iodide, methoxy, —OMs or —OTs.

The Y in scheme 1 is different to, and not to be confused with the Y used in the claims.

The reaction between II and III to form either I, I-PG or IV can be performed in the presence or absence of an acid (such as HCl) or a base (such as Et$_3$N or K$_2$CO$_3$), in a suitable solvent (such as DMF or EtOH) at a suitable temperature such as from room temperature to 200° C. by conventional heating or microwave induced heating. Alternatively, the reaction between II and III to form either I, I-PG or IV can be performed in the presence of a transition metal based catalysis with a suitable ligand and a suitable base and in a suitable solvent, at a suitable temperature such as from room temperature to 200° C. by conventional heating or microwave induced heating. Typical transition metals includes Pd and Cu, suitable ligands includes P-based ligands like 2,2'-bis(diphenylphosphino)1,1'-binaphthyl and 4,5-bis-diphenylphosphanyl-9,9-dimethyl-9H-xanthene, and N-based ligands like N,N'-dimethylcyclohexane-1,2-diamine, suitable bases includes Cs$_2$CO$_3$, sodium tert-butoxide and K$_3$PO$_4$, and suitable solvents include dioxane and toluene.

Any protecting group represented by Y and W can in general be introduced and removed by standard procedures known to a chemist skilled in the art of organic synthesis (e.g "*Protective Groups in Organic Synthesis*", 3$^{rd}$ ed., Greene T. W. and Wuts P. G. M., John Wiley & Sons Inc.).

Compounds of the general formula II and III are either commercially available or are prepared from commercially available molecules by synthetic transformations according to standard procedures known to a chemist skilled in the art of organic synthesis.

Compounds of the general formula III can for example be prepared by reduction of monoketopiperazines, either commercially available or prepared by methods known to a chemist skilled in the art of organic synthesis.

Compounds of the general formula III can for example be prepared by derivatisation of monoketopiperazines, either commercially available or prepared by methods known to a chemist skilled in the art of organic synthesis.

For example by cyclopropanation of appropriately substituted monoketopiperazines.

Compounds of the general formula III can for example be prepared by reduction of diketopiperazines, prepared via cyclization of suitable dipeptides which again are prepared by coupling of suitable aminoacids, aminoacid esters or suitable amino acid derivatives.

Introduction of R$_4$ in compounds of general formula III can for example be achieved by reacting compounds of general formula III (Y=H) with suitable derivatives of R$_4$, such as, but not restricted to, carboxylic acid halide or ester derivatives of R$_4$, isocyanate derivatives of R$_4$, isothiocyanate derivatives of R$_4$, sulfonylhalide or ester derivatives of R$_4$, sulfinylhalide or ester derivatives of R$_4$, carboxylic acid derivatives of R$_4$ under suitable coupling conditions, and amine derivatives of R$_4$ with a suitable carbonylating agent.

Introduction of R$_4$ in compounds of general formula IV (Y=H), V and VI can for example be achieved by reacting compounds of general formula IV (Y=H), V and VI with suitable derivatives of R$_4$, such as, but not restricted to, carboxylic acid halide or ester derivatives of R$_4$, isocyanate derivatives of R$_4$, isothiocyanate derivatives of R$_4$, sulfonylhalide or ester derivatives of R$_4$, sulfinylhalide or ester derivatives of R$_4$, carboxylic acid derivatives of R$_4$ under suitable coupling conditions, and amine derivatives of R$_4$ with a suitable carbonylating agent. Typical conditions for such reactions are described in further detail in the following for introduction of R$_4$ in compounds of general formula IV (Y=H), V and VI.

Compounds of the general formula I where R$_4$=R$_{4-a}$, R$_{4-c}$, R$_{4-f}$, R$_{4-h}$ or R$_{4-j}$ and X=O can for example be prepared by reacting compounds of the general formula IV (Y=H), V and VI with appropriate carboxylic acid halide derivatives of R$_{4-a}$, R$_{4-c}$, R$_{4-e}$, R$_{4-f}$, R$_{4-h}$ and R$_{4-j}$ in the presence or absence of a base such as Et$_3$N in a suitable solvent such as DCM, THF or DMF at an appropriate temperature such as from 0° C. to 150° C. Furthermore, compounds of the general formula I where R$_4$=R$_{4-a}$, R$_{4-c}$, R$_{4-e}$, R$_{4-f}$, R$_{4-h}$ or R$_{4-j}$ and X=O can for example be prepared by reacting compounds of the general formula IV (Y=H), V and VI with appropriate carboxylic acid derivatives of R$_{4-a}$, R$_{4-c}$, R$_{4-e}$, R$_{4-f}$, R$_{4-h}$ and R$_{4-j}$ in the presence of a suitable amide coupling reagent (E. Valeur, M. Bradley *Chem. Soc. Rev.* 2009, 38, 606-631) such as DCC, HATU, EDC or PyBroP, in the presence or absence of a base such as Et$_3$N, and in a suitable solvent such as DCM or DMF at a suitable temperature such as from room temperature to 150° C.

Compounds of the general formula I where R$_4$=R$_{4-b}$, R$_{4-d}$, R$_{4-g}$ or R$_{4-i}$ and Y=N can for example be prepared by reacting compounds of the general formula IV (Y=H), V and VI with appropriate isocyanato (X=O) or isothiocyanato (X=S) derivatives of R$_{4-b}$, R$_{4-d}$, R$_{4-g}$ or R$_{4-i}$ in a suitable solvent such as DCM, THF or DMF at an appropriate temperature such as from 0° C. to 150° C.

Furthermore, compounds of the general formula I where R$_4$=R$_{4-b}$, R$_{4-d}$, R$_{4-g}$ or R$_{4-i}$ and Y=N can for example be prepared by reacting compounds of the general formula IV (Y=H), V and VI with appropriate amino derivatives of R$_{4-b}$, R$_{4-d}$, R$_{4-g}$ or R$_{4-i}$ in the presence of a suitable carbonylating reagent such as appropriate carbonates, CDI or CBT (J. Org. Chem. 1997, 62, 4155-4158) in a suitable solvent such as DCM, THF or DMF at an appropriate temperature such as from 0° C. to 150° C.

Compounds of the general formula I where R$_4$=R$_{4-b}$, R$_{4-d}$, R$_{4-g}$ or R$_{4-i}$ and Y=O can for example be prepared by reacting compounds of the general formula IV (Y=H), V and VI with appropriate chloroformate or dicarbonate derivatives of R$_{4-b}$, R$_{4-d}$, R$_{4-g}$ or R$_{4-i}$ in a suitable solvent such as DCM, THF or DMF at an appropriate temperature such as from 0° C. to 150° C.

Compounds of the general formula I where R$_4$=R$_{4-k}$, R$_{4-l}$, R$_{4-m}$, R$_{4-q}$, R$_{4-r}$ or R$_{4-s}$ can for example be prepared by reacting compounds of the general formula IV (Y=H), V and VI with appropriate sulfonic acid halide or ester derivatives of R$_{4-k}$, R$_{4-l}$, R$_{4-m}$, R$_{4-q}$, R$_{4-r}$ or R$_{4-s}$ in the presence or absence of a base such as Et$_3$N in a suitable solvent such as DCM, THF or DMF at an appropriate temperature such as from 0° C. to 150° C.

Compounds of the general formula I where R$_4$=R$_{4-n}$, R$_{4-o}$, R$_{4-p}$, R$_{4-t}$, R$_{4-u}$ or R$_{4-v}$ can for example be prepared by reacting compounds of the general formula IV (Y=H), V and VI with appropriate sulfinic acid halide or ester derivatives of R$_{4-n}$, R$_{4-o}$, R$_{4-p}$, R$_{4-t}$, R$_{4-u}$ or R$_{4-v}$, in the presence or absence of a base such as Et$_3$N in a suitable solvent such as DCM, THF or DMF at an appropriate temperature such as from 0° C. to 150° C.

Compounds of the general formula I where X=S can for example be prepared by reacting compounds of the general formula I where X=O with Lawessons reagent.

Compounds of the general formula I where R$_4$=R$_{4-c}$, R$_{4-e}$, R$_{4-f}$, R$_{4-h}$, or R$_{4-j}$ and where the C=X (X=O) is directly followed by a —CH₂— group can be reacted with oxidising reagents to form compounds of the general formula I where R₄=R₄₋c, R₄₋f, R₄₋h, or R₄₋j and where the C=X (X=O) is directly followed by a —C(=O)— group.

Intermediates

Intermediate 1

Example 45

7-(7H-pyrrolo[2,3-d]pyrimidin-4-yl)-4,7-diazaspiro[2.5]octane-4-carboxylic acid tert-butyl ester

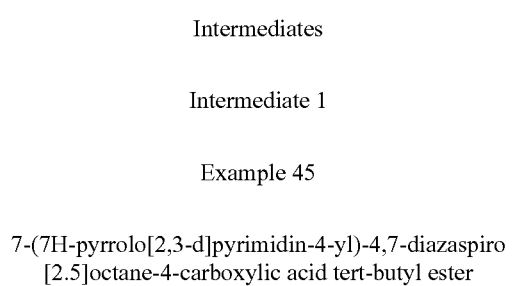

To commercially available 4-chloro-7H-pyrrolo[2,3-d]pyrimidine (1.0 g, 6.5 mmol) dissolved in DMF (5 ml) was added Et₃N (1.3 ml, 9.8 mmol) followed by commercially available 4,7-diaza-spiro[2.5]octane-4-carboxylic acid tert-butyl ester (1.5 g, 7.2 mmol). The reaction mixture was heated for 16 hours at 110° C. After evaporation of the solvent in vacuo the crude mixture was treated with water (25 mL) and extracted with EtOAc (4×30 mL) the combined organic phases were washed with brine (2×20 mL), dried over Na₂SO₄, filtered and concentrated in vacuo to provide 1.5 g crude. The product was purified by flash chromatography on silica using EtOAc in heptane as eluent.

¹H NMR (300 MHz, DMSO) δ=11.70 (s, 1H), 8.15 (s, 1H), 7.18 (m, 1H), 6.59 (m, 1H), 3.90 (m, 2H), 3.73 (m, 2H), 3.62-3.53 (m, 2H), 1.68-1.11 (m, 9H), 1.01-0.57 (m, 5H).

Intermediate 2

4-(4,7-Diaza-spiro[2.5]oct-7-yl)-7H-pyrrolo[2,3-d]pyrimidine

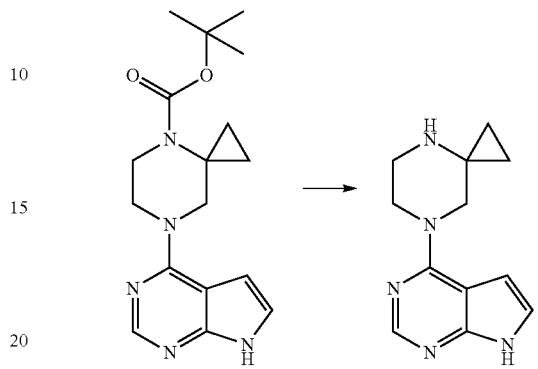

To 7-(7H-pyrrolo[2,3-d]pyrimidin-4-yl)-4,7-diazaspiro[2.5]octane-4-carboxylic acid tert-butyl ester (intermediate 1) (0.5 g, mmol) dissolved in diethyl ether (20 ml) was added HCl in dioxane (ml, M) and the reaction mixture was stirred for 5 hours at room temperature. The precipitate was isolated by filtration, and washed with diethyl ether (2×5 ml). The precipitate was suspended in THF (50 ml) and stirred vigorously with K₂CO₃ (5 gram) for 3 hours. After filtration and evaporation of the solvent in vacuo, the product was obtained as an off-white compound.

¹H NMR (300 MHz, DMSO) δ=11.64 (s, 1H), 8.09 (s, 1H), 7.21-7.08 (m, 1H), 6.53 (m, 1H), 3.92-3.79 (m, 2H), 3.71 (s, 2H), 2.94-2.81 (m, 2H), 1.29 (br s, 1H), 0.59-0.37 (m, 4H).

Alternatively Synthesis of Intermediate 2

4-(4,7-Diaza-spiro[2.5]oct-7-yl)-7H-pyrrolo[2,3-d]pyrimidine

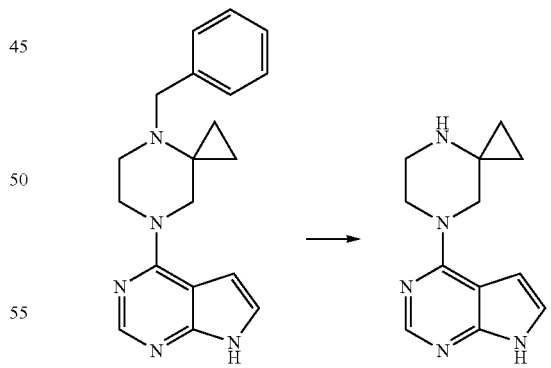

To 4-(4-benzyl-4,7-diaza-spiro[2.5]oct-7-yl)-7H-pyrrolo[2,3-d]pyrimidine (intermediate 20) (50 g, 78.36 mmol) in MeOH, was added 10% Pd/C (20 g) and HCOONH4 (98 g, 783.69 mmol) and the reaction mixture was heated to reflux for 30 min. The reaction mixture was filtered through celite bed and washed with MeOH and concentrated under reduced pressure. The crude compound was treated with 50% NaOH solution (200 ml) and stirred for 15 min and solid was obtained by filtration. And the solid was wash with 50 ml of water and dried under vacuum. The crude compound (33 g) in acetone (10 times) was heated to reflux for 30 min. The reaction mixture was cooled and filtered and the solid was washed with acetone to afford the title compound as a solid (29.78 g, 83%).

Intermediate 3

Example 9

3-(7H-Pyrrolo[2,3-d]pyrimidin-4-yl)-3,8-diaza-bicyclo[3.2.1]octane-8-carboxylic acid tert-butyl ester

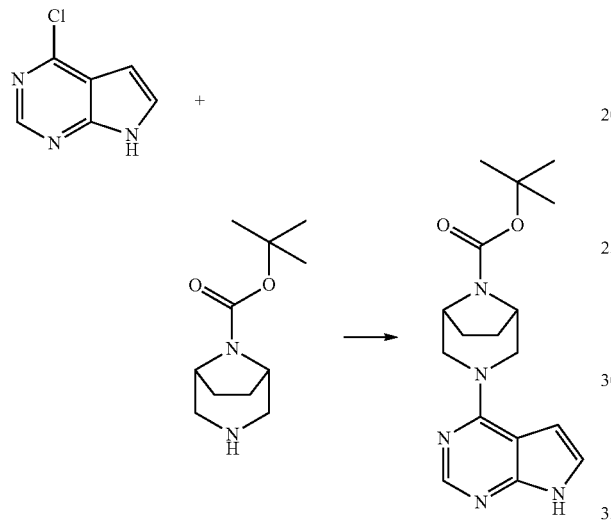

Prepared in a way similar to Intermediate 1, using 3,8-diaza-bicyclo[3.2.1]octane-8-carboxylic acid tert-butyl ester, instead of 4,7-diaza-spiro[2.5]octane-4-carboxylic acid tert-butyl ester.

$^1$H NMR (300 MHz, CDC$_{l3}$) δ=10.64 (s, 1H), 8.33 (s, 1H), 7.08 (d, J=3.2, 1H), 6.52 (d, J=3.5, 1H), 4.83-4.25 (m, 4H), 3.44 (m, 2H), 2.03-1.91 (m, 2H), 1.81 (m, 2H), 1.50 (s, 9H).

Intermediate 4

4-(3,8-Diaza-bicyclo[3.2.1]oct-3-yl)-7H-pyrrolo[2,3-d]pyrimidine

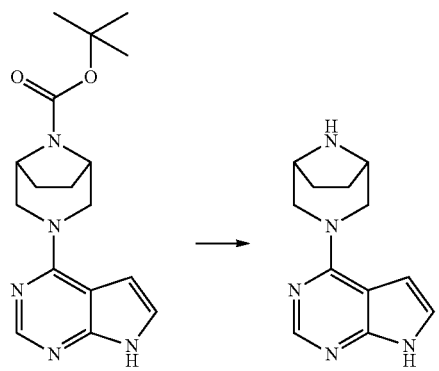 [SMILES: CC(C)(C)OC(=O)N1C2CCC1CN(c1ncnc3[nH]ccc13)C2 ; c1nc(N2CC3CCC(C2)N3)c2cc[nH]c2n1]

Prepared in a way similar to Intermediate 2, using 3-(7H-Pyrrolo[2,3-d]pyrimidin-4-yl)-3,8-diaza-bicyclo[3.2.1]octane-8-carboxylic acid tert-butyl ester (intermediate 3) instead of intermediate 1.

$^1$H NMR (300 MHz, DMSO) δ=11.61 (s, 1H), 8.09 (s, 1H), 7.12 (d, J=3.6, 1H), 6.56 (d, J=3.5, 1H), 4.29 (m, 2H), 3.51 (m, 2H), 3.17 (m, 2H), 1.74-1.56 (m, 4H).

Intermediate 5

5-(7H-pyrrolo[2,3-d]pyrimidin-4-yl)-2,5-diaza-bicyclo[2.2.1]heptane-2-carboxylic acid tert-butyl ester

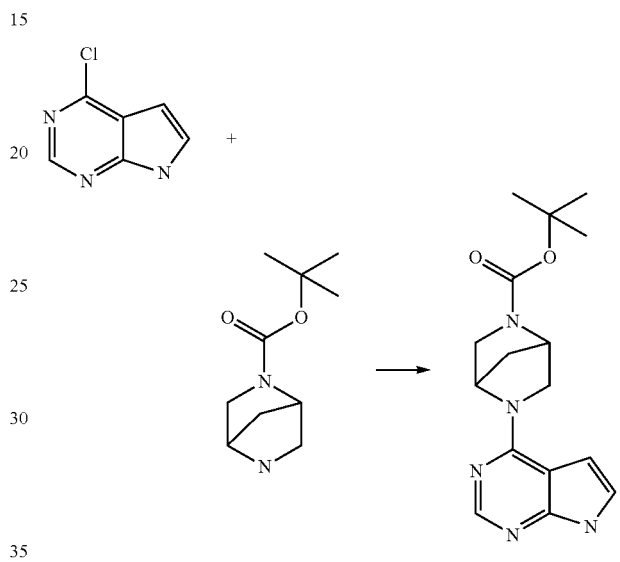

Prepared in a way similar to Intermediate 1, using 2,5-diaza-bicyclo[2.2.1]heptane-2-carboxylic acid tert-butyl ester, instead of 4,7-diaza-spiro[2.5]octane-4-carboxylic acid tert-butyl ester.

1H NMR (300 MHz, DMSO) δ=11.66 (s, 1H), 8.11 (s, 1H), 7.16 (m, 1H), 6.58 (br, 1H), 5.11 (br, 1H), 4.52 (m, 1H), 3.87 (br, 1H), 3.64 (m, 1H), 3.27 (m, 2H), 1.98 (m, 2H), 1.37 (br, 9H).

Intermediate 6

4-(2,5-Diaza-bicyclo[2.2.1]hept-2-yl)-7H-pyrrolo[2,3-d]pyrimidine

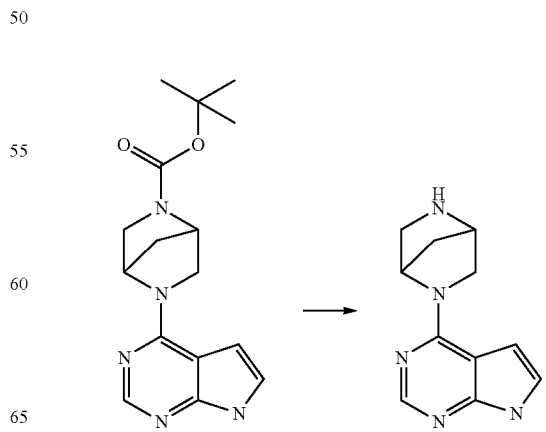

Prepared in a way similar to intermediate 2, using intermediate 5, instead of intermediate 1.

1H NMR (300 MHz, DMSO) δ=11.56 (s, 1H), 8.06 (s, 1H), 7.09 (br, 1H), 6.48 (br, 1H), 4.96 (br, 1H), 3.63 (br, 3H), 2.89 (br, 2H), 1.73 (br, 2H).

Intermediate 7

4-(4-tert-Butoxycarbonyl-4,7-diazaspiro[2.5]oct-7-yl)-7H-pyrrolo[2,3-d]pyrimidine-6-carboxylic acid methyl ester

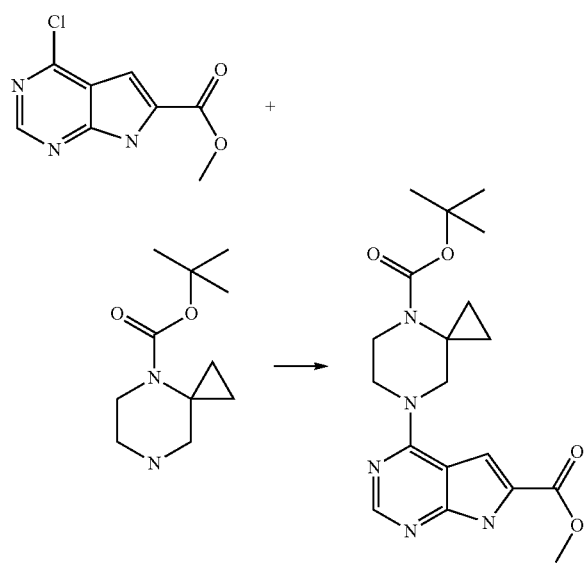

Prepared in a way similar to intermediate 1.

1H NMR (300 MHz, DMSO) δ=12.56 (s, 1H), 8.21 (s, 1H), 7.38 (s, 1H), 3.96 (m, 2H), 3.85 (s, 3H), 3.78 (m, 2H), 3.59 (m, 2H), 1.43 (s, 9H), 0.90 (br, 4H).

Intermediate 8

4-(4,7-Diaza-spiro[2.5]oct-7-yl)-7H-pyrrolo[2,3-d]pyrimidine-6-carboxylic acid methyl ester

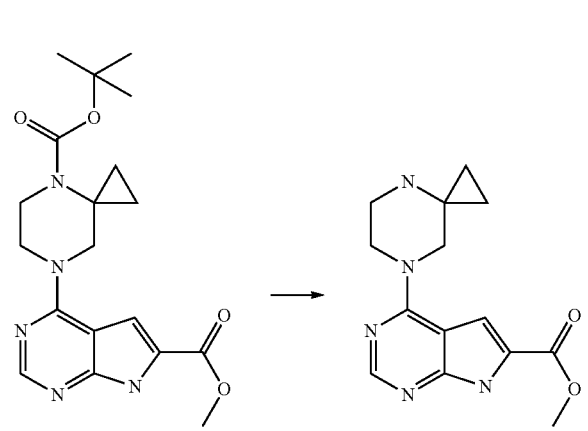 [SMILES: COC(=O)c1cc2c(N3CCN(C(=O)OC(C)(C)C)C4(CC4)C3)ncnc2[nH]1 ; COC(=O)c1cc2c(N3CCNC4(CC4)C3)ncnc2[nH]1]

Prepared in a way similar to intermediate 2, using intermediate 7, instead of intermediate 1.

1H NMR (300 MHz, DMSO) δ=8.22 (s, 1H), 7.30 (s, 1H), 3.89 (br, 2H), 3.84 (s, 3H), 3.76 (br, 2H), 2.88 (br, 2H), 0.50 (br, 4H).

Intermediate 9

7-(2-Amino-7H-pyrrolo[2,3-d]pyrimidin-4-yl)-4,7-diaza-spiro[2.5]octane-4-carboxylic acid tert-butyl ester

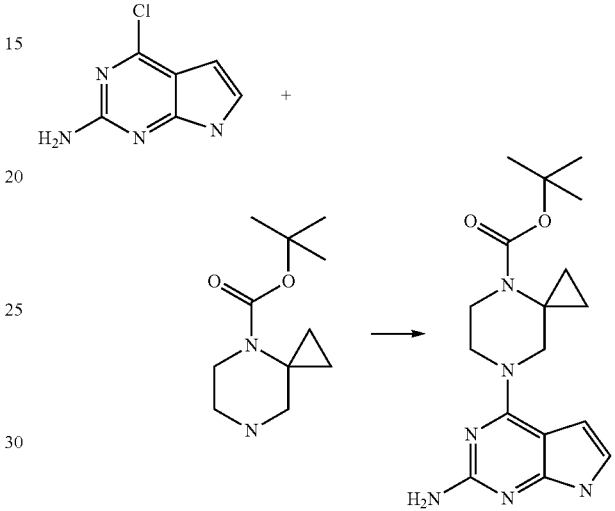

Prepared in a way similar to intermediate 1.

1H NMR (600 MHz, DMSO) δ=11.62 (s, 1H), 6.89 (br, 3H), 6.56 (m, 1H), 3.97 (m, 2H), 3.76 (m, 2H), 3.59 (m, 2H), 1.43 (s, 9H), 0.89 (m, 4H).

Intermediate 10

4-(4,7-Diaza-spiro[2.5]oct-7-yl)-7H-pyrrolo[2,3-d]pyrimidin-2-ylamine

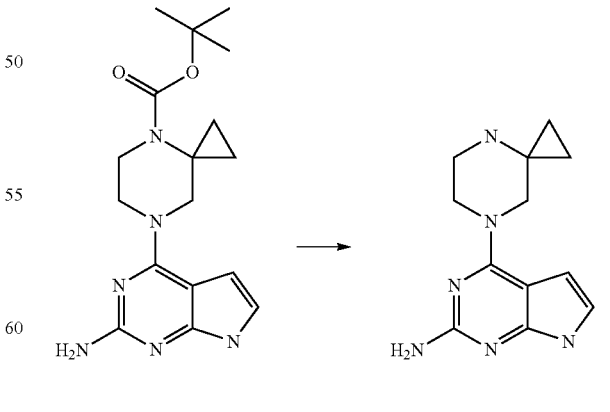

Prepared in a way similar to intermediate 2, using intermediate 9, instead of intermediate 1.

1H NMR (300 MHz, DMSO) δ=12.08 (s, 1H), 9.50 (br, 2H), 7.03 (m, 1H), 6.71 (m, 1H), 4.05 (br, 6H), 0.99 (br, 4H).

Intermediate 11

7-(5-Chloro-7H-pyrrolo[2,3-d]pyrimidin-4-yl)-4,7-diaza-spiro[2.5]octane-4-carboxylic acid tert-butyl ester

Intermediate 13

7-(5-Methyl-7H-pyrrolo[2,3-d]pyrimidin-4-yl)-4,7-diaza-spiro[2.5]octane-4-carboxylic acid tert-butyl ester

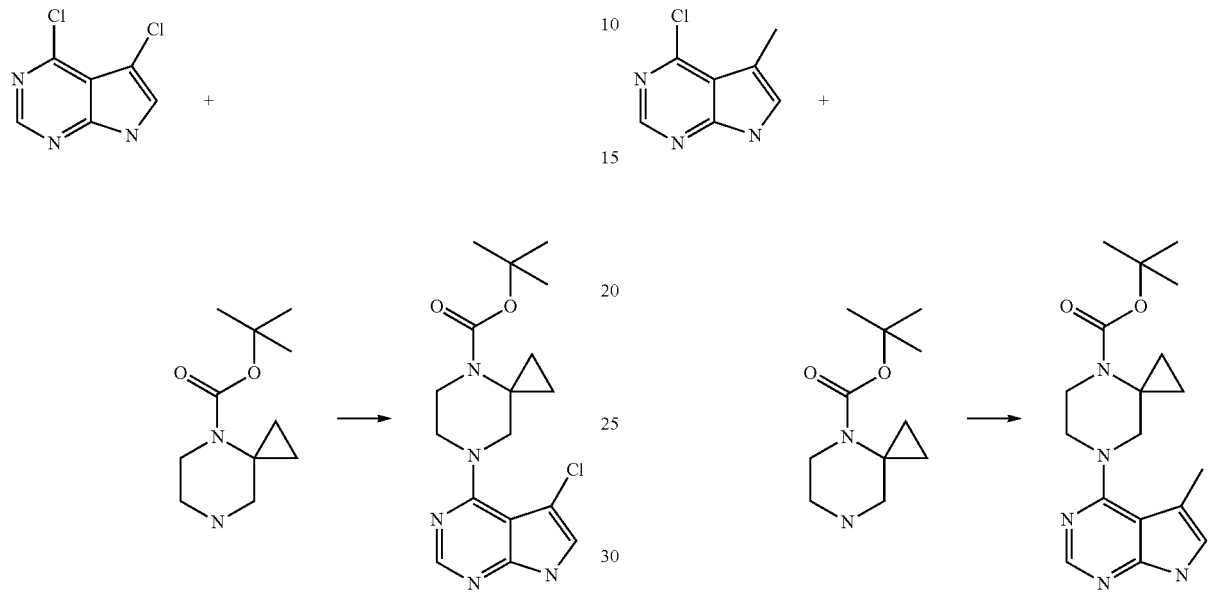

Prepared in a way similar to intermediate 1.

1H NMR (300 MHz, DMSO) δ=12.17 (s, 1H), 8.25 (s, 1H), 7.48 (s, 1H), 3.64 (br, 4H), 3.49 (br, 2H), 1.42 (s, 9H), 0.84 (br, 4H).

Prepared in a way similar to intermediate 1.

1H NMR (300 MHz, DMSO) δ=11.52 (s, 1H), 8.21 (s, 1H), 7.05 (s, 1H), 3.52 (br, 6H), 2.31 (s, 3H), 1.42 (s, 9H), 0.82 (br, 4H).

Intermediate 12

5-Chloro-4-(4,7-diaza-spiro[2.5]oct-7-yl)-7H-pyrrolo[2,3-d]pyrimidine

Intermediate 14

4-(4,7-Diaza-spiro[2.5]oct-7-yl)-5-methyl-7H-pyrrolo[2,3-d]pyrimidine

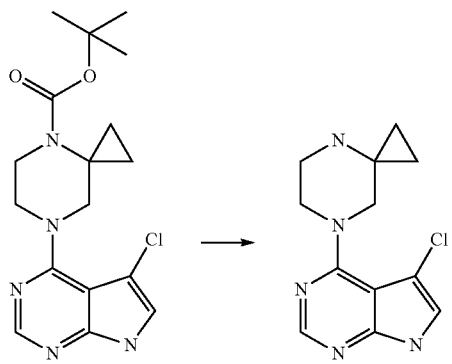 [SMILES: CC(C)(C)OC(=O)N1CCN(c2ncnc3[nH]cc(Cl)c23)CC12CC2 ; Clc1c[nH]c2ncnc(N3CCNC4(CC4)C3)c12]

Prepared in a way similar to intermediate 2, using intermediate 11, instead of intermediate 1.

1H NMR (300 MHz, DMSO) δ=12.35 (br, 1H), 9.38 (br, 1H), 8.35 (s, 1H), 7.52 (s, 1H), 3.89 (br, 4H), 3.45 (br, 2H), 0.99 (br, 4H).

Prepared in a way similar to intermediate 2, using intermediate 13, instead of intermediate 1.

1H NMR (300 MHz, DMSO) δ=12.18 (s, 1H), 9.53 (br, 1H), 8.39 (s, 1H), 7.24 (s, 1H), 3.91 (br, 2H), 3.77 (br, 2H), 3.46 (br, 2H), 2.40 (s, 3H), 1.01 (br, 4H).

Intermediate 15

4-(4,7-Diaza-spiro[2.5]oct-7-yl)-1H-pyrrolo[2,3-b]pyridine

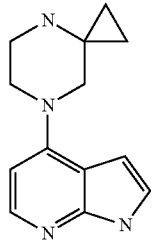 [SMILES: c1cc(N2CCNC3(CC3)C2)c2cc[nH]c2n1]

Prepared in a sequence similar to the sequence described for intermediates 1 and 2, starting from 4-chloro-1H-pyrrolo[2,3-b]pyridine and 4,7-diaza-spiro[2.5]octane-4-carboxylic acid tert-butyl ester.

1H NMR (300 MHz, DMSO) δ=11.34 (s, 1H), 7.92 (m, 1H), 7.19 (m, 1H), 6.36 (br, 2H), 3.19 (br, 2H), 2.94 (m, 2H), 2.50 (m, 2H), 0.53 (br, 4H).

Intermediate 16

4-(4,7-Diaza-spiro[2.5]oct-7-yl)-5-methoxy-1H-pyrrolo[2,3-b]pyridine

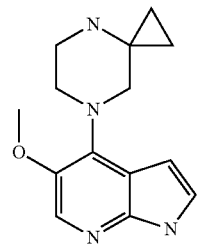 [SMILES: COc1cnc2[nH]ccc2c1N1CCNC2(CC2)C1]

Prepared in a sequence similar to the sequence described for intermediates 1 and 2, starting from 4-chloro-5-methoxy-1H-pyrrolo[2,3-b]pyridine and 4,7-diaza-spiro[2.5]octane-4-carboxylic acid tert-butyl ester.

1H NMR (300 MHz, DMSO) δ=11.24 (s, 1H), 7.84 (s, 1H), 7.21 (m, 2H), 6.48 (m, 2H), 3.80 (s, 3H), 3.43 (br, 2H), 3.25 (br, 2H), 2.91 (m, 2H), 0.49 (br, 4H).

Intermediate 17

4-(6,9-Diaza-spiro[4.5]dec-9-yl)-7H-pyrrolo[2,3-d]pyrimidine

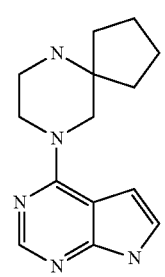

Prepared in a sequence similar to the sequence described for intermediates 1 and 2, starting from 4-chloro-7H-pyrrolo[2,3-d]pyrimidine and 6,9-diaza-spiro[4.5]decane-6-carboxylic acid tert-butyl ester.

1H NMR (300 MHz, DMSO) δ=11.66 (s, 1H), 8.10 (s, 1H), 7.15 (d, J=3.5, 1H), 6.53 (d, J=3.6, 1H), 3.78 (m, 2H), 3.68 (br, 2H), 2.82 (m, 2H), 1.54 (br, 8H).

Intermediate 20

4-(4-Benzyl-4,7-diaza-spiro[2.5]oct-7-yl)-7H-pyrrolo[2,3-d]pyrimidine

To a stirred solution of 4-chloro-7H-pyrrolo[2,3-d]pyrimidine (29.2 g, 190.98 mmol) in water, was added intermediate 19 (50 g, 210 mmol) and K$_2$CO$_3$ (79 g, 572.9 mmol) and the resultant reaction mixture was heated to 100° C. for 16 h. The reaction mixture was cooled to RT and filtered. The obtained solid was washed with diethyl ether to afford the title compound. (50 g, 80%).

$^1$H NMR (300 MHz, DMSO) δ=11.70 (br, 1H), 8.10 (s, 1H), 7.32 (m, 5H), 7.14 (d, 1H), 6.58 (d, 1H), 3.95 (br, 4H), 3.80 (br, 2H), 2.82 (m, 2H), 0.64 (m, 4H)

Intermediate 19

4-benzyl-4,7-diaza-spiro[2.5]octane

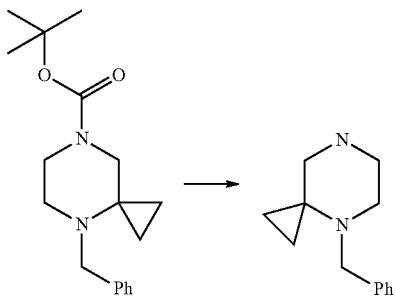 [SMILES: CC(C)(C)OC(=O)N1CCN(Cc2ccccc2)C2(CC2)C1 ; c1ccc(CN2CCNCC23CC3)cc1]

To a stirred solution of intermediate 18 (96 g) in THF (500 mL) was added 4N HCl in dioxane (200 mL) and the resultant reaction mixture was stirred at RT for 16 h. The reaction mixture was concentrated under reduced pressure. The crude was washed with n-pentane to afford title compound as a solid (75 g, 100%).

$^1$H NMR (300 MHz, DMSO) δ=7.4 (br, 5H), 4.00-4.40 (br, 2H), 3.00-3.80 (br, 6H), 0.81 (br, 4H)

Intermediate 18

4-benzyl-4,7-diaza-spiro[2.5]octane-7-carboxylic acid tert-butyl ester

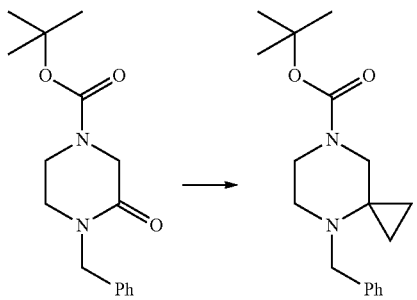 [SMILES: CC(C)(C)OC(=O)N1CCN(Cc2ccccc2)C(=O)C1 ; CC(C)(C)OC(=O)N1CCN(Cc2ccccc2)C2(CC2)C1]

To EtMgBr (344 mL) in THF cooled to −78° C. was added Ti(O$^i$Pr)$_4$ (39 g, 137.93 mmol), followed by commercially available 4-benzyl-3-oxo-piperazine-1-carboxylic acid tert-butyl ester (40 g, 137.93 mmol) and the resultant reaction mixture was heated to reflux for 1 h. After cooling the reaction mixture to 5° C., another portion of EtMgBr (344 ml) and Ti(O$^i$Pr)$_4$ (39 g, 137.93 mmol) was added. The mixture was stirred for 16 h at RT. The reaction mixture was quenched with NH$_4$Cl solution and stirred for 15 min and filtered through a celite bed and washed with EtOAc. The aqueous layer was again extracted with EtOAc (3×). The combined EtOAc layers were washed with water and dried over Na$_2$SO$_4$ and concentrated under reduced pressure. Purification by column chromatography to afforded the title compound as a solid (24 g, 58%).

$^1$H NMR (300 MHz, DMSO) δ=7.20 (m, 5H), 3.80 (s, 2H), 3.40 (m, 2H), 3.22 (m, 2H), 2.63 (m, 2H), 1.38 (s, 9H), 0.58 (br, 4H)

Intermediate 21

2-carboxy-thiophene-5-chlorosulfonate

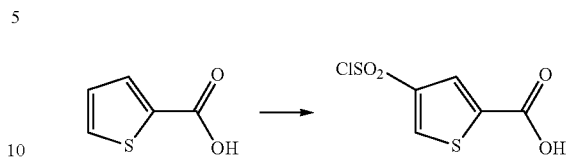

A mixture of chlorosulfonic (5 ml) and thiophene-2-carboxylic acid (1 g) was heated to 120° C. for 5 h. After cooling the mixture was added dropwise to ice and the white precipitate formed was washed with cold water and dried in vacuo to give the intermediate 21.

Intermediate 22

2-carboxy-thiophene-5-aminosulfonate

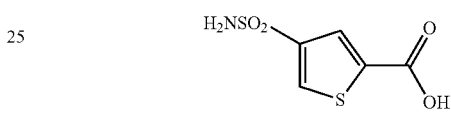

2-carboxy-thiophene-5-chlorosulfonate was added slowly to a cold solution of 2N ammonium hydroxide to afford intermediate 22 after filteration and drying in vacuo (300 mg)

$^1$H NMR (300 MHz, DMSO) δ 8.30 (s, 1H), 7.80 (s, 1H), 7.49 (s, 2H).

Intermediate 23

2-carboxy-thiophene-5-methylaminosulfonate

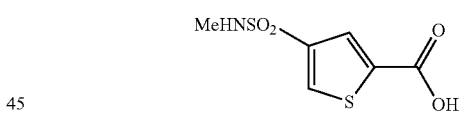

2-carboxy-thiophene-5-chlorosulfonate was added slowly to a cold aqueous solution of methylamine to afford intermediate 23 (100 mg).

$^1$H NMR (300 MHz, DMSO) δ 8.40 (s, 1H), 7.60 (s, 1H), 7.40-7.55 (m, 1H), 2.49 (d, 3H)

Intermediate 24

2-carboxy-5-methyl thiophene-5-aminosulfonate

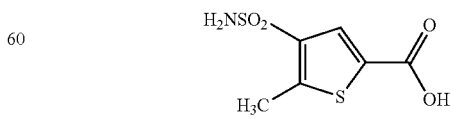

Intermediate 24 was prepared from 5-methylthiophene carboxylic acid using a similar method to that described for intermediate 22.

$^1$H NMR (300 MHz, DMSO) δ 7.80 (s, 1H), 7.50 (s, 2H), 2.70 (s, 3H)

Intermediate 25

2-carboxy-5-methyl thiophene-5-methylaminosulfonate

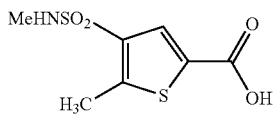

Intermediate 25 was prepared from 5-methylthiophene carboxylic acid using a similar method to that described for intermediate 23.

$^1$H NMR (300 MHz, DMSO) δ 7.70 (s, 1H), 7.50-7.60 (m, 1H), 2.65 (s, 3H), 2.49 (d, 3H)

Intermediate 26

2-carboxy-3-methyl thiophene-4 and -5-methylaminosulfonate

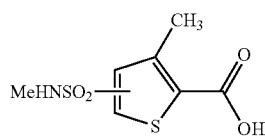

Intermediate F was prepared from 3-methylthiophene carboxylic acid using a similar method to that described for intermediate 23 to give a mixture of the 5 and -6 sulfonamide regioisomers which was used without further purification.

Intermediate 27

4-Acetyl-benzenesulfonamide

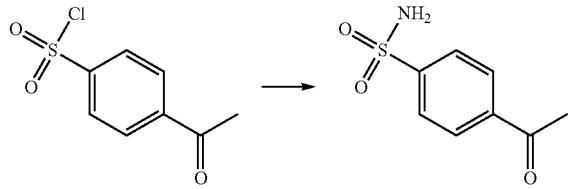

Commercially available 4-acetyl-benzenesulfonyl chloride (1.25 g, 5.7 mmol) was dissolved in THF (20 mL) and slowly added to a stirred solution of 25% NH$_3$ in H$_2$O (50 mL). The reaction mixture was stirred at it for 1 h. The reaction mixture was acidified using conc. HCl to pH=2. The white precipitation was collected by filtration, washed with H$_2$O and dried in vacuo affording 975 mg of the title compound as off-white crystals.

$^1$H NMR (300 MHz, DMSO) δ 8.12 (d, J=8.5 Hz, 2H), 7.95 (d, J=8.5 Hz, 2H), 7.53 (s, 2H), 2.63 (s, 3H).

Intermediate 28

Oxo-(4-sulfamoyl-phenyl)-acetic acid

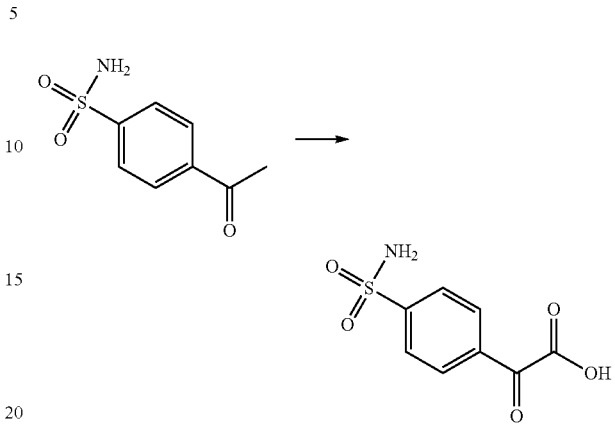

4-Acetyl-benzenesulfonamide (460 mg, 2.31 mmol) was dissolved in dry pyridine (12 mL). This solution was heated to 90° C. before being added SeO$_2$ (384 mg, 3.46 mmol). The reaction mixture was stirred at 90° C. for 3 h, cooled to rt, filtered and concentrated in vacuo. The obtained residue was added H2O (25 mL) and washed with Et$_2$O (2×25 mL). The aqueous phase was cooled to 0° C. before being acidified to pH=2 using conc. HCl. Brine (25 mL) was added and the obtained solution was extracted with Et$_2$O (6×25 mL). The combined organic phases were dried (Na$_2$SO$_4$), filtered and concentrated in vacuo. The obtained was purified by either Prep HPLC or by flash chromatography on silica using a gradient of Heptane:EtOAc (1:1) to EtOAc:AcOH (99:1) as eluent affording the title compound as off-white crystals.

$^1$H NMR (300 MHz, DMSO) δ 8.18-8.09 (m, 2H), 8.07-7.97 (m, 2H), 7.62 (s, 2H).

Intermediate 29

2-Methoxy-4-sulfamoyl-benzoic acid

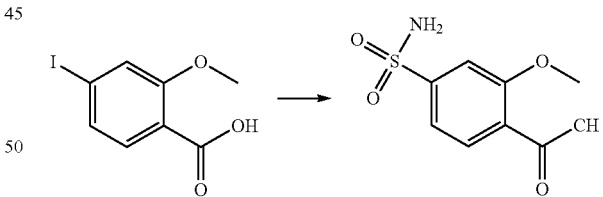

4-Iodo-2-methoxy-benzoic acid (556 mg, 2 mmol) was dissolved in dry THF (10 mL), cooled to 0° C. and dropwise added isopropylmagnesium chloride (2M in THF, 2 mmol, 1 mL). The reaction mixture was stirred at 0° C. for 10 min before being cooled to −78° C. and added t-BuLi (1.7M in heptanes, 4 mmol, 2.35 mL) dropwise. The reaction mixture was stirred at −78° C. for 30 min. SO$_2$ was slowly added/condensed into the reaction mixture over a period of 10 min. The reaction mixture was allowed to reach rt and the precipitated lithium sulfinate was collected by filtration affording an orange compound (650 mg). The obtained lithium sulfinate was suspended in dry DCM (6 mL) and added N-chlorosuccinimide. The reaction mixture was stirred at rt for 1 h before being quenched into a stirred solution of 25% NH$_3$ in H$_2$O.

The obtained mixture was extracted with EtOAc (2×10 mL). The aqueous layer was acidified to pH=2 using conc. HCl followed by extraction with EtOAc (3×50 mL). The combined organic phases were dried (Na₂SO₄), filtered and concentrated in vacuo. The obtained oil was crystallised in MeOH:heptane. Solvent removed in vacuo and the obtained compound was suspended in EtOAc, collected by filtration and washed with EtOAc affording the title compound as light yellow crystals (131 mg).

¹H NMR (600 MHz, MeOD) δ 7.88 (d, J=8.0 Hz, 1H), 7.60 (d, J=1.4 Hz, 1H), 7.51 (dd, J=8.0, 1.6 Hz, 1H), 3.96 (s, 3H).

Intermediate 30

3-Methoxy-4-sulfamoyl-benzoic acid

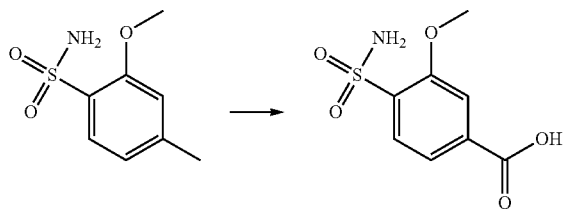

2-Methoxy-4-methyl-benzenesulfonamide (201 mg, 1 mmol) was dissolved in H₂O (10 mL). NaHCO₃ (67 mg, 0.8 mmol) and KMnO₄ (653 mg, 4.13 mmol) was added. The reaction mixture was stirred at reflux for 4 h. The reaction mixture was cooled to rt and filtered. the filtrate was acidified to pH=2 using conc. HCl. The precipitate was collected by filtration, washed with H₂O affording the title compound as a white powder (117 mg).

¹H NMR (300 MHz, DMSO) δ 13.40 (br, 1H), 7.85 (d, J=7.8 Hz, 1H), 7.69-7.59 (m, 2H), 7.23 (s, 2H), 3.97 (s, 3H).

Intermediate 31

2-Methyl-4-sulfamoyl-benzoic acid

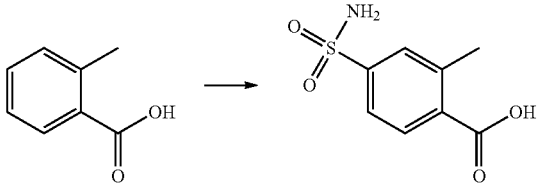

2-Methyl-benzoic acid (1.36 g, 10 mmol) was dissolved in CHCl₃ (8 mL), added ClSO₃H (5.83 g, 3.32 mL, 50 mmol) and stirred at 60° C. for 22 h. The reaction mixture was cooled to rt and then added carefully to a stirred solution of 25% NH₃ in H₂O (75 mL). The obtained solution was acidified to pH=2 using conc. HCl. The precipitate was collected by filtration, washed with H₂O affording the title compound as a white powder (1.37 g).

¹H NMR (600 MHz, DMSO) δ 13.26 (br, 1H), 8.27 (d, J=2.1 Hz, 1H), 7.85 (dd, J=8.0, 2.1 Hz, 1H), 7.51 (d, J=18.1 Hz, 1H), 7.42 (s, 2H), 2.59 (s, 3H).

Intermediate 32

3-Methyl-4-sulfamoyl-benzoic acid

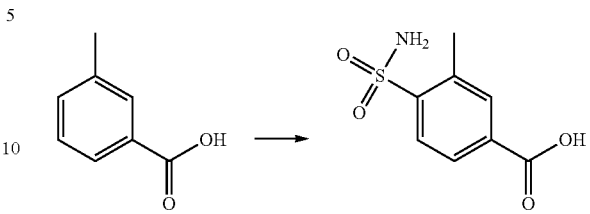

3-Methyl-benzoic acid (1.36 g, 10 mmol) was dissolved in CHCl₃ (8 mL), added ClSO₃H (5.83 g, 3.32 mL, 50 mmol) and stirred at 60° C. for 3 h. The reaction mixture was cooled to rt and then added carefully to a stirred solution of 25% NH₃ in H₂O (75 mL). The obtained solution was acidified to pH=2 using conc. HCl. and extracted with EtOAc (3×50 mL). The combined organic phases were dried (Na₂SO₄), filtered and concentrated in vacuo. The obtained was purified by flash chromatography on silica using a gradient of Heptane:AcOH (99:1) to EtOAc:AcOH (99:1) as eluent affording the title compound as off-white compound.

¹H NMR (600 MHz, DMSO) δ 13.34 (br, 1H), 8.20 (s, 1H), 7.96 (s, 1H), 7.86 (s, 1H), 7.44 (s, 2H), 2.45 (s, 3H).

EXAMPLES

Example 1

[3-(7H-Pyrrolo[2,3-d]pyrimidin-4-yl)-3,8-diazabicyclo[3.2.1]oct-8-yl]-(4-trifluoromethylphenyl)methanone

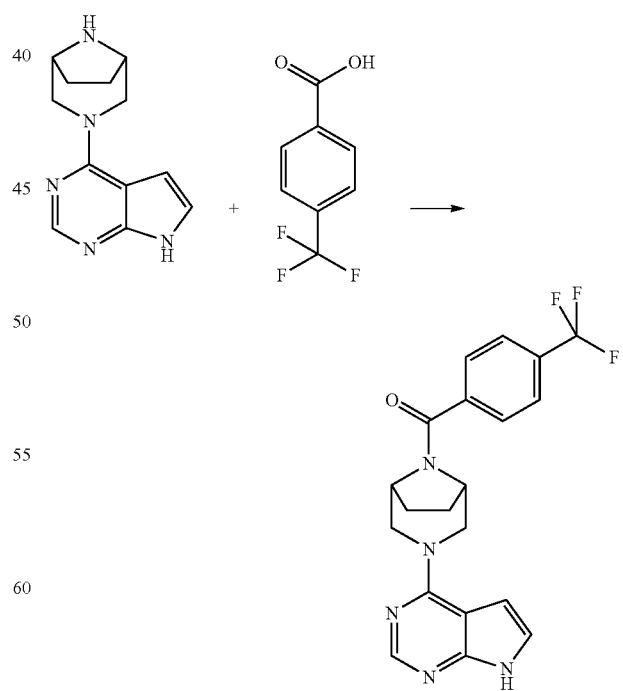

4-(3,8-Diaza-bicyclo[3.2.1]oct-3-yl)-7H-pyrrolo[2,3-d]pyrimidine (intermediate 4) (0.05 mmol) was dissolved in dry DMF (0.3 mL). Triethylamine (0.18 mmol) and HATU (0.09 mmol) was added followed by 4-trifluoromethylbenzoic acid (0.07 mmol). The reaction mixture was left at it for 16 hours. The pure compounds were obtained by standard preparative HPLC purification of the reaction mixture.

$^1$H NMR (300 MHz, DMSO) δ=11.84 (s, 1H), 8.16 (d, J=14.8, 1H), 7.82 (dd, J=8.2, 24.8, 4H), 7.29-7.16 (m, 1H), 6.67 (dd, J=1.7, 3.5, 1H), 4.86 (m, 1H), 4.52 (m, 2H), 4.12 (m, 1H), 3.38 (m, 2H), 1.96 (m, 2H), 1.74 (m, 2H).

Using this procedure the following compounds were obtained:

Example 30

1-[3-(7H-Pyrrolo[2,3-d]pyrimidin-4-yl)-3,8-diazabicyclo[3.2.1]oct-8-yl]propan-1-one $^1$H NMR (300 MHz, DMSO) δ=11.70 (s, 1H), 8.13 (s, 1H), 7.18 (dd, J=2.5, 3.5, 1H), 6.61 (dd, J=1.8, 3.6, 1H), 4.66 (m, 1H), 4.57-4.36 (m, 3H), 3.18 (m, 2H), 2.44-2.25 (m, 2H), 1.99-1.59 (m, 4H), 1.04 (t, J=7.4, 3H).

Example 31

4-[3-(7H-Pyrrolo[2,3-d]pyrimidin-4-yl)-3,8-diazabicyclo[3.2.1]octane-8-carbonyl]benzonitrile $^1$H NMR (300 MHz, DMSO) δ=11.73 (s, 1H), 8.14 (s, 1H), 8.03-7.88 (m, 2H), 7.81-7.64 (m, 2H), 7.25-7.12 (m, 1H), 6.62 (dd, J=1.7, 3.6, 1H), 4.84 (m, 1H), 4.69-4.35 (m, 2H), 4.07 (m, 1H), 3.42 (m, 2H), 1.82 (m, 4H).

Example 32

2-Phenyl-1-[3-(7H-pyrrolo[2,3-d]pyrimidin-4-yl)-3,8-diazabicyclo[3.2.1]oct-8-yl]ethanone $^1$H NMR (300 MHz, DMSO) δ=11.69 (s, 1H), 8.15 (s, 1H), 7.40-7.11 (m, 6H), 6.59 (d, J=2.1, 1H), 4.55 (dd, J=19.4, 57.6, 4H), 3.76 (d, J=6.6, 2H), 3.18 (d, J=11.0, 1H), 3.06 (d, J=11.5, 1H), 1.91-1.56 (m, 4H).

Example 33

Phenyl-[3-(7H-pyrrolo[2,3-d]pyrimidin-4-yl)-3,8-diazabicyclo[3.2.1]oct-8-yl]methanone $^1$H NMR (300 MHz, DMSO) δ=11.70 (s, 1H), 8.16 (s, 1H), 7.67-7.41 (m, 5H), 7.31-7.05 (m, 1H), 6.64 (d, J=2.2, 1H), 5.08-3.99 (m, 4H), 3.48-3.46 (m, 2H), 1.90 (s, 2H), 1.71 (m, 2H).

Example 34

N-{2-Oxo-2-[3-(7H-pyrrolo[2,3-d]pyrimidin-4-yl)-3,8-diaza-bicyclo[3.2.1]oct-8-yl]-ethyl}acetamide $^1$H NMR (300 MHz, DMSO) δ=11.72 (s, 1H), 8.14 (s, 1H), 8.07 (s, 1H), 7.29-7.07 (m, 1H), 6.62 (dd, J=1.9, 3.6, 1H), 4.62-4.28 (m, 4H), 4.06-3.92 (m, 2H), 3.18 (m, 1H), 1.95 (m, 1H), 1.87 (s, 3H), 1.85-1.54 (m, 4H).

Example 38

2-Cyclopentyl-1-[3-(7H-pyrrolo[2,3-d]pyrimidin-4-yl)-3,8-diazabicyclo[3.2.1]oct-8-yl]ethanone $^1$H NMR (300 MHz, DMSO) δ=11.71 (s, 1H), 8.13 (s, 1H), 7.18 (m, 1H), 6.61 (dd, J=1.6, 3.6, 1H), 4.68 (d, J=6.0, 1H), 4.48 (t, J=11.2, 3H), 3.21 (dd, J=12.1, 17.8, 2H), 2.44-2.32 (m, 2H), 2.19 (m, 1H), 1.98-1.38 (m, 10H), 1.15 (s, 2H).

Example 40

3,3,3-Trifluoro-1-[3-(7H-pyrrolo[2,3-d]pyrimidin-4-yl)-3,8-diaza-bicyclo[3.2.1]oct-8-yl]propan-1-one $^1$H NMR (300 MHz, DMSO) δ=11.72 (s, 1H), 8.24-8.03 (m, 1H), 7.28-7.04 (m, 1H), 6.60 (dd, J=1.7, 3.6, 1H), 4.70 (s, 1H), 4.49 (m, 2H), 3.82-3.16 (m, 5H), 2.06-1.59 (m, 4H).

Example 53

3-Oxo-3-[3-(7H-pyrrolo[2,3-d]pyrimidin-4-yl)-3,8-diazabicyclo[3.2.1]oct-8-yl]propionitrile $^1$H NMR (300 MHz, DMSO) δ=11.71 (s, 1H), 8.14 (s, 1H), 7.19 (d, J=3.6, 1H), 6.60 (d, J=3.6, 1H), 4.68 (m, 1H), 4.48 (m, 2H), 4.36 (m, 1H), 4.08 (m, 2H), 3.28 (m, 2H), 1.69 (m, 4H).

Example 57

Pyridin-3-yl-[3-(7H-pyrrolo[2,3-d]pyrimidin-4-yl)-3,8-diazabicyclo[3.2.1]oct-8-yl]methanone $^1$H NMR (300 MHz, DMSO) δ=11.72 (s, 1H), 8.76 (s, 1H), 8.71 (m, 4.8, 1H), 8.44 (s, 1H), 8.14 (s, 1H), 8.04-7.93 (m, 1H), 7.52 (m, 1H), 7.22-7.13 (m, 1H), 6.69-6.58 (m, 1H), 4.84 (m, 1H), 4.51 (s, 2H), 4.15 (s, 1H), 3.48-3.45 (m, 2H) 1.92 (br s, 2H), 1.73 (br s, 2H).

Example 71

5-[3-(7H-Pyrrolo[2,3-d]pyrimidin-4-yl)-3,8-diazabicyclo[3.2.1]octane-8-carbonyl]-thiophene-2-carbonitrile 1H NMR (300 MHz, DMSO) δ=11.69 (s, 1H), 8.14 (s, 1H), 7.97 (m, 1H), 7.71 (m, 1H), 7.19 (m, 1H), 6.64 (m, 1H), 4.76 (br, 1H), 4.58 (br, 2H), 3.72 (br, 1H), 3.47 (br, 2H), 1.92 (br, 2H), 1.73 (br, 2H).

Example 72

(3-Methyl-pyrazin-2-yl)-[3-(7H-pyrrolo[2,3-d]pyrimidin-4-yl)-3,8-diaza-bicyclo[3.2.1]oct-8-yl]-methanone 1H NMR (300 MHz, DMSO) δ=11.50 (br, 1H), 8.65 (m, 1H), 8.53 (m, 1H), 8.15 (m, 1H), 7.19 (m, 1H), 6.63 (m, 1H), 4.92 (br, 1H), 4.64 (br, 1H), 4.43 (br, 1H), 3.94 (br, 1H), 3.81 (s, 3H), 3.33 (br, 2H), 1.93 (m, 2H), 1.75 (m, 2H).

Example 73

(6-Methyl-pyrazin-2-yl)-[3-(7H-pyrrolo[2,3-d]pyrimidin-4-yl)-3,8-diaza-bicyclo[3.2.1]oct-8-yl]-methanone 1H NMR (300 MHz, DMSO) δ=11.69 (s, 1H), 8.77 (s, 1H), 8.68 (br, 1H), 8.14 (br, 1H), 7.18 (br, 1H), 6.63 (br, 1H), 4.89 (br, 1H), 4.71 (br, 1H), 4.56 (br, 2H), 3.57 (br, 2H), 2.58 (s, 3H), 1.94 (br, 2H), 1.74 (br, 2H).

Example 74

(5-Methyl-pyrazin-2-yl)-[3-(7H-pyrrolo[2,3-d]pyrimidin-4-yl)-3,8-diaza-bicyclo[3.2.1]oct-8-yl]-methanone 1H NMR (300 MHz, DMSO) δ=11.70 (s, 1H), 8.88 (br, 1H), 8.61 (br, 1H), 8.14 (br, 1H), 7.18 (d, J=3.5, 1H), 6.63 (d, J=3.6, 1H), 4.89 (br, 1H), 4.81 (br, 1H), 4.62 (br, 1H), 4.51 (r, 1H), 3.42 (br, 2H), 2.59 (1, 3H), 1.95 (br, 2H), 1.75 (br, 2H).

Example 75

Benzo[b]thiophen-2-yl-[9-(7H-pyrrolo[2,3-d]pyrimidin-4-yl)-6,9-diaza-spiro[4.5]dec-6-yl]-methanone Using Intermediate 17

1H NMR (300 MHz, DMSO) δ=12.02 (s, 1H), 8.23 (s, 1H), 8.04 (m, 1H), 7.94 (m, 1H), 7.81 (s, 1H), 7.47 (m, 2H), 7.26 (m, 1H), 6.72 (m, 1H), 4.23 (br, 2H), 4.13 (br, 2H), 4.00 (br, 2H), 2.35 (br, 2H), 1.95 (br, 2H), 1.59 (br, 4H).

Example 108

(5-Methoxy-thiophen-3-yl)-[3-(7H-pyrrolo[2,3-d]pyrimidin-4-yl)-3,8-diaza-bicyclo[3.2.1]oct-8-yl]-methanone 1H NMR (300 MHz, DMSO) δ=11.71 (s, 1H), 8.14 (s, 1H), 7.17 (m, 2H), 6.65 (m, 1H), 6.50 (m, 1H), 4.54 (br, 2H), 3.89 (s, 3H), 3.01 (br, 2H), 1.75 (br, 6H).

Example 109

1-[3-(7H-Pyrrolo[2,3-d]pyrimidin-4-yl)-3,8-diaza-bicyclo[3.2.1]oct-8-yl]-2-thiophen-2-yl-ethanone 1H NMR (300 MHz, DMSO) δ=11.70 (s, 1H), 8.13 (s, 1H), 7.38 (m, 1H), 7.18 (m, 1H), 6.96 (m, 2H), 6.60 (m, 1H), 4.65 (br, 2H), 4.47 (br, 2H), 4.02 (br, 2H), 3.15 (br, 2H), 1.78 (br, 4H).

Example 110

(5-Fluoro-6-methyl-1H-indol-2-yl)-[3-(7H-pyrrolo[2,3-d]pyrimidin-4-yl)-3,8-diaza-bicyclo[3.2.1]oct-8-yl]-methanone 1H NMR (300 MHz, DMSO) δ=11.72 (br, 1H), 11.60 (br, 1H), 8.16 (s, 1H), 7.31 (m, 2H), 7.20 (d, J=3.4, 1H), 6.98 (s, 1H), 6.68 (d, J=3.4, 1H), 4.95 (br, 2H), 4.63 (br, 2H), 3.42 (br, 2H), 2.33 (s, 3H), 1.90 (br, 2H), 1.76 (br, 2H).

Example 112

1-{4-[3-(7H-Pyrrolo[2,3-d]pyrimidin-4-yl)-3,8-diaza-bicyclo[3.2.1]octane-8-carbonyl]-thiophen-2-yl}-ethanone 1H NMR (300 MHz, DMSO) δ=11.71 (s, 1H), 8.36 (d, J=1.2, 1H), 8.15 (s, 1H), 8.09 (d, J=1.2, 1H), 7.20 (m, 1H), 6.64 (m, 1H), 4.81 (br, 1H), 4.54 (br, 3H), 3.40 (br, 2H), 2.59 (s, 3H), 1.91 (br, 2H), 1.72 (br, 2H).

Example 127

2-Chloro-5-{2-oxo-2-[3-(7H-pyrrolo[2,3-d]pyrimidin-4-yl)-3,8-diaza-bicyclo[3.2.1]oct-8-yl]-ethoxy}-benzenesulfonamide 1H NMR (300 MHz, DMSO) δ=12.04 (s, 1H), 8.24 (s, 1H), 7.54 (br, 4H), 7.29 (m, 1H), 7.19 (m, 1H), 6.73 (m, 1H), 4.99 (br, 2H), 4.70 (br, 1H), 4.54 (br, 3H), 2.04 (br, 2H), 1.77 (br, 4H).

Example 128

4-{2-Oxo-2-[3-(7H-pyrrolo[2,3-d]pyrimidin-4-yl)-3,8-diaza-bicyclo[3.2.1]oct-8-yl]-acetyl}-benzonitrile 1H NMR (300 MHz, DMSO) δ=11.74 (s, 1H), 8.11 (br, 5H), 7.20 (m, 1H), 6.62 (m, 1H), 4.87 (br, 1H), 4.66 (br, 1H), 4.53 (br, 1H), 4.25 (br, 1H), 3.42 (br, 2H), 1.96 (br, 2H), 1.77 (br, 2H).

Example 129

2-[3-(7H-Pyrrolo[2,3-d]pyrimidin-4-yl)-3,8-diaza-bicyclo[3.2.1]octane-8-carbonyl]-1H-indole-5-carbonitrile 1H NMR (300 MHz, DMSO) δ=12.22 (s, 1H), 11.73 (s, 1H), 8.20 (m, 1H), 8.16 (s, 1H), 7.56 (m, 2H), 7.20 (m, 2H), 6.68 (m, 1H), 4.95 (br, 2H), 4.64 (br, 2H), 3.45 (br, 2H), 1.94 (br, 2H), 1.77 (br, 2H).

Example 130

(5-Methanesulfonyl-1H-indol-2-yl)-[3-(7H-pyrrolo[2,3-d]pyrimidin-4-yl)-3,8-diaza-bicyclo[3.2.1]oct-8-yl]-methanone 1H NMR (300 MHz, DMSO) δ=12.22 (s, 1H), 11.73 (s, 1H), 8.27 (m, 1H), 8.17 (s, 1H), 7.73 (m, 1H), 7.65 (m, 1H), 7.28 (br, 1H), 7.21 (m, 1H), 6.67 (m, 1H), 4.95 (br, 2H), 4.64 (br, 2H), 3.42 (s, 3H), 3.18 (br, 2H), 1.94 (br, 2H), 1.78 (br, 2H).

Example 131

(3-Fluoro-4-methanesulfonyl-phenyl)-[3-(7H-pyrrolo[2,3-d]pyrimidin-4-yl)-3,8-diaza-bicyclo[3.2.1]oct-8-yl]-methanone 1H NMR (300 MHz, DMSO) δ=11.72 (br, 1H), 8.16 (s, 1H), 7.42 (m, 2H), 7.20 (m, 1H), 7.06 (m, 1H), 6.68 (m, 1H), 4.95 (br, 2H), 4.63 (br, 2H), 3.47 (br, 2H), 2.07 (s, 3H), 1.91 (br, 2H), 1.76 (br, 2H).

Example 132

Bicyclo[4.2.0]octa-1(6),2,4-trien-7-yl-[3-(7H-pyrrolo[2,3-d]pyrimidin-4-yl)-3,8-diaza-bicyclo[3.2.1]oct-8-yl]-methanone 1H NMR (300 MHz, DMSO) δ=11.73 (s, 1H), 8.16 (s, 1H), 7.22 (m, 4H), 7.13 (m, 1H), 6.65 (m, 1H), 4.56 (br, 4H), 3.44 (br, 4H), 1.77 (br, 4H).

Example 133

2-[3-(7H-Pyrrolo[2,3-d]pyrimidin-4-yl)-3,8-diaza-bicyclo[3.2.1]octane-8-carbonyl]-indan-1-one 1H NMR (300 MHz, DMSO) δ=11.72 (s, 1H), 8.16 (s, 1H), 7.71 (m, 2H), 7.49 (m, 2H), 7.20 (m, 1H), 6.63 (m, 1H), 4.71 (m, 6H), 2.90 (br, 2H), 1.82 (br, 4H).

Example 134

2-(4-Methanesulfonyl-phenyl)-1-[3-(7H-pyrrolo[2,3-d]pyrimidin-4-yl)-3,8-diaza-bicyclo[3.2.1]oct-8-yl]-ethanone 1H NMR (300 MHz, DMSO) δ=11.70 (s, 1H), 8.26 (s, 1H), 7.87 (m, 2H), 7.55 (m, 2H), 7.18 (m, 1H), 6.60 (m, 1H), 4.66 (br, 2H), 4.49 (br, 2H), 3.92 (br, 4H), 3.19 (br, 3H), 1.76 (br, 4H).

Example 135

(3-Methanesulfonyl-phenyl)-[3-(7H-pyrrolo[2,3-d]pyrimidin-4-yl)-3,8-diaza-bicyclo[3.2.1]oct-8-yl]-methanone 1H NMR (300 MHz, DMSO) δ=11.70 (s, 1H), 8.17 (s, 1H), 7.90 (m, 3H), 7.76 (m, 1H), 7.18 (m, 1H), 6.63 (m, 1H), 4.72 (br, 4H), 4.15 (br, 2H), 3.21 (s, 3H), 1.94 (br, 2H), 1.73 (br, 2H).

Example 136

(5-Fluoro-1H-indol-2-yl)-[3-(7H-pyrrolo[2,3-d]pyrimidin-4-yl)-3,8-diaza-bicyclo[3.2.1]oct-8-yl]-methanone 1H NMR (300 MHz, DMSO) δ=11.72 (s, 2H), 8.16 (br, 2H), 7.42 (m, 2H), 7.20 (m, 2H), 7.06 (m, 1H), 6.68 (m, 1H), 4.95 (br, 2H), 4.63 (br, 2H), 3.47 (br, 2H), 1.91 (br, 2H), 1.76 (br, 2H).

Example 137

[3-(7H-Pyrrolo[2,3-d]pyrimidin-4-yl)-3,8-diaza-bicyclo[3.2.1]oct-8-yl]-(1,2,3,4-tetrahydro-naphthalen-1-yl)-methanone 1H NMR (300 MHz, DMSO) δ=11.71 (s, 1H), 8.15 (s, 1H), 7.19 (m, 1H), 7.06 (br, 3H), 6.89 (m, 1H), 6.62 (m, 1H), 4.74 (br, 1H), 4.57 (br, 3H), 4.17 (br, 1H), 2.75 (br, 2H), 1.84 (br, 10H).

Example 138

2-Methyl-5-[3-(7H-pyrrolo[2,3-d]pyrimidin-4-yl)-3,8-diaza-bicyclo[3.2.1]octane-8-carbonyl]-benzenesulfonamide 1H NMR (300 MHz, DMSO) δ=11.72 (br, 1H), 8.15 (s, 1H), 7.76 (m, 2H), 7.53 (m, 1H), 7.19 (m, 1H), 6.62 (m, 1H), 4.89 (br, 1H), 4.63 (br, 2H), 4.44 (br, 1H), 3.79 (br, 3H), 2.36 (s, 4H), 1.96 (br, 2H), 1.74 (br, 2H).

Example 139

(5,6-Dihydro-4H-cyclopenta[b]thiophen-2-yl)-[3-(7H-pyrrolo[2,3-d]pyrimidin-4-yl)-3,8-diaza-bicyclo[3.2.1]oct-8-yl]-methanone 1H NMR (300 MHz, DMSO) δ=11.72 (s, 1H), 8.16 (s, 1H), 7.41 (s, 1H), 7.19 (m, 1H), 6.67 (m, 1H), 4.81 (br, 2H), 4.59 (br, 2H), 3.28 (br, 2H), 2.90 (br, 2H), 2.73 (br, 2H), 2.41 (br, 2H), 1.88 (br, 2H), 1.73 (br, 2H).

Example 140

(5,7-Difluoro-1H-indol-2-yl)-[3-(7H-pyrrolo[2,3-d]pyrimidin-4-yl)-3,8-diaza-bicyclo[3.2.1]oct-8-yl]-methanone 1H NMR (300 MHz, DMSO) δ=11.72 (br, 2H), 8.16 (s, 1H), 7.25 (m, 2H), 7.09 (br, 2H), 6.67 (br, 1H), 4.88 (br, 2H), 4.62 (br, 2H), 3.43 (br, 2H), 1.93 (br, 2H), 1.76 (br, 2H).

Example 141

1-Methyl-5-[3-(7H-pyrrolo[2,3-d]pyrimidin-4-yl)-3,8-diaza-bicyclo[3.2.1]octane-8-carbonyl]-1H-pyrrole-2-sulfonic acid amide 1H NMR (300 MHz, DMSO) δ=11.33 (br, 1H), 8.18 (s, 1H), 7.44 (d, J=1.7, 1H), 7.19 (d, J=3.7, 1H), 6.76 (d, J=1.7, 1H), 6.66 (d, J=3.7, 1H), 4.69 (br, 2H), 4.57 (br, 2H), 3.76 (s, 3H), 3.39 (br, 2H), 1.90 (br, 2H), 1.73 (br, 2H).

Example 142

1-Methyl-5-[3-(7H-pyrrolo[2,3-d]pyrimidin-4-yl)-3,8-diaza-bicyclo[3.2.1]octane-8-carbonyl]-1H-pyrrole-3-sulfonic acid amide 1H NMR (300 MHz, DMSO) δ=8.15 (s, 1H), 7.44 (d, J=1.7, 1H), 7.19 (d, J=3.6, 1H), 6.76 (d, J=1.7, 1H), 6.66 (d, J=3.6, 1H), 4.69 (br, 2H), 4.57 (br, 2H), 3.76 (s, 3H), 3.42 (br, 2H), 1.90 (br, 2H), 1.73 (br, 2H).

Example 144

[3-(7H-Pyrrolo[2,3-d]pyrimidin-4-yl)-3,8-diaza-bicyclo[3.2.1]oct-8-yl]-(tetrahydro-furan-3-yl)-methanone 1H NMR (300 MHz, DMSO) δ=11.70 (s, 1H), 8.14 (s, 1H), 7.19 (m, 1H), 6.61 (m, 1H), 4.69 (br, 1H), 4.50 (br, 3H), 3.93 (m, 1H), 3.72 (br, 4H), 3.20 (br, 2H), 2.01 (br, 3H), 1.73 (br, 3H).

Example 65

4-{1,1-Difluoro-2-oxo-2-[3-(7H-pyrrolo[2,3-d]pyrimidin-4-yl)-3,8-diaza-bicyclo[3.2.1]oct-8-yl]-ethyl}-benzonitrile 1H NMR (300 MHz, DMSO) δ=11.72 (m, 1H), 8.13 (s, 1H), 8.05 (d, J=8.3, 11H), 7.84 (m, 1H), 7.19 (m, 1H), 6.60 (m, 1H), 4.78 (br, 1H), 4.53 (m, 3H), 3.23 (s, 1H), 2.99 (br, 1H), 1.75 (br, 4H).

Example 168

3-Phenyl-1-[3-(7H-pyrrolo[2,3-d]pyrimidin-4-yl)-3,8-diaza-bicyclo[3.2.1]oct-8-yl]-propan-1-one 1H NMR (600 MHz, DMSO) δ=11.70 (s, 1H), 8.13 (s, 1H), 7.27 (m, 4H), 7.16 (m, 2H), 6.58 (m, 1H), 4.68 (m, 1H), 4.43 (m, 3H), 3.12 (m, 2H), 2.86 (m, 2H), 2.67 (m, 2H), 1.70 (m, 4H).

Example 169

Benzo[b]thiophen-2-yl-[3-(7H-pyrrolo[2,3-d]pyrimidin-4-yl)-3,8-diaza-bicyclo[3.2.1]oct-8-yl]-methanone 1H NMR (600 MHz, DMSO) δ=11.74 (s, 1H), 8.17 (s, 1H), 8.05 (m, 1H), 7.99 (m, 2H), 7.48 (m, 2H), 7.21 (m, 1H), 6.68 (m, 1H), 4.87 (m, 2H), 4.62 (m, 2H), 3.41 (m, 2H), 1.95 (m, 2H), 1.76 (m, 2H).

Example 170

2-(1H-Indol-3-yl)-1-[3-(7H-pyrrolo[2,3-d]pyrimidin-4-yl)-3,8-diaza-bicyclo[3.2.1]oct-8-yl]-ethanone 1H NMR (600 MHz, DMSO) δ=11.69 (s, 1H), 10.90 (s, 1H), 8.10 (s, 1H), 7.61 (d, J=7.9, 1H), 7.34 (d, J=7.9, 1H), 7.27 (m, 1H), 7.16 (m, 1H), 7.06 (m, 1H), 6.98 (m, 1H), 6.55 (m, 1H), 4.67 (m, 2H), 4.41 (m, 2H), 3.82 (m, 2H), 3.13 (m, 1H), 2.96 (m, 1H), 1.71 (m, 4H).

Example 171

2-Pyridin-4-yl-1-[3-(7H-pyrrolo[2,3-d]pyrimidin-4-yl)-3,8-diaza-bicyclo[3.2.1]oct-8-yl]-ethanone 1H NMR (600 MHz, DMSO) δ=11.76 (s, 1H), 8.54 (s, 2H), 8.15 (s, 1H), 7.39 (m, 2H), 7.19 (m, 1H), 6.62 (m, 1H), 4.65 (m, 2H), 4.48 (m, 2H), 3.87 (m, 2H), 3.22 (m, 2H), 1.79 (m, 4H).

Example 172

2-Pyridin-3-yl-1-[3-(7H-pyrrolo[2,3-d]pyrimidin-4-yl)-3,8-diaza-bicyclo[3.2.1]oct-8-yl]-ethanone 1H NMR (600 MHz, DMSO) δ=11.75 (s, 1H), 8.47 (m, 2H), 8.15 (s, 1H), 7.72 (m, 1H), 7.37 (m, 1H), 7.19 (m, 1H), 6.62 (m, 1H), 4.66 (m, 2H), 4.49 (m, 2H), 3.83 (m, 2H), 3.23 (m, 2H), 1.78 (m, 4H).

Example 173

3-[3-(7H-Pyrrolo[2,3-d]pyrimidin-4-yl)-3,8-diaza-bicyclo[3.2.1]octane-8-carbonyl]-benzonitrile 1H NMR (600 MHz, DMSO) δ=11.72 (s, 1H), 8.14 (s, 1H), 8.03 (m, 1H), 7.99 (m, 1H), 7.89 (m, 1H), 7.70 (m, 1H), 7.19 (m, 1H), 6.63 (m, 1H), 4.83 (m, 1H), 4.60 (m, 1H), 4.44 (m, 1H), 4.11 (m, 1H), 3.31 (m, 2H), 1.94 (m, 2H), 1.71 (m, 2H).

Example 175

{4-[3-(7H-Pyrrolo[2,3-d]pyrimidin-4-yl)-3,8-diaza-bicyclo[3.2.1]octane-8-carbonyl]-phenyl}-acetonitrile 1H NMR (600 MHz, DMSO) δ=11.72 (s, 1H), 8.14 (s, 1H), 7.60 (m, 2H), 7.46 (d, J=8.1, 2H), 7.18 (m, 1H), 6.64 (m, 1H), 4.83 (m, 1H), 4.53 (m, 2H), 4.15 (br, 3H), 3.35 (br, 2H), 1.89 (br, 2H), 1.70 (br, 2H).

Example 176

N-{3-Oxo-3-[3-(7H-pyrrolo[2,3-d]pyrimidin-4-yl)-3,8-diaza-bicyclo[3.2.1]oct-8-yl]-propyl}-methanesulfonamide 1H NMR (600 MHz, DMSO) δ=11.74 (s, 1H), 8.14 (br, 1H), 6.98 (m, 1H), 6.63 (br, 1H), 4.69 (m, 1H), 4.47 (m, 3H), 3.22 (m, 2H), 2.92 (s, 3H), 2.59 (m, 4H), 1.94 (m, 1H), 1.72 (m, 3H).

Example 177

Oxazol-2-yl-[3-(7H-pyrrolo[2,3-d]pyrimidin-4-yl)-3,8-diaza-bicyclo[3.2.1]oct-8-yl]-methanone 1H NMR (600 MHz, DMSO) δ=11.73 (s, 1H), 8.30 (s, 1H), 8.14 (m, 1H), 7.52 (s, 1H), 7.18 (m, 1H), 6.66 (m, 1H), 5.50 (br, 1H), 4.87 (br, 1H), 4.63 (br, 2H), 3.30 (br, sH), 2.00 (m, 1H), 1.88 (m, 1H), 1.76 (m, 2H).

Example 178

Biphenyl-3-yl-[3-(7H-pyrrolo[2,3-d]pyrimidin-4-yl)-3,8-diaza-bicyclo[3.2.1]oct-8-yl]-methanone 1H NMR (600 MHz, DMSO) δ=8.15 (s, 1H), 7.81 (m, 2H), 7.74 (m, 2H), 7.59 (m, 1H), 7.54 (m, 1H), 7.50 (m, 2H), 7.40 (m, 1H), 7.18 (m, 1H), 6.64 (m, 1H), 4.86 (br, 1H), 4.55 (br, 2H), 4.24 (br, 1H), 3.40 (br, 2H), 1.93 (br, 2H), 1.71 (br, 2H).

Example 179

3-{2-Oxo-2-[3-(7H-pyrrolo[2,3-d]pyrimidin-4-yl)-3,8-diaza-bicyclo[3.2.1]oct-8-yl]-ethyl}-benzonitrile 1H NMR (600 MHz, DMSO) δ=11.72 (s, 1H), 8.14 (s, 1H), 7.76 (s, 1H), 7.71 (m, 1H), 7.64 (m, 1H), 7.53 (m, 1H), 7.19 (m, 1H), 6.61 (m, 1H), 4.65 (br, 2H), 4.49 (br, 2H), 3.87 (br, 2H), 3.23 (br, 2H), 1.92 (m, 1H), 1.74 (m, 3H).

Example 180

4-{2-Oxo-2-[3-(7H-pyrrolo[2,3-d]pyrimidin-4-yl)-3,8-diaza-bicyclo[3.2.1]oct-8-yl]-ethyl}-benzonitrile 1H NMR (600 MHz, DMSO) δ=11.72 (s, 1H), 8.14 (s, 1H), 7.79 (m, 2H), 7.50 (m, 2H), 7.19 (m, 1H), 6.60 (m, 1H), 4.64 (m, 2H), 4.48 (m, 2H), 3.90 (m, 2H), 3.20 (m, 2H), 1.78 (m, 4H).

Example 181

4,4,4-Trifluoro-1-[3-(7H-pyrrolo[2,3-d]pyrimidin-4-yl)-3,8-diaza-bicyclo[3.2.1]oct-8-yl]-butan-1-one 1H NMR (600 MHz, DMSO) δ=11.72 (s, 1H), 8.14 (s, 1H), 7.19 (m, 1H), 6.61 (m, 1H), 4.68 (m, 1H), 4.49 (br m, 3H), 3.31 (br, 1H), 3.19 (br, 1H), 2.66 (m, 2H), 2.58 (m, 2H), 1.96 (br, 1H), 1.73 (m, 3H).

Example 182

4-Oxo-4-[3-(7H-pyrrolo[2,3-d]pyrimidin-4-yl)-3,8-diaza-bicyclo[3.2.1]oct-8-yl]-butyronitrile 1H NMR (600 MHz, DMSO) δ=11.75 (s, 1H), 8.15 (s, 1H), 7.20 (m, 1H), 6.63 (m, 1H), 4.69 (m, 1H), 4.47 (m, 3H), 3.12 (m, 2H), 2.79 (m, 2H), 2.67 (m, 2H), 1.96 (m, 1H), 1.73 (m, 3H).

Example 199

5-[3-(7H-Pyrrolo[2,3-d]pyrimidin-4-yl)-3,8-diaza-bicyclo[3.2.1]octane-8-carbonyl]-thiophene-3-carbonitrile 1H NMR (300 MHz, DMSO) δ=11.72 (s, 1H), 8.77 (s, 1H), 8.16 (s, 1H), 8.06 (m, 1H), 7.21 (d, J=3.6, 1H), 6.65 (d, J=3.6, 1H), 4.80 (br, 2H), 4.59 (br, 2H), 3.38 (m, 2H), 1.92 (m, 2H), 1.73 (m, 2H).

Example 200

(5-Methyl-1H-indol-2-yl)-[3-(7H-pyrrolo[2,3-d]pyrimidin-4-yl)-3,8-diaza-bicyclo[3.2.1]oct-8-yl]-methanone 1H NMR (300 MHz, DMSO) δ=11.72 (s, 1H), 11.49 (s, 1H), 8.19 (m, 1H), 7.41 (s, 1H), 7.33 (m, 1H), 7.20 (m, 1H), 7.04 (m, 1H), 6.93 (s, 1H), 6.69 (d, 1H), 4.96 (br, 2H), 4.63 (br, 2H), 3.41 (br, 2H), 2.37 (s, 3H), 1.84 (br, 4H).

Example 201

(5-Fluoro-3-methyl-1H-indol-2-yl)-[3-(7H-pyrrolo[2,3-d]pyrimidin-4-yl)-3,8-diaza-bicyclo[3.2.1]oct-8-yl]-methanone 1H NMR (300 MHz, DMSO) δ=11.71 (s, 1H), 11.37 (s, 1H), 8.14 (s, 1H), 7.36 (m, 2H), 7.17 (m, 1H), 7.04 (m, 1H), 6.63 (m, 1H), 4.55 (br, 4H), 3.40 (br, 2H), 2.33 (s, 3H), 1.96 (br, 2H), 1.75 (br, 2H).

Example 202

[4-(Propane-2-sulfonyl)-phenyl]-[3-(7H-pyrrolo[2,3-d]pyrimidin-4-yl)-3,8-diaza-bicyclo[3.2.1]oct-8-yl]-methanone 1H NMR (300 MHz, DMSO) δ=11.72 (s, 1H), 8.15 (s, 1H), 7.94 (m, 2H), 7.82 (m, 2H), 7.20 (m, 1H), 6.63 (m, 1H), 4.59 (m, 4H), 3.49 (m, 1H), 3.37 (br, 2H), 1.80 (br, 4H), 1.18 (m, 6H).

Example 203

[4-(Propane-2-sulfonyl)-phenyl]-[3-(7H-pyrrolo[2,3-d]pyrimidin-4-yl)-3,8-diaza-bicyclo[3.2.1]oct-8-yl]-methanone 1H NMR (300 MHz, DMSO) δ=11.69 (s, 1H), 8.59 (s, 1H), 8.15 (m, 1H), 7.22 (br, 2H), 7.08 (m, 2H), 6.63 (br, 1H), 4.91 (br, 2H), 4.61 (br, 4H), 3.35 (br, 2H), 1.94 (br, 2H).

Example 239

2,2-Dimethyl-3-oxo-3-[3-(7H-pyrrolo[2,3-d]pyrimidin-4-yl)-3,8-diaza-bicyclo[3.2.1]oct-8-yl]-propionitrile 1H NMR (600 MHz, DMSO) δ=11.74 (s, 1H), 8.15 (s, 1H), 7.21 (m, 1H), 6.64 (m, 1H), 4.70 (br, 4H), 3.40 (br, 2H), 1.83 (br, 4H), 1.57 (s, 6H).

Example 240

Phenyl-[3-(7H-pyrrolo[2,3-d]pyrimidin-4-yl)-3,8-diaza-bicyclo[3.2.1]oct-8-yl]-methanone 1H NMR (600 MHz, DMSO) δ=11.71 (s, 1H), 8.16 (s, 1H), 7.52 (br m, 5H), 7.19 (m, 1H), 6.64 (m, 1H), 4.83 (m, 1H), 4.53 (m, 2H), 4.15 (m, 1H), 3.29 (br, 2H), 1.86 (m, 2H), 1.72 (m, 2H).

Example 241

Pyridin-2-yl-[3-(7H-pyrrolo[2,3-d]pyrimidin-4-yl)-3,8-diaza-bicyclo[3.2.1]oct-8-yl]-methanone 1H NMR (600 MHz, DMSO) δ=11.72 (s, 1H), 8.64 (s, 1H), 8.14 (s, 1H), 7.96 (m, 1H), 7.79 (m, 1H), 7.55 (m, 1H), 7.19 (m, 1H), 6.64 (m, 1H), 4.84 (m, 2H), 4.56 (m, 2H), 3.42 (m, 2H), 1.92 (m, 2H), 1.74 (m, 2H).

Example 242

Pyridin-4-yl-[3-(7H-pyrrolo[2,3-d]pyrimidin-4-yl)-3,8-diaza-bicyclo[3.2.1]oct-8-yl]-methanone 1H NMR (600 MHz, DMSO) δ=11.90 (s, 1H), 8.73 (m, 2H), 8.19 (s, 1H), 7.55 (m, 2H), 7.24 (m, 1H), 6.70 (m, 1H), 4.86 (s, 1H), 4.49 (m, 2H), 4.10 (s, 1H), 3.43 (s, 2H), 1.93 (m, 2H), 1.72 (m, 2H).

Example 243

(3-Methyl-thiophen-2-yl)-[3-(7H-pyrrolo[2,3-d]pyrimidin-4-yl)-3,8-diaza-bicyclo[3.2.1]oct-8-yl]-methanone 1H NMR (600 MHz, DMSO) δ=11.72 (s, 1H), 8.17 (s, 1H), 7.60 (m, 1H), 7.19 (m, 1H), 7.00 (m, 1H), 6.64 (m, 1H), 4.54 (br, 4H), 3.29 (m, 2H), 2.29 (s, 3H), 1.89 (m, 2H), 1.73 (m, 2H).

Example 244

[3-(7H-Pyrrolo[2,3-d]pyrimidin-4-yl)-3,8-diaza-bicyclo[3.2.1]oct-8-yl]-(3-trifluoromethoxy-phenyl)-methanone 1H NMR (600 MHz, DMSO) δ=11.72 (s, 1H), 8.14 (s, 1H), 7.62 (m, 2H), 7.53 (m, 2H), 7.19 (m, 1H), 6.63 (m, 1H), 4.83 (s, 1H), 4.53 (br, 2H), 4.12 (s, 1H), 3.29 (m, 2H), 1.92 (m, 2H), 1.71 (m, 2H).

Example 245

(3-Methyl-benzo[b]thiophen-2-yl)-[3-(7H-pyrrolo[2,3-d]pyrimidin-4-yl)-3,8-diaza-bicyclo[3.2.1]oct-8-yl]-methanone 1H NMR (600 MHz, DMSO) δ=11.73 (s, 1H), 8.14 (s, 1H), 8.02 (m, 1H), 7.88 (m, 1H), 7.49 (m, 2H), 7.20 (m, 1H), 6.62 (m, 1H), 4.41 (m, 4H), 3.29 (m, 2H), 2.47 (s, 3H), 1.95 (br, 2H), 1.75 (br, 2H).

Example 246

Benzo[b]thiophen-3-yl-[3-(7H-pyrrolo[2,3-d]pyrimidin-4-yl)-3,8-diaza-bicyclo[3.2.1]oct-8-yl]-methanone 1H NMR (600 MHz, DMSO) δ=11.72 (s, 1H), 8.17 (s, 1H), 8.14 (s, 1H), 8.08 (m, 1H), 7.93 (m, 1H), 7.46 (m, 2H), 7.18 (m, 1H), 6.63 (m, 1H), 4.55 (m, 4H), 3.41 (m, 2H), 1.95 (m, 2H), 1.73 (m, 2H).

Example 247

(5-Methyl-benzo[b]thiophen-2-yl)-[3-(7H-pyrrolo[2,3-d]pyrimidin-4-yl)-3,8-diaza-bicyclo[3.2.1]oct-8-yl]-methanone 1H NMR (600 MHz, DMSO) δ=11.74 (s, 1H), 8.16 (s, 1H), 7.91 (m, 1H), 7.89 (s, 1H), 7.77 (s, 1H), 7.32 (m, 1H), 7.21 (m, 1H), 6.67 (m, 1H), 4.85 (m, 2H), 4.61 (m, 2H), 3.43 (br, 2H), 2.44 (s, 3H), 1.94 (m, 2H), 1.75 (m, 2H).

Example 248

4-[3-(7H-Pyrrolo[2,3-d]pyrimidin-4-yl)-3,8-diaza-bicyclo[3.2.1]octane-8-carbonyl]-tetrahydro-pyran-4-carbonitrile 1H NMR (600 MHz, DMSO) δ=11.74 (s, 1H), 8.15 (s, 1H), 7.21 (m, 1H), 6.63 (m, 1H), 4.86 (m, 2H), 4.55 (m, 2H), 3.93 (m, 2H), 3.60 (m, 2H), 3.27 (m, 2H), 2.00 (m, 4H), 1.77 (m, 4H).

Example 249

2-[3-(7H-Pyrrolo[2,3-d]pyrimidin-4-yl)-3,8-diaza-bicyclo[3.2.1]octane-8-carbonyl]-benzonitrile 1H NMR (600 MHz, DMSO) δ=11.74 (s, 1H), 8.15 (s, 1H), 7.99 (m, 1H), 7.83 (m, 1H), 7.70 (m, 2H), 7.19 (m, 1H), 6.62 (m, 1H), 4.88 (m, 1H), 4.64 (m, 1H), 4.44 (m, 1H), 3.91 (m, 1H), 3.22 (m, 2H), 1.93 (m, 2H), 1.74 (m, 2H).

Example 250

2-{2-Oxo-2-[3-(7H-pyrrolo[2,3-d]pyrimidin-4-yl)-3,8-diaza-bicyclo[3.2.1]oct-8-yl]-ethyl}-benzonitrile 1H NMR (600 MHz, DMSO) δ=11.73 (s, 1H), 8.15 (s, 1H), 7.80 (m, 1H), 7.65 (m, 1H), 7.50 (m, 1H), 7.45 (m, 1H), 7.20 (m, 1H), 6.64 (m, 1H), 4.68 (m, 2H), 4.53 (m, 2H), 4.04 (m, 2H), 3.24 (m, 2H), 1.86 (m, 4H).

Example 251

[3-(7H-Pyrrolo[2,3-d]pyrimidin-4-yl)-3,8-diaza-bicyclo[3.2.1]oct-8-yl]-(4-trifluoromethoxy-phenyl)-methanone 1H NMR (600 MHz, DMSO) δ=11.72 (s, 1H), 8.14 (s, 1H), 7.71 (m, 2H), 7.46 (m, 2H), 7.20 (m, 1H), 6.63 (m, 1H), 4.83 (s, 1H), 4.54 (m, 2H), 4.16 (s, 1H), 3.29 (br, 2H), 1.91 (m, 2H), 1.71 (m, 2H).

Example 341

(1H-Indol-5-yl)-[3-(7H-pyrrolo[2,3-d]pyrimidin-4-yl)-3,8-diaza-bicyclo[3.2.1]oct-8-yl]-methanone 1H NMR (600 MHz, DMSO) δ=11.71 (s, 1H), 11.33 (s, 1H), 8.14 (s, 1H), 7.81 (s, 1H), 7.45 (m, 2H), 7.32 (m, 1H), 7.18 (m, 1H), 6.64 (m, 1H), 6.54 (m, 1H), 4.48 (br, 4H), 3.40 (br, 2H), 1.90 (br, 2H), 1.72 (br, 2H).

Example 342

{4-[3-(7H-Pyrrolo[2,3-d]pyrimidin-4-yl)-3,8-diaza-bicyclo[3.2.1]octane-8-carbonyl]-phenoxy}-acetonitrile 1H NMR (600 MHz, DMSO) δ=11.71 (s, 1H), 8.14 (s, 1H), 7.61 (m, 2H), 7.16 (br, 3H), 6.64 (m, 1H), 5.26 (s, 2H), 4.53 (br, 4H), 3.40 (br, 2H), 1.89 (br, 2H), 1.70 (br, 2H).

Example 343

{3-[3-(7H-Pyrrolo[2,3-d]pyrimidin-4-yl)-3,8-diaza-bicyclo[3.2.1]octane-8-carbonyl]-phenoxy}-acetonitrile 1H NMR (600 MHz, DMSO) δ=11.72 (s, 1H), 8.14 (s, 1H), 7.48 (m, 1H), 7.24 (m, 2H), 7.20 (m, 2H), 6.63 (m, 1H), 5.26 (s, 2H), 4.83 (br, 1H), 4.53 (m, 2H), 4.16 (br, 1H), 3.39 (br, 2H), 1.88 (br, 2H), 1.71 (br, 2H).

Example 344

(1H-Indol-4-yl)-[3-(7H-pyrrolo[2,3-d]pyrimidin-4-yl)-3,8-diaza-bicyclo[3.2.1]oct-8-yl]-methanone 1H NMR (600 MHz, DMSO) δ=11.70 (s, 1H), 11.35 (s, 1H), 8.13 (s, 1H), 7.52 (m, 1H), 7.45 (m, 1H), 7.15 (m, 3H), 6.60 (m, 1H), 6.45 (m, 1H), 4.48 (br, 4H), 3.22 (br, 2H), 1.94 (br, 2H), 1.72 (br, 2H).

Example 345

[3-(7H-Pyrrolo[2,3-d]pyrimidin-4-yl)-3,8-diaza-bicyclo[3.2.1]oct-8-yl]-quinoxalin-2-yl-methanone 1H NMR (600 MHz, DMSO) δ=11.73 (s, 1H), 9.24 (s, 1H), 8.20 (m, 3H), 7.98 (m, 2H), 7.21 (m, 1H), 6.66 (m, 1H), 4.95 (br, 2H), 4.59 (br, 2H), 3.51 (m, 2H), 2.00 (m, 2H), 1.79 (m, 2H).

Example 346

(3-{2-Oxo-2-[3-(7H-pyrrolo[2,3-d]pyrimidin-4-yl)-3,8-diaza-bicyclo[3.2.1]oct-8-yl]-ethyl}-phenyl)-acetonitrile 1H NMR (600 MHz, DMSO) δ=11.71 (s, 1H), 8.13 (s, 1H), 7.33 (m, 1H), 7.26 (m, 2H), 7.19 (m, 2H), 6.59 (m, 1H), 4.64 (br, 2H), 4.47 (br, 2H), 4.02 (br, 2H), 3.77 (br, 2H), 3.16 (br, 2H), 1.76 (m, 4H).

Example 347

(4-{2-Oxo-2-[3-(7H-pyrrolo[2,3-d]pyrimidin-4-yl)-3,8-diaza-bicyclo[3.2.1]oct-8-yl]-ethyl}-phenyl)-acetonitrile 1H NMR (600 MHz, DMSO) δ=11.71 (s, 1H), 8.13 (s, 1H), 7.29 (m, 4H), 7.19 (m, 1H), 6.60 (m, 1H), 4.63 (br, 2H), 4.46 (br, 2H), 4.00 (s, 2H), 3.74 (br, 2H), 3.15 (br, 2H), 1.75 (br, 4H).

Example 348

(1H-Indol-2-yl)-[3-(7H-pyrrolo[2,3-d]pyrimidin-4-yl)-3,8-diaza-bicyclo[3.2.1]oct-8-yl]-methanone 1H NMR (600 MHz, DMSO) δ=11.73 (s, 1H), 11.64 (s, 1H), 8.16 (s, 1H), 7.65 (m, 1H), 7.45 (m, 1H), 7.22 (m, 2H), 7.06 (m, 2H), 6.69 (m, 1H), 4.97 (br, 2H), 4.64 (br, 2H), 3.42 (m, 2H), 1.96 (br, 2H), 1.74 (m, 2H).

Example 349

1-[3-(7H-Pyrrolo[2,3-d]pyrimidin-4-yl)-3,8-diaza-bicyclo[3.2.1]oct-8-yl]-2-(4-trifluoromethyl-phenyl)-ethanone 1H NMR (600 MHz, DMSO) δ=11.72 (s, 1H), 8.13 (s, 1H), 7.68 (m, 2H), 7.52 (m, 2H), 7.17 (m, 1H), 6.60 (m, 1H), 4.65 (br, 2H), 4.48 (br, 2H), 3.89 (br, 2H), 3.21 (br, 2H), 1.76 (br, 4H).

Example 350

2-Fluoro-4-[3-(7H-pyrrolo[2,3-d]pyrimidin-4-yl)-3,8-diaza-bicyclo[3.2.1]octane-8-carbonyl]-benzonitrile 1H NMR (600 MHz, DMSO) δ=11.72 (s, 1H), 8.14 (s, 1H), 8.07 (m, 1H), 7.73 (m, 1H), 7.57 (m, 1H), 7.19 (m, 1H), 6.61 (m, 1H), 4.82 (br, 1H), 4.51 (br, 1H), 4.07 (br, 1H), 3.38 (br, 2H), 1.89 (br, 2H), 1.72 (m, 2H).

Example 351

3-Fluoro-4-[3-(7H-pyrrolo[2,3-d]pyrimidin-4-yl)-3,8-diaza-bicyclo[3.2.1]octane-8-carbonyl]-benzonitrile 1H NMR (600 MHz, DMSO) δ=11.73 (s, 1H), 8.14 (s, 1H), 8.05 (m, 1H), 7.84 (m, 1H), 7.78 (m, 1H), 7.19 (m, 1H), 6.60 (m, 1H), 4.86 (br, 1H), 4.62 (br, 1H), 4.45 (br, 1H), 3.92 (br, 1H), 3.21 (m, 1H), 1.90 (m, 2H), 1.73 (br, 2H).

Example 352

5-Oxo-5-[3-(7H-pyrrolo[2,3-d]pyrimidin-4-yl)-3,8-diaza-bicyclo[3.2.1]oct-8-yl]-pentanenitrile 1H NMR (600 MHz, DMSO) δ=11.71 (s, 1H), 8.13 (s, 1H), 7.19 (d, J=3.6, 1H), 6.61 (d, J=3.6, 1H), 4.68 (br, 1H), 4.48 (m, 3H), 3.28 (br, 1H), 3.18 (br, 1H), 2.54 (br, 4H), 1.92 (m, 1H), 1.79 (m, 4H), 1.64 (br, 1H).

Example 353

4-[3-(7H-Pyrrolo[2,3-d]pyrimidin-4-yl)-3,8-diaza-bicyclo[3.2.1]octane-8-carbonyl]-benzenesulfonamide 1H NMR (600 MHz, DMSO) δ=11.72 (s, 1H), 8.15 (s, 1H), 7.92 (m, 2H), 7.75 (m, 2H), 7.51 (s, 2H), 7.19 (m, 1H), 6.64 (m, 1H), 4.85 (s, 1H), 4.61 (br, 1H), 4.47 (br, 1H), 4.11 (s, 1H), 3.36 (s, 2H), 1.94 (br, 2H), 1.71 (br, 2H).

Example 354

N-{4-[3-(7H-Pyrrolo[2,3-d]pyrimidin-4-yl)-3,8-diaza-bicyclo[3.2.1]octane-8-carbonyl]-phenyl}-acetamide 1H NMR (600 MHz, DMSO) δ=11.71 (s, 1H), 10.16 (s, 1H), 8.14 (s, 1H), 7.68 (m, 2H), 7.53 (m, 2H), 7.18 (m, 1H), 6.64 (m, 1H), 4.53 (br, 4H), 3.37 (br, 2H), 2.08 (s, 3H), 1.87 (m, 2H), 1.69 (m, 2H).

Example 355

6-[3-(7H-Pyrrolo[2,3-d]pyrimidin-4-yl)-3,8-diaza-bicyclo[3.2.1]octane-8-carbonyl]-1H-quinolin-2-one 1H NMR (600 MHz, DMSO) δ=11.94 (s, 1H), 11.77 (s, 1H), 8.16 (s, 1H), 8.01 (m, 1H), 7.93 (m, 1H), 7.70 (m, 1H), 7.37 (m, 1H), 7.20 (m, 1H), 6.66 (m, 1H), 6.57 (m, 1H), 4.56 (br, 4H), 3.40 (br, 2H), 1.91 (br, 2H), 1.71 (br, 2H).

Example 356

(4-Methanesulfonyl-phenyl)-[3-(7H-pyrrolo[2,3-d]pyrimidin-4-yl)-3,8-diaza-bicyclo[3.2.1]oct-8-yl]-methanone 1H NMR (600 MHz, DMSO) δ=11.72 (s, 1H), 8.14 (m, 1H), 8.03 (m, 2H), 7.81 (m, 2H), 7.20 (m, 1H), 6.64 (m, 1H), 4.85 (br, 1H), 4.62 (m, 1H), 4.45 (m, 1H), 4.09 (m, 1H), 3.37 (m, 2H), 3.30 (s, 3H), 1.93 (m, 2H), 1.71 (m, 2H).

Example 357

(1H-Indol-6-yl)-[3-(7H-pyrrolo[2,3-d]pyrimidin-4-yl)-3,8-diaza-bicyclo[3.2.1]oct-8-yl]-methanone 1H NMR (600 MHz, DMSO) δ=11.71 (s, 1H), 11.29 (s, 1H), 8.14 (s, 1H), 7.62 (m, 2H), 7.50 (m, 1H), 7.22 (m, 1H), 7.18 (m, 1H), 6.64 (m, 1H), 6.51 (m, 1H), 4.70 (br, 4H), 3.39 (m, 2H), 1.89 (br, 2H), 1.71 (br, 2H).

Example 358

4-[3-(7H-Pyrrolo[2,3-d]pyrimidin-4-yl)-3,8-diaza-bicyclo[3.2.1]octane-8-carbonyl]-benzamide 1H NMR (600 MHz, DMSO) δ=11.75 (s, 1H), 8.15 (s, 1H), 8.09 (s, 1H), 7.96 (m, 2H), 7.62 (m, 2H), 7.49 (s, 1H), 7.19 (m, 1H), 6.64 (m, 1H), 4.84 (s, 1H), 4.53 (m, 2H), 4.13 (s, 1H), 3.37 (br, 2H), 1.91 (m, 2H), 1.72 (m, 2H).

Example 359

(6-Hydroxy-naphthalen-1-yl)-[3-(7H-pyrrolo[2,3-d]pyrimidin-4-yl)-3,8-diaza-bicyclo[3.2.1]oct-8-yl]-methanone 1H NMR (600 MHz, DMSO) δ=11.71 (s, 1H), 9.90 (s, 1H), 8.13 (s, 1H), 7.75 (m, 2H), 7.45 (m, 1H), 7.31 (s, 1H), 7.16 (br, 3H), 6.59 (m, 1H), 4.98 (br, 1H), 4.66 (br, 1H), 4.35 (br, 1H), 3.74 (s, 1H), 3.43 (br, 1H), 3.08 (m, 1H), 2.02 (br, 1H), 1.81 (m, 2H), 1.63 (m, 1H).

Example 360

(6-Bromo-benzo[d]isothiazol-3-yl)-[3-(7H-pyrrolo[2,3-d]pyrimidin-4-yl)-3,8-diaza-bicyclo[3.2.1]oct-8-yl]-methanone 1H NMR (600 MHz, DMSO) δ=11.73 (s, 1H), 8.65 (s, 1H), 8.29 (d, J=8.8, 1H), 8.15 (s, 1H), 7.73 (d, J=8.8, 1H), 7.19 (m, 1H), 6.65 (m, 1H), 4.98 (m, 1H), 4.83 (m, 1H), 4.68 (m, 1H), 4.56 (m, 1H), 3.41 (m, 2H), 1.95 (m, 2H), 1.77 (m, 2H).

Example 390

2-Methoxy-4-[3-(7H-pyrrolo[2,3-d]pyrimidin-4-yl)-3,8-diaza-bicyclo[3.2.1]octane-8-carbonyl]-benzene-sulfonamide 1H NMR (600 MHz, DMSO) δ=11.73 (s, 1H), 8.15 (s, 1H), 7.81 (m, 1H), 7.31 (m, 1H), 7.20 (br, 4H), 6.66 (m, 1H), 4.84 (s, 1H), 4.62 (br, 1H), 4.47 (br, 1H), 4.11 (br, 1H), 3.96 (s, 3H), 3.39 (m, 2H), 1.90 (br, 2H), 1.70 (br, 2H).

Example 391

3-Methyl-4-[3-(7H-pyrrolo[2,3-d]pyrimidin-4-yl)-3,8-diaza-bicyclo[3.2.1]octane-8-carbonyl]-benzene-sulfonamide 1H NMR (600 MHz, DMSO) δ=11.74 (s, 1H), 8.14 (s, 1H), 7.78 (m, 1H), 7.74 (s, 1H), 7.52 (m, 1H), 7.39 (br, 2H), 7.19 (m, 1H), 6.62 (m, 1H), 4.89 (br, 1H), 4.62 (br, 1H), 4.43 (br, 1H), 3.78 (br, 1H), 3.38 (br, 2H), 3.17 (br, 1H), 2.35 (s, 3H), 1.96 (m, 2H), 1.74 (m, 2H).

Example 392

2-Methyl-4-[3-(7H-pyrrolo[2,3-d]pyrimidin-4-yl)-3,8-diaza-bicyclo[3.2.1]octane-8-carbonyl]-benzene-sulfonamide 1H NMR (600 MHz, DMSO) δ=11.73 (s, 1H), 8.15 (s, 1H), 7.77 (s, 2H), 7.60 (s, 1H), 7.37 (br, 2H), 7.19 (m, 1H), 6.64 (m, 1H), 4.84 (br, 1H), 4.51 (m, 2H), 4.17 (br, 1H), 3.40 (m, 2H), 2.46 (s, 3H), 1.94 (m, 2H), 1.75 (m, 2H).

Example 393

3-Methoxy-4-[3-(7H-pyrrolo[2,3-d]pyrimidin-4-yl)-3,8-diaza-bicyclo[3.2.1]octane-8-carbonyl]-benzene-sulfonamide 1H NMR (300 MHz, DMSO) δ=12.03 (s, 1H), 8.22 (s, 1H), 7.50 (br, 5H), 7.27 (m, 1H), 6.73 (m, 1H), 4.88 (br, 1H), 4.58 (br, 1H), 4.41 (br, 1H), 3.91 (s, 3H), 3.80 (m, 1H), 3.40 (br, 2H), 1.91 (br, 2H), 1.72 (m, 2H).

Example 421

Pyrazin-2-yl-[3-(7H-pyrrolo[2,3-d]pyrimidin-4-yl)-3,8-diaza-bicyclo[3.2.1]oct-8-yl]-methanone 1H NMR (300 MHz, DMSO) δ=11.65 (s, 1H), 8.98 (s, 1H), 8.78 (m, 1H), 8.71 (m, 1H), 8.12 (m, 1H), 7.17 (m, 1H), 6.63 (m, 1H), 4.89 (s, 1H), 4.72 (s, 1H), 4.54 (br, 2H), 3.38 (m, 2H), 1.93 (m, 2H), 1.74 (br, 2H).

Example 2

Pyridin-2-yl-[7-(7H-pyrrolo[2,3-d]pyrimidin-4-yl)-4,7-diazaspiro[2.5]oct-4-yl]methanone

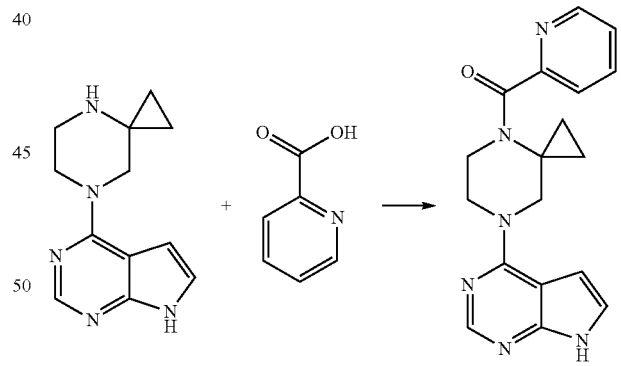

4-(4,7-Diaza-spiro[2.5]oct-7-yl)-7H-pyrrolo[2,3-d]pyrimidine (intermediate 2) (0.05 mmol) was dissolved in dry DMF (0.3 mL). Triethylamine (0.18 mmol) and HATU (0.09 mmol) was added followed by 2-pyridincarboxylic acid (0.07 mmol). The reaction mixture was left at rt for 16 hours. The pure compounds were obtained by standard preparative HPLC purification of the reaction mixture.

¹H NMR (300 MHz, DMSO) δ=11.74 (s, 1H), 8.61 (m, 1H), 8.15 (m, 1H), 7.93 (br m, 1H), 7.72-7.61 (br m, 1H), 7.52-7.48 (m, 1H), 7.23-7.19 (m, 1H), 6.65-6.60 (br, 1H), 3.91 (br m, 2H), 3.71 (br, 2H), 2.96-2.77 (m, 2H), 0.61-0.36 (m, 4H).

Using this procedure the following compounds were obtained:

Example 3

Pyridin-4-yl-[7-(7H-pyrrolo[2,3-d]pyrimidin-4-yl)-4,7-diazaspiro[2.5]oct-4-yl]-methanone $^1$H NMR (300 MHz, DMSO) δ=11.76 (s, 1H), 8.69 (m, 2H), 8.15 (m, 1H), 7.48 (m, 2H), 7.21 (m, 1H), 6.63 (m, 1H), 4.43-3.73 (m, 4H), 3.81-3.47 (m, 2H), 1.12-0.40 (m, 4H).

Example 4

2-Pyridin-3-yl-1-[7-(7H-pyrrolo[2,3-d]pyrimidin-4-yl)-4,7-diazaspiro[2.5]oct-4-yl]ethanone $^1$H NMR (300 MHz, DMSO) δ=11.79 (s, 1H), 8.60-8.36 (m, 2H), 8.16 (s, 1H), 7.75 (br, 1H), 7.40 (br, 1H), 7.23-7.20 (m, 1H), 6.63 (s, 1H), 4.12-3.64 (br, 8H), 1.40-0.69 (m, 4H).

Example 5

Biphenyl-4-yl-[7-(7H-pyrrolo[2,3-d]pyrimidin-4-yl)-4,7-diazaspiro[2.5]oct-4-yl]methanone $^1$H NMR (300 MHz, DMSO) δ=11.73 (s, 1H), 8.14 (s, 1H), 7.75 (m, 4H), 7.59 (m, 2H), 7.50 (m, 2H), 7.41 (m, 1H), 7.27-7.13 (m, 1H), 6.62 (m, 1H), 4.10-3.73 (m, 6H), 0.88 (br, 4H).

Example 6

Biphenyl-3-yl-[7-(7H-pyrrolo[2,3-d]pyrimidin-4-yl)-4,7-diazaspiro[2.5]oct-4-yl]methanone $^1$H NMR (300 MHz, DMSO) δ=11.73 (s, 1H), 8.14 (s, 1H), 7.79 (dd, J=3.6, 5.3, 1H), 7.77-7.63 (m, 3H), 7.55 (t, J=7.7, 1H), 7.49 (dd, J=7.7, 15.7, 3H), 7.40 (t, J=7.4, 1H), 7.19 (s, 1H), 6.62 (s, 1H), 3.97 (br, 4H), 3.89-3.62 (br, 2H), 0.85 (br, 4H).

Example 7

[7-(7H-Pyrrolo[2,3-d]pyrimidin-4-yl)-4,7-diazaspiro[2.5]oct-4-yl]-(tetrahydrofuran-3-yl)methanone $^1$H NMR (300 MHz, DMSO) δ=11.78 (s, 1H), 8.15 (s, 1H), 7.18 (m, 1H), 6.63 (m, 1H), 4.11-3.52 (m, 10H), 2.10-2.05 (br, 1H), 2.02-1.86 (m, 1H), 1.20-1.10 (br, 3H), 0.93-0.88 (br, 2H).

Example 8

2-{3-[7-(7H-Pyrrolo[2,3-d]pyrimidin-4-yl)-4,7-diazaspiro[2.5]octane-4-carbonyl]phenyl}propionitrile $^1$H NMR (300 MHz, DMSO) δ=12.52-11.00 (br, 1H), 8.14 (s, 1H), 7.60-7.39 (m, 4H), 7.19 (d, J=3.6, 1H), 6.61 (d, J=3.6, 1H), 4.38 (q, J=7.2, 1H), 4.08-3.92 (br, 4H), 3.84-3.68 (br, 2H), 1.58 (d, J=7.2, 3H), 0.95-0.60 (br, 4H).

Example 13

(1,1-Dioxo-hexahydro-1lambda*6*-thiopyran-4-yl)[7-(7H-pyrrolo[2,3-d]pyrimidin-4-yl)-4,7-diazaspiro[2.5]oct-4-yl]methanone $^1$H NMR (300 MHz, DMSO) δ=11.72 (s, 1H), 8.14 (s, 1H), 7.26-7.13 (m, 1H), 6.59 (m, 1H), 4.04-3.88 (br, 2H), 3.82-3.70 (br, 4H), 3.20-3.05 (br, 4H), 2.10-19.5 (br, 5H), 1.14-1.00 (br, 3H), 1.00-0.84 (br, 1H).

Example 14

2-(1H-Indol-3-yl)-1-[7-(7H-pyrrolo[2,3-d]pyrimidin-4-yl)-4,7-diazaspiro[2.5]oct-4-yl]ethanone $^1$H NMR (300 MHz, DMSO) δ=11.71 (s, 1H), 10.88 (s, 1H), 8.11 (s, 1H), 7.52 (br, 1H), 7.33 (d, J=8.1, 1H), 7.17 (br, 2H), 7.05 (t, J=7.5, 1H), 6.94 (br, 1H), 6.57 (br, 1H), 4.14-3.48 (m, 8H), 1.51-0.40 (m, 4H).

Example 16

(1H-Indol-3-yl)-[7-(7H-pyrrolo[2,3-d]pyrimidin-4-yl)-4,7-diazaspiro[2.5]oct-4-yl]methanone $^1$H NMR (300 MHz, DMSO) δ=11.71 (s, 1H), 11.66 (s, 1H), 8.13 (s, 1H), 7.82 (br, 1H), 7.70 (d, J=7.9, 1H), 7.45 (d, J=8.1, 1H), 7.23-7.13 (m, 2H), 7.13-7.05 (m, 1H), 6.61 (m, 1H), 3.98 (br m, 2H), 3.90 (br m, 4H), 0.98 (br m, 2H), 0.87 (br m, 2H).

Example 17

3-Oxo-3-[7-(7H-pyrrolo[2,3-d]pyrimidin-4-yl)-4,7-diazaspiro[2.5]oct-4-yl]propane-1-sulfonic acid amide $^1$H NMR (300 MHz, DMSO) δ=11.85 (s, 1H), 8.17 (s, 1H), 7.23 (br s, 1H), 6.88 (br s, 2H), 6.65 (br s, 1H), 4.17-3.59 (br m, 8H), 2.96 (br, 2H), 1.15-0.87 (br m, 4H).

Example 18

{4-[7-(7H-Pyrrolo[2,3-d]pyrimidin-4-yl)-4,7-diazaspiro[2.5]octane-4-carbonyl]-phenyl}acetonitrile $^1$H NMR (300 MHz, DMSO) δ=11.71 (s, 1H), 8.14 (s, 1H), 7.52 (d, J=8.2, 2H), 7.43 (d, J=8.2, 2H), 7.24-7.13 (m, 1H), 6.61 (br s, 1H), 4.13 (br s, 2H), 4.00 (br s, 2H), 3.93 (br s, 2H), 3.75 (br s, 2H), 0.84 (br s, 4H).

Example 19

Pyrazin-2-yl-[7-(7H-pyrrolo[2,3-d]pyrimidin-4-yl)-4,7-diazaspiro[2.5]oct-4-yl]methanone $^1$H NMR (300 MHz, DMSO) δ=11.86 (s, 1H), 8.86 (s, 1H), 8.78 (m, 1H), 8.72 (br, 1H), 8.19 (br, 1H), 7.24 (br, 1H), 6.68 (br, 1H), 4.20-3.90 (br m, 6H), 0.70 (br s, 2H), 0.47 (br s, 2H).

Example 20

[7-(7H-Pyrrolo[2,3-d]pyrimidin-4-yl)-4,7-diazaspiro[2.5]oct-4-yl]-(3-trifluoromethylphenyl)methanone $^1$H NMR (300 MHz, DMSO) δ=11.74 (s, 1H), 8.14 (s, 1H), 7.93-7.77 (br m, 3H), 7.71 (t, J=7.7, 1H), 7.20 (br s, 1H), 6.62 (br s, 1H), 4.00-3.90 (br, 6H), 1.15-0.30 (br, 4H).

Example 21

2-Pyridin-4-yl-1-[7-(7H-pyrrolo[2,3-d]pyrimidin-4-yl)-4,7-diazaspiro[2.5]oct-4-yl]ethanone $^1$H NMR (600 MHz, DMSO) δ=11.76 (s, 1H), 8.51 (m, 2H), 8.14 (s, 1H), 7.34 (br s, 2H), 7.25-7.18 (m, 1H), 6.62 (br s, 1H), 4.10-3.75 (m, 8H), 1.28-0.85 (m, 4H).

Example 22

[7-(7H-Pyrrolo[2,3-d]pyrimidin-4-yl)-4,7-diazaspiro[2.5]oct-4-yl]-(tetrahydrofuran-2-yl)methanone $^1$H NMR (600 MHz, DMS) δ=11.73 (s, 1H), 8.13 (s, 1H), 7.18 (m, 1H), 6.60 (s, 1H), 4.95-4.57 (br, 1H), 4.10-3.67 (br m, 9H), 2.17-1.78 (br m, 3H), 1.05-0.87 (m, 4H).

Example 23

4-[7-(7H-Pyrrolo[2,3-d]pyrimidin-4-yl)-4,7-diazaspiro[2.5]octane-4-carbonyl]cyclohexanone $^1$H NMR (600 MHz, DMSO) δ=11.73 (s, 1H), 8.13 (br, 1H), 7.31-7.09 (m, 1H), 6.62 (s, 1H), 4.05-3.73 (br, 5H), 3.40 (br s, 1H), 3.30 (br, 3H), 2.25 (br, 2H), 2.04 (br, 2H), 1.79 (br, 2H), 1.27-0.99 (br, 2H), 0.95-0.89 (br, 2H).

Example 24

3,3,3-Trifluoro-1-[7-(7H-pyrrolo[2,3-d]pyrimidin-4-yl)-4,7-diazaspiro[2.5]oct-4-yl]propan-1-one $^1$H NMR (600 MHz, DMSO) δ=11.73 (s, 1H), 8.13 (m, 1H), 7.20 (m, 1H), 6.60 (s, 1H), 4.20-3.60 (br m, 8H), 1.120-0.90 (br m, 4H).

Example 25

3-{2-Oxo-2-[7-(7H-pyrrolo[2,3-d]pyrimidin-4-yl)-4,7-diazaspiro[2.5]oct-4-yl]-ethyl}benzonitrile $^1$H NMR (600 MHz, DMSO) δ=11.73 (s, 1H), 8.14 (s, 1H), 7.75 (m, 2H), 7.59 (m, 1H), 7.51 (m, 1H), 7.20 (m, 1H), 6.61 (br, 1H), 4.05-3.70 (m, 8H), 1.25-1.00 (br, 3H), 1.00-0.88 (br, 1H).

Example 26

Benzo[b]thiophen-2-yl-[7-(7H-pyrrolo[2,3-d]pyrimidin-4-yl)-4,7-diazaspiro[2.5]oct-4-yl]methanone $^1$H NMR (600 MHz, DMSO) δ=11.75 (s, 1H), 8.16 (s, 1H), 8.07-8.01 (m, 1H), 8.00-7.95 (m, 1H), 7.87 (s, 1H), 7.52-7.42 (m, 2H), 7.21 (dd, J=2.7, 3.2, 1H), 6.65 (d, J=1.6, 1H), 4.28-3.83 (m, 6H), 1.04-0.86 (m, 4H).

Example 27

Phenyl-[7-(7H-pyrrolo[2,3-d]pyrimidin-4-yl)-4,7-diazaspiro[2.5]oct-4-yl]methanone $^1$H NMR (300 MHz, DMSO) δ=11.98-11.46 (m, 1H), 8.14 (s, 1H), 7.55-7.39 (m, 5H), 7.19 (d, J=3.6, 1H), 6.61 (d, J=3.6, 1H), 4.10-3.65 (m, 6H), 0.97-0.57 (br, 4H).

Example 28

4,4,4-Trifluoro-1-[7-(7H-pyrrolo[2,3-d]pyrimidin-4-yl)-4,7-diazaspiro[2.5]oct-4-yl]butan-1-one $^1$H NMR (300 MHz, DMSO) δ=12.11-11.45 (br 1, 1H), 8.13 (s, 1H), 7.19 (s, 1H), 6.60 (s, 1H), 4.05-3.67 (br m, 6H), 2.82-2.70 (m, 2H), 2.70-2.45 (m, 2H), 1.16-0.85 (br, 4H).

Example 35

4-{2-Oxo-2-[7-(7H-pyrrolo[2,3-d]pyrimidin-4-yl)-4,7-diazaspiro[2.5]oct-4-yl]-ethyl}benzonitrile $^1$H NMR (600 MHz, DMSO) δ=11.73 (s, 1H), 8.13 (s, 1H), 7.76 (d, J=8.3, 2H), 7.45 (d, J=7.7, 2H), 7.22-7.14 (m, 1H), 6.60 (s, 1H), 4.07-3.71 (br m, 8H), 1.20-1.105 (br, 3H), 0.95-0.87 (br, 1H).

Example 36

(1H-Indol-6-yl)-[7-(7H-pyrrolo[2,3-d]pyrimidin-4-yl)-4,7-diazaspiro[2.5]oct-4-yl]methanone $^1$H NMR (300 MHz, DMSO) δ=11.79-11.48 (br, 1H), 11.34 (m, 1H), 8.26 (s, 1H), 7.94 (m, 1H), 7.73 (m, 2H), 7.70 (m, 1H), 7.51-7.44 (m, 2H), 7.17 (m, 6.61 (m, 1H), 4.03-3.8 (br, 6H), 0.88-0.76 (br, 4H).

Example 37

3-Methanesulfonyl-1-[7-(7H-pyrrolo[2,3-d]pyrimidin-4-yl)-4,7-diazaspiro[2.5]oct-4-yl]propan-1-one $^1$H NMR (300 MHz, DMSO) δ=11.91-10.80 (br, 1H), 8.14 (s, 1H), 7.19 (d, J=3.6, 1H), 6.60 (s, 1H), 4.08-3.70 (br m, 6H), 3.50-3.43 (br, 4H), 3.01 (br, 3H), 1.12-0.85 (br, 4H).

Example 41

2-Methyl-5-[7-(7H-pyrrolo[2,3-d]pyrimidin-4-yl)-4,7-diazaspiro[2.5]octane-4-carbonyl]-N-(3-trifluoromethylphenyl)benzamide $^1$H NMR (300 MHz, DMSO) δ=11.75 (s, 1H), 10.67-10.52 (br, 1H), 8.30-7.76 (br m, 4H), 7.68-7.53 (m, 2H), 7.48-7.38 (m, 2H), 7.22-7.16 (m, 1H), 6.64-6.59 (m, 1H), 4.10-3.70 (br, 5H), 3.50-3.17 (br, 4H), 1.10-0.65 (br, 4H).

Example 42

Pyridin-3-yl-[7-(7H-pyrrolo[2,3-d]pyrimidin-4-yl)-4,7-diazaspiro[2.5]oct-4-yl]methanone $^1$H NMR (600 MHz, DMSO) δ=11.75 (s, 1H), 8.74-8.61 (m, 2H), 8.15 (s, 1H), 7.93 (m, 1H), 7.50 (m, 1H), 7.20 (s, 1H), 6.63 (br s, 1H), 4.20-3.80 (br, 6H), 1.05-0.75 (br, 4H).

Example 43

1-{4-[7-(7H-Pyrrolo[2,3-d]pyrimidin-4-yl)-4,7-diazaspiro[2.5]octane-4-carbonyl]piperidin-1-yl}ethanone $^1$H NMR (600 MHz, DMSO) δ=11.73 (s, 1H), 8.13 (s, 1H), 7.26-7.16 (m, 1H), 6.61 (br s, 1H), 4.45-3.60 (br m, 8H), 3.08 (m, 2H), 1.99 (m, 3H), 1.78-0.72 (m, 8H).

Example 44

3-[7-(7H-Pyrrolo[2,3-d]pyrimidin-4-yl)-4,7-diazaspiro[2.5]octane-4-carbonyl]benzonitrile $^1$H NMR (300 MHz, DMSO) δ=11.72 (s, 1H), 8.14 (s, 1H), 8.03-7.91 (m, 2H), 7.82 (dd, J=3.9, 5.3, 1H), 7.67 (t, J=7.9, 1H), 7.19 (d, J=3.5, 1H), 6.61 (s, 1H), 4.20-3.62 (br m, 6H), 1.00-0.55 (br, 4H).

Example 48

[7-(7H-Pyrrolo[2,3-d]pyrimidin-4-yl)-4,7-diaza-spiro[2.5]oct-4-yl]-(4-trifluoromethylphenyl)methanone $^1$H NMR (600 MHz, DMSO) δ=11.74 (s, 1H), 8.14 (s, 1H), 7.83 (d, J=8.2, 2H), 7.72 (d, J=7.9, 2H), 7.20 (s, 1H), 6.61 (s, 1H), 4.15-3.85 (br, 5H), 3.68-3.48 (br, 1H), 1.15-0.46 (br, 4H).

Example 49

4-[7-(7H-Pyrrolo[2,3-d]pyrimidin-4-yl)-4,7-diaza-spiro[2.5]octane-4-carbonyl]benzamide $^1$H NMR (600 MHz, DMSO) δ=11.79 (s, 1H), 8.16 (s, 1H), 7.93 (m, 2H), 7.56 (d, J=8.2, 2H), 7.21 (s, 1H), 6.64 (s, 1H), 4.15-3.75 (br, 6H), 1.04-0.40 (br, 4H).

Example 50

1-{2-[7-(7H-Pyrrolo[2,3-d]pyrimidin-4-yl)-4,7-diazaspiro[2.5]octane-4-carbonyl]pyrrolidin-1-yl}ethanone $^1$H NMR (600 MHz, DMSO) δ=11.71 (s, 1H), 8.14 (d, J=8.9, 1H), 7.21-7.15 (m, 1H), 6.59 (s, 1H), 4.98 (m, 1H), 4.45-3.60 (br, 6H), 3.59-3.45 (m, 2H), 2.21-1.68 (br m, 7H), 1.31-0.70 (br m, 4H).

Example 54

3-Oxo-3-[7-(7H-pyrrolo[2,3-d]pyrimidin-4-yl)-4,7-diazaspiro[2.5]oct-4-yl]propionitrile $^1$H NMR (600 MHz, DMSO) δ=11.93 (s, 1H), 8.19 (s, 1H), 7.26 (s, 1H), 6.66 (s, 1H), 4.18 (s, 2H), 4.12-3.56 (br m, 6H), 1.16-0.95 (br m, 4H).

Example 55

(1H-Indol-2-yl)-[7-(7H-pyrrolo[2,3-d]pyrimidin-4-yl)-4,7-diazaspiro[2.5]oct-4-yl]methanone $^1$H NMR (600 MHz, DMSO) δ=11.73 (s, 1H), 11.57 (s, 1H), 8.15 (s, 1H), 7.63 (d, J=7.9, 1H), 7.47-7.37 (m, 1H), 7.25-7.15 (m, 2H), 7.09-7.03 (m, 1H), 6.93 (s, 1H), 6.64 (m, 1H), 4.02 (br s, 6H), 1.10 (br s, 2H), 0.92 (br s, 2H).

Example 56

5-[7-(7H-Pyrrolo[2,3-d]pyrimidin-4-yl)-4,7-diazaspiro[2.5]octane-4-carbonyl]-1H-pyridin-2-one $^1$H NMR (300 MHz, DMSO) δ=11.71 (br s, 2H), 8.14 (m, 1H), 8.04 (d, J=2.6, 1H), 7.79 (m, 1H), 7.57 (m, 1H), 7.24-7.17 (m, 1H), 6.60 (m, 1H), 4.02-3.73 (m, 6H), 0.94 (br, 2H), 0.83 (br, 2H).

Example 15

4-[7-(7H-Pyrrolo[2,3-d]pyrimidin-4-yl)-4,7-diaza-spiro[2.5]octane-4-carbonyl]benzonitrile $^1$H NMR (300 MHz, DMSO) δ=11.74 (s, 1H), 8.14 (s, 1H), 7.94 (d, J=8.3, 2H), 7.69 (d, J=7.8, 2H), 7.20 (br s, 1H), 6.61 (br s, 1H), 4.32-3.66 (br m, 6H), 1.42-0.23 (m, 4H).

Example 60

5-[7-(7H-Pyrrolo[2,3-d]pyrimidin-4-yl)-4,7-diaza-spiro[2.5]octane-4-carbonyl]-thiophene-3-carbonitrile 1H NMR (300 MHz, DMSO) δ=11.72 (s, 1H), 8.75 (d, J=1.1, 1H), 8.15 (s, 1H), 7.92 (d, J=1.1, 1H), 7.20 (d, J=3.6, 1H), 6.63 (d, J=3.6, 1H), 3.95 (m, 6H), 0.98 (m, 4H).

Example 61

(5,6-Dihydro-4H-cyclopenta[b]thiophen-2-yl)[7-(7H-pyrrolo[2,3-d]pyrimidin-4-yl)-4,7-diaza-spiro[2.5]oct-4-yl]-methanone 1H NMR (600 MHz, DMSO) δ=11.73 (s, 1H), 8.15 (s, 1H), 7.30 (s, 1H), 7.20 (m, 1H), 6.63 (m, 1H), 4.02 (m, 6H), 2.88 (t, J=7.3, 2H), 2.72 (t, J=7.2, 2H), 2.39 (m, 2H), 0.93 (m, 4H).

Example 62

(4-Methyl-thiophen-2-yl)-[7-(7H-pyrrolo[2,3-d]pyrimidin-4-yl)-4,7-diaza-spiro[2.5]oct-4-yl]-methanone 1H NMR (600 MHz, DMSO) δ=11.77 (s, 1H), 8.15 (s, 1H), 7.38 (s, 1H), 7.36 (s, 1H), 7.21 (d, J=3.6, 1H), 6.64 (d, J=3.6, 1H), 3.96 (m, 6H), 2.25 (s, 3H), 0.91 (m, 4H).

Example 63

4-{2-Oxo-2-[7-(7H-pyrrolo[2,3-d]pyrimidin-4-yl)-4,7-diaza-spiro[2.5]oct-4-yl]-acetyl}-benzenesulfonamide 1H NMR (300 MHz, DMSO) δ=11.76 (s, 1H), 8.08 (m, 4H), 7.64 (br, 2H), 7.22 (m, 1H), 6.62 (m, 1H), 3.99 (br m, 6H), 1.01 (br, 4H).

Example 64

4-{1,1-Difluoro-2-oxo-2-[7-(7H-pyrrolo[2,3-d]pyrimidin-4-yl)-4,7-diaza-spiro[2.5]oct-4-yl]-ethyl}-benzonitrile 1H NMR (600 MHz, DMSO) δ=11.74 (s, 1H), 8.11 (s, 1H), 8.00 (d, J=8.4, 2H), 7.78 (d, J=8.4, 2H), 7.19 (s, 1H), 6.56 (s, 1H), 3.85 (br, 6H), 1.00 (br, 4H).

Example 143

4-Oxo-4-[7-(7H-pyrrolo[2,3-d]pyrimidin-4-yl)-4,7-diaza-spiro[2.5]oct-4-yl]-butane-1-sulfonic acid amide 1H NMR (300 MHz, DMSO) δ=11.70 (s, 1H), 8.20 (s, 1H), 7.18 (m, 1H), 6.77 (s, 2H), 6.59 (s, 1H), 3.75 (br, 6H), 3.03 (m, 2H), 2.70 (m, 2H), 1.98 (m, 2H), 1.06 (br, 4H).

Example 66

2-Fluoro-5-{2-oxo-2-[7-(7H-pyrrolo[2,3-d]pyrimidin-4-yl)-4,7-diaza-spiro[2.5]oct-4-yl]-ethyl}-benzonitrile 1H NMR (600 MHz, DMSO) δ=11.78 (s, 1H), 8.15 (s, 1H), 7.82 (m, 1H), 7.66 (m, 1H), 7.46 (m, 1H), 7.21 (m, 1H), 6.62 (m, 1H), 3.81 (br, 8H), 1.12 (br, 4H).

Example 67

{3-[7-(7H-Pyrrolo[2,3-d]pyrimidin-4-yl)-4,7-diaza-spiro[2.5]octane-4-carbonyl]-phenoxy}-acetonitrile 1H NMR (600 MHz, DMSO) δ=11.74 (s, 1H), 8.14 (s, 1H), 7.45 (m, 1H), 7.17 (br, 4H), 6.60 (m, 1H), 5.24 (s, 2H), 3.92 (br, 6H), 0.99 (br, 4H).

Example 68

{4-[7-(7H-Pyrrolo[2,3-d]pyrimidin-4-yl)-4,7-diaza-spiro[2.5]octane-4-carbonyl]-phenoxy}-acetonitrile 1H NMR (600 MHz, DMSO) δ=11.72 (s, 1H), 8.14 (s, 1H), 7.53 (m, 2H), 7.19 (d, J=3.6, 1H), 7.13 (m, 2H), 6.57 (d, J=3.6, 1H), 5.24 (s, 2H), 4.01 (br, 4H), 3.78 (br, 2H), 0.80 (br, 4H).

Example 69

(4-{2-Oxo-2-[7-(7H-pyrrolo[2,3-d]pyrimidin-4-yl)-4,7-diaza-spiro[2.5]oct-4-yl]-ethyl}-phenoxy)-acetonitrile 1H NMR (600 MHz, DMSO) δ=11.72 (s, 1H), 8.13 (s, 1H), 7.23 (m, 2H), 7.19 (m, 1H), 6.99 (m, 2H), 6.59 (s, 1H), 5.13 (s, 2H), 3.87 (br, 4H), 3.72 (br, 4H), 0.99 (br, 4H).

Example 70

(3-{2-Oxo-2-[7-(7H-pyrrolo[2,3-d]pyrimidin-4-yl)-4,7-diaza-spiro[2.5]oct-4-yl]-ethyl}-phenoxy)-acetonitrile 1H NMR (600 MHz, DMSO) δ=11.72 (s, 1H), 8.12 (s, 1H), 7.29 (m, 1H), 7.18 (m, 1H), 6.94 (br, 3H), 6.56 (m, 3H), 5.14 (s, 2H), 3.83 (br, 8H), 0.99 (br, 4H).

Example 91

(5-Methyl-thiophen-2-yl)-[7-(7H-pyrrolo[2,3-d]pyrimidin-4-yl)-4,7-diaza-spiro[2.5]oct-4-yl]-methanone 1H NMR (600 MHz, DMSO) δ=11.75 (s, 1H), 8.16 (s, 1H), 7.35 (d, J=3.6, 1H), 7.21 (d, J=3.6, 1H), 6.85 (m, 1H), 6.63 (d, J=3.6, 1H), 4.00 (m, 6H), 0.93 (br, 4H).

Example 151

N-{2-Oxo-2-[7-(7H-pyrrolo[2,3-d]pyrimidin-4-yl)-4,7-diaza-spiro[2.5]oct-4-yl]-ethyl}-acetamide 1H NMR (600 MHz, DMSO) δ=11.83 (s, 1H), 8.16 (br, 2H), 7.22 (m, 1H), 6.64 (m, 1H), 3.74 (br, 8H), 1.86 (s, 3H), 1.15 (m, 4H).

Example 152

2-Phenyl-1-[7-(7H-pyrrolo[2,3-d]pyrimidin-4-yl)-4,7-diaza-spiro[2.5]oct-4-yl]-ethanone 1H NMR (600 MHz, DMSO) δ=11.72 (s, 1H), 8.13 (s, 1H), 7.30 (m, 2H), 7.23 (m, 3H), 7.19 (m, 1H), 6.57 (m, 1H), 3.82 (br, 8H), 1.03 (m, 4H).

Example 153

3-Phenyl-1-[7-(7H-pyrrolo[2,3-d]pyrimidin-4-yl)-4,7-diaza-spiro[2.5]oct-4-yl]-propan-1-one 1H NMR (600 MHz, DMSO) δ=11.71 (s, 1H), 8.12 (s, 1H), 7.25 (d, J=3.9, 4H), 7.18 (m, 1H), 7.13 (d, J=3.9, 1H), 6.56 (s, 1H), 3.70 (br, 6H), 2.86 (m, 4H), 0.99 (br, 4H).

Example 154

(1-Phenyl-cyclopropyl)-[7-(7H-pyrrolo[2,3-d]pyrimidin-4-yl)-4,7-diaza-spiro[2.5]oct-4-yl]-methanone 1H NMR (600 MHz, DMSO) δ=11.69 (s, 1H), 8.09 (s, 1H), 7.30 (m, 2H), 7.17 (br m, 4H), 6.52 (s, 1H), 3.61 (m, 6H), 1.34 (m, 2H), 1.11 (m, 2H), 0.92 (m, 4H).

Example 155

(4-Hydroxymethyl-phenyl)-[7-(7H-pyrrolo[2,3-d]pyrimidin-4-yl)-4,7-diaza-spiro[2.5]oct-4-yl]-methanone 1H NMR (600 MHz, DMSO) δ=11.73 (s, 1H), 8.14 (s, 1H), 7.45 (d, J=8.1, 2H), 7.38 (m, 2H), 7.19 (m, 1H), 6.61 (s, 1H), 5.31 (t, J=5.7, 1H), 4.55 (m, 2H), 3.89 (br, 6H), 1.04 (m, 4H).

Example 157

(1H-Indol-5-yl)-[7-(7H-pyrrolo[2,3-d]pyrimidin-4-yl)-4,7-diaza-spiro[2.5]oct-4-yl]-methanone 1H NMR (600 MHz, DMSO) δ=11.72 (s, 1H), 11.32 (s, 1H), 8.14 (s, 1H), 7.74 (s, 1H), 7.43 (m, 2H), 7.24 (m, 1H), 7.18 (m, 1H), 6.60 (m, 1H), 6.52 (m, 1H), 3.96 (br, 4H), 3.79 (br, 2H), 0.81 (m, 4H).

Example 158

(4-Hydroxy-cyclohexyl)-[7-(7H-pyrrolo[2,3-d]pyrimidin-4-yl)-4,7-diaza-spiro[2.5]oct-4-yl]-methanone 1H NMR (600 MHz, DMSO) δ=11.72 (s, 1H), 8.13 (s, 1H), 7.19 (m, 1H), 6.60 (m, 1H), 4.28 (m, 1H), 3.78 (m, 7H), 2.91 (m, 1H), 1.76 (m, 4H), 1.45 (m, 2H), 1.36 (m, 2H), 1.01 (m, 4H).

Example 159

(1H-Indol-4-yl)-[7-(7H-pyrrolo[2,3-d]pyrimidin-4-yl)-4,7-diaza-spiro[2.5]oct-4-yl]-methanone 1H NMR (600 MHz, DMSO) δ=11.71 (s, 1H), 11.32 (s, 1H), 8.13 (s, 1H), 7.51 (m, 1H), 7.42 (m, 1H), 7.15 (m, 3H), 6.58 (m, 1H), 6.36 (m, 1H), 3.93 (br, 4H), 3.65 (br, 2H), 1.10 (m, 4H).

Example 160

[7-(7H-Pyrrolo[2,3-d]pyrimidin-4-yl)-4,7-diaza-spiro[2.5]oct-4-yl]-(3-trifluoromethoxy-phenyl)-methanone 1H NMR (600 MHz, DMSO) δ=11.74 (s, 1H), 8.15 (s, 1H), 7.61 (m, 1H), 7.52 (m, 3H), 7.20 (s, 1H), 6.62 (s, 1H), 3.88 (br, 6H), 0.82 (m, 4H).

Example 161

[7-(7H-Pyrrolo[2,3-d]pyrimidin-4-yl)-4,7-diaza-spiro[2.5]oct-4-yl]-quinoxalin-2-yl-methanone 1H NMR (600 MHz, DMSO) δ=11.79 (s, 1H), 9.18 (s, 1H), 8.18 (br, 3H), 7.97 (br, 2H), 7.22 (m, 1H), 6.63 (m, 1H), 4.04 (m, 6H), 1.99 (br, 1H), 0.57 (br, 3H). Rotamers observed.

Example 162

(1H-Benzoimidazol-5-yl)-[7-(7H-pyrrolo[2,3-d]pyrimidin-4-yl)-4,7-diaza-spiro[2.5]oct-4-yl]-methanone 1H NMR (600 MHz, DMSO) δ=12.6 (br, 1H), 11.73 (s, 1H), 8.33 (s, 1H), 8.15 (m, 1H), 7.75 (s, 1H), 7.63 (m, 1H), 7.35 (m, 1H), 7.18 (m, 1H), 6.61 (m, 1H), 4.01 (br, 4H), 3.83 (br5, 2H), 0.81 (m, 4H).

Example 163

[7-(7H-Pyrrolo[2,3-d]pyrimidin-4-yl)-4,7-diaza-spiro[2.5]oct-4-yl]-quinolin-3-yl-methanone 1H NMR (600 MHz, DMSO) δ=11.75 (s, 1H), 9.00 (s, 1H), 8.57 (m, 1H), 8.15 (m, 1H), 8.10 (m, 2H), 7.87 (m, 1H), 7.70 (m, 1H), 7.21 (s, 1H), 6.69 (m, 1H), 4.04 (br, 6H), 0.84 (m, 4H).

Example 164

[7-(7H-Pyrrolo[2,3-d]pyrimidin-4-yl)-4,7-diaza-spiro[2.5]oct-4-yl]-quinolin-8-yl-methanone 1H NMR (600 MHz, DMSO) δ=11.72 (s, 1H), 8.92 (s, 1H), 8.44 (m, 1H), 8.13 (m, 1H), 8.05 (m, 1H), 7.69 (m, 2H), 7.59 (m, 1H), 7.17 (m, 1H), 6.56 (m, 1H), 4.01 (br, 6H), 1.15 (m, 2H), 0.40 (m, 2H).

Example 165

1-[7-(7H-Pyrrolo[2,3-d]pyrimidin-4-yl)-4,7-diaza-spiro[2.5]octane-4-carbonyl]-cyclopropanecarbonitrile 1H NMR (300 MHz, DMSO) δ=11.72 (s, 1H), 8.15 (s, 1H), 7.20 (m, 1H), 6.61 (m, 1H), 3.98 (br, 6H), 1.57 (m, 4H), 1.09 (m, 4H).

Example 166

(6-Hydroxy-pyridin-2-yl)-[7-(7H-pyrrolo[2,3-d]pyrimidin-4-yl)-4,7-diaza-spiro[2.5]oct-4-yl]-methanone 1H NMR (600 MHz, DMSO) δ=11.81 (s, 1H), 8.17 (s, 1H), 7.57 (m, 1H), 7.22 (m, 1H), 6.59 (br m, 3H), 3.83 (br, 6H), 0.89 (m, 4H).

Example 167

4-Oxo-4-[7-(7H-pyrrolo[2,3-d]pyrimidin-4-yl)-4,7-diaza-spiro[2.5]oct-4-yl]-butyronitrile 1H NMR (600 MHz, DMSO) δ=11.73 (s, 1H), 8.14 (s, 1H), 7.20 (m, 1H), 6.59 (m, 1H), 3.83 (br, 6H), 2.91 (m, 2H), 2.67 (m, 2H), 1.04 (m, 4H).

Example 183

(2-Fluoro-4-methanesulfonyl-phenyl)-[7-(7H-pyrrolo[2,3-d]pyrimidin-4-yl)-4,7-diaza-spiro[2.5]oct-4-yl]-methanone 1H NMR (300 MHz, DMSO) δ=11.80 (s, 1H), 8.18 (s, 1H), 7.88 (m, 3H), 7.22 (s, 1H), 6.62 (m, 1H), 3.98 (b, 6H), 3.34 (s, 3H), 1.10 (m, 2H), 0.68 (m, 2H).

Example 184

(5-Methyl-1H-indol-2-yl)-[7-(7H-pyrrolo[2,3-d]pyrimidin-4-yl)-4,7-diaza-spiro[2.5]oct-4-yl]-methanone 1H NMR (300 MHz, DMSO) δ=11.85 (s, 1H), 11.43 (s, 1H), 8.17 (m, 1H), 7.39 (s, 1H), 7.33 (m, 1H), 7.24 (m, 1H), 7.03 (m, 1H), 6.83 (m, 1H), 6.69 (m, 1H), 4.04 (br, 6H), 2.37 (s, 3H), 1.01 (m, 4H).

Example 185

(5-Fluoro-3-methyl-1H-indol-2-yl)-[7-(7H-pyrrolo[2,3-d]pyrimidin-4-yl)-4,7-diaza-spiro[2.5]oct-4-yl]-methanone 1H NMR (300 MHz, DMSO) δ=11.93 (s, 1H), 11.34 (s, 1H), 8.21 (s, 1H), 7.35 (m, 2H), 7.25 (m, 1H), 7.04 (m, 1H), 6.67 (m, 1H), 3.97 (br, 4H), 3.79 (br, 2H), 2.25 (s, 3H), 0.97 (m, 4H).

Example 186

2-[7-(7H-Pyrrolo[2,3-d]pyrimidin-4-yl)-4,7-diaza-spiro[2.5]octane-4-carbonyl]-1H-indole-5-sulfonic acid amide 1H NMR (300 MHz, DMSO) δ=11.99 (s, 1H), 11.73 (s, 1H), 8.14 (m, 2H), 7.63 (m, 2H), 7.18 (m, 4H), 6.64 (m, 1H), 4.04 (br, 6H), 0.98 (m, 4H).

Example 187

1-Methyl-5-[7-(7H-pyrrolo[2,3-d]pyrimidin-4-yl)-4,7-diaza-spiro[2.5]octane-4-carbonyl]-1H-pyrrole-2-sulfonic acid amide 1H NMR (300 MHz, DMSO) δ=12.65 (s, 1H), 8.41 (s, 1H), 7.47 (s, 1H), 7.43 (m, 1H), 6.98 (br, 3H), 6.69 (m, 1H), 3.87 (br, 9H), 0.96 (m, 4H).

Example 188

1-Methyl-5-[7-(7H-pyrrolo[2,3-d]pyrimidin-4-yl)-4,7-diaza-spiro[2.5]octane-4-carbonyl]-1H-pyrrole-3-sulfonic acid amide 1H NMR (300 MHz, DMSO) δ=11.74 (s, 1H), 8.15 (s, 1H), 7.41 (d, J=1.7, 1H), 7.20 (m, 1H), 7.03 (s, 2H), 6.68 (d, J=1.7, 1H), 6.63 (m, 1H), 3.93 (br, 6H), 3.70 (s, 3H), 0.94 (m, 2H), 0.84 (m, 2H).

Example 189

N,N-Dimethyl-4-[7-(7H-pyrrolo[2,3-d]pyrimidin-4-yl)-4,7-diaza-spiro[2.5]octane-4-carbonyl]-benzene-sulfonamide 1H NMR (300 MHz, DMSO) δ=11.82 (s, 1H), 8.16 (s, 1H), 7.82 (d, J=8.3, 2H), 7.75 (d, J=8.3, 2H), 7.22 (m, 1H), 6.65 (m, 1H), 3.69 (m, 6H), 2.65 (s, 6H), 0.84 (m, 4H).

Example 190

1-[7-(7H-Pyrrolo[2,3-d]pyrimidin-4-yl)-4,7-diaza-spiro[2.5]oct-4-yl]-2-thiophen-2-yl-ethanone 1H NMR (300 MHz, DMSO) δ=11.76 (s, 1H), 8.14 (1, 1H), 7.37 (m, 1H), 7.20 (m, 1H), 6.96 (m, 2H), 6.60 (s, 1H), 3.89 (br, 8H), 1.09 (m, 4H).

Example 191

4-{2-Oxo-2-[7-(7H-pyrrolo[2,3-d]pyrimidin-4-yl)-4,7-diaza-spiro[2.5]oct-4-yl]-ethyl}-benzenesulfonamide 1H NMR (300 MHz, DMSO) δ=11.81 (s, 1H), 8.17 (s, 1H), 7.75 (m, 2H), 7.41 (m, 2H), 7.30 (s, 2H), 7.22 (m, 1H), 6.63 (s, 1H), 3.86 (br, 8H), 1.15 (m, 4H).

Example 192

(5,7-Difluoro-1H-indol-2-yl)-[7-(7H-pyrrolo[2,3-d]pyrimidin-4-yl)-4,7-diaza-spiro[2.5]oct-4-yl]-methanone 1H NMR (300 MHz, DMSO) δ=12.18 (s, 1H), 11.83 (s, 1H), 8.18 (s, 1H), 7.25 (m, 2H), 7.08 (m, 1H), 6.95 (m, 1H), 6.67 (m, 1H), 4.00 (br, 6H), 0.97 (m, 4H).

Example 193

5-[7-(7H-Pyrrolo[2,3-d]pyrimidin-4-yl)-4,7-diaza-spiro[2.5]octane-4-carbonyl]-thiophene-2-carbonitrile 1H NMR (300 MHz, DMSO) δ=11.81 (s, 1H), 8.17 (s, 1H), 7.99 (d, J=4.0, 1H), 7.64 (d, J=4.0, 1H), 7.23 (m, 1H), 6.65 (m, 1H), 3.99 (br, 6H), 1.01 (m, 2H), 0.88 (m, 2H).

Example 194

(4-Methanesulfonyl-3-pyrrolidin-1-yl-phenyl)-[7-(7H-pyrrolo[2,3-d]pyrimidin-4-yl)-4,7-diaza-spiro[2.5]oct-4-yl]-methanone 1H NMR (300 MHz, DMSO) δ=11.79 (s, 1H), 8.16 (s, 1H), 7.94 (d, J=8.2, 1H), 7.50 (s, 1H), 7.29 (d, J=8.2, 1H), 7.22 (m, 1H), 6.64 (s, 1H), 3.87 (br, 6H), 3.25 (br, 7H), 1.91 (m, 4H), 0.85 (m, 4H).

Example 195

5-{2-Oxo-2-[7-(7H-pyrrolo[2,3-d]pyrimidin-4-yl)-4,7-diaza-spiro[2.5]oct-4-yl]-ethyl}-thiophene-2-sulfonic acid amide 1H NMR (300 MHz, DMSO) δ=11.92 (s, 1H), 8.21 (s, 1H), 7.55 (s, 2H), 7.37 (m, 1H), 7.26 (m, 1H), 6.97 (s, 1H), 6.67 (s, 1H), 3.99 (br, 8H), 1.10 (m, 4H).

Example 196

[4-(Propane-2-sulfonyl)-phenyl]-[7-(7H-pyrrolo[2,3-d]pyrimidin-4-yl)-4,7-diaza-spiro[2.5]oct-4-yl]-methanone 1H NMR (300 MHz, DMSO) δ=11.75 (s, 1H), 8.15 (s, 1H), 7.93 (d, J=8.3, 2H), 7.77 (d, J=8.3, 2H), 7.20 (m, 1H), 6.62 (s, 1H), 4.00 (br, 6H), 3.49 (m, 1H), 1.18 (d, J=6.8, 6H), 0.79 (m, 4H).

Example 197

4-{3-Oxo-3-[7-(7H-pyrrolo[2,3-d]pyrimidin-4-yl)-4,7-diaza-spiro[2.5]oct-4-0]-propenyl}-benzene-sulfonamide 1H NMR (300 MHz, DMSO) δ=11.72 (s, 1H), 8.15 (s, 1H), 7.85 (br m, 5H), 7.42 (br, 3H), 7.20 (m, 1H), 6.61 (m, 1H), 3.95 (br, 6H), 1.10 (m, 4H).

Example 198

5-[7-(7H-Pyrrolo[2,3-d]pyrimidin-4-yl)-4,7-diaza-spiro[2.5]octane-4-carbonyl]-furan-2-sulfonic acid amide 1H NMR (300 MHz, DMSO) δ=11.74 (s, 1H), 8.15 (s, 1H), 7.95 (br, 2H), 7.21 (m, 1H), 7.09 (m, 2H), 6.63 (m, 1H), 3.98 (br, 6H), 0.98 (m, 2H), 0.81 (m, 2H).

Example 204

4-[7-(7H-Pyrrolo[2,3-d]pyrimidin-4-yl)-4,7-diaza-spiro[2.5]octane-4-carbonyl]-N-thiophen-2-ylmethyl-benzenesulfonamide 1H NMR (300 MHz, DMSO) δ=11.73 (s, 1H), 8.40 (s, 1H), 8.15 (s, 1H), 7.85 (br, 2H), 7.66 (br, 2H), 7.39 (br, 1H), 7.20 (br, 1H), 6.90 (br, 2H), 6.62 (s, 1H), 4.24 (s, 2H), 3.92 (br, 6H), 0.84 (br, 4H).

Example 205

1-[7-(7H-Pyrrolo[2,3-d]pyrimidin-4-yl)-4,7-diaza-spiro[2.5]oct-4-yl]-2-thiophen-2-yl-ethane-1,2-dlone 1H NMR (300 MHz, DMSO) δ=11.84 (s, 1H), 8.24 (m, 1H), 8.19 (s, 1H), 7.83 (m, 1H), 7.32 (m, 1H), 7.23 (m, 1H), 6.65 (m, 1H), 4.13 (br, 2H), 3.95 (br, 4H), 0.85 (m, 4H).

Example 206

(5-Methoxy-thiophen-2-yl)-[7-(7H-pyrrolo[2,3-d]pyrimidin-4-yl)-4,7-diaza-spiro[2.5]oct-4-yl]-methanone 1H NMR (300 MHz, DMSO) δ=11.80 (s, 1H), 8.16 (s, 1H), 7.30 (d, J=4.2, 1H), 7.22 (m, 1H), 6.65 (m, 1H), 6.36 (d, J=4.2, 1H), 4.03 (br, 2H), 3.96 (br, 4H), 3.92 (s, 3H), 1.02 (m, 2H), 0.90 (m, 2H).

Example 207

(5-Propyl-thiophen-3-yl)-[7-(7H-pyrrolo[2,3-d]pyrimidin-4-yl)-4,7-diaza-spiro[2.5]oct-4-yl]-methanone 1H NMR (300 MHz, DMSO) δ=11.88 (s, 1H), 8.19 (s, 1H), 7.64 (m, 1H), 7.24 (m, 1H), 6.97 (s, 1H), 6.68 (s, 1H), 3.93 (br, 6H), 2.78 (m, 2H), 1.65 (m, 2H), 0.91 (br m, 5H), 0.77 (m, 2H).

Example 208

(4-Bromo-5-methyl-thiophen-2-yl)-[7-(7H-pyrrolo[2,3-d]pyrimidin-4-yl)-4,7-diaza-spiro[2.5]oct-4-yl]-methanone 1H NMR (300 MHz, DMSO) δ=11.76 (s, 1H), 8.20 (s, 1H), 7.45 (s, 1H), 7.21 (s, 1H), 6.67 (s, 1H), 3.97 (br, 6H), 2.40 (s, 3H), 0.95 (m, 4H).

Example 209

(4-Bromo-5-ethyl-thiophen-2-yl)-[7-(7H-pyrrolo[2,3-d]pyrimidin-4-yl)-4,7-diaza-spiro[2.5]oct-4-yl]-methanone 1H NMR (300 MHz, DMSO) δ=11.80 (s, 1H), 8.15 (s, 1H), 7.46 (s, 1H), 7.22 (m, 1H), 6.66 (m, 1H), 3.98 (br, 6H), 2.79 (q, J=7.5, 2H), 1.24 (t, J=7.5, 3H), 0.98 (m, 4H).

Example 210

Ethanesulfonic acid {4-[7-(7H-pyrrolo[2,3-d]pyrimidin-4-yl)-4,7-diaza-spiro[2.5]octane-4-carbonyl]-phenyl}-amide 1H NMR (300 MHz, DMSO) δ=11.73 (s, 1H), 10.22 (s, 1H), 8.14 (s, 1H), 7.47 (m, 2H), 7.27 (m, 2H), 7.19 (m, 1H), 6.61 (m, 1H), 3.89 (br, 6H), 3.17 (m, 2H), 1.19 (m, 3H), 0.79 (m, 4H).

Example 211

[7-(7H-Pyrrolo[2,3-d]pyrimidin-4-yl)-4,7-diaza-spiro[2.5]oct-4-yl]-thiophen-2-yl-methanone 1H NMR (600 MHz, DMSO) δ=11.73 (s, 1H), 8.14 (s, 1H), 7.79 (m, 1H), 7.54 (m, 1H), 7.20 (m, 1H), 7.16 (m, 1H), 6.63 (m, 1H), 3.98 (br, 6H), 0.99 (m, 2H), 0.84 (m, 2H).

Example 212

(2,3-Dimethoxy-phenyl)-[7-(7H-pyrrolo[2,3-d]pyrimidin-4-yl)-4,7-diaza-spiro[2.5]oct-4-yl]-methanone 1H NMR (600 MHz, DMSO) δ=11.72 (s, 1H), 8.13 (br, 1H), 7.18 (m, 1H), 7.11 (m, 2H), 6.84 (m, 1H), 6.60 (m, 1H), 3.97 (m, 4H), 3.84 (s, 3H), 3.76 (s, 3H), 3.70 (br, 2H), 1.05 (m, 2H), 0.59 (m, 2H).

Example 213

(3,5-Dimethoxy-phenyl)-[7-(7H-pyrrolo[2,3-d]pyrimidin-4-yl)-4,7-diaza-spiro[2.5]oct-4-yl]-methanone 1H NMR (600 MHz, DMSO) δ=11.73 (s, 1H), 7.19 (m, 1H), 6.58 (br m, 4H), 3.87 br, 4H), 3.77 (s, 6H), 3.64 (br, 2H), 0.84 (m, 4H).

Example 214

Benzo[b]thiophen-3-yl-[7-(7H-pyrrolo[2,3-d]pyrimidin-4-yl)-4,7-diaza-spiro[2.5]oct-4-yl]-methanone 1H NMR (600 MHz, DMSO) δ=11.73 (s, 1H), 8.14 (s, 1H), 8.11 (m, 1H), 8.07 (m, 1H), 7.83 (m, 1H), 7.44 (m, 2H), 7.19 (m, 1H), 6.61 (m, 1H), 3.92 (br, 6H), 1.03 (m, 4H).

Example 215

(5-Phenyl-thiophen-2-yl)-[7-(7H-pyrrolo[2,3-d]pyrimidin-4-yl)-4,7-diaza-spiro[2.5]oct-4-yl]-methanone 1H NMR (600 MHz, DMSO) δ=11.74 (s, 1H), 8.15 (s, 1H), 7.73 (m, 2H), 7.55 (m, 2H), 7.46 (m, 2H), 7.38 (m, 1H), 7.21 (m, 1H), 6.65 (m, 1H), 4.01 (br, 6H), 1.03 (m, 2H), 0.91 (m, 2H).

Example 216

(2-Methoxy-pyridin-3-yl)-[7-(7H-pyrrolo[2,3-d]pyrimidin-4-yl)-4,7-diaza-spiro[2.5]oct-4-yl]-methanone 1H NMR (600 MHz, DMSO) δ=11.73 (s, 1H), 8.25 (m, 1H), 8.14 (m, 1H), 7.73 (m, 1H), 7.19 m, 1H), 7.08 (m, 1H), 6.60 (m, 1H), 3.93 (br, 9H), 1.05 (m, 2H), 0.60 (m, 2H).

Example 217

2-[7-(7H-Pyrrolo[2,3-d]pyrimidin-4-yl)-4,7-diaza-spiro[2.5]octane-4-carbonyl]-1H-indole-5-carbonitrile 1H NMR (600 MHz, DMSO) δ=12.16 (s, 1H), 11.74 (s, 1H), 8.20 (s, 1H), 8.15 (s, 1H), 7.59 (d, J=8.6, 1H), 7.54 (d, J=8.6, 1H), 7.21 (m, 1H), 7.08 (s, 1H), 6.64 (s, 1H), 4.03 (br, 6H), 1.05 (m, 2H), 0.92 (m, 2H).

Example 218

[7-(7H-Pyrrolo[2,3-d]pyrimidin-4-yl)-4,7-diaza-spiro[2.5]oct-4-yl]-(5,6,7,8-tetrahydro-naphthalen-2-yl)-methanone 1H NMR (600 MHz, DMSO) δ=11.72 (s, 1H), 8.14 (s, 1H), 7.17 (m, 3H), 7.11 (m, 1H), 6.60 (s, 1H), 3.86 (br, 6H), 2.75 (m, 4H), 1.75 (m, 4H), 0.86 (m, 4H).

Example 219

2-Fluoro-4-[7-(7H-pyrrolo[2,3-d]pyrimidin-4-yl)-4,7-diaza-spiro[2.5]octane-4-carbonyl]-benzonitrile 1H NMR (300 MHz, DMSO) δ=11.73 (s, 1H), 8.14 (s, 1H), 8.04 (m, 1H), 7.70 (m, 1H), 7.53 (m, 1H), 7.20 (s, 1H), 6.61 (m, 1H), 3.91 (br, 6H), 0.67 (m, 4H).

Example 220

Using Intermediate 15

3-Oxo-3-[7-(1H-pyrrolo[2,3-b]pyridin-4-yl)-4,7-diaza-spiro[2.5]oct-4-yl]-propionitrile 1H NMR (600 MHz, DMSO) δ=11.41 (s, 1H), 7.94 (d, J=5.4, 1H), 7.23 (m, 1H), 6.42 (s, 1H), 6.38 (d, J=5.4, 1H), 4.17 (br, 2H), 3.81 (br, 6H), 1.08 (m, 4H).

Example 221

Using Intermediate 15

Phenyl-[7-(1H-pyrrolo[2,3-b]pyridin-4-yl)-4,7-diaza-spiro[2.5]oct-4-yl]-methanone 1H NMR (600 MHz, DMSO) δ=11.41 (s, 1H), 7.94 (d, J=5.4, 1H), 7.47 (m, 5H), 7.23 (m, 1H), 6.43 (m, 2H), 3.81 (br, 2H), 3.42 (br, 4H), 1.03 (m, 4H).

Example 222

Using Intermediate 15

Pyridin-2-yl-[7-(1H-pyrrolo[2,3-b]pyridin-4-yl)-4,7-diaza-spiro[2.5]oct-4-yl]-methanone 1H NMR (600 MHz, DMSO) δ=11.41 (s, 1H), 8.60 (d, J=4.6, 1H), 7.94 (m, 2H), 7.54 (m, 2H), 7.23 (s, 1H), 6.43 (m, 2H), 3.66 (br, 6H), 1.07 (m, 1H), 0.56 (m, 3H). Rotamers observed.

Example 223

Using Intermediate 15

Pyridin-3-yl-[7-(1H-pyrrolo[2,3-b]pyridin-4-yl)-4,7-diaza-spiro[2.5]oct-4-yl]-methanone 1H NMR (600 MHz, DMSO) δ=11.41 (s, 1H), 8.68 (m, 2H), 7.92 (m, 2H), 7.49 (m, 1H), 7.23 (m, 1H), 6.39 (m, 2H), 3.48 (br, 6H), 0.97 (m, 4H).

Example 224

Using Intermediate 15

Pyridin-4-yl-[7-(1H-pyrrolo[2,3-b]pyridin-4-yl)-4,7-diaza-spiro[2.5]oct-4-yl]-methanone 1H NMR (600 MHz, DMSO) δ=11.42 (s, 1H), 8.68 (m, 2H), 7.94 (m, 1H), 7.47 (s, 2H), 7.24 (s, 1H), 6.41 (m, 2H), 3.67 (br, 6H), 1.09 (m, 2H), 0.65 (m, 2H). Rotamers observed.

Example 225

Using Intermediate 15

Pyrazin-2-yl-[7-(1H-pyrrolo[2,3-b]pyridin-4-yl)-4,7-diaza-spiro[2.5]oct-4-yl]-methanone 1H NMR (600 MHz, DMSO) δ=11.42 (s, 1H), 8.88 (m, 1H), 8.74 (m, 2H), 7.95 (m, 1H), 7.24 (s, 1H), 6.43 (m, 2H), 3.61 br, 6H), 1.08 (m, 1H), 0.60 (m, 3H).

Example 226

Using Intermediate 15

4-[7-(1H-Pyrrolo[2,3-b]pyridin-4-yl)-4,7-diaza-spiro[2.5]octane-4-carbonyl]-benzonitrile 1H NMR (600 MHz, DMSO) δ=11.41 (s, 1H), 7.94 (m, 3H), 7.68 (m, 2H), 7.23 (s, 1H), 6.44 (s, 2H), 3.64 (m, 6H), 0.93 (m, 4H).

Example 227

Using Intermediate 15

3-[7-(1H-Pyrrolo[2,3-b]pyridin-4-yl)-4,7-diaza-spiro[2.5]octane-4-carbonyl]-benzonitrile 1H NMR (600 MHz, DMSO) δ=11.41 (s, 1H), 7.96 (m, 3H), 7.82 (m, 1H), 7.67 (m, 1H), 7.23 (m, 1H), 6.40 (m, 2H), 3.56 (m, 6H), 0.93 (m, 4H).

Example 228

Using Intermediate 15

(3-Methyl-thiophen-2-yl)-[7-(1H-pyrrolo[2,3-b]pyridin-4-yl)-4,7-diaza-spiro[2.5]oct-4-yl]-methanone 1H NMR (600 MHz, DMSO) δ=11.41 (s, 1H), 7.94 (m, 1H), 7.61 (d, J=5.0, 1H), 7.23 (m, 1H), 6.96 (d, J=5.0, 1H), 6.43 (m, 2H), 3.78 (br, 2H), 3.41 (br, 4H), 2.21 (s, 3H), 0.93 (m, 4H).

Example 229

Using Intermediate 15

[7-(1H-Pyrrolo[2,3-b]pyridin-4-yl)-4,7-diaza-spiro[2.5]oct-4-yl]-(3-trifluoromethoxy-phenyl)-methanone 1H NMR (600 MHz, DMSO) δ=11.41 (s, 1H), 7.95 (m, 1H), 7.60 (m, 1H), 7.51 (m, 3H), 7.23 (m, 1H), 6.44 (s, 2H), 3.62 (m, 6H), 1.04 (m, 4H).

Example 230

Using Intermediate 15

{4-[7-(1H-Pyrrolo[2,3-b]pyridin-4-yl)-4,7-diaza-spiro[2.5]octane-4-carbonyl]-phenyl}-acetonitrile 1H NMR (600 MHz, DMSO) δ=11.41 (s, 1H), 7.92 (m, 1H), 7.52 (d, J=8.2, 2H), 7.43 (d, J=8.2, 2H), 7.23 (m, 1H), 6.44 (s, 2H), 4.12 (s, 2H), 3.64 (br, 6H), 1.01 (m, 4H).

Example 231

Using Intermediate 15

(5-Methyl-thiophen-2-yl)-[7-(1H-pyrrolo[2,3-b]pyridin-4-yl)-4,7-diaza-spiro[2.5]oct-4-yl]-methanone 1H NMR (600 MHz, DMSO) δ=11.41 (s, 1H), 7.94 (m, 1H), 7.34 (m, 1H), 7.23 (m, 1H), 6.85 (m, 1H), 6.46 (m, 1H), 6.42 (m, 1H), 3.96 (br, 2H), 3.45 (br, 4H), 2.48 (s, 3H), 1.01 (m, 2H), 0.89 (m, 2H).

Example 232

Using Intermediate 15

(3-Methyl-benzo[b]thiophen-2-yl)-[7-(1H-pyrrolo[2,3-b]pyridin-4-yl)-4,7-diaza-spiro[2.5]oct-4-yl]-methanone 1H NMR (600 MHz, DMSO) δ=11.42 (s, 1H), 8.00 (m, 1H), 7.95 (m, 1H), 7.86 (m, 1H), 7.48 (m, 2H), 7.23 (m, 1H), 6.43 (m, 2H), 3.83 (br, 2H), 3.47 (br, 4H), 2.40 (s, 3H), 0.99 (m, 4H).

Example 233

Using Intermediate 15

Benzo[b]thiophen-3-yl-[7-(1H-pyrrolo[2,3-b]pyridin-4-yl)-4,7-diaza-spiro[2.5]oct-4-yl]-methanone 1H NMR (600 MHz, DMSO) δ=11.37 (s, 1H), 8.07 (m, 2H), 7.93 m, 1H), 7.79 (m, 1H), 7.44 (m, 2H), 7.21 (m, 1H), 6.43 (m, 2H), 3.83 (br, 2H), 3.45 (br, 4H), 0.94 (m, 4H).

Example 234

Using Intermediate 15

(5-Methyl-benzo[b]thiophen-2-yl)-[7-(1H-pyrrolo[2,3-b]pyridin-4-yl)-4,7-diaza-spiro[2.5]oct-4-yl]-methanone 1H NMR (600 MHz, DMSO) δ=11.42 (s, 1H), 7.96 (m, 1H), 7.90 (m, 1H), 7.75 (m, 2H), 7.30 (m, 1H), 7.25 (m, 1H), 6.47 (m, 2H), 4.02 (br, 2H), 3.49 b (r, 4H), 2.43 (s, 3H), 1.02 (m, 2H), 0.93 (m, 2H).

Example 235

Using Intermediate 15

2-[7-(1H-Pyrrolo[2,3-b]pyridin-4-yl)-4,7-diaza-spiro[2.5]octane-4-carbonyl]-benzonitrile 1H NMR (600 MHz, DMSO) δ=11.43 (s, 1H), 7.96 m, 2H), 7.79 (m, 1H), 7.68 (m, 2H), 7.24 (s, 1H), 6.40 (m, 2H), 4.04 (br, 2H), 3.56 (br, 4H), 1.13 (m, 2H), 0.65 (m, 2H).

Example 236

Using Intermediate 15

3-{2-Oxo-2-[7-(1H-pyrrolo[2,3-b]pyridin-4-yl)-4,7-diaza-spiro[2.5]oct-4-yl]-ethyl}-benzonitrile 1H NMR (600 MHz, DMSO) δ=11.41 (s, 1H), 7.94 (m, 1H), 7.70 (m, 2H), 7.58 (m, 1H), 7.51 (m, 1H), 7.23 (m, 1H), 6.41 (m, 2H), 3.99 (br, 2H), 3.83 (br, 2H), 3.43 (br, 4H), 1.01 (m, 4H).

Example 237

Using Intermediate 15

2-{2-Oxo-2-[7-(1H-pyrrolo[2,3-b]pyridin-4-yl)-4,7-diaza-spiro[2.5]oct-4-yl]-ethyl}-benzonitrile 1H NMR (600 MHz, DMSO) δ=11.41 (s, 1H), 7.95 (m, 1H), 7.80 (m, 1H), 7.64 (m, 1H), 7.45 (m, 2H), 7.24 (m, 1H), 6.45 (m, 1H), 6.40 (m, 1H), 4.16 (br, 2H), 3.95 (br, 2H), 3.55 (br, 4H), 1.07 (m, 4H).

Example 238

Using Intermediate 15

[7-(1H-Pyrrolo[2,3-b]pyridin-4-yl)-4,7-diaza-spiro[2.5]oct-4-yl]-(4-trifluoromethoxy-phenyl)-methanone 1H NMR (600 MHz, DMSO) δ=11.41 (s, 1H), 7.94 (m, 1H), 7.63 (m, 2H), 7.44 (d, J=8.1, 2H), 7.23 (m, 1H), 6.40 (d, J=8.1, 2H), 3.63 (br, 6H), 0.90 (m, 4H).

Example 369

4-[7-(7H-Pyrrolo[2,3-d]pyrimidin-4-yl)-4,7-diaza-spiro[2.5]octane-4-carbonyl]-benzenesulfonamide 1H NMR (600 MHz, DMSO) δ=11.79 (s, 1H), 8.15 (s, 1H), 7.90 (d, J=8.3, 2H), 7.68 (d, J=8.0, 2H), 7.55 (s, 2H), 7.20 (m, 1H), 6.62 (m, 1H), 3.82 (br, 6H), 0.93 (br, 4H).

Example 381

4-{2-Oxo-2-[7-(7H-pyrrolo[2,3-d]pyrimidin-4-yl)-4,7-diaza-spiro[2.5]oct-4-yl]-acetyl}-benzonitrile 1H NMR (600 MHz, DMSO) δ=11.79 (s, 1H), 8.10 (m, 5H), 7.22 (m, 1H), 6.61 (1, 2H), 3.98 (br, 6H), 1.04 (br, 4H). Rotamers observed

Example 386

(4-Methoxy-thiophen-2-yl)-[7-(7H-pyrrolo[2,3-d]pyrimidin-4-yl)-4,7-diaza-spiro[2.5]oct-4-yl]-methanone 1H NMR (600 MHz, DMSO) δ=11.74 (s, 1H), 8.15 (s, 1H), 7.19 (br, 2H), 6.87 (m, 1H), 6.63 (m, 1H), 3.94 (br, 6H), 3.78 (s, 3H), 0.92 (br, 4H).

Example 373

5-[7-(7H-Pyrrolo[2,3-d]pyrimidin-4-yl)-4,7-diaza-spiro[2.5]octane-4-carbonyl]-thiophene-3-sulfonic acid methylamide $^1$H NMR (300 MHz, DMSO) δ 11.8 (br, 1H), 8.38 (s, 1H), 8.20 (s, 1H), 7.60 (s, 1H), 7.4-7.50 (m, 1H), 7.23-7.26 (m, 1H), 6.65-6.70 (m, 1H), 3.0-4.2 (6H, m), 2.5 (s, 3H), 0.8-1.20 (m, 4H).

Example 374

2-Methyl-5-[7-(7H-pyrrolo[2,3-d]pyrimidin-4-yl)-4,7-diaza-spiro[2.5]octane-4-carbonyl]-thiophene-3-sulfonic acid amide $^1$H NMR (300 MHz, DMSO) δ 11.7 (br, 1H), 8.20 (s, 1H), 7.60 (s, 1H), 7.40 (s, 2H), 7.23-7.26 (m, 1H), 6.65-6.70 (m, 1H), 3.0-4.2 (6H, m), 2.60 (s, 3H), 0.8-1.20 (m, 4H).

Example 375

2-Methyl-5-[7-(7H-pyrrolo[2,3-d]pyrimidin-4-yl)-4,7-diaza-spiro[2.5]octane-4-carbonyl]-thiophene-3-sulfonic acid methylamide $^1$H NMR (300 MHz, DMSO) δ 11.8 (br, 1H), 8.20 (s, 1H), 7.50 (s, 1H), 7.49-7.52 (m, 1H), 7.20-2.25 (m, 1H), 6.65-6.70 (m, 1H), 3.0-4.2 (6H, m), 2.70 (s, 3H), 2.50 (s, 3H), 0.8-1.30 (m, 4H).

Example 376

4-Methyl-5-[7-(7H-pyrrolo[2,3-d]pyrimidin-4-yl)-4,7-diaza-spiro[2.5]octane-4-carbonyl]-thiophene-3-sulfonic acid methylamide $^1$H NMR (300 MHz, DMSO) δ 11.70 (br, 1H), 8.25 (s, 1H), 8.20 (s, 1H), 7.4-7.50 (m, 1H), 7.23-7.26 (m, 1H), 6.65-6.70 (m, 1H), 3.0-4.2 (6H, m), 2.5 (s, 3H), 2.25 (s, 3H), 0.8-1.20 (m, 4H).

Example 79

4-[7-(7H-Pyrrolo[2,3-d]pyrimidin-4-yl)-4,7-diaza-spiro[2.5]octane-4-sulfonylmethyl]-benzonitrile 1H NMR (300 MHz, DMSO) δ=11.73 (s, 1H), 8.13 (s, 1H), 7.86 (d, J=8.3, 2H), 7.50 (d, J=8.3, 2H), 7.19 (d, J=3.4, 1H), 6.57 (d, J=3.4, 1H), 4.60 (br, 2H), 4.00 (br, 2H), 3.78 (br, 2H), 3.42 (br, 2H), 0.76 (br, 2H), 0.60 (br, 2H).

Example 82

Benzo[b]thiophen-2-yl-[7-(1H-pyrrolo[2,3-b]pyridin-4-yl)-4,7-diaza-spiro[2.5]oct-4-yl]-methanone Using Intermediate 15

1H NMR (300 MHz, DMSO) δ=11.44 (s, 1H), 7.98 (m, 3H), 7.86 (m, 1H), 7.46 (m, 2H), 7.25 (m, 1H), 6.46 (m, 2H), 4.03 (br, 2H), 3.56 (br, 4H), 1.03 (br, 2H), 0.94 (br, 2H).

Example 85

1-[7-(7H-Pyrrolo[2,3-d]pyrimidin-4-yl)-4,7-diaza-spiro[2.5]octane-4-carbonyl]-cyclopropanecarboxylic acid 1H NMR (300 MHz, DMSO) δ=11.79 (s, 1H), 8.15 (s, 1H), 7.21 (d, J=3.5, 1H), 6.63 (d, J=3.5, 1H), 4.05 (br, 2H), 3.75 (br, 4H), 1.19 (br, 8H).

Example 86

1-[7-(7H-Pyrrolo[2,3-d]pyrimidin-4-yl)-4,7-diaza-spiro[2.5]octane-4-carbonyl]-cyclopropanecarboxylic acid cyanomethyl-methyl-amide 1H NMR (300 MHz, DMSO) δ=11.70 (s, 1H), 8.13 (s, 1H), 7.18 (m, 1H), 6.61 (m, 1H), 4.39 (br, 2H), 3.98 (br, 2H), 3.75 (br, 4H), 2.95 (s, 3H), 1.18 (br, 8H).

Example 87

1-[7-(7H-Pyrrolo[2,3-d]pyrimidin-4-yl)-4,7-diaza-spiro[2.5]octane-4-carbonyl]-cyclopropanecarboxylic acid (2-cyano-ethyl)-methyl-amide 1H NMR (300 MHz, DMSO) δ=11.70 (s, 1H), 8.14 (s, 1H), 7.18 (m, 1H), 6.61 (m, 1H), 3.97 (br, 2H), 3.76 (br, 4H), 3.52 (br, 2H), 2.92 (s, 3H), 2.73 (br, 2H), 1.15 (br, 8H).

Example 88

1-{1-[7-(7H-Pyrrolo[2,3-d]pyrimidin-4-yl)-4,7-diaza-spiro[2.5]octane-4-carbonyl]-cyclopropanecarbonyl}-pyrrolidine-3-carbonitrile 1H NMR (300 MHz, DMSO) δ=11.88 (s, 1H), 8.18 (s, 1H), 7.23 (m, 1H), 6.68 (s, 1H), 3.70 (br, 13H), 1.14 (br, 4H), 0.93 (br, 4H).

Example 90

(3-Methyl-thiophen-2-yl)[7-(7H-pyrrolo[2,3-d]pyrimidin-4-yl)-4,7-diaza-spiro[2.5]oct-4-yl]-methanone 1H NMR (300 MHz, DMSO) δ=11.73 (s, 1H), 8.14 (s, 1H), 7.62 (d, J=5.0, 1H), 7.19 (m, 1H), 6.96 (d, J=5.0, 1H), 6.60 (m, 1H), 3.96 (br, 2H), 3.91 (br, 2H), 3.72 (br, 2H), 2.20 (s, 3H), 0.93 (br, 2H), 0.84 (br, 2H).

Example 92

3-Fluoro-4-[7-(7H-pyrrolo[2,3-d]pyrimidin-4-yl)-4,7-diaza-spiro[2.5]octane-4-carbonyl]-benzonitrile 1H NMR (300 MHz, DMSO) δ=11.74 (s, 1H), 8.15 (s, 1H), 8.02 (m, 1H), 7.77 (m, 2H), 7.20 (m, 1H), 6.59 (m, 1H), 4.13 (br, 2H), 3.89 (br, 4H), 1.11 (br, 2H), 0.75 (br, 1H), 0.56 (br, 1H).

Example 94

{3-[7-(7H-Pyrrolo[2,3-d]pyrimidin-4-yl)-4,7-diaza-spiro[2.5]octane-4-carbonyl]-piperidin-1-yl}-acetonitrile 1H NMR (300 MHz, DMSO) δ=11.71 (s, 1H), 8.14 (s, 1H), 7.19 (m, 1H), 6.60 (m, 1H), 3.77 (br, 8H), 2.78 (m, 3H), 2.25 (m, 1H), 2.11 (m, 1H), 1.67 (br, 2H), 1.55 (m, 1H), 1.34 (br, 1H), 1.15 (br, 4H).

Example 95

3-{3-[7-(7H-Pyrrolo[2,3-d]pyrimidin-4-yl)-4,7-diaza-spiro[2.5]octane-4-carbonyl]-piperidin-1-yl}-propionitrile 1H NMR (300 MHz, DMSO) δ=11.70 (s, 1H), 8.13 (s, 1H), 7.19 (m, 1H), 6.60 (m, 1H), 3.78 (br, 6H), 2.85 (m, 2H), 2.61 (br, 5H), 2.03 (br, 2H), 1.62 (br, 4H), 1.02 (br, 4H).

Example 97

3-{4-[7-(7H-Pyrrolo[2,3-d]pyrimidin-4-yl)-4,7-diaza-spiro[2.5]octane-4-carbonyl]-piperidin-1-yl}-propionitrile 1H NMR (300 MHz, DMSO) δ=11.70 (s, 1H), 8.13 (s, 1H), 7.18 (m, 1H), 6.59 (s, 1H), 3.85 (br, 6H), 2.89 (m, 3H), 2.65 (br, 2H), 2.56 (m, 2H), 2.02 (m, 2H), 1.63 (br, 4H), 1.02 (br, 4H).

Example 101

2-(3-Methanesulfonyl-phenyl)-1-[7-(7H-pyrrolo[2,3-d]pyrimidin-4-yl)-4,7-diaza-spiro[2.5]oct-4-yl]-ethanone 1H NMR (300 MHz, DMSO) δ=11.71 (s, 1H), 8.14 (s, 1H), 7.80 (m, 2H), 7.57 (m, 2H), 7.19 (m, 1H), 6.60 (m, 1H), 3.81 (br, 11H), 1.09 (br, 4H).

Example 102

2-Chloro-5-{2-oxo-2-[7-(7H-pyrrolo[2,3-d]pyrimidin-4-yl)-4,7-diaza-spiro[2.5]oct-4-yl]-ethoxy}-benzenesulfonamide 1H NMR (300 MHz, DMSO) δ=11.73 (s, 1H), 8.19 (s, 1H), 7.59 (br, 2H), 7.48 (m, 2H), 7.20 (m, 1H), 7.13 (m, 1H), 6.60 (m, 1H), 5.11 (s, 2H), 3.82 (br, 6H), 1.09 (br, 4H).

Example 103

2-Chloro-4-[7-(7H-pyrrolo[2,3-d]pyrimidin-4-yl)-4,7-diaza-spiro[2.5]octane-4-carbonyl]-benzene-sulfonamide 1H NMR (300 MHz, DMSO) δ=11.73 (s, 1H), 8.15 (s, 1H), 8.07 (m, 1H), 7.73 (br, 4H), 7.20 (m, 1H), 6.61 (m, 1H), 3.91 (br, 6H), 0.88 (br, 4H).

Example 104

N-Methyl-4-[7-(7H-pyrrolo[2,3-d]pyrimidin-4-yl)-4,7-diaza-spiro[2.5]octane-4-carbonyl]-benzene-sulfonamide 1H NMR (300 MHz, DMSO) δ=11.77 (s, 1H), 8.16 (s, 1H), 7.84 (d, J=8.3, 2H), 7.71 (d, J=8.3, 2H), 7.57 (m, 1H), 7.21 (m, 1H), 6.63 (m, 1H), 3.93 (br, 9H), 0.84 (br, 4H).

Example 105

Indan-1-yl-[7-(7H-pyrrolo[2,3-d]pyrimidin-4-yl)-4,7-diaza-spiro[2.5]oct-4-yl]-methanone 1H NMR (300 MHz, DMSO) δ=11.73 (s, 1H), 8.16 (s, 1H), 7.14 (br, 5H), 6.62 (m, 1H), 3.88 (br, 4H), 2.89 (br, 3H), 1.15 (br, 4H), 0.96 (br, 4H).

Example 106

Benzo[b]thiophen-5-yl-[7-(7H-pyrrolo[2,3-d]pyrimidin-4-yl)-4,7-diaza-spiro[2.5]oct-4-yl]-methanone 1H NMR (300 MHz, DMSO) δ=11.71 (s, 1H), 8.14 (s, 1H), 8.09 (d, J=8.3, 1H), 8.04 (s, 1H), 7.86 (d, J=5.4, 1H), 7.54 (d, J=5.4, 1H), 7.47 (d, J=8.3, 1H), 7.19 (m, 1H), 6.61 (m, 1H), 3.97 (br, 4H), 3.79 (br, 2H), 0.86 (br, 4H).

Example 107

2-(4-Methanesulfonyl-phenyl)-1-[7-(7H-pyrrolo[2,3-d]pyrimidin-4-yl)-4,7-diaza-spiro[2.5]oct-4-yl]-ethanone 1H NMR (300 MHz, DMSO) δ=11.72 (s, 1H), 8.14 (s, 1H), 7.85 (d, J=8.3, 2H), 7.52 (d, J=8.3, 2H), 7.19 (m, 1H), 6.60 (m, 1H), 3.90 (br, 8H), 3.19 (s, 3H), 1.10 (br, 4H).

Example 113

2-{2-Oxo-2-[7-(7H-pyrrolo[2,3-d]pyrimidin-4-yl)-4,7-diaza-spiro[2.5]oct-4-yl]-ethyl}-benzonitrile 1H NMR (300 MHz, DMSO) δ=11.72 (s, 1H), 8.14 (s, 1H), 7.81 (m, 1H), 7.66 (m, 1H), 7.48 (m, 2H), 7.20 (m, 1H), 6.57 (m, 1H), 3.99 (m, 6H), 2.53 (br, 2H), 1.15 (br, 4H).

Example 114

1-[7-(7H-Pyrrolo[2,3-d]pyrimidin-4-yl)-4,7-diaza-spiro[2.5]octane-4-carbonyl]-cyclopentanecarbonitrile 1H NMR (300 MHz, DMSO) δ=11.78 (s, 1H), 8.15 (s, 1H), 7.22 (m, 1H), 6.63 (m, 1H), 4.06 (br, 2H), 3.93 (br, 2H), 3.81 (br, 2H), 2.53 (br, 1H), 2.26 (br, 4H), 1.74 (br, 4H), 0.95 (br, 4H).

Example 115

4-{2-Oxo-2-[7-(1H-pyrrolo[2,3-b]pyridin-4-yl)-4,7-diaza-spiro[2.5]oct-4-yl]-ethyl}-benzonitrile Using Intermediate 15

1H NMR (300 MHz, DMSO) δ=11.41 (s, 1H), 7.94 (d, J=5.4, 1H), 7.75 (d, J=8.2, 2H), 7.44 (d, J=8.2, 2H), 7.23 (d, J=3.4, 1H), 6.43 (d, J=3.4, 1H), 6.39 (d, J=5.4, 1H), 3.56 (br, 8H), 1.06 (br, 4H).

Example 116

4-Oxo-4-[7-(1H-pyrrolo[2,3-b]pyridin-4-yl)-4,7-diaza-spiro[2.5]oct-4-yl]-butyronitrile Using intermediate 15

1H NMR (300 MHz, DMSO) δ=12.28 (s, 1H), 8.00 (d, J=7.2, 1H), 7.40 (m, 1H), 6.90 (br, 1H), 6.79 (d, J=7.2, 1H), 3.96 (br, 2H), 3.82 (br, 4H), 2.91 (m, 2H), 2.65 (m, 2H), 1.16 (br, 4H).

Example 117

1-[7-(1H-Pyrrolo[2,3-b]pyridin-4-yl)-4,7-diaza-spiro[2.5]octane-4-carbonyl]-cyclopropanecarbonitrile Using Intermediate 15

1H NMR (300 MHz, DMSO) δ=12.27 (s, 1H), 8.02 (d, J=7.1, 1H), 7.41 (d, J=2.4, 1H), 6.90 (d, J=2.4, 1H), 6.81 (d, J=7.1, 1H), 4.09 (br, 2H), 3.91 (br, 4H), 1.63 (br, 4H), 1.23 (br, 4H).

Example 118

4-[7-(5-Methyl-7H-pyrrolo[2,3-d]pyrimidin-4-yl)-4,7-diaza-spiro[2.5]octane-4-carbonyl]-benzonitrile Using Intermediate 14

1H NMR (300 MHz, DMSO) δ=11.55 (s, 1H), 8.19 (s, 1H), 7.93 (d, J=8.2, 2H), 7.66 (d, J=8.2, 2H), 7.07 (s, 1H), 3.53 (br, 6H), 2.34 (s, 3H), 0.88 (br, 4H).

Example 119

3-[7-(5-Methyl-7H-pyrrolo[2,3-d]pyrimidin-4-yl)-4,7-diaza-spiro[2.5]octane-4-carbonyl]-benzonitrile Using Intermediate 14

1H NMR (300 MHz, DMSO) δ=11.55 (s, 1H), 8.20 (s, 1H), 7.95 (m, 2H), 7.81 (m, 1H), 7.67 (m, 1H), 7.07 (s, 1H), 3.53 (br, 6H), 2.35 (s, 3H), 0.76 (br, 4H).

Example 120

[7-(5-Methyl-7H-pyrrolo[2,3-d]pyrimidin-4-yl)-4,7-diaza-spiro[2.5]oct-4-yl]-quinoxalin-2-yl-methanone Using Intermediate 14

1H NMR (300 MHz, DMSO) δ=11.53 (s, 1H), 9.11 (s, 1H), 8.17 (br, 3H), 7.98 (m, 2H), 7.08 (b, 1H), 3.88 (br, 6H), 2.40 (s, 3H), 0.52 (br, 4H).

Example 121

4-{4-[2-(3-Cyanomethyl-phenyl)-acetyl]-4,7-diaza-spiro[2.5]oct-7-yl}-7H-pyrrolo[2,3-d]pyrimidine-6-carboxylic acid methyl ester Using Intermediate 8

1H NMR (300 MHz, DMSO) δ=12.56 (s, 1H), 8.22 (s, 1H), 7.32 (m, 2H), 7.21 (m, 3H), 4.00 (br, 4H), 3.93 (s, 3H), 3.85 (br, 6H), 1.06 (br, 4H).

Example 122

4-{4-[2-(4-Cyanomethyl-phenyl)-acetyl]-4,7-diaza-spiro[2.5]oct-7-yl}-7H-pyrrolo[2,3-d]pyrimidine-6-carboxylic acid methyl ester Using Intermediate 8

1H NMR (300 MHz, DMSO) δ=12.56 (s, 1H), 8.22 (s, 1H), 7.35 (s, 1H), 7.26 (br, 4H), 3.89 (br, 13H), 1.03 (br, 4H).

Example 123

4-{4-[2-(3-Cyano-phenyl)-acetyl]-4,7-diaza-spiro[2.5]oct-7-yl}-7H-pyrrolo[2,3-d]pyrimidine-6-carboxylic acid methyl ester Using Intermediate 8

1H NMR (300 MHz, DMSO) δ=12.48 (br, 1H), 8.41 (s, 1H), 7.70 (m, 2H), 7.58 (m, 1H), 7.50 (m, 1H), 7.37 (m, 1H), 3.96 (br, 4H), 3.85 (s, 3H), 3.74 (br, 4H), 1.11 (br, 4H).

Example 124

4-{4-[2-(4-Cyano-phenyl)-acetyl]-4,7-diaza-spiro[2.5]oct-7-yl}-7H-pyrrolo[2,3-d]pyrimidine-6-carboxylic acid methyl ester Using Intermediate 8

1H NMR (300 MHz, DMSO) δ=12.56 (s, 1H), 8.22 (s, 1H), 7.75 (d, J=8.1, 2H), 7.45 (d, J=8.1, 2H), 7.35 (s, 1H), 4.03 (br, 4H), 3.85 (s, 3H), 3.79 (br, 4H), 1.03 (br, 4H).

Example 125

Bicyclo[4.2.0]octa-1(6),2,4-trien-7-yl-[7-(7H-pyrrolo[2,3-d]pyrimidin-4-yl)-4,7-diaza-spiro[2.5]oct-4-yl]-methanone 1H NMR (300 MHz, DMSO) δ=11.72 (s, 1H), 8.15 (s, 1H), 7.19 (br, 5H), 6.62 (m, 1H), 4.75 (br, 1H), 4.11 (s, 2H), 3.83 (br, 4H), 3.51 (br, 1H), 1.13 (br, 4H).

Example 126

3-[7-(7H-Pyrrolo[2,3-d]pyrimidin-4-yl)-4,7-diaza-spiro[2.5]octane-4-carbonyl]-indan-1-one 1H NMR (300 MHz, DMSO) δ=11.74 (s, 1H), 8.17 (s, 1H), 7.65 (m, 2H), 7.48 (m, 2H), 7.21 (m, 1H), 6.64 (m, 1H), 3.95 (br, 6H), 2.79 (br, 2H), 1.04 (br, 4H).

Example 145

3-[6-Methyl-7-(7H-pyrrolo[2,3-d]pyrimidin-4-yl)-4,7-diaza-spiro[2.5]octane-4-carbonyl]-benzonitrile 1H NMR (300 MHz, dmso) δ=11.72 (s, 1H), 8.14 (s, 1H), 7.98 (m, 1H), 7.85 (s, 1H), 7.70 (m, 1H), 7.20 (s, 1H), 6.54 (m, 2H), 4.54 (br, 5H), 1.30 (br, 3H), 0.84 (m, 4H).

Example 146

3-{2-[6-Methyl-7-(7H-pyrrolo[2,3-d]pyrimidin-4-yl)-4,7-diaza-spiro[2.5]oct-4-yl]-2-oxo-ethyl}-benzonitrile 1H NMR (300 MHz, dmso) δ=11.71 (s, 1H), 8.13 (s, 1H), 7.73 (m, 2H), 7.57 (m, 2H), 7.20 (m, 1H), 6.57 (s, 1H), 4.39 (br m, 2H), 3.97 (br m, 5H), 1.25 (m, 2H), 1.07 (d, J=6.6, 3H), 0.71 (m, 4H).

Example 147

4-{2-[6-Methyl-7-(7H-pyrrolo[2,3-d]pyrimidin-4-yl)-4,7-diaza-spiro[2.5]oct-4-yl]-2-oxo-ethyl}-benzonitrile 1H NMR (300 MHz, dmso) δ=11.71 (s, 1H), 8.12 (s, 1H), 7.78 (d, J=8.1, 2H), 7.49 (d, J=8.1, 2H), 7.19 (m, 1H), 6.57 (m, 1H), 5.00 (br, 1H), 4.39 (br, 1H), 4.01 (br m, 5H), 1.18 (m, 2H), 1.07 (d, 3H), 0.70 (m, 2H).

Example 148

4-[6-Methyl-7-(7H-pyrrolo[2,3-d]pyrimidin-4-yl)-4,7-diaza-spiro[2.5]octane-4-carbonyl]-benzonitrile 1H NMR (300 MHz, dmso) δ=11.74 (s, 1H), 8.14 (s, 1H), 7.95 (m, 2H), 7.70 (m, 2H), 7.20 (m, 1H), 6.61 (m, 1H), 3.91 (br m, 5H), 1.28 (br, 3H), 0.84 (m, 4H).

Example 149

1-[6-Methyl-7-(7H-pyrrolo[2,3-d]pyrimidin-4-yl)-4,7-diaza-spiro[2.5]octane-4-carbonyl]-cyclopropanecarbonitrile 1H NMR (300 MHz, dmso) δ=11.74 (s, 1H), 8.14 (s, 1H), 7.22 (m, 1H), 6.60 (m, 1H), 4.28 (br, 2H), 3.92 (br, 3H), 1.40 (m, 4H), 1.17 (br d, 3H), 0.77 (m, 4H).

Example 150

4-[6-Methyl-7-(7H-pyrrolo[2,3-d]pyrimidin-4-yl)-4,7-diaza-spiro[2.5]oct-4-yl]-4-oxo-butyronitrile 1H NMR (300 MHz, dmso) δ=11.70 (s, 1H), 8.11 (s, 1H), 7.19 (m, 1H), 6.56 (m, 1H), 3.71 (br, 5H), 2.95 (m, 2H), 2.67 (m, 2H), 1.10 (d, J=6.8, 3H), 0.65 (m, 4H).

Example 312

4-{2-[7-(2-Amino-7H-pyrrolo[2,3-d]pyrimidin-4-yl)-4,7-diaza-spiro[2.5]oct-4-yl]-2-oxo-ethyl}-benzonitrile 1H NMR (600 MHz, DMSO) δ=10.84 (s, 1H), 7.78 (d, J=8.0, 2H), 7.45 (d, J=8.0, 2H), 6.74 (br, 1H), 6.32 (br, 1H), 5.51 (br, 2H), 4.02 (br, 2H), 3.72 (br, 6H), 1.01 (br, 4H).

Example 93

N-(4-{4-[2-(4-Cyano-phenyl)-acetyl]-4,7-diaza-spiro[2.5]oct-7-yl}-7H-pyrrolo[2,3-d]pyrimidin-2-yl)-acetamide Using example 312.

1H NMR (600 MHz, DMSO) δ=11.55 (s, 1H), 9.71 (s, 1H), 7.78 (m, 2H), 7.46 (m, 2H), 7.05 (m, 1H), 6.53 (m, 1H), 3.88 (br, 8H), 2.18 (s, 3H), 1.06 (br, 4H).

Example 96

N-(4-{4-[2-(4-Cyano-phenyl)-acetyl]-4,7-diaza-spiro[2.5]oct-7-yl}-7H-pyrrolo[2,3-d]pyrimidin-2-yl)-2-(2-methoxy-ethoxy)-acetamide Using Example 312

1H NMR (300 MHz, DMSO) δ=11.60 (s, 1H), 9.54 (s, 1H), 7.76 (d, J=8.3, 2H), 7.45 (d, J=8.3, 2H), 7.08 (m, 1H), 6.55 (m, 1H), 4.22 (br, 2H), 3.90 (br, 8H), 3.66 (m, 2H), 3.51 (m, 2H), 3.29 (s, 3H), 1.01 (br, 4H).

Example 98

N-(4-{4-[2-(4-Cyano-phenyl)-acetyl]-4,7-diaza-spiro[2.5]oct-7-yl}-7H-pyrrolo[2,3-d]pyrimidin-2-yl)-benzamide Using Example 312

1H NMR (300 MHz, DMSO) δ=11.60 (s, 1H), 10.20 (s, 1H), 7.88 (d, J=7.6, 2H), 7.76 (d, J=7.6, 2H), 7.51 (m, 5H), 7.11 (m, 1H), 6.56 (m, 1H), 3.82 (br, 8H), 1.07 (br, 4H).

Example 99

Isoxazole-5-carboxylic acid (4-{4-[2-(4-cyano-phenyl)-acetyl]-4,7-diaza-spiro[2.5]oct-7-yl}-7H-pyrrolo[2,3-d]pyrimidin-2-yl)-amide Using Example 312

1H NMR (300 MHz, DMSO) δ=11.72 (s, 1H), 10.65 (s, 1H), 8.77 (d, J=1.9, 1H), 7.76 (d, J=8.2, 2H), 7.46 (d, J=8.2, 2H), 7.29 (d, J=1.9, 1H), 7.15 (m, 1H), 6.59 (s, 1H), 3.89 (br, 8H), 1.02 (br, 4H).

Example 100

Acetic acid (4-{4-[2-(4-cyano-phenyl)-acetyl]-4,7-diaza-spiro[2.5]oct-7-yl}-7H-pyrrolo[2,3-d]pyrimidin-2-ylcarbamoyl)-methyl ester Using Example 312

1H NMR (300 MHz, DMSO) δ=11.56 (s, 1H), 10.00 (s, 1H), 7.76 (d, J=8.2, 2H), 7.45 (d, J=8.2, 2H), 7.07 (m, 1H), 6.53 (m, 1H), 4.97 (s, 2H), 3.89 (br, 8H), 2.10 (s, 3H), 1.01 (br, 4H).

Example 253

Phenyl-[5-(7H-pyrrolo[2,3-d]pyrimidin-4-yl)-2,5-diaza-bicyclo[2.2.1]hept-2-yl]-methanone Using Intermediate 6

1H NMR (600 MHz, DMSO) δ=11.66 (s, 1H), 8.10 (br, 1H), 7.47 (br, 5H), 7.14 (m, 1H), 6.55 (m, 1H), 5.17 (br, 1H), 4.72 (br, 1H), 3.78 (br, 3H), 3.43 (br, 1H), 2.03 (br, 2H).
Mixture of isomers.

Example 258

4-[5-(7H-Pyrrolo[2,3-d]pyrimidin-4-yl)-2,5-diaza-bicyclo[2.2.1]heptane-2-carbonyl]-benzonitrile Using Intermediate 6

1H NMR (600 MHz, DMSO) δ=11.65 (br, 1H), 8.10 (br, 1H), 7.91 (br, 2H), 7.71 (br, 2H), 7.14 (br, 1H), 6.53 (br, 1H), 5.19 (br, 1H), 4.59 (br, 1H), 3.85 (br, 2H), 3.71 (br, 1H), 3.28 (br, 1H), 2.02 (br, 2H).

Example 265

(5-Methyl-thiophen-2-yl)-[5-(7H-pyrrolo[2,3-d]pyrimidin-4-yl)-2,5-diaza-bicyclo[2.2.1]hept-2-yl]-methanone Using Intermediate 6

1H NMR (600 MHz, DMSO-SPE) δ=11.66 (s, 1H), 8.10 (s, 1H), 7.41 (m, 1H), 7.15 (m, 1H), 6.84 (m, 1H), 6.53 (m, 1H), 5.22 (br, 1H), 5.00 (br, 1H), 3.82 (br, 4H), 2.42 (br, 3H), 2.05 (br, 2H).

Example 270

1-[5-(7H-Pyrrolo[2,3-d]pyrimidin-4-yl)-2,5-diaza-bicyclo[2.2.1]heptane-2-carbonyl]-cyclopropanecarbonitrile Using Intermediate 6

1H NMR (600 MHz, DMSO) δ=11.67 (s, 1H), 8.13 (s, 1H), 7.16 (m, 2H), 6.53 (s, 1H), 5.05 (br, 2H), 3.75 (br, 4H), 2.02 (br, 2H), 1.56 (br, 4H).

Example 278

4-{2-Oxo-2-[5-(7H-pyrrolo[2,3-d]pyrimidin-4-yl)-2,5-diaza-bicyclo[2.2.1]hept-2-yl]-ethyl}-benzonitrile Using Intermediate 6

1H NMR (600 MHz, DMSO) δ=11.65 (s, 1H), 8.10 (s, 1H), 7.72 (br, 2H), 7.40 (br, 2H), 7.15 (m, 1H), 6.51 (br, 1H), 5.16 (br, 1H), 4.88 (br, 1H), 3.90 (br, 2H), 3.65 (m, 4H), 1.99 (br, 2H).

Example 283

[7-(5-Methoxy-1H-pyrrolo[2,3-b]pyridin-4-yl)-4,7-diaza-spiro[2.5]oct-4-yl]-phenyl-methanone Using Intermediate 16

1H NMR (600 MHz, DMSO) δ=11.30 (s, 1H), 7.89 (s, 1H), 7.47 (m, 5H), 7.25 (m, 1H), 6.51 (s, 1H), 3.81 (s, 3H), 3.43 (br, 4H), 3.28 (br, 2H), 1.00 (br, 4H).

Example 284

Benzo[b]thiophen-2-yl-[7-(5-methoxy-1H-pyrrolo[2,3-b]pyridin-4-yl)-4,7-diaza-spiro[2.5]oct-4-yl]-methanone Using Intermediate 16

1H NMR (600 MHz, DMSO) δ=11.32 (s, 1H), 8.03 (s, 1H), 7.97 (m, 1H), 7.89 (m, 2H), 7.46 (m, 2H), 7.27 (m, 1H), 6.55 (m, 1H), 3.83 (s, 3H), 3.45 (br, 4H), 3.28 (br, 2H), 0.97 (br, 4H).

Example 285

[7-(5-Methoxy-1H-pyrrolo[2,3-b]pyridin-4-yl)-4,7-diaza-spiro[2.5]oct-4-yl]-pyrazin-2-yl-methanone Using Intermediate 16

1H NMR (600 MHz, DMSO) δ=11.36 (1, 1H), 8.89 (br, 1H), 8.75 (m, 2H), 8.70 (m, 1H), 7.89 (m, 1H), 7.26 (m, 1H), 6.48 (m, 2H), 3.81 (s, 3H), 3.52 (br, 4H), 3.27 (br, 2H), 1.09 (br, 1H), 0.58 br, 3H).
Rotamers observed

Example 286

4-[7-(5-Methoxy-1H-pyrrolo[2,3-b]pyridin-4-yl)-4,7-diaza-spiro[2.5]octane-4-carbonyl]-benzonitrile Using Intermediate 16

1H NMR (600 MHz, DMSO) δ=11.31 (s, 1H), 7.92 (m, 2H), 7.89 (s, 1H), 7.69 (m, 2H), 7.26 (m, 1H), 6.53 (m, 1H), 3.79 (s, 3H), 3.45 (br, 6H), 0.95 (br, 4H).

Example 287

3-[7-(5-Methoxy-1H-pyrrolo[2,3-b]pyridin-4-yl)-4,7-diaza-spiro[2.5]octane-4-carbonyl]-benzonitrile Using Intermediate 16

1H NMR (600 MHz, DMSO) δ=11.30 (s, 1H), 7.98 (m, 1H), 7.95 (m, 1H), 7.89 (s, 1H), 7.84 (m, 1H), 7.67 (m, 1H), 7.26 (s, 1H), 6.45 (m, 1H), 3.81 (s, 3H), 3.44 (br, 6H), 0.92 (br, 4H).

Example 288

(1H-Indol-2-yl)-[7-(5-methoxy-1H-pyrrolo[2,3-b]pyridin-4-yl)-4,7-diaza-spiro[2.5]oct-4-yl]-methanone Using Intermediate 16

1H NMR (600 MHz, DMSO) δ=11.56 (s, 1H), 11.31 (s, 1H), 7.90 (s, 1H), 7.62 (d, J=8.0, 1H), 7.43 (m, 1H), 7.26 (m, 1H), 7.19 (m, 1H), 7.05 (m, 1H), 6.92 (s, 1H), 6.53 (s, 1H), 4.01 (br, 2H), 3.84 (s, 3H), 3.55 (br, 4H), 1.09 (m, 2H), 0.94 (m, 2H).

Example 289

Benzo[b]thiophen-3-yl-[7-(5-methoxy-1H-pyrrolo[2,3-b]pyridin-4-yl)-4,7-diaza-spiro[2.5]oct-4-yl]-methanone Using Intermediate 16

1H NMR (600 MHz, DMSO) δ=11.30 (s, 1H), 8.12 (s, 1H), 8.06 (m, 1H), 7.89 (m, 1H), 7.82 (m, 1H), 7.45 (m, 2H), 7.25 (m, 1H), 6.52 (s, 1H), 3.82 (s, 3H), 3.51 (br, 4H), 3.26 (br, 2H), 0.92 (br, 4H).

Example 290

[7-(5-Methoxy-1H-pyrrolo[2,3-b]pyridin-4-yl)-4,7-diaza-spiro[2.5]oct-4-yl]-(5-phenyl-thiophen-2-yl)-methanone Using Intermediate 16

1H NMR (600 MHz, DMSO) δ=11.31 (s, 1H), 7.90 (s, 1H), 7.73 (m, 2H), 7.54 (m, 2H), 7.46 (m, 2H), 7.38 (m, 1H), 7.26 (m, 1H), 6.54 (m, 1H), 3.95 (br, 2H), 3.83 (s, 3H), 3.45 (br, 4H), 1.02 (br, 2H), 0.93 (br, 2H).

Example 291

2-[7-(5-Methoxy-1H-pyrrolo[2,3-b]pyridin-4-yl)-4,7-diaza-spiro[2.5]octane-4-carbonyl]-1H-indole-5-carbonitrile Using Intermediate 16

1H NMR (600 MHz, DMSO) δ=12.18 (s, 1H), 11.36 (s, 1H), 8.20 (s, 1H), 7.90 (s, 1H), 7.59 (m, 1H), 7.53 (m, 1H), 7.26 (m, 1H), 7.07 (s, 1H), 6.53 (s, 1H), 3.93 (br, 2H), 3.84 (s, 3H), 3.63 (br, 4H), 1.05 (br, 2H), 0.94 (br, 2H).

Example 292

2-Fluoro-4-[7-(5-methoxy-1H-pyrrolo[2,3-b]pyridin-4-yl)-4,7-diaza-spiro[2.5]octane-4-carbonyl]-benzonitrile Using Intermediate 16

1H NMR (600 MHz, DMSO) δ=11.30 (s, 1H), 8.03 (s, 1H), 7.89 (s, 1H), 7.70 (m, 1H), 7.53 (m, 1H), 7.26 (s, 1H), 6.55 (m, 1H), 3.81 (s, 3H), 3.53 (br, 6H), 0.91 (br, 4H).

Example 293

5-[7-(5-Methoxy-1H-pyrrolo[2,3-b]pyridin-4-yl)-4,7-diaza-spiro[2.5]oct-4-yl]-5-oxo-pentanenitrile Using Intermediate 16

1H NMR (600 MHz, DMSO) δ=11.29 (s, 1H), 7.88 (s, 1H), 7.25 (m, 1H), 6.47 (s, 1H), 3.81 (s, 3H), 3.55 (br, 6H), 3.11 (br, 2H), 2.66 (br, 2H), 1.83 (br, 2H), 1.08 (br, 4H).

Example 294

3-{2-[7-(5-Methoxy-1H-pyrrolo[2,3-b]pyridin-4-yl)-4,7-diaza-spiro[2.5]oct-4-yl]-2-oxo-ethyl}-benzonitrile Using Intermediate 16

1H NMR (600 MHz, DMSO) δ=11.35 (s, 1H), 7.88 (s, 1H), 7.71 (m, 2H), 7.62 (m, 1H), 7.53 (m, 1H), 7.25 (m, 1H), 6.46 (m, 1H), 4.02 (br, 2H), 3.81 (s, 3H), 3.05 (br, 6H), 1.06 (m, 4H).

Example 295

4-{2-[7-(5-Methoxy-1H-pyrrolo[2,3-b]pyridin-4-yl)-4,7-diaza-spiro[2.5]oct-4-yl]-2-oxo-ethyl}-benzonitrile Using Intermediate 16

1H NMR (600 MHz, DMSO) δ=11.34 (s, sH), 7.88 (s, 1H), 7.78 (d, J=8.2, 2H), 7.48 (d, J=8.2, 2H), 7.25 (m, 1H), 6.43 (m, 1H), 4.05 (br, 2H), 3.80 (s, 3H), 3.49 (br, 6H), 1.04 (m, 4H).

Example 296

(3-Methyl-benzo[b]thiophen-2-yl)-[7-(7H-pyrrolo[2,3-d]pyrimidin-4-yl)-4,7-diaza-spiro[2.5]oct-4-yl]-methanone 1H NMR (600 MHz, DMSO) δ=11.74 (s, 1H), 8.15 (s, 1H), 8.00 (m, 1H), 7.85 (m, 1H), 7.47 (m, 2H), 7.19 (m, 1H), 6.60 (m, 1H), 3.97 (br, 4H), 3.79 (br, 2H), 2.39 (s, 3H), 0.95 (br, 4H).

Example 297

(5-Methyl-benzo[b]thiophen-2-yl)-[7-(7H-pyrrolo[2,3-d]pyrimidin-4-yl)-4,7-diaza-spiro[2.5]oct-4-yl]-methanone 1H NMR (600 MHz, DMSO) δ=11.75 (s, 1H), 8.16 (s, 1H), 7.90 (m, 1H), 7.77 (m, 2H), 7.31 (m, 1H), 7.21 (m, 1H), 6.64 (m, 1H), 4.02 (br, 6H), 2.44 (s, 3H), 0.96 (br, 2H), 0.88 (br, 2H).

Example 298

5-Oxo-5-[7-(7H-pyrrolo[2,3-d]pyrimidin-4-yl)-4,7-diaza-spiro[2.5]oct-4-yl]-pentanenitrile 1H NMR (600 MHz, DMSO) δ=11.72 (s, 1H), 8.13 (s, 1H), 7.19 (m, 3H), 6.60 (s, 1H), 3.83 (br, 6H), 2.63 (m, 2H), 2.42 (m, 2H), 1.84 (m, 2H), 0.95 (br, 4H).

Example 299

2-[7-(7H-Pyrrolo[2,3-d]pyrimidin-4-yl)-4,7-diaza-spiro[2.5]octane-4-carbonyl]-benzonitrile 1H NMR (600 MHz, DMSO) δ=11.75 (s, 1H), 8.15 (s, 1H), 7.97 (m, 1H), 7.74 (br, 3H), 7.20 (s, 1H), 6.61 (m, 1H), 4.04 (br, 4H), 3.40 (br, 2H), 1.03 (br, 2H), 0.62 (br, 2H).

Example 300

{2-[7-(7H-Pyrrolo[2,3-d]pyrimidin-4-yl)-4,7-diaza-spiro[2.5]octane-4-carbonyl]-phenyl}-acetonitrile 1H NMR (600 MHz, DMSO) δ=11.73 (s, 1H), 8.13 (s, 1H), 7.50 (m, 1H), 7.44 (br, 3H), 7.19 (m, 1H), 6.61 (m, 1H), 4.01 (br, 6H), 3.42 (br, 2H), 1.07 (dbr, 2H), 0.66 (br, 2H).

Example 301

3-[7-(7H-Pyrrolo[2,3-d]pyrimidin-4-yl)-4,7-diaza-spiro[2.5]octane-4-carbonyl]-1H-indazole-6-carbonitrile 1H NMR (600 MHz, DMSO) δ=14.12 (s, 1H), 11.72 (s, 1H), 8.21 (m, 3H), 7.57 (m, 1H), 7.19 (s, 1H), 6.62 (s, 1H), 4.02 (br, 6H), 0.90 (br, 4H).

Example 302

[7-(2-Amino-7H-pyrrolo[2,3-d]pyrimidin-4-yl)-4,7-diaza-spiro[2.5]oct-4-yl]-pyrazin-2-yl-methanone Using Intermediate 10

1H NMR (600 MHz, DMSO) δ=10.97 (s, 1H), 8.86 (m, 1H), 8.77 (m, 1H), 8.71 (m, 1H), 6.78 (br, 1H), 6.37 (m, 1H), 5.74 (br, 2H), 3.82 (br, 6H), 0.46-1.05 (br, 4H).
Rotamers observed

Example 303

4-[7-(2-Amino-7H-pyrrolo[2,3-d]pyrimidin-4-yl)-4,7-diaza-spiro[2.5]octane-4-carbonyl]-benzonitrile Using Intermediate 10

1H NMR (600 MHz, DMSO) δ=10.85 (s, 1H), 7.95 (d, J=7.92H), 7.68 (d, J=7.9, 2H), 6.74 (br, 1H), 6.34 (br, 1H), 5.52 (br s, 2H), 4.01 (br, 6H), 0.77 (br, 4H).

Example 304

3-[7-(2-Amino-7H-pyrrolo[2,3-d]pyrimidin-4-yl)-4,7-diaza-spiro[2.5]octane-4-carbonyl]-benzonitrile Using Intermediate 10

1H NMR (600 MHz, DMSO) δ=11.13 (s, 1H), 7.97 (br, 2H), 7.82 (m, 1H), 7.68 (m, 1H), 6.82 (br, 1H), 6.44 (br, 1H), 6.02 (br s, 2H), 3.91 (br, 6H), 0.81 (br, 4H).

Example 305

[7-(2-Amino-7H-pyrrolo[2,3-d]pyrimidin-4-yl)-4,7-diaza-spiro[2.5]oct-4-yl]-quinoxalin-2-yl-methanone Using Intermediate 10

1H NMR (600 MHz, DMSO) δ=10.86 (s, 1H), 9.17 (m, 1H), 8.17 (m, 2H), 7.97 (m, 2H), 6.76 (m, 1H), 6.36 (m, 1H), 5.53 (br s, 2H), 3.95 (br, 6H), 1.11 (br, 1H), 0.57 (br, 3H).
Rotamers observed.

Example 306

(3-{2-[7-(2-Amino-7H-pyrrolo[2,3-d]pyrimidin-4-yl)-4,7-diaza-spiro[2.5]oct-4-yl]-2-oxo-ethyl}-phenyl)-acetonitrile Using Intermediate 10

1H NMR (600 MHz, DMSO) δ=10.83 (s, 1H), 7.33 (m, 1H), 7.21 (br, 3H), 6.74 (m, 1H), 6.31 (m, 1H), 5.50 (br s, 2H), 4.01 (s, 2H), 3.92 (br, 2H), 3.70 (br, 6H), 0.98 (br, 4H).

Example 307

(4-{2-[7-(2-Amino-7H-pyrrolo[2,3-d]pyrimidin-4-yl)-4,7-diaza-spiro[2.5]oct-4-yl]-2-oxo-ethyl}-phenyl)-acetonitrile Using Intermediate 10

1H NMR (600 MHz, DMSO) δ=11.04 (s, 1H), 7.27 (br, 4H), 6.79 (m, 1H), 6.38 (m, 1H), 5.87 (br s, 2H), 4.00 (br s, 2H), 3.90 (br s, 2H), 3.73 (br, 4H), 0.98 (m, 4H).

Example 308

1-[7-(2-Amino-7H-pyrrolo[2,3-d]pyrimidin-4-yl)-4,7-diaza-spiro[2.5]octane-4-carbonyl]-cyclopropanecarbonitrile Using Intermediate 10

1H NMR (600 MHz, DMSO) δ=10.85 (s, 1H), 6.75 (dd, J=3.5, 2.1, 1H), 6.34 (dd, J=3.5, 2.1, 1H), 5.54 (br s, 2H), 3.65 (br, 6H), 1.71 (m, 4H), 1.17 (m, 4H).

Example 309

1-[7-(2-Amino-7H-pyrrolo[2,3-d]pyrimidin-4-yl)-4,7-diaza-spiro[2.5]oct-4-yl]-2-(4-trifluoromethyl-phenyl)-ethanone Using Intermediate 10

1H NMR (600 MHz, DMSO) δ=10.84 (s, 1H), 7.66 (d, 2H), 7.47 (d, J=7.8, 2H), 6.74 (m, 1H), 6.32 (s, 1H), 5.51 (br s, 2H), 4.02 (s, 2H), 3.76 (br, 6H), 1.05 (m, 4H).

Example 310

5-[7-(2-Amino-7H-pyrrolo[2,3-d]pyrimidin-4-yl)-4,7-diaza-spiro[2.5]oct-4-yl]-5-oxo-pentanenitrile Using Intermediate 10

1H NMR (600 MHz, DMSO) δ=10.83 (s, 1H), 6.74 (m, 1H), 6.32 (m, 1H), 5.50 (s, 2H), 3.72 (br, 6H), 3.40 (br, 2H), 2.63 (m, 2H), 1.85 (m, 2H), 1.00 (m, 4H).

Example 311

3-{2-[7-(2-Amino-7H-pyrrolo[2,3-d]pyrimidin-4-yl)-4,7-diaza-spiro[2.5]oct-4-yl]-2-oxo-ethyl}-benzonitrile Using Intermediate 10

1H NMR (600 MHz, DMSO) δ=10.84 (s, 1H), 7.73 (s, 1H), 7.70 (m, 1H), 7.59 (m, 1H), 7.51 (m, 1H), 6.74 (m, 1H), 6.33 (m, 1H), 5.51 (s, 2H), 4.00 (br s, 2H), 3.73 (br, 6H), 1.01 (m, 4H).

Example 313

4-[7-(2-Amino-7H-pyrrolo[2,3-d]pyrimidin-4-yl)-4,7-diaza-spiro[2.5]oct-4-yl]-4-oxo-butyronitrile Using Intermediate 10

1H NMR (600 MHz, DMSO) δ=10.87 (s, 1H), 6.75 (m, 1H), 6.34 (m, 1H), 5.57 (s, 2H), 3.77 (br, 6H), 2.91 (m, 2H), 2.67 (m, 2H), 1.08 (br, 4H).

Example 314

[7-(5-Chloro-7H-pyrrolo[2,3-d]pyrimidin-4-yl)-4,7-diaza-spiro[2.5]oct-4-yl]-pyrazin-2-yl-methanone Using Intermediate 12

1H NMR (600 MHz, DMSO) δ=12.21 (s, 1H), 8.87 (s, 1H), 8.77 (m, 1H), 8.70 (s, 1H), 8.26 (m, 1H), 7.51 (s, 1H), 3.68 (br, 6H), 1.02 (br, 1H), 0.51 (br, 3H).
Rotamers observed

Example 315

4-[7-(5-Chloro-7H-pyrrolo[2,3-d]pyrimidin-4-yl)-4,7-diaza-spiro[2.5]octane-4-carbonyl]-benzonitrile Using Intermediate 12

1H NMR (600 MHz, DMSO) δ=12.21 (s, 1H), 8.31 (m, 1H), 7.93 (d, 2H), 7.68 (d, 2H), 7.55 (m, 1H), 3.70 (br, 6H), 0.91 (br, 4H).

Example 316

3-[7-(5-Chloro-7H-pyrrolo[2,3-d]pyrimidin-4-yl)-4,7-diaza-spiro[2.5]octane-4-carbonyl]-benzonitrile Using Intermediate 12

1H NMR (600 MHz, DMSO) δ=12.21 (s, 1H), 8.24 (m, 1H), 7.95 (m, 2H), 7.82 (m, 1H), 7.67 (m, 1H), 7.51 (m, 1H), 3.81 (br, 6H), 0.89 (br, 4H).

Example 317

[7-(5-Chloro-7H-pyrrolo[2,3-d]pyrimidin-4-yl)-4,7-diaza-spiro[2.5]oct-4-yl]-quinoxalin-2-yl-methanone Using Intermediate 12

1H NMR (600 MHz, DMSO) δ=12.24 (s, 1H), 9.14 (m, 1H), 8.28 (m, 1H), 8.16 (m, 2H), 7.97 (m, 2H), 7.53 (m, 1H), 3.90 (br, 6H), 1.09 (br, 1H), 0.54 (br, 3H). Rotamers observed.

Example 318

(3-{2-[7-(5-Chloro-7H-pyrrolo[2,3-d]pyrimidin-4-yl)-4,7-diaza-spiro[2.5]oct-4-yl]-2-oxo-ethyl}-phenyl)-acetonitrile Using Intermediate 12

1H NMR (600 MHz, DMSO-SPE) δ=12.18 (s, 1H), 8.25 (s, 1H), 7.49 (s, 1H), 7.32 (m, 1H), 7.21 (br, 3H), 4.02 (s, 2H), 3.92 (s, 2H), 3.63 (br, 6H), 1.16 (m, 4H).

Example 319

(4-{2-[7-(5-Chloro-7H-pyrrolo[2,3-d]pyrimidin-4-yl)-4,7-diaza-spiro[2.5]oct-4-yl]-2-oxo-ethyl}-phenyl)-acetonitrile Using Intermediate 12

1H NMR (600 MHz, DMSO) δ=12.18 (s, 1H), 8.25 (s, 1H), 7.49 (s, 1H), 7.26 (br, 4H), 4.00 (s, 2H), 3.90 (s, 2H), 3.62 (br, 6H), 1.03 (br, 4H).

Example 320

1-[7-(5-Chloro-7H-pyrrolo[2,3-d]pyrimidin-4-yl)-4,7-diaza-spiro[2.5]oct-4-yl]-2-(4-fluoro-phenyl)-ethanone Using Intermediate 12

1H NMR (600 MHz, DMSO) δ=12.19 (s, 1H), 8.25 (s, 1H), 7.49 (s, 1H), 7.26 (br, 2H), 7.11 (br, 2H), 3.71 (br, 8H), 1.03 (br, 4H).

Example 321

1-[7-(5-Chloro-7H-pyrrolo[2,3-d]pyrimidin-4-yl)-4,7-diaza-spiro[2.5]oct-4-yl]-2-(4-trifluoromethyl-phenyl)-ethanone Using Intermediate 12

1H NMR (600 MHz, DMSO) δ=12.19 (s, 1H), 8.26 (s, 1H), 7.66 (m, 2H), 7.48 (m, 3H), 4.03 (s, 2H), 3.85 (s, 2H), 3.60 (br, 4H), 1.11 (m, 4H).

Example 322

5-[7-(5-Chloro-7H-pyrrolo[2,3-d]pyrimidin-4-yl)-4,7-diaza-spiro[2.5]oct-4-yl]-5-oxo-pentanenitrile Using Intermediate 12

1H NMR (600 MHz, DMSO) δ=12.19 (s, 1H), 8.25 (s, 1H), 7.50 (s, 1H), 3.75 (br, 2H), 3.52 (br, 2H), 3.39 (br, 2H), 2.62 (m, 2H), 2.41 (br, 2H), 1.82 (m, 2H), 1.12 (br, 4H).

Example 323

3-{2-[7-(5-Chloro-7H-pyrrolo[2,3-d]pyrimidin-4-yl)-4,7-diaza-spiro[2.5]oct-4-yl]-2-oxo-ethyl}-benzonitrile Using Intermediate 12

1H NMR (600 MHz, DMSO) δ=12.19 (s, 1H), 8.26 (s, 1H), 7.71 (m, 2H), 7.59 (m, 1H), 7.51 (m, 2H), 4.00 (s, 2H), 3.66 (br, 6H), 1.03 (br, 4H).

Example 324

4-{2-[7-(5-Chloro-7H-pyrrolo[2,3-d]pyrimidin-4-yl)-4,7-diaza-spiro[2.5]oct-4-yl]-2-oxo-ethyl}-benzonitrile Using Intermediate 12

1H NMR (600 MHz, DMSO) δ=12.19 (s, 1H), 8.26 (s, 1H), 7.76 (d, J=8.0, 2H), 7.50 (s, 1H), 7.44 (d, J=8.0, 2H), 4.03 (s, 2H), 3.70 (br, 6H), 1.03 br, 4H).

Example 325

4-[7-(5-Chloro-7H-pyrrolo[2,3-d]pyrimidin-4-yl)-4,7-diaza-spiro[2.5]oct-4-yl]-4-oxo-butyronitrile Using Intermediate 12

1H NMR (600 MHz, DMSO) δ=12.19 (s, 1H), 8.26 (s, 1H), 7.50 (s, 1H), 3.52 (br, 6H), 2.91 (m, 2H), 2.66 (m, 2H), 1.03 (br, 4H).

Example 326

[7-(5-Methyl-7H-pyrrolo[2,3-d]pyrimidin-4-yl)-4,7-diaza-spiro[2.5]oct-4-yl]-pyrazin-2-yl-methanone Using Intermediate 14

1H NMR (600 MHz, DMSO) δ=11.59 (s, 1H), 8.86 (s, 1H), 8.77 (m, 1H), 8.71 (m, 1H), 8.20 (m, 1H), 7.08 (m, 1H), 3.56 (br, 6H), 2.35 (s, 3H), 1.00 (br, 1H), 0.49 (br, 3H).
Rotamers observed.

Example 327

(3-{2-[7-(5-Methyl-7H-pyrrolo[2,3-d]pyrimidin-4-yl)-4,7-diaza-spiro[2.5]oct-4-yl]-2-oxo-ethyl}-phenyl)-acetonitrile Using Intermediate 14

1H NMR (600 MHz, DMSO) δ=11.57 (s, 1H), 8.19 (s, 1H), 7.33 (m, 1H), 7.21 (br, 3H), 7.06 (s, 1H), 4.03 (s, 2H), 3.92 (s, 2H), 3.77 (br, 2H), 3.49 (br, 2H), 3.42 (br, 2H), 2.31 (s, 3H), 1.05 (m, 4H).

Example 328

(4-{2-[7-(5-Methyl-7H-pyrrolo[2,3-d]pyrimidin-4-yl)-4,7-diaza-spiro[2.5]oct-4-yl]-2-oxo-ethyl}-phenyl)-acetonitrile Using Intermediate 14

1H NMR (600 MHz, DMSO) δ=11.57 (s, 1H), 8.19 (s, 1H), 7.26 (br, 4H), 7.07 (s, 1H), 4.01 (br, 2H), 3.90 (br, 2H), 3.76 (br, 2H), 3.45 (br, 4H), 2.31 (s, 3H), 1.01 (br, 4H).

Example 329

1-[7-(5-Methyl-7H-pyrrolo[2,3-d]pyrimidin-4-yl)-4,7-diaza-spiro[2.5]octane-4-carbonyl]-cyclopropanecarbonitrile Using Intermediate 14

1H NMR (600 MHz, DMSO-SPE) δ=11.60 (s, 1H), 8.21 (s, 1H), 7.09 (m, 1H), 3.82 (br, 6H), 2.35 (s, 3H), 1.64 (br, 4H), 0.98 (br, 4H).

Example 330

2-(4-Fluoro-phenyl)-1-[7-(5-methyl-7H-pyrrolo[2,3-d]pyrimidin-4-yl)-4,7-diaza-spiro[2.5]oct-4-yl]-ethanone Using Intermediate 14

1H NMR (600 MHz, DMSO) δ=11.57 (s, 1H), 8.19 (s, 1H), 7.26 (m, 2H), 7.12 (m, 2H), 7.07 (s, 1H), 3.94 (s, 2H), 3.58 (br, 6H), 2.32 (s, 3H), 1.00 (br, 4H).

Example 331

1-[7-(5-Methyl-7H-pyrrolo[2,3-d]pyrimidin-4-yl)-4,7-diaza-spiro[2.5]oct-4-yl]-2-(4-trifluoromethyl-phenyl)-ethanone Using Intermediate 14

1H NMR (600 MHz, DMSO) δ=11.58 (s, 1H), 8.19 (s, 1H), 7.66 (d, J=8.1, 2H), 7.46 (d, J=8.1, 2H), 7.07 (s, 1H), 4.03 (s, 2H), 3.88 (br, 2H), 3.50 (br, 4H), 2.32 (s, 3H), 1.01 (br, 4H).

Example 332

5-[7-(5-Methyl-7H-pyrrolo[2,3-d]pyrimidin-4-yl)-4,7-diaza-spiro[2.5]oct-4-yl]-5-oxo-pentanenitrile Using Intermediate 14

1H NMR (600 MHz, DMSO) δ=11.57 (s, 1H), 8.19 (s, 1H), 7.07 (s, 1H), 3.51 (br, 6H), 3.32 (br, 2H), 2.64 (m, 2H), 2.33 (s, 3H), 1.84 (m, 2H), 1.07 (br, 4H).

Example 333

3-{2-[7-(5-Methyl-7H-pyrrolo[2,3-d]pyrimidin-4-yl)-4,7-diaza-spiro[2.5]oct-4-yl]-2-oxo-ethyl}-benzonitrile Using Intermediate 14

1H NMR (600 MHz, DMSO) δ=11.58 (s, 1H), 8.19 (s, 1H), 7.74 (m, 1H), 7.71 (m, 1H), 7.57 (m, 1H), 7.51 (m, 1H), 7.07 (s, 1H), 4.00 (s, 2H), 3.52 (br, 6H), 2.33 (s, 3H), 1.03 (br, 4H).

Example 334

4-{2-[7-(5-Methyl-7H-pyrrolo[2,3-d]pyrimidin-4-yl)-4,7-diaza-spiro[2.5]oct-4-yl]-2-oxo-ethyl}-benzonitrile 1H NMR (600 MHz, DMSO) δ=11.58 (s, 1H), 8.19 (s, 1H), 7.74 m, 2H), 7.48 (m, 2H), 7.07 (s, 1H), 4.02 (s, 2H), 3.86 (br, 2H), 3.46 (br, 4H), 2.32 (s, 3H), 1.05 (br, 4H).

Example 335

4-[7-(5-Methyl-7H-pyrrolo[2,3-d]pyrimidin-4-yl)-4,7-diaza-spiro[2.5]oct-4-yl]-4-oxo-butyronitrile Using Intermediate 14

1H NMR (600 MHz, DMSO) δ=11.58 (s, 1H), 8.19 (s, 1H), 7.07 (s, 1H), 3.55 (br, 6H), 2.92 (m, 2H), 2.67 (m, 2H), 2.33 (s, 3H), 0.98 (br, 4H).

Example 336

4-[4-(1-Cyano-cyclopropanecarbonyl)-4,7-diaza-spiro[2.5]oct-7-yl]-7H-pyrrolo[2,3-d]pyrimidine-6-carboxylic acid methyl ester Using Intermediate 8

1H NMR (600 MHz, DMSO) δ=12.58 (s, 1H), 8.24 (s, 1H), 7.40 (s, 1H), 3.90 (br, 6H), 3.85 (s, 3H), 1.64 (br, 4H), 1.08 (br, 4H).

Example 337

4-{4-[2-(4-Fluoro-phenyl)-acetyl]-4,7-diaza-spiro[2.5]oct-7-yl}-7H-pyrrolo[2,3-d]pyrimidine-6-carboxylic acid methyl ester Using Intermediate 8

1H NMR (600 MHz, DMSO) δ=12.57 (s, 1H), 8.22 (s, 1H), 7.35 (s, 1H), 7.27 (m, 2H), 7.10 (m, 2H), 3.85 (br, 11H), 1.07 (br, 4H).

Example 338

4-{4-[2-(4-Trifluoromethyl-phenyl)-acetyl]-4,7-diaza-spiro[2.5]oct-7-yl}-7H-pyrrolo[2,3-d]pyrimidine-6-carboxylic acid methyl ester Using Intermediate 8

1H NMR (600 MHz, DMSO) δ=12.60 (s, 1H), 8.23 (s, 1H), 7.65 (d, J=8.1, 2H), 7.47 (d, J=8.1, 2H), 7.37 (s, 1H), 4.01 (br, 4H), 3.84 (br, 7H), 1.13 (m, 4H).

Example 339

4-[4-(4-Cyano-butyryl)-4,7-diaza-spiro[2.5]oct-7-yl]-7H-pyrrolo[2,3-d]pyrimidine-6-carboxylic acid methyl ester Using Intermediate 8

1H NMR (600 MHz, DMSO) δ=12.57 (s, 1H), 8.22 (s, 1H), 7.38 (s, 1H), 4.05 (br, 2H), 3.85 (br, 7H), 2.64 (m, 2H), 2.46 (m, 2H), 1.84 (m, 2H), 1.08 (br, 4H).

Example 340

4-[4-(4-Cyano-butyryl)-4,7-diaza-spiro[2.5]oct-7-yl]-7H-pyrrolo[2,3-d]pyrimidine-6-carboxylic acid methyl ester Using Intermediate 8

1H NMR (600 MHz, DMSO) δ=12.59 (s, 1H), 8.23 (s, 1H), 7.39 (s, 1H), 3.99 (br, 2H), 3.84 (br, 7H), 2.93 m, 2H), 2.66 (m, 2H), 1.09 (br, 4H).

Example 361

(5-Fluoro-1H-indol-2-yl)-[7-(7H-pyrrolo[2,3-d]pyrimidin-4-yl)-4,7-diaza-spiro[2.5]oct-4-yl]-methanone 1H NMR (300 MHz, DMSO) δ=11.70 (br, 2H), 8.15 (s, 1H), 7.40 (m, 2H), 7.20 (m, 1H), 7.06 (m, 1H), 6.91 (m, 1H), 6.64 (m, 1H), 4.02 (br, 6H), 1.01 (m, 2H), 0.91 (m, 2H).

Example 362

(7-Fluoro-1H-indol-2-yl)-[7-(7H-pyrrolo[2,3-d]pyrimidin-4-yl)-4,7-diaza-spiro[2.5]oct-4-yl]-methanone 1H NMR (300 MHz, DMSO) δ=12.02 (s, 1H), 11.79 (s, 1H), 8.17 (s, 1H), 7.45 (m, 1H), 7.22 (m, 1H), 7.01 (m, 3H), 6.66 (m, 1H), 3.99 (br, 6H), 0.96 (br, 4H).

Example 363

(6-Fluoro-1H-indol-2-yl)-[7-(7H-pyrrolo[2,3-d]pyrimidin-4-yl)-4,7-diaza-spiro[2.5]oct-4-yl]-methanone 1H NMR (300 MHz, DMSO) δ=11.82 (s, 1H), 11.65 (s, 1H), 8.18 (s, 1H), 7.65 (m, 1H), 7.23 (m, 1H), 7.15 (m, 1H), 6.94 (m, 2H), 6.67 (m, 1H), 4.03 (br, 6H), 1.05 (br, 2H), 0.94 (br, 2H).

Example 364

(4-Methanesulfonyl-phenyl)-[7-(7H-pyrrolo[2,3-d]pyrimidin-4-yl)-4,7-diaza-spiro[2.5]oct-4-yl]-methanone 1H NMR (300 MHz, DMSO) δ=11.81 (s, 1H), 8.17 (s, 1H), 8.01 (d, J=8.4, 2H), 7.75 (d, J=8.4, 2H), 7.22 (m, 1H), 6.64 (m, 1H), 3.62 (br, 9H), 0.97 (br, 4H).

Example 365

(5-Methanesulfonyl-1H-indol-2-yl)-[7-(7H-pyrrolo[2,3-d]pyrimidin-4-yl)-4,7-diaza-spiro[2.5]oct-4-yl]-methanone 1H NMR (300 MHz, DMSO) δ=12.14 (s, 1H), 11.87 (s, 1H), 8.27 (s, 1H), 8.20 (s, 1H), 7.69 (m, 2H), 7.23 (m, 2H), 6.69 (m, 1H), 4.05 (br, 6H), 3.18 (s, 3H), 1.04 (br, 2H), 0.94 (br, 2H).

Example 366

(4-Fluoro-3-methanesulfonyl-phenyl)-[7-(7H-pyrrolo[2,3-d]pyrimidin-4-yl)-4,7-diaza-spiro[2.5]oct-4-yl]-methanone 1H NMR (300 MHz, DMSO) δ=11.88 (s, 1H), 8.19 (s, 1H), 7.96 m, 2H), 7.63 (m, 1H), 7.25 (m, 1H), 6.67 (m, 1H), 4.02 (br, 4H), 3.79 (br, 2H), 3.59 (br, 3H), 0.90 (br, 4H).

Example 367

(3-Methanesulfonyl-phenyl)-[7-(7H-pyrrolo[2,3-d]pyrimidin-4-yl)-4,7-diaza-spiro[2.5]oct-4-yl]-methanone 1H NMR (300 MHz, DMSO) δ=11.81 (s, 1H), 8.18 (s, 1H), 8.05 (m, 2H), 7.85 (m, 1H), 7.75 (m, 1H), 7.22 (m, 1H), 6.65 (m, 1H), 4.02 (br, 4H), 3.80 (br, 2H), 3.59 (br, 3H), 0.86 (br, 4H).

Example 368

(4-Fluoro-1H-indol-2-yl)-[7-(7H-pyrrolo[2,3-d]pyrimidin-4-yl)-4,7-diaza-spiro[2.5]oct-4-yl]-methanone 1H NMR (300 MHz, DMSO) δ=12.02 (s, 1H), 11.89 (s, 1H), 8.13 (s, 1H), 7.45 (m, 1H), 7.24 (s, 1H), 7.02 (m, 2H), 6.96 (m, 1H), 6.69 (m, 1H), 3.99 (dbr, 6H), 1.01 (br, 2H), 0.91 (br, 2H).

Example 370

(3-Fluoro-4-methanesulfonyl-phenyl)-[7-(7H-pyrrolo[2,3-d]pyrimidin-4-yl)-4,7-diaza-spiro[2.5]oct-4-yl]-methanone 1H NMR (300 MHz, DMSO) δ=11.81 (s, 1H), 8.17 (s, 1H), 7.95 (m, 1H), 7.70 (m, 1H), 7.59 (m, 1H), 7.23 (m, 1H), 6.65 (m, 1H), 3.96 (br, 5H), 3.54 (br, 4H), 1.04 (m, 4H).

Example 371

3-[7-(7H-Pyrrolo[2,3-d]pyrimidin-4-yl)-4,7-diaza-spiro[2.5]octane-4-carbonyl]-benzenesulfonamide 1H NMR (300 MHz, DMSO) δ=11.87 (s, 1H), 8.20 (s, 1H), 7.94 (m, 2H), 7.71 (m, 2H), 7.49 (br, 2H), 7.25 (m, 1H), 6.67 (m, 1H), 3.87 (br, 6H), 0.89 (br, 4H).

Example 372

5-[7-(7H-Pyrrolo[2,3-d]pyrimidin-4-yl)-4,7-diaza-spiro[2.5]octane-4-carbonyl]-thiophene-3-sulfonic acid amide 1H NMR (300 MHz, DMSO) δ=11.89 (s, 1H), 8.27 (s, 1H), 8.20 (m, 1H), 7.74 (m, 1H), 7.52 (br, 2H), 7.26 (m, 1H), 6.69 (m, 1H), 3.97 (br, 6H), 1.06 (br, 2H), 0.94 (br, 2H).

Example 377

N-Propyl-4-[7-(7H-pyrrolo[2,3-d]pyrimidin-4-yl)-4,7-diaza-spiro[2.5]octane-4-carbonyl]-benzenesulfonamide 1H NMR (300 MHz, DMSO) δ=11.80 (s, 1H), 8.15 (s, 1H), 7.86 (m, 2H), 7.72 (m, 3H), 7.22 (m, 1H), 6.65 (m, 1H), 3.71 (br, 6H), 2.74 (m, 2H), 1.38 (m, 2H), 0.80 (t, 3H), 0.58 (br, 4H).

Example 378

2-Methoxy-4-[7-(7H-pyrrolo[2,3-d]pyrimidin-4-yl)-4,7-diaza-spiro[2.5]octane-4-carbonyl]-benzenesulfonamide 1H NMR (300 MHz, DMSO) δ=11.82 (s, 1H), 8.18 (s, 1H), 7.78 (m, 1H), 7.22 (br, 5H), 6.66 (m, 1H), 3.91 (br, 9H), 0.87 (br, 4H).

Example 379

3-Methyl-4-[7-(7H-pyrrolo[2,3-d]pyrimidin-4-yl)-4,7-diaza-spiro[2.5]octane-4-carbonyl]-benzenesulfonamide 1H NMR (300 MHz, DMSO) δ=11.80 (s, 1H), 8.19 (s, 1H), 7.76 (m, 2H), 7.48 (m, 1H), 7.37 (m, 2H), 7.22 (m, 1H), 6.63 (m, 1H), 3.89 (br, 3H), 3.40 (br, 3H), 2.28 (s, 3H), 0.95 (br, 4H).

Example 380

2-Methyl-4-[7-(7H-pyrrolo[2,3-d]pyrimidin-4-yl)-4,7-diaza-spiro[2.5]octane-4-carbonyl]-benzenesulfonamide 1H NMR (300 MHz, DMSO) δ=11.79 (s, 1H), 8.18 (s, 1H), 7.73 (m, 2H), 7.52 (m, 1H), 7.42 (m, 2H), 7.22 (m, 1H), 6.64 (m, 1H), 3.98 (br, 5H), 3.77 (br, 2H), 3.40 (br, 2H), 1.06 (br, 4H).

Example 382

(2-Chloro-4-methanesulfonyl-phenyl)-[7-(7H-pyrrolo[2,3-d]pyrimidin-4-yl)-4,7-diaza-spiro[2.5]oct-4-yl]-methanone 1H NMR (300 MHz, DMSO) δ=11.79 (s, 1H), 8.12 (m, 2H), 7.97 (m, 2H), 7.21 (m, 1H), 6.62 (m, 1H), 4.52 (br, 1H), 4.42 (br, 4H), 3.90 (br, 2H), 3.37 (br, 2H), 1.16 (m, 2H), 0.68 (m, 2H).

Example 383

4-{3-Oxo-3-[7-(7H-pyrrolo[2,3-d]pyrimidin-4-yl)-4,7-diaza-spiro[2.5]oct-4-yl]-propyl}-benzenesulfonamide 1H NMR (300 MHz, DMSO) δ=12.16 (s, 1H), 8.13 (s, 1H), 7.72 (m, 2H), 7.43 (m, 2H), 7.29 (m, 3H), 6.74 (m, 1H), 3.95 (br, 2H), 3.80 (br, 6H), 2.90 (br, 2H), 1.04 (br, 4H).

Example 384

(5-Methoxy-thiophen-3-yl)-[7-(7H-pyrrolo[2,3-d]pyrimidin-4-yl)-4,7-diaza-spiro[2.5]oct-4-yl]-methanone 1H NMR (300 MHz, DMSO) δ=11.79 (s, 1H), 8.15 (m, 1H), 7.21 (m, 1H), 7.09 (m, 1H), 6.64 (m, 1H), 6.44 (m, 1H), 3.91 (br, 9H), 0.88 (m, 4H).

Example 385

(4-Hydroxy-thiophen-2-yl)-[7-(7H-pyrrolo[2,3-d]pyrimidin-4-yl)-4,7-diaza-spiro[2.5]oct-4-yl]-methanone 1H NMR (300 MHz, DMSO) δ=11.91 (s, 1H), 9.72 (s, 1H), 8.20 (m, 1H), 7.25 (m, 1H), 7.06 (d, J=1.7, 1H), 6.69 (m, 1H), 6.55 (d, J=1.7, 1H), 3.92 (br, 6H), 0.99 (m, 2H), 0.88 (m, 2H).

Example 387

2-(4-Bromo-thiophen-2-yl)-1-[7-(7H-pyrrolo[2,3-d]pyrimidin-4-yl)-4,7-diaza-spiro[2.5]oct-4-yl]-ethanone 1H NMR (300 MHz, DMSO) δ=11.83 (s, 1H), 8.15 (m, 1H), 7.50 (m, 1H), 7.23 (m, 1H), 6.98 (m, 1H), 6.63 (m, 1H), 4.16 (s, 2H), 3.96 (br, 2H), 3.81 (br, 4H), 1.10 (m, 4H).

Example 388

4-Methyl-3-[7-(7H-pyrrolo[2,3-d]pyrimidin-4-yl)-4,7-diaza-spiro[2.5]octane-4-carbonyl]-benzenesulfonamide 1H NMR (300 MHz, DMSO) δ=11.80 (s, 1H), 8.19 (s, 1H), 7.76 (m, 2H), 7.48 (m, 1H), 7.37 (m, 2H), 7.22 (m, 1H), 6.62 (m, 1H), 3.92 (br, 4H), 3.46 (br, 2H), 2.27 (br, 3H), 1.02 (br, 4H).

Example 389

3-Methoxy-4-[7-(7H-pyrrolo[2,3-d]pyrimidin-4-yl)-4,7-diaza-spiro[2.5]octane-4-carbonyl]-benzenesulfonamide 1H NMR (300 MHz, DMSO) δ=11.89 (s, 1H), 8.17 (s, 1H), 7.45 (br, 5H), 7.24 (br, 1H), 6.67 (m, 1H), 3.93 (br, 7H), 3.42 (br, 2H), 1.01 (br, 4H).

Example 394

4-[7-(7H-Pyrrolo[2,3-d]pyrimidin-4-yl)-4,7-diaza-spiro[2.5]octane-4-carbonyl]-N-(tetrahydro-furan-2-ylmethyl)-benzenesulfonamide 1H NMR (600 MHz, DMSO) δ=11.75 (s, 1H), 8.17 (s, 1H), 7.88 (br, 3H), 7.70 (m, 2H), 7.20 (s, 1H), 6.58 (m, 1H), 4.04 (br, 6H), 3.80 (m, 1H), 3.67 (m, 1H), 3.57 (m, 1H), 2.83 (m, 2H), 1.84 (m, 1H), 1.76 (m, 2H), 1.52 (m, 1H), 0.91 (br, 4H).

Example 395

N-(2-Cyano-ethyl)-4-[7-(7H-pyrrolo[2,3-d]pyrimidin-4-yl)-4,7-diaza-spiro[2.5]octane-4-carbonyl]-benzenesulfonamide 1H NMR (600 MHz, DMSO) δ=8.22 (s, 1H), 8.17 (s, 1H), 7.88 (d, J=8.3, 2H), 7.72 (d, J=8.3, 2H), 7.20 (m, 1H), 6.62 (m, 1H), 3.92 (br, 6H), 3.05 (t, J=6.4, 2H), 2.65 (t, J=6.4, 2H), 0.92 (br, 4H).

Example 396

N-(2-Methoxy-ethyl)-4-[7-(7H-pyrrolo[2,3-d]pyrimidin-4-yl)-4,7-diaza-spiro[2.5]octane-4-carbonyl]-benzenesulfonamide 1H NMR (600 MHz, DMSO) δ=11.75 (s, 1H), 8.17 (m, 1H), 7.87 (m, 3H), 7.70 (m, 2H), 7.20 (m, 1H), 6.62 (m, 1H), 4.06 (br, 4H), 3.66 (br, 2H), 3.30 (m, 2H), 3.17 (s, 3H), 2.95 (t, J=5.4, 2H), 0.99 (m, 4H).

Example 397

4-[7-(7H-Pyrrolo[2,3-d]pyrimidin-4-yl)-4,7-diaza-spiro[2.5]octane-4-carbonyl]-N-(2-thiophen-2-yl-ethyl)-benzenesulfonamide 1H NMR (600 MHz, DMSO) δ=11.75 (s, 1H), 8.17 (s, 1H), 7.95 (m, 1H), 7.87 (m, 2H), 7.72 (m, 2H), 7.33 (m, 1H), 7.18 (m, 1H), 6.94 (m, 1H), 6.87 (m, 1H), 6.62 (m, 1H), 3.94 (br, 6H), 3.03 (br, 2H), 2.92 (t, J=7.2, 2H), 0.94 (br, 4H).

Example 398

3-{2-Oxo-2-[7-(7H-pyrrolo[2,3-d]pyrimidin-4-yl)-4,7-diaza-spiro[2.5]oct-4-yl]-ethyl}-benzenesulfonamide 1H NMR (300 MHz, DMSO) δ=11.71 (s, 1H), 8.14 (s, 1H), 7.70 (m, 2H), 7.48 (m, 2H), 7.32 (s, 2H), 7.19 (m, 1H), 6.59 (m, 1H), 3.92 (br, 8H), 1.11 (br, 4H).

Example 399

4-{2-Oxo-2-[7-(7H-pyrrolo[2,3-d]pyrimidin-4-yl)-4,7-diaza-spiro[2.5]oct-4-yl]-ethoxy}-benzenesulfonamide 1H NMR (600 MHz, DMSO) δ=11.74 (s, 1H), 8.15 (s, 1H), 7.72 (m, 2H), 7.21 (br, 3H), 7.05 (m, 2H), 6.64 (br, 1H), 5.04 (m, 2H), 3.87 (br, 6H), 1.02 (m, 4H).

Example 400

4-{5-[7-(7H-Pyrrolo[2,3-d]pyrimidin-4-yl)-4,7-diaza-spiro[2.5]octane-4-carbonyl]-furan-2-yl}-benzenesulfonamide 1H NMR (300 MHz, DMSO) δ=11.74 (s, 1H), 8.17 (s, 1H), 7.99 (d, J=8.6, 2H), 7.92 (d, J=8.6, 2H), 7.44 (br s, 2H), 7.30 (m, 1H), 7.21 (m, 2H), 6.68 (m, 1H), 4.11 (br, 4H), 3.96 (br, 2H), 0.99 (m, 2H), 0.84 (m, 2H).

Example 401

2-Oxo-2-[7-(7H-pyrrolo[2,3-d]pyrimidin-4-yl)-4,7-diaza-spiro[2.5]oct-4-yl]-N-(4-sulfamoyl-phenyl)-acetamide 1H NMR (600 MHz, DMSO) δ=11.75 (br s, 1H), 11.14 (br s, 1H), 8.15 (m, 1H), 7.82 (m, 4H), 7.32 (br s, 2H), 7.20 (m, 1H), 6.61 (m, 1H), 3.89 (br, 6H), 1.02 (br, 4H).

Example 402

5-[7-(7H-Pyrrolo[2,3-d]pyrimidin-4-yl)-4,7-diaza-spiro[2.5]octane-4-carbonyl]-1H-pyrrole-3-sulfonic acid amide 1H NMR (300 MHz, DMSO) δ=8.26 (s, 0.6H), 8.15 (s, 1H), 7.26 (s, 0.3H), 7.20 (m, 1H), 6.86 (m, 0.2H), 6.62 (m, 1H), 5.97 (br, 6H), 3.94 (br, 3H), 3.83 (br, 2H), 3.61 (br, 2H), 0.93 (br, 4H).

Example 403

(4-Methanesulfonyl-3-methyl-phenyl)-[7-(7H-pyrrolo[2,3-d]pyrimidin-4-yl)-4,7-diaza-spiro[2.5]oct-4-yl]-methanone 1H NMR (300 MHz, DMSO) δ=12.96 (s, 1H), 8.40 (s, 1H), 7.98 (m, 1H), 7.58 (m, 2H), 7.49 (m, 1H), 7.00 (m, 1H), 4.18 (br, 4H), 3.81 (br, 2H), 3.27 (s, 3H), 2.71 (s, 3H), 1.15 (m, 4H).

Example 404

4-{2-Oxo-2-[7-(7H-pyrrolo[2,3-d]pyrimidin-4-yl)-4,7-diaza-spiro[2.5]oct-4-yl]-ethylsulfanyl}-benzenesulfonamide 1H NMR (300 MHz, DMSO) δ=12.09 (s, 1H), 8.19 (s, 1H), 7.71 (d, J=8.5, 2H), 7.49 (d, J=8.5, 2H), 7.30 (br m, 3H), 6.72 (m, 1H), 4.08 (br, 8H), 1.09 (br, 4H).

Example 405

5-[7-(7H-Pyrrolo[2,3-d]pyrimidin-4-yl)-4,7-diaza-spiro[2.5]octane-4-carbonyl]-thiophene-2-sulfonic acid amide 1H NMR (300 MHz, DMSO) δ=12.82 (s, 1H), 8.39 (s, 1H), 7.88 (br, 2H), 7.52 (br m, 3H), 6.98 (m, 1H), 4.13 (br, 6H), 1.12 (br, 4H).

Example 406

[4-(2-Hydroxy-ethanesulfonyl)-phenyl]-[7-(7H-pyrrolo[2,3-d]pyrimidin-4-yl)-4,7-diaza-spiro[2.5]oct-4-yl]-methanone 1H NMR (300 MHz, DMSO) δ=8.15 (s, 1H), 7.97 (d, J=8.4, 2H), 7.73 (d, J=8.4, 2H), 7.20 (m, 1H), 6.61 (m, 1H), 4.00 (br, 6H), 3.71 (t, J=6.2, 2H), 3.51 (t, J=6.2, 2H), 0.80 (br, 4H).

Example 407

(4-Cyclopentanesulfonyl-phenyl)-[7-(7H-pyrrolo[2,3-d]pyrimidin-4-yl)-4,7-diaza-spiro[2.5]oct-4-yl]-methanone 1H NMR (300 MHz, DMSO) δ=11.73 (s, 1H), 8.15 (s, 1H), 7.96 (d, J=8.3, 2H), 7.75 (d, J=8.3, 2H), 7.20 (m, 1H), 6.62 (m, 1H), 3.86 (br, 7H), 1.85 (m, 4H), 1.60 (m, 4H), 0.96 (m, 4H).

Example 408

4-{4-[7-(7H-Pyrrolo[2,3-d]pyrimidin-4-yl)-4,7-diaza-spiro[2.5]octane-4-carbonyl]-benzenesulfonyl}-butyronitrile 1H NMR (300 MHz, DMSO) δ=11.74 (s, 1H), 8.15 (s, 1H), 7.99 (d, J=8.3, 2H), 7.78 (d, J=8.3, 2H), 7.20 (m, 1H), 6.62 (m, 1H), 4.00 (br, 6H), 3.46 (m, 2H), 2.63 (t, J=7.2, 2H), 1.88 (m, 2H), 0.86 (br, 4H).

Example 409

{4-[7-(7H-Pyrrolo[2,3-d]pyrimidin-4-yl)-4,7-diaza-spiro[2.5]octane-4-carbonyl]-phenyl}-methanesulfonamide 1H NMR (300 MHz, DMSO) δ=11.72 (s, 1H), 8.14 (s, 1H), 7.47 (br, 4H), 7.19 (m, 1H), 6.88 (s, 2H), 6.58 (m, 1H), 4.34 (br s, 2H), 3.97 (br, 4H), 3.76 (br, 2H), 0.93 (br, 4H).

Example 410

N-{2-Oxo-2-[7-(7H-pyrrolo[2,3-d]pyrimidin-4-yl)-4, 7-diaza-spiro[2.5]oct-4-yl]-ethyl}-4-sulfamoyl-benzamide 1H NMR (300 MHz, DMSO) δ=11.72 (s, 1H), 8.99 (s, 1H), 8.14 (m, 1H), 8.02 (m, 2H), 7.91 (m, 2H), 7.47 (s, 2H), 7.20 (m, 1H), 6.62 (m, 1H), 4.29 (br, 2H), 3.88 (br, 6H), 1.03 (br, 4H).

Example 411

3-Methyl-4-{2-oxo-2-[7-(7H-pyrrolo[2,3-d]pyrimidin-4-yl)-4,7-diaza-spiro[2.5]oct-4-yl]-ethoxy}-benzenesulfonamide 1H NMR (300 MHz, DMSO) δ=11.72 (s, 1H), 8.15 (s, 1H), 7.58 (m, 2H), 7.20 (m, 1H), 7.13 (s, 2H), 6.96 (m, 1H), 6.60 (m, 1H), 5.13 (br, 2H), 3.88 (br, 6H), 2.26 (s, 3H), 1.11 (br, 4H).

Example 412

1-{2-Oxo-2-[7-(7H-pyrrolo[2,3-d]pyrimidin-4-yl)-4, 7-diaza-spiro[2.5]oct-4-yl]-ethyl}-1H-pyrazole-4-sulfonic acid amide 1H NMR (600 MHz, DMSO) δ=11.75 (s, 1H), 8.16 (br, 3H), 7.30 (s, 2H), 7.19 (m, 1H), 6.60 (m, 1H), 5.36 (s, 1H), 3.92 (br, 8H), 1.01 (m, 4H).

Example 413

Indan-1-yl-[7-(7H-pyrrolo[2,3-d]pyrimidin-4-yl)-4, 7-diaza-spiro[2.5]oct-4-yl]-methanone 1H NMR (600 MHz, DMSO) δ=11.74 (s, 1H), 8.16 (s, 1H), 7.25 (m, 1H), 7.21 (m, 1H), 7.16 (m, 1H), 7.06 (m, 2H), 6.63 (m, 1H), 4.75 (br s, 1H), 4.05 (br, 6H), 2.96 (br, 2H), 2.29 (br, 2H), 1.01 (br, 4H).

Example 414

(5-Methyl-pyrazin-2-yl)-[7-(7H-pyrrolo[2,3-d]pyrimidin-4-yl)-4,7-diaza-spiro[2.5]oct-4-yl]-methanone 1H NMR (600 MHz, DMSO) δ=11.74 (s, 1H), 8.76 (s, 1H), 8.60 (s, 1H), 8.15 (br, 1H), 7.21 (br, 1H), 6.60 (br, 1H), 3.95 (br, 6H), 2.58 (s, 3H), 0.92 (m, 4H).

Example 415

[7-(7H-Pyrrolo[2,3-d]pyrimidin-4-yl)-4,7-diaza-spiro[2.5]oct-4-yl]-(1,2,3,4-tetrahydro-naphthalen-1-yl)-methanone 1H NMR (600 MHz, DMSO) δ=11.7 (s, 1H), 8.15 (s, 1H), 7.20 (m, 1H), 7.09 (m, 2H), 7.00 (m, 1H), 6.84 (m, 1H), 6.61 (m, 1H), 4.50 (br, 1H), 3.91 (br, 6H), 2.72 (br, 2H), 1.80 (br, 4H), 1.10 (br, 4H).

Example 416

[7-(7H-Pyrrolo[2,3-d]pyrimidin-4-yl)-4,7-diaza-spiro[2.5]oct-4-yl]-(1,2,3,4-tetrahydro-naphthalen-1-yl)-methanone 1H NMR (600 MHz, DMSO) δ=11.74 (s, 1H), 8.16 (s, 1H), 7.20 (m, 1H), 7.09 (m, 2H), 6.99 (m, 1H), 6.84 (m, 1H), 6.61 (m, 1H), 4.50 (br, 1H), 3.92 (br, 6H), 2.75 (br, 2H), 1.80 (br, 4H), 1.09 (br, 4H).

Example 417

(3-Methyl-pyrazin-2-yl)-[7-(7H-pyrrolo[2,3-d]pyrimidin-4-yl)-4,7-diaza-spiro[2.5]oct-4-yl]-methanone 1H NMR (600 MHz, DMSO) δ=11.75 (s, 1H), 8.63 (s, 1H), 8.52 (m, 1H), 8.15 (m, 1H), 7.20 (m, 1H), 6.60 (m, 1H), 3.99 (br, 6H), 2.46 (s, 3H), 0.54 (br, 4H).
Rotamers observed

Example 418

(6-Methyl-pyrazin-2-yl)-[7-(7H-pyrrolo[2,3-d]pyrimidin-4-yl)-4,7-diaza-spiro[2.5]oct-4-yl]-methanone 1H NMR (600 MHz, DMSO) δ=11.74 (br, 1H), 8.66 (br, 2H), 8.16 (m, 1H), 7.20 (m, 1H), 6.61 (m, 1H), 3.95 (br, 6H), 2.54 (s, 3H), 0.69 (br, 4H).
Rotamers observed

Example 419

(3-Methyl-quinoxalin-2-yl)-[7-(7H-pyrrolo[2,3-d]pyrimidin-4-yl)-4,7-diaza-spiro[2.5]oct-4-yl]-methanone 1H NMR (600 MHz, DMSO) δ=11.76 (br, 1H), 8.16 (br, 1H), 8.09 (m, 2H), 7.88 (m, 2H), 7.21 (br, 1H), 6.61 (br, 1H), 4.05 (m, 6H), 2.66 (s, 3H), 0.54 (br, 4H).
Rotamers observed

Example 420

2-(4-Methanesulfonyl-phenyl)-1-[7-(7H-pyrrolo[2,3-d]pyrimidin-4-yl)-4,7-diaza-spiro[2.5]oct-4-yl]-ethanone 1H NMR (600 MHz, DMSO) δ=11.73 (s, 1H), 8.14 (s, 1H), 7.85 (m, 2H), 7.52 (m, 2H), 7.20 (m, 1H), 6.59 (m, 1H), 3.91 (br, 8H), 3.20 (s, 3H), 1.02 (br, 4H).

Example 422

5-[7-(7H-Pyrrolo[2,3-d]pyrimidin-4-yl)-4,7-diaza-spiro[2.5]octane-4-carbonyl]-thiophene-3-sulfonic acid isobutyl-amide 1H NMR (300 MHz, DMSO) δ=11.72 (s, 1H), 11.53 (s, 1H), 8.14 (s, 1H), 7.32 (m, 2H), 7.20 (m, 1H), 6.90 (m, 1H), 6.64 (m, 1H), 4.03 (br, 6H), 2.31 (s, 3H), 1.01 (br, 2H), 0.91 (br, 2H).

Example 423

5-[7-(7H-Pyrrolo[2,3-d]pyrimidin-4-yl)-4,7-diaza-spiro[2.5]octane-4-carbonyl]-thiophene-3-sulfonic acid isobutyl-amide 1H NMR (300 MHz, DMSO) δ=11.76 (s, 1H), 8.33 (s, 1H), 8.16 (s, 1H), 7.69 (m, 2H), 7.22 (m, 1H), 6.64 (m, 1H), 4.01 (br, 6H), 2.61 (t, J=6.4, 2H), 1.67 (m, 1H), 0.97 (br, 2H), 0.85 (br, 8H).

Example 426

N-Furan-2-ylmethyl-4-[7-(7H-pyrrolo[2,3-d]pyrimidin-4-yl)-4,7-diaza-spiro[2.5]octane-4-carbonyl]-benzenesulfonamide 1H NMR (300 MHz, DMSO) δ=11.65 (br, 1H), 8.24 (t, J=5.8, 1H), 8.10 (m, 1H), 7.75 (d, J=8.4, 2H), 7.58 (d, J=8.4, 2H), 7.42 (m, 1H), 7.13 (m, 1H), 6.55 (m, 1H), 6.23 m, 1H), 6.10 (m, 1H), 4.00 (br, 4H), 3.87 (br, 2H), 3.68 (br, 2H), 0.78 (br, 4H).

Example 427

N-(5-Methyl-furan-2-ylmethyl)-4-[7-(7H-pyrrolo[2,3-d]pyrimidin-4-yl)-4,7-diaza-spiro[2.5]octane-4-carbonyl]-benzenesulfonamide 1H NMR (300 MHz, DMSO) δ=11.76 (s, 1H), 8.25 (t, J=6.0, 1H), 8.15 (br, 1H), 7.81 (d, J=8.4, 2H), 7.64 (d, J=8.4, 2H), 7.21 (m, 1H), 6.63 (m, 1H), 6.02 (m, 1H), 5.87 (m, 1H), 3.98 (br, 6H), 3.76 (s, 2H), 2.12 (s, 3H), 0.85 (br, 4H).

Example 428

(2-{4-[7-(7H-Pyrrolo[2,3-d]pyrimidin-4-yl)-4,7-diaza-spiro[2.5]octane-4-carbonyl]-benzenesulfonylamino}-ethyl)-carbamic acid tert-butyl ester 1H NMR (300 MHz, DMSO) δ=11.77 (s, 1H), 8.16 (s, 1H), 7.85 (d, J=8.4, 2H), 7.79 (t, J=5.8, 1H), 7.70 (d, J=8.4, 2H), 7.21 (m, 1H), 6.78 (br, 1H), 6.63 (m, 1H), 3.92 (br, 6H), 2.95 (m, 2H), 2.79 (m, 2H), 1.36 (s, 9H), 0.83 (br, 4H).

Example 429

4-{1-[7-(7H-Pyrrolo[2,3-d]pyrimidin-4-yl)-4,7-diaza-spiro[2.5]octane-4-carbonyl-cyclopropyl}-benzonitrile 1H NMR (300 MHz, DMSO) δ=11.72 (s, 1H), 8.10 (s, 1H), 7.74 (m, 2H), 7.34 (m, 2H), 7.17 (m, 1H), 6.53 (m, 1H), 3.68 (br, 6H), 1.38 (m, 4H), 0.94 (m, 4H).

Example 430

N-{4-[7-(7H-Pyrrolo[2,3-d]pyrimidin-4-yl)-4,7-diaza-spiro[2.5]octane-4-carbonyl]-phenyl}-methanesulfonamide 1H NMR (600 MHz, DMSO) δ=11.73 (s, 1H), 10.05 (s, 1H), 8.14 (s, 1H), 7.47 (m, 2H), 7.24 (m, 2H), 7.19 (m, 1H), 6.61 (m, 1H), 3.96 (br, 4H), 3.78 (br, 2H), 3.06 (s, 3H), 0.79 (br, 4H).

Example 431

Propane-1-sulfonic acid {4-[7-(7H-pyrrolo[2,3-d]pyrimidin-4-yl)-4,7-diaza-spiro[2.5]octane-4-carbonyl]-phenyl}-amide 1H NMR (300 MHz, DMSO) δ=11.77 (s, 1H), 10.10 (s, 1H), 8.14 (s, 1H), 7.47 (m, 2H), 7.22 (m, 3H), 6.63 (m, 1H), 4.01 (br, 4H), 3.76 (br, 2H), 3.14 (m, 2H), 1.69 (m, 2H), 0.94 (t, J=7.4, 3H), 0.79 (br, 4H).

Example 432

Propane-2-sulfonic acid {4-[7-(7H-pyrrolo[2,3-d]pyrimidin-4-yl)-4,7-diaza-spiro[2.5]octane-4-carbonyl]-phenyl}-amide 1H NMR (300 MHz, DMSO) δ=11.76 (s, 1H), 10.06 (s, 1H), 8.14 (s, 1H), 7.46 (d, J=8.6, 2H), 7.28 (d, J=8.6, 2H), 7.20 (m, 1H), 6.62 (m, 1H), 3.96 (br, 4H), 3.75 (br, 2H), 3.28 (m, 1H), 1.26 (d, J=6.8, 6H), 0.78 (br, 4H).

Example 433

[4-(2-Methoxy-ethanesulfonyl)-phenyl]-[7-(7H-pyrrolo[2,3-d]pyrimidin-4-yl)-4,7-diaza-spiro[2.5]oct-4-yl]-methanone 1H NMR (300 MHz, DMSO) δ=11.73 (s, 1H), 8.15 (s, 1H), 7.96 (d, J=8.4, 2H), 7.73 (d, J=8.4, 2H), 7.20 (m, 1H), 6.61 (s, 1H), 4.01 (br, 6H), 3.66 (br, 4H), 3.08 (s, 3H), 0.81 (br, 4H).

Example 434

3-Fluoro-4-{2-oxo-2-[7-(7H-pyrrolo[2,3-d]pyrimidin-4-yl)-4,7-diaza-spiro[2.5]oct-4-yl]-ethoxy}-benzenesulfonamide 1H NMR (300 MHz, DMSO) δ=11.73 (br, 1H), 8.15 (s, 1H), 7.62 (m, 1H), 7.55 (m, 1H), 7.32 (s, 2H), 7.20 (m, 2H), 6.60 (m, 1H), 5.24 (s, 2H), 3.82 (br, 6H), 1.11 (br, 4H).

Example 435

1-{3-Oxo-3-[7-(7H-pyrrolo[2,3-d]pyrimidin-4-yl)-4,7-diaza-spiro[2.5]oct-4-yl]-propyl}-1H-pyrazole-4-sulfonic acid amide 1H NMR (300 MHz, DMSO) δ=11.71 (s, 1H), 8.13 (s, 1H), 7.69 (s, 1H), 7.19 (br, 3H), 6.58 (br, 2H), 4.42 (br, 5H), 3.80 (br, 5H), 0.95 (br, 4H).

Example 442

2-Phenoxy-1-[7-(7H-pyrrolo[2,3-d]pyrimidin-4-yl)-4,7-diaza-spiro[2.5]oct-4-yl]-ethanone 1H NMR (300 MHz, DMSO) δ=11.77 (s, 1H), 8.15 (br, 1H), 7.23 (br, 3H), 6.91 (br, 3H), 6.62 (m, 1H), 4.95 (s, 2H), 3.83 (br, 6H), 1.09 (br, 4H).

Example 443

2-Methoxy-1-[7-(7H-pyrrolo[2,3-d]pyrimidin-4-yl)-4,7-diaza-spiro[2.5]oct-4-yl]-ethanone 1H NMR (300 MHz, DMSO) δ=11.71 (br, 1H), 8.14 (s, 1H), 7.19 (m, 1H), 6.59 (m, 1H), 4.18 (s, 2H), 3.96 (br, 4H), 3.81 (s, 3H), 3.62 (br, 2H), 0.95 (br, 4H).

Example 451

2-Phenylamino-1-[7-(7H-pyrrolo[2,3-d]pyrimidin-4-yl)-4,7-diaza-spiro[2.5]oct-4-yl]-ethanone 1H NMR (300 MHz, DMSO) δ=11.72 (s, 1H), 8.14 (s, 1H), 7.19 (m, 1H), 7.05 (m, 2H), 6.57 (m, 4H), 5.59 (br, 1H), 3.92 (br, 16H), 1.16 (br, 8H).

Example 452

4-{3-Oxo-3-[7-(7H-pyrrolo[2,3-d]pyrimidin-4-yl)-4,7-diaza-spiro[2.5]oct-4-yl]-propoxy}-benzene-sulfonamide 1H NMR (300 MHz, DMSO) δ=11.71 (s, 1H), 8.14 (s, 1H), 7.72 (d, J=8.5, 2H), 7.19 (m, 3H), 7.03 (d, J=8.5, 2H), 6.60 (m, 1H), 4.33 (br, 2H), 3.85 (br, 6H), 3.04 (s, 2H), 1.08 (br, 4H).

Example 453

4-{3-Oxo-3-[7-(7H-pyrrolo[2,3-d]pyrimidin-4-yl)-4,7-diaza-spiro[2.5]oct-4-yl]-propylamino}-benzene-sulfonamide 1H NMR (300 MHz, DMSO) δ=11.71 (s, 1H), 8.13 (s, 1H), 7.51 (d, J=8.8, 2H), 7.18 (m, 1H), 6.90 (br, 2H), 6.61 (m, 3H), 6.37 (br, 1H), 3.94 (br, 2H), 3.77 (br, 4H), 3.37 (br, 2H), 2.81 (br, 2H), 1.02 (br, 4H).

Example 454

4-{2-Oxo-2-[7-(7H-pyrrolo[2,3-d]pyrimidin-4-yl)-4,7-diaza-spiro[2.5]oct-4-yl]-ethylamino}-benzene-sulfonamide 1H NMR (300 MHz, DMSO) δ=11.72 (s, 1H), 8.14 (s, 1H), 7.49 (m, 2H), 7.20 (m, 1H), 6.91 (m, 2H), 6.69 (m, 2H), 6.60 (m, 1H), 6.40 (s, 1H), 3.96 (br, 8H), 1.09 (br, 4H).

Example 455

3-Methylsulfanyl-1-[7-(7H-pyrrolo[2,3-d]pyrimidin-4-yl)-4,7-diaza-spiro[2.5]oct-4-yl]-propan-1-one 1H NMR (300 MHz, DMSO) δ=11.71 (s, 1H), 8.13 (s, 1H), 7.19 (m, 1H), 6.59 (m, 1H), 3.83 (br, 6H), 2.77 (br, 4H), 2.08 (s, 3H), 0.99 (br, 4H).

Example 456

3-Methoxy-1-[7-(7H-pyrrolo[2,3-d]pyrimidin-4-yl)-4,7-diaza-spiro[2.5]oct-4-yl]-propan-1-one 1H NMR (300 MHz, DMSO) δ=11.85 (br, 1H), 8.13 (s, 1H), 7.19 (m, 1H), 6.59 (m, 1H), 3.69 (br, 106H), 3.22 (br, 10H), 2.76 (s, 3H), 1.05 (br, 4H).

Example 457

3-Dimethylamino-1-[7-(7H-pyrrolo[2,3-d]pyrimidin-4-yl)-4,7-diaza-spiro[2.5]oct-4-yl]-propan-1-one 1H NMR (300 MHz, DSO) δ=11.79 (br, 1H), 8.33 (s, 1H), 7.38 (m, 1H), 6.79 (m, 1H), 4.01 (br, 6H), 2.83 (br, 2H), 2.34 (s, 6H), 1.25 (br, 4H).

Example 12

3-(7H-Pyrrolo[2,3-d]pyrimidin-4-yl)-3,8-diazabicyclo[3.2.1]octane-8-carboxylic acid 2-methoxyethyl ester

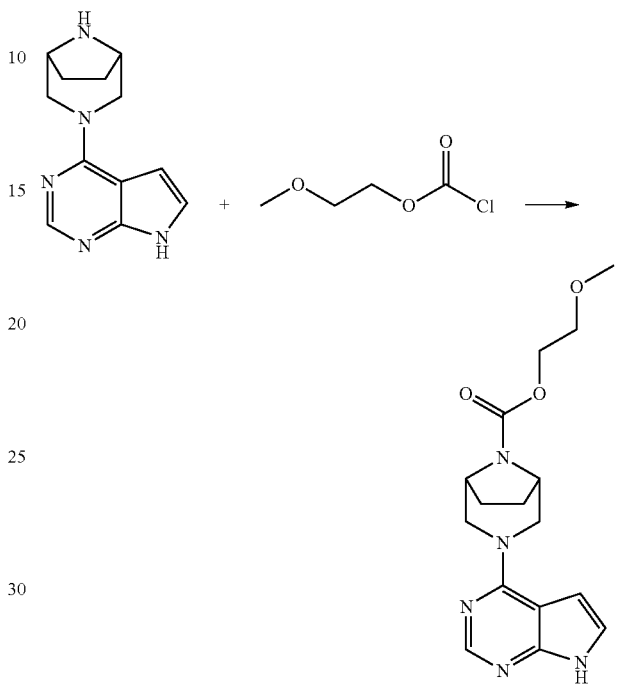

4-(3,8-Diaza-bicyclo[3.2.1]oct-3-yl)-7H-pyrrolo[2,3-d]pyrimidine (intermediate 4) (0.05 mmol) was dissolved in THF (1.0 mL). Triethylamine (0.12 mmol) and 2-methoxyethyl chloroformate (0.06 mmol) was added. The reaction mixture was left at rt for 16 hours. The pure compounds were obtained by standard preparative HPLC purification of the reaction mixture.

¹H NMR (300 MHz, DMSO) δ=11.70 (s, 1H), 8.13 (s, 1H), 7.18 (dd, J=2.5, 3.4, 1H), 6.63 (dd, J=1.8, 3.5, 1H), 4.56-4.28 (m, 4H), 4.25-4.11 (m, 2H), 3.53 (m, 2H), 3.43-3.14 (m, 5H), 1.85 (m, 2H), 1.66 (m, 2H).

Using this procedure the following compounds were obtained:

Example 52

3-(7H-Pyrrolo[2,3-d]pyrimidin-4-yl)-3,8-diazabicyclo[3.2.1]octane-8-carboxylic acid ethyl ester ¹H NMR (300 MHz, DMSO) δ=11.70 (s, 1H), 8.13 (s, 1H), 7.23-7.11 (m, 1H), 6.62 (m, 1H), 4.56-4.27 (m, 4H), 4.10 (q, 2H), 3.23 (m, 2H), 1.83 (m, 2H), 1.66 (m, 2H), 1.21 (t, J=7.1, 3H).

Example 58

3-(7H-Pyrrolo[2,3-d]pyrimidin-4-yl)-3,8-diazabicyclo[3.2.1]octane-8-carboxylic acid benzyl ester ¹H NMR (300 MHz, DMSO) δ=11.71 (s, 1H), 8.13 (s, 1H), 7.46-7.25 (m, 5H), 7.24-7.11 (m, 1H), 6.62 (d, J=1.8, 1H), 5.14 (s, 2H), 4.58-4.31 (m, 4H), 3.22 (m, 2H), 1.85 (m, 2H), 1.67 (m, 2H).

Example 59

3-(7H-Pyrrolo[2,3-d]pyrimidin-4-yl)-3,8-diazabicyclo[3.2.1]octane-8-carboxylic acid prop-2-ynyl ester $^1$H NMR (300 MHz, DMSO) δ=11.70 (s, 1H), 8.14 (s, 1H), 7.25-7.12 (m, 1H), 6.63 (d, J=1.9, 1H), 4.74 (m, 2H), 4.58-4.29 (m, 4H), 3.59-3.14 (br m, 3H), 1.86 (s, 2H), 1.67 (m, 2H).

Example 89

7-(7H-Pyrrolo[2,3-d]pyrimidin-4-yl)-4,7-diaza-spiro[2.5]octane-4-carboxylic acid but-2-ynyl ester 1H NMR (300 MHz, DMSO) δ=11.71 (s, 1H), 8.13 (s, 1H), 7.18 (m, 1H), 6.60 (m, 1H), 4.68 (m, 2H), 3.95 (m, 2H), 3.76 (m, 2H), 3.63 (s, 2H), 1.83 (br, 3H), 0.95 (br, 4H).

Example 446

7-(7H-Pyrrolo[2,3-d]pyrimidin-4-yl)-4,7-diaza-spiro[2.5]octane-4-carboxylic acid 4-chloro-phenyl ester 1H NMR (300 MHz, DMF) δ=11.95 (s, 1H), 8.35 (s, 1H), 7.66 (m, 2H), 7.42 (m, 3H), 6.82 (m, 1H), 4.28 (br, 2H), 4.07 (br, 2H), 3.93 (br, 2H), 1.30 (br, 2H), 1.16 (br, 2H).

Example 450

7-(7H-Pyrrolo[2,3-d]pyrimidin-4-yl)-4,7-diaza-spiro[2.5]octane-4-carboxylic acid cyclopentyl ester 1H NMR (300 MHz, DMSO) δ=11.71 (s, 1H), 8.13 (s, 1H), 7.18 (m, 1H), 6.59 (m, 1H), 5.05 (m, 1H), 3.91 (m, 2H), 3.73 (br s, 2H), 3.60 (m, 2H), 1.71 (br, 8H), 0.89 (br, 4H).

Example 11

3-(7H-Pyrrolo[2,3-d]pyrimidin-4-yl)-3,8-diazabicyclo[3.2.1]octane-8-carbothioic acid benzylamide

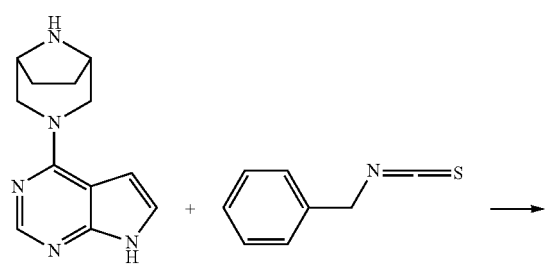

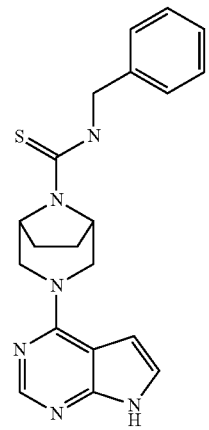

4-(3,8-Diaza-bicyclo[3.2.1]oct-3-yl)-7H-pyrrolo[2,3-d]pyrimidine (intermediate 4) (0.05 mmol) was dissolved in THF (1 mL), and benzyl isothiocyanate (0.06 mmol) was added. The reaction mixture was left at rt for 16 hours. The pure compounds were obtained by standard preparative HPLC purification of the reaction mixture.

$^1$H NMR (300 MHz, DMSO) δ=11.72 (s, 1H), 8.15 (m, 1H), 7.39-7.12 (m, 6H), 6.62 (m, 1H), 5.03 (s, 2H), 4.83 (m, 2H), 4.46 (m, 2H), 3.37 (m, 2H), 1.84 (m, 4H).

Using this procedure the following compounds were obtained:

Example 10

3-(7H-Pyrrolo[2,3-d]pyrimidin-4-yl)-3,8-diaza-bicyclo[3.2.1]octane-8-carbothioic acid isobutyl-amide $^1$H NMR (300 MHz, DMSO) δ=11.71 (s, 1H), 8.17 (m, 1H), 7.83 (m, 1H), 7.18 (m, 1H), 6.61 (m, 1H), 5.00 (m, 2H), 4.42 (m, 2H), 3.78-3.21 (m, 4H), 2.13-1.65 (m, 5H), 0.85 (m, 6H).

Example 29

[3-(7H-Pyrrolo[2,3-d]pyrimidin-4-yl)-3,8-diazabicyclo[3.2.1]octane-8-carbothioyl]carbamic acid ethyl ester $^1$H NMR (300 MHz, DMSO) δ=11.74 (s, 1H), 8.15 (s, 1H), 7.26-7.13 (m, 1H), 6.64 (m, 1H), 5.10 (m, 1H), 4.56 (m, 3H), 4.21-4.00 (m, 2H), 3.39 (m, 3H), 2.11-1.67 (m, 4H), 1.21 (m, 3H).

Example 39

3-(7H-Pyrrolo[2,3-d]pyrimidin-4-yl)-3,8-diazabicyclo[3.2.1]octane-8-carbothioic acid (3-methoxy-propyl)amide $^1$H NMR (300 MHz, DMSO) δ=11.71 (s, 1H), 8.17 (m, 1H), 7.79 (m, 1H), 7.27-7.11 (m, 1H), 6.60 (m, 1H), 4.96 (m, 2H), 4.41 (m, 2H), 3.55 (m, 2H), 3.48-3.28 (m, 4H), 3.23 (m, 3H), 2.01-1.64 (m, 6H).

Example 46

Using Isocyanate 3-(7H-Pyrrolo[2,3-d]pyrimidin-4-yl)-3,8-diaza-bicyclo[3.2.1]octane-8-carboxylic acid cyclohexylamide ¹H NMR (300 MHz, DMSO) δ=11.67 (s, 1H), 8.12 (s, 1H), 7.25-7.12 (m, 1H), 6.69-6.55 (m, 1H), 6.42 (m, 1H), 4.36 (m, 4H), 3.44 (m, 3H), 1.88-1.00 (m, 14H).

Example 47

3-(7H-Pyrrolo[2,3-d]pyrimidin-4-yl)-3,8-diaza-bicyclo[3.2.1]octane-8-carbothioic acid (2-oxo-tetrahydro-furan-3-yl)-amide ¹H NMR (300 MHz, DMSO) δ=11.73 (s, 1H), 8.24-8.07 (m, 2H), 7.28-7.13 (m, 1H), 6.62 (dd, J=1.7, 3.6, 1H), 5.57 (m, 1H), 4.96 (m, 2H), 4.55-4.19 (m, 4H), 3.37 (m, 3H), 2.22 (m, 1H), 1.96 (m, 2H), 1.78 (m, 2H).

Example 437

7-(7H-Pyrrolo[2,3-d]pyrimidin-4-yl)-4,7-diaza-spiro[2.5]octane-4-carbothioic acid cyclohexylamide 1H NMR (300 MHz, DMSO) δ=11.72 (s, 1H), 8.13 (s, 1H), 7.20 (br m, 2H), 6.59 (m, 1H), 4.19 (m, 2H), 3.92 (m, 2H), 3.80 (m, 2H), 1.90 (m, 2H), 1.70 (m, 2H), 1.59 (m, 1H), 1.27 (br, 10H).

Example 438

7-(7H-Pyrrolo[2,3-d]pyrimidin-4-yl)-4,7-diaza-spiro[2.5]octane-4-carbothioic acid benzylamide 1H NMR (300 MHz, DMSO) δ=11.72 (s, 1H), 8.34 (m, 1H), 8.14 (s, 1H), 7.26 (br m, 6H), 6.60 (m, 1H), 4.86 (d, J=5.6, 2H), 4.04 (m, 6H), 1.13 (m, 4H).

Example 436

Using Isocyanate 7-(7H-Pyrrolo[2,3-d]pyrimidin-4-yl)-4,7-diaza-spiro[2.5]octane-4-carboxylic acid cyclohexylamide 1H NMR (300 MHz, DMSO) δ=11.69 (s, 1H), 8.12 (s, 1H), 7.17 (m, 1H), 6.57 (m, 1H), 5.94 (m, 1H), 3.71 (br m, 7H), 1.66 (br m, 5H), 1.24 (br m, 5H), 0.90 (m, 4H).

Example 444

Using Isocyanate 7-(7H-Pyrrolo[2,3-d]pyrimidin-4-yl)-4,7-diaza-spiro[2.5]octane-4-carboxylic acid butylamide 1H NMR (300 MHz, DMSO) δ=11.70 (s, 1H), 8.12 (s, 1H), 7.18 (m, 1H), 6.56 (m, 1H), 6.38 (m, 1H), 3.81 (m, 2H), 3.74 (br, 2H), 3.61 (m, 2H), 3.10 (m, 2H), 1.43 (m, 2H), 1.27 (m, 2H), 0.90 (br m, 7H).

Example 445

Using Isocyanate 7-(7H-Pyrrolo[2,3-d]pyrimidin-4-yl)-4,7-diaza-spiro[2.5]octane-4-carboxylic acid phenethyl-amide 1H NMR (300 MHz, DMSO) δ=11.70 (s, 1H), 8.12 (s, 1H), 7.21 (m, 6H), 6.55 (m, 1H), 6.39 (m, 1H), 3.65 (br, 6H), 3.35 (m, 2H), 2.77 (m, 2H), 0.84 (m, 4H).

Example 51

4-[8-(Propane-1-sulfonyl)-3,8-diaza-bicyclo[3.2.1]oct-3-yl]-7H-pyrrolo[2,3-d]pyrimidine

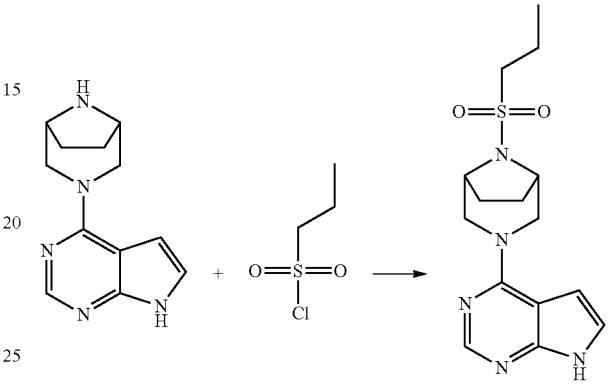

4-(3,8-Diaza-bicyclo[3.2.1]oct-3-yl)-7H-pyrrolo[2,3-d]pyrimidine (intermediate 4) (0.05 mmol) was dissolved in THF (1.0 mL). Triethylamine (0.12 mmol) and propane-1-sulfonyl chloride (0.06 mmol) was added. The reaction mixture was left at it for 16 hours. The pure compounds were obtained by standard preparative HPLC purification of the reaction mixture.

¹H NMR (300 MHz, DMSO) δ=11.70 (s, 1H), 8.14 (m, 1H), 7.19 (m, 1H), 6.61 (m, 1H), 4.66-4.25 (m, 3H), 3.46 (m, 4H), 1.73 (m, 6H), 1.31-0.85 (m, 4H).

Using this procedure the following compounds were obtained:

Example 76

3-[7-(7H-Pyrrolo[2,3-d]pyrimidin-4-yl)-4,7-diaza-spiro[2.5]octane-4-sulfonylmethyl]-benzonitrile 1H NMR (300 MHz, DMSO) δ=11.78 (s, 1H), 8.15 (br, 1H), 7.86 (m, 1H), 7.78 (br, 1H), 7.63 (m, 2H), 7.22 (m, 1H), 6.61 (m, 1H), 4.56 (br, 2H), 4.00 (br, 2H), 3.76 (br, 2H), 3.44 (br, 2H), 0.78 (br, 2H), 0.55 (br, 2H).

Example 77

3-[3-(7H-Pyrrolo[2,3-d]pyrimidin-4-yl)-3,8-diaza-bicyclo[3.2.1]octane-8-sulfonylmethyl]-benzonitrile 1H NMR (300 MHz, DMSO) δ=11.82 (s, 1H), 8.16 (s, 1H), 7.85 (m, 3H), 7.64 (m, 1H), 7.22 (m, 1H), 6.63 (m, 1H), 4.66 (br, 2H), 4.47 (br, 2H), 4.19 (br, 2H), 3.20 (br, 2H), 1.86 (br, 2H), 1.69 (br, 2H).

Example 78

4-[3-(7H-Pyrrolo[2,3-d]pyrimidin-4-yl)-3,8-diaza-bicyclo[3.2.1]octane-8-sulfonylmethyl]-benzonitrile 1H NMR (300 MHz, DMSO) δ=11.80 (s, 1H), 8.16 (s, 1H), 7.88 (d, J=8.3, 2H), 7.67 (d, J=8.3, 2H), 7.22 (m, 3H, 1H), 6.62 (d, J=3.4, 1H), 4.70 (s, 2H), 4.47 (br, 2H), 4.19 (s, 2H), 3.19 (br, 2H), 1.86 (br, 2H), 1.68 (br, 2H).

Example 439

4-[4-(Toluene-4-sulfonyl)-4,7-diazaspiro[2.5]oct-7-yl]-7H-pyrrolo[2,3-d]pyrimidine 1H NMR (300 MHz, DMSO) δ=11.75 (s, 1H), 8.11 (s, 1H), 7.73 (d, J=8.3, 2H), 7.35 (d, J=8.3, 2H), 7.18 (m, 1H), 6.50 (m, 1H), 3.91 (m, 2H), 3.75 (br, 2H), 3.43 (br, 4H), 2.33 (s, 3H), 1.07 (m, 2H), 0.85 (m, 2H).

Example 458

7-(7H-Pyrrolo[2,3-d]pyrimidin-4-yl)-4,7-diaza-spiro[2.5]octane-4-sulfonic acid (2-cyano-ethyl)-methyl-amide

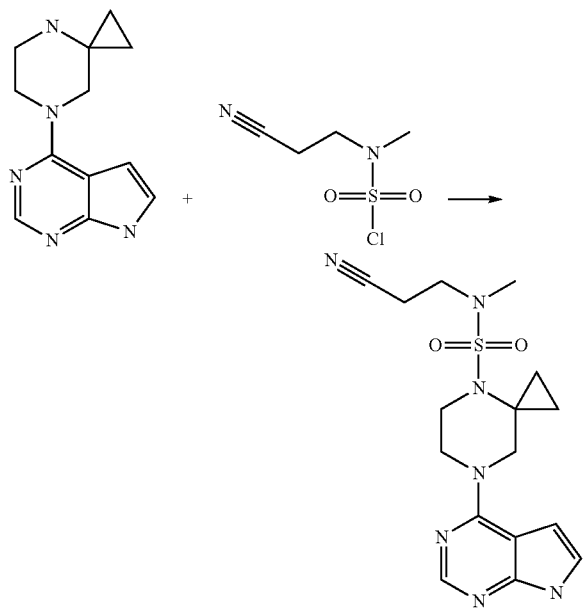

Intermediate 2 (0.05 mmol) was dissolved in THF (1.0 mL). Triethylamine (0.12 mmol) and 2-cyanoethyl(methyl)sulfamoyl chloride (0.06 mmol) was added. The reaction mixture was left at it for 16 hours. The pure compounds were obtained by standard preparative HPLC purification of the reaction mixture.

1H NMR (300 MHz, DMSO) δ=11.73 (s, 1H), 8.14 (s, 1H), 7.19 (m, 1H), 6.59 (m, 1H), 4.05 (m, 2H), 3.84 (br, 2H), 3.56 (m, 2H), 3.35 (m, 2H), 2.78 (br, 5H), 1.04 (m, 2H), 0.88 (m, 2H).

Using this procedure the following compounds were obtained:

Example 459

7-(7H-Pyrrolo[2,3-d]pyrimidin-4-yl)-4,7-diaza-spiro[2.5]octane-4-sulfonic acid diethylamide 1H NMR (300 MHz, DMSO) δ=11.72 (s, 1H), 8.13 (s, 1H), 7.18 (m, 1H), 6.59 (m, 1H), 4.04 (m, 2H), 3.84 (s, 2H), 3.51 (m, 2H), 3.15 (q, J=7.1, 4H), 1.08 (t, J=7.1, 6H), 0.99 (br, 2H), 0.86 (br, 2H).

Example 460

7-(7H-Pyrrolo[2,3-d]pyrimidin-4-yl)-4,7-diaza-spiro[2.5]octane-4-sulfonic acid cyclohexyl-methyl-amide 1H NMR (300 MHz, DMSO) δ=11.71 (s, 1H), 8.13 (s, 1H), 7.18 (m, 1H), 6.59 (m, 1H), 4.04 (m, 2H), 3.83 (s, 2H), 3.51 (m, 2H), 2.61 (s, 3H), 1.25 (br, 14H).

Example 449

4-[4-(2-Methyl-propane-2-sulfinyl)-4,7-diaza-spiro[2.5]oct-7-yl]-7H-pyrrolo[2,3-d]pyrimidine

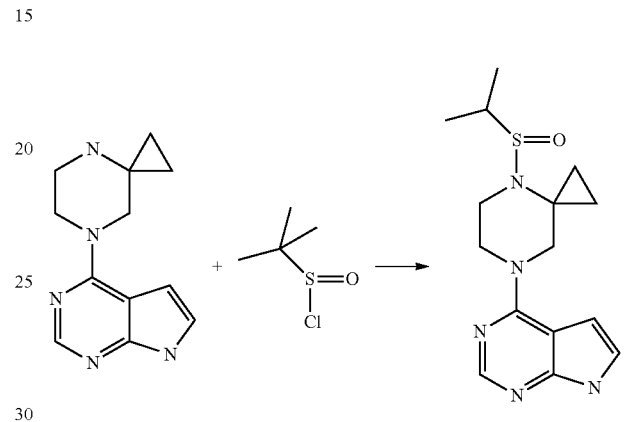

Intermediate 2 (0.05 mmol) was dissolved in THF (1.0 mL). Triethylamine (0.12 mmol) and 2-methylpropane-2-sulfinyl chloride (0.06 mmol) was added. The reaction mixture was left at rt for 16 hours. The pure compounds were obtained by standard preparative HPLC purification of the reaction mixture.

1H NMR (300 MHz, DMSO) δ=11.69 (s, 1H), 8.12 (s, 1H), 7.17 (m, 1H), 6.57 (m, 1H), 4.41 (m, 1H), 3.98 (m, 1H), 3.71 (m, 2H), 3.57 (m, 2H), 1.03 (s, 9H), 0.89 (m, 2H), 0.64 (m, 2H).

Example 440

(5,6-Dihydro-4H-cyclopenta[b]thiophen-2-yl)-[7-(7H-pyrrolo[2,3-d]Pyrimidin-4-yl)-4,7-diaza-spiro[2.5]oct-4-yl]-methanethione

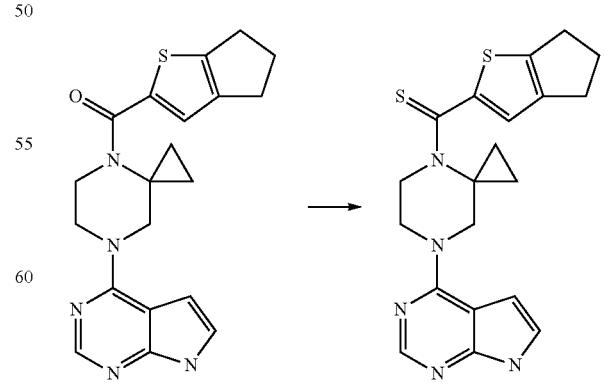

To example 61 (20 mg) in THF (5 mL) is added Lawessons reagent (30 mg) and the suspension is heated to 60° C. for 18 h. The pure compounds were obtained by standard preparative HPLC purification of the reaction mixture.

1H NMR (600 MHz, DMSO) δ=11.72 (s, 1H), 8.19 (s, 1H), 7.27 (s, 1H), 7.17 (m, 1H), 6.55 (m, 1H), 4.02 (m, 6H), 2.92 (t, J=7.1, 2H), 2.73 (t, J=7.1, 2H), 2.34 (m, 2H), 0.97 (m, 4H).

Using a similar procedure the following compound where prepared from their corresponding amides:

Example 441

4-{2-[7-(7H-Pyrrolo[2,3-d]pyrimidin-4-yl)-4,7-diaza-spiro[2.5]oct-4-yl]-2-thioxo-ethyl}-benzonitrile 1H NMR (300 MHz, DMSO) δ=11.74 (s, 1H), 8.13 (s, 1H), 7.74 (m, 2H), 7.46 (m, 2H), 7.20 (m, 1H), 6.57 (m, 1H), 4.47 (s, 2H), 4.10 (br, 4H), 3.76 (br, 2H), 1.22 (m, 4H).

Example 447

2-Methoxy-1-[7-(7H-pyrrolo[2,3-d]pyrimidin-4-yl)-4,7-diaza-spiro[2.5]oct-4-yl]-ethanethione 1H NMR (300 MHz, DMSO) δ=11.74 (s, 1H), 8.15 (m, 1H), 7.20 (m, 1H), 6.62 (m, 1H), 4.46 (br, 3H), 4.12 (br, 4H), 3.93 (br, 2H), 3.26 (br, 2H), 1.20 (m, 4H).

Example 448

2-Phenoxy-1-[7-(7H-pyrrolo[2,3-d]pyrimidin-4-yl)-4,7-diaza-spiro[2.5]oct-4-yl]-ethanethione 1H NMR (300 MHz, DMSO) δ=11.74 (s, 1H), 8.15 (m, 1H), 7.26 (m, 3H), 6.95 (m, 3H), 6.61 (m, 1H), 5.14 (m, 2H), 4.45 (br, 2H), 4.14 (br, 2H), 3.96 (s, 2H), 1.13 (m, 4H).

JAK Kinase Assays:

Human baculovirus-expressed JAK1, 2, 3 and TYK2 were purchased from Carna Biosciences, Inc. All four purified enzymes contain only the catalytic domain. JAK1 (aa 850-1154) and TYK2 (aa 871-1187) are expressed with an N-terminally fused GST-tag, and JAK2 and JAK3 with an N-terminally fused His-tag.

Inhibition of phosphorylation of a synthetic peptide was measured in an HTRF-based assay using the TK substrate-Biotin from the Cisbio HTRFKinEASE TK kit. First, 2 μl of TK solution (TK substrate-biotin in kinase buffer [1× enzymatic buffer from HTRFKinEASE TK kit, 1 mM DTT]) is added to a plate containing 1 μl prediluted compound (final assay concentration DMSO: 0.75%). Then, 5 μl kinase-ATP mix (prepared in kinase buffer) is added to the wells and the plates are incubated at RT for 20-30 min. For all four kinases a concentration of ATP that corresponded to the Km for ATP was used. The final concentrations of buffers, substrate, kinase and ATP were: JAK1: 50 mM Hepes buffer pH 7.0, 0.01% BSA, 10 mM $MgCl_2$, 1 mM DTT, 7 μM ATP, 50 nM SEB, 1 μM TK Substrate-Biotin and 5 ng JAK1; JAK2: 50 mM Hepes buffer pH 7.0, 0.01% BSA, 5 mM $MgCl_2$, 1 mM DTT, 4 μM ATP, 1 μM TK Substrate-Biotin and 0.1 ng JAK2; JAK3: 50 mM Hepes buffer pH 7.0, 0.01% BSA, 5 mM $MgCl_2$, 1 mM DTT, 2 μM ATP, 1 μM TK Substrate-Biotin and 0.3 ng JAK3; TYK2: 50 mM Hepes buffer pH 7.0, 0.01% BSA, 5 mM $MgCl_2$, 1 mM DTT, 13 μM ATP, 50 nM SEB, 1 μM TK Substrate-Biotin and 0.8 ng TYK2. Thereafter, the kinase reaction is stopped by adding 4 μl detection mix (final concentrations: 50 mM Hepes buffer pH 7.0, 0.01% BSA, 0.8 M KF, 20 mM EDTA, 42 nM Streptavidin-XL665 and 1:400 STK Ab Cryptate) and the plates are incubated overnight in the dark. The HTRF signal is read using an Envision plate reader.

In Table 1 selected JAK kinase inhibitory activities are listed with the following indicators: I: $EC_{50}$<100 nM, II: 100 nM≤$EC_{50}$≤500 nM and III: $EC_{50}$>500 nM

TABLE 1

| Example number | Structure | JAK1 | JAK2 | JAK3 | TYK2 |
|---|---|---|---|---|---|
| 1 | 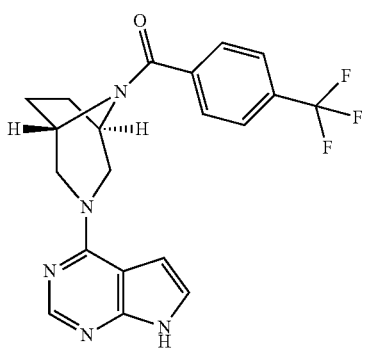 [SMILES: O=C(c1ccc(C(F)(F)F)cc1)N1[C@@H]2CC[C@H]1CN(c1ncnc3[nH]ccc13)C2] | I | II | III | III |

TABLE 1-continued
| Example number | Structure | JAK1 | JAK2 | JAK3 | TYK2 |
|---|---|---|---|---|---|
| 2 | 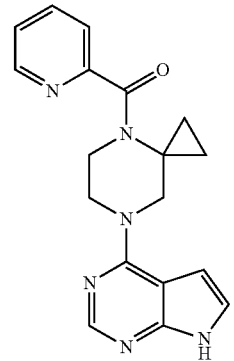 [SMILES: O=C(c1ccccn1)N1CCN(c2ncnc3[nH]ccc23)CC12CC2] | I | I | II | II |
| 3 | 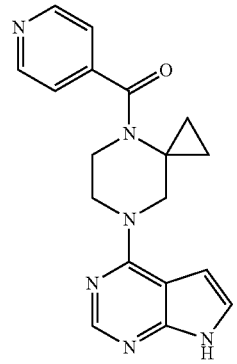 [SMILES: O=C(c1ccncc1)N1CCN(c2ncnc3[nH]ccc23)CC12CC2] | I | I | II | II |
| 4 | 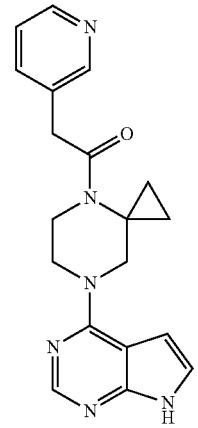 [SMILES: O=C(Cc1cccnc1)N1CCN(c2ncnc3[nH]ccc23)CC12CC2] | II | I | II | III |
| 5 | 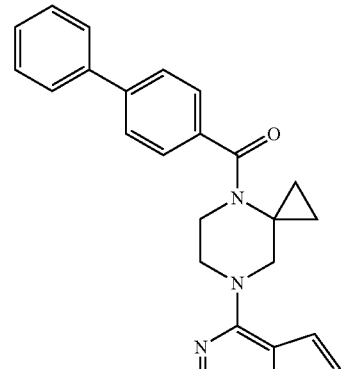 | I | I | II | III |

TABLE 1-continued

| Example number | Structure | JAK1 | JAK2 | JAK3 | TYK2 |
|---|---|---|---|---|---|
| 6 | 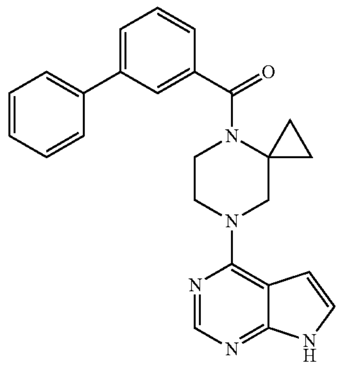 [SMILES: O=C(c1cccc(-c2ccccc2)c1)N1CCN(c2ncnc3[nH]ccc23)CC12CC2] | I | I | II | II |
| 7 | 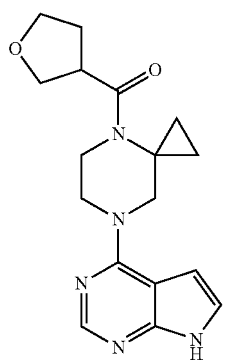 [SMILES: O=C(C1CCOC1)N1CCN(c2ncnc3[nH]ccc23)CC12CC2] | II | I | II | III |
| 8 | 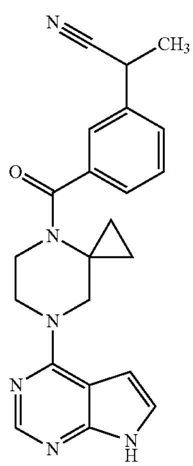 [SMILES: CC(C#N)c1cccc(C(=O)N2CCN(c3ncnc4[nH]ccc34)CC23CC3)c1] | I | I | II | III |
| 9 | 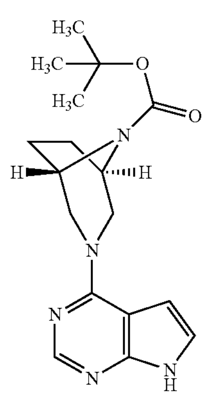 [SMILES: CC(C)(C)OC(=O)N1[C@@H]2CC[C@H]1CN(c1ncnc3[nH]ccc13)C2] | II | I | II | III |

TABLE 1-continued
| Example number | Structure | JAK1 | JAK2 | JAK3 | TYK2 |
|---|---|---|---|---|---|
| 10 | 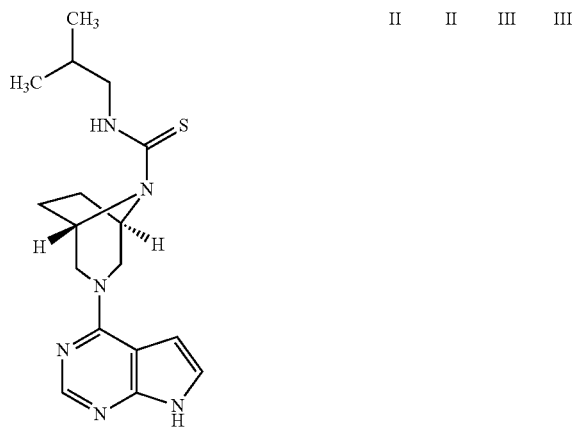 | II | II | III | III |
| 11 | 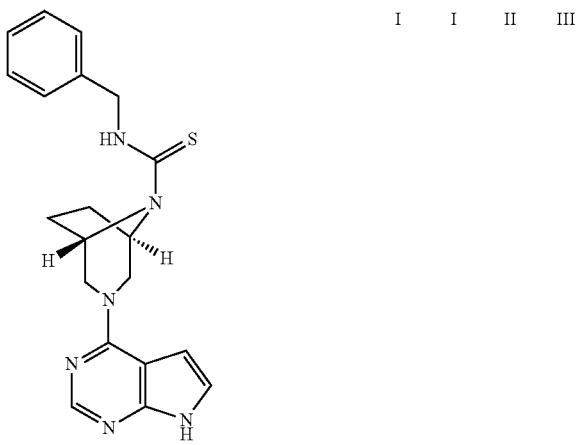 | I | I | II | III |
| 12 | 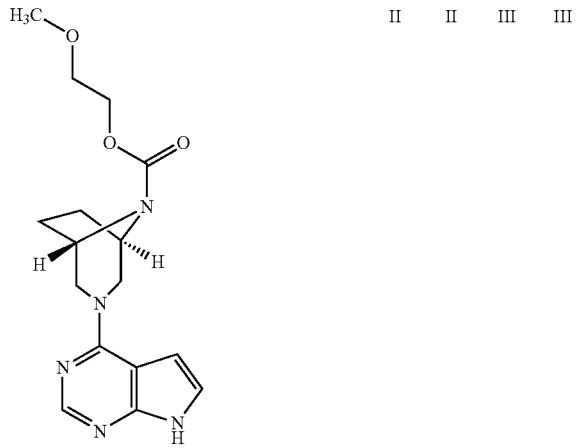 | II | II | III | III |

TABLE 1-continued
| Example number | Structure | JAK1 | JAK2 | JAK3 | TYK2 |
|---|---|---|---|---|---|
| 13 | 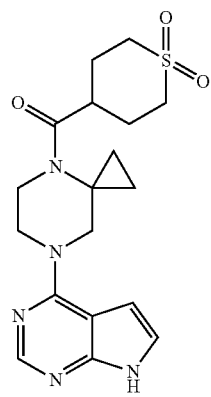 [SMILES: O=C(C1CCS(=O)(=O)CC1)N1CCN(c2ncnc3[nH]ccc23)CC12CC2] | II | II | II | III |
| 14 | 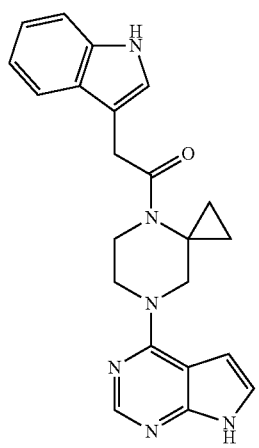 [SMILES: O=C(Cc1c[nH]c2ccccc12)N1CCN(c2ncnc3[nH]ccc23)CC12CC2] | II | I | II | III |
| 15 | 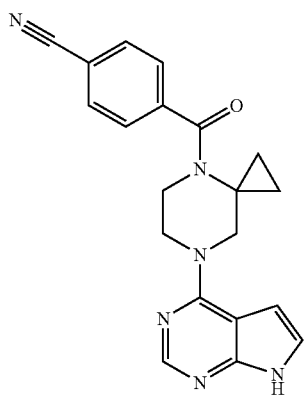 [SMILES: N#Cc1ccc(C(=O)N2CCN(c3ncnc4[nH]ccc34)CC23CC3)cc1] | I | I | II | II |

TABLE 1-continued

| Example number | Structure | JAK1 | JAK2 | JAK3 | TYK2 |
|---|---|---|---|---|---|
| 16 | 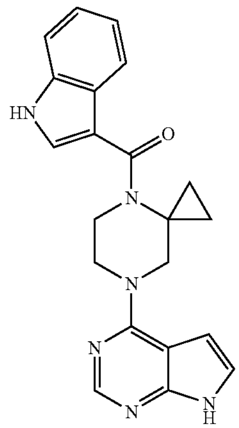 [SMILES: O=C(c1c[nH]c2ccccc12)N1CCN(c2ncnc3[nH]ccc23)CC12CC2] | I | I | I | II |
| 17 | 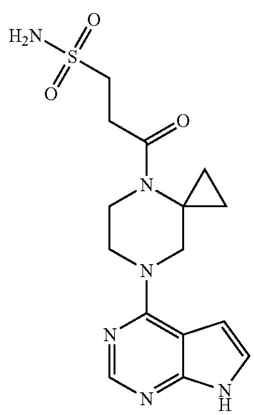 [SMILES: NS(=O)(=O)CCC(=O)N1CCN(c2ncnc3[nH]ccc23)CC12CC2] | I | I | I | II |
| 18 | 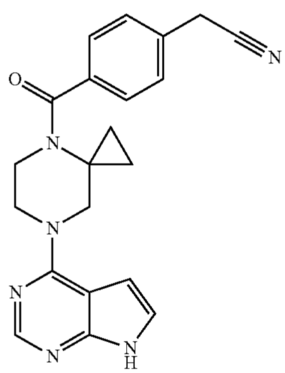 [SMILES: N#CCc1ccc(C(=O)N2CCN(c3ncnc4[nH]ccc34)CC23CC3)cc1] | I | I | II | II |
| 19 | 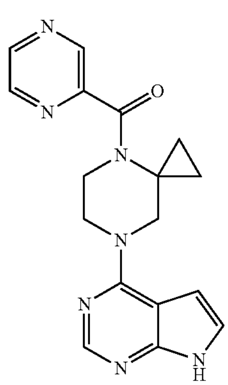 [SMILES: O=C(c1cnccn1)N1CCN(c2ncnc3[nH]ccc23)CC12CC2] | I | I | I | II |

TABLE 1-continued
| Example number | Structure | JAK1 | JAK2 | JAK3 | TYK2 |
|---|---|---|---|---|---|
| 20 | 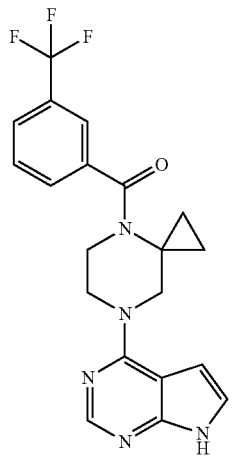 [SMILES: O=C(c1cccc(C(F)(F)F)c1)N1CCN(c2ncnc3[nH]ccc23)CC12CC2] | I | I | II | II |
| 21 | 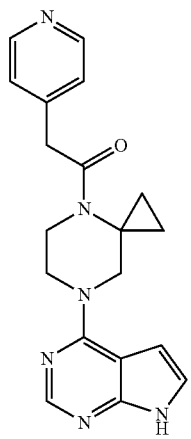 [SMILES: O=C(Cc1ccncc1)N1CCN(c2ncnc3[nH]ccc23)CC12CC2] | I | I | II | III |
| 22 | 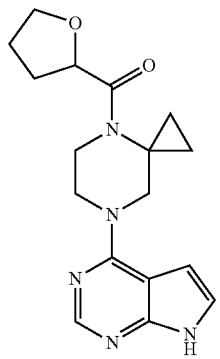 [SMILES: O=C(C1CCCO1)N1CCN(c2ncnc3[nH]ccc23)CC12CC2] | II | I | II | III |

TABLE 1-continued
| Example number | Structure | JAK1 | JAK2 | JAK3 | TYK2 |
|---|---|---|---|---|---|
| 23 | 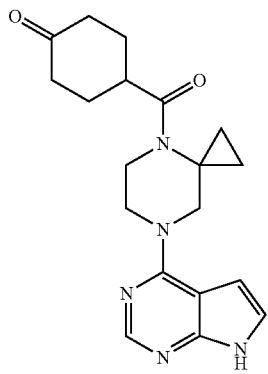 [SMILES: O=C1CCC(C(=O)N2CCN(c3ncnc4[nH]ccc34)CC23CC3)CC1] | I | I | I | II |
| 24 | 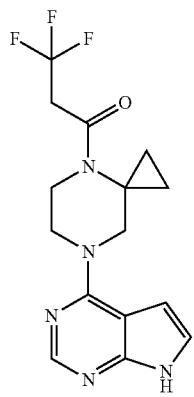 [SMILES: O=C(CC(F)(F)F)N1CCN(c2ncnc3[nH]ccc23)CC12CC2] | I | I | I | III |
| 25 | 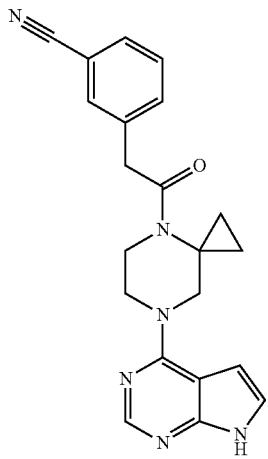 [SMILES: N#Cc1cccc(CC(=O)N2CCN(c3ncnc4[nH]ccc34)CC23CC3)c1] | II | I | II | III |

TABLE 1-continued
| Example number | Structure | JAK1 | JAK2 | JAK3 | TYK2 |
|---|---|---|---|---|---|
| 26 | 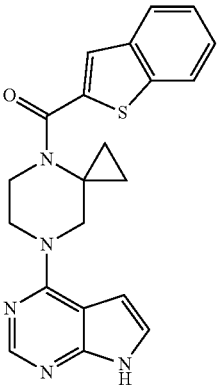 [SMILES: O=C(c1cc2ccccc2s1)N1CCN(c2ncnc3[nH]ccc23)CC12CC2] | I | I | II | II |
| 27 | 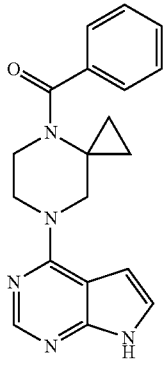 [SMILES: O=C(c1ccccc1)N1CCN(c2ncnc3[nH]ccc23)CC12CC2] | I | I | II | II |
| 28 | 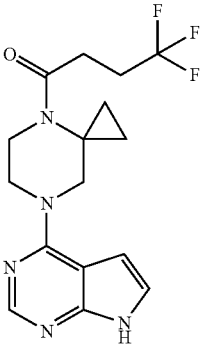 | I | I | I | II |
| 29 | 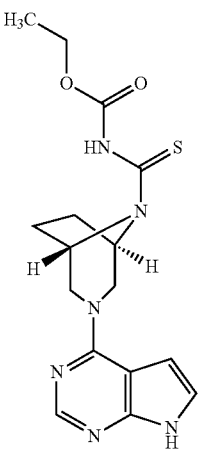 [SMILES: CCOC(=O)NC(=S)N1[C@@H]2CC[C@H]1CN(c1ncnc3[nH]ccc13)C2] | II | II | III | III |

TABLE 1-continued

| Example number | Structure | JAK1 | JAK2 | JAK3 | TYK2 |
|---|---|---|---|---|---|
| 30 | 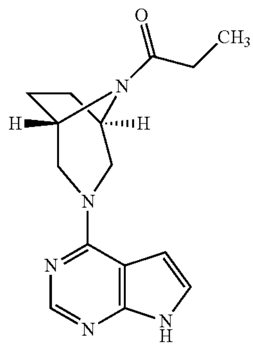 [SMILES: CCC(=O)N1[C@@H]2CC[C@H]1CN(c1ncnc3[nH]ccc13)C2] | II | II | III | III |
| 31 | 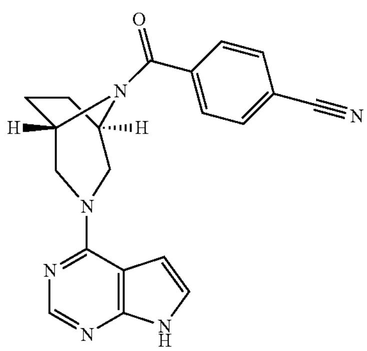 [SMILES: N#Cc1ccc(C(=O)N2[C@@H]3CC[C@H]2CN(c2ncnc4[nH]ccc24)C3)cc1] | I | I | II | III |
| 32 | 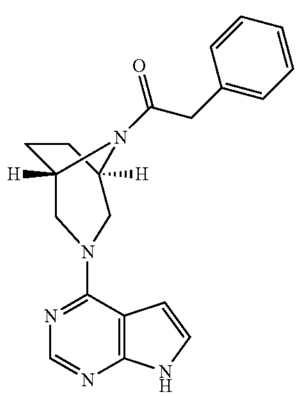 [SMILES: O=C(Cc1ccccc1)N1[C@@H]2CC[C@H]1CN(c1ncnc3[nH]ccc13)C2] | II | II | III | III |
| 33 | 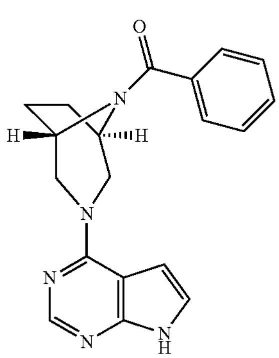 [SMILES: O=C(c1ccccc1)N1[C@@H]2CC[C@H]1CN(c1ncnc3[nH]ccc13)C2] | I | I | II | II |

TABLE 1-continued
| Example number | Structure | JAK1 | JAK2 | JAK3 | TYK2 |
|---|---|---|---|---|---|
| 34 | 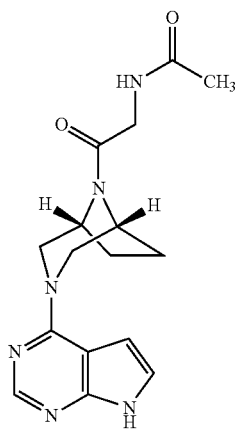 [SMILES: CC(=O)NCC(=O)N1[C@@H]2CC[C@@H]1CN(c1ncnc3[nH]ccc13)C2] | III | III | III | III |
| 35 | 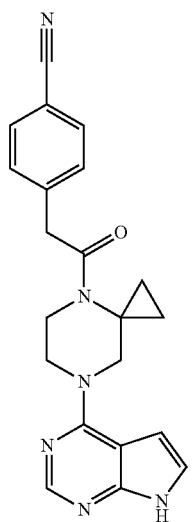 [SMILES: N#Cc1ccc(CC(=O)N2CCN(c3ncnc4[nH]ccc34)CC23CC3)cc1] | I | I | I | I |
| 36 | 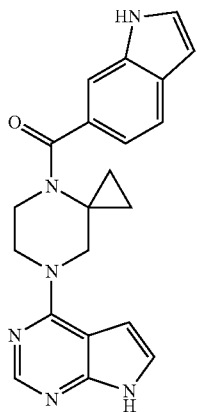 [SMILES: O=C(c1ccc2cc[nH]c2c1)N1CCN(c2ncnc3[nH]ccc23)CC12CC2] | II | II | III | III |

TABLE 1-continued
| Example number | Structure | JAK1 | JAK2 | JAK3 | TYK2 |
|---|---|---|---|---|---|
| 37 | 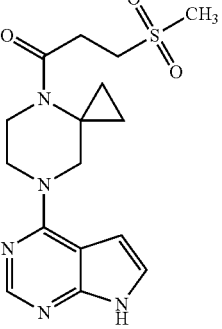 | I | I | II | III |
| 38 | 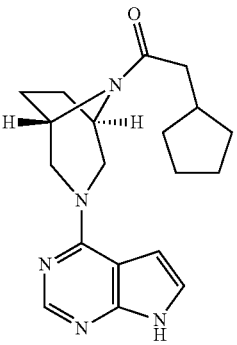 [SMILES: O=C(CC1CCCC1)N1[C@@H]2CC[C@H]1CN(c1ncnc3[nH]ccc13)C2] | I | I | II | III |
| 39 | 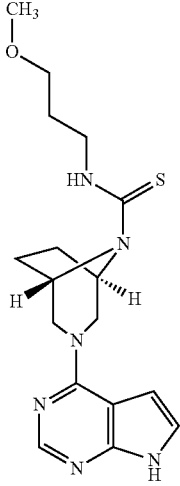 [SMILES: COCCCNC(=S)N1[C@@H]2CC[C@H]1CN(c1ncnc3[nH]ccc13)C2] | III | II | III | III |
| 40 | 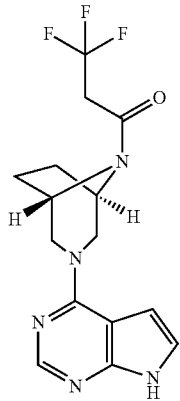 | II | II | III | III |

TABLE 1-continued
| Example number | Structure | JAK1 | JAK2 | JAK3 | TYK2 |
|---|---|---|---|---|---|
| 41 | 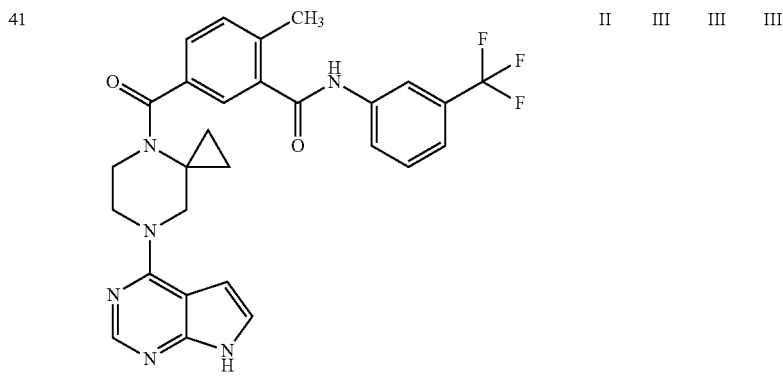 | II | III | III | III |
| 42 | 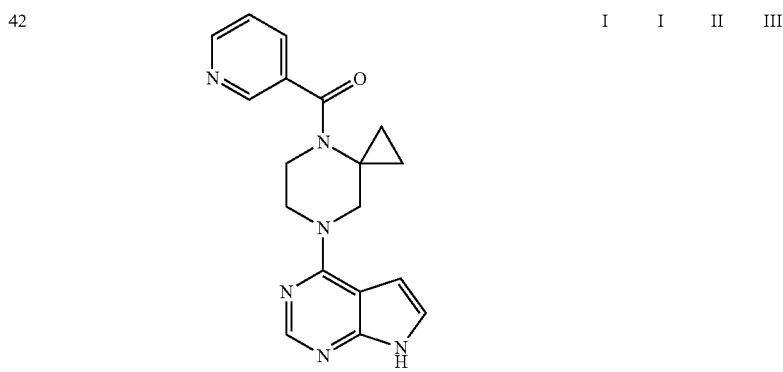 | I | I | II | III |
| 43 | 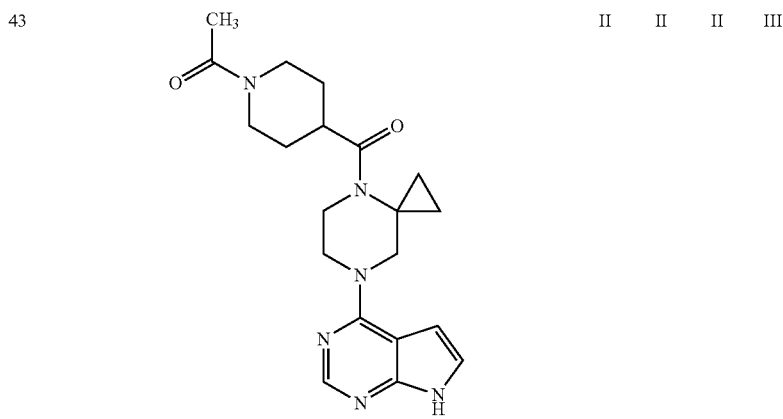 | II | II | II | III |

TABLE 1-continued

| Example number | Structure | JAK1 | JAK2 | JAK3 | TYK2 |
|---|---|---|---|---|---|
| 44 | 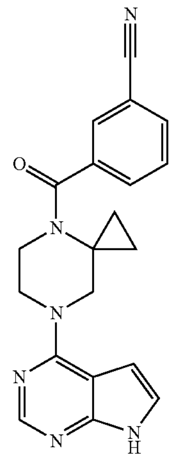 [SMILES: N#Cc1cccc(C(=O)N2CCN(c3ncnc4[nH]ccc34)CC23CC3)c1] | I | I | I | I |
| 45 | 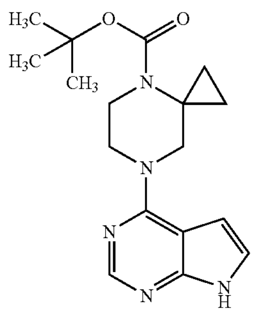 [SMILES: CC(C)(C)OC(=O)N1CCN(c2ncnc3[nH]ccc23)CC12CC2] | I | I | I | III |
| 46 | 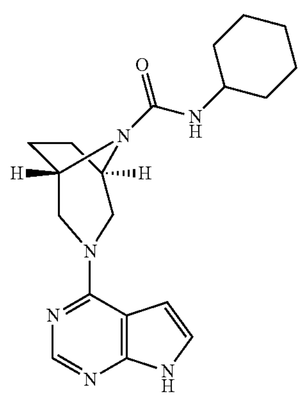 [SMILES: O=C(NC1CCCCC1)N1[C@@H]2CC[C@H]1CN(c1ncnc3[nH]ccc13)C2] | II | II | III | III |
| 47 | 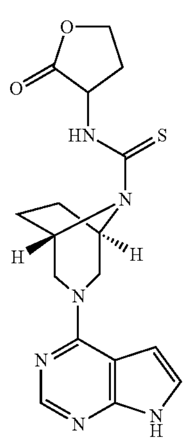 [SMILES: O=C1OCCC1NC(=S)N1[C@@H]2CC[C@H]1CN(c1ncnc3[nH]ccc13)C2] | II | II | II | III |

TABLE 1-continued
| Example number | Structure | JAK1 | JAK2 | JAK3 | TYK2 |
|---|---|---|---|---|---|
| 48 | 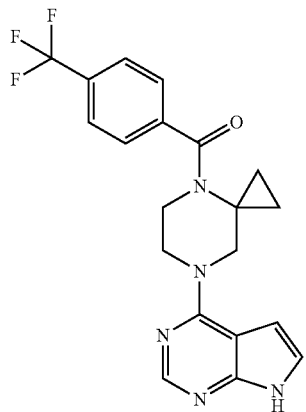 [SMILES: O=C(c1ccc(C(F)(F)F)cc1)N1CCN(c2ncnc3[nH]ccc23)CC12CC2] | I | I | II | III |
| 49 | 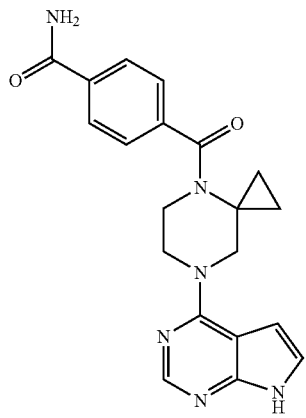 [SMILES: NC(=O)c1ccc(C(=O)N2CCN(c3ncnc4[nH]ccc34)CC23CC3)cc1] | I | I | II | III |
| 50 | 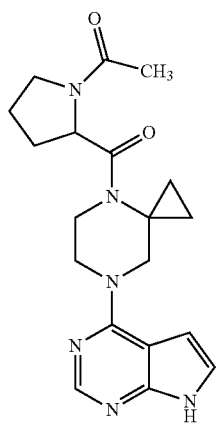 [SMILES: CC(=O)N1CCCC1C(=O)N1CCN(c2ncnc3[nH]ccc23)CC12CC2] | III | III | III | III |

TABLE 1-continued

| Example number | Structure | JAK1 | JAK2 | JAK3 | TYK2 |
|---|---|---|---|---|---|
| 51 | 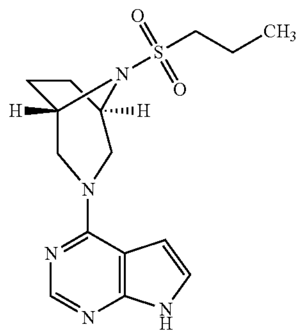 [SMILES: CCCS(=O)(=O)N1[C@@H]2CC[C@H]1CN(c1ncnc3[nH]ccc13)C2] | II | II | III | III |
| 52 | 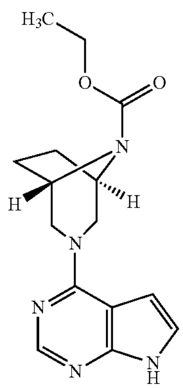 [SMILES: CCOC(=O)N1[C@@H]2CC[C@H]1CN(c1ncnc3[nH]ccc13)C2] | II | I | II | II |
| 53 | 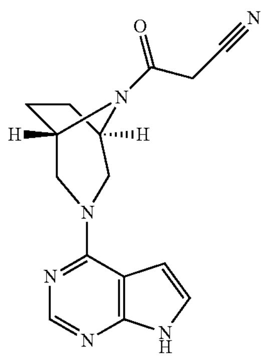 [SMILES: N#CCC(=O)N1[C@@H]2CC[C@H]1CN(c1ncnc3[nH]ccc13)C2] | II | II | II | III |
| 54 | 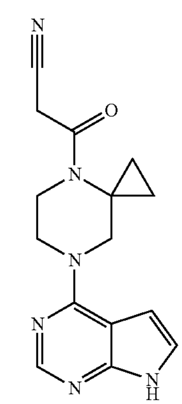 [SMILES: N#CCC(=O)N1CCN(c2ncnc3[nH]ccc23)CC12CC2] | I | I | I | III |

TABLE 1-continued
| Example number | Structure | JAK1 | JAK2 | JAK3 | TYK2 |
|---|---|---|---|---|---|
| 55 | 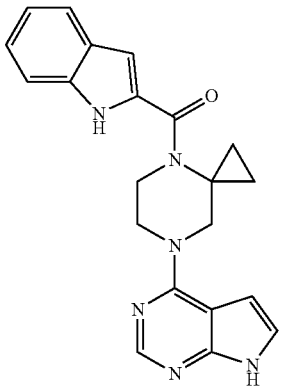 [SMILES: O=C(c1cc2ccccc2[nH]1)N1CCN(c2ncnc3[nH]ccc23)CC12CC2] | I | I | I | II |
| 56 | 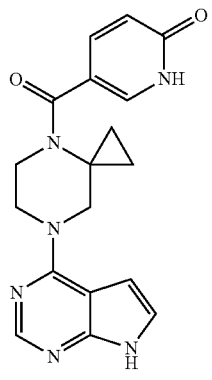 [SMILES: O=C(c1ccc(=O)[nH]c1)N1CCN(c2ncnc3[nH]ccc23)CC12CC2] | I | I | II | III |
| 57 | 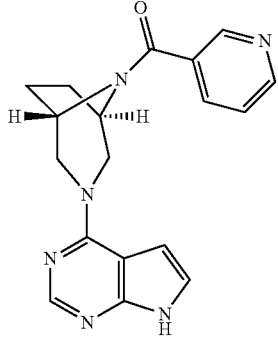 [SMILES: O=C(c1cccnc1)N1[C@@H]2CC[C@H]1CN(c1ncnc3[nH]ccc13)C2] | II | II | III | III |
| 58 | 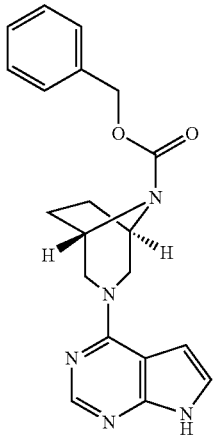 [SMILES: O=C(OCc1ccccc1)N1[C@@H]2CC[C@H]1CN(c1ncnc3[nH]ccc13)C2] | I | I | II | III |

TABLE 1-continued
| Example number | Structure | JAK1 | JAK2 | JAK3 | TYK2 |
|---|---|---|---|---|---|
| 59 | 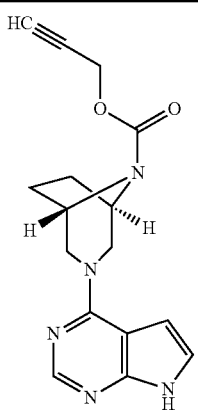 | II | II | II | III |
| 60 | 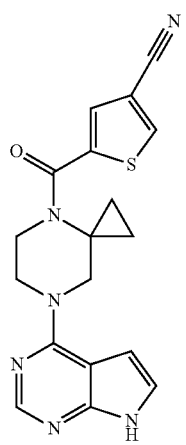 [SMILES: N#Cc1csc(C(=O)N2CCN(c3ncnc4[nH]ccc34)CC23CC3)c1] | I | I | I | I |
| 61 | 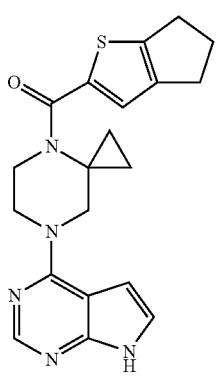 [SMILES: O=C(c1cc2c(s1)CCC2)N1CCN(c2ncnc3[nH]ccc23)CC12CC2] | I | I | I | I |

TABLE 1-continued
| Example number | Structure | JAK1 | JAK2 | JAK3 | TYK2 |
|---|---|---|---|---|---|
| 62 | 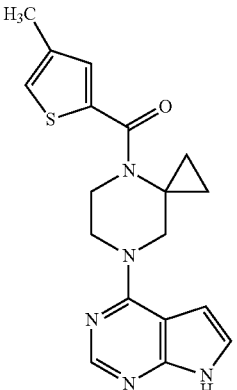 | I | I | I | I |
| 63 | 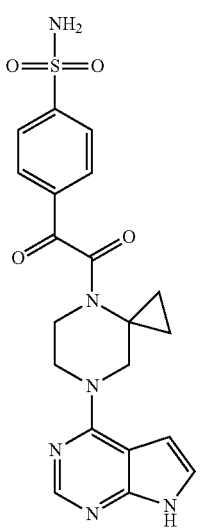 [SMILES: NS(=O)(=O)c1ccc(C(=O)C(=O)N2CCN(c3ncnc4[nH]ccc34)CC23CC3)cc1] | I | I | I | I |
| 64 | 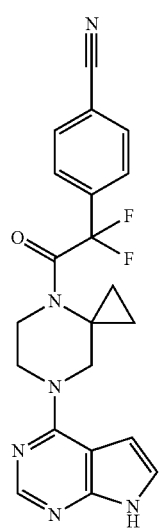 [SMILES: N#Cc1ccc(C(F)(F)C(=O)N2CCN(c3ncnc4[nH]ccc34)CC23CC3)cc1] | I | I | II | III |

TABLE 1-continued
| Example number | Structure | JAK1 | JAK2 | JAK3 | TYK2 |
|---|---|---|---|---|---|
| 65 | 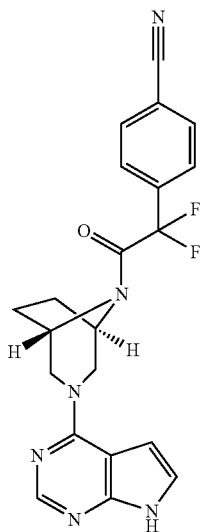 [SMILES: N#Cc1ccc(C(F)(F)C(=O)N2[C@@H]3CC[C@H]2CN(c2ncnc4[nH]ccc24)C3)cc1] | II | I | II | III |
| 66 | 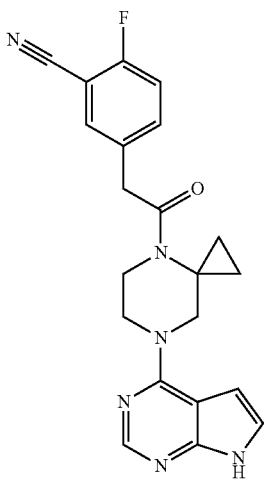 [SMILES: N#Cc1cc(CC(=O)N2CCN(c3ncnc4[nH]ccc34)CC23CC3)ccc1F] | I | I | II | III |
| 67 | 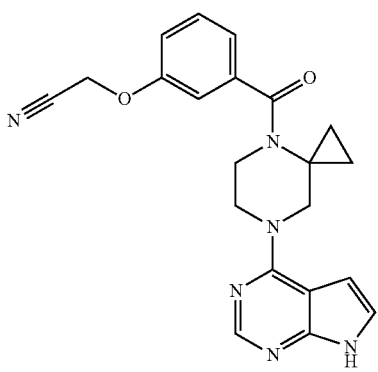 [SMILES: N#CCOc1cccc(C(=O)N2CCN(c3ncnc4[nH]ccc34)CC23CC3)c1] | I | I | II | II |

TABLE 1-continued
| Example number | Structure | JAK1 | JAK2 | JAK3 | TYK2 |
|---|---|---|---|---|---|
| 68 | 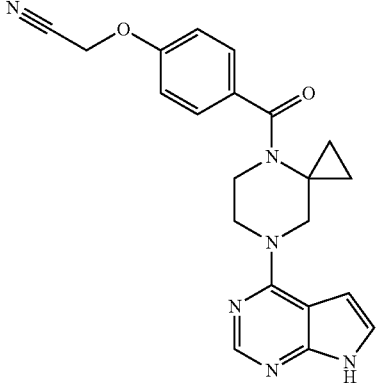 [SMILES: N#CCOc1ccc(C(=O)N2CCN(c3ncnc4[nH]ccc34)CC23CC3)cc1] | I | I | II | II |
| 69 | 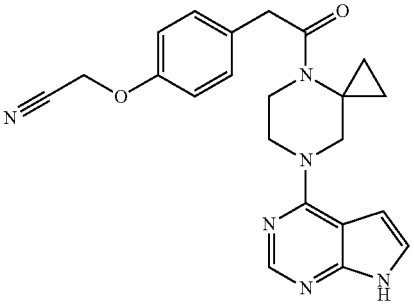 [SMILES: N#CCOc1ccc(CC(=O)N2CCN(c3ncnc4[nH]ccc34)CC23CC3)cc1] | I | I | I | III |
| 70 | 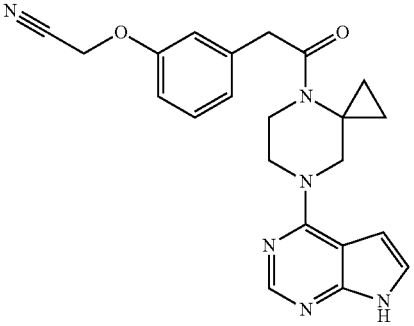 [SMILES: N#CCOc1cccc(CC(=O)N2CCN(c3ncnc4[nH]ccc34)CC23CC3)c1] | II | II | II | III |
| 71 | 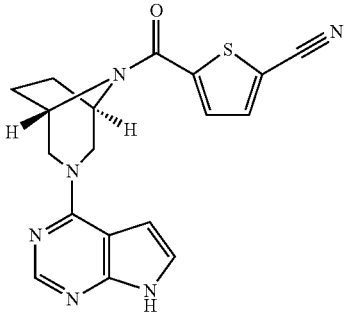 [SMILES: N#Cc1ccc(C(=O)N2[C@@H]3CC[C@H]2CN(c2ncnc4[nH]ccc24)C3)s1] | I | I | I | II |

TABLE 1-continued

| Example number | Structure | JAK1 | JAK2 | JAK3 | TYK2 |
|---|---|---|---|---|---|
| 72 | 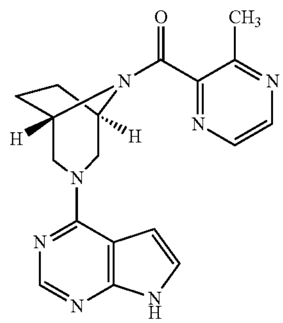 [SMILES: Cc1nccnc1C(=O)N1[C@@H]2CC[C@H]1CN(c1ncnc3[nH]ccc13)C2] | II | I | II | III |
| 73 | 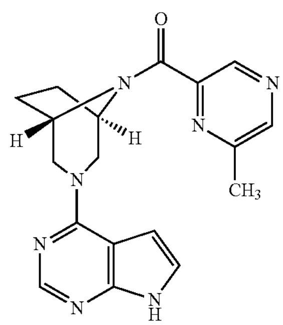 [SMILES: Cc1cncc(C(=O)N2[C@@H]3CC[C@H]2CN(c2ncnc4[nH]ccc24)C3)n1] | I | II | II | III |
| 74 | 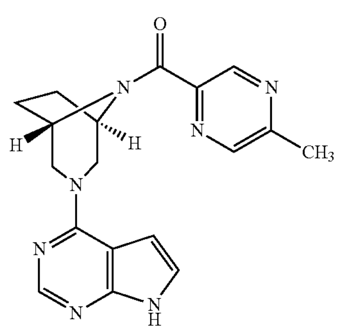 [SMILES: Cc1cnc(C(=O)N2[C@@H]3CC[C@H]2CN(c2ncnc4[nH]ccc24)C3)cn1] | II | II | III | III |
| 75 | 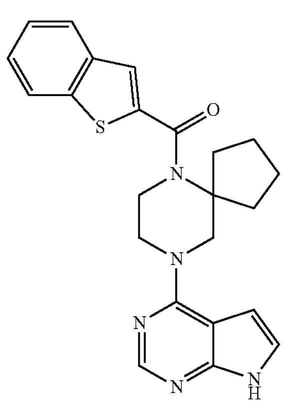 [SMILES: O=C(c1cc2ccccc2s1)N1CCN(c2ncnc3[nH]ccc23)CC12CCCC2] | III | III | III | III |

TABLE 1-continued
| Example number | Structure | JAK1 | JAK2 | JAK3 | TYK2 |
|---|---|---|---|---|---|
| 76 | 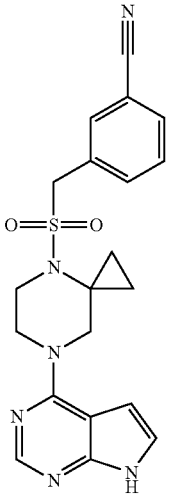 [SMILES: N#Cc1cccc(CS(=O)(=O)N2CCN(c3ncnc4[nH]ccc34)CC23CC3)c1] | I | I | II | III |
| 77 | 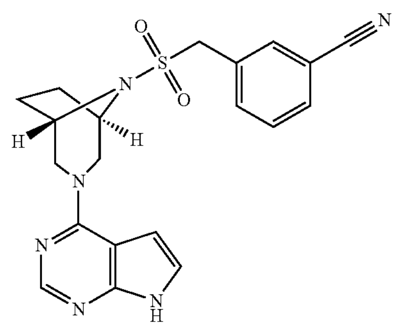 [SMILES: N#Cc1cccc(CS(=O)(=O)N2[C@@H]3CC[C@H]2CN(c2ncnc4[nH]ccc24)C3)c1] | I | I | II | III |
| 78 | 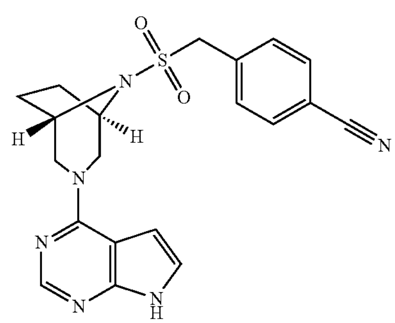 [SMILES: N#Cc1ccc(CS(=O)(=O)N2[C@@H]3CC[C@H]2CN(c2ncnc4[nH]ccc24)C3)cc1] | I | II | II | III |
| 79 | 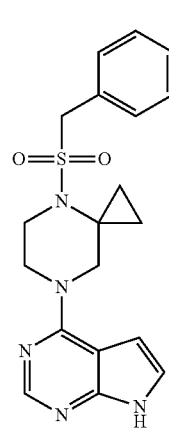 | I | I | II | III |

TABLE 1-continued

| Example number | Structure | JAK1 | JAK2 | JAK3 | TYK2 |
|---|---|---|---|---|---|
| 82 | 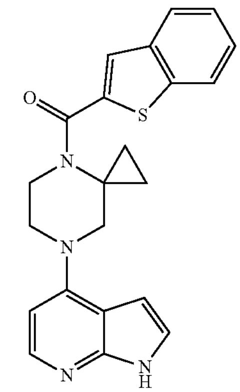 [SMILES: O=C(c1cc2ccccc2s1)N1CCN(c2ccnc3[nH]ccc23)CC12CC2] | II | II | III | III |
| 85 | 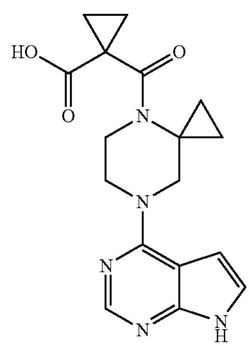 [SMILES: O=C(O)C1(C(=O)N2CCN(c3ncnc4[nH]ccc34)CC23CC3)CC1] | III | II | III | III |
| 86 | 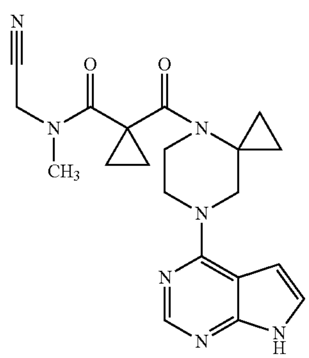 [SMILES: CN(CC#N)C(=O)C1(C(=O)N2CCN(c3ncnc4[nH]ccc34)CC23CC3)CC1] | III | II | III | III |
| 87 | 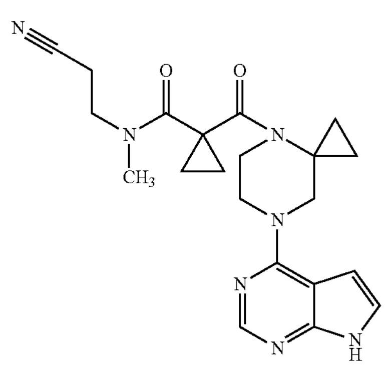 [SMILES: CN(CCC#N)C(=O)C1(C(=O)N2CCN(c3ncnc4[nH]ccc34)CC23CC3)CC1] | III | III | III | III |

TABLE 1-continued
| Example number | Structure | JAK1 | JAK2 | JAK3 | TYK2 |
|---|---|---|---|---|---|
| 88 | 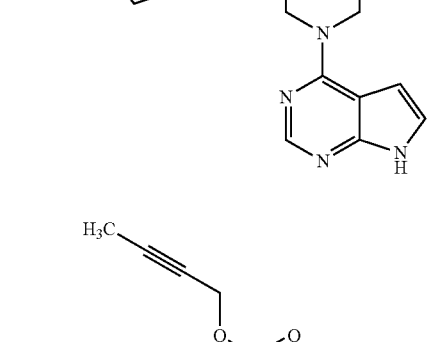 | III | II | III | III |
| 89 | 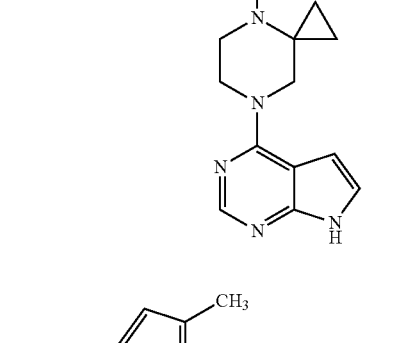 | I | I | II | III |
| 90 | 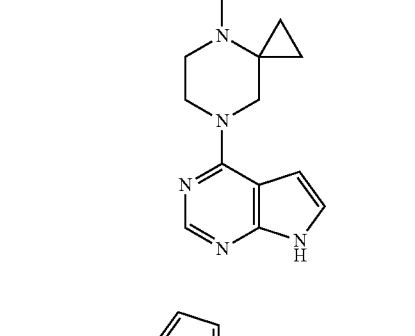 | I | I | II | II |
| 91 | 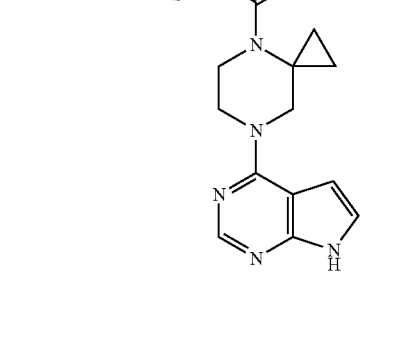 | I | I | I | I |

TABLE 1-continued
| Example number | Structure | JAK1 | JAK2 | JAK3 | TYK2 |
|---|---|---|---|---|---|
| 92 | 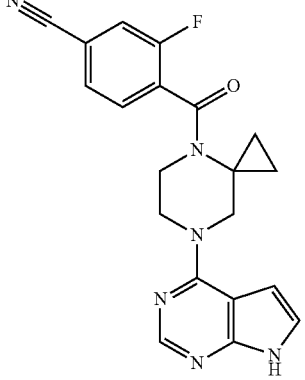 | I | I | II | II |
| 93 | 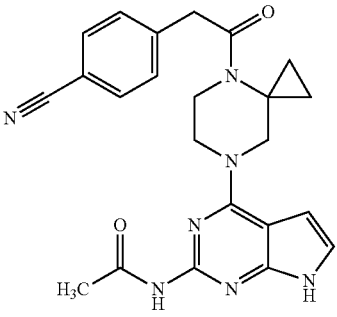 [SMILES: CC(=O)Nc1nc(N2CCN(C(=O)Cc3ccc(C#N)cc3)C3(CC3)C2)c2cc[nH]c2n1] | I | I | I | II |
| 94 | 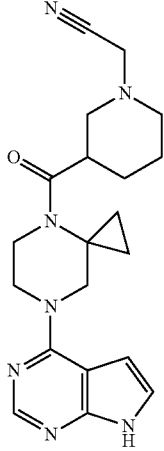 [SMILES: N#CCN1CCCC(C(=O)N2CCN(c3ncnc4[nH]ccc34)CC23CC3)C1] | II | I | II | II |
| 95 | 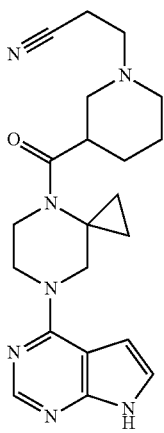 [SMILES: N#CCCN1CCCC(C(=O)N2CCN(c3ncnc4[nH]ccc34)CC23CC3)C1] | II | II | III | III |

TABLE 1-continued
| Example number | Structure | JAK1 | JAK2 | JAK3 | TYK2 |
|---|---|---|---|---|---|
| 96 | 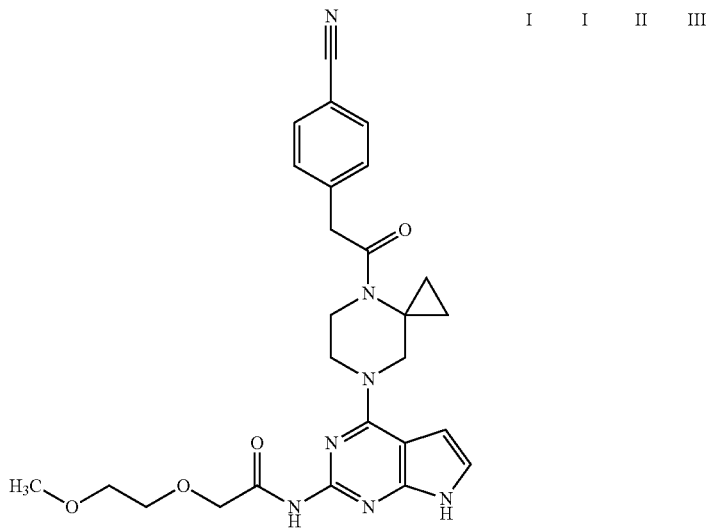 | I | I | II | III |
| 97 | 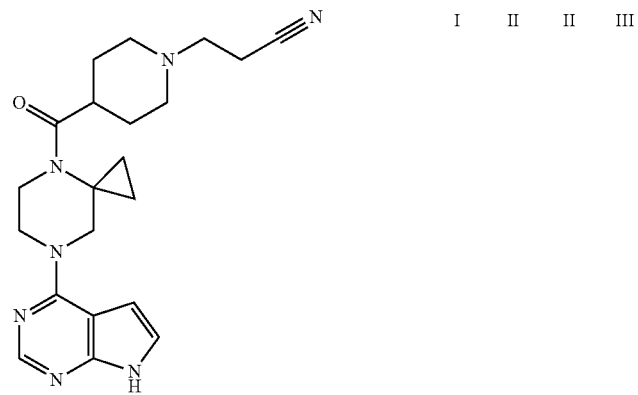 | I | II | II | III |
| 98 | 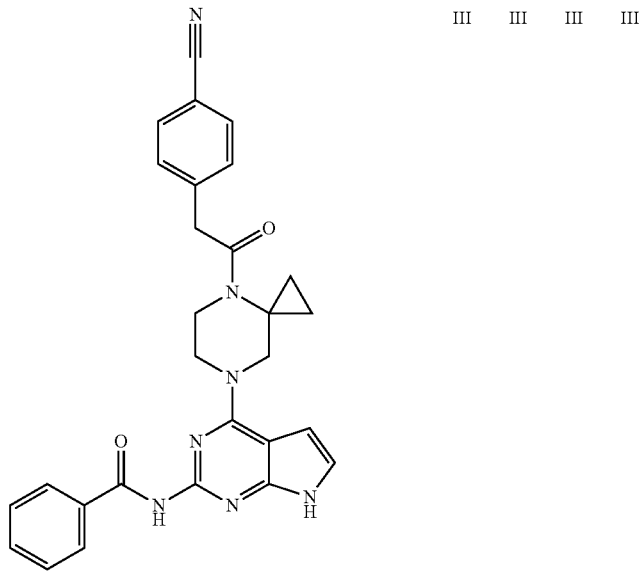 | III | III | III | III |

TABLE 1-continued
| Example number | Structure | JAK1 | JAK2 | JAK3 | TYK2 |
|---|---|---|---|---|---|
| 99 | 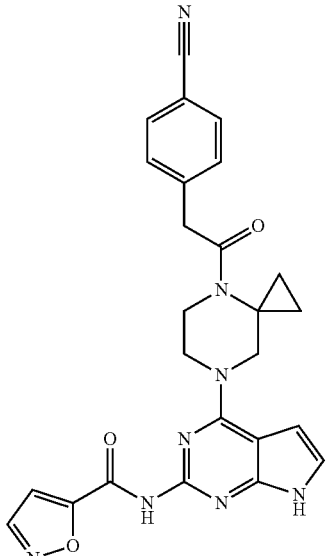 | II | I | III | III |
| 100 | 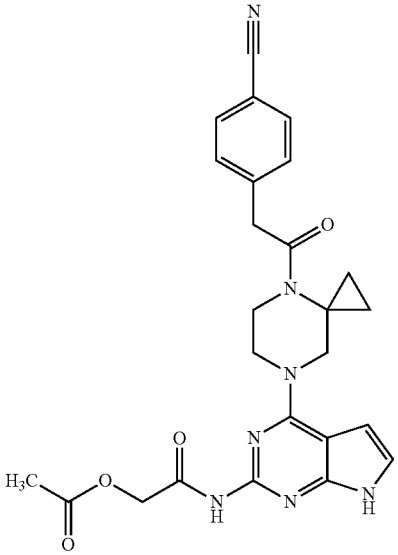 [SMILES: CC(=O)OCC(=O)Nc1nc(N2CCN(C(=O)Cc3ccc(C#N)cc3)C3(CC3)C2)c2cc[nH]c2n1] | I | I | I | II |
| 101 | 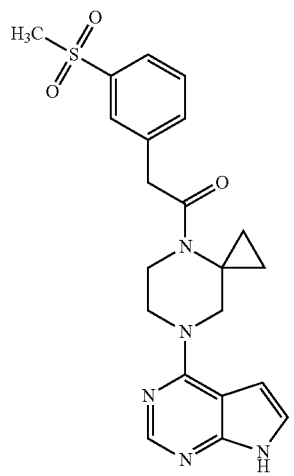 [SMILES: CS(=O)(=O)c1cccc(CC(=O)N2CCN(c3ncnc4[nH]ccc34)CC23CC3)c1] | II | II | II | III |

TABLE 1-continued
| Example number | Structure | JAK1 | JAK2 | JAK3 | TYK2 |
|---|---|---|---|---|---|
| 102 | 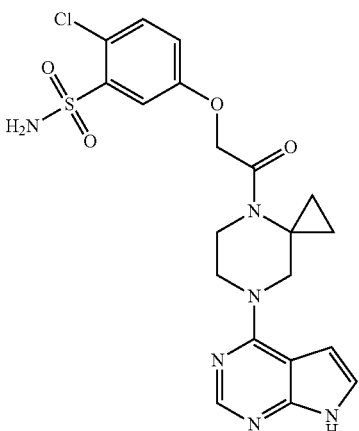 | I | I | I | II |
| 103 | 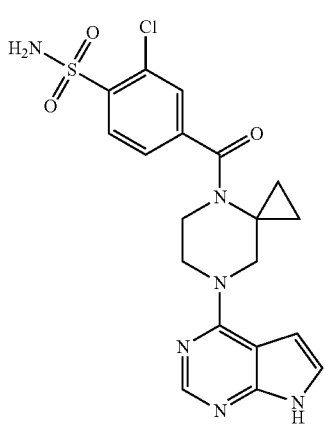 | I | I | I | I |
| 104 | 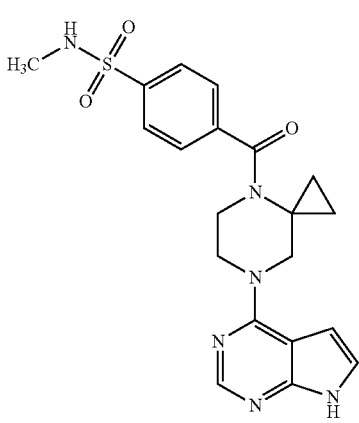 [SMILES: CNS(=O)(=O)c1ccc(C(=O)N2CCN(c3ncnc4[nH]ccc34)CC23CC3)cc1] | I | I | I | I |

TABLE 1-continued
| Example number | Structure | JAK1 | JAK2 | JAK3 | TYK2 |
|---|---|---|---|---|---|
| 105 | 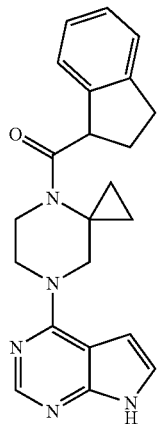 [SMILES: O=C(C1CCc2ccccc21)N1CCN(c2ncnc3[nH]ccc23)CC12CC2] | II | I | II | III |
| 106 | 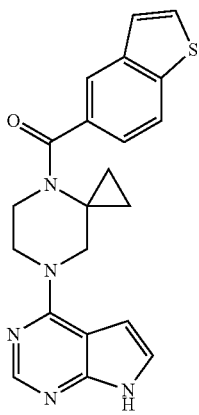 [SMILES: O=C(c1ccc2sccc2c1)N1CCN(c2ncnc3[nH]ccc23)CC12CC2] | I | I | II | II |
| 107 | 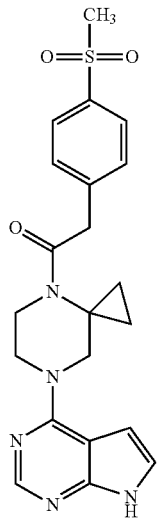 [SMILES: CS(=O)(=O)c1ccc(CC(=O)N2CCN(c3ncnc4[nH]ccc34)CC23CC3)cc1] | I | I | I | III |

TABLE 1-continued

| Example number | Structure | JAK1 | JAK2 | JAK3 | TYK2 |
|---|---|---|---|---|---|
| 108 | 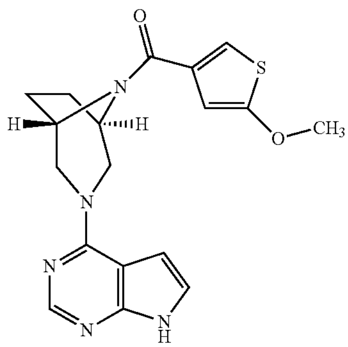 [SMILES: COc1cc(C(=O)N2[C@@H]3CC[C@H]2CN(c2ncnc4[nH]ccc24)C3)cs1] | I | I | I | III |
| 109 | 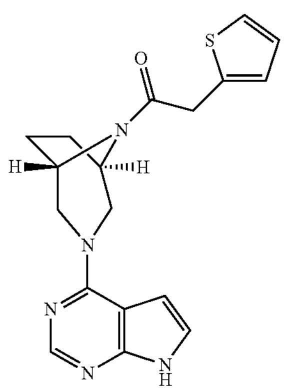 [SMILES: O=C(Cc1cccs1)N1[C@@H]2CC[C@H]1CN(c1ncnc3[nH]ccc13)C2] | I | I | II | III |
| 110 | 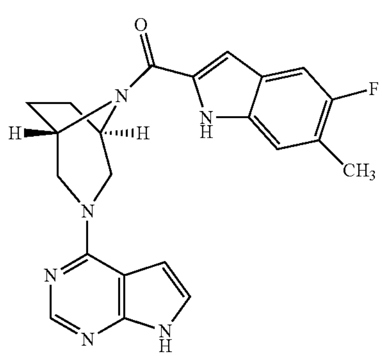 [SMILES: Cc1cc2[nH]c(C(=O)N3[C@@H]4CC[C@H]3CN(c3ncnc5[nH]ccc35)C4)cc2cc1F] | I | II | II | III |
| 112 | 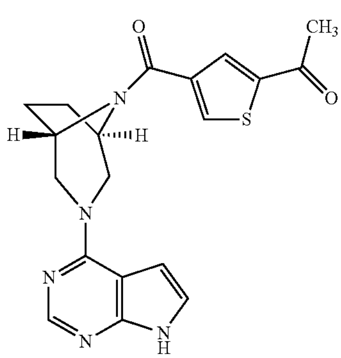 [SMILES: CC(=O)c1cc(C(=O)N2[C@@H]3CC[C@H]2CN(c2ncnc4[nH]ccc24)C3)cs1] | I | I | II | III |

TABLE 1-continued

| Example number | Structure | JAK1 | JAK2 | JAK3 | TYK2 |
|---|---|---|---|---|---|
| 113 | 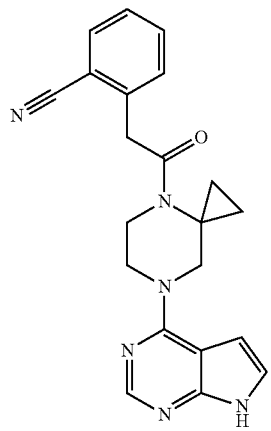 [SMILES: N#Cc1ccccc1CC(=O)N1CCN(c2ncnc3[nH]ccc23)CC12CC2] | II | I | II | III |
| 114 | 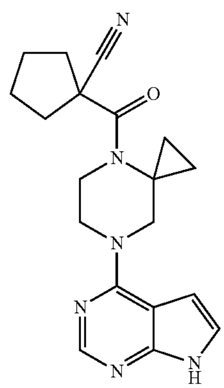 [SMILES: N#CC1(C(=O)N2CCN(c3ncnc4[nH]ccc34)CC23CC3)CCCC1] | II | I | II | III |
| 115 | 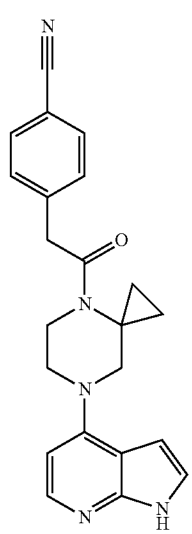 [SMILES: N#Cc1ccc(CC(=O)N2CCN(c3ccnc4[nH]ccc34)CC23CC3)cc1] | I | I | I | III |

TABLE 1-continued
| Example number | Structure | JAK1 | JAK2 | JAK3 | TYK2 |
|---|---|---|---|---|---|
| 116 | 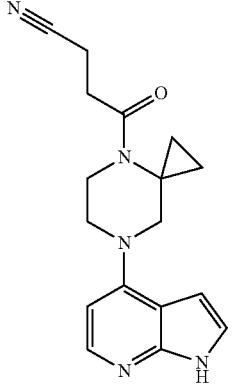 [SMILES: N#CCCC(=O)N1CCN(c2ccnc3[nH]ccc23)CC12CC2] | II | II | II | III |
| 117 | 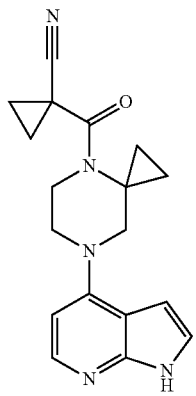 [SMILES: N#CC1(C(=O)N2CCN(c3ccnc4[nH]ccc34)CC23CC3)CC1] | II | II | II | III |
| 118 | 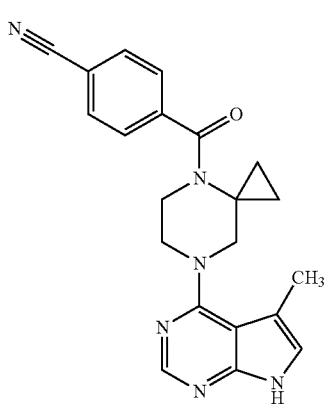 [SMILES: Cc1c[nH]c2ncnc(N3CCN(C(=O)c4ccc(C#N)cc4)C4(CC4)C3)c12] | III | III | III | III |

TABLE 1-continued
| Example number | Structure | JAK1 | JAK2 | JAK3 | TYK2 |
|---|---|---|---|---|---|
| 119 | 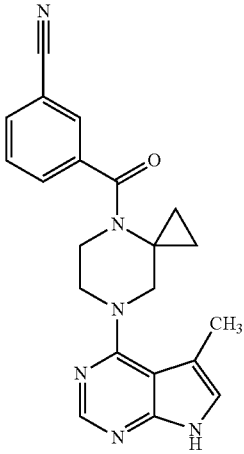 [SMILES: Cc1c[nH]c2ncnc(N3CCN(C(=O)c4cccc(C#N)c4)C4(CC4)C3)c12] | III | III | III | III |
| 120 | 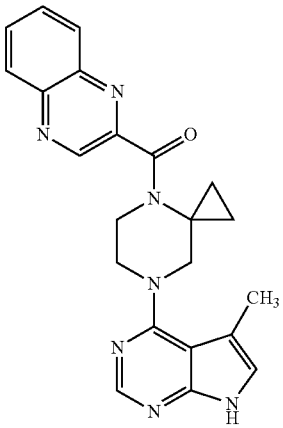 [SMILES: Cc1c[nH]c2ncnc(N3CCN(C(=O)c4cnc5ccccc5n4)C4(CC4)C3)c12] | III | III | III | III |
| 121 | 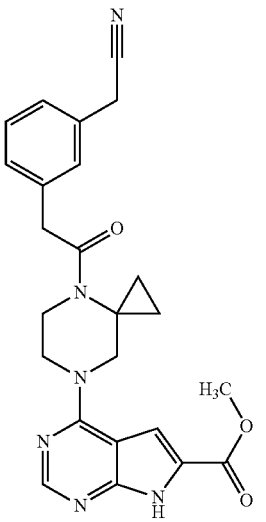 [SMILES: COC(=O)c1cc2c(N3CCN(C(=O)Cc4cccc(CC#N)c4)C4(CC4)C3)ncnc2[nH]1] | III | III | III | III |

TABLE 1-continued

| Example number | Structure | JAK1 | JAK2 | JAK3 | TYK2 |
|---|---|---|---|---|---|
| 122 | 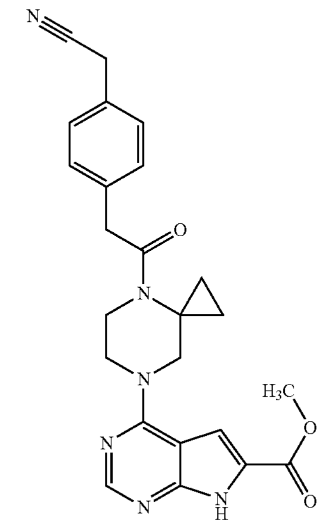 [SMILES: COC(=O)c1cc2c(N3CCN(C(=O)Cc4ccc(CC#N)cc4)C4(CC4)C3)ncnc2[nH]1] | III | III | III | III |
| 123 | 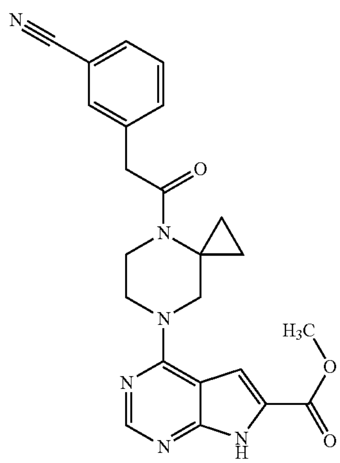 [SMILES: COC(=O)c1cc2c(N3CCN(C(=O)Cc4cccc(C#N)c4)C4(CC4)C3)ncnc2[nH]1] | III | III | III | III |
| 124 | 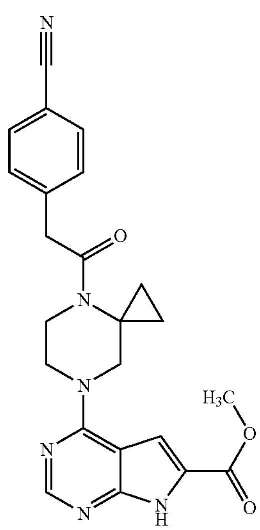 [SMILES: COC(=O)c1cc2c(N3CCN(C(=O)Cc4ccc(C#N)cc4)C4(CC4)C3)ncnc2[nH]1] | III | III | III | III |

TABLE 1-continued

| Example number | Structure | JAK1 | JAK2 | JAK3 | TYK2 |
|---|---|---|---|---|---|
| 125 | 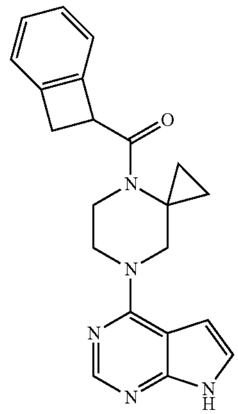 [SMILES: O=C(C1Cc2ccccc21)N1CCN(c2ncnc3[nH]ccc23)CC12CC2] | I | I | II | III |
| 126 | 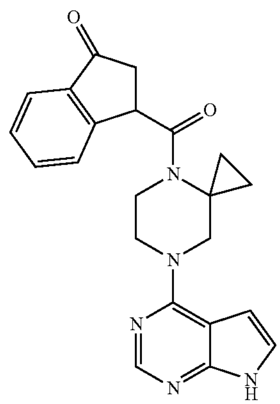 [SMILES: O=C1CC(C(=O)N2CCN(c3ncnc4[nH]ccc34)CC23CC3)c2ccccc21] | I | I | II | III |
| 127 | 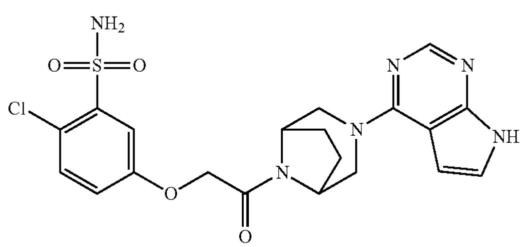 [SMILES: NS(=O)(=O)c1cc(OCC(=O)N2C3CCC2CN(c2ncnc4[nH]ccc24)C3)ccc1Cl] | I | I | I | III |
| 128 | 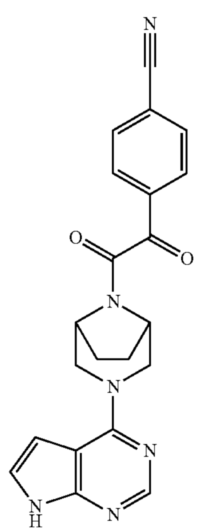 [SMILES: N#Cc1ccc(C(=O)C(=O)N2C3CCC2CN(c2ncnc4[nH]ccc24)C3)cc1] | I | I | II | III |

TABLE 1-continued
| Example number | Structure | JAK1 | JAK2 | JAK3 | TYK2 |
|---|---|---|---|---|---|
| 129 | 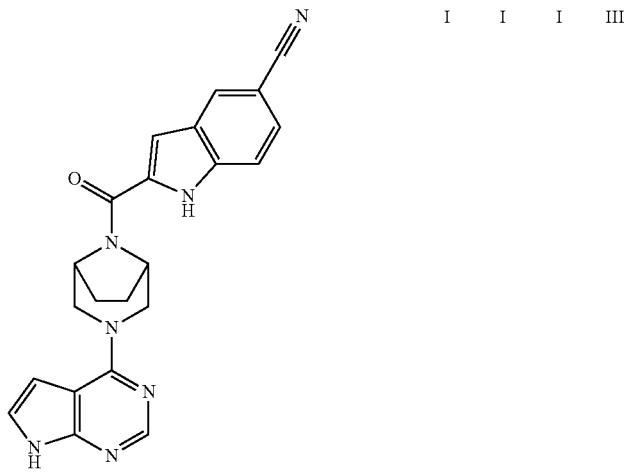 | I | I | I | III |
| 130 | 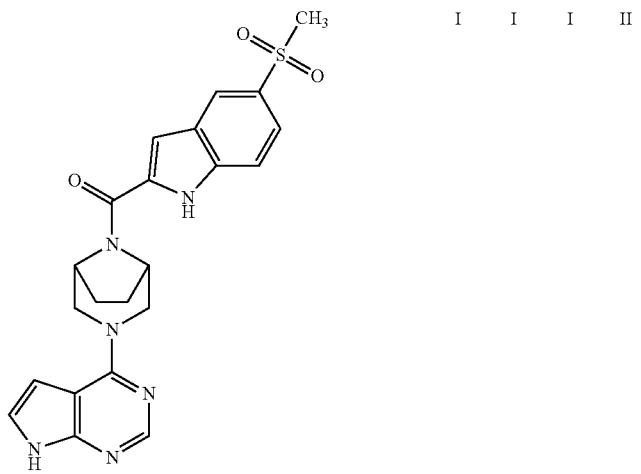 | I | I | I | II |
| 131 | 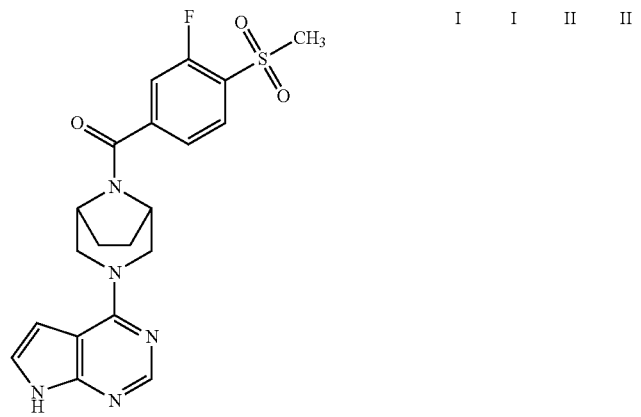 | I | I | II | II |

TABLE 1-continued
| Example number | Structure | JAK1 | JAK2 | JAK3 | TYK2 |
|---|---|---|---|---|---|
| 132 | 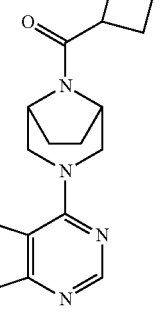 | II | II | II | III |
| 133 | 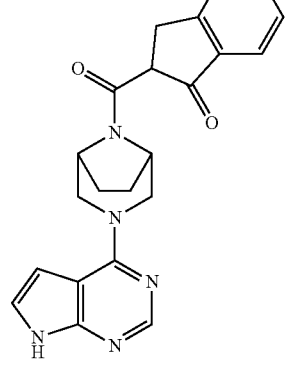 | III | II | III | III |
| 134 | 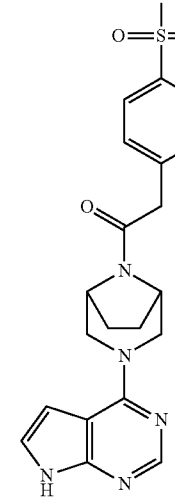 | II | II | III | III |

TABLE 1-continued
| Example number | Structure | JAK1 | JAK2 | JAK3 | TYK2 |
|---|---|---|---|---|---|
| 135 | 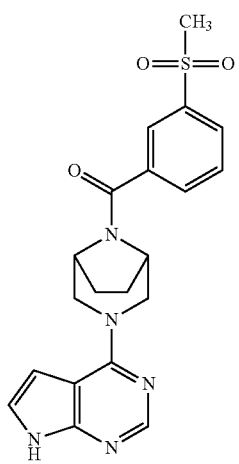 [SMILES: CS(=O)(=O)c1cccc(C(=O)N2C3CCC2CN(c2ncnc4[nH]ccc24)C3)c1] | I | I | II | III |
| 136 | 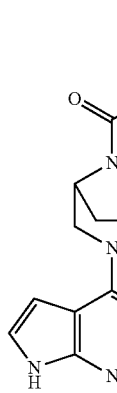 | I | I | I | II |
| 137 | 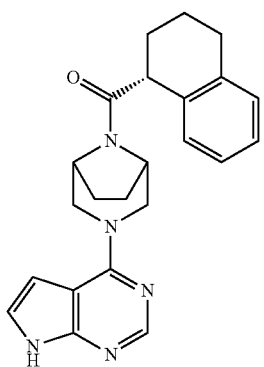 [SMILES: O=C([C@@H]1CCCc2ccccc21)N1C2CCC1CN(c1ncnc3[nH]ccc13)C2] | III | II | III | III |

TABLE 1-continued
| Example number | Structure | JAK1 | JAK2 | JAK3 | TYK2 |
|---|---|---|---|---|---|
| 138 | 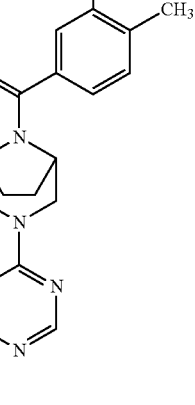 | I | I | I | III |
| 139 | 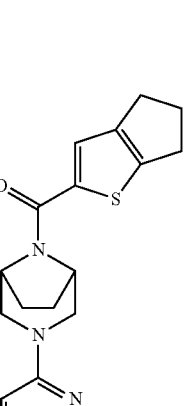 | I | I | II | III |
| 140 | 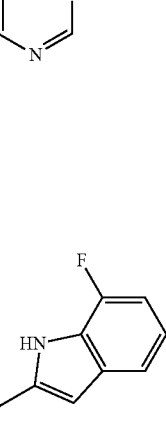 | I | I | I | III |

TABLE 1-continued
| Example number | Structure | JAK1 | JAK2 | JAK3 | TYK2 |
|---|---|---|---|---|---|
| 141 | 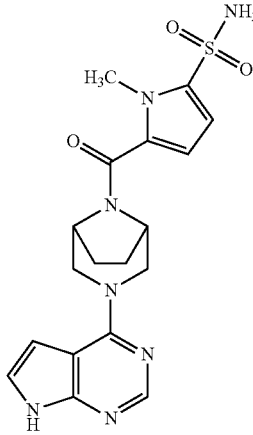 | I | I | I | III |
| 142 | 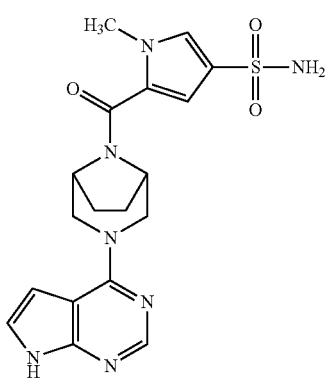 [SMILES: Cn1cc(S(N)(=O)=O)cc1C(=O)N1C2CCC1CN(c1ncnc3[nH]ccc13)C2] | I | I | I | II |
| 143 | 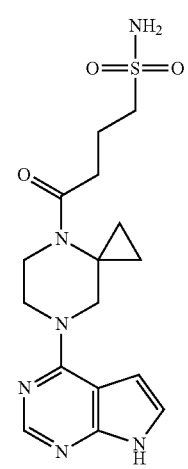 [SMILES: NS(=O)(=O)CCCC(=O)N1CCN(c2ncnc3[nH]ccc23)CC12CC2] | I | I | I | III |

TABLE 1-continued

| Example number | Structure | JAK1 | JAK2 | JAK3 | TYK2 |
|---|---|---|---|---|---|
| 144 | 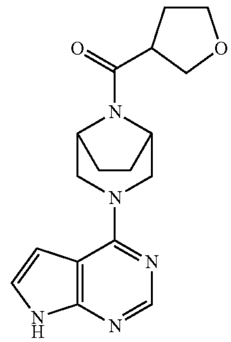 [SMILES: O=C(C1CCOC1)N1C2CCC1CN(c1ncnc3[nH]ccc13)C2] | II | I | III | III |
| 145 | 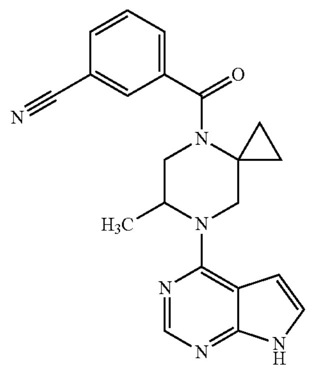 [SMILES: CC1CN(C(=O)c2cccc(C#N)c2)C2(CC2)CN1c1ncnc2[nH]ccc12] | I | I | II | II |
| 146 | 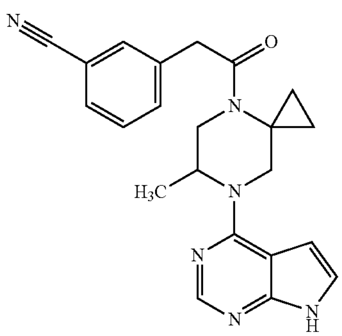 [SMILES: CC1CN(C(=O)Cc2cccc(C#N)c2)C2(CC2)CN1c1ncnc2[nH]ccc12] | II | I | II | III |
| 147 | 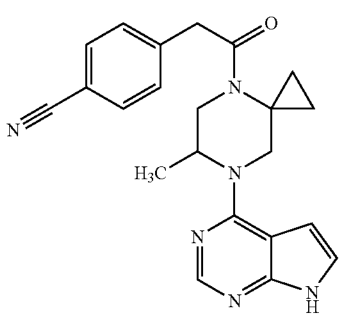 [SMILES: CC1CN(C(=O)Cc2ccc(C#N)cc2)C2(CC2)CN1c1ncnc2[nH]ccc12] | I | I | I | I |

TABLE 1-continued
| Example number | Structure | JAK1 | JAK2 | JAK3 | TYK2 |
|---|---|---|---|---|---|
| 148 | 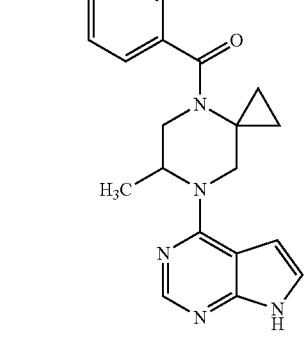 | I | I | II | III |
| 149 | 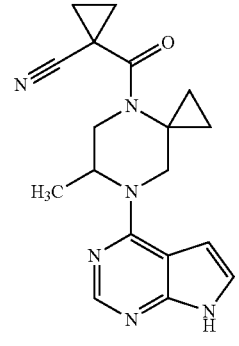 [SMILES: CC1CN(C(=O)C2(C#N)CC2)C2(CC2)CN1c1ncnc2[nH]ccc12] | I | I | II | II |
| 150 | 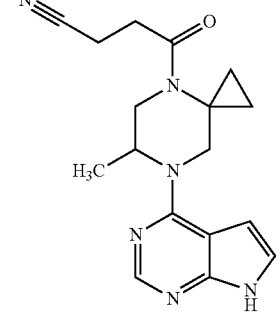 | I | I | I | III |
| 151 | 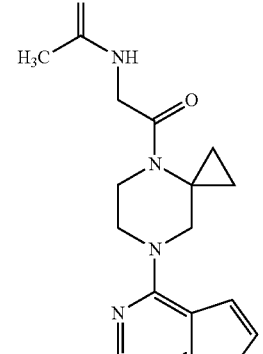 | II | II | III | III |

TABLE 1-continued
| Example number | Structure | JAK1 | JAK2 | JAK3 | TYK2 |
|---|---|---|---|---|---|
| 152 | 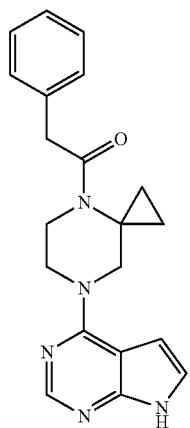 [SMILES: O=C(Cc1ccccc1)N1CCN(c2ncnc3[nH]ccc23)CC12CC2] | I | I | I | II |
| 153 | 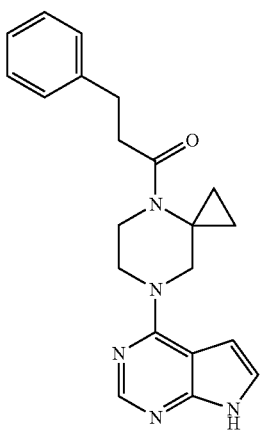 [SMILES: O=C(CCc1ccccc1)N1CCN(c2ncnc3[nH]ccc23)CC12CC2] | I | I | II | III |
| 154 | 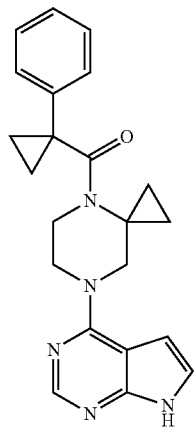 [SMILES: O=C(N1CCN(c2ncnc3[nH]ccc23)CC12CC2)C1(c2ccccc2)CC1] | II | I | III | III |

TABLE 1-continued
| Example number | Structure | JAK1 | JAK2 | JAK3 | TYK2 |
|---|---|---|---|---|---|
| 155 | 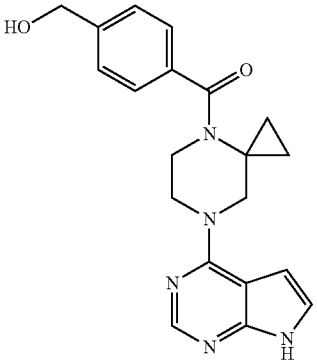 [SMILES: O=C(c1ccc(CO)cc1)N1CCN(c2ncnc3[nH]ccc23)CC12CC2] | I | I | II | II |
| 157 | 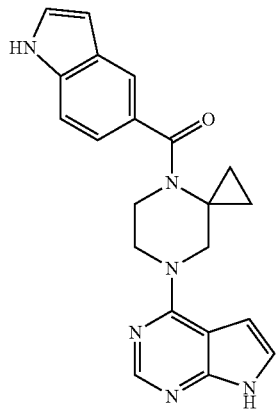 [SMILES: O=C(c1ccc2[nH]ccc2c1)N1CCN(c2ncnc3[nH]ccc23)CC12CC2] | I | I | I | II |
| 158 | 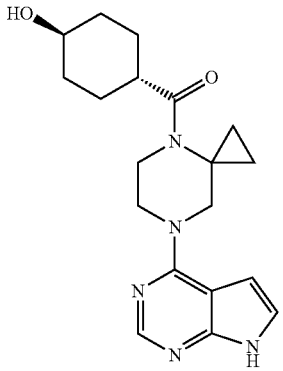 [SMILES: O=C([C@H]1CC[C@H](O)CC1)N1CCN(c2ncnc3[nH]ccc23)CC12CC2] | II | I | II | III |
| 159 | 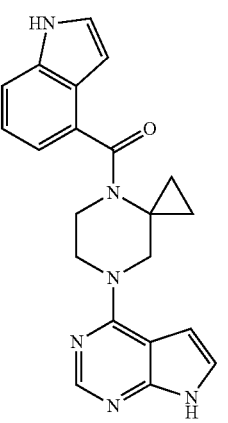 [SMILES: O=C(c1cccc2[nH]ccc12)N1CCN(c2ncnc3[nH]ccc23)CC12CC2] | I | I | II | II |

TABLE 1-continued

| Example number | Structure | JAK1 | JAK2 | JAK3 | TYK2 |
|---|---|---|---|---|---|
| 160 | 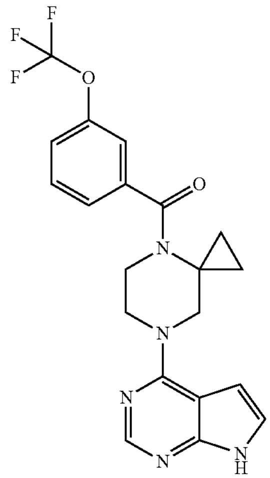 [SMILES: O=C(c1cccc(OC(F)(F)F)c1)N1CCN(c2ncnc3[nH]ccc23)CC12CC2] | I | I | II | II |
| 161 | 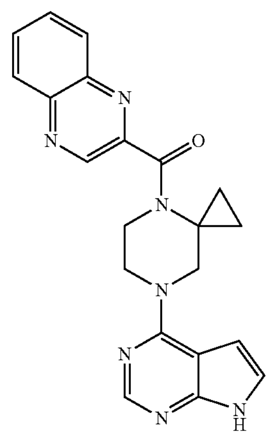 [SMILES: O=C(c1cnc2ccccc2n1)N1CCN(c2ncnc3[nH]ccc23)CC12CC2] | I | I | I | I |
| 162 | 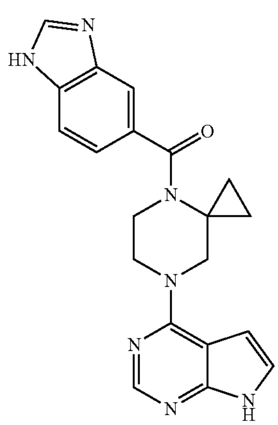 [SMILES: O=C(c1ccc2[nH]cnc2c1)N1CCN(c2ncnc3[nH]ccc23)CC12CC2] | I | I | II | III |

TABLE 1-continued
| Example number | Structure | JAK1 | JAK2 | JAK3 | TYK2 |
|---|---|---|---|---|---|
| 163 | 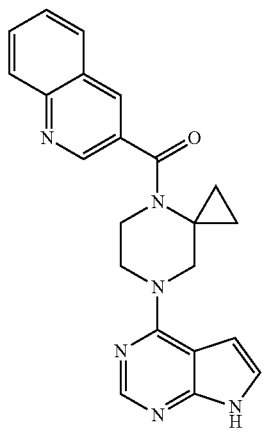 [SMILES: O=C(c1cnc2ccccc2c1)N1CCN(c2ncnc3[nH]ccc23)CC12CC2] | I | I | III | II |
| 164 | 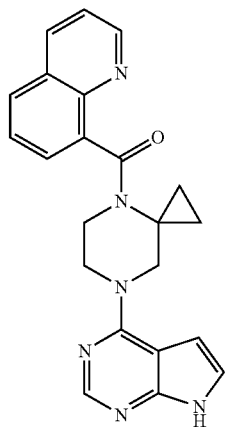 [SMILES: O=C(c1cccc2cccnc12)N1CCN(c2ncnc3[nH]ccc23)CC12CC2] | II | I | II | III |
| 165 | 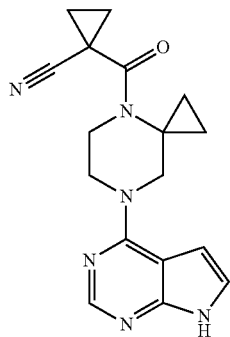 [SMILES: N#CC1(C(=O)N2CCN(c3ncnc4[nH]ccc34)CC23CC3)CC1] | I | I | I | II |

TABLE 1-continued
| Example number | Structure | JAK1 | JAK2 | JAK3 | TYK2 |
|---|---|---|---|---|---|
| 166 | 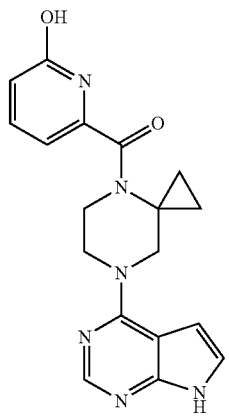 [SMILES: O=C(c1cccc(O)n1)N1CCN(c2ncnc3[nH]ccc23)CC12CC2] | I | I | II | III |
| 167 | 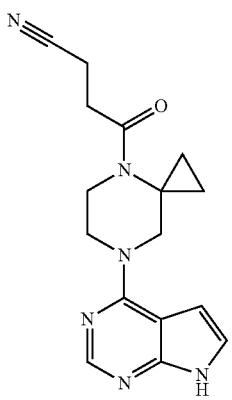 [SMILES: N#CCCC(=O)N1CCN(c2ncnc3[nH]ccc23)CC12CC2] | I | I | I | II |
| 168 | 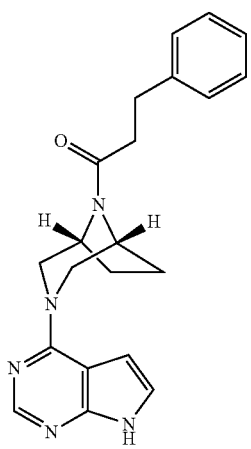 [SMILES: O=C(CCc1ccccc1)N1[C@@H]2CC[C@@H]1CN(c1ncnc3[nH]ccc13)C2] | I | I | II | III |

TABLE 1-continued
| Example number | Structure | JAK1 | JAK2 | JAK3 | TYK2 |
|---|---|---|---|---|---|
| 169 | 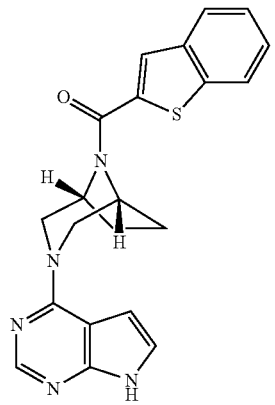 [SMILES: O=C(c1cc2ccccc2s1)N1[C@@H]2CC[C@@H]1CN(c1ncnc3[nH]ccc13)C2] | I | I | I | III |
| 170 | 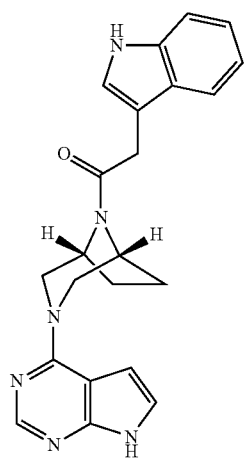 [SMILES: O=C(Cc1c[nH]c2ccccc12)N1[C@@H]2CC[C@@H]1CN(c1ncnc3[nH]ccc13)C2] | II | II | II | III |
| 171 | 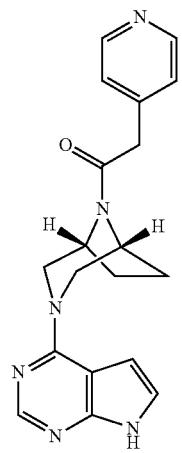 [SMILES: O=C(Cc1ccncc1)N1[C@@H]2CC[C@@H]1CN(c1ncnc3[nH]ccc13)C2] | II | II | III | III |

TABLE 1-continued
| Example number | Structure | JAK1 | JAK2 | JAK3 | TYK2 |
|---|---|---|---|---|---|
| 172 | 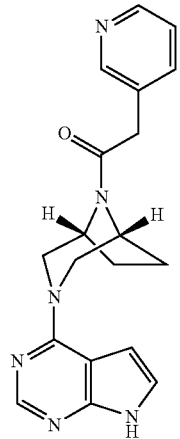 [SMILES: O=C(Cc1cccnc1)N1[C@@H]2CC[C@@H]1CN(c1ncnc3[nH]ccc13)C2] | III | II | III | III |
| 173 | 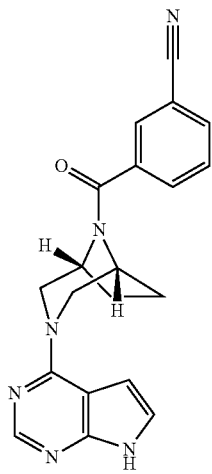 [SMILES: N#Cc1cccc(C(=O)N2[C@@H]3CC[C@@H]2CN(c2ncnc4[nH]ccc24)C3)c1] | I | I | I | II |
| 175 | 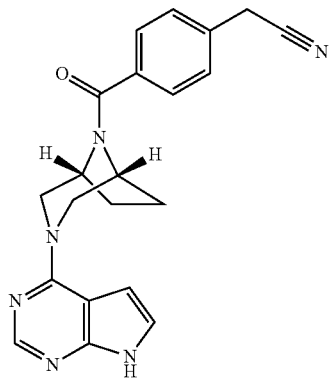 [SMILES: N#CCc1ccc(C(=O)N2[C@@H]3CC[C@@H]2CN(c2ncnc4[nH]ccc24)C3)cc1] | I | I | II | III |

TABLE 1-continued
| Example number | Structure | JAK1 | JAK2 | JAK3 | TYK2 |
|---|---|---|---|---|---|
| 176 | 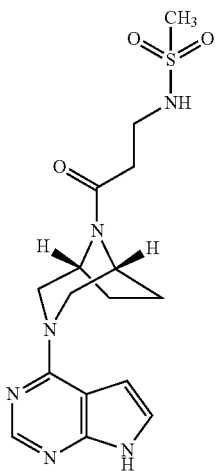 [SMILES: CS(=O)(=O)NCCC(=O)N1[C@@H]2CC[C@@H]1CN(c1ncnc3[nH]ccc13)C2] | II | II | III | III |
| 177 | 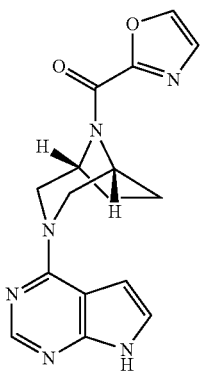 [SMILES: O=C(c1ncco1)N1[C@@H]2CC[C@@H]1CN(c1ncnc3[nH]ccc13)C2] | II | II | II | III |
| 178 | 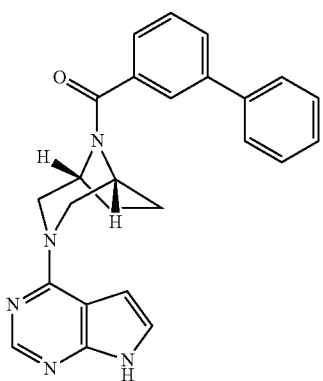 [SMILES: O=C(c1cccc(-c2ccccc2)c1)N1[C@@H]2CC[C@@H]1CN(c1ncnc3[nH]ccc13)C2] | II | II | II | III |

TABLE 1-continued

| Example number | Structure | JAK1 | JAK2 | JAK3 | TYK2 |
|---|---|---|---|---|---|
| 179 | 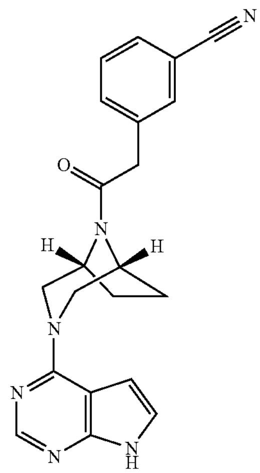 [SMILES: N#Cc1cccc(CC(=O)N2[C@@H]3CC[C@@H]2CN(c2ncnc4[nH]ccc24)C3)c1] | II | II | III | III |
| 180 | 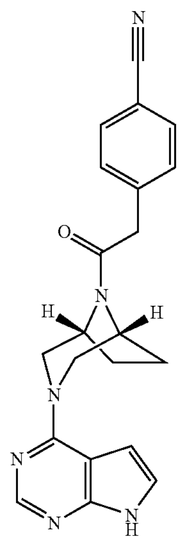 [SMILES: N#Cc1ccc(CC(=O)N2[C@@H]3CC[C@@H]2CN(c2ncnc4[nH]ccc24)C3)cc1] | II | II | II | III |
| 181 | 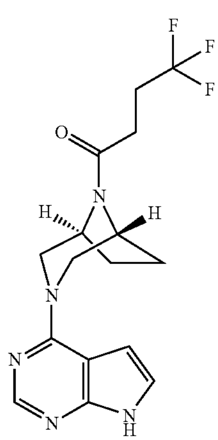 [SMILES: O=C(CCC(F)(F)F)N1[C@@H]2CC[C@H]1CN(c1ncnc3[nH]ccc13)C2] | I | I | II | II |

TABLE 1-continued
| Example number | Structure | JAK1 | JAK2 | JAK3 | TYK2 |
|---|---|---|---|---|---|
| 182 | 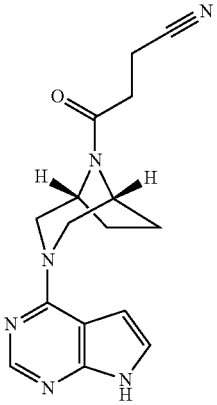 [SMILES: N#CCCC(=O)N1[C@@H]2CC[C@@H]1CN(c1ncnc3[nH]ccc13)C2] | I | I | II | II |
| 183 | 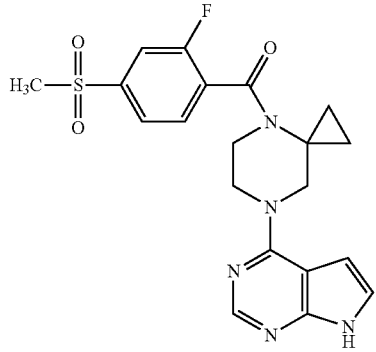 [SMILES: CS(=O)(=O)c1ccc(C(=O)N2CCN(c3ncnc4[nH]ccc34)CC23CC3)c(F)c1] | I | I | I | I |
| 184 | 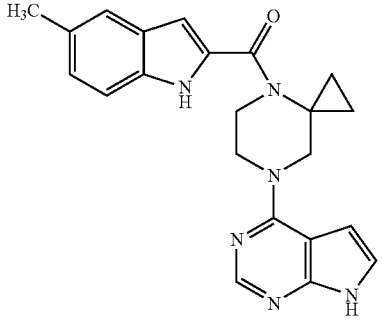 [SMILES: Cc1ccc2[nH]c(C(=O)N3CCN(c4ncnc5[nH]ccc45)CC34CC4)cc2c1] | I | I | I | II |
| 185 | 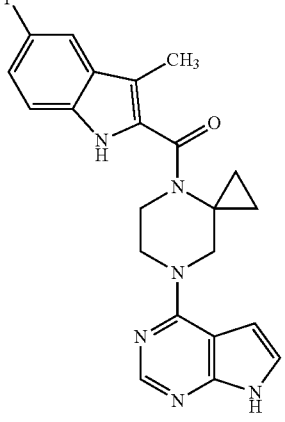 | II | II | III | III |

TABLE 1-continued
| Example number | Structure | JAK1 | JAK2 | JAK3 | TYK2 |
|---|---|---|---|---|---|
| 186 | 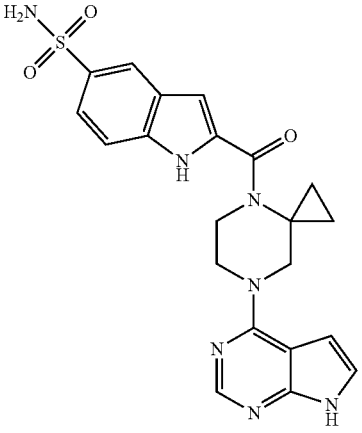 [SMILES: NS(=O)(=O)c1ccc2[nH]c(C(=O)N3CCN(c4ncnc5[nH]ccc45)CC34CC4)cc2c1] | I | I | I | I |
| 187 | 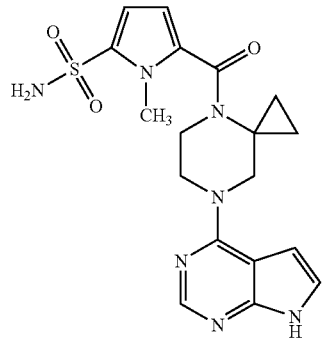 [SMILES: Cn1c(C(=O)N2CCN(c3ncnc4[nH]ccc34)CC23CC3)ccc1S(N)(=O)=O] | I | I | I | I |
| 188 | 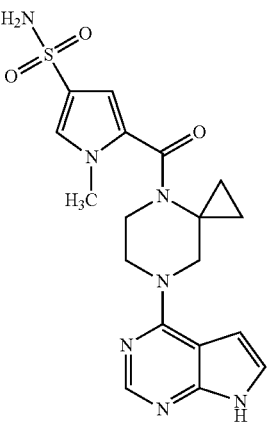 [SMILES: Cn1cc(S(N)(=O)=O)cc1C(=O)N1CCN(c2ncnc3[nH]ccc23)CC12CC2] | I | I | I | I |

TABLE 1-continued
| Example number | Structure | JAK1 | JAK2 | JAK3 | TYK2 |
|---|---|---|---|---|---|
| 189 | 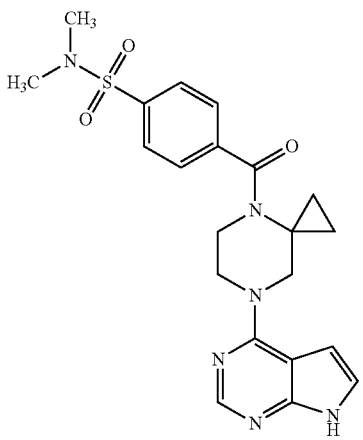 [SMILES: CN(C)S(=O)(=O)c1ccc(C(=O)N2CCN(c3ncnc4[nH]ccc34)CC23CC3)cc1] | I | I | II | II |
| 190 | 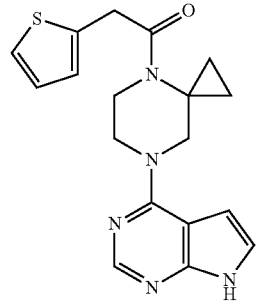 [SMILES: O=C(Cc1cccs1)N1CCN(c2ncnc3[nH]ccc23)CC12CC2] | I | I | I | II |
| 191 | 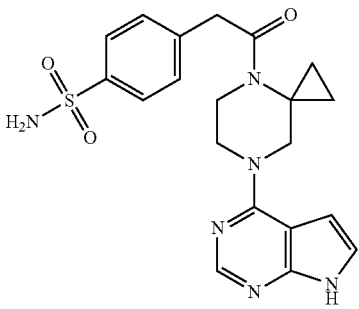 [SMILES: NS(=O)(=O)c1ccc(CC(=O)N2CCN(c3ncnc4[nH]ccc34)CC23CC3)cc1] | I | I | I | III |
| 192 | 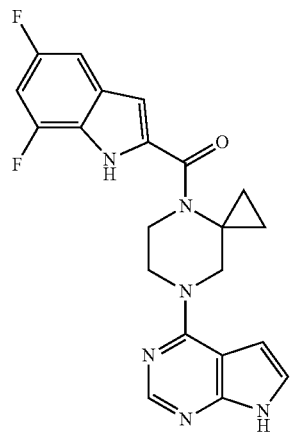 [SMILES: O=C(c1cc2cc(F)cc(F)c2[nH]1)N1CCN(c2ncnc3[nH]ccc23)CC12CC2] | I | I | I | I |

TABLE 1-continued
| Example number | Structure | JAK1 | JAK2 | JAK3 | TYK2 |
|---|---|---|---|---|---|
| 193 | 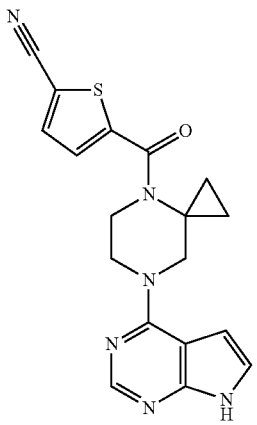 [SMILES: N#Cc1ccc(C(=O)N2CCN(c3ncnc4[nH]ccc34)CC23CC3)s1] | I | I | I | I |
| 194 | 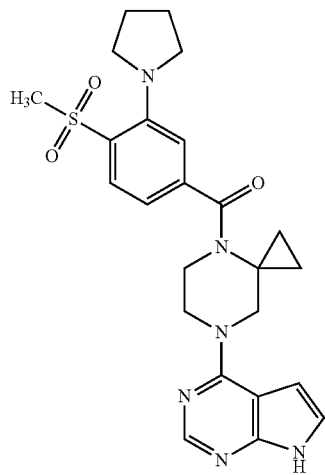 [SMILES: CS(=O)(=O)c1ccc(C(=O)N2CCN(c3ncnc4[nH]ccc34)CC23CC3)cc1N1CCCC1] | I | I | II | III |
| 195 | 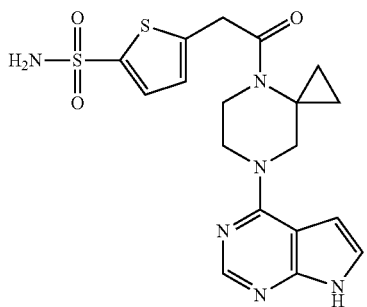 [SMILES: NS(=O)(=O)c1ccc(CC(=O)N2CCN(c3ncnc4[nH]ccc34)CC23CC3)s1] | I | I | I | II |

TABLE 1-continued
| Example number | Structure | JAK1 | JAK2 | JAK3 | TYK2 |
|---|---|---|---|---|---|
| 196 | 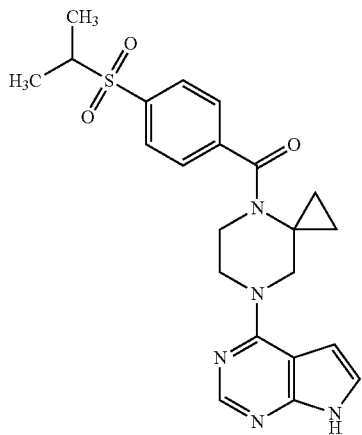 [SMILES: CC(C)S(=O)(=O)c1ccc(C(=O)N2CCN(c3ncnc4[nH]ccc34)CC23CC3)cc1] | I | I | II | III |
| 197 | 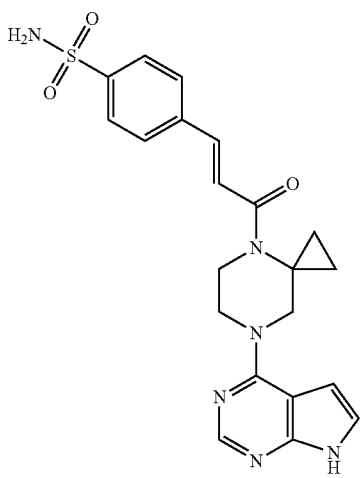 [SMILES: NS(=O)(=O)c1ccc(/C=C/C(=O)N2CCN(c3ncnc4[nH]ccc34)CC23CC3)cc1] | I | I | I | I |
| 198 | 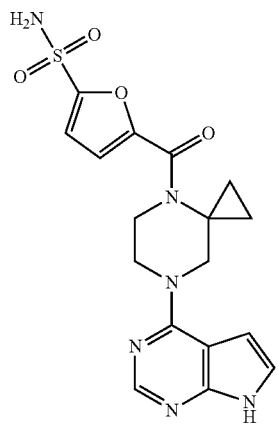 [SMILES: NS(=O)(=O)c1ccc(C(=O)N2CCN(c3ncnc4[nH]ccc34)CC23CC3)o1] | I | I | I | I |

TABLE 1-continued
| Example number | Structure | JAK1 | JAK2 | JAK3 | TYK2 |
|---|---|---|---|---|---|
| 199 | 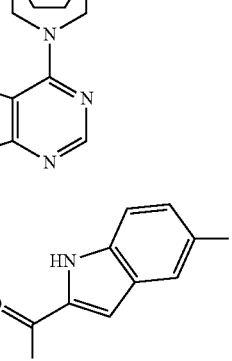 | I | I | I | II |
| 200 | 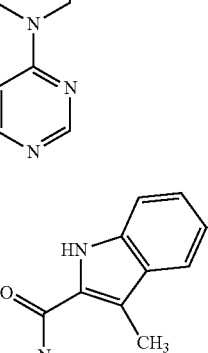 | I | I | II | III |
| 201 | 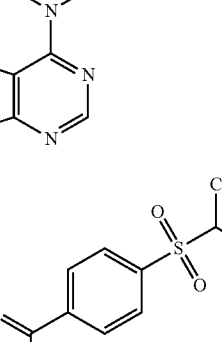 | I | II | II | III |
| 202 | 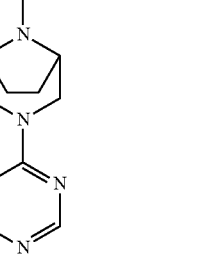 | II | II | III | III |

TABLE 1-continued
| Example number | Structure | JAK1 | JAK2 | JAK3 | TYK2 |
|---|---|---|---|---|---|
| 203 | 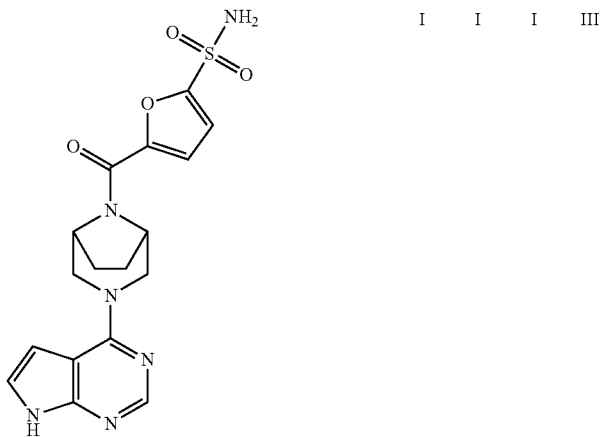 | I | I | I | III |
| 204 | 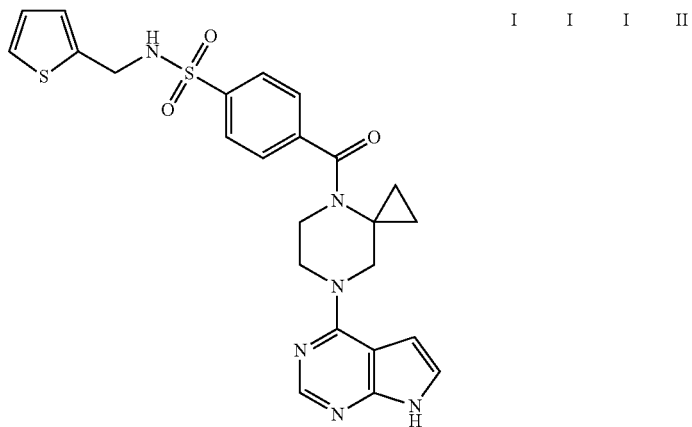 | I | I | I | II |
| 205 | 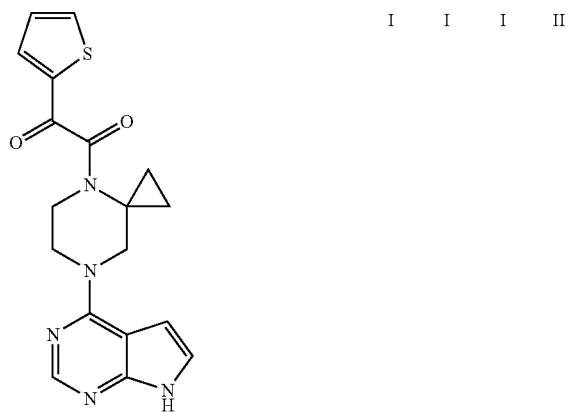 | I | I | I | II |

TABLE 1-continued

| Example number | Structure | JAK1 | JAK2 | JAK3 | TYK2 |
|---|---|---|---|---|---|
| 206 | 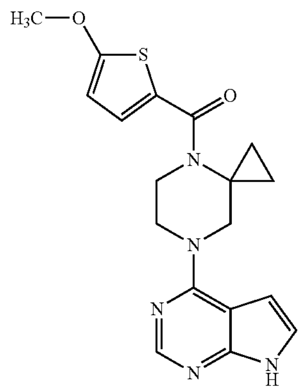 [SMILES: COc1ccc(C(=O)N2CCN(c3ncnc4[nH]ccc34)CC23CC3)s1] | I | I | I | I |
| 207 | 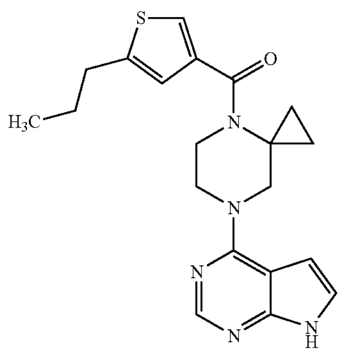 [SMILES: CCCc1cc(C(=O)N2CCN(c3ncnc4[nH]ccc34)CC23CC3)cs1] | I | I | II | II |
| 208 | 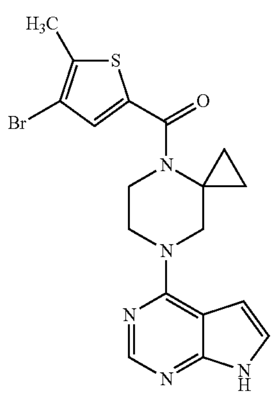 [SMILES: Cc1sc(C(=O)N2CCN(c3ncnc4[nH]ccc34)CC23CC3)cc1Br] | I | I | I | I |
| 209 | 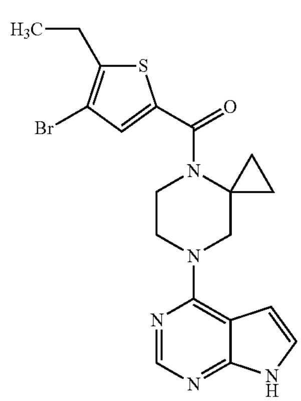 [SMILES: CCc1sc(C(=O)N2CCN(c3ncnc4[nH]ccc34)CC23CC3)cc1Br] | I | I | II | I |

TABLE 1-continued
| Example number | Structure | JAK1 | JAK2 | JAK3 | TYK2 |
|---|---|---|---|---|---|
| 210 | 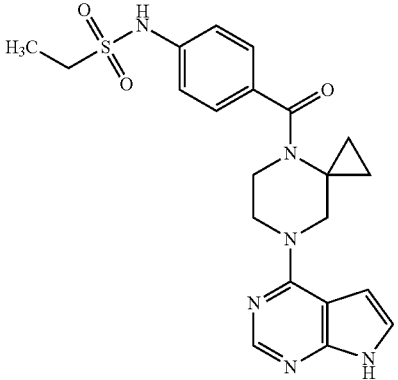 [SMILES: CCS(=O)(=O)Nc1ccc(C(=O)N2CCN(c3ncnc4[nH]ccc34)CC23CC3)cc1] | I | I | I | I |
| 211 | 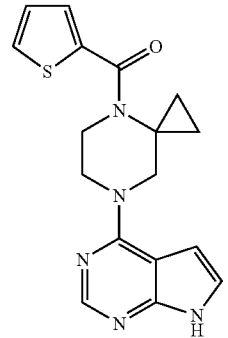 [SMILES: O=C(c1cccs1)N1CCN(c2ncnc3[nH]ccc23)CC12CC2] | I | I | I | II |
| 212 | 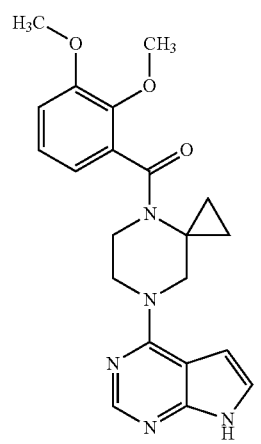 [SMILES: COc1cccc(C(=O)N2CCN(c3ncnc4[nH]ccc34)CC23CC3)c1OC] | II | I | III | III |

TABLE 1-continued
| Example number | Structure | JAK1 | JAK2 | JAK3 | TYK2 |
|---|---|---|---|---|---|
| 213 | 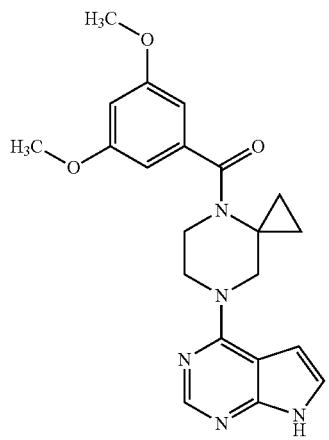 [SMILES: COc1cc(OC)cc(C(=O)N2CCN(c3ncnc4[nH]ccc34)CC23CC3)c1] | I | I | II | II |
| 214 | 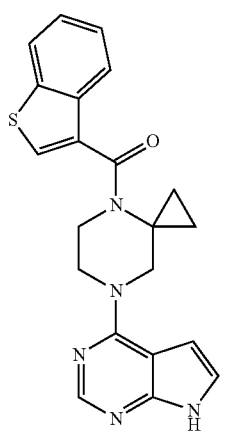 [SMILES: O=C(c1csc2ccccc12)N1CCN(c2ncnc3[nH]ccc23)CC12CC2] | I | I | I | I |
| 215 | 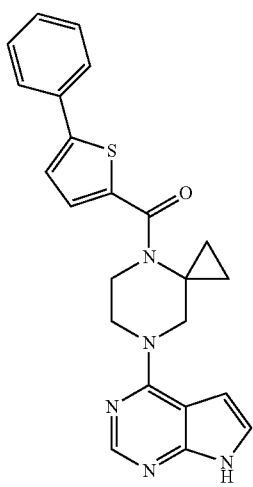 [SMILES: O=C(c1ccc(-c2ccccc2)s1)N1CCN(c2ncnc3[nH]ccc23)CC12CC2] | I | I | II | II |

TABLE 1-continued
| Example number | Structure | JAK1 | JAK2 | JAK3 | TYK2 |
|---|---|---|---|---|---|
| 216 | 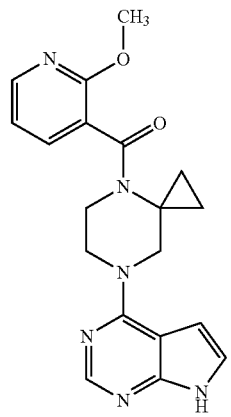 [SMILES: COc1ncccc1C(=O)N1CCN(c2ncnc3[nH]ccc23)CC12CC2] | II | II | III | III |
| 217 | 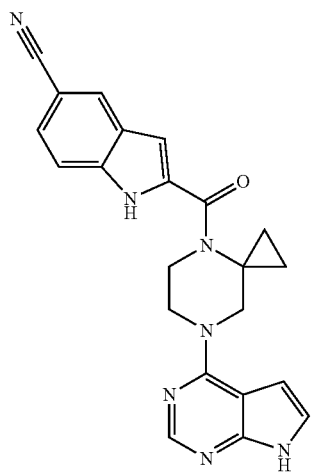 [SMILES: N#Cc1ccc2[nH]c(C(=O)N3CCN(c4ncnc5[nH]ccc45)CC34CC4)cc2c1] | I | I | I | II |
| 218 | 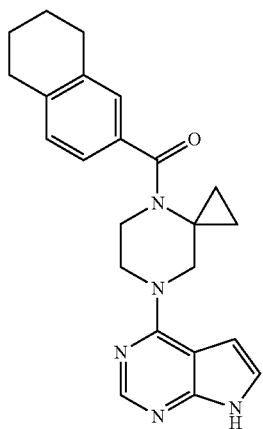 [SMILES: O=C(c1ccc2c(c1)CCCC2)N1CCN(c2ncnc3[nH]ccc23)CC12CC2] | I | I | III | III |

TABLE 1-continued

| Example number | Structure | JAK1 | JAK2 | JAK3 | TYK2 |
|---|---|---|---|---|---|
| 219 | 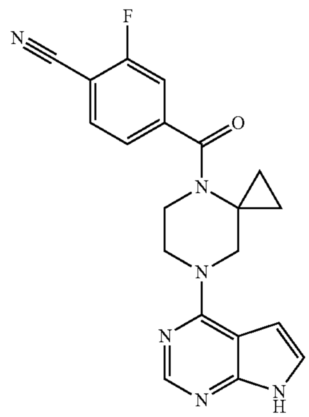 [SMILES: N#Cc1ccc(C(=O)N2CCN(c3ncnc4[nH]ccc34)CC23CC3)cc1F] | I | I | II | II |
| 220 | 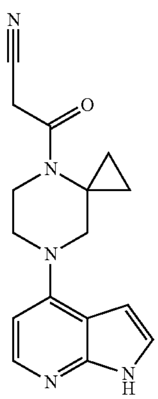 [SMILES: N#CCC(=O)N1CCN(c2ccnc3[nH]ccc23)CC12CC2] | II | II | II | III |
| 221 | 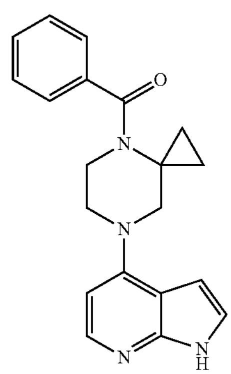 [SMILES: O=C(c1ccccc1)N1CCN(c2ccnc3[nH]ccc23)CC12CC2] | I | I | II | III |
| 222 | 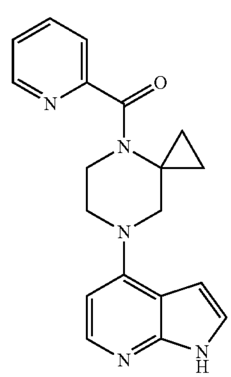 [SMILES: O=C(c1ccccn1)N1CCN(c2ccnc3[nH]ccc23)CC12CC2] | II | II | III | III |

TABLE 1-continued

| Example number | Structure | JAK1 | JAK2 | JAK3 | TYK2 |
|---|---|---|---|---|---|
| 223 | 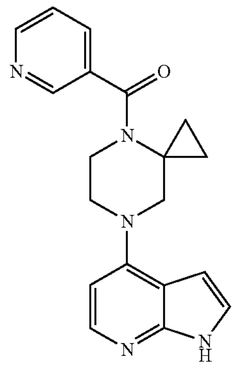 [SMILES: O=C(c1cccnc1)N1CCN(c2ccnc3[nH]ccc23)CC12CC2] | II | II | III | III |
| 224 | 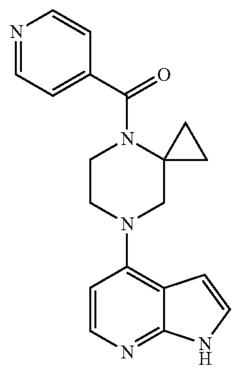 [SMILES: O=C(c1ccncc1)N1CCN(c2ccnc3[nH]ccc23)CC12CC2] | II | II | III | III |
| 225 | 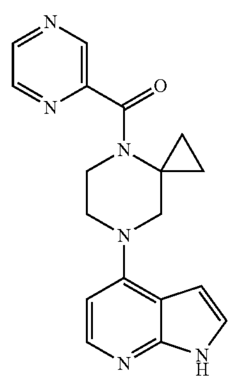 [SMILES: O=C(c1cnccn1)N1CCN(c2ccnc3[nH]ccc23)CC12CC2] | II | I | III | III |
| 226 | 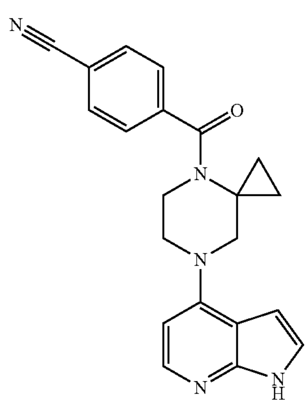 [SMILES: N#Cc1ccc(C(=O)N2CCN(c3ccnc4[nH]ccc34)CC23CC3)cc1] | I | II | III | III |

TABLE 1-continued
| Example number | Structure | JAK1 | JAK2 | JAK3 | TYK2 |
|---|---|---|---|---|---|
| 227 | 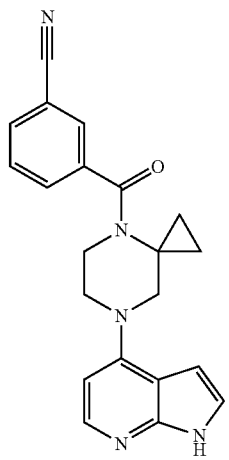 [SMILES: N#Cc1cccc(C(=O)N2CCN(c3ccnc4[nH]ccc34)CC23CC3)c1] | I | I | II | III |
| 228 | 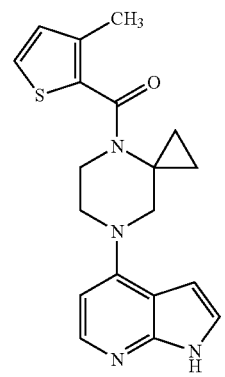 [SMILES: Cc1ccsc1C(=O)N1CCN(c2ccnc3[nH]ccc23)CC12CC2] | II | I | III | III |
| 229 | 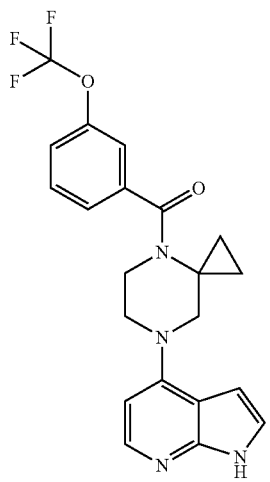 [SMILES: O=C(c1cccc(OC(F)(F)F)c1)N1CCN(c2ccnc3[nH]ccc23)CC12CC2] | II | II | III | III |

TABLE 1-continued
| Example number | Structure | JAK1 | JAK2 | JAK3 | TYK2 |
|---|---|---|---|---|---|
| 230 | 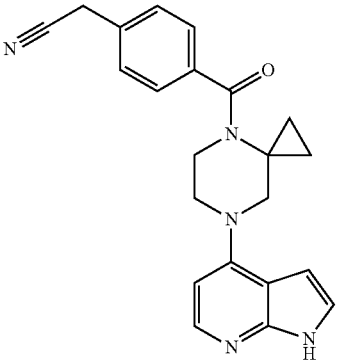 [SMILES: N#CCc1ccc(C(=O)N2CCN(c3ccnc4[nH]ccc34)CC23CC3)cc1] | II | I | II | III |
| 231 | 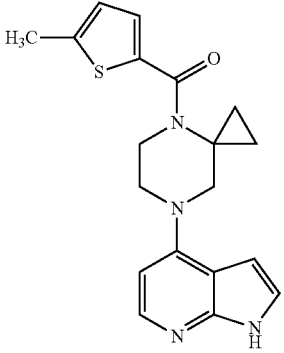 [SMILES: Cc1ccc(C(=O)N2CCN(c3ccnc4[nH]ccc34)CC23CC3)s1] | I | I | II | II |
| 232 | 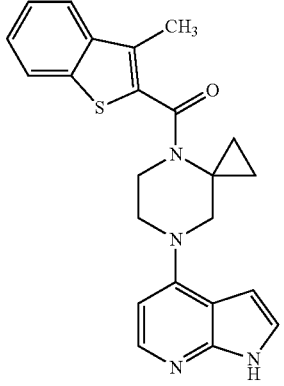 [SMILES: Cc1c(C(=O)N2CCN(c3ccnc4[nH]ccc34)CC23CC3)sc2ccccc12] | I | I | III | II |
| 233 | 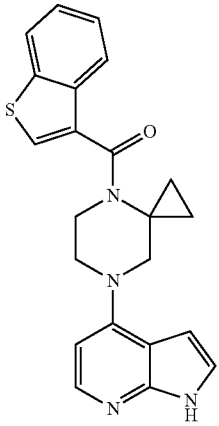 | II | I | III | III |

TABLE 1-continued
| Example number | Structure | JAK1 | JAK2 | JAK3 | TYK2 |
|---|---|---|---|---|---|
| 234 | 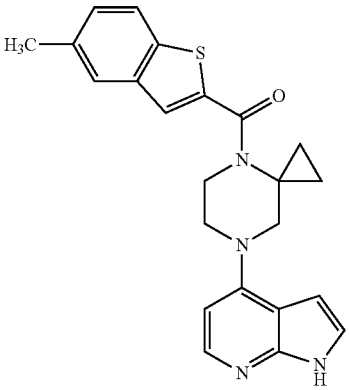 | II | II | III | III |
| 235 | 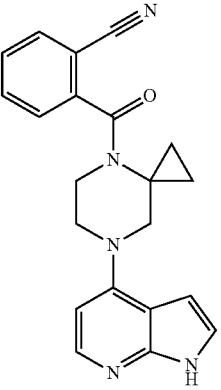 [SMILES: N#Cc1ccccc1C(=O)N1CCN(c2ccnc3[nH]ccc23)CC12CC2] | II | I | III | III |
| 236 | 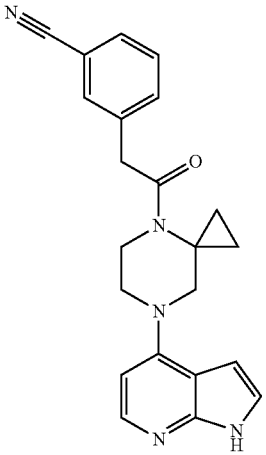 [SMILES: N#Cc1cccc(CC(=O)N2CCN(c3ccnc4[nH]ccc34)CC23CC3)c1] | III | III | III | III |

TABLE 1-continued
| Example number | Structure | JAK1 | JAK2 | JAK3 | TYK2 |
|---|---|---|---|---|---|
| 237 | 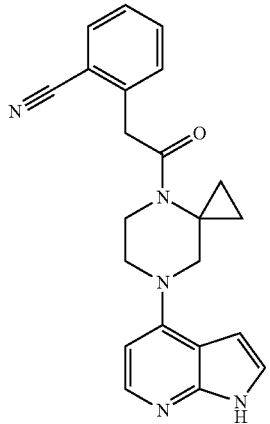 [SMILES: N#Cc1ccccc1CC(=O)N1CCN(c2ccnc3[nH]ccc23)CC12CC2] | III | II | II | III |
| 238 | 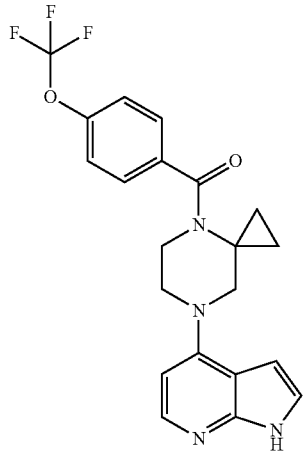 [SMILES: O=C(c1ccc(OC(F)(F)F)cc1)N1CCN(c2ccnc3[nH]ccc23)CC12CC2] | I | II | III | III |
| 239 | 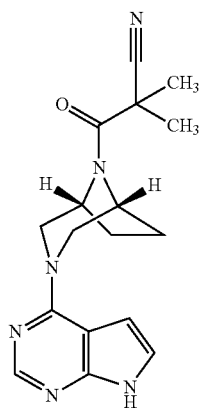 [SMILES: CC(C)(C#N)C(=O)N1[C@@H]2CC[C@@H]1CN(c1ncnc3[nH]ccc13)C2] | II | II | II | III |

TABLE 1-continued

| Example number | Structure | JAK1 | JAK2 | JAK3 | TYK2 |
|---|---|---|---|---|---|
| 240 | 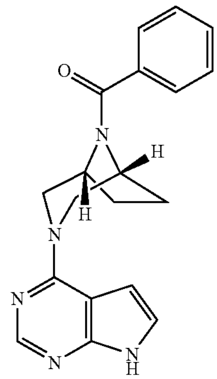 [SMILES: O=C(c1ccccc1)N1[C@@H]2CC[C@@H]1CN(c1ncnc3[nH]ccc13)C2] | I | I | II | III |
| 241 | 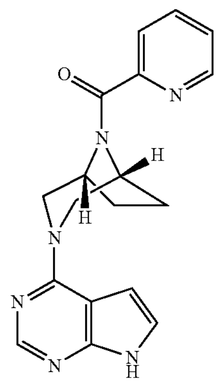 [SMILES: O=C(c1ccccn1)N1[C@@H]2CC[C@@H]1CN(c1ncnc3[nH]ccc13)C2] | I | I | II | III |
| 242 | 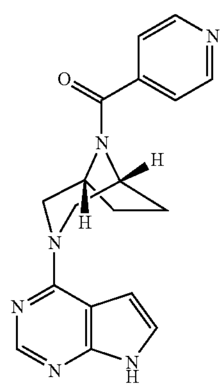 [SMILES: O=C(c1ccncc1)N1[C@@H]2CC[C@@H]1CN(c1ncnc3[nH]ccc13)C2] | I | I | II | III |
| 243 | 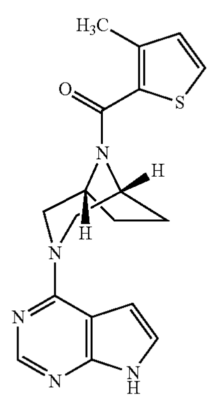 [SMILES: Cc1ccsc1C(=O)N1[C@@H]2CC[C@@H]1CN(c1ncnc3[nH]ccc13)C2] | II | I | II | III |

TABLE 1-continued

| Example number | Structure | JAK1 | JAK2 | JAK3 | TYK2 |
|---|---|---|---|---|---|
| 244 | 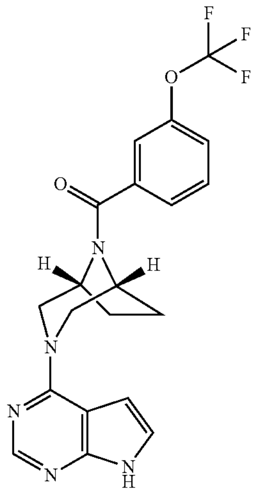 [SMILES: O=C(c1cccc(OC(F)(F)F)c1)N1[C@@H]2CC[C@@H]1CN(c1ncnc3[nH]ccc13)C2] | I | I | I | III |
| 245 | 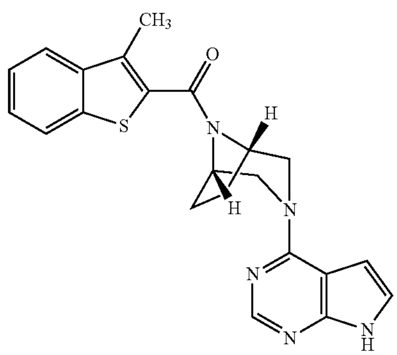 [SMILES: Cc1c(C(=O)N2[C@H]3CC[C@H]2CN(c2ncnc4[nH]ccc24)C3)sc2ccccc12] | I | I | I | III |
| 246 | 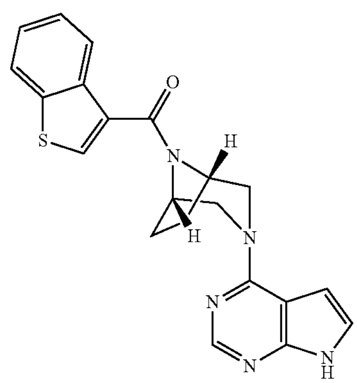 [SMILES: O=C(c1csc2ccccc12)N1[C@H]2CC[C@H]1CN(c1ncnc3[nH]ccc13)C2] | I | I | I | II |
| 247 | 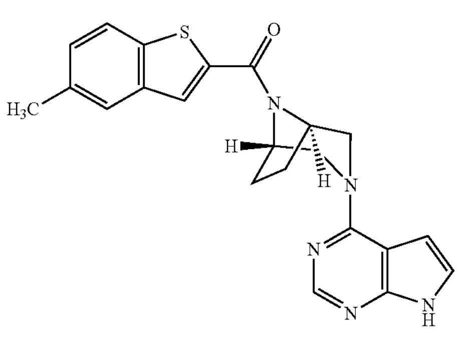 [SMILES: Cc1ccc2sc(C(=O)N3[C@@H]4CC[C@H]3CN(c3ncnc5[nH]ccc35)C4)cc2c1] | I | I | II | III |

TABLE 1-continued
| Example number | Structure | JAK1 | JAK2 | JAK3 | TYK2 |
|---|---|---|---|---|---|
| 248 | 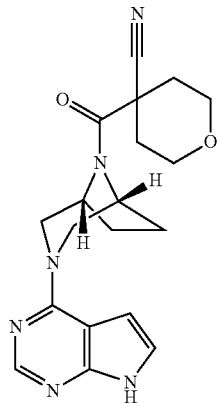 [SMILES: N#CC1(C(=O)N2[C@@H]3CC[C@@H]2CN(c2ncnc4[nH]ccc24)C3)CCOCC1] | II | I | II | III |
| 249 | 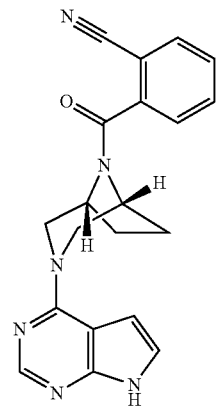 [SMILES: N#Cc1ccccc1C(=O)N1[C@@H]2CC[C@@H]1CN(c1ncnc3[nH]ccc13)C2] | II | I | II | III |
| 250 | 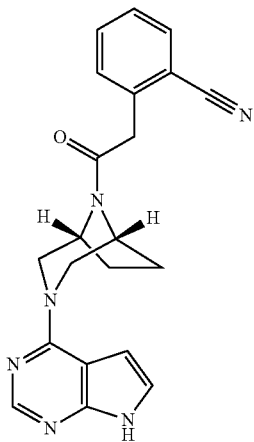 [SMILES: N#Cc1ccccc1CC(=O)N1[C@@H]2CC[C@@H]1CN(c1ncnc3[nH]ccc13)C2] | II | II | II | III |

TABLE 1-continued
| Example number | Structure | JAK1 | JAK2 | JAK3 | TYK2 |
|---|---|---|---|---|---|
| 251 | 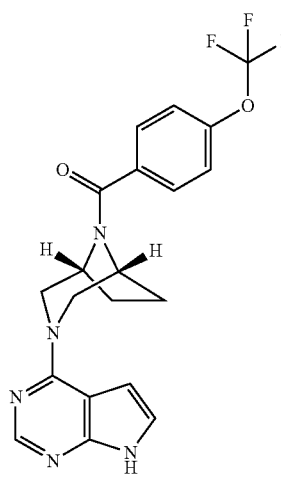 | I | II | II | III |
| 253 | 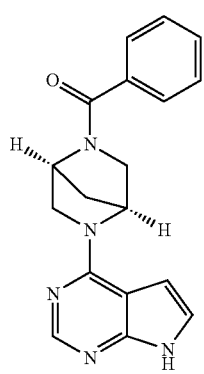 [SMILES: O=C(c1ccccc1)N1C[C@@H]2C[C@H]1CN2c1ncnc2[nH]ccc12] | III | III | III | III |
| 258 | 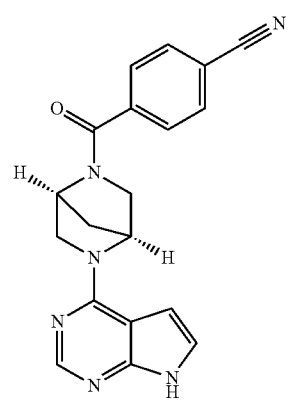 [SMILES: N#Cc1ccc(C(=O)N2C[C@@H]3C[C@H]2CN3c2ncnc3[nH]ccc23)cc1] | III | III | III | III |

TABLE 1-continued
| Example number | Structure | JAK1 | JAK2 | JAK3 | TYK2 |
|---|---|---|---|---|---|
| 265 | 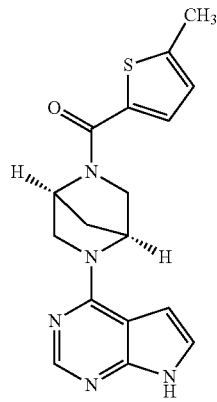 [SMILES: Cc1ccc(C(=O)N2C[C@@H]3C[C@H]2CN3c2ncnc3[nH]ccc23)s1] | III | III | III | III |
| 270 | 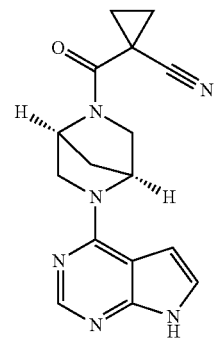 [SMILES: N#CC1(C(=O)N2C[C@@H]3C[C@H]2CN3c2ncnc3[nH]ccc23)CC1] | III | III | III | III |
| 278 | 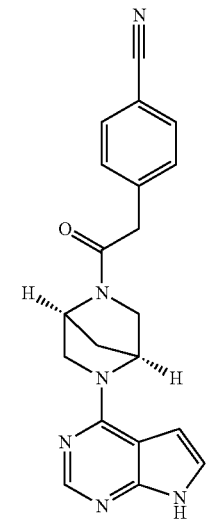 [SMILES: N#Cc1ccc(CC(=O)N2C[C@@H]3C[C@H]2CN3c2ncnc3[nH]ccc23)cc1] | III | III | III | III |

TABLE 1-continued
| Example number | Structure | JAK1 | JAK2 | JAK3 | TYK2 |
|---|---|---|---|---|---|
| 283 | 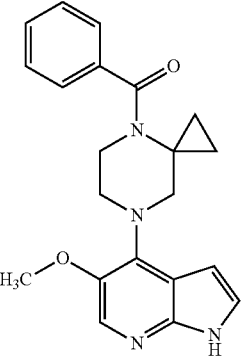 [SMILES: COc1cnc2[nH]ccc2c1N1CCN(C(=O)c2ccccc2)C2(CC2)C1] | III | II | II | III |
| 284 | 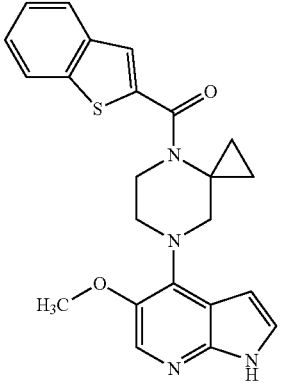 [SMILES: COc1cnc2[nH]ccc2c1N1CCN(C(=O)c2cc3ccccc3s2)C2(CC2)C1] | III | III | III | III |
| 285 | 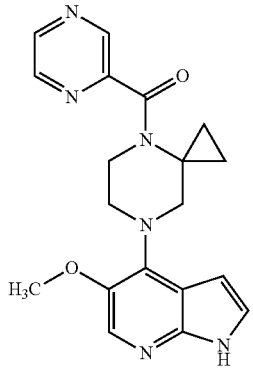 [SMILES: COc1cnc2[nH]ccc2c1N1CCN(C(=O)c2cnccn2)C2(CC2)C1] | III | II | II | III |
| 286 | 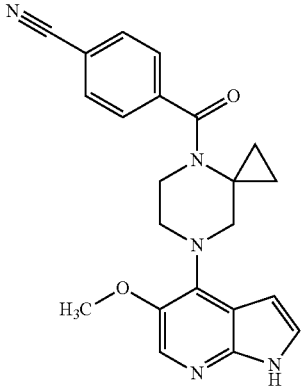 [SMILES: COc1cnc2[nH]ccc2c1N1CCN(C(=O)c2ccc(C#N)cc2)C2(CC2)C1] | III | III | III | III |

TABLE 1-continued
| Example number | Structure | JAK1 | JAK2 | JAK3 | TYK2 |
|---|---|---|---|---|---|
| 287 | 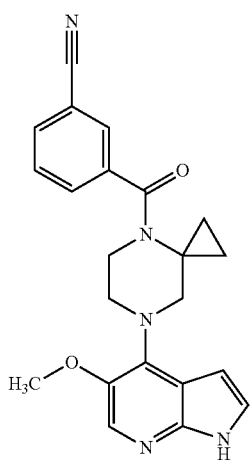 [SMILES: COc1cnc2[nH]ccc2c1N1CCN(C(=O)c2cccc(C#N)c2)C2(CC2)C1] | III | II | II | III |
| 288 | 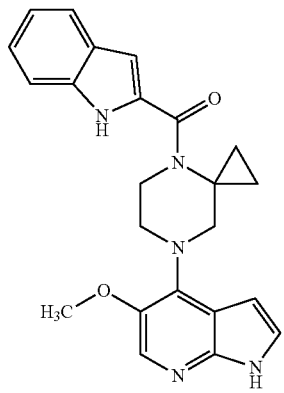 [SMILES: COc1cnc2[nH]ccc2c1N1CCN(C(=O)c2cc3ccccc3[nH]2)C2(CC2)C1] | III | III | II | III |
| 289 | 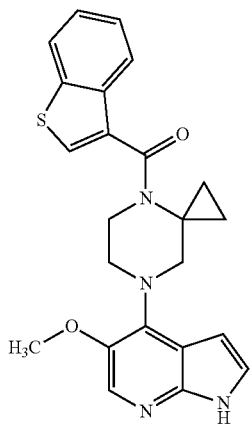 [SMILES: COc1cnc2[nH]ccc2c1N1CCN(C(=O)c2csc3ccccc23)C2(CC2)C1] | II | II | II | III |

TABLE 1-continued
| Example number | Structure | JAK1 | JAK2 | JAK3 | TYK2 |
|---|---|---|---|---|---|
| 290 | 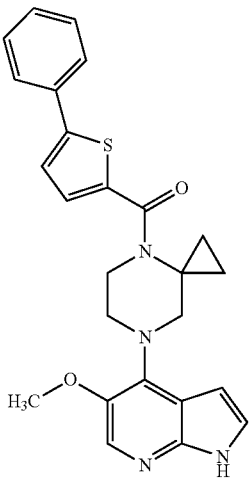 [SMILES: COc1cnc2[nH]ccc2c1N1CCN(C(=O)c2ccc(-c3ccccc3)s2)C2(CC2)C1] | III | III | III | III |
| 291 | 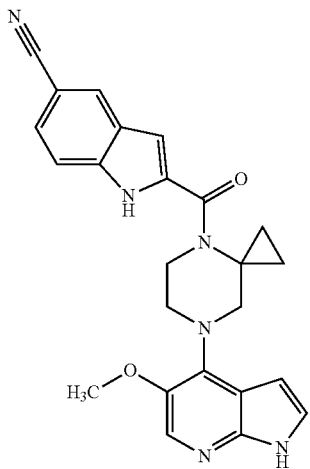 [SMILES: COc1cnc2[nH]ccc2c1N1CCN(C(=O)c2cc3cc(C#N)ccc3[nH]2)C2(CC2)C1] | III | III | II | III |
| 292 | 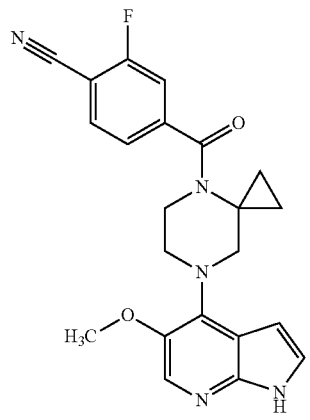 [SMILES: COc1cnc2[nH]ccc2c1N1CCN(C(=O)c2ccc(C#N)c(F)c2)C2(CC2)C1] | III | II | II | III |

TABLE 1-continued
| Example number | Structure | JAK1 | JAK2 | JAK3 | TYK2 |
|---|---|---|---|---|---|
| 293 | 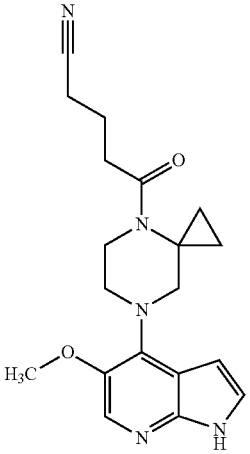 [SMILES: COc1cnc2[nH]ccc2c1N1CCN(C(=O)CCCC#N)C2(CC2)C1] | I | I | I | II |
| 294 | 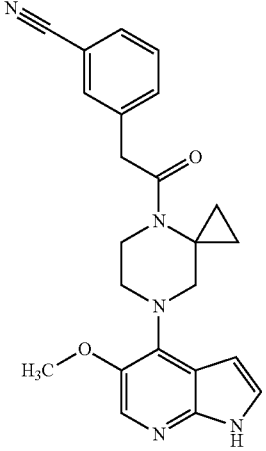 [SMILES: COc1cnc2[nH]ccc2c1N1CCN(C(=O)Cc2cccc(C#N)c2)C2(CC2)C1] | II | II | II | III |
| 295 | 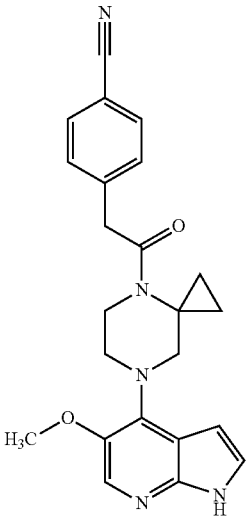 [SMILES: COc1cnc2[nH]ccc2c1N1CCN(C(=O)Cc2ccc(C#N)cc2)C2(CC2)C1] | II | I | I | III |

TABLE 1-continued
| Example number | Structure | JAK1 | JAK2 | JAK3 | TYK2 |
|---|---|---|---|---|---|
| 296 | 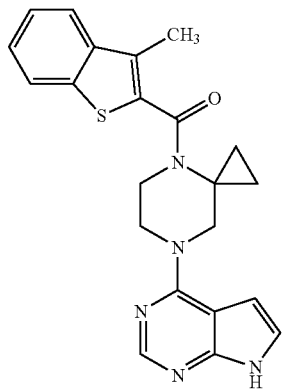 | I | I | II | I |
| 297 | 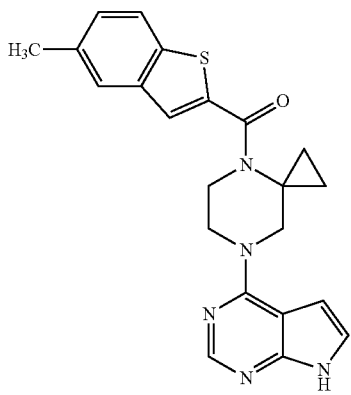 [SMILES: Cc1ccc2sc(C(=O)N3CCN(c4ncnc5[nH]ccc45)CC34CC4)cc2c1] | I | I | II | II |
| 298 | 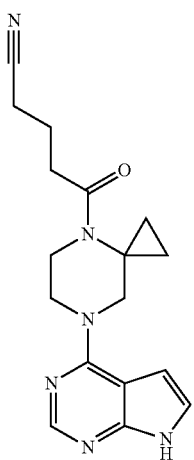 [SMILES: N#CCCCC(=O)N1CCN(c2ncnc3[nH]ccc23)CC12CC2] | I | I | I | II |

TABLE 1-continued
| Example number | Structure | JAK1 | JAK2 | JAK3 | TYK2 |
|---|---|---|---|---|---|
| 299 | 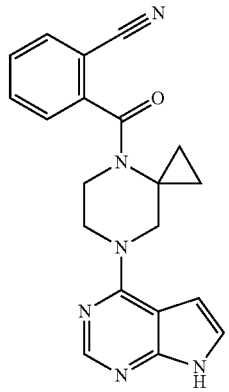 [SMILES: N#Cc1ccccc1C(=O)N1CCN(c2ncnc3[nH]ccc23)CC12CC2] | I | I | II | II |
| 300 | 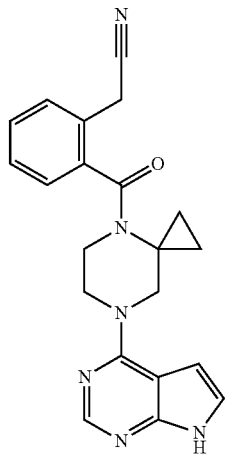 [SMILES: N#CCc1ccccc1C(=O)N1CCN(c2ncnc3[nH]ccc23)CC12CC2] | I | I | II | II |
| 301 | 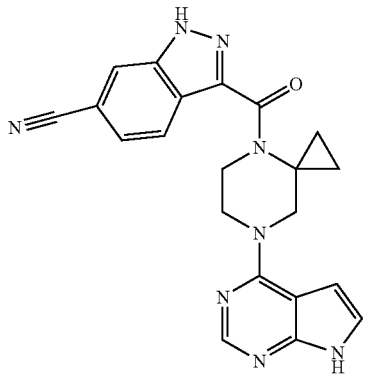 [SMILES: N#Cc1ccc2c(C(=O)N3CCN(c4ncnc5[nH]ccc45)CC34CC4)n[nH]c2c1] | I | I | I | II |

TABLE 1-continued
| Example number | Structure | JAK1 | JAK2 | JAK3 | TYK2 |
|---|---|---|---|---|---|
| 302 | 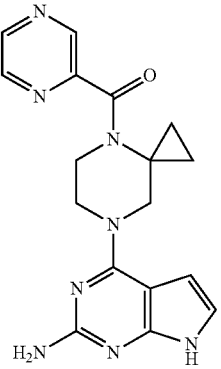 [SMILES: Nc1nc(N2CCN(C(=O)c3cnccn3)C3(CC3)C2)c2cc[nH]c2n1] | II | I | II | III |
| 303 | 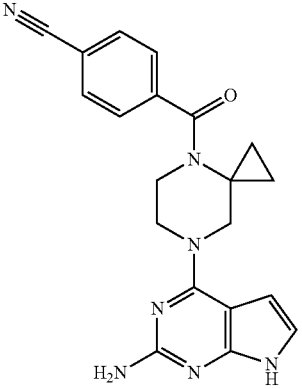 [SMILES: N#Cc1ccc(C(=O)N2CCN(c3nc(N)nc4[nH]ccc34)CC23CC3)cc1] | I | I | II | III |
| 304 | 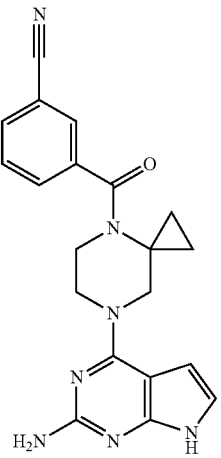 [SMILES: N#Cc1cccc(C(=O)N2CCN(c3nc(N)nc4[nH]ccc34)CC23CC3)c1] | I | I | I | II |

TABLE 1-continued

| Example number | Structure | JAK1 | JAK2 | JAK3 | TYK2 |
|---|---|---|---|---|---|
| 305 | 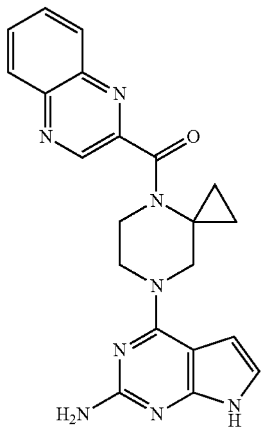 [SMILES: Nc1nc(N2CCN(C(=O)c3cnc4ccccc4n3)C3(CC3)C2)c2cc[nH]c2n1] | I | I | II | II |
| 306 | 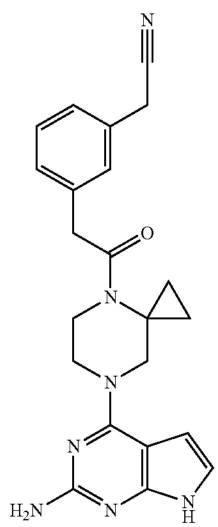 [SMILES: N#CCc1cccc(CC(=O)N2CCN(c3nc(N)nc4[nH]ccc34)CC23CC3)c1] | II | II | II | III |
| 307 | 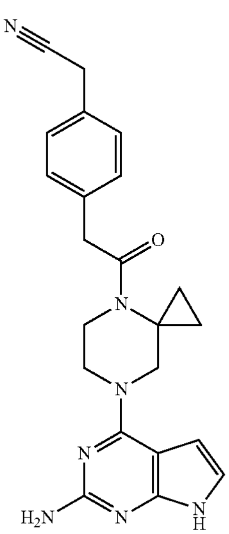 [SMILES: N#CCc1ccc(CC(=O)N2CCN(c3nc(N)nc4[nH]ccc34)CC23CC3)cc1] | II | II | II | III |

TABLE 1-continued
| Example number | Structure | JAK1 | JAK2 | JAK3 | TYK2 |
|---|---|---|---|---|---|
| 308 | 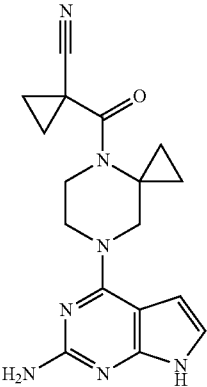 [SMILES: N#CC1(C(=O)N2CCN(c3nc(N)nc4[nH]ccc34)CC23CC3)CC1] | II | I | II | III |
| 309 | 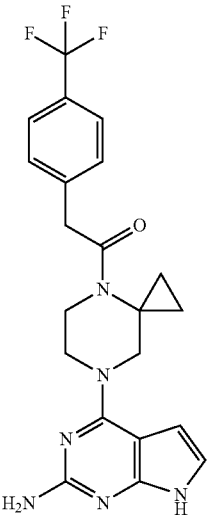 [SMILES: Nc1nc(N2CCN(C(=O)Cc3ccc(C(F)(F)F)cc3)C3(CC3)C2)c2cc[nH]c2n1] | I | I | I | III |
| 310 | 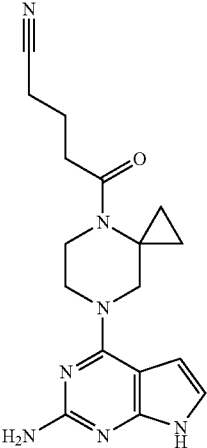 [SMILES: N#CCCCC(=O)N1CCN(c2nc(N)nc3[nH]ccc23)CC12CC2] | I | I | I | III |

TABLE 1-continued
| Example number | Structure | JAK1 | JAK2 | JAK3 | TYK2 |
|---|---|---|---|---|---|
| 311 | 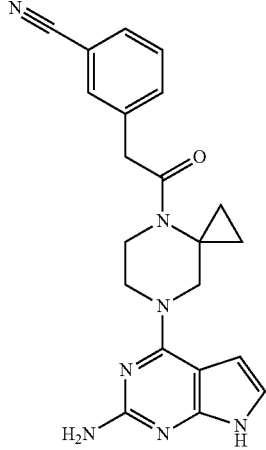 [SMILES: N#Cc1cccc(CC(=O)N2CCN(c3nc(N)nc4[nH]ccc34)CC23CC3)c1] | II | II | II | III |
| 312 | 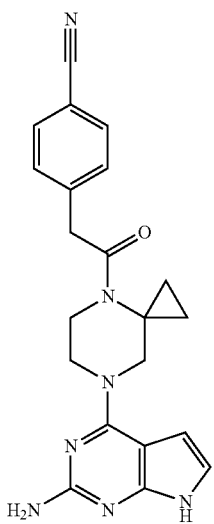 [SMILES: N#Cc1ccc(CC(=O)N2CCN(c3nc(N)nc4[nH]ccc34)CC23CC3)cc1] | I | I | I | II |
| 313 | 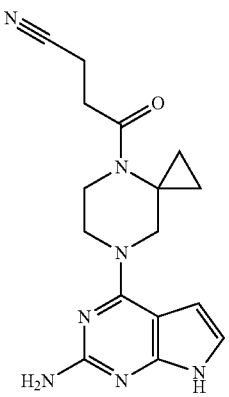 [SMILES: N#CCCC(=O)N1CCN(c2nc(N)nc3[nH]ccc23)CC12CC2] | I | I | I | II |

TABLE 1-continued
| Example number | Structure | JAK1 | JAK2 | JAK3 | TYK2 |
|---|---|---|---|---|---|
| 314 | 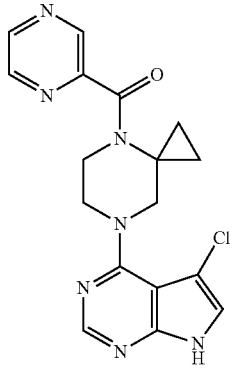 [SMILES: O=C(c1cnccn1)N1CCN(c2ncnc3[nH]cc(Cl)c23)CC12CC2] | III | II | III | III |
| 315 | 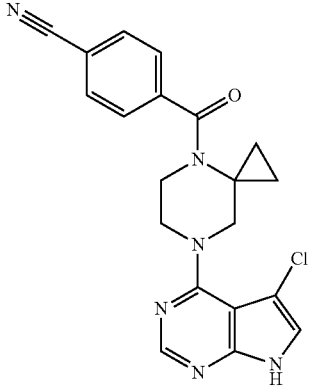 [SMILES: N#Cc1ccc(C(=O)N2CCN(c3ncnc4[nH]cc(Cl)c34)CC23CC3)cc1] | III | III | III | III |
| 316 | 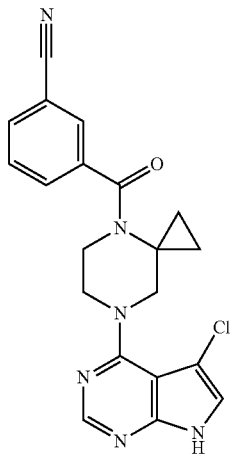 [SMILES: N#Cc1cccc(C(=O)N2CCN(c3ncnc4[nH]cc(Cl)c34)CC23CC3)c1] | III | II | II | III |

TABLE 1-continued

| Example number | Structure | JAK1 | JAK2 | JAK3 | TYK2 |
| --- | --- | --- | --- | --- | --- |
| 317 | 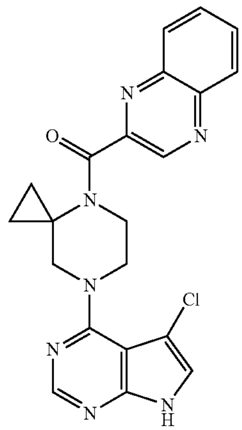 [SMILES: O=C(c1cnc2ccccc2n1)N1CCN(c2ncnc3[nH]cc(Cl)c23)CC12CC2] | III | II | III | III |
| 318 | 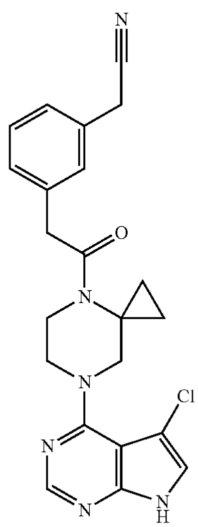 [SMILES: N#CCc1cccc(CC(=O)N2CCN(c3ncnc4[nH]cc(Cl)c34)CC23CC3)c1] | III | III | III | III |
| 319 | 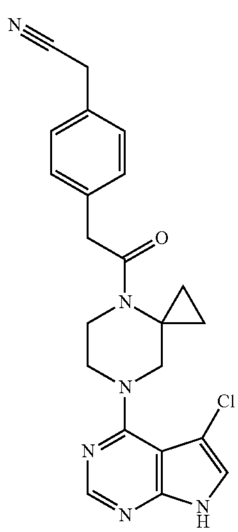 [SMILES: N#CCc1ccc(CC(=O)N2CCN(c3ncnc4[nH]cc(Cl)c34)CC23CC3)cc1] | III | II | II | III |

TABLE 1-continued
| Example number | Structure | JAK1 | JAK2 | JAK3 | TYK2 |
|---|---|---|---|---|---|
| 320 | 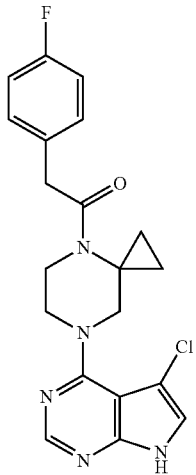 [SMILES: O=C(Cc1ccc(F)cc1)N1CCN(c2ncnc3[nH]cc(Cl)c23)CC12CC2] | II | I | II | III |
| 321 | 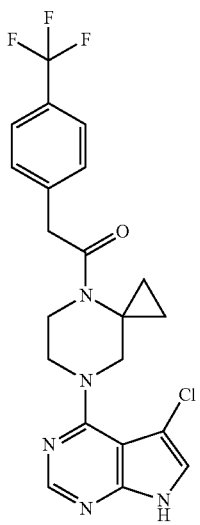 | II | II | I | III |
| 322 | 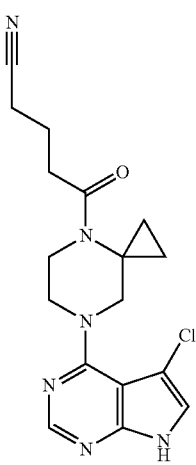 [SMILES: N#CCCCC(=O)N1CCN(c2ncnc3[nH]cc(Cl)c23)CC12CC2] | III | III | II | III |

TABLE 1-continued
| Example number | Structure | JAK1 | JAK2 | JAK3 | TYK2 |
|---|---|---|---|---|---|
| 323 | 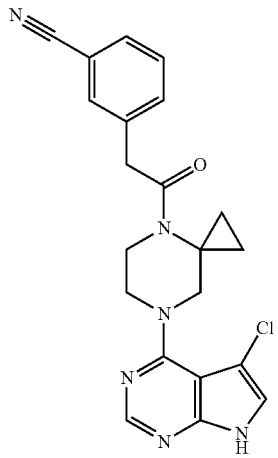 [SMILES: N#Cc1cccc(CC(=O)N2CCN(c3ncnc4[nH]cc(Cl)c34)CC23CC3)c1] | III | I | II | III |
| 324 | 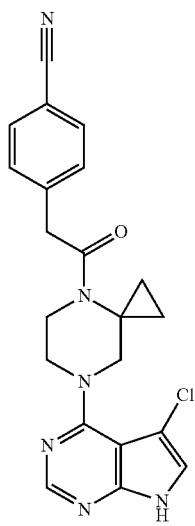 [SMILES: N#Cc1ccc(CC(=O)N2CCN(c3ncnc4[nH]cc(Cl)c34)CC23CC3)cc1] | I | I | I | III |
| 325 | 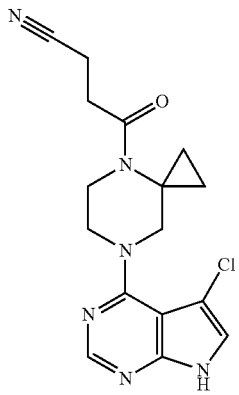 [SMILES: N#CCCC(=O)N1CCN(c2ncnc3[nH]cc(Cl)c23)CC12CC2] | III | II | II | III |

TABLE 1-continued
| Example number | Structure | JAK1 | JAK2 | JAK3 | TYK2 |
|---|---|---|---|---|---|
| 326 | 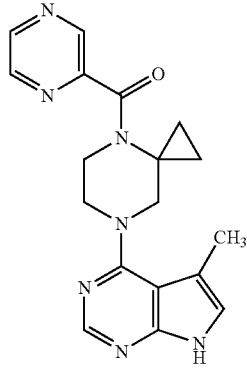 [SMILES: Cc1c[nH]c2ncnc(N3CCN(C(=O)c4cnccn4)C4(CC4)C3)c12] | III | III | III | III |
| 327 | 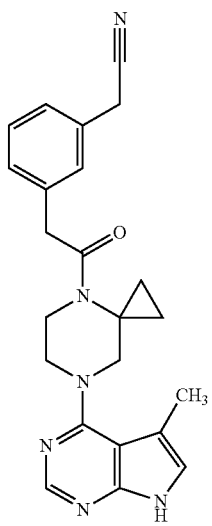 [SMILES: Cc1c[nH]c2ncnc(N3CCN(C(=O)Cc4cccc(CC#N)c4)C4(CC4)C3)c12] | III | III | III | III |
| 328 | 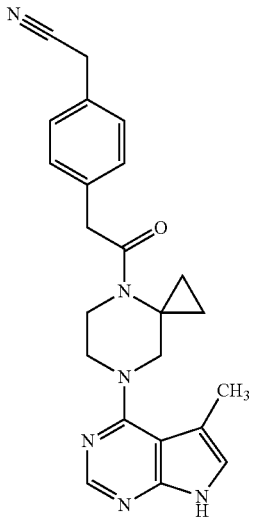 [SMILES: Cc1c[nH]c2ncnc(N3CCN(C(=O)Cc4ccc(CC#N)cc4)C4(CC4)C3)c12] | III | III | II | III |

TABLE 1-continued
| Example number | Structure | JAK1 | JAK2 | JAK3 | TYK2 |
|---|---|---|---|---|---|
| 329 | 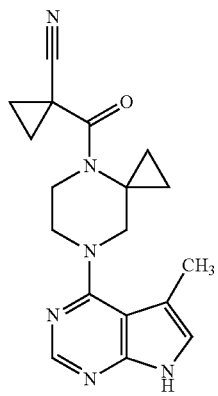 [SMILES: Cc1c[nH]c2ncnc(N3CCN(C(=O)C4(C#N)CC4)C4(CC4)C3)c12] | III | III | III | III |
| 330 | 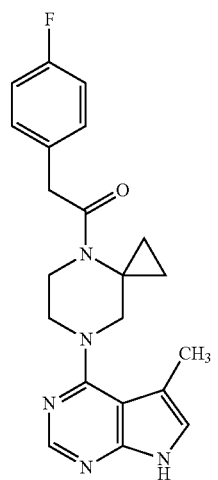 [SMILES: Cc1c[nH]c2ncnc(N3CCN(C(=O)Cc4ccc(F)cc4)C4(CC4)C3)c12] | II | II | II | III |
| 331 | 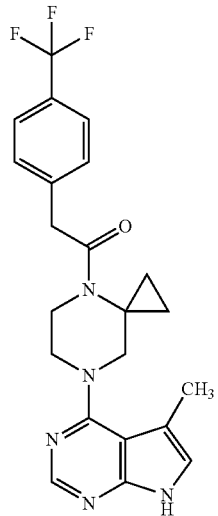 [SMILES: Cc1c[nH]c2ncnc(N3CCN(C(=O)Cc4ccc(C(F)(F)F)cc4)C4(CC4)C3)c12] | II | II | I | III |

TABLE 1-continued
| Example number | Structure | JAK1 | JAK2 | JAK3 | TYK2 |
|---|---|---|---|---|---|
| 332 | 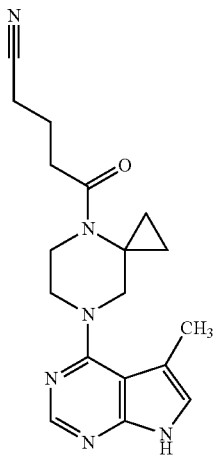 [SMILES: Cc1c[nH]c2ncnc(N3CCN(C(=O)CCCC#N)C4(CC4)C3)c12] | III | III | III | III |
| 333 | 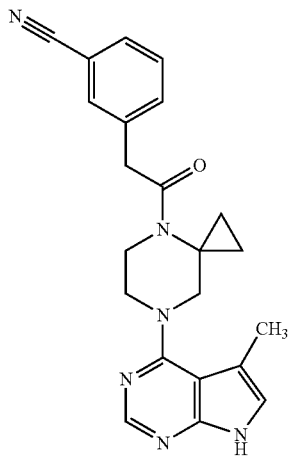 [SMILES: Cc1c[nH]c2ncnc(N3CCN(C(=O)Cc4cccc(C#N)c4)C4(CC4)C3)c12] | III | III | III | III |
| 334 | 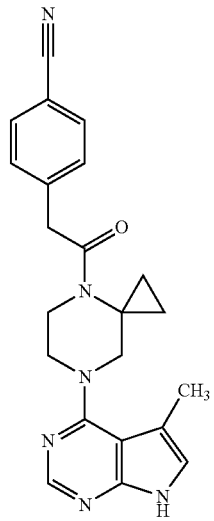 [SMILES: Cc1c[nH]c2ncnc(N3CCN(C(=O)Cc4ccc(C#N)cc4)C4(CC4)C3)c12] | II | I | I | III |

TABLE 1-continued
| Example number | Structure | JAK1 | JAK2 | JAK3 | TYK2 |
|---|---|---|---|---|---|
| 335 | 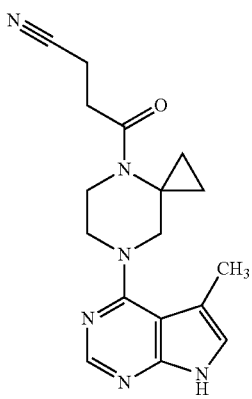 [SMILES: Cc1c[nH]c2ncnc(N3CCN(C(=O)CCC#N)C4(CC4)C3)c12] | III | III | III | III |
| 336 | 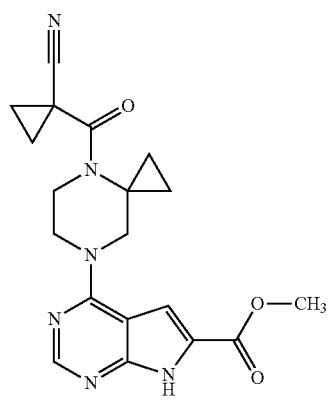 [SMILES: COC(=O)c1cc2c(N3CCN(C(=O)C4(C#N)CC4)C4(CC4)C3)ncnc2[nH]1] | III | III | III | III |
| 337 | 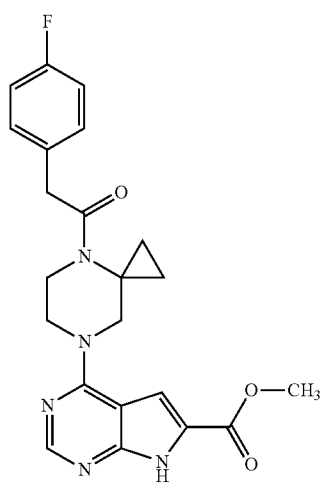 [SMILES: COC(=O)c1cc2c(N3CCN(C(=O)Cc4ccc(F)cc4)C4(CC4)C3)ncnc2[nH]1] | III | III | III | III |

TABLE 1-continued
| Example number | Structure | JAK1 | JAK2 | JAK3 | TYK2 |
|---|---|---|---|---|---|
| 338 | 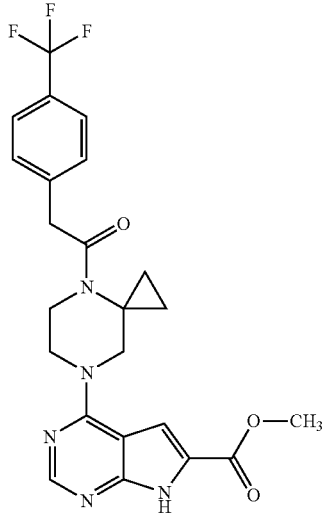 [SMILES: COC(=O)c1cc2c(N3CCN(C(=O)Cc4ccc(C(F)(F)F)cc4)C4(CC4)C3)ncnc2[nH]1] | III | III | III | III |
| 339 | 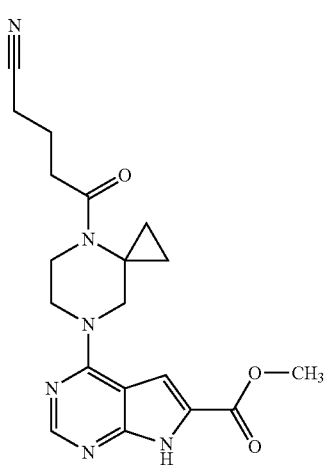 [SMILES: COC(=O)c1cc2c(N3CCN(C(=O)CCCC#N)C4(CC4)C3)ncnc2[nH]1] | III | III | III | III |
| 340 | 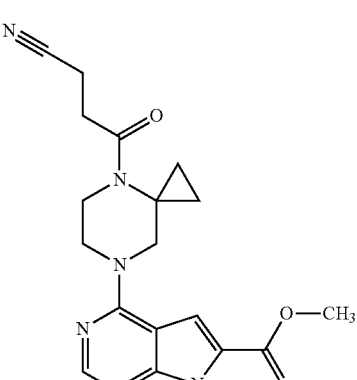 | III | III | III | III |

TABLE 1-continued
| Example number | Structure | JAK1 | JAK2 | JAK3 | TYK2 |
|---|---|---|---|---|---|
| 341 | 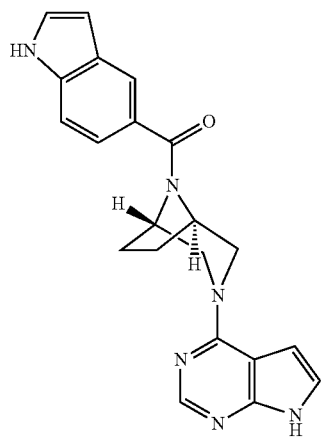 [SMILES: O=C(c1ccc2[nH]ccc2c1)N1[C@@H]2CC[C@H]1CN(c1ncnc3[nH]ccc13)C2] | I | I | I | II |
| 342 | 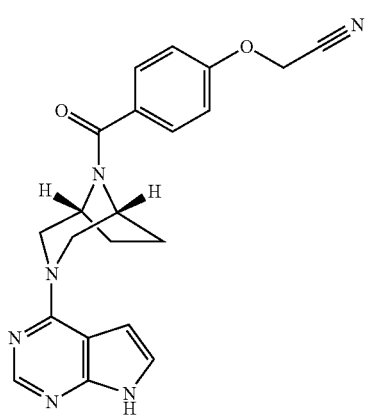 [SMILES: N#CCOc1ccc(C(=O)N2[C@@H]3CC[C@@H]2CN(c2ncnc4[nH]ccc24)C3)cc1] | I | I | II | III |
| 343 | 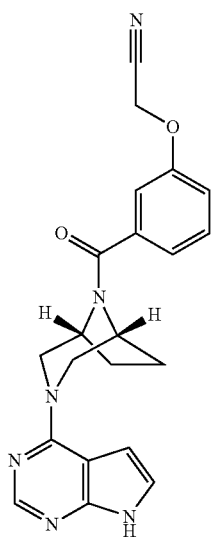 [SMILES: N#CCOc1cccc(C(=O)N2[C@@H]3CC[C@@H]2CN(c2ncnc4[nH]ccc24)C3)c1] | I | I | II | III |

TABLE 1-continued

| Example number | Structure | JAK1 | JAK2 | JAK3 | TYK2 |
|---|---|---|---|---|---|
| 344 | 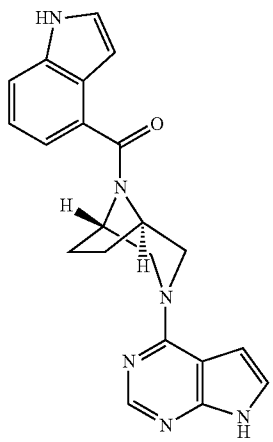 [SMILES: O=C(c1cccc2[nH]ccc12)N1[C@@H]2CC[C@H]1CN(c1ncnc3[nH]ccc13)C2] | II | I | I | II |
| 345 | 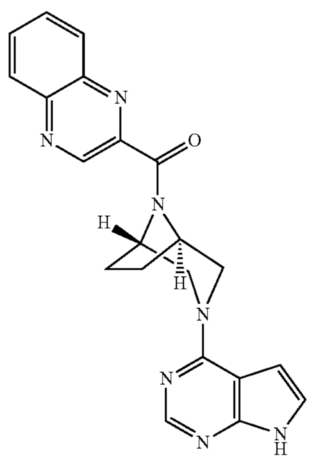 [SMILES: O=C(c1cnc2ccccc2n1)N1[C@@H]2CC[C@H]1CN(c1ncnc3[nH]ccc13)C2] | I | I | II | III |
| 346 | 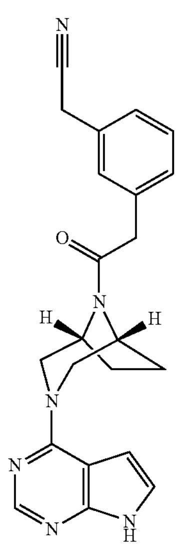 [SMILES: N#CCc1cccc(CC(=O)N2[C@@H]3CC[C@@H]2CN(c2ncnc4[nH]ccc24)C3)c1] | II | II | III | III |

TABLE 1-continued

| Example number | Structure | JAK1 | JAK2 | JAK3 | TYK2 |
|---|---|---|---|---|---|
| 347 | 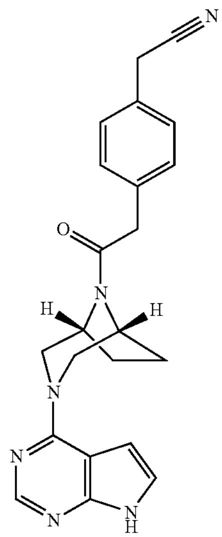 [SMILES: N#CCc1ccc(CC(=O)N2[C@@H]3CC[C@@H]2CN(c2ncnc4[nH]ccc24)C3)cc1] | II | II | III | III |
| 348 | 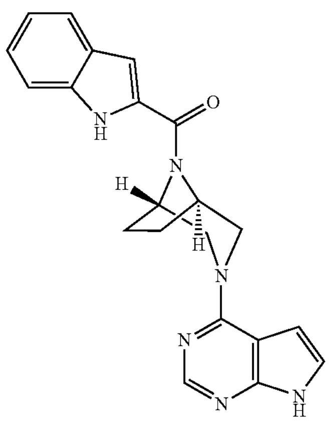 [SMILES: O=C(c1cc2ccccc2[nH]1)N1[C@@H]2CC[C@H]1CN(c1ncnc3[nH]ccc13)C2] | I | I | I | III |
| 349 | 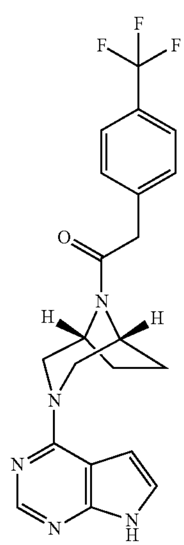 [SMILES: O=C(Cc1ccc(C(F)(F)F)cc1)N1[C@@H]2CC[C@@H]1CN(c1ncnc3[nH]ccc13)C2] | II | II | II | III |

TABLE 1-continued
| Example number | Structure | JAK1 | JAK2 | JAK3 | TYK2 |
|---|---|---|---|---|---|
| 350 | 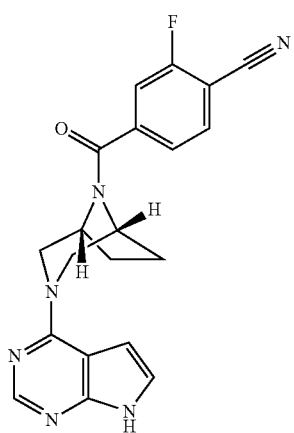 [SMILES: N#Cc1ccc(C(=O)N2[C@@H]3CC[C@@H]2CN(c2ncnc4[nH]ccc24)C3)cc1F] | I | I | I | II |
| 351 | 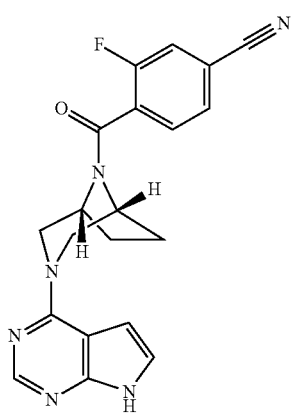 [SMILES: N#Cc1ccc(C(=O)N2[C@@H]3CC[C@@H]2CN(c2ncnc4[nH]ccc24)C3)c(F)c1] | I | I | II | III |
| 352 | 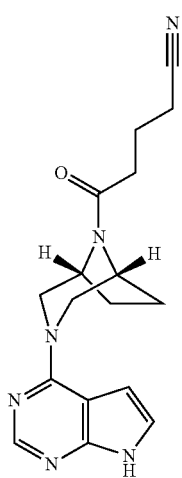 [SMILES: N#CCCCC(=O)N1[C@@H]2CC[C@@H]1CN(c1ncnc3[nH]ccc13)C2] | I | I | II | III |

TABLE 1-continued

| Example number | Structure | JAK1 | JAK2 | JAK3 | TYK2 |
|---|---|---|---|---|---|
| 353 | 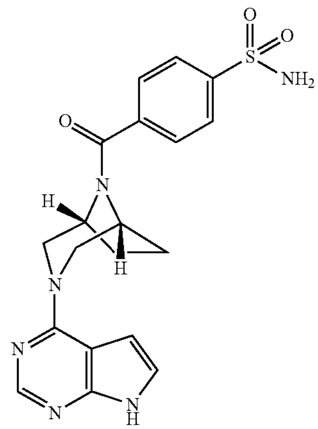 [SMILES: NS(=O)(=O)c1ccc(C(=O)N2[C@@H]3CC[C@@H]2CN(c2ncnc4[nH]ccc24)C3)cc1] | I | I | I | I |
| 354 | 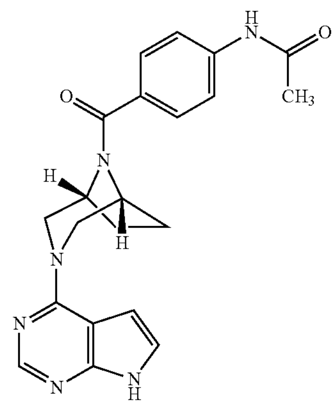 [SMILES: CC(=O)Nc1ccc(C(=O)N2[C@@H]3CC[C@@H]2CN(c2ncnc4[nH]ccc24)C3)cc1] | I | I | II | III |
| 355 | 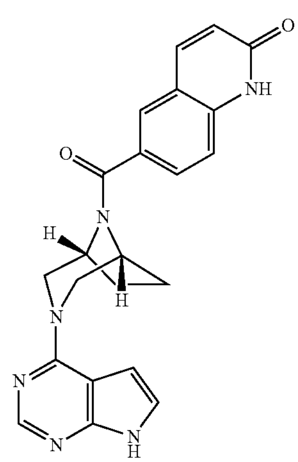 [SMILES: O=C(c1ccc2[nH]c(=O)ccc2c1)N1[C@@H]2CC[C@@H]1CN(c1ncnc3[nH]ccc13)C2] | I | I | II | III |

TABLE 1-continued

| Example number | Structure | JAK1 | JAK2 | JAK3 | TYK2 |
|---|---|---|---|---|---|
| 356 | 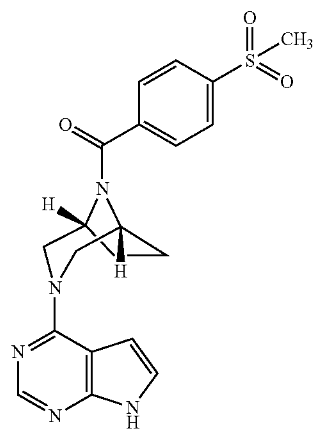 [SMILES: CS(=O)(=O)c1ccc(C(=O)N2[C@@H]3CC[C@@H]2CN(c2ncnc4[nH]ccc24)C3)cc1] | I | I | II | III |
| 357 | 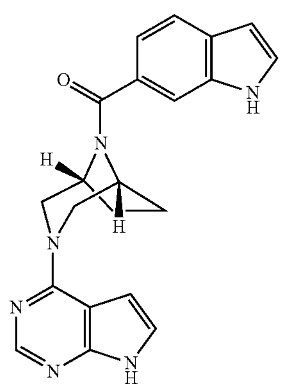 [SMILES: O=C(c1ccc2cc[nH]c2c1)N1[C@@H]2CC[C@@H]1CN(c1ncnc3[nH]ccc13)C2] | I | I | I | II |
| 358 | 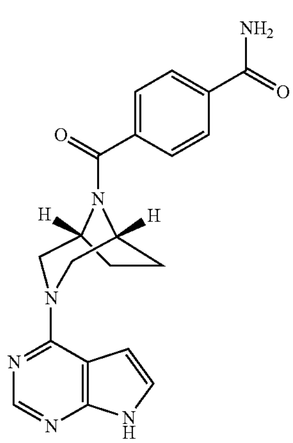 [SMILES: NC(=O)c1ccc(C(=O)N2[C@@H]3CC[C@@H]2CN(c2ncnc4[nH]ccc24)C3)cc1] | I | I | II | II |

TABLE 1-continued
| Example number | Structure | JAK1 | JAK2 | JAK3 | TYK2 |
|---|---|---|---|---|---|
| 359 | 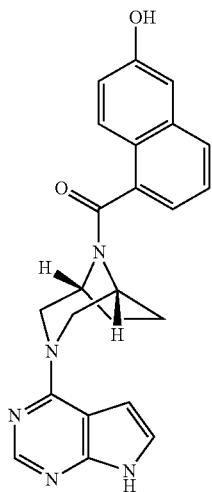 [SMILES: O=C(c1cccc2cc(O)ccc12)N1[C@@H]2CC[C@@H]1CN(c1ncnc3[nH]ccc13)C2] | I | I | I | II |
| 360 | 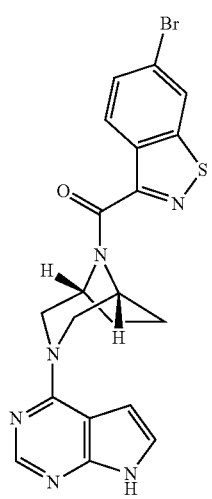 [SMILES: O=C(c1nsc2cc(Br)ccc12)N1[C@@H]2CC[C@@H]1CN(c1ncnc3[nH]ccc13)C2] | II | II | II | III |
| 361 | 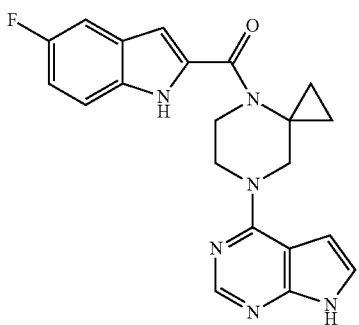 [SMILES: O=C(c1cc2cc(F)ccc2[nH]1)N1CCN(c2ncnc3[nH]ccc23)CC12CC2] | I | I | I | I |

TABLE 1-continued

| Example number | Structure | JAK1 | JAK2 | JAK3 | TYK2 |
|---|---|---|---|---|---|
| 362 | 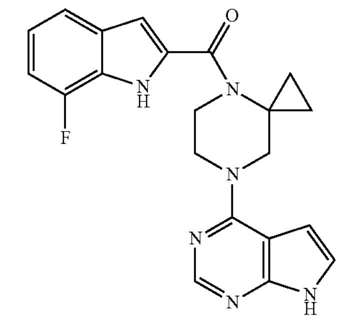 [SMILES: O=C(c1cc2cccc(F)c2[nH]1)N1CCN(c2ncnc3[nH]ccc23)CC12CC2] | I | I | I | II |
| 363 | 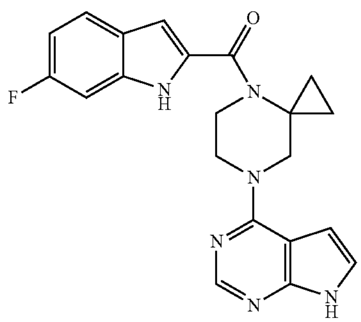 [SMILES: O=C(c1cc2ccc(F)cc2[nH]1)N1CCN(c2ncnc3[nH]ccc23)CC12CC2] | I | I | I | II |
| 364 | 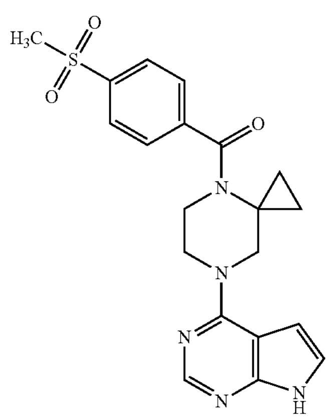 [SMILES: CS(=O)(=O)c1ccc(C(=O)N2CCN(c3ncnc4[nH]ccc34)CC23CC3)cc1] | I | I | II | II |
| 365 | 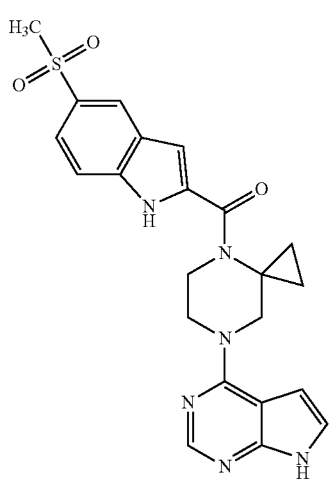 [SMILES: CS(=O)(=O)c1ccc2[nH]c(C(=O)N3CCN(c4ncnc5[nH]ccc45)CC34CC4)cc2c1] | I | I | I | I |

TABLE 1-continued

| Example number | Structure | JAK1 | JAK2 | JAK3 | TYK2 |
|---|---|---|---|---|---|
| 366 | 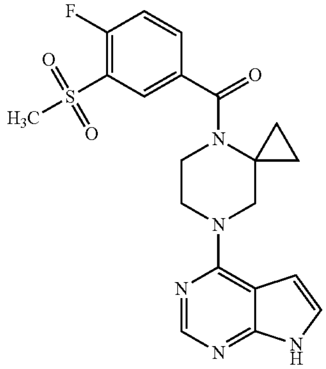 [SMILES: CS(=O)(=O)c1cc(C(=O)N2CCN(c3ncnc4[nH]ccc34)CC23CC3)ccc1F] | I | I | II | III |
| 367 | 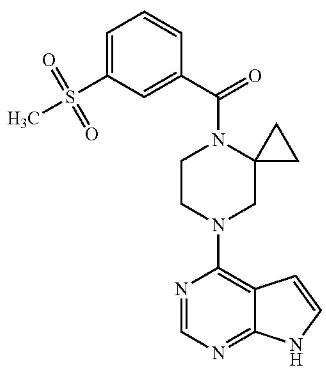 [SMILES: CS(=O)(=O)c1cccc(C(=O)N2CCN(c3ncnc4[nH]ccc34)CC23CC3)c1] | I | I | II | II |
| 368 | 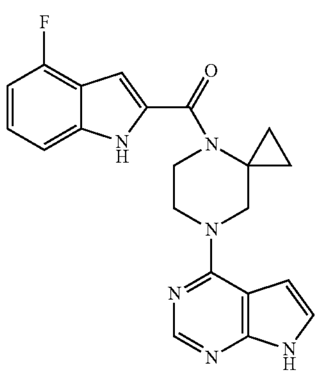 [SMILES: O=C(c1cc2c(F)cccc2[nH]1)N1CCN(c2ncnc3[nH]ccc23)CC12CC2] | I | I | II | II |
| 369 | 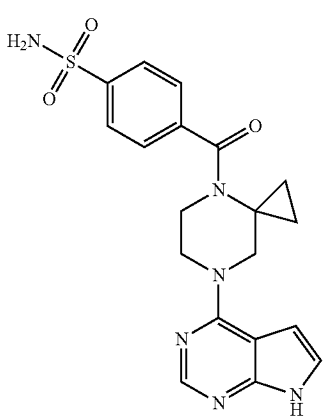 [SMILES: NS(=O)(=O)c1ccc(C(=O)N2CCN(c3ncnc4[nH]ccc34)CC23CC3)cc1] | I | I | I | I |

TABLE 1-continued

| Example number | Structure | JAK1 | JAK2 | JAK3 | TYK2 |
| --- | --- | --- | --- | --- | --- |
| 370 | 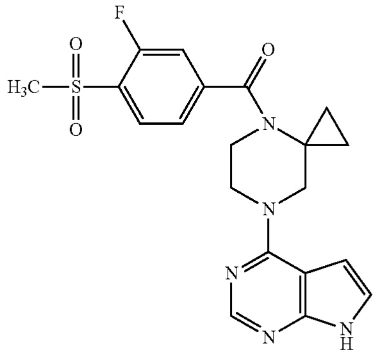 [SMILES: CS(=O)(=O)c1ccc(C(=O)N2CCN(c3ncnc4[nH]ccc34)CC23CC3)cc1F] | I | I | I | II |
| 371 | 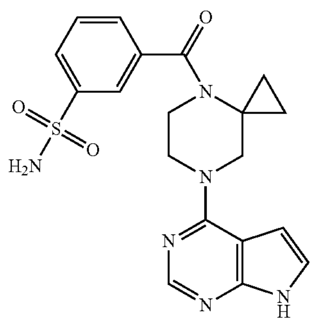 [SMILES: NS(=O)(=O)c1cccc(C(=O)N2CCN(c3ncnc4[nH]ccc34)CC23CC3)c1] | I | I | I | I |
| 372 | 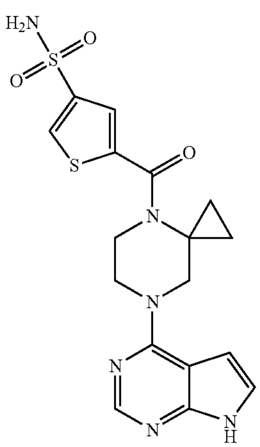 [SMILES: NS(=O)(=O)c1csc(C(=O)N2CCN(c3ncnc4[nH]ccc34)CC23CC3)c1] | I | I | I | I |
| 373 | 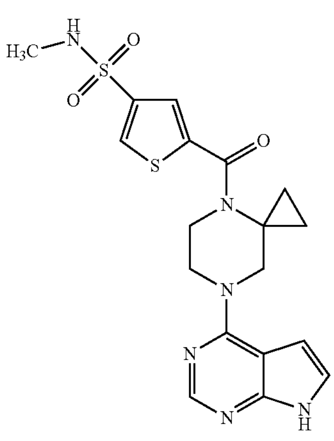 [SMILES: CNS(=O)(=O)c1csc(C(=O)N2CCN(c3ncnc4[nH]ccc34)CC23CC3)c1] | I | I | I | I |

TABLE 1-continued
| Example number | Structure | JAK1 | JAK2 | JAK3 | TYK2 |
|---|---|---|---|---|---|
| 374 | 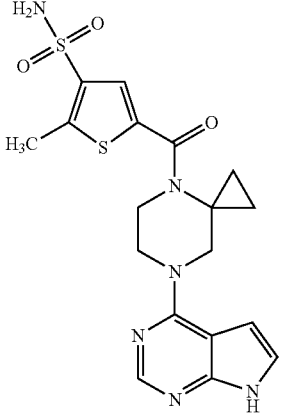 [SMILES: Cc1sc(C(=O)N2CCN(c3ncnc4[nH]ccc34)CC23CC3)cc1S(N)(=O)=O] | I | I | I | I |
| 375 | 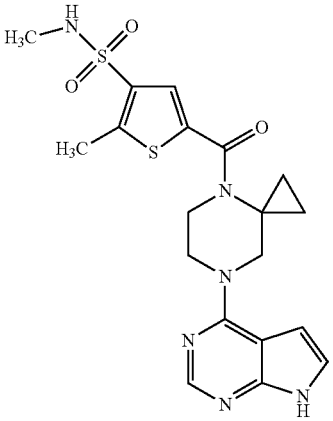 [SMILES: CNS(=O)(=O)c1cc(C(=O)N2CCN(c3ncnc4[nH]ccc34)CC23CC3)sc1C] | I | I | I | II |
| 376 | 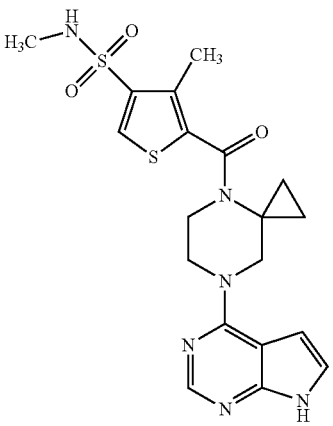 [SMILES: CNS(=O)(=O)c1csc(C(=O)N2CCN(c3ncnc4[nH]ccc34)CC23CC3)c1C] | I | I | I | II |

TABLE 1-continued
| Example number | Structure | JAK1 | JAK2 | JAK3 | TYK2 |
|---|---|---|---|---|---|
| 377 | 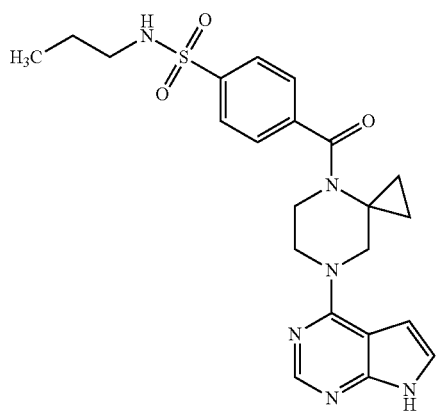 [SMILES: CCCNS(=O)(=O)c1ccc(C(=O)N2CCN(c3ncnc4[nH]ccc34)CC23CC3)cc1] | I | I | I | II |
| 378 | 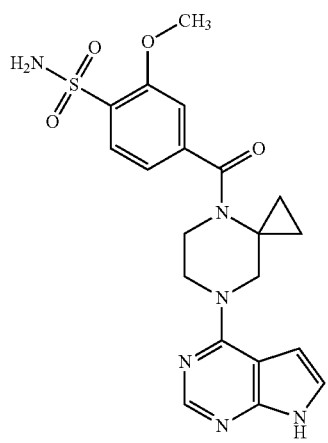 [SMILES: COc1cc(C(=O)N2CCN(c3ncnc4[nH]ccc34)CC23CC3)ccc1S(N)(=O)=O] | I | I | I | I |
| 379 | 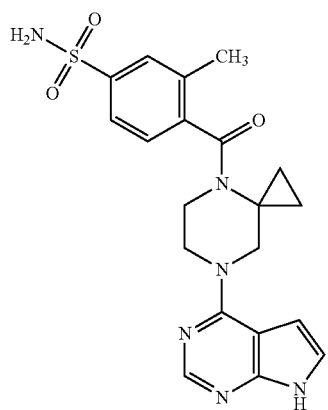 | I | I | I | II |

TABLE 1-continued
| Example number | Structure | JAK1 | JAK2 | JAK3 | TYK2 |
|---|---|---|---|---|---|
| 380 | 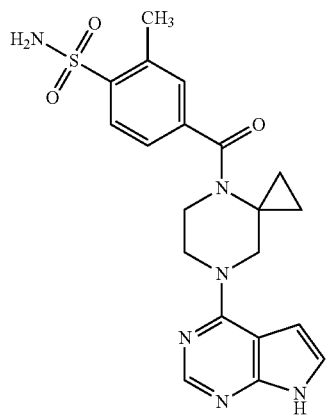 [SMILES: Cc1cc(C(=O)N2CCN(c3ncnc4[nH]ccc34)CC23CC3)ccc1S(N)(=O)=O] | I | I | I | I |
| 381 | 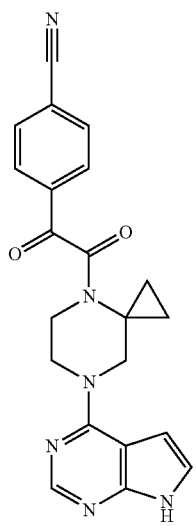 [SMILES: N#Cc1ccc(C(=O)C(=O)N2CCN(c3ncnc4[nH]ccc34)CC23CC3)cc1] | I | I | II | II |
| 382 | 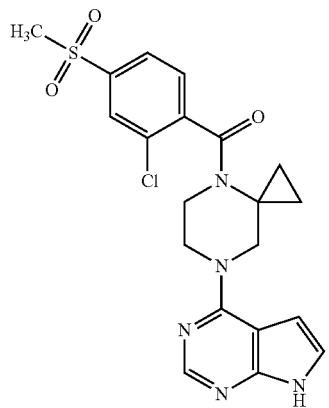 [SMILES: CS(=O)(=O)c1ccc(C(=O)N2CCN(c3ncnc4[nH]ccc34)CC23CC3)c(Cl)c1] | I | I | III | II |

TABLE 1-continued
| Example number | Structure | JAK1 | JAK2 | JAK3 | TYK2 |
|---|---|---|---|---|---|
| 383 | 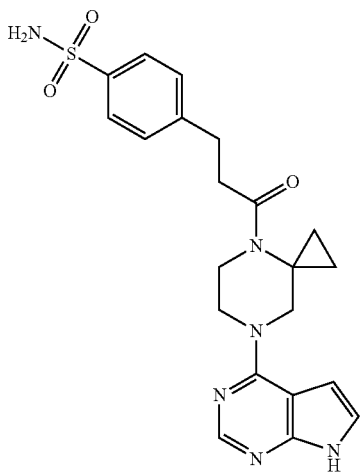 [SMILES: NS(=O)(=O)c1ccc(CCC(=O)N2CCN(c3ncnc4[nH]ccc34)CC23CC3)cc1] | I | I | I | I |
| 384 | 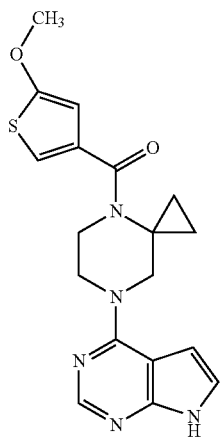 [SMILES: COc1cc(C(=O)N2CCN(c3ncnc4[nH]ccc34)CC23CC3)cs1] | I | I | I | I |
| 385 | 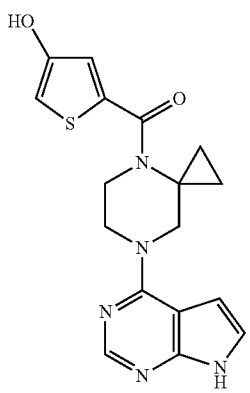 [SMILES: O=C(c1cc(O)cs1)N1CCN(c2ncnc3[nH]ccc23)CC12CC2] | I | I | I | I |

TABLE 1-continued
| Example number | Structure | JAK1 | JAK2 | JAK3 | TYK2 |
|---|---|---|---|---|---|
| 386 | 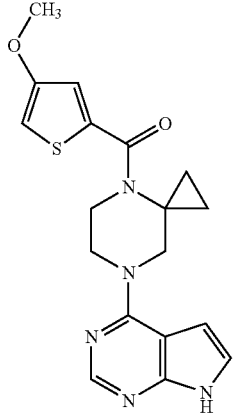 [SMILES: COc1csc(C(=O)N2CCN(c3ncnc4[nH]ccc34)CC23CC3)c1] | I | I | I | I |
| 387 | 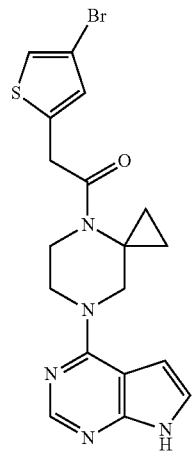 [SMILES: O=C(Cc1cc(Br)cs1)N1CCN(c2ncnc3[nH]ccc23)CC12CC2] | I | I | I | II |
| 388 | 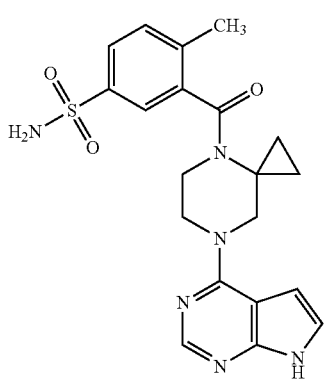 [SMILES: Cc1ccc(S(N)(=O)=O)cc1C(=O)N1CCN(c2ncnc3[nH]ccc23)CC12CC2] | I | I | I | III |

TABLE 1-continued
| Example number | Structure | JAK1 | JAK2 | JAK3 | TYK2 |
|---|---|---|---|---|---|
| 389 | 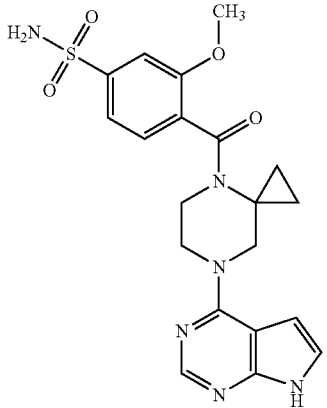 [SMILES: COc1cc(S(N)(=O)=O)ccc1C(=O)N1CCN(c2ncnc3[nH]ccc23)CC12CC2] | I | I | I | II |
| 390 | 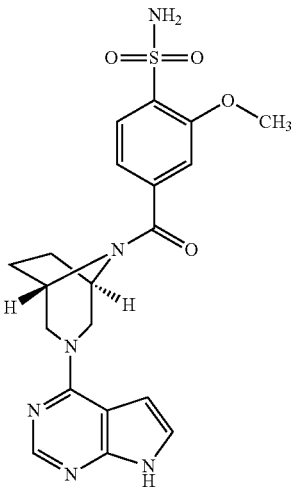 [SMILES: COc1cc(C(=O)N2[C@@H]3CC[C@H]2CN(c2ncnc4[nH]ccc24)C3)ccc1S(N)(=O)=O] | I | I | I | I |
| 391 | 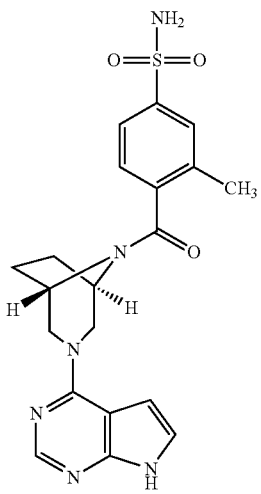 [SMILES: Cc1cc(S(N)(=O)=O)ccc1C(=O)N1[C@@H]2CC[C@H]1CN(c1ncnc3[nH]ccc13)C2] | II | II | II | III |

| Example number | Structure | JAK1 | JAK2 | JAK3 | TYK2 |
|---|---|---|---|---|---|
| 392 | 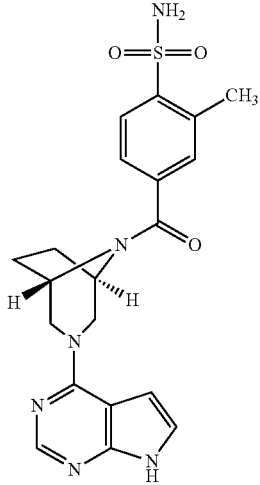 [SMILES: Cc1cc(C(=O)N2[C@@H]3CC[C@H]2CN(c2ncnc4[nH]ccc24)C3)ccc1S(N)(=O)=O] | I | I | I | III |
| 393 | 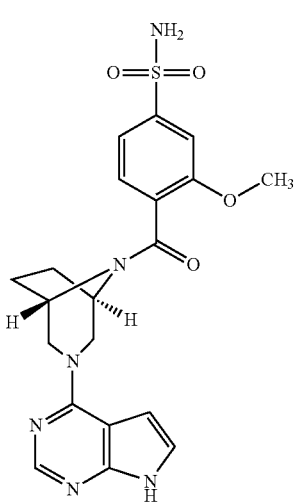 [SMILES: COc1cc(S(N)(=O)=O)ccc1C(=O)N1[C@@H]2CC[C@H]1CN(c1ncnc3[nH]ccc13)C2] | I | I | I | II |
| 394 | 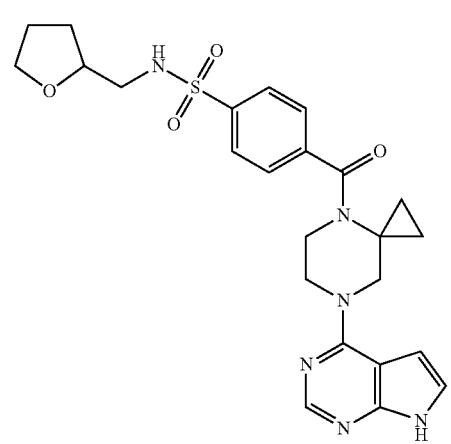 [SMILES: O=C(c1ccc(S(=O)(=O)NCC2CCCO2)cc1)N1CCN(c2ncnc3[nH]ccc23)CC12CC2] | I | I | II | II |

TABLE 1-continued

| Example number | Structure | JAK1 | JAK2 | JAK3 | TYK2 |
|---|---|---|---|---|---|
| 395 | 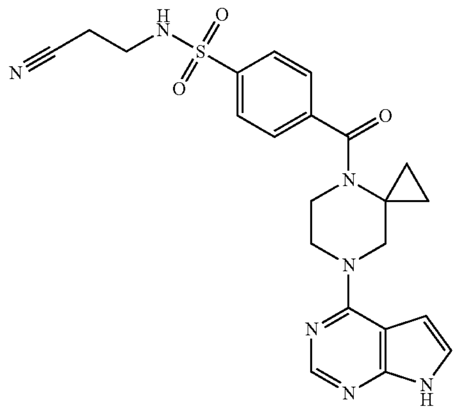 [SMILES: N#CCCNS(=O)(=O)c1ccc(C(=O)N2CCN(c3ncnc4[nH]ccc34)CC23CC3)cc1] | I | I | I | I |
| 396 | 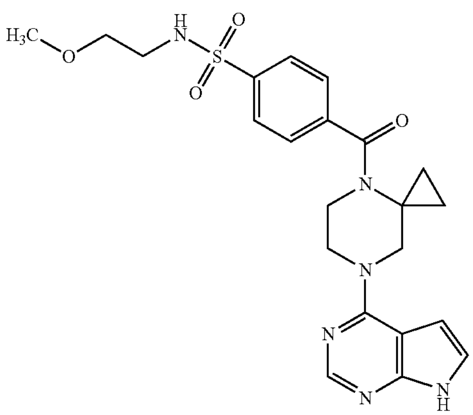 [SMILES: COCCNS(=O)(=O)c1ccc(C(=O)N2CCN(c3ncnc4[nH]ccc34)CC23CC3)cc1] | I | I | I | II |
| 397 | 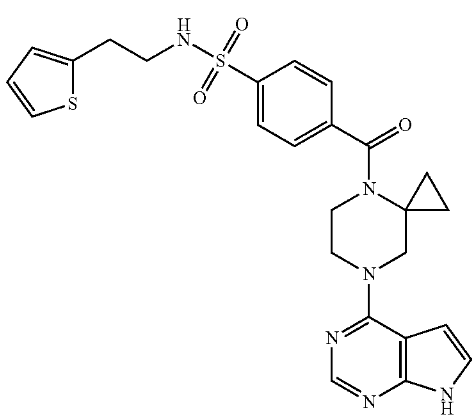 [SMILES: O=C(c1ccc(S(=O)(=O)NCCc2cccs2)cc1)N1CCN(c2ncnc3[nH]ccc23)CC12CC2] | I | I | II | II |

TABLE 1-continued

| Example number | Structure | JAK1 | JAK2 | JAK3 | TYK2 |
|---|---|---|---|---|---|
| 398 | 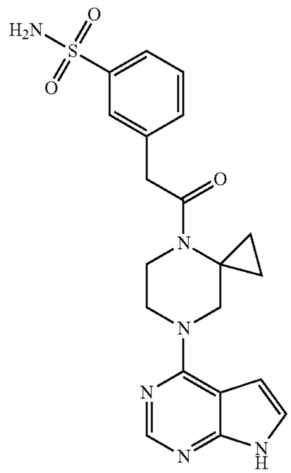 [SMILES: NS(=O)(=O)c1cccc(CC(=O)N2CCN(c3ncnc4[nH]ccc34)CC23CC3)c1] | I | I | I | III |
| 399 | 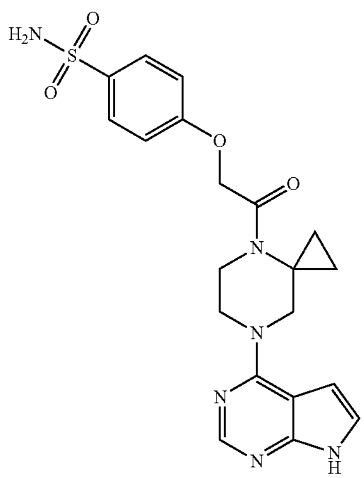 [SMILES: NS(=O)(=O)c1ccc(OCC(=O)N2CCN(c3ncnc4[nH]ccc34)CC23CC3)cc1] | I | I | I | I |
| 400 | 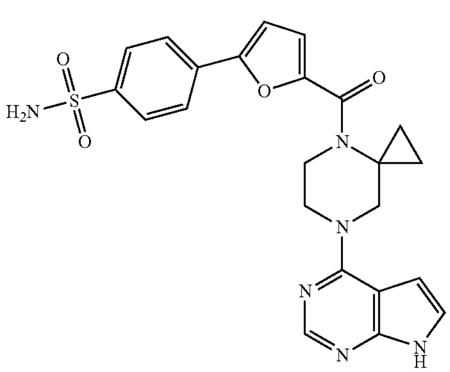 [SMILES: NS(=O)(=O)c1ccc(-c2ccc(C(=O)N3CCN(c4ncnc5[nH]ccc45)CC34CC4)o2)cc1] | I | I | II | II |

TABLE 1-continued
| Example number | Structure | JAK1 | JAK2 | JAK3 | TYK2 |
|---|---|---|---|---|---|
| 401 | 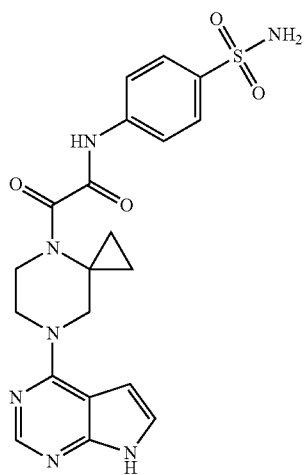 [SMILES: NS(=O)(=O)c1ccc(NC(=O)C(=O)N2CCN(c3ncnc4[nH]ccc34)CC23CC3)cc1] | I | I | I | I |
| 402 | 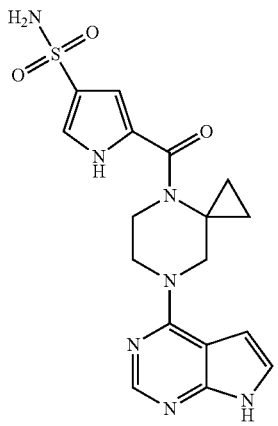 [SMILES: NS(=O)(=O)c1c[nH]c(C(=O)N2CCN(c3ncnc4[nH]ccc34)CC23CC3)c1] | I | I | I | I |
| 403 | 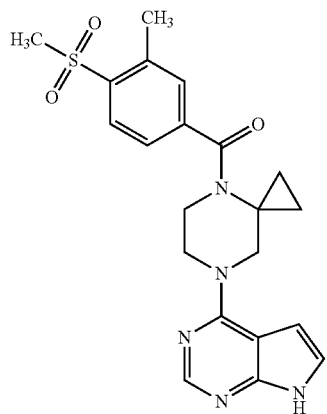 [SMILES: Cc1cc(C(=O)N2CCN(c3ncnc4[nH]ccc34)CC23CC3)ccc1S(C)(=O)=O] | I | I | II | II |

TABLE 1-continued
| Example number | Structure | JAK1 | JAK2 | JAK3 | TYK2 |
|---|---|---|---|---|---|
| 404 | 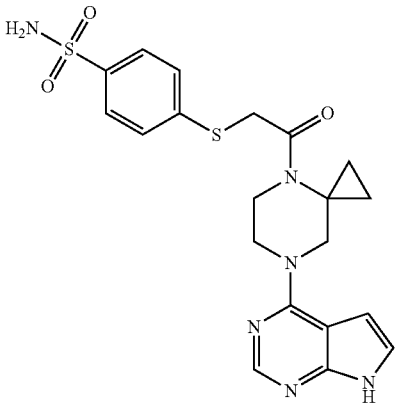 [SMILES: NS(=O)(=O)c1ccc(SCC(=O)N2CCN(c3ncnc4[nH]ccc34)CC23CC3)cc1] | I | I | I | I |
| 405 | 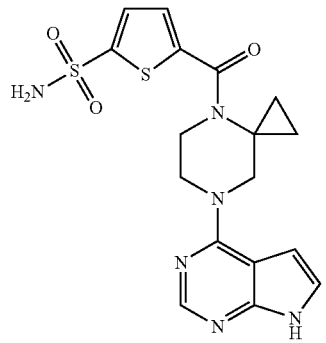 [SMILES: NS(=O)(=O)c1ccc(C(=O)N2CCN(c3ncnc4[nH]ccc34)CC23CC3)s1] | I | I | I | I |
| 406 | 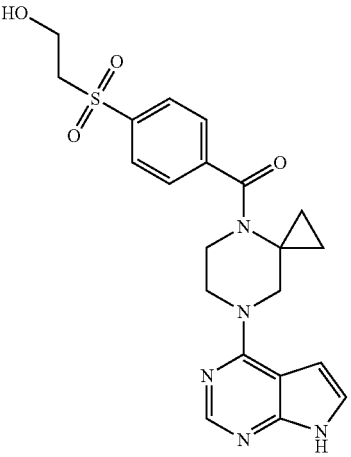 [SMILES: O=C(c1ccc(S(=O)(=O)CCO)cc1)N1CCN(c2ncnc3[nH]ccc23)CC12CC2] | I | I | II | II |

TABLE 1-continued
| Example number | Structure | JAK1 | JAK2 | JAK3 | TYK2 |
|---|---|---|---|---|---|
| 407 | 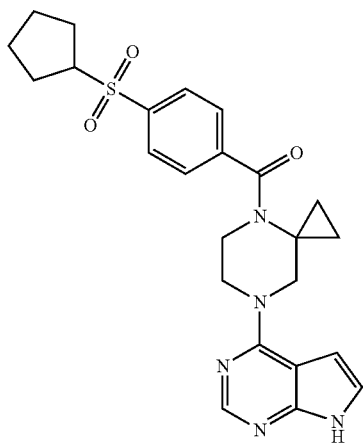 [SMILES: O=C(c1ccc(S(=O)(=O)C2CCCC2)cc1)N1CCN(c2ncnc3[nH]ccc23)CC12CC2] | I | I | III | III |
| 408 | 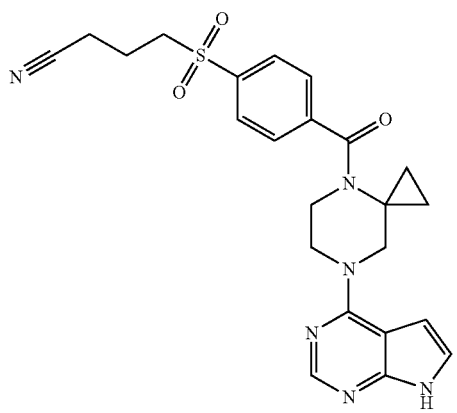 [SMILES: N#CCCCS(=O)(=O)c1ccc(C(=O)N2CCN(c3ncnc4[nH]ccc34)CC23CC3)cc1] | I | I | III | III |
| 409 | 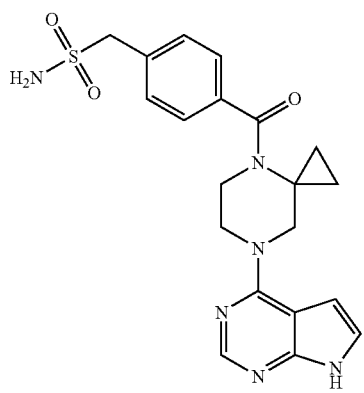 [SMILES: NS(=O)(=O)Cc1ccc(C(=O)N2CCN(c3ncnc4[nH]ccc34)CC23CC3)cc1] | I | I | I | II |

TABLE 1-continued
| Example number | Structure | JAK1 | JAK2 | JAK3 | TYK2 |
|---|---|---|---|---|---|
| 410 | 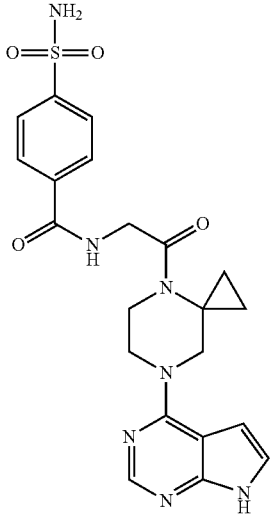 [SMILES: NS(=O)(=O)c1ccc(C(=O)NCC(=O)N2CCN(c3ncnc4[nH]ccc34)CC23CC3)cc1] | I | I | I | I |
| 411 | 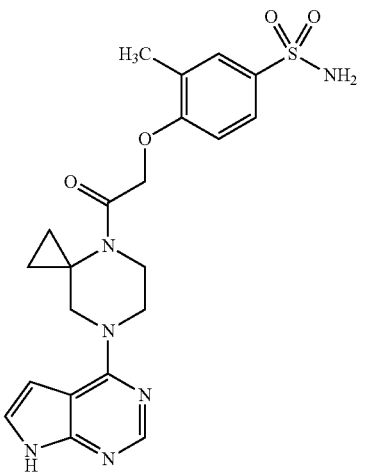 [SMILES: Cc1cc(S(N)(=O)=O)ccc1OCC(=O)N1CCN(c2ncnc3[nH]ccc23)CC12CC2] | I | I | I | I |
| 412 | 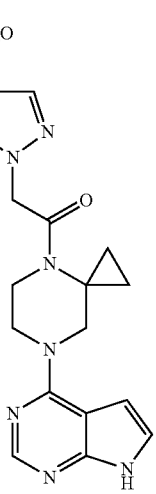 | I | I | I | III |

TABLE 1-continued
| Example number | Structure | JAK1 | JAK2 | JAK3 | TYK2 |
|---|---|---|---|---|---|
| 413 | 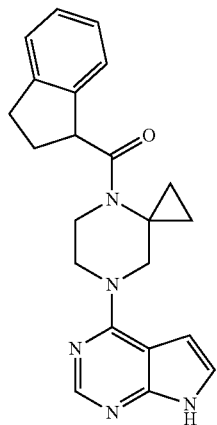 [SMILES: O=C(C1CCc2ccccc21)N1CCN(c2ncnc3[nH]ccc23)CC12CC2] | II | I | II | III |
| 414 | 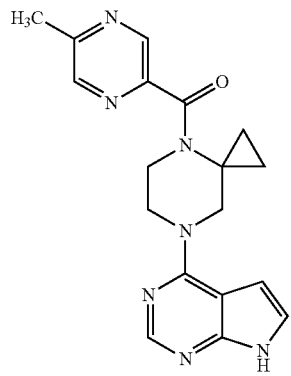 [SMILES: Cc1cnc(C(=O)N2CCN(c3ncnc4[nH]ccc34)CC23CC3)cn1] | I | I | I | II |
| 415 | 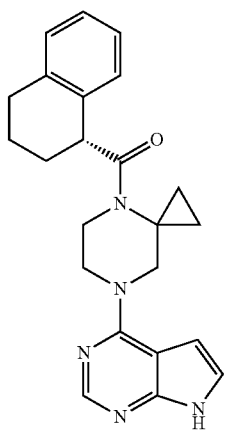 [SMILES: O=C([C@@H]1CCCc2ccccc21)N1CCN(c2ncnc3[nH]ccc23)CC12CC2] | II | II | III | III |

TABLE 1-continued
| Example number | Structure | JAK1 | JAK2 | JAK3 | TYK2 |
|---|---|---|---|---|---|
| 416 | 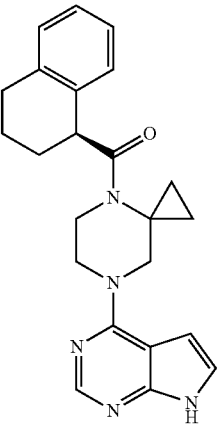 [SMILES: O=C([C@H]1CCCc2ccccc21)N1CCN(c2ncnc3[nH]ccc23)CC12CC2] | II | I | II | III |
| 417 | 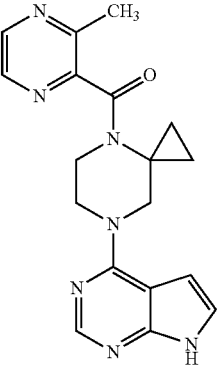 [SMILES: Cc1nccnc1C(=O)N1CCN(c2ncnc3[nH]ccc23)CC12CC2] | I | I | I | I |
| 418 | 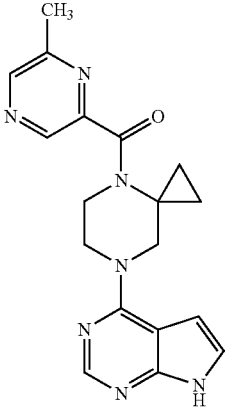 [SMILES: Cc1cncc(C(=O)N2CCN(c3ncnc4[nH]ccc34)CC23CC3)n1] | I | I | I | I |
| 419 | 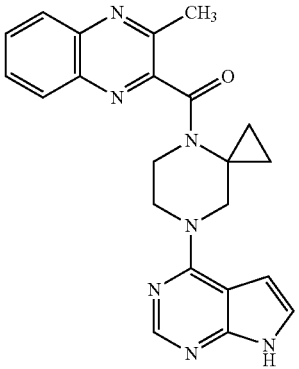 [SMILES: Cc1nc2ccccc2nc1C(=O)N1CCN(c2ncnc3[nH]ccc23)CC12CC2] | I | I | I | I |

TABLE 1-continued
| Example number | Structure | JAK1 | JAK2 | JAK3 | TYK2 |
|---|---|---|---|---|---|
| 420 | 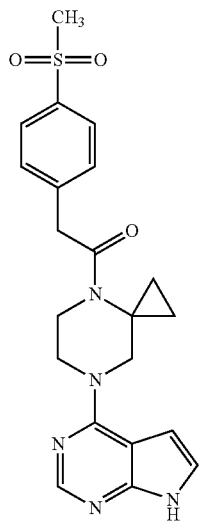 [SMILES: CS(=O)(=O)c1ccc(CC(=O)N2CCN(c3ncnc4[nH]ccc34)CC23CC3)cc1] | I | I | I | III |
| 421 | 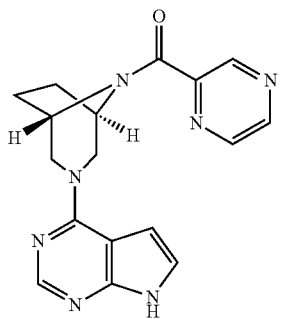 [SMILES: O=C(c1cnccn1)N1[C@@H]2CC[C@H]1CN(c1ncnc3[nH]ccc13)C2] | I | I | II | III |
| 422 | 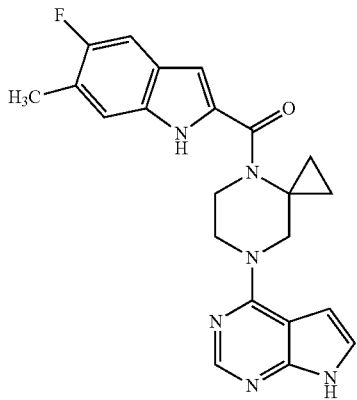 [SMILES: Cc1cc2[nH]c(C(=O)N3CCN(c4ncnc5[nH]ccc45)CC34CC4)cc2cc1F] | I | I | II | II |

TABLE 1-continued
| Example number | Structure | JAK1 | JAK2 | JAK3 | TYK2 |
|---|---|---|---|---|---|
| 423 | 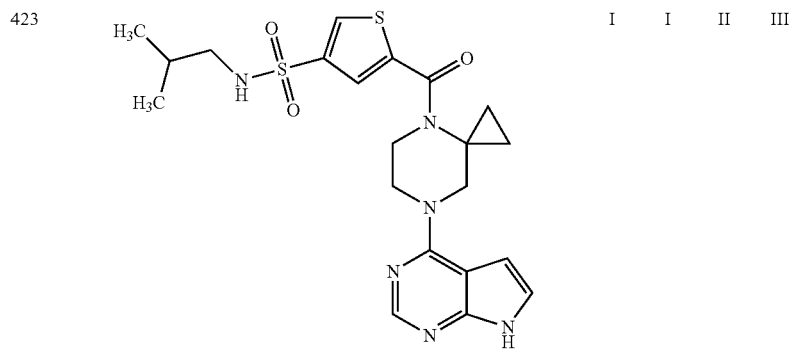 | I | I | II | III |
| 426 | 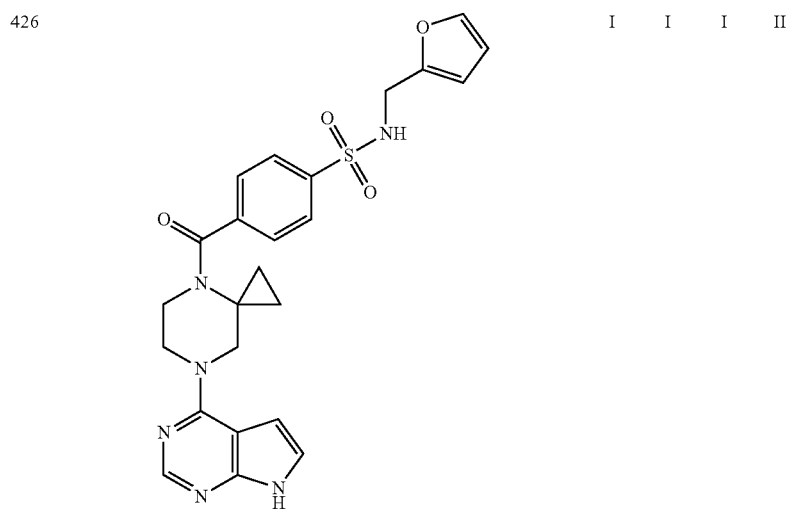 | I | I | I | II |
| 427 | 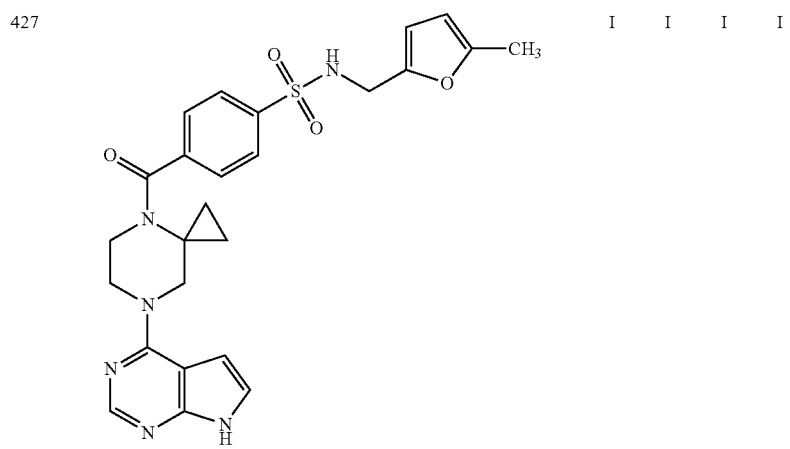 | I | I | I | I |

TABLE 1-continued
| Example number | Structure | JAK1 | JAK2 | JAK3 | TYK2 |
|---|---|---|---|---|---|
| 428 | 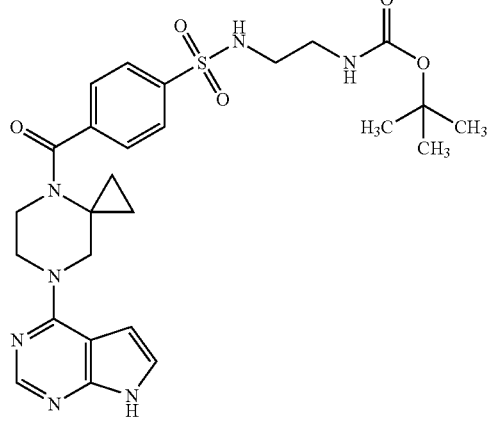 | I | I | I | II |
| 429 | 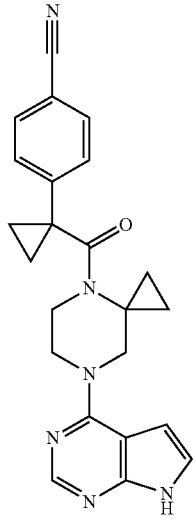 [SMILES: N#Cc1ccc(C2(C(=O)N3CCN(c4ncnc5[nH]ccc45)CC34CC4)CC2)cc1] | I | I | I | II |
| 430 | 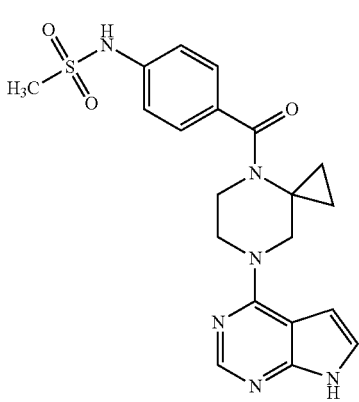 [SMILES: CS(=O)(=O)Nc1ccc(C(=O)N2CCN(c3ncnc4[nH]ccc34)CC23CC3)cc1] | I | I | I | I |

TABLE 1-continued
| Example number | Structure | JAK1 | JAK2 | JAK3 | TYK2 |
|---|---|---|---|---|---|
| 431 | 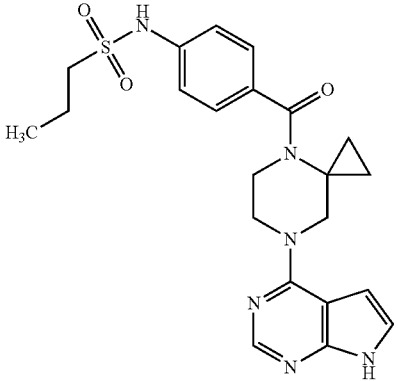 [SMILES: CCCS(=O)(=O)Nc1ccc(C(=O)N2CCN(c3ncnc4[nH]ccc34)CC23CC3)cc1] | I | I | II | II |
| 432 | 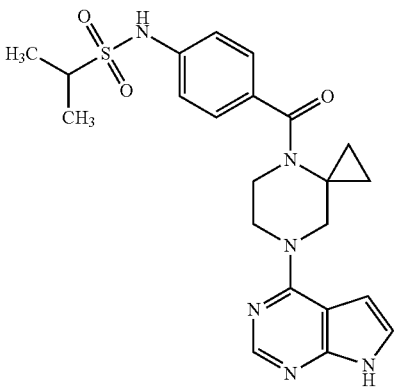 [SMILES: CC(C)S(=O)(=O)Nc1ccc(C(=O)N2CCN(c3ncnc4[nH]ccc34)CC23CC3)cc1] | I | I | I | II |
| 433 | 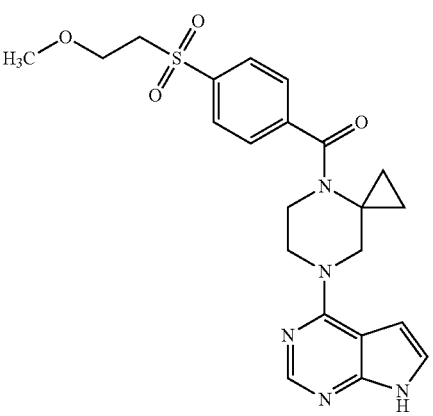 [SMILES: COCCS(=O)(=O)c1ccc(C(=O)N2CCN(c3ncnc4[nH]ccc34)CC23CC3)cc1] | I | I | II | II |
| 434 | 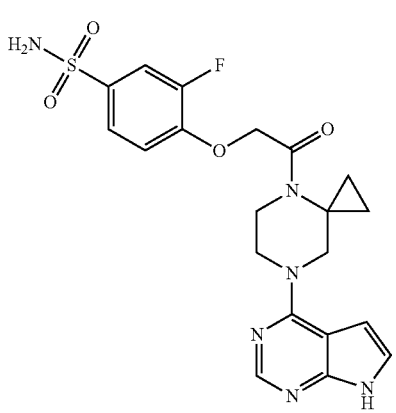 [SMILES: NS(=O)(=O)c1ccc(OCC(=O)N2CCN(c3ncnc4[nH]ccc34)CC23CC3)c(F)c1] | I | I | I | I |

TABLE 1-continued
| Example number | Structure | JAK1 | JAK2 | JAK3 | TYK2 |
|---|---|---|---|---|---|
| 435 | 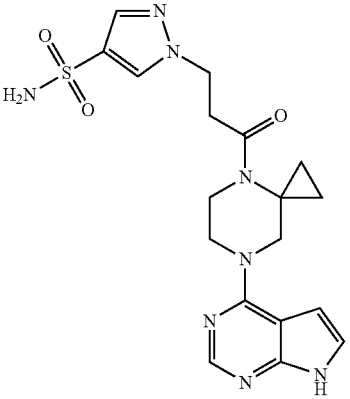 [SMILES: NS(=O)(=O)c1cnn(CCC(=O)N2CCN(c3ncnc4[nH]ccc34)CC23CC3)c1] | I | I | I | II |
| 436 | 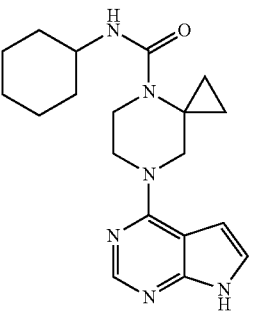 [SMILES: O=C(NC1CCCCC1)N1CCN(c2ncnc3[nH]ccc23)CC12CC2] | I | I | I | II |
| 437 | 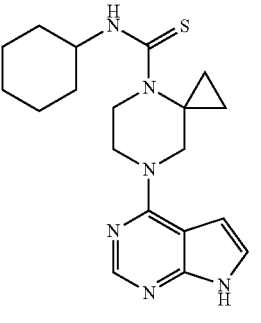 [SMILES: S=C(NC1CCCCC1)N1CCN(c2ncnc3[nH]ccc23)CC12CC2] | III | II | III | III |
| 438 | 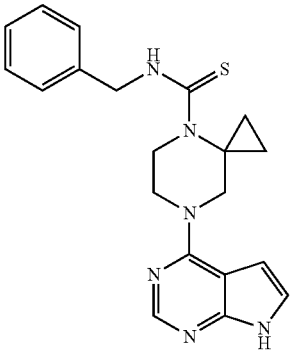 [SMILES: S=C(NCc1ccccc1)N1CCN(c2ncnc3[nH]ccc23)CC12CC2] | I | I | II | II |

TABLE 1-continued
| Example number | Structure | JAK1 | JAK2 | JAK3 | TYK2 |
|---|---|---|---|---|---|
| 439 | 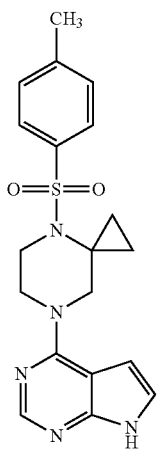 [SMILES: Cc1ccc(S(=O)(=O)N2CCN(c3ncnc4[nH]ccc34)CC23CC3)cc1] | I | I | I | II |
| 440 | 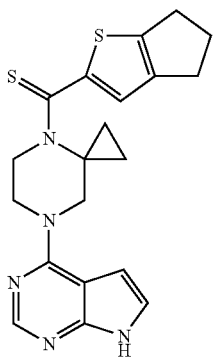 [SMILES: S=C(c1cc2c(s1)CCC2)N1CCN(c2ncnc3[nH]ccc23)CC12CC2] | I | I | II | II |
| 441 | 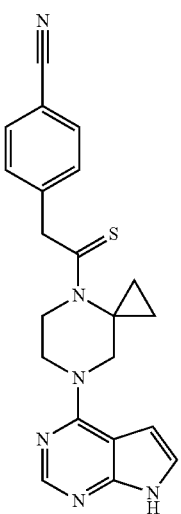 [SMILES: N#Cc1ccc(CC(=S)N2CCN(c3ncnc4[nH]ccc34)CC23CC3)cc1] | I | I | I | I |

TABLE 1-continued
| Example number | Structure | JAK1 | JAK2 | JAK3 | TYK2 |
|---|---|---|---|---|---|
| 442 | 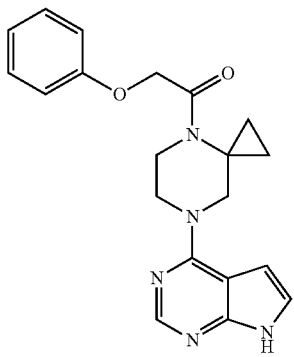 [SMILES: O=C(COc1ccccc1)N1CCN(c2ncnc3[nH]ccc23)CC12CC2] | I | I | I | II |
| 443 | 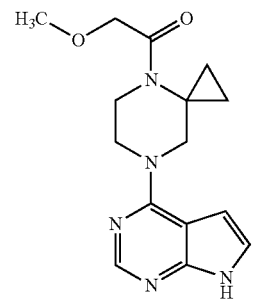 [SMILES: COCC(=O)N1CCN(c2ncnc3[nH]ccc23)CC12CC2] | I | I | III | III |
| 444 | 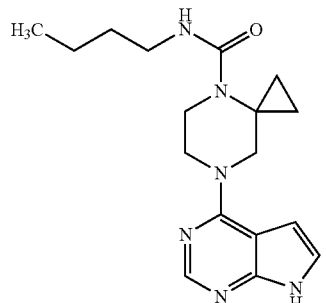 | I | I | II | III |
| 445 | 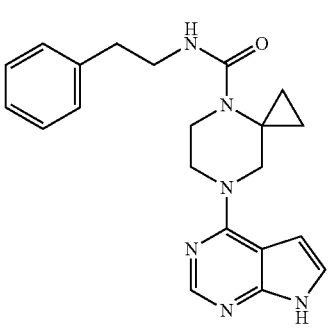 [SMILES: O=C(NCCc1ccccc1)N1CCN(c2ncnc3[nH]ccc23)CC12CC2] | I | I | II | III |
| 446 | 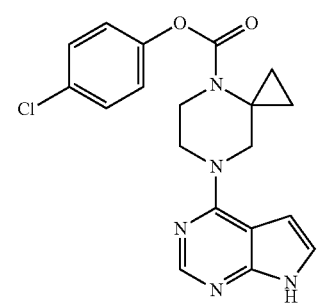 [SMILES: O=C(Oc1ccc(Cl)cc1)N1CCN(c2ncnc3[nH]ccc23)CC12CC2] | I | I | II | III |

TABLE 1-continued

| Example number | Structure | JAK1 | JAK2 | JAK3 | TYK2 |
|---|---|---|---|---|---|
| 447 | 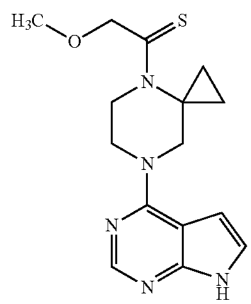 [SMILES: COCC(=S)N1CCN(c2ncnc3[nH]ccc23)CC12CC2] | I | I | II | II |
| 448 | 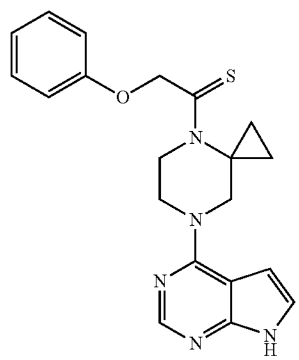 [SMILES: S=C(COc1ccccc1)N1CCN(c2ncnc3[nH]ccc23)CC12CC2] | I | I | I | II |
| 449 | 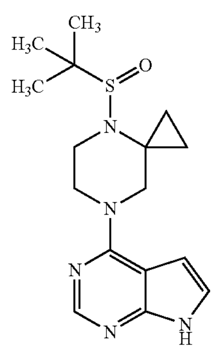 [SMILES: CC(C)(C)S(=O)N1CCN(c2ncnc3[nH]ccc23)CC12CC2] | III | II | III | III |
| 450 | 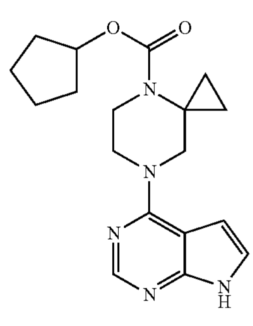 [SMILES: O=C(OC1CCCC1)N1CCN(c2ncnc3[nH]ccc23)CC12CC2] | I | I | I | I |

TABLE 1-continued

| Example number | Structure | JAK1 | JAK2 | JAK3 | TYK2 |
|---|---|---|---|---|---|
| 451 | 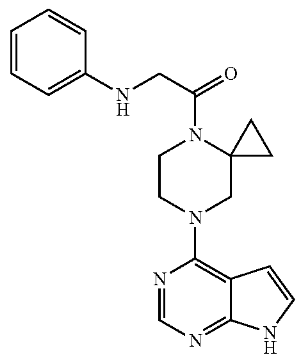 [SMILES: O=C(CNc1ccccc1)N1CCN(c2ncnc3[nH]ccc23)CC12CC2] | I | I | II | III |
| 452 | 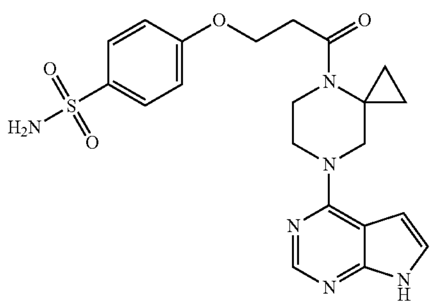 [SMILES: NS(=O)(=O)c1ccc(OCCC(=O)N2CCN(c3ncnc4[nH]ccc34)CC23CC3)cc1] | I | I | I | III |
| 453 | 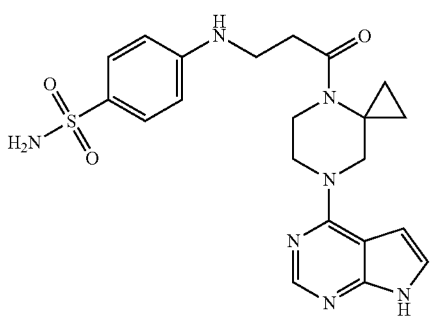 [SMILES: NS(=O)(=O)c1ccc(NCCC(=O)N2CCN(c3ncnc4[nH]ccc34)CC23CC3)cc1] | I | I | II | III |
| 454 | 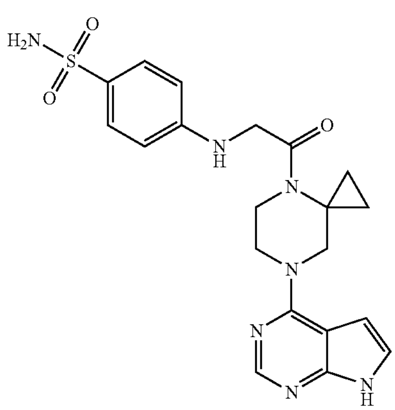 [SMILES: NS(=O)(=O)c1ccc(NCC(=O)N2CCN(c3ncnc4[nH]ccc34)CC23CC3)cc1] | I | I | II | II |

TABLE 1-continued

| Example number | Structure | JAK1 | JAK2 | JAK3 | TYK2 |
|---|---|---|---|---|---|
| 455 | 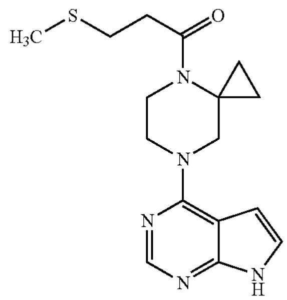 [SMILES: CSCCC(=O)N1CCN(c2ncnc3[nH]ccc23)CC12CC2] | I | I | I | II |
| 456 | 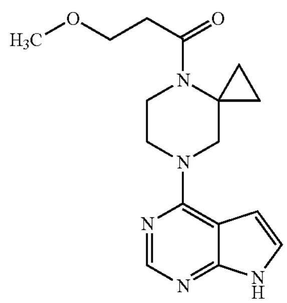 [SMILES: COCCC(=O)N1CCN(c2ncnc3[nH]ccc23)CC12CC2] | II | II | II | III |
| 457 | 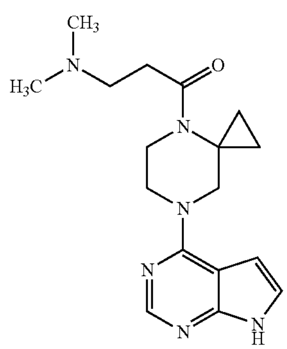 [SMILES: CN(C)CCC(=O)N1CCN(c2ncnc3[nH]ccc23)CC12CC2] | III | III | III | III |
| 458 | 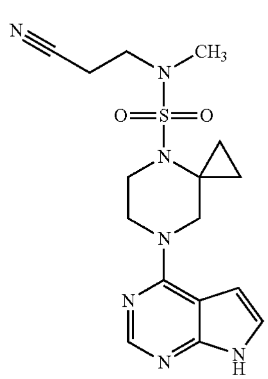 [SMILES: CN(CCC#N)S(=O)(=O)N1CCN(c2ncnc3[nH]ccc23)CC12CC2] | I | I | I | I |

TABLE 1-continued

| Example number | Structure | JAK1 | JAK2 | JAK3 | TYK2 |
|---|---|---|---|---|---|
| 459 | 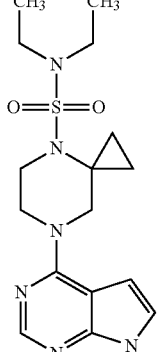 | I | I | II | II |
| 460 | 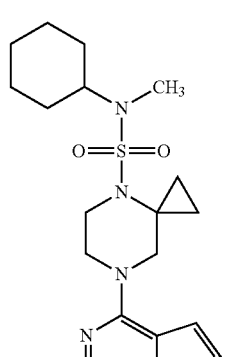 | I | I | II | II |

The invention claimed is:

1. A compound of general formula I

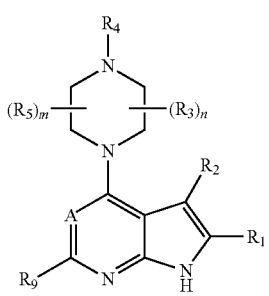

wherein m is 0-3;

n is 2, 4, 6, or 8;

A is N;

$R_2$ is hydrogen;

$R_1$ and $R_9$ independently are selected from the group consisting of hydrogen, halogen, cyano, —$NH_2$, —$SO_2NH_2$, —$SONH_2$, and —$CONH_2$;

or $R_1$ and $R_9$ independently are selected from the group consisting of alkyl-, alkenyl-, alkynyl-, alkenylalkyl-, alkynylalkyl-, cycloalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, $R_{1a}$O-L-, $R_{1a}$S-L, $(R_{1a})_2$N-L-, $R_{1b}$—C(=O)-L-, $R_{1b}$O—C(=O)-L, $(R_{1b})_2$N—C(=O)-L-, $R_{1b}$—C(=O)N($R_{1c}$)-L-, $R_{1b}$O—C(=O)N($R_{1c}$)-L-, $(R_{1b})_2$N—C(=O)N($R_{1c}$)-L-, $R_{1b}$—C(=O)O-L-, $R_{1b}$O—C(=O)O-L-, $(R_{1b})_2$N—C(=O)O-L-, $R_{1b}$—S(=O)-L-, $R_{1b}$—S(=O)$_2$-L-, $R_{1b}$O—S(=O)-L-, $R_{1b}$O—S(=O)$_2$-L-, $(R_{1b})_2$N—S(=O)-L-, $(R_{1b})_2$N—S(=O)$_2$-L-, $R_{1b}$—S(=O)N($R_{1c}$)-L-, $R_{1b}$—S(=O)$_2$N($R_{1c}$)-L-, $R_{1b}$O—S(=O)N($R_{1c}$)-L-, $R_{1b}$O—S(=O)$_2$N($R_{1c}$)-L-, $(R_{1b})_2$N—S(=O)$_2$N($R_{10}$)-L-, $R_{1b}$—S(=O)O-L-, $R_{1b}$—S(=O)$_2$O-L-, $R_{1b}$O—S(=O)O-L-, $R_{1b}$O—S(=O)$_2$O-L-, $(R_{1b})_2$N—S(=O)O-L-, $(R_{1b})_2$N—S(=O)$_2$O-L-, aryl-, arylalkyl-, arylalkenyl-, arylalkynyl-, arylcycloalkyl-, aryloxy-, aryloxyalkyl-, aryloxycycloalkyl-, heteroaryl-, heteroarylalkyl-, heteroarylalkenyl-, heteroarylalkynyl, heteroarylcycloalkyl-, heteroaryloxy-, heteroaryloxyalkyl-, and heteroaryloxycycloalkyl-, either of which may be optionally substituted with one or more $R_{1d}$;

L is a covalent bond or L is independently at each occurrence selected from the group consisting of alkyl-, cycloalkyl-, alkylcycloalkyl- and cycloalkylalkyl-;

$R_{1a}$ is hydrogen;

or $R_{1a}$ independently at each occurrence is selected from the group consisting of alkyl-, alkenyl-, alkynyl-, cycloalkyl, -heterocyclyl-, aryl- and heteroaryl-, either of which may be optionally substituted with one or more $R_{1e}$;

or in the case where two $R_{1a}$s are attached to the same N, they may together with the N atom to which they are attached form a heterocycle which may be optionally substituted with one or more $R_{1e}$;

$R_{1b}$ and $R_{1c}$ independently at each occurrence are selected from the group consisting of alkyl-, alkenyl-, alkynyl-, cycloalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, aryl-, arylalkyl-, arylalkenyl-, arylalkynyl-, arylcycloalkyl-, aryloxyalkyl-, aryloxycycloalkyl-, heteroaryl-, heteroarylalkyl-, heteroarylalkenyl-, heteroarylalkynyl-, heteroarylcycloalkyl, heteroaryloxyalkyl-, and heteroaryloxycycloalkyl-, either of which may be optionally substituted with one or more $R_{1e}$;

or in the case where two $R_{1b}$s or two $R_{1c}$s are attached to the same N, they may together with the N atom to which they are attached form a heterocycle which may be optionally substituted with one or more $R_{1e}$;

$R_{1d}$ and $R_{1e}$ independently at each occurrence are selected from the group consisting of halogen, cyano, hydroxy, oxo, —$NH_2$, —$SO_2NH_2$, —$SONH_2$, —$CONH_2$, alkyl-, alkenyl-, alkynyl-, cycloalkyl-, cycloalkenyl-, heterocyclyl-, $R_{1f}$O-L-, $R_{1f}$S-L-, $(R_{1f})_2$N-L-, $R_{1f}$O—$R_{1f}$O-L-, $R_{1f}$—C(=O)-L-, $R_{1f}$O—C(=O)-L-, $(R_{1f})_2$N—C(=O)-L-, $R_{1f}$—C(=O)N($R_{1f}$)-L-, $R_{1f}$O—C(=O)N($R_{1f}$)-L-, $(R_{1f})_2$N—C(=O)N($R_{1f}$)-L-, $R_{1f}$—C(=O)O-L-, $R_{1f}$O—C(=O)O-L-, $(R_{1f})_2$N—C(=O)O-L-, $R_{1f}$O—S(=O)$_2$-L-, $(R_{1f})_2$N—S(=O)$_2$-L-, $R_{1f}$—S(=O)$_2$N($R_{1f}$)-L-, $R_{1f}$O—S(=O)$_2$N($R_{1f}$)-L-, $(R_{1f})_2$N—S(=O)$_2$N($R_{1f}$)-L-, $R_{1f}$—S(=O)$_2$O-L-, $R_{1f}$O—S(=O)$_2$O-L-, $(R_{1f})_2$N—S(=O)$_2$O-L-, aryl-, aryloxy-, heteroaryl-, and heteroaryloxy-;

$R_{1f}$ independently at each occurrence is selected from the group consisting of alkyl-, alkenyl-, alkynyl-, cycloalkyl-, heterocyclyl-, aryl- and heteroaryl-;

$R_3$ is independently at each occurrence a covalent bond or alkyl- or heteroalkyl-, which may be optionally substituted with one or more $R_{3a}$, wherein any two $R_3$s form, together with the ring atom(s) to which they are attached, a cycloalkyl or heterocycle, with the proviso that said two $R_3$s are either attached to the same C atom or to two non-adjacent C atoms;

$R_{3a}$ independently at each occurrence is selected from the group consisting of halogen, cyano, hydroxy, oxo, —$NH_2$, —$SO_2NH_2$, —$SONH_2$, —$CONH_2$, alkyl-, alkenyl-, alkynyl-, alkenylalkyl-, alkynylalkyl-, cycloalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, $R_{3b}$O-L-, $R_{3b}$S-L-, $(R_{3b})_2$N-L-, $R_{3b}$—C(=O)-L-, $R_{3b}$O—C(=O)-L-, $(R_{3b})_2$N—C(=O)-L-, $R_{3b}$—C(=O)N($R_{3c}$)-L-, $R_{3b}$O—C(=O)N($R_{3c}$)-L-, $(R_{3b})_2$N—C(=O)N($R_{3c}$)-L-, $R_{3b}$—C(=O)O-L-, $R_{3b}$O—C(=O)O-L-, $(R_{3b})_2$N—C(=O)O-L-, $R_{3b}$—S(=O)-L-, $R_{3b}$—S(=O)$_2$-L-, $R_{3b}$O—S(=O)-L-, $R_{3b}$O—S(=O)$_2$-L-, $(R_{3b})_2$N—S(=O)-L-, $(R_{3b})_2$N—S(=O)$_2$-L-, $R_{3b}$—S(=O)N($R_{3c}$)-L-, $R_{3b}$—S(=O)$_2$N($R_{3c}$)-L-, $R_{3b}$O—S(=O)N($R_{3c}$)-L-, $R_{3b}$O—S(=O)$_2$N($R_{3c}$)-L-, $(R_{3b})_2$N—S(=O)$_2$N($R_{3c}$)-L-, $R_{3b}$—S(=O)O-L-, $R_{3b}$—S(=O)$_2$O-L-, $R_{3b}$O—S(=O)O-L-, $R_{3b}$O—S(=O)$_2$O-L-, $(R_{3b})_2$N—S(=O)O-L-, $(R_{3b})_2$N—S(=O)$_2$O-L-, aryl-, arylalkyl-, arylalkenyl-, arylalkynyl-, arylcycloalkyl-, aryloxy-, aryloxyalkyl-, aryloxycycloalkyl-, heteroaryl-, heteroarylalkyl-, heteroarylalkenyl-, heteroarylalkynyl-, heteroarylcycloalkyl, heteroaryloxy-, heteroaryloxyalkyl-, and heteroaryloxycycloalkyl-;

$R_{3b}$ and $R_{3c}$ independently at each occurrence are selected from the group consisting of hydrogen, alkyl-, alkenyl-, alkynyl-, cycloalkyl-, heterocyclyl-, aryl- and heteroaryl-;

$R_5$ independently at each occurrence is selected from the group consisting of halogen, cyano, hydroxy, oxo, —$NH_2$, —$SO_2NH_2$, —$SONH_2$, —$CONH_2$, alkyl-, alkenyl-, alkynyl-, alkenylalkyl-, alkynylalkyl-, cycloalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, $R_{5a}$O-L-, $R_{5a}$S-L-, $(R_{5a})_2$N-L-, $R_{5a}$—C(=O)-L-, $R_{5a}$O—C(=O)-L-, $(R_{5a})_2$N—C(=O)-L-, $R_{5a}$—C(=O)N($R_{5b}$)-L-, $R_{5a}$O—C(=O)N($R_{5b}$)-L-, $(R_{5a})_2$N—C(=O)N($R_{5b}$)-L-, $R_{5a}$—C(=O)O-L-, $R_{5a}$O—C(=O)O-L-, $(R_{5a})_2$N—C(=O)O-L-, $R_{5a}$—S(=O)-L-, $R_{5a}$—S(=O)$_2$-L-, $R_{5a}$O—S(=O)-L-, $R_{5a}$O—S(=O)$_2$-L-, $(R_{5a})_2$N—S(=O)-L-, $(R_{5a})_2$N—S(=O)$_2$-L-, $R_{5a}$—S(=O)N($R_{5b}$)-L-, $R_{5a}$—S(=O)$_2$N($R_{5b}$)-L-, $R_{5a}$O—S(=O)N($R_{5b}$)-L-, $R_{5a}$O—S(=O)$_2$N($R_{5b}$)-L-, $(R_{5a})_2$N—S(=O)$_2$N($R_{5b}$)-L-, $R_{5a}$—S(=O)O-L-, $R_{5a}$—S(=O)$_2$O-L-, $R_{5a}$O—S(=O)O-L-, $R_{5a}$O—S(=O)$_2$O-L-, $(R_{5a})_2$N—S(=O)O-L-, $(R_{5a})_2$N—S(=O)$_2$O-L-, aryl-, arylalkyl-, arylalkenyl-, arylalkynyl-, arylcycloalkyl-, aryloxy-, aryloxyalkyl-, aryloxycycloalkyl-, heteroaryl-, heteroarylalkyl-, heteroarylalkenyl-, heteroarylalkynyl-, heteroarylcycloalkyl, heteroaryloxy-, heteroaryloxyalkyl-, and heteroaryloxycycloalkyl-;

$R_{5a}$ and $R_{5b}$ independently at each occurrence are selected from the group consisting of hydrogen, alkyl-, alkenyl-, alkynyl-, cycloalkyl-, heterocyclyl-, aryl- and heteroaryl-;

$R_4$ is selected from the group consisting of

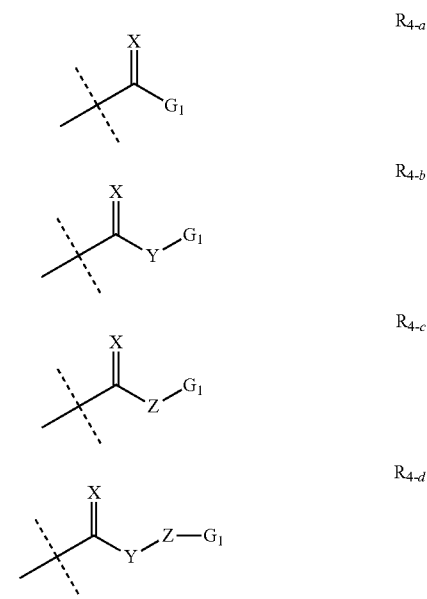

R4-e 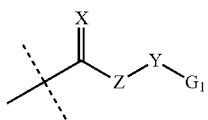

R4-f 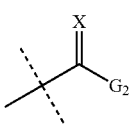

R4-g 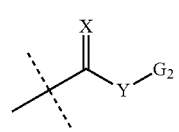

R4-h 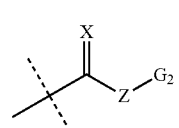

R4-i 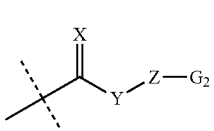

R4-j 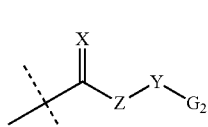

R4-k 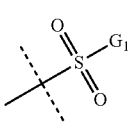

R4-l 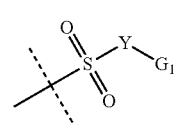

R4-m 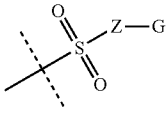

R4-n 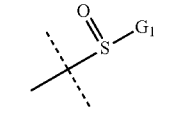

R4-o 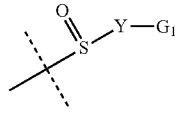

R4-p 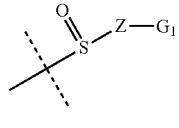

R4-q 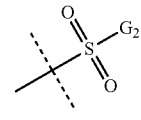

R4-r 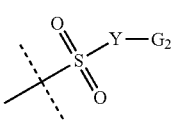

R4-s 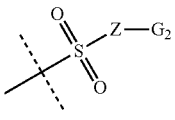

R4-t 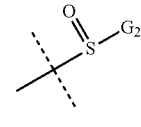

R4-u 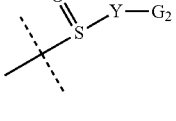

R4-v 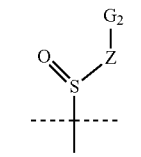

wherein
X is O or S;
Y is O or N—$R_7$;
Z is $C_{1-6}$-alkylene, $C_{2-6}$-alkenylene, or $C_{2-6}$-alkynylene, either of which may be optionally substituted with one or more $R_8$;
$G_1$ is selected from the group consisting of cycloalkyl-, cycloalkenyl-, heterocyclyl-, aryl- and heteroaryl-, either of which may be optionally substituted with one or more $R_G$;
$G_2$ is selected from the group consisting of alkyl-, alkenyl-, alkynyl-, $R_{G2a}$O-L-, $R_{G2a}$S-L-, $(R_{G2a})_2$N-L-, $R_{G2a}$—C(=O)-L-, $R_{G2a}$O—C(=O)-L-, $(R_{G2a})_2$N—C(=O)-L-, $R_{G2a}$—C(=O)N($R_{G2b}$)-L-, $R_{G2a}$O—C(=O)N($R_{G2b}$)-L-, $(R_{G2a})_2$N—C(=O)N($R_{G2b}$)-L-, $R_{G2a}$—C(=O)O-L-, $R_{G2a}$O—C(=O)O-L-, $(R_{G2a})_2$N—C(=O)O-L-, $R_{G2a}$—S(=O)-L-, $R_{G2a}$—S(=O)$_2$-L-, $R_{G2a}$O—S(=O)-L-, $R_{G2a}$O—S(=O)$_2$-L-, $(R_{G2a})_2$N—S(=O)-L-, $(R_{G2a})_2$N—S(=O)$_2$-L-, $R_{G2a}$—S(=O)N($R_{G2b}$)-L-, $R_{G2a}$—S(=O)$_2$N($R_{G2b}$)-L-, $R_{G2a}$O—S(=O)N($R_{G2b}$)-L-, $R_{G2a}$O—S(=O)$_2$N($R_{G2b}$)-L-, $(R_{G2a})_2$N—S(=O)$_2$N($R_{G2b}$)-L-, $R_{G2a}$—S(=O)O-L-, $R_{G2a}$—S(=O)$_2$O-L-, $R_{G2a}$O—S(=O)O-L-, $R_{G2a}$—S(=O)$_2$O-L-, $(R_{G2a})_2$N—S(=O)O-L-, and $(R_{G2a})_2$N—S(=O)$_2$O-L-; either of which may be optionally substituted with one or more $R_G$;
$R_{G2a}$ and $R_{G2b}$ independently at each occurrence are selected from the group consisting of hydrogen, alkyl-, alkenyl-, alkynyl-, cycloalkyl-, heterocyclyl-, aryl- and heteroaryl-;
$R_G$ is selected from the group consisting of halogen, cyano, hydroxy, oxo, —NH$_2$, —SO$_2$NH$_2$, —SONH$_2$, —$CONH_2$, alkyl- and cycloalkyl-, wherein said alkyl- or cycloalkyl- is optionally substituted by one or more substituents selected from the group consisting of halogen, cyano, hydroxy, trifluoromethyl and —$NH_2$; or $R_G$ is selected from the group consisting of alkenyl-, alkynyl-, alkenylalkyl-, alkynylalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, $R_{Ga}$O-L-, $R_{Ga}$S-L-, $(R_{Ga})_2$N-L-, $R_{Ga}$—C(=O)-L-, $R_{Ga}$O—C(=O)-L-, $(R_{Ga})_2$N—C(=O)-L-, $R_{Ga}$—C(=O)N($R_{Gb}$)-L-, $R_{Ga}$O—C(=O)N($R_G$O-L-, $(R_{Ga})_2$N—C(=O)N($R_{Gb}$)-L-, $R_{Ga}$—C(=O)O-L-, $R_{Ga}$O—C(=O)O-L-, $(R_{Ga})_2$N—C(=O)O-L-, $R_{Ga}$—S(=O)-L-, $R_{Ga}$—S(=O)$_2$-L-, $R_{Ga}$O—S(=O)-L-, $R_{Ga}$O—S(=O)$_2$-L-, $(R_{Ga})_2$N—S(=O)-L-, $(R_{Ga})_2$N—S(=O)$_2$-L-, $R_{Gb}$—C(=O)—$(R_{Ga})$N—$(R_{Ga})_2$N—S(=O)$_2$-L, $R_{Gb}$O—C(=O)—$(R_{Ga})$N—$(R_{Ga})_2$N—S(=O)$_2$-L, $R_{Ga}$—S(=O)N($R_{Gb}$)-L-, $R_{Ga}$—S(=O)$_2$N($R_{Gb}$)-L-, $R_{Ga}$O—S(=O)N($R_{Gb}$)-L-, $R_{Ga}$O—S(=O)$_2$N($R_{Gb}$)-L-, $(R_{Ga})_2$N—S(=O)$_2$N($R_{Gb}$)-L-, $R_{Ga}$—S(=O)O-L-, $R_{Ga}$—S(=O)$_2$O-L-, $R_{Ga}$O—S(=O)O-L-, $R_{Ga}$O—S(=O)$_2$O-L-, $(R_{Ga})_2$N—S(=O)O-L-, $(R_{Ga})_2$N—S(=O)$_2$O-L-, aryl-, arylalkyl-, arylalkenyl-, arylalkynyl-, arylcycloalkyl-, aryloxy-, aryloxyalkyl-, aryloxycycloalkyl-, heteroaryl-, heteroarylalkyl-, heteroarylalkenyl-, heteroarylalkynyl-, heteroarylcycloalkyl, heteroaryloxy-, heteroaryloxyalkyl-, and heteroaryloxycycloalkyl-;

$R_{Ga}$ and $R_{Gb}$ independently at each occurrence are selected from the group consisting of hydrogen, alkyl-, alkenyl-, alkynyl-, cycloalkyl-, heterocyclyl-, heterocyclylalkyl, aryl-, heteroaryl- and heteroarylalkyl; wherein said alkyl-, alkenyl-, alkynyl-, cycloalkyl-, heterocyclyl-, heterocyclylalkyl, aryl-, heteroaryl- or heteroarylalkyl group is optionally substituted one or more times by a substituent selected from the group consisting of halogen, cyano, hydroxy, methyl, trifluoromethyl, methoxy and —$NH_2$;

$R_7$ is hydrogen or is independently at each occurrence selected from the group consisting of alkyl-, alkenyl-, alkynyl-, cycloalkyl-, heterocyclyl-, aryl- and heteroaryl-, either of which may be optionally substituted with one or more $R_{7a}$;

$R_{7a}$ independently at each occurrence is selected from the group consisting of halogen, cyano, hydroxy, oxo, —$NH_2$, —$SO_2NH_2$, —$SONH_2$, —$CONH_2$, alkyl-, alkenyl-, alkynyl-, cycloalkyl-, heterocyclyl-, aryl- and heteroaryl-;

$R_8$ independently at each occurrence is selected from the group consisting of hydrogen, halogen, cyano, hydroxy, oxo, —$NH_2$, —$SO_2NH_2$, —$SONH_2$, —$CONH_2$, alkyl- and cycloalkyl, wherein said alkyl- or cycloalkyl- is optionally substituted by one or more substituents selected from the group consisting of halogen, cyano, hydroxy, trifluoromethyl and —$NH_2$;

or two $R_8$s may, together with the C atom(s) to which they are attached, form an optionally substituted cycloalkyl or heterocycle;

and pharmaceutically acceptable salts, hydrates, or solvates thereof.

2. The compound according to claim 1, wherein $R_{Ga}$ and $R_{Gb}$ independently at each occurrence are selected from the group consisting of hydrogen, alkyl-, alkenyl-, alkynyl-, cycloalkyl-, heterocyclyl-, aryl- and heteroaryl-; wherein said alkyl-, alkenyl-, alkynyl-, cycloalkyl-, heterocyclyl-, aryl- or heteroaryl- group is optionally substituted one or more times by a substituent selected from the group consisting of halogen, cyano, hydroxy, trifluoromethyl and —$NH_2$.

3. The compound according to claim 1, wherein m is 0.

4. The compound according to claim 1, wherein n is 2 or 4.

5. The compound according to claim 1, wherein n is 2.

6. The compound according to claim 1, wherein $R_1$ and $R_9$ independently are selected from the group consisting of hydrogen, halogen, cyano, —$SO_2NH_2$, —$SONH_2$, and —$CONH_2$;

or $R_1$ and $R_9$ independently are selected from the group consisting of $C_{1-6}$-alkyl-, $C_{3-6}$-cycloalkyl-, $C_{3-6}$-cycloalkyl-$C_{1-6}$-alkyl-, $C_{2-6}$-heterocyclyl-, $C_{2-6}$-heterocyclyl-$C_{1-6}$-alkyl-, $R_{1a}$O-L-, $(R_{1a})_2$N-L-, $(R_{1b})_2$N—C(=O)-L-, $R_{1b}$—C(=O)N($R_{1c}$)-L-, $R_{1b}$O—C(=O)N($R_1$ $(R_{1b})_2$N—C(=O)N($R_{1c}$)-L-, $(R_{1b})_2$N—C(=O)O-L-, $(R_{1b})_2$N—S(=O)$_2$-L-, $R_{1b}$—S(=O)$_2$N($R_{1c}$)-L-, $R_{1b}$O—S(=O)$_2$N($R_{1c}$)-L-, $(R_{1b})_2$N—S(=O)$_2$N($R_{1c}$)-L-, $(R_{1b})_2$N—S(=O)$_2$O-L-, aryl-, arylalkyl-, arylcycloalkyl-, aryloxy-, aryloxyalkyl-, aryloxycycloalkyl-, heteroaryl-, heteroarylalkyl-, heteroarylcycloalkyl-, heteroaryloxy-, heteroaryloxyalkyl-, and heteroaryloxycycloalkyl-, either of which may be optionally substituted with one or more $R_{1d}$;

wherein $R_{1a}$ is hydrogen or $C_{1-6}$-alkyl-, $C_{3-6}$-cycloalkyl-, $C_{2-6}$-heterocyclyl-, or $C_{6-10}$-aryl;

$R_{1b}$ and $R_{1c}$ independently at each occurrence are selected from the group consisting of $C_{1-6}$-alkyl-, $C_{3-6}$-cycloalkyl-, $C_{3-6}$-cycloalkyl-$C_{1-6}$-alkyl-, $C_{2-6}$-heterocyclyl-, $C_{2-6}$-heterocyclyl-$C_{1-6}$-alkyl-, $C_{6-10}$-aryl-, and $C_{2-8}$-heteroaryl-, either of which may be optionally substituted with one or more $R_{1e}$;

or in the case where two $R_{1b}$s or two $R_{1c}$s are attached to the same N, they may together with the N atom to which they are attached form a heterocycle which may be optionally substituted with one or more $R_{1e}$;

$R_{1d}$ and $R_{1e}$ independently at each occurrence are selected from the group consisting of cyano, hydroxy, oxo, —$SO_2NH_2$, —$CONH_2$, $C_{1-6}$-alkyl-, $C_{3-6}$-cycloalkyl-, $C_{2-6}$-heterocyclyl-, $R_{1f}$O-L-, $R_{1f}$S-L-, $(R_{1f})_2$N-L-, $(R_{1f})_2$N—C(=O)-L-, $R_{1f}$—C(=O)N($R_{1f}$)-L-, $R_{1f}$O—C(=O)N($R_{1f}$)-L-, $(R_{1f})_2$N—C(=O)N($R_{1f}$)-L-, $(R_{1f})_2$N—C(=O)O-L-, $(R_{1f})_2$N—S(=O)$_2$-L-, $R_{1f}$—S(=O)$_2$N($R_{1f}$)-L-, $R_{1f}$O—S(=O)$_2$N($R_{1f}$)-L-, and $(R_{1f})_2$N—S(=O)$_2$N($R_{1f}$)-L-;

and $R_{1f}$ independently at each occurrence is selected from the group consisting of $C_{1-6}$-alkyl-, $C_{3-6}$-cycloalkyl-, and $C_{2-6}$-heterocyclyl-.

7. The compound according to claim 1, wherein $R_1$ and $R_9$ independently are selected from the group consisting of hydrogen, halogen, cyano, —$SO_2NH_2$, —$SONH_2$, and —$CONH_2$;

or $R_1$ and $R_9$ independently are selected from the group consisting of $C_{1-6}$-alkyl-, $C_{3-6}$-cycloalkyl-, $C_{2-6}$-heterocyclyl-, $R_{1a}$O-L-, $(R_{1a})_2$N-L-, $R_{1b}$O—C(=O)-L, $(R_{1b})_2$N—C(=O)-L-, $R_{1b}$—C(=O)N($R_{1c}$)-L-, $R_{1b}$O—C(=O)N($R_{1c}$)-L-, $(R_{1b})_2$N—C(=O)N($R_{1c}$)-L-, $(R_{1b})_2$N—C(=O)O-L-, $(R_{1b})_2$N—S(=O)$_2$-L-, $R_{1b}$—S(=O)$_2$ N($R_{1c}$)-L-, $R_{1b}$O—S(=O)$_2$N($R_{1c}$)-L-, $(R_{1b})_2$N—S(=O)$_2$N($R_{1c}$)-L-, and $(R_{1b})_2$N—S(=O)$_2$O-L- either of which may be optionally substituted with one or more $R_{1d}$; wherein $R_{1a}$ is hydrogen or $C_{1-6}$-alkyl-, $C_{3-6}$-cycloalkyl-, $C_{2-6}$-heterocyclyl-, or $C_{6-10}$-aryl;

$R_{1b}$ and $R_{1c}$ independently at each occurrence are selected from the group consisting of $C_{1-6}$-alkyl-, $C_{3-6}$-cycloalkyl-, $C_{3-6}$-cycloalkyl-$C_{1-6}$-alkyl-, $C_{2-6}$-heterocyclyl-, $C_{2-6}$-heterocyclyl-$C_{1-6}$-alkyl-, $C_{6-10}$-aryl-, and $C_{2-8}$-heteroaryl-, which may be optionally substituted with one or more $R_{1e}$;

or in the case where two $R_{1b}$s are attached to the same N, they may together with the N atom to which they are attached form a heterocycle which may be optionally substituted with one or more $R_{1e}$;

$R_{1d}$ and $R_{1e}$ independently at each occurrence are selected from the group consisting of cyano, hydroxy, oxo, —$SO_2NH_2$, —$CONH_2$, $C_{1-6}$-alkyl-, $C_{3-6}$-cycloalkyl-, $C_{2-6}$-heterocyclyl-, $R_{1f}$O-L-, $R_{1f}$S-L-, $(R_{1f})_2$N-L-, $(R_{1f})_2$N—C(=O)-L-, $R_{1f}$—C(=O)N($R_{1f}$)-L-, $R_{1f}$O—C(=O)N($R_{1f}$)-L-, $(R_{1f})_2$N—C(=O)N($R_{1f}$)-L-, $(R_{1f})_2$N—C(=O)O-L-, $(R_{1f})_2$N—S(=O)$_2$-L-, $R_{1f}$—S(=O)$_2$N($R_{1f}$)-L-, $R_{1f}$O—S(=O)$_2$N($R_{1f}$)-L-, and $(R_{1f})_2$N—S(=O)$_2$N($R_{1f}$)-L-;

and $R_{1f}$ independently at each occurrence is selected from the group consisting of $C_{1-6}$-alkyl-, $C_{3-6}$-cycloalkyl-, and $C_{2-6}$-heterocyclyl-.

8. The compound according to claim 1, wherein $R_1$ is hydrogen or $R_{1b}$O—C(=O)-L, wherein $R_{1b}$ is $C_{1-6}$-alkyl-.

9. The compound according to claim 1, wherein $R_1$ is hydrogen.

10. The compound according to claim 1, wherein $R_9$ is selected from the group consisting of hydrogen, $(R_{1a})_2$N-L-, $(R_{1b})_2$N—C(=O)-L-, and $R_{1b}$—C(=O)N($R_{1c}$)-L-, wherein $R_{1a}$ is hydrogen, and $R_{1b}$ and $R_{1c}$ are selected from the group consisting of $C_{1-6}$-alkyl-, $C_{6-10}$-aryl-, and $C_{2-8}$-heteroaryl-.

11. The compound according to claim 1, wherein $R_9$ is hydrogen.

12. The compound according to claim 1, wherein $R_3$ is a covalent bond or $C_{1-3}$-alkyl or $C_{1-3}$-heteroalkyl, and any two $R_3$s form, together with the ring atom(s) to which they are attached, a cycloalkyl or heterocycle, with the proviso that said two $R_3$s are either attached to the same carbon atom or to two non-adjacent carbon atoms, $R_3$ being optionally substituted by one or more $R_{3a}$, wherein $R_{3a}$ independently at each occurrence is selected from the group consisting of cyano, hydroxy, oxo, —$NH_2$, —$SO_2NH_2$, —$CONH_2$, alkyl-, cycloalkyl-, heterocyclyl-, $R_{3b}$O-L-, $R_{3b}$S-L-, $(R_{3b})_2$N-L-, $R_{3b}$—C(=O)-L-, $R_{3b}$O—C(=O)-L-, $(R_{3b})_2$N—C(=O)-L-, $R_{3b}$—C(=O)N($R_{3c}$)-L-, $R_{3b}$O—C(=O)N($R_{3c}$)-L-, $(R_{3b})_2$N—C(=O)N($R_{3c}$)-L-, $(R_{3b})_2$N—C(=O)O-L-, $R_{3b}$—S(=O)$_2$-L-, $R_{3b}$O—S(=O)$_2$-L-, $(R_{3b})_2$N—S(=O)$_2$-L-, $R_{3b}$—S(=O)$_2$N($R_{3c}$)-L-, $R_{3b}$O—S(=O)$_2$N($R_{3c}$)-L-, $(R_{3b})_2$N—S(=O)$_2$N($R_{3c}$)-L-, $R_{3b}$—S(=O)$_2$O-L-, $R_{3b}$O—S(=O)$_2$O-L-, and $(R_{3b})_2$N—S(=O)$_2$O-L-;

wherein $R_{3b}$ independently at each occurrence is selected from the group consisting of $C_{1-6}$-alkyl-, $C_{3-6}$-cycloalkyl-, and $C_{2-6}$-heterocyclyl-.

13. The compound according to claim 12, wherein the n $R_3$ together with the piperazine ring and the ring atom(s) to which they are attached, form a structure selected from the group consisting of:

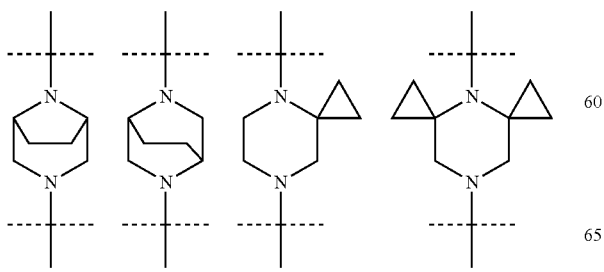

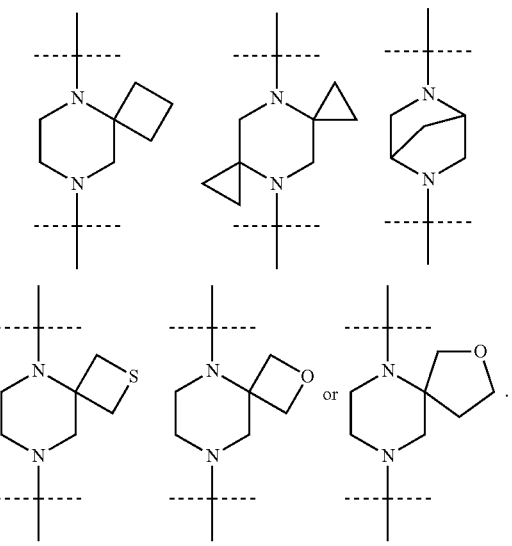

14. The compound according to claim 13, wherein the n $R_3$ together with the piperazine ring and the ring atom(s) to which they are attached, form a structure selected from the group consisting of:

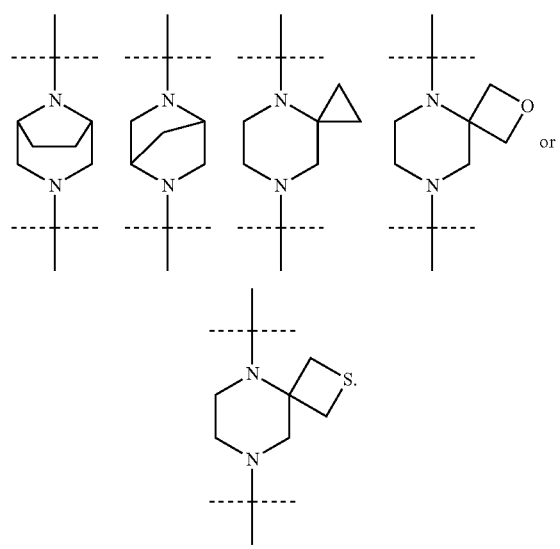

15. The compound according to claim 1, wherein $R_5$ is hydrogen or $C_{1-6}$-alkyl-.

16. The compound according to claim 1, wherein $R_4$ is selected from the group consisting of:

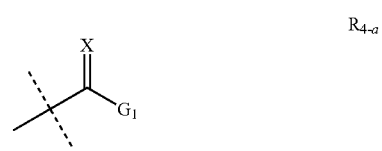

$R_{4-a}$ wherein
 X is O or S;
 Y is O or N—R$_7$;
 Z is C$_{1-6}$-alkylene which may be optionally substituted with one or more R$_8$;
 G$_1$ is selected from the group consisting of C$_{3-8}$-cycloalkyl-, C$_{3-8}$-cycloalkenyl-, C$_{2-8}$-heterocyclyl-, C$_{6-10}$-aryl- and C$_{2-10}$-heteroaryl-, either of which may be optionally substituted with one or more R$_G$;
 G$_2$ is selected from the group consisting of C$_{1-6}$-alkyl-, C$_{2-6}$-alkenyl-, C$_{2-6}$-alkynyl-, R$_{G2a}$O-L-, R$_{G2a}$S-L-, (R$_{G2a}$)$_2$N-L-, R$_{G2a}$—C(=O)-L-, R$_{G2a}$O—C(=O)-L-, (R$_{G2a}$)$_2$N—C(=O)-L-, R$_{G2a}$—C(=O)N(R$_{G2b}$)-L-, R$_{G2a}$O—C(=O)N(R$_{G2b}$)-L-, (R$_{G2a}$)$_2$N—C(=O)N(R$_{G2b}$)-L-, R$_{G2a}$—C(=O)O-L-, (R$_{G2a}$)$_2$N—C(=O)O-L-, R$_{G2a}$—S(=O)-L-, R$_{G2a}$—S(=O)$_2$-L-, R$_{G2a}$O—S(=O)$_2$-L-, (R$_{G2a}$)$_2$N—S(=O)-L-, (R$_{G2a}$)$_2$N—S (=O)₂-L-, R$_{G2a}$—S(=O)N(R$_{G2b}$)-L-, R$_{G2a}$—S(=O)₂N(R$_{G2b}$)-L-, R$_{G2a}$O—S(=O)₂N(R$_{G2b}$)-L-, (R$_{G2a}$)₂N—S(=O)₂N(R$_{G2b}$)-L-, R$_{G2a}$—S(=O)₂O-L-, and R$_{G2a}$O—S(=O)₂O-L-either of which may be optionally substituted with one or more R$_G$;

wherein L is a covalent bond or L is independently at each occurrence selected from the group consisting of C$_{1-6}$-alkyl- or C$_{3-6}$-cycloalkyl-;

R$_{G2a}$ and R$_{G2b}$ independently at each occurrence are selected from the group consisting of hydrogen, C$_{1-6}$-alkyl-, C$_{3-6}$-cycloalkyl-, and C$_{2-6}$-heterocyclyl-;

R$_G$ is selected from the group consisting of halogen, cyano, hydroxy, oxo, —NH₂, —SO₂NH₂, —SONH₂, —CONH₂, C$_{1-6}$-alkyl- and C$_{3-6}$-cycloalkyl-, wherein said C$_{1-6}$-alkyl- or C$_{3-6}$-cycloalkyl- is optionally substituted by one or more substituents selected from the group consisting of halogen, cyano, hydroxy, trifluoromethyl and —NH₂; or R$_G$ is selected from the group consisting of C$_{2-6}$-heterocyclyl-, C$_{2-6}$-heterocyclyl-C$_{1-6}$-alkyl-, R$_{Ga}$O-L-, R$_{Ga}$S-L-, (R$_{Ga}$)₂N-L-, R$_{Ga}$—C(=O)-L-, R$_{Ga}$O—C(=O)-L-, (R$_{Ga}$)₂N—C(=O)-L-, R$_{Ga}$—C(=O)N(R$_{Gb}$)-L-, R$_{Ga}$O—C(=O)N(R$_{Gb}$)-L-, (R$_{Ga}$)₂N—C(=O)N(R$_{Gb}$)-L-, R$_{Ga}$—C(=O)O-L-, R$_{Ga}$O—C(=O)O-L-, (R$_{Ga}$)₂N—C(=O)O-L-, R$_{Ga}$—S(=O)₂-L-, R$_{Ga}$O—S(=O)₂-L-, (R$_{Ga}$)₂N—S(=O)₂-L-, R$_{Ga}$—S(=O)₂N(R$_{Gb}$)-L-, R$_{Ga}$O—S(=O)₂N(R$_{Gb}$)-L-, (R$_{Ga}$)₂N—S(=O)₂N(R$_{Gb}$)-L-, R$_{Ga}$—S(=O)₂O-L-, R$_{Ga}$O—S(=O)₂O-L-, (R$_{Ga}$)₂N—S(=O)₂O-L-, aryl-, arylalkyl-, aryloxy-, aryloxyalkyl-, heteroaryl-, heteroarylalkyl-, heteroaryloxy- and heteroaryloxyalkyl-;

wherein L is a covalent bond or L is independently at each occurrence selected from the group consisting of C$_{1-6}$-alkyl- and C$_{3-6}$-cycloalkyl-;

R$_{Ga}$ and R$_{Gb}$ independently at each occurrence are selected from the group consisting of hydrogen, C$_{1-6}$-alkyl-, C$_{3-6}$-cycloalkyl-, C$_{2-6}$-heterocyclyl-, C$_{6-10}$-aryl- and C$_{3-8}$-heteroaryl-; wherein said C$_{1-6}$-alkyl-, C$_{3-6}$-cycloalkyl-, C$_{2-6}$-heterocyclyl-, C$_{6-10}$-aryl- and C$_{3-8}$-heteroaryl-group is optionally substituted one or more times by a substituent selected from the group consisting of halogen, cyano, hydroxy, trifluoromethyl and —NH₂;

R$_7$ is hydrogen or is independently at each occurrence selected from the group consisting of C$_{1-6}$-alkyl-, C$_{3-6}$-cycloalkyl-, C$_{2-6}$-heterocyclyl-, C$_{6-10}$-aryl- and C$_{3-8}$-heteroaryl-, either of which may be optionally substituted with one or more R$_{7a}$;

wherein R$_{7a}$ independently at each occurrence is selected from the group consisting of cyano, hydroxy, oxo, —SO₂NH₂, —CONH₂, C$_{1-6}$-alkyl-, C$_{3-6}$-cycloalkyl-, C$_{2-6}$-heterocyclyl-, C$_{6-10}$-aryl- and C$_{3-8}$-heteroaryl-.

17. The compound according to claim 1, wherein R$_4$ is selected from the group consisting of:

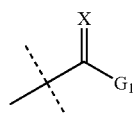

R$_{4\text{-}a}$

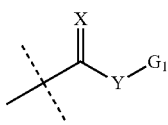

R$_{4\text{-}b}$

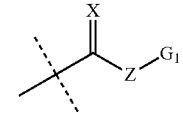

R$_{4\text{-}c}$

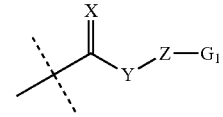

R$_{4\text{-}d}$

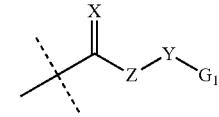

R$_{4\text{-}e}$

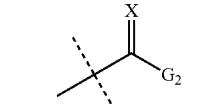

R$_{4\text{-}f}$

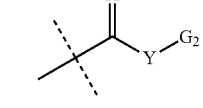

R$_{4\text{-}g}$

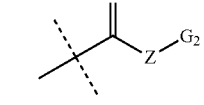

R$_{4\text{-}h}$

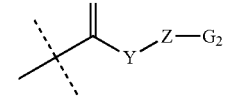

R$_{4\text{-}i}$

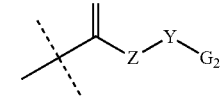

R$_{4\text{-}j}$

R$_{4\text{-}k}$

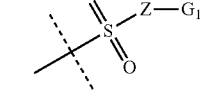

R$_{4\text{-}m}$

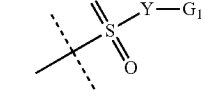

R$_{4\text{-}o}$

R$_{4\text{-}l}$

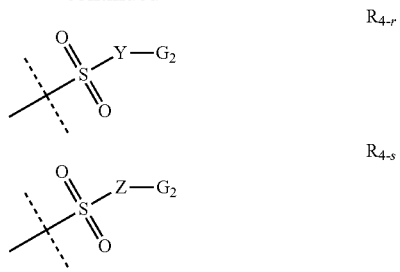

X is O or S;
Y is O or N—$R_7$;
Z is $C_{1-6}$-alkylene;
$G_1$ is selected from the group consisting of $C_{3-6}$-cycloalkyl-, $C_{3-6}$-heterocyclyl-, $C_{6-10}$-aryl- and $C_{3-8}$-heteroaryl-, either of which may be optionally substituted with one or more $R_G$;
$G_2$ is selected from the group consisting of $C_{1-6}$-alkyl-, $C_{2-6}$-alkenyl-, $C_{2-6}$-alkynyl-, $R_{G2a}$O-L-, $R_{G2a}$S-L-, $(R_{G2a})_2$N-L-, $R_{G2a}$—C(=O)-L-, $R_{G2a}$O—C(=O)-L-, $(R_{G2a})_2$N—C(=O)-L-, $R_{G2a}$—C(=O)N($R_{G2b}$)-L-, $R_{G2a}$O—C(=O)N($R_{G2b}$)-L-, $(R_{G2a})_2$N—C(=O)N($R_{G2b}$)-L-, $R_{G2a}$—C(=O)O-L-, $(R_{G2a})_2$N—C(=O)O-L-, $R_{G2a}$—S(=O)$_2$-L-, $(R_{G2a})_2$N—S(=O)$_2$-L-, $R_{G2a}$—S(=O)$_2$N($R_{G2b}$)-L-, and $(R_{G2a})_2$N—S(=O)$_2$N($R_{G2b}$)-L-; either of which may be optionally substituted with one or more $R_G$;
wherein L is a covalent bond or $C_{1-6}$-alkylene-;
$R_{G2a}$ and $R_{G2b}$ independently at each occurrence are hydrogen or $C_{1-6}$-alkyl-;
$R_G$ is selected from the group consisting of halogen, cyano, hydroxy, oxo, —NH$_2$, —SO$_2$NH$_2$, —SONH$_2$, —CONH$_2$, $C_{1-6}$-alkyl- and $C_{3-6}$-cycloalkyl-, wherein said $C_{1-6}$-alkyl- or $C_{3-6}$-cycloalkyl- is optionally substituted by one or more substituents selected from the group consisting of halogen, cyano, hydroxy, trifluoromethyl and —NH$_2$; or $R_G$ is selected from the group consisting of $R_{Ga}$O-L-, $R_{Ga}$S-L-, $(R_{Ga})_2$N-L-, $R_{Ga}$—C(=O)-L-, $R_{Ga}$O—C(=O)-L-, $(R_{Ga})_2$N—C(=O)-L-, $R_{Ga}$—C(=O)N($R_{Gb}$)-L-, $R_{Ga}$O—C(=O)N($R_{Gb}$)-L-, $(R_{Ga})_2$N—C(=O)N($R_{Gb}$)-L-, $R_{Ga}$—C(=O)O-L-, $(R_{Ga})_2$N—C(=O)O-L-, $R_{Ga}$—S(=O)$_2$-L-, $(R_{Ga})_2$N—S(=O)$_2$-L-, $R_{Ga}$—S(=O)$_2$N($R_{Gb}$)-L-, aryl-, arylalkyl-, heteroaryl-, and heteroarylalkyl-;
wherein L is a covalent bond or $C_{1-6}$-alkylene-;
$R_{Ga}$ and $R_{Gb}$ are hydrogen, $C_{1-6}$-alkyl- or aryl, each of which may be substituted one or more times by a substituent selected from the group consisting of halogen, cyano, hydroxy, trifluoromethyl and —NH$_2$; and
$R_7$ is hydrogen.

18. The compound according to claim 16 or 17, wherein X is O.

19. The compound according to claim 16 or 17, wherein X is S.

20. The compound according to claim 16, wherein Y is O.

21. The compound according to claim 16, wherein Y is NR$_7$.

22. The compound according to claim 21, wherein R$_7$ is hydrogen.

23. The compound according to claim 16, wherein G$_2$ is selected from the group consisting of $C_{1-6}$-alkyl, $C_{2-6}$-alkenyl, $C_{2-6}$-alkynyl, $R_{G2a}$O-L-, $R_{G2a}$—C(=O)-L-, $R_{G2a}$O—C(=O)-L-, $(R_{G2a})_2$N—C(=O)-L-, and $R_{G2a}$—S(=O)$_2$-L-; either of which may be optionally substituted with one or more $R_G$.

24. The compound according to claim 16, wherein G$_1$ is selected from the group consisting of cyclopropyl, cyclobutyl, cyclopentyl, cyclohexyl, phenyl, biphenyl, indolyl, piperidinyl, pyridinyl, pyrimidinyl, pyrrolidinyl, thienyl, quinoxalinyl, benzo[b]thienyl, tetrahydrofuranyl, 5,6-dihydro-4H-cyclopenta[b]thiophenyl, and tetrahydrothiopyranyl; either of which may be optionally substituted with one or more $R_G$.

25. The compound according to claim 16, wherein R$_G$ is selected from the group consisting of fluoro, chloro, bromo, iodo, cyano, oxo, —SO$_2$NH$_2$, —CONH$_2$, $C_{1-6}$-alkyl, $C_{1-6}$-haloalkyl, $C_{1-6}$-cyanoalkyl, R$_G$, O-L-, $R_{Ga}$O—C(=O)-L-, $R_{Ga}$—C(=O)-L-, $(R_{Ga})_2$N—C(=O)-L-, phenyl- or pyridinyl.

26. The compound according to claim 25, wherein R$_{Ga}$ is hydrogen or is selected from the group consisting of $C_{1-6}$-alkyl and phenyl-, which may be substituted one or more times by halogen or trifluoromethyl.

27. The compound according to claim 1, wherein L is a covalent bond.

28. The compound according to claim 1, wherein L is $C_{1-6}$-alkyl.

29. The compound according to claim 1 selected from the group consisting of:
[3-(7H-Pyrrolo[2,3-d]pyrimidin-4-yl)-3,8-diazabicyclo [3.2.1]oct-8-yl]-(4-trifluoromethylphenyl)-methanone,
Pyridin-2-yl-[7-(7H-pyrrolo[2,3-d]pyrimidin-4-yl)-4,7-diazaspiro[2.5]oct-4-yl]-methanone,
Pyridin-4-yl-[7-(7H-pyrrolo[2,3-d]pyrimidin-4-yl)-4,7-diazaspiro[2.5]oct-4-yl]-methanone,
2-Pyridin-3-yl-1-[7-(7H-pyrrolo[2,3-d]pyrimidin-4-yl)-4,7-diazaspiro[2.5]oct-4-yl]-ethanone,
Biphenyl-4-yl-[7-(7H-pyrrolo[2,3-d]pyrimidin-4-yl)-4,7-diazaspiro[2.5]oct-4-yl]-methanone,
Biphenyl-3-yl-[7-(7H-pyrrolo[2,3-d]pyrimidin-4-yl)-4,7-diazaspiro[2.5]oct-4-yl]-methanone,
[7-(7H-Pyrrolo[2,3-d]pyrimidin-4-yl)-4,7-diazaspiro[2.5] oct-4-yl]-(tetrahydro-furan-3-yl)-methanone,
2-{3-[7-(7H-Pyrrolo[2,3-d]pyrimidin-4-yl)-4,7-diazaspiro[2.5]octane-4-carbonyl]-phenyl}-propionitrile,
3-(7H-Pyrrolo[2,3-d]pyrimidin-4-yl)-3,8-diazabicyclo [3.2.1]octane-8-carboxylic acid tert-butyl ester,
3-(7H-Pyrrolo[2,3-d]pyrimidin-4-yl)-3,8-diazabicyclo [3.2.1]octane-8-carbothioic acid isobutyl-amide,
3-(7H-Pyrrolo[2,3-d]pyrimidin-4-yl)-3,8-diazabicyclo [3.2.1]octane-8-carbothioic acid benzylamide,
3-(7H-Pyrrolo[2,3-d]pyrimidin-4-yl)-3,8-diazabicyclo [3.2.1]octane-8-carboxylic acid 2-methoxy-ethyl ester,
(1,1-Dioxo-hexahydro-1lambda*6*-thiopyran-4-yl)-[7-(7H-pyrrolo[2,3-d]pyrimidin-4-yl)-4,7-diazaspiro[2.5] oct-4-yl]-methanone,
2-(1H-Indol-3-yl)-1-[7-(7H-pyrrolo[2,3-d]pyrimidin-4-yl)-4,7-diazaspiro[2.5]oct-4-yl]-ethanone,
4-[7-(7H-Pyrrolo[2,3-d]pyrimidin-4-yl)-4,7-diazaspiro [2.5]octane-4-carbonyl]-benzonitrile,
(1H-Indol-3-yl)-[7-(7H-pyrrolo[2,3-d]pyrimidin-4-yl)-4, 7-diazaspiro[2.5]oct-4-yl]-methanone,
3-Oxo-3-[7-(7H-pyrrolo[2,3-d]pyrimidin-4-yl)-4,7-diazaspiro[2.5]oct-4-yl]-propane-1-sulfonic acid amide,
{4-[7-(7H-Pyrrolo[2,3-d]pyrimidin-4-yl)-4,7-diazaspiro [2.5]octane-4-carbonyl]-phenyl}-acetonitrile,
Pyrazin-2-yl-[7-(7H-pyrrolo[2,3-d]pyrimidin-4-yl)-4,7-diazaspiro[2.5]oct-4-yl]-methanone,

[7-(7H-Pyrrolo[2,3-d]pyrimidin-4-yl)-4,7-diazaspiro[2.5]oct-4-yl]-(3-trifluoromethylphenyl)-methanone,
2-Pyridin-4-yl-1-[7-(7H-pyrrolo[2,3-d]pyrimidin-4-yl)-4,7-diazaspiro[2.5]oct-4-yl]-ethanone,
[7-(7H-Pyrrolo[2,3-d]pyrimidin-4-yl)-4,7-diazaspiro[2.5]oct-4-yl]-(tetrahydrofuran-2-yl)-methanone,
4-[7-(7H-Pyrrolo[2,3-d]pyrimidin-4-yl)-4,7-diazaspiro[2.5]octane-4-carbonyl]-cyclohexanone,
3,3,3-Trifluoro-1-[7-(7H-pyrrolo[2,3-d]pyrimidin-4-yl)-4,7-diazaspiro[2.5]oct-4-yl]-propan-1-one,
3-{2-Oxo-2-[7-(7H-pyrrolo[2,3-d]pyrimidin-4-yl)-4,7-diazaspiro[2.5]oct-4-yl]-ethyl}-benzonitrile,
Benzo[b]thiophen-2-yl-[7-(7H-pyrrolo[2,3-d]pyrimidin-4-yl)-4,7-diazaspiro[2.5]oct-4-yl]-methanone,
Phenyl-[7-(7H-pyrrolo[2,3-d]pyrimidin-4-yl)-4,7-diazaspiro[2.5]oct-4-yl]-methanone,
4,4,4-Trifluoro-1-[7-(7H-pyrrolo[2,3-d]pyrimidin-4-yl)-4,7-diazaspiro[2.5]oct-4-yl]-butan-1-one,
[3-(7H-Pyrrolo[2,3-d]pyrimidin-4-yl)-3,8-diazabicyclo[3.2.1]octane-8-carbothioyl]-carbamic acid ethyl ester,
1-[3-(7H-Pyrrolo[2,3-d]pyrimidin-4-yl)-3,8-diazabicyclo[3.2.1]oct-8-yl]-propan-1-one,
4-[3-(7H-Pyrrolo[2,3-d]pyrimidin-4-yl)-3,8-diazabicyclo[3.2.1]octane-8-carbonyl]-benzonitrile,
2-Phenyl-1-[3-(7H-pyrrolo[2,3-d]pyrimidin-4-yl)-3,8-diazabicyclo[3.2.1]oct-8-yl]-ethanone,
Phenyl-[3-(7H-pyrrolo[2,3-d]pyrimidin-4-yl)-3,8-diazabicyclo[3.2.1]oct-8-yl]-methanone,
N-{2-Oxo-2-[3-(7H-pyrrolo[2,3-d]pyrimidin-4-yl)-3,8-diazabicyclo[3.2.1]oct-8-yl]-ethyl}-acetamide,
(1H-Indol-6-yl)-[7-(7H-pyrrolo[2,3-d]pyrimidin-4-yl)-4,7-diazaspiro[2.5]oct-4-yl]-methanone,
3-Methanesulfonyl-1-[7-(7H-pyrrolo[2,3-d]pyrimidin-4-yl)-4,7-diazaspiro[2.5]oct-4-yl]-propan-1-one,
2-Cyclopentyl-1-[3-(7H-pyrrolo[2,3-d]pyrimidin-4-yl)-3,8-diazabicyclo[3.2.1]oct-8-yl]-ethanone,
3-(7H-Pyrrolo[2,3-d]pyrimidin-4-yl)-3,8-diazabicyclo[3.2.1]octane-8-carbothioic acid (3-methoxypropyl)-amide,
3,3,3-Trifluoro-1-[3-(7H-pyrrolo[2,3-d]pyrimidin-4-yl)-3,8-diazabicyclo[3.2.1]oct-8-yl]-propan-1-one,
2-Methyl-5-[7-(7H-pyrrolo[2,3-d]pyrimidin-4-yl)-4,7-diazaspiro[2.5]octane-4-carbonyl]-N-(3-trifluoromethylphenyl)-benzamide,
Pyridin-3-yl-[7-(7H-pyrrolo[2,3-d]pyrimidin-4-yl)-4,7-diazaspiro[2.5]oct-4-yl]-methanone,
1-{4-[7-(7H-Pyrrolo[2,3-d]pyrimidin-4-yl)-4,7-diazaspiro[2.5]octane-4-carbonyl]-piperidin-1-yl}-ethanone,
3-[7-(7H-Pyrrolo[2,3-d]pyrimidin-4-yl)-4,7-diazaspiro[2.5]octane-4-carbonyl]-benzonitrile,
7-(7H-Pyrrolo[2,3-d]pyrimidin-4-yl)-4,7-diazaspiro[2.5]octane-4-carboxylic acid tert-butyl ester,
3-(7H-Pyrrolo[2,3-d]pyrimidin-4-yl)-3,8-diazabicyclo[3.2.1]octane-8-carboxylic acid cyclohexylamide,
3-(7H-Pyrrolo[2,3-d]pyrimidin-4-yl)-3,8-diazabicyclo[3.2.1]octane-8-carbothioic acid (2-oxotetrahydrofuran-3-yl)-amide,
[7-(7H-Pyrrolo[2,3-d]pyrimidin-4-yl)-4,7-diazaspiro[2.5]oct-4-yl]-(4-trifluoromethylphenyl)-methanone,
4-[7-(7H-Pyrrolo[2,3-d]pyrimidin-4-yl)-4,7-diazaspiro[2.5]octane-4-carbonyl]-benzamide,
1-{2-[7-(7H-Pyrrolo[2,3-d]pyrimidin-4-yl)-4,7-diazaspiro[2.5]octane-4-carbonyl]-pyrrolidin-1-yl}-ethanone,
4-[8-(Propane-1-sulfonyl)-3,8-diazabicyclo[3.2.1]oct-3-yl]-7H-pyrrolo[2,3-d]pyrimidine,
3-(7H-Pyrrolo[2,3-d]pyrimidin-4-yl)-3,8-diazabicyclo[3.2.1]octane-8-carboxylic acid ethyl ester,
3-Oxo-3-[3-(7H-pyrrolo[2,3-d]pyrimidin-4-yl)-3,8-diazabicyclo[3.2.1]oct-8-yl]-propionitrile,
3-Oxo-3-[7-(7H-pyrrolo[2,3-d]pyrimidin-4-yl)-4,7-diazaspiro[2.5]oct-4-yl]-propionitrile,
(1H-Indol-2-yl)-[7-(7H-pyrrolo[2,3-d]pyrimidin-4-yl)-4,7-diazaspiro[2.5]oct-4-yl]-methanone,
5-[7-(7H-Pyrrolo[2,3-d]pyrimidin-4-yl)-4,7-diazaspiro[2.5]octane-4-carbonyl]-1H-pyridin-2-one,
Pyridin-3-yl-[3-(7H-pyrrolo[2,3-d]pyrimidin-4-yl)-3,8-diazabicyclo[3.2.1]oct-8-yl]-methanone,
3-(7H-Pyrrolo[2,3-d]pyrimidin-4-yl)-3,8-diazabicyclo[3.2.1]octane-8-carboxylic acid benzyl ester,
3-(7H-Pyrrolo[2,3-d]pyrimidin-4-yl)-3,8-diazabicyclo[3.2.1]octane-8-carboxylic acid prop-2-ynyl ester,
5-[7-(7H-Pyrrolo[2,3-d]pyrimidin-4-yl)-4,7-diaza-spiro[2.5]octane-4-carbonyl]-thiophene-3-carbonitrile,
(5,6-Dihydro-4H-cyclopenta[b]thiophen-2-yl)-[7-(7H-pyrrolo[2,3-d]pyrimidin-4-yl)-4,7-diaza-spiro[2.5]oct-4-yl]-methanone,
(4-Methyl-thiophen-2-yl)-[7-(7H-pyrrolo[2,3-d]pyrimidin-4-yl)-4,7-diaza-spiro[2.5]oct-4-yl]-methanone,
4-{2-Oxo-2-[7-(7H-pyrrolo[2,3-d]pyrimidin-4-yl)-4,7-diaza-spiro[2.5]oct-4-yl]-acetyl}-benzenesulfonamide,
4-{1,1-Difluoro-2-oxo-2-[7-(7H-pyrrolo[2,3-d]pyrimidin-4-yl)-4,7-diaza-spiro[2.5]oct-4-yl]-ethyl}-benzonitrile,
4-{1,1-Difluoro-2-oxo-2-[3-(7H-pyrrolo[2,3-d]pyrimidin-4-yl)-3,8-diaza-bicyclo[3.2.1]oct-8-yl]-ethyl}-benzonitrile,
2-Fluoro-5-{2-oxo-2-[7-(7H-pyrrolo[2,3-d]pyrimidin-4-yl)-4,7-diaza-spiro[2.5]oct-4-yl]-ethyl}-benzonitrile,
{3-[7-(7H-Pyrrolo[2,3-d]pyrimidin-4-yl)-4,7-diaza-spiro[2.5]octane-4-carbonyl]-phenoxy}-acetonitrile,
{4-[7-(7H-Pyrrolo[2,3-d]pyrimidin-4-yl)-4,7-diaza-spiro[2.5]octane-4-carbonyl]-phenoxy}-acetonitrile,
(4-{2-Oxo-2-[7-(7H-pyrrolo[2,3-d]pyrimidin-4-yl)-4,7-diaza-spiro[2.5]oct-4-yl]-ethyl}-phenoxy)-acetonitrile,
(3-{2-Oxo-2-[7-(7H-pyrrolo[2,3-d]pyrimidin-4-yl)-4,7-diaza-spiro[2.5]oct-4-yl]-ethyl}-phenoxy)-acetonitrile,
5-[3-(7H-Pyrrolo[2,3-d]pyrimidin-4-yl)-3,8-diaza-bicyclo[3.2.1]octane-8-carbonyl]-thiophene-2-carbonitrile,
(3-Methyl-pyrazin-2-yl)-[3-(7H-pyrrolo[2,3-d]pyrimidin-4-yl)-3,8-diaza-bicyclo[3.2.1]oct-8-yl]-methanone,
(6-Methyl-pyrazin-2-yl)-[3-(7H-pyrrolo[2,3-d]pyrimidin-4-yl)-3,8-diaza-bicyclo[3.2.1]oct-8-yl]-methanone,
(5-Methyl-pyrazin-2-yl)-[3-(7H-pyrrolo[2,3-d]pyrimidin-4-yl)-3,8-diaza-bicyclo[3.2.1]oct-8-yl]-methanone,
Benzo[b]thiophen-2-yl-[9-(7H-pyrrolo[2,3-d]pyrimidin-4-yl)-6,9-diaza-spiro[4.5]dec-6-yl]-methanone,
3-[7-(7H-Pyrrolo[2,3-d]pyrimidin-4-yl)-4,7-diaza-spiro[2.5]octane-4-sulfonylmethyl]-benzonitrile,
3-[3-(7H-Pyrrolo[2,3-d]pyrimidin-4-yl)-3,8-diaza-bicyclo[3.2.1]octane-8-sulfonylmethyl]-benzonitrile,
4-[3-(7H-Pyrrolo[2,3-d]pyrimidin-4-yl)-3,8-diaza-bicyclo[3.2.1]octane-8-sulfonylmethyl]-benzonitrile,
4-[7-(7H-Pyrrolo[2,3-d]pyrimidin-4-yl)-4,7-diaza-spiro[2.5]octane-4-sulfonylmethyl]-benzonitrile,
Benzo[b]thiophen-2-yl-[4-(1H-pyrrolo[2,3-b]pyridin-4-yl)-piperazin-1-yl]-methanone,
1-[4-(7H-Pyrrolo[2,3-d]pyrimidin-4-yl)-piperazine-1-carbonyl]-cyclopropanecarbonitrile,
Benzo[b]thiophen-2-yl-[7-(1H-pyrrolo[2,3-b]pyridin-4-yl)-4,7-diaza-spiro[2.5]oct-4-yl]-methanone,
Benzo[b]thiophen-2-yl-[4-(7H-pyrrolo[2,3-d]pyrimidin-4-yl)-piperazin-1-yl]-methanone, 1-[4-(1H-Pyrrolo[2,3-b]pyridin-4-yl)-piperazine-1-carbonyl]-cyclopropanecarbonitrile,
1-[7-(7H-Pyrrolo[2,3-d]pyrimidin-4-yl)-4,7-diaza-spiro[2.5]octane-4-carbonyl]-cyclopropanecarboxylic acid,
1-[7-(7H-Pyrrolo[2,3-d]pyrimidin-4-yl)-4,7-diaza-spiro[2.5]octane-4-carbonyl]-cyclopropanecarboxylic acid cyanomethyl-methyl-amide,
1-[7-(7H-Pyrrolo[2,3-d]pyrimidin-4-yl)-4,7-diaza-spiro[2.5]octane-4-carbonyl]-cyclopropanecarboxylic acid (2-cyano-ethyl)-methyl-amide,
1-{1-[7-(7H-Pyrrolo[2,3-d]pyrimidin-4-yl)-4,7-diaza-spiro[2.5]octane-4-carbonyl]-cyclopropanecarbonyl}-pyrrolidine-3-carbonitrile,
7-(7H-Pyrrolo[2,3-d]pyrimidin-4-yl)-4,7-diaza-spiro[2.5]octane-4-carboxylic acid but-2-ynyl ester,
(3-Methyl-thiophen-2-yl)-[7-(7H-pyrrolo[2,3-d]pyrimidin-4-yl)-4,7-diaza-spiro[2.5]oct-4-yl]-methanone,
(5-Methyl-thiophen-2-yl)-[7-(7H-pyrrolo[2,3-d]pyrimidin-4-yl)-4,7-diaza-spiro[2.5]oct-4-yl]-methanone,
3-Fluoro-4-[7-(7H-pyrrolo[2,3-d]pyrimidin-4-yl)-4,7-diaza-spiro[2.5]octane-4-carbonyl]-benzonitrile,
N-(4-{4-[2-(4-Cyano-phenyl)-acetyl]-4,7-diaza-spiro[2.5]oct-7-yl}-7H-pyrrolo[2,3-d]pyrimidin-2-yl)-acetamide,
{3-[7-(7H-Pyrrolo[2,3-d]pyrimidin-4-yl)-4,7-diaza-spiro[2.5]octane-4-carbonyl]-piperidin-1-yl}-acetonitrile,
3-{3-[7-(7H-Pyrrolo[2,3-d]pyrimidin-4-yl)-4,7-diaza-spiro[2.5]octane-4-carbonyl]-piperidin-1-yl}-propionitrile,
N-(4-{4-[2-(4-Cyano-phenyl)-acetyl]-4,7-diaza-spiro[2.5]oct-7-yl}-7H-pyrrolo[2,3-d]pyrimidin-2-yl)-2-(2-methoxy-ethoxy)-acetamide,
3-{4-[7-(7H-Pyrrolo[2,3-d]pyrimidin-4-yl)-4,7-diaza-spiro[2.5]octane-4-carbonyl]-piperidin-1-yl}-propionitrile,
N-(4-{4-[2-(4-Cyano-phenyl)-acetyl]-4,7-diaza-spiro[2.5]oct-7-yl}-7H-pyrrolo[2,3-d]pyrimidin-2-yl)-benzamide,
Isoxazole-5-carboxylic acid (4-{4-[2-(4-cyano-phenyl)-acetyl]-4,7-diaza-spiro[2.5]oct-7-yl}-7H-pyrrolo[2,3-d]pyrimidin-2-yl)-amide,
Acetic acid (4-{4-[2-(4-cyano-phenyl)-acetyl]-4,7-diaza-spiro[2.5]oct-7-yl}-7H-pyrrolo[2,3-d]pyrimidin-2-yl-carbamoyl)-methyl ester,
2-(3-Methanesulfonyl-phenyl)-1-[7-(7H-pyrrolo[2,3-d]pyrimidin-4-yl)-4,7-diaza-spiro[2.5]oct-4-yl]-ethanone,
2-Chloro-5-{2-oxo-2-[7-(7H-pyrrolo[2,3-d]pyrimidin-4-yl)-4,7-diaza-spiro[2.5]oct-4-yl]-ethoxy}-benzene sulfonamide,
2-Chloro-4-[7-(7H-pyrrolo[2,3-d]pyrimidin-4-yl)-4,7-diaza-spiro[2.5]octane-4-carbonyl]-benzenesulfonamide,
N-Methyl-4-[7-(7H-pyrrolo[2,3-d]pyrimidin-4-yl)-4,7-diaza-spiro[2.5]octane-4-carbonyl]-benzenesulfonamide,
Indan-1-yl-[7-(7H-pyrrolo[2,3-d]pyrimidin-4-yl)-4,7-diaza-spiro[2.5]oct-4-yl]-methanone,
Benzo[b]thiophen-5-yl-[7-(7H-pyrrolo[2,3-d]pyrimidin-4-yl)-4,7-diaza-spiro[2.5]oct-4-yl]-methanone,
2-(4-Methanesulfonyl-phenyl)-1-[7-(7H-pyrrolo[2,3-d]pyrimidin-4-yl)-4,7-diaza-spiro[2.5]oct-4-yl]-ethanone,
(5-Methoxy-thiophen-3-yl)-[3-(7H-pyrrolo[2,3-d]pyrimidin-4-yl)-3,8-diaza-bicyclo[3.2.1]oct-8-yl]-methanone,
1-[3-(7H-Pyrrolo[2,3-d]pyrimidin-4-yl)-3,8-diaza-bicyclo[3.2.1]oct-8-yl]-2-thiophen-2-yl-ethanone,
(5-Fluoro-6-methyl-1H-indol-2-yl)-[3-(7H-pyrrolo[2,3-d]pyrimidin-4-yl)-3,8-diaza-bicyclo[3.2.1]oct-8-yl]-methanone,
(4-Hydroxymethyl-thiophen-2-yl)-[3-(7H-pyrrolo[2,3-d]pyrimidin-4-yl)-3,8-diaza-bicyclo[3.2.1]oct-8-yl]-methanone,
1-{4-[3-(7H-Pyrrolo[2,3-d]pyrimidin-4-yl)-3,8-diaza-bicyclo[3.2.1]octane-8-carbonyl]-thiophen-2-yl}-ethanone,
2-{2-Oxo-2-[7-(7H-pyrrolo[2,3-d]pyrimidin-4-yl)-4,7-diaza-spiro[2.5]oct-4-yl]-ethyl}-benzonitrile,
1-[7-(7H-Pyrrolo[2,3-d]pyrimidin-4-yl)-4,7-diaza-spiro[2.5]octane-4-carbonyl]-cyclopentanecarbonitrile,
4-{2-Oxo-2-[7-(1H-pyrrolo[2,3-b]pyridin-4-yl)-4,7-diaza-spiro[2.5]oct-4-yl]-ethyl}-benzonitrile,
4-{4-[2-(3-Cyanomethyl-phenyl)-acetyl]-4,7-diaza-spiro[2.5]oct-7-yl}-7H-pyrrolo[2,3-d]pyrimidine-6-carboxylic acid methyl ester,
4-{4-[2-(4-Cyanomethyl-phenyl)-acetyl]-4,7-diaza-spiro[2.5]oct-7-yl}-7H-pyrrolo[2,3-d]pyrimidine-6-carboxylic acid methyl ester,
4-{4-[2-(3-Cyano-phenyl)-acetyl]-4,7-diaza-spiro[2.5]oct-7-yl}-7H-pyrrolo[2,3-d]pyrimidine-6-carboxylic acid methyl ester,
4-{4-[2-(4-Cyano-phenyl)-acetyl]-4,7-diaza-spiro[2.5]oct-7-yl}-7H-pyrrolo[2,3-d]pyrimidine-6-carboxylic acid methyl ester,
Bicyclo[4.2.0]octa-1(6),2,4-trien-7-yl-[7-(7H-pyrrolo[2,3-d]pyrimidin-4-yl)-4,7-diaza-spiro[2.5]oct-4-yl]-methanone,
3-[7-(7H-Pyrrolo[2,3-d]pyrimidin-4-yl)-4,7-diaza-spiro[2.5]octane-4-carbonyl]-indan-1-one,
2-Chloro-5-{2-oxo-2-[3-(7H-pyrrolo[2,3-d]pyrimidin-4-yl)-3,8-diaza-bicyclo[3.2.1]oct-8-yl]-ethoxy}-benzene sulfonamide,
4-{2-Oxo-2-[3-(7H-pyrrolo[2,3-d]pyrimidin-4-yl)-3,8-diaza-bicyclo[3.2.1]oct-8-yl]-acetyl}-benzonitrile,
2-[3-(7H-Pyrrolo[2,3-d]pyrimidin-4-yl)-3,8-diaza-bicyclo[3.2.1]octane-8-carbonyl]-1H-indole-5-carbonitrile,
(5-Methanesulfonyl-1H-indol-2-yl)-[3-(7H-pyrrolo[2,3-d]pyrimidin-4-yl)-3,8-diaza-bicyclo[3.2.1]oct-8-yl]-methanone,
(3-Fluoro-4-methanesulfonyl-phenyl)-[3-(7H-pyrrolo[2,3-d]pyrimidin-4-yl)-3,8-diaza-bicyclo[3.2.1]oct-8-yl]-methanone,
Bicyclo[4.2.0]octa-1(6),2,4-trien-7-yl-[3-(7H-pyrrolo[2,3-d]pyrimidin-4-yl)-3,8-diaza-bicyclo[3.2.1]oct-8-yl]-methanone,
2-[3-(7H-Pyrrolo[2,3-d]pyrimidin-4-yl)-3,8-diaza-bicyclo[3.2.1]octane-8-carbonyl]-indan-1-one,
2-(4-Methanesulfonyl-phenyl)-1-[3-(7H-pyrrolo[2,3-d]pyrimidin-4-yl)-3,8-diaza-bicyclo[3.2.1]oct-8-yl]-ethanone,
(3-Methanesulfonyl-phenyl)-[3-(7H-pyrrolo[2,3-d]pyrimidin-4-yl)-3,8-diaza-bicyclo[3.2.1]oct-8-yl]-methanone,
(5-Fluoro-1H-indol-2-yl)-[3-(7H-pyrrolo[2,3-d]pyrimidin-4-yl)-3,8-diaza-bicyclo[3.2.1]oct-8-yl]-methanone,
[3-(7H-Pyrrolo[2,3-d]pyrimidin-4-yl)-3,8-diaza-bicyclo[3.2.1]oct-8-yl]-(1,2,3,4-tetrahydro-naphthalen-1-yl)-methanone,
2-Methyl-5-[3-(7H-pyrrolo[2,3-d]pyrimidin-4-yl)-3,8-diaza-bicyclo[3.2.1]octane-8-carbonyl]-benzene-sulfonamide,
(5,6-Dihydro-4H-cyclopenta[b]thiophen-2-yl)-[3-(7H-pyrrolo[2,3-d]pyrimidin-4-yl)-3,8-diaza-bicyclo[3.2.1]oct-8-yl]-methanone, (5,7-Difluoro-1H-indol-2-yl)-[3-(7H-pyrrolo[2,3-d]pyrimidin-4-yl)-3,8-diaza-bicyclo[3.2.1]oct-8-yl]-methanone, 1-Methyl-5-[3-(7H-pyrrolo[2,3-d]pyrimidin-4-yl)-3,8-diaza-bicyclo[3.2.1]octane-8-carbonyl]-1H-pyrrole-2-sulfonic acid amide, 1-Methyl-5-[3-(7H-pyrrolo[2,3-d]pyrimidin-4-yl)-3,8-diaza-bicyclo[3.2.1]octane-8-carbonyl]-1H-pyrrole-3-sulfonic acid amide, 4-Oxo-4-[7-(7H-pyrrolo[2,3-d]pyrimidin-4-yl)-4,7-diaza-spiro[2.5]oct-4-yl]-butane-1-sulfonic acid amide,

[3-(7H-Pyrrolo[2,3-d]pyrimidin-4-yl)-3,8-diaza-bicyclo[3.2.1]oct-8-yl]-(tetrahydro-furan-3-yl)-methanone, 3-[6-Methyl-7-(7H-pyrrolo[2,3-d]pyrimidin-4-yl)-4,7-diaza-spiro[2.5]octane-4-carbonyl]-benzonitrile, 3-{2-[6-Methyl-7-(7H-pyrrolo[2,3-d]pyrimidin-4-yl)-4,7-diaza-spiro[2.5]oct-4-yl]-2-oxo-ethyl}-benzonitrile, 4-{2-[6-Methyl-7-(7H-pyrrolo[2,3-d]pyrimidin-4-yl)-4,7-diaza-spiro[2.5]oct-4-yl]-2-oxo-ethyl}-benzonitrile, 4-[6-Methyl-7-(7H-pyrrolo[2,3-d]pyrimidin-4-yl)-4,7-diaza-spiro[2.5]octane-4-carbonyl]-benzonitrile, 1-[6-Methyl-7-(7H-pyrrolo[2,3-d]pyrimidin-4-yl)-4,7-diaza-spiro[2.5]octane-4-carbonyl]-cyclopropanecarbonitrile, 4-[6-Methyl-7-(7H-pyrrolo[2,3-d]pyrimidin-4-yl)-4,7-diaza-spiro[2.5]oct-4-yl]-4-oxo-butyronitrile, N-{2-Oxo-2-[7-(7H-pyrrolo[2,3-d]pyrimidin-4-yl)-4,7-diaza-spiro[2.5]oct-4-yl]-ethyl}-acetamide, 2-Phenyl-1-[7-(7H-pyrrolo[2,3-d]pyrimidin-4-yl)-4,7-diaza-spiro[2.5]oct-4-yl]-ethanone, 3-Phenyl-1-[7-(7H-pyrrolo[2,3-d]pyrimidin-4-yl)-4,7-diaza-spiro[2.5]oct-4-yl]-propan-1-one, (1-Phenyl-cyclopropyl)-[7-(7H-pyrrolo[2,3-d]pyrimidin-4-yl)-4,7-diaza-spiro[2.5]oct-4-yl]-methanone, (4-Hydroxymethyl-phenyl)-[7-(7H-pyrrolo[2,3-d]pyrimidin-4-yl)-4,7-diaza-spiro[2.5]oct-4-yl]-methanone, 4-Oxo-4-[7-(7H-pyrrolo[2,3-d]pyrimidin-4-yl)-4,7-diaza-spiro[2.5]oct-4-yl]-butyramide, (1H-Indol-5-yl)-[7-(7H-pyrrolo[2,3-d]pyrimidin-4-yl)-4,7-diaza-spiro[2.5]oct-4-yl]-methanone, (4-Hydroxy-cyclohexyl)-[7-(7H-pyrrolo[2,3-d]pyrimidin-4-yl)-4,7-diaza-spiro[2.5]oct-4-yl]-methanone, (1H-Indol-4-yl)-[7-(7H-pyrrolo[2,3-d]pyrimidin-4-yl)-4,7-diaza-spiro[2.5]oct-4-yl]-methanone,

[7-(7H-Pyrrolo[2,3-d]pyrimidin-4-yl)-4,7-diaza-spiro[2.5]oct-4-yl]-(3-trifluoromethoxy-phenyl)-methanone,

[7-(7H-Pyrrolo[2,3-d]pyrimidin-4-yl)-4,7-diaza-spiro[2.5]oct-4-yl]-quinoxalin-2-yl-methanone, (1H-Benzoimidazol-5-yl)-[7-(7H-pyrrolo[2,3-d]pyrimidin-4-yl)-4,7-diaza-spiro[2.5]oct-4-yl]-methanone,

[7-(7H-Pyrrolo[2,3-d]pyrimidin-4-yl)-4,7-diaza-spiro[2.5]oct-4-yl]-quinolin-3-yl-methanone,

[7-(7H-Pyrrolo[2,3-d]pyrimidin-4-yl)-4,7-diaza-spiro[2.5]oct-4-yl]-quinolin-8-yl-methanone, 1-[7-(7H-Pyrrolo[2,3-d]pyrimidin-4-yl)-4,7-diaza-spiro[2.5]octane-4-carbonyl]-cyclopropanecarbonitrile, (6-Hydroxy-pyridin-2-yl)-[7-(7H-pyrrolo[2,3-d]pyrimidin-4-yl)-4,7-diaza-spiro[2.5]oct-4-yl]-methanone, 4-Oxo-4-[7-(7H-pyrrolo[2,3-d]pyrimidin-4-yl)-4,7-diaza-spiro[2.5]oct-4-yl]-butyronitrile, 3-Phenyl-1-[3-(7H-pyrrolo[2,3-d]pyrimidin-4-yl)-3,8-diaza-bicyclo[3.2.1]oct-8-yl]-propan-1-one, Benzo[b]thiophen-2-yl-[3-(7H-pyrrolo[2,3-d]pyrimidin-4-yl)-3,8-diaza-bicyclo[3.2.1]oct-8-yl]-methanone, 2-(1H-Indol-3-yl)-1-[3-(7H-pyrrolo[2,3-d]pyrimidin-4-yl)-3,8-diaza-bicyclo[3.2.1]oct-8-yl]-ethanone, 2-Pyridin-4-yl-1-[3-(7H-pyrrolo[2,3-d]pyrimidin-4-yl)-3,8-diaza-bicyclo[3.2.1]oct-8-yl]-ethanone, 2-Pyridin-3-yl-1-[3-(7H-pyrrolo[2,3-d]pyrimidin-4-yl)-3,8-diaza-bicyclo[3.2.1]oct-8-yl]-ethanone, 3-[3-(7H-Pyrrolo[2,3-d]pyrimidin-4-yl)-3,8-diaza-bicyclo[3.2.1]octane-8-carbonyl]-benzonitrile, 4-Oxo-4-[3-(7H-pyrrolo[2,3-d]pyrimidin-4-yl)-3,8-diaza-bicyclo[3.2.1]oct-8-yl]-butyramide, {4-[3-(7H-Pyrrolo[2,3-d]pyrimidin-4-yl)-3,8-diaza-bicyclo[3.2.1]octane-8-carbonyl]-phenyl}-acetonitrile, N-{3-Oxo-3-[3-(7H-pyrrolo[2,3-d]pyrimidin-4-yl)-3,8-diaza-bicyclo[3.2.1]oct-8-yl]-propyl}-methanesulfonamide, Oxazol-2-yl-[3-(7H-pyrrolo[2,3-d]pyrimidin-4-yl)-3,8-diaza-bicyclo[3.2.1]oct-8-yl]-methanone, Biphenyl-3-yl-[3-(7H-pyrrolo[2,3-d]pyrimidin-4-yl)-3,8-diaza-bicyclo[3.2.1]oct-8-yl]-methanone, 3-{2-Oxo-2-[3-(7H-pyrrolo[2,3-d]pyrimidin-4-yl)-3,8-diaza-bicyclo[3.2.1]oct-8-yl]-ethyl}-benzonitrile, 4-{2-Oxo-2-[3-(7H-pyrrolo[2,3-d]pyrimidin-4-yl)-3,8-diaza-bicyclo[3.2.1]oct-8-yl]-ethyl}-benzonitrile, 4,4,4-Trifluoro-1-[3-(7H-pyrrolo[2,3-d]pyrimidin-4-yl)-3,8-diaza-bicyclo[3.2.1]oct-8-yl]-butan-1-one, 4-Oxo-4-[3-(7H-pyrrolo[2,3-d]pyrimidin-4-yl)-3,8-diaza-bicyclo[3.2.1]oct-8-yl]-butyronitrile, (2-Fluoro-4-methanesulfonyl-phenyl)-[7-(7H-pyrrolo[2,3-d]pyrimidin-4-yl)-4,7-diaza-spiro[2.5]oct-4-yl]-methanone, (5-Methyl-1H-indol-2-yl)-[7-(7H-pyrrolo[2,3-d]pyrimidin-4-yl)-4,7-diaza-spiro[2.5]oct-4-yl]-methanone, (5-Fluoro-3-methyl-1H-indol-2-yl)-[7-(7H-pyrrolo[2,3-d]pyrimidin-4-yl)-4,7-diaza-spiro[2.5]oct-4-yl]-methanone, 2-[7-(7H-Pyrrolo[2,3-d]pyrimidin-4-yl)-4,7-diaza-spiro[2.5]octane-4-carbonyl]-1H-indole-5-sulfonic acid amide, 1-Methyl-5-[7-(7H-pyrrolo[2,3-d]pyrimidin-4-yl)-4,7-diaza-spiro[2.5]octane-4-carbonyl]-1H-pyrrole-2-sulfonic acid amide, 1-Methyl-5-[7-(7H-pyrrolo[2,3-d]pyrimidin-4-yl)-4,7-diaza-spiro[2.5]octane-4-carbonyl]-1H-pyrrole-3-sulfonic acid amide, N,N-Dimethyl-4-[7-(7H-pyrrolo[2,3-d]pyrimidin-4-yl)-4,7-diaza-spiro[2.5]octane-4-carbonyl]-benzenesulfonamide, 1-[7-(7H-Pyrrolo[2,3-d]pyrimidin-4-yl)-4,7-diaza-spiro[2.5]oct-4-yl]-2-thiophen-2-yl-ethanone, 4-{2-Oxo-2-[7-(7H-pyrrolo[2,3-d]pyrimidin-4-yl)-4,7-diaza-spiro[2.5]oct-4-yl]-ethyl}-benzenesulfonamide, (5,7-Difluoro-1H-indol-2-yl)-[7-(7H-pyrrolo[2,3-d]pyrimidin-4-yl)-4,7-diaza-spiro[2.5]oct-4-yl]-methanone, 5-[7-(7H-Pyrrolo[2,3-d]pyrimidin-4-yl)-4,7-diaza-spiro[2.5]octane-4-carbonyl]-thiophene-2-carbonitrile, (4-Methanesulfonyl-3-pyrrolidin-1-yl-phenyl)-[7-(7H-pyrrolo[2,3-d]pyrimidin-4-yl)-4,7-diaza-spiro[2.5]oct-4-yl]-methanone, 5-{2-Oxo-2-[7-(7H-pyrrolo[2,3-d]pyrimidin-4-yl)-4,7-diaza-spiro[2.5]oct-4-yl]-ethyl}-thiophene-2-sulfonic acid amide,

[4-(Propane-2-sulfonyl)-phenyl]-[7-(7H-pyrrolo[2,3-d]pyrimidin-4-yl)-4,7-diaza-spiro[2.5]oct-4-yl]-methanone, 4-{3-Oxo-3-[7-(7H-pyrrolo[2,3-d]pyrimidin-4-yl)-4,7-diaza-spiro[2.5]oct-4-yl]-propenyl}-benzenesulfonamide, 5-[7-(7H-Pyrrolo[2,3-d]pyrimidin-4-yl)-4,7-diaza-spiro[2.5]octane-4-carbonyl]-furan-2-sulfonic acid amide, 5-[3-(7H-Pyrrolo[2,3-d]pyrimidin-4-yl)-3,8-diaza-bicyclo[3.2.1]octane-8-carbonyl]-thiophene-3-carbonitrile,
(5-Methyl-1H-indol-2-yl)-[3-(7H-pyrrolo[2,3-d]pyrimidin-4-yl)-3,8-diaza-bicyclo[3.2.1]oct-8-yl]-methanone,
(5-Fluoro-3-methyl-1H-indol-2-yl)-[3-(7H-pyrrolo[2,3-d]pyrimidin-4-yl)-3,8-diaza-bicyclo[3.2.1]oct-8-yl]-methanone,
[4-(Propane-2-sulfonyl)-phenyl]-[3-(7H-pyrrolo[2,3-d]pyrimidin-4-yl)-3,8-diaza-bicyclo[3.2.1]oct-8-yl]-methanone,
[4-(Propane-2-sulfonyl)-phenyl]-[3-(7H-pyrrolo[2,3-d]pyrimidin-4-yl)-3,8-diaza-bicyclo[3.2.1]oct-8-yl]-methanone,
4-[7-(7H-Pyrrolo[2,3-d]pyrimidin-4-yl)-4,7-diaza-spiro[2.5]octane-4-carbonyl]-N-thiophen-2-ylmethyl-benzenesulfonamide,
1-[7-(7H-Pyrrolo[2,3-d]pyrimidin-4-yl)-4,7-diaza-spiro[2.5]oct-4-yl]-2-thiophen-2-yl-ethane-1,2-dione,
(5-Methoxy-thiophen-2-yl)-[7-(7H-pyrrolo[2,3-d]pyrimidin-4-yl)-4,7-diaza-spiro[2.5]oct-4-yl]-methanone,
(5-Propyl-thiophen-3-yl)-[7-(7H-pyrrolo[2,3-d]pyrimidin-4-yl)-4,7-diaza-spiro[2.5]oct-4-yl]-methanone,
(4-Bromo-5-methyl-thiophen-2-yl)-[7-(7H-pyrrolo[2,3-d]pyrimidin-4-yl)-4,7-diaza-spiro[2.5]oct-4-yl]-methanone,
(4-Bromo-5-ethyl-thiophen-2-yl)-[7-(7H-pyrrolo[2,3-d]pyrimidin-4-yl)-4,7-diaza-spiro[2.5]oct-4-yl]-methanone,
Ethanesulfonic acid {4-[7-(7H-pyrrolo[2,3-d]pyrimidin-4-yl)-4,7-diaza-spiro[2.5]octane-4-carbonyl]-phenyl}-amide,
[7-(7H-Pyrrolo[2,3-d]pyrimidin-4-yl)-4,7-diaza-spiro[2.5]oct-4-yl]-thiophen-2-yl-methanone,
(2,3-Dimethoxy-phenyl)-[7-(7H-pyrrolo[2,3-d]pyrimidin-4-yl)-4,7-diaza-spiro[2.5]oct-4-yl]-methanone,
(3,5-Dimethoxy-phenyl)-[7-(7H-pyrrolo[2,3-d]pyrimidin-4-yl)-4,7-diaza-spiro[2.5]oct-4-yl]-methanone,
Benzo[b]thiophen-3-yl-[7-(7H-pyrrolo[2,3-d]pyrimidin-4-yl)-4,7-diaza-spiro[2.5]oct-4-yl]-methanone,
(5-Phenyl-thiophen-2-yl)-[7-(7H-pyrrolo[2,3-d]pyrimidin-4-yl)-4,7-diaza-spiro[2.5]oct-4-yl]-methanone,
(2-Methoxy-pyridin-3-yl)-[7-(7H-pyrrolo[2,3-d]pyrimidin-4-yl)-4,7-diaza-spiro[2.5]oct-4-yl]-methanone,
2-[7-(7H-Pyrrolo[2,3-d]pyrimidin-4-yl)-4,7-diaza-spiro[2.5]octane-4-carbonyl]-1H-indole-5-carbonitrile,
[7-(7H-Pyrrolo[2,3-d]pyrimidin-4-yl)-4,7-diaza-spiro[2.5]oct-4-yl]-(5,6,7,8-tetrahydro-naphthalen-2-yl)-methanone,
2-Fluoro-4-[7-(7H-pyrrolo[2,3-d]pyrimidin-4-yl)-4,7-diaza-spiro[2.5]octane-4-carbonyl]-benzonitrile,
2,2-Dimethyl-3-oxo-3-[3-(7H-pyrrolo[2,3-d]pyrimidin-4-yl)-3,8-diaza-bicyclo[3.2.1]oct-8-yl]-propionitrile,
Phenyl-[3-(7H-pyrrolo[2,3-d]pyrimidin-4-yl)-3,8-diaza-bicyclo[3.2.1]oct-8-yl]-methanone,
Pyridin-2-yl-[3-(7H-pyrrolo[2,3-d]pyrimidin-4-yl)-3,8-diaza-bicyclo[3.2.1]oct-8-yl]-methanone,
Pyridin-4-yl-[3-(7H-pyrrolo[2,3-d]pyrimidin-4-yl)-3,8-diaza-bicyclo[3.2.1]oct-8-yl]-methanone,
(3-Methyl-thiophen-2-yl)-[3-(7H-pyrrolo[2,3-d]pyrimidin-4-yl)-3,8-diaza-bicyclo[3.2.1]oct-8-yl]-methanone,
[3-(7H-Pyrrolo[2,3-d]pyrimidin-4-yl)-3,8-diaza-bicyclo[3.2.1]oct-8-yl]-(3-trifluoromethoxy-phenyl)-methanone,
(3-Methyl-benzo[b]thiophen-2-yl)-[3-(7H-pyrrolo[2,3-d]pyrimidin-4-yl)-3,8-diaza-bicyclo[3.2.1]oct-8-yl]-methanone,
Benzo[b]thiophen-3-yl-[3-(7H-pyrrolo[2,3-d]pyrimidin-4-yl)-3,8-diaza-bicyclo[3.2.1]oct-8-yl]-methanone,
(5-Methyl-benzo[b]thiophen-2-yl)-[3-(7H-pyrrolo[2,3-d]pyrimidin-4-yl)-3,8-diaza-bicyclo[3.2.1]oct-8-yl]-methanone,
4-[3-(7H-Pyrrolo[2,3-d]pyrimidin-4-yl)-3,8-diaza-bicyclo[3.2.1]octane-8-carbonyl]-tetrahydro-pyran-4-carbonitrile,
2-[3-(7H-Pyrrolo[2,3-d]pyrimidin-4-yl)-3,8-diaza-bicyclo[3.2.1]octane-8-carbonyl]-benzonitrile,
2-{2-Oxo-2-[3-(7H-pyrrolo[2,3-d]pyrimidin-4-yl)-3,8-diaza-bicyclo[3.2.1]oct-8-yl]-ethyl}-benzonitrile,
[3-(7H-Pyrrolo[2,3-d]pyrimidin-4-yl)-3,8-diaza-bicyclo[3.2.1]oct-8-yl]-(4-trifluoromethoxy-phenyl)-methanone,
{2-[5-(7H-Pyrrolo[2,3-d]pyrimidin-4-yl)-2,5-diaza-bicyclo[2.2.1]heptane-2-carbonyl]-phenyl}-acetonitrile,
Phenyl-[5-(7H-pyrrolo[2,3-d]pyrimidin-4-yl)-2,5-diaza-bicyclo[2.2.1]hept-2-yl]-methanone,
Pyridin-2-yl-[5-(7H-pyrrolo[2,3-d]pyrimidin-4-yl)-2,5-diaza-bicyclo[2.2.1]hept-2-yl]-methanone,
Pyridin-3-yl-[5-(7H-pyrrolo[2,3-d]pyrimidin-4-yl)-2,5-diaza-bicyclo[2.2.1]hept-2-yl]-methanone,
Pyridin-4-yl-[5-(7H-pyrrolo[2,3-d]pyrimidin-4-yl)-2,5-diaza-bicyclo[2.2.1]hept-2-yl]-methanone,
Pyrazin-2-yl-[5-(7H-pyrrolo[2,3-d]pyrimidin-4-yl)-2,5-diaza-bicyclo[2.2.1]hept-2-yl]-methanone,
4-[5-(7H-Pyrrolo[2,3-d]pyrimidin-4-yl)-2,5-diaza-bicyclo[2.2.1]heptane-2-carbonyl]-benzonitrile,
3-[5-(7H-Pyrrolo[2,3-d]pyrimidin-4-yl)-2,5-diaza-bicyclo[2.2.1]heptane-2-carbonyl]-benzonitrile,
(3-Methyl-thiophen-2-yl)-[5-(7H-pyrrolo[2,3-d]pyrimidin-4-yl)-2,5-diaza-bicyclo[2.2.1]hept-2-yl]-methanone,
1-[5-(7H-Pyrrolo[2,3-d]pyrimidin-4-yl)-2,5-diaza-bicyclo[2.2.1]heptane-2-carbonyl]-cyclopentanecarbonitrile,
(1H-Indol-4-yl)-[5-(7H-pyrrolo[2,3-d]pyrimidin-4-yl)-2,5-diaza-bicyclo[2.2.1]hept-2-yl]-methanone,
{4-[5-(7H-Pyrrolo[2,3-d]pyrimidin-4-yl)-2,5-diaza-bicyclo[2.2.1]heptane-2-carbonyl]-phenyl}-acetonitrile,
(1H-Indol-2-yl)-[5-(7H-pyrrolo[2,3-d]pyrimidin-4-yl)-2,5-diaza-bicyclo[2.2.1]hept-2-yl]-methanone,
(5-Methyl-thiophen-2-yl)-[5-(7H-pyrrolo[2,3-d]pyrimidin-4-yl)-2,5-diaza-bicyclo[2.2.1]hept-2-yl]-methanone,
(3-Methyl-benzo[b]thiophen-2-yl)-[5-(7H-pyrrolo[2,3-d]pyrimidin-4-yl)-2,5-diaza-bicyclo[2.2.1]hept-2-yl]-methanone,
Benzo[b]thiophen-3-yl-[5-(7H-pyrrolo[2,3-d]pyrimidin-4-yl)-2,5-diaza-bicyclo[2.2.1]hept-2-yl]-methanone,
(5-Methyl-benzo[b]thiophen-2-yl)-[5-(7H-pyrrolo[2,3-d]pyrimidin-4-yl)-2,5-diaza-bicyclo[2.2.1]hept-2-yl]-methanone,
(5-Phenyl-thiophen-2-yl)-[5-(7H-pyrrolo[2,3-d]pyrimidin-4-yl)-2,5-diaza-bicyclo[2.2.1]hept-2-yl]-methanone,
1-[5-(7H-Pyrrolo[2,3-d]pyrimidin-4-yl)-2,5-diaza-bicyclo[2.2.1]heptane-2-carbonyl]-cyclopropanecarbonitrile,
2-[5-(7H-Pyrrolo[2,3-d]pyrimidin-4-yl)-2,5-diaza-bicyclo[2.2.1]heptane-2-carbonyl]-1H-indole-5-carbonitrile,
2-Fluoro-4-[5-(7H-pyrrolo[2,3-d]pyrimidin-4-yl)-2,5-diaza-bicyclo[2.2.1]heptane-2-carbonyl]-benzonitrile,
3-Fluoro-4-[5-(7H-pyrrolo[2,3-d]pyrimidin-4-yl)-2,5-diaza-bicyclo[2.2.1]heptane-2-carbonyl]-benzonitrile, 4-[5-(7H-Pyrrolo[2,3-d]pyrimidin-4-yl)-2,5-diaza-bicyclo[2.2.1]heptane-2-carbonyl]-tetrahydro-pyran-4-carbonitrile,
5-Oxo-5-[5-(7H-pyrrolo[2,3-d]pyrimidin-4-yl)-2,5-diaza-bicyclo[2.2.1]hept-2-yl]-pentanenitrile,
2-[5-(7H-Pyrrolo[2,3-d]pyrimidin-4-yl)-2,5-diaza-bicyclo[2.2.1]heptane-2-carbonyl]-benzonitrile,
3-{2-Oxo-2-[5-(7H-pyrrolo[2,3-d]pyrimidin-4-yl)-2,5-diaza-bicyclo[2.2.1]hept-2-yl]-ethyl}-benzonitrile,
4-{2-Oxo-2-[5-(7H-pyrrolo[2,3-d]pyrimidin-4-yl)-2,5-diaza-bicyclo[2.2.1]hept-2-yl]-ethyl}-benzonitrile,
2-{2-Oxo-2-[5-(7H-pyrrolo[2,3-d]pyrimidin-4-yl)-2,5-diaza-bicyclo[2.2.1]hept-2-yl]-ethyl}-benzonitrile,
4-Oxo-4-[5-(7H-pyrrolo[2,3-d]pyrimidin-4-yl)-2,5-diaza-bicyclo[2.2.1]hept-2-yl]-butyronitrile,
{2-[5-(7H-Pyrrolo[2,3-d]pyrimidin-4-yl)-2,5-diaza-bicyclo[2.2.1]heptane-2-carbonyl]-phenyl}-acetonitrile,
[5-(7H-Pyrrolo[2,3-d]pyrimidin-4-yl)-2,5-diaza-bicyclo[2.2.1]hept-2-yl]-(4-trifluoromethoxy-phenyl)-methanone,
(3-Methyl-benzo[b]thiophen-2-yl)-[7-(7H-pyrrolo[2,3-d]pyrimidin-4-yl)-4,7-diaza-spiro[2.5]oct-4-yl]-methanone,
(5-Methyl-benzo[b]thiophen-2-yl)-[7-(7H-pyrrolo[2,3-d]pyrimidin-4-yl)-4,7-diaza-spiro[2.5]oct-4-yl]-methanone,
5-Oxo-5-[7-(7H-pyrrolo[2,3-d]pyrimidin-4-yl)-4,7-diaza-spiro[2.5]oct-4-yl]-pentanenitrile,
2-[7-(7H-Pyrrolo[2,3-d]pyrimidin-4-yl)-4,7-diaza-spiro[2.5]octane-4-carbonyl]-benzonitrile,
{2-[7-(7H-Pyrrolo[2,3-d]pyrimidin-4-yl)-4,7-diaza-spiro[2.5]octane-4-carbonyl]-phenyl}-acetonitrile,
3-[7-(7H-Pyrrolo[2,3-d]pyrimidin-4-yl)-4,7-diaza-spiro[2.5]octane-4-carbonyl]-1H-indazole-6-carbonitrile,
[7-(2-Amino-7H-pyrrolo[2,3-d]pyrimidin-4-yl)-4,7-diaza-spiro[2.5]oct-4-yl]-pyrazin-2-yl-methanone,
4-[7-(2-Amino-7H-pyrrolo[2,3-d]pyrimidin-4-yl)-4,7-diaza-spiro[2.5]octane-4-carbonyl]-benzonitrile,
3-[7-(2-Amino-7H-pyrrolo[2,3-d]pyrimidin-4-yl)-4,7-diaza-spiro[2.5]octane-4-carbonyl]-benzonitrile,
[7-(2-Amino-7H-pyrrolo[2,3-d]pyrimidin-4-yl)-4,7-diaza-spiro[2.5]oct-4-yl]-quinoxalin-2-yl-methanone,
(3-{2-[7-(2-Amino-7H-pyrrolo[2,3-d]pyrimidin-4-yl)-4,7-diaza-spiro[2.5]oct-4-yl]-2-oxo-ethyl}-phenyl)-acetonitrile,
(4-{2-[7-(2-Amino-7H-pyrrolo[2,3-d]pyrimidin-4-yl)-4,7-diaza-spiro[2.5]oct-4-yl]-2-oxo-ethyl}-phenyl)-acetonitrile,
1-[7-(2-Amino-7H-pyrrolo[2,3-d]pyrimidin-4-yl)-4,7-diaza-spiro[2.5]octane-4-carbonyl]-cyclopropanecarbonitrile,
1-[7-(2-Amino-7H-pyrrolo[2,3-d]pyrimidin-4-yl)-4,7-diaza-spiro[2.5]oct-4-yl]-2-(4-trifluoromethyl-phenyl)-ethanone,
5-[7-(2-Amino-7H-pyrrolo[2,3-d]pyrimidin-4-yl)-4,7-diaza-spiro[2.5]oct-4-yl]-5-oxo-pentanenitrile,
3-{2-[7-(2-Amino-7H-pyrrolo[2,3-d]pyrimidin-4-yl)-4,7-diaza-spiro[2.5]oct-4-yl]-2-oxo-ethyl}-benzonitrile,
4-{2-[7-(2-Amino-7H-pyrrolo[2,3-d]pyrimidin-4-yl)-4,7-diaza-spiro[2.5]oct-4-yl]-2-oxo-ethyl}-benzonitrile,
4-[7-(2-Amino-7H-pyrrolo[2,3-d]pyrimidin-4-yl)-4,7-diaza-spiro[2.5]oct-4-yl]-4-oxo-butyronitrile,
[7-(5-Chloro-7H-pyrrolo[2,3-d]pyrimidin-4-yl)-4,7-diaza-spiro[2.5]oct-4-yl]-pyrazin-2-yl-methanone,
4-[7-(5-Chloro-7H-pyrrolo[2,3-d]pyrimidin-4-yl)-4,7-diaza-spiro[2.5]octane-4-carbonyl]-benzonitrile,
3-[7-(5-Chloro-7H-pyrrolo[2,3-d]pyrimidin-4-yl)-4,7-diaza-spiro[2.5]octane-4-carbonyl]-benzonitrile,
[7-(5-Chloro-7H-pyrrolo[2,3-d]pyrimidin-4-yl)-4,7-diaza-spiro[2.5]oct-4-yl]-quinoxalin-2-yl-methanone,
(3-{2-[7-(5-Chloro-7H-pyrrolo[2,3-d]pyrimidin-4-yl)-4,7-diaza-spiro[2.5]oct-4-yl]-2-oxo-ethyl}-phenyl)-acetonitrile,
(4-{2-[7-(5-Chloro-7H-pyrrolo[2,3-d]pyrimidin-4-yl)-4,7-diaza-spiro[2.5]oct-4-yl]-2-oxo-ethyl}-phenyl)-acetonitrile,
1-[7-(5-Chloro-7H-pyrrolo[2,3-d]pyrimidin-4-yl)-4,7-diaza-spiro[2.5]oct-4-yl]-2-(4-fluoro-phenyl)-ethanone,
1-[7-(5-Chloro-7H-pyrrolo[2,3-d]pyrimidin-4-yl)-4,7-diaza-spiro[2.5]oct-4-yl]-2-(4-trifluoromethyl-phenyl)-ethanone,
5-[7-(5-Chloro-7H-pyrrolo[2,3-d]pyrimidin-4-yl)-4,7-diaza-spiro[2.5]oct-4-yl]-5-oxo-pentanenitrile,
3-{2-[7-(5-Chloro-7H-pyrrolo[2,3-d]pyrimidin-4-yl)-4,7-diaza-spiro[2.5]oct-4-yl]-2-oxo-ethyl}-benzonitrile,
4-{2-[7-(5-Chloro-7H-pyrrolo[2,3-d]pyrimidin-4-yl)-4,7-diaza-spiro[2.5]oct-4-yl]-2-oxo-ethyl}-benzonitrile,
4-[7-(5-Chloro-7H-pyrrolo[2,3-d]pyrimidin-4-yl)-4,7-diaza-spiro[2.5]oct-4-yl]-4-oxo-butyronitrile,
4-[4-(1-Cyano-cyclopropanecarbonyl)-4,7-diaza-spiro[2.5]oct-7-yl]-7H-pyrrolo[2,3-d]pyrimidine-6-carboxylic acid methyl ester,
4-{4-[2-(4-Fluoro-phenyl)-acetyl]-4,7-diaza-spiro[2.5]oct-7-yl}-7H-pyrrolo[2,3-d]pyrimidine-6-carboxylic acid methyl ester,
4-{4-[2-(4-Trifluoromethyl-phenyl)-acetyl]-4,7-diaza-spiro[2.5]oct-7-yl}-7H-pyrrolo[2,3-d]pyrimidine-6-carboxylic acid methyl ester,
4-[4-(4-Cyano-butyryl)-4,7-diaza-spiro[2.5]oct-7-yl]-7H-pyrrolo[2,3-d]pyrimidine-6-carboxylic acid methyl ester,
4-[4-(4-Cyano-butyryl)-4,7-diaza-spiro[2.5]oct-7-yl]-7H-pyrrolo[2,3-d]pyrimidine-6-carboxylic acid methyl ester,
(1H-Indol-5-yl)-[3-(7H-pyrrolo[2,3-d]pyrimidin-4-yl)-3,8-diaza-bicyclo[3.2.1]oct-8-yl]-methanone,
{4-[3-(7H-Pyrrolo[2,3-d]pyrimidin-4-yl)-3,8-diaza-bicyclo[3.2.1]octane-8-carbonyl]-phenoxy}-acetonitrile,
{3-[3-(7H-Pyrrolo[2,3-d]pyrimidin-4-yl)-3,8-diaza-bicyclo[3.2.1]octane-8-carbonyl]-phenoxy}-acetonitrile,
(1H-Indol-4-yl)-[3-(7H-pyrrolo[2,3-d]pyrimidin-4-yl)-3,8-diaza-bicyclo[3.2.1]oct-8-yl]-methanone,
[3-(7H-Pyrrolo[2,3-d]pyrimidin-4-yl)-3,8-diaza-bicyclo[3.2.1]oct-8-yl]-quinoxalin-2-yl-methanone,
(3-{2-Oxo-2-[3-(7H-pyrrolo[2,3-d]pyrimidin-4-yl)-3,8-diaza-bicyclo[3.2.1]oct-8-yl]-ethyl}-phenyl)-acetonitrile,
(4-{2-Oxo-2-[3-(7H-pyrrolo[2,3-d]pyrimidin-4-yl)-3,8-diaza-bicyclo[3.2.1]oct-8-yl]-ethyl}-phenyl)-acetonitrile,
(1H-Indol-2-yl)-[3-(7H-pyrrolo[2,3-d]pyrimidin-4-yl)-3,8-diaza-bicyclo[3.2.1]oct-8-yl]-methanone,
1-[3-(7H-Pyrrolo[2,3-d]pyrimidin-4-yl)-3,8-diaza-bicyclo[3.2.1]oct-8-yl]-2-(4-trifluoromethyl-phenyl)-ethanone,
2-Fluoro-4-[3-(7H-pyrrolo[2,3-d]pyrimidin-4-yl)-3,8-diaza-bicyclo[3.2.1]octane-8-carbonyl]-benzonitrile,
3-Fluoro-4-[3-(7H-pyrrolo[2,3-d]pyrimidin-4-yl)-3,8-diaza-bicyclo[3.2.1]octane-8-carbonyl]-benzonitrile,
5-Oxo-5-[3-(7H-pyrrolo[2,3-d]pyrimidin-4-yl)-3,8-diaza-bicyclo[3.2.1]oct-8-yl]-pentanenitrile, 4-[3-(7H-Pyrrolo[2,3-d]pyrimidin-4-yl)-3,8-diaza-bicyclo[3.2.1]octane-8-carbonyl]-benzenesulfonamide,
N-{4-[3-(7H-Pyrrolo[2,3-d]pyrimidin-4-yl)-3,8-diaza-bicyclo[3.2.1]octane-8-carbonyl]-phenyl}-acetamide,
6-[3-(7H-Pyrrolo[2,3-d]pyrimidin-4-yl)-3,8-diaza-bicyclo[3.2.1]octane-8-carbonyl]-1H-quinolin-2-one,
(4-Methanesulfonyl-phenyl)-[3-(7H-pyrrolo[2,3-d]pyrimidin-4-yl)-3,8-diaza-bicyclo[3.2.1]oct-8-yl]-methanone,
(1H-Indol-6-yl)-[3-(7H-pyrrolo[2,3-d]pyrimidin-4-yl)-3,8-diaza-bicyclo[3.2.1]oct-8-yl]-methanone,
4-[3-(7H-Pyrrolo[2,3-d]pyrimidin-4-yl)-3,8-diaza-bicyclo[3.2.1]octane-8-carbonyl]-benzamide,
(6-Hydroxy-naphthalen-1-yl)-[3-(7H-pyrrolo[2,3-d]pyrimidin-4-yl)-3,8-diaza-bicyclo[3.2.1]oct-8-yl]-methanone,
(6-Bromo-benzo[d]isothiazol-3-yl)-[3-(7H-pyrrolo[2,3-d]pyrimidin-4-yl)-3,8-diaza-bicyclo[3.2.1]oct-8-yl]-methanone
(5-Fluoro-1H-indol-2-yl)-[7-(7H-pyrrolo[2,3-d]pyrimidin-4-yl)-4,7-diaza-spiro[2.5]oct-4-yl]-methanone,
(7-Fluoro-1H-indol-2-yl)-[7-(7H-pyrrolo[2,3-d]pyrimidin-4-yl)-4,7-diaza-spiro[2.5]oct-4-yl]-methanone,
(6-Fluoro-1H-indol-2-yl)-[7-(7H-pyrrolo[2,3-d]pyrimidin-4-yl)-4,7-diaza-spiro[2.5]oct-4-yl]-methanone,
(4-Methanesulfonyl-phenyl)-[7-(7H-pyrrolo[2,3-d]pyrimidin-4-yl)-4,7-diaza-spiro[2.5]oct-4-yl]-methanone,
(5-Methanesulfonyl-1H-indol-2-yl)-[7-(7H-pyrrolo[2,3-d]pyrimidin-4-yl)-4,7-diaza-spiro[2.5]oct-4-yl]-methanone,
(4-Fluoro-3-methanesulfonyl-phenyl)-[7-(7H-pyrrolo[2,3-d]pyrimidin-4-yl)-4,7-diaza-spiro[2.5]oct-4-yl]-methanone,
(3-Methanesulfonyl-phenyl)-[7-(7H-pyrrolo[2,3-d]pyrimidin-4-yl)-4,7-diaza-spiro[2.5]oct-4-yl]-methanone,
(4-Fluoro-1H-indol-2-yl)-[7-(7H-pyrrolo[2,3-d]pyrimidin-4-yl)-4,7-diaza-spiro[2.5]oct-4-yl]-methanone,
4-[7-(7H-Pyrrolo[2,3-d]pyrimidin-4-yl)-4,7-diaza-spiro[2.5]octane-4-carbonyl]-benzenesulfonamide,
(3-Fluoro-4-methanesulfonyl-phenyl)-[7-(7H-pyrrolo[2,3-d]pyrimidin-4-yl)-4,7-diaza-spiro[2.5]oct-4-yl]-methanone,
3-[7-(7H-Pyrrolo[2,3-d]pyrimidin-4-yl)-4,7-diaza-spiro[2.5]octane-4-carbonyl]-benzenesulfonamide,
5-[7-(7H-Pyrrolo[2,3-d]pyrimidin-4-yl)-4,7-diaza-spiro[2.5]octane-4-carbonyl]-thiophene-3-sulfonic acid amide,
5-[7-(7H-Pyrrolo[2,3-d]pyrimidin-4-yl)-4,7-diaza-spiro[2.5]octane-4-carbonyl]-thiophene-3-sulfonic acid methylamine,
2-Methyl-5-[7-(7H-pyrrolo[2,3-d]pyrimidin-4-yl)-4,7-diaza-spiro[2.5]octane-4-carbonyl]-thiophene-3-sulfonic acid amide,
2-Methyl-5-[7-(7H-pyrrolo[2,3-d]pyrimidin-4-yl)-4,7-diaza-spiro[2.5]octane-4-carbonyl]-thiophene-3-sulfonic acid methylamide,
4-Methyl-5-[7-(7H-pyrrolo[2,3-d]pyrimidin-4-yl)-4,7-diaza-spiro[2.5]octane-4-carbonyl]-thiophene-3-sulfonic acid methylamide,
N-Propyl-4-[7-(7H-pyrrolo[2,3-d]pyrimidin-4-yl)-4,7-diaza-spiro[2.5]octane-4-carbonyl]-benzenesulfonamide,
2-Methoxy-4-[7-(7H-pyrrolo[2,3-d]pyrimidin-4-yl)-4,7-diaza-spiro[2.5]octane-4-carbonyl]-benzenesulfonamide,
3-Methyl-4-[7-(7H-pyrrolo[2,3-d]pyrimidin-4-yl)-4,7-diaza-spiro[2.5]octane-4-carbonyl]-benzenesulfonamide,
2-Methyl-4-[7-(7H-pyrrolo[2,3-d]pyrimidin-4-yl)-4,7-diaza-spiro[2.5]octane-4-carbonyl]-benzenesulfonamide,
4-{2-Oxo-2-[7-(7H-pyrrolo[2,3-d]pyrimidin-4-yl)-4,7-diaza-spiro[2.5]oct-4-yl]-acetyl}-benzonitrile,
(2-Chloro-4-methanesulfonyl-phenyl)-[7-(7H-pyrrolo[2,3-d]pyrimidin-4-yl)-4,7-diaza-Spiro[2.5]oct-4-yl]-methanone,
4-{3-Oxo-3-[7-(7H-pyrrolo[2,3-d]pyrimidin-4-yl)-4,7-diaza-spiro[2.5]oct-4-yl]-propyl}-benzenesulfonamide,
(5-Methoxy-thiophen-3-yl)-[7-(7H-pyrrolo[2,3-d]pyrimidin-4-yl)-4,7-diaza-spiro[2.5]oct-4-yl]-methanone,
(4-Hydroxy-thiophen-2-yl)-[7-(7H-pyrrolo[2,3-d]pyrimidin-4-yl)-4,7-diaza-spiro[2.5]oct-4-yl]-methanone,
(4-Methoxy-thiophen-2-yl)-[7-(7H-pyrrolo[2,3-d]pyrimidin-4-yl)-4,7-diaza-spiro[2.5]oct-4-yl]-methanone,
2-(4-Bromo-thiophen-2-yl)-1-[7-(7H-pyrrolo[2,3-d]pyrimidin-4-yl)-4,7-diaza-spiro[2.5]oct-4-yl]-ethanone,
4-Methyl-3-[7-(7H-pyrrolo[2,3-d]pyrimidin-4-yl)-4,7-diaza-spiro[2.5]octane-4-carbonyl]-benzenesulfonamide,
3-Methoxy-4-[7-(7H-pyrrolo[2,3-d]pyrimidin-4-yl)-4,7-diaza-spiro[2.5]octane-4-carbonyl]-benzenesulfonamide,
2-Methoxy-4-[3-(7H-pyrrolo[2,3-d]pyrimidin-4-yl)-3,8-diaza-bicyclo[3.2.1]octane-8-carbonyl]-benzenesulfonamide,
3-Methyl-4-[3-(7H-pyrrolo[2,3-d]pyrimidin-4-yl)-3,8-diaza-bicyclo[3.2.1]octane-8-carbonyl]-benzenesulfonamide,
2-Methyl-4-[3-(7H-pyrrolo[2,3-d]pyrimidin-4-yl)-3,8-diaza-bicyclo[3.2.1]octane-8-carbonyl]-benzenesulfonamide,
3-Methoxy-4-[3-(7H-pyrrolo[2,3-d]pyrimidin-4-yl)-3,8-diaza-bicyclo[3.2.1]octane-8-carbonyl]-benzenesulfonamide,
4-[7-(7H-Pyrrolo[2,3-d]pyrimidin-4-yl)-4,7-diaza-spiro[2.5]octane-4-carbonyl]-N-(tetrahydro-furan-2-ylmethyl)-benzenesulfonamide,
N-(2-Cyano-ethyl)-4-[7-(7H-pyrrolo[2,3-d]pyrimidin-4-yl)-4,7-diaza-spiro[2.5]octane-4-carbonyl]-benzene sulfonamide,
N-(2-Methoxy-ethyl)-4-[7-(7H-pyrrolo[2,3-d]pyrimidin-4-yl)-4,7-diaza-spiro[2.5]octane-4-carbonyl]-benzenesulfonamide,
4-[7-(7H-Pyrrolo[2,3-d]pyrimidin-4-yl)-4,7-diaza-spiro[2.5]octane-4-carbonyl]-N-(2-thiophen-2-yl-ethyl)-benzenesulfonamide,
3-{2-Oxo-2-[7-(7H-pyrrolo[2,3-d]pyrimidin-4-yl)-4,7-diaza-spiro[2.5]oct-4-yl]-ethyl}-benzenesulfonamide,
4-{2-Oxo-2-[7-(7H-pyrrolo[2,3-d]pyrimidin-4-yl)-4,7-diaza-spiro[2.5]oct-4-yl]-ethoxy}-benzenesulfonamide,
4-{5-[7-(7H-Pyrrolo[2,3-d]pyrimidin-4-yl)-4,7-diaza-spiro[2.5]octane-4-carbonyl]-furan-2-yl}-benzenesulfonamide,
2-Oxo-2-[7-(7H-pyrrolo[2,3-d]pyrimidin-4-yl)-4,7-diaza-spiro[2.5]oct-4-yl]-N-(4-sulfamoyl-phenyl)-acetamide,
5-[7-(7H-Pyrrolo[2,3-d]pyrimidin-4-yl)-4,7-diaza-spiro[2.5]octane-4-carbonyl]-1H-pyrrole-3-sulfonic acid amide, (4-Methanesulfonyl-3-methyl-phenyl)-[7-(7H-pyrrolo[2,3-d]pyrimidin-4-yl)-4,7-diaza-spiro[2.5]oct-4-yl]-methanone,
4-{2-Oxo-2-[7-(7H-pyrrolo[2,3-d]pyrimidin-4-yl)-4,7-diaza-spiro[2.5]oct-4-yl]-ethyl sulfanyl}-benzene-sulfonamide,
5-[7-(7H-Pyrrolo[2,3-d]pyrimidin-4-yl)-4,7-diaza-spiro[2.5]octane-4-carbonyl]-thiophene-2-sulfonic acid amide,
[4-(2-Hydroxy-ethanesulfonyl)-phenyl]-[7-(7H-pyrrolo[2,3-d]pyrimidin-4-yl)-4,7-diaza-spiro[2.5]oct-4-yl]-methanone,
(4-Cyclopentanesulfonyl-phenyl)-[7-(7H-pyrrolo[2,3-d]pyrimidin-4-yl)-4,7-diaza-spiro[2.5]oct-4-yl]-methanone,
4-{4-[7-(7H-Pyrrolo[2,3-d]pyrimidin-4-yl)-4,7-diaza-spiro[2.5]octane-4-carbonyl]-benzenesulfonyl}-butyronitrile,
{4-[7-(7H-Pyrrolo[2,3-d]pyrimidin-4-yl)-4,7-diaza-spiro[2.5]octane-4-carbonyl]-phenyl}-methanesulfonamide,
N-{2-Oxo-2-[7-(7H-pyrrolo[2,3-d]pyrimidin-4-yl)-4,7-diaza-spiro[2.5]oct-4-yl]-ethyl}-4-sulfamoyl-benzamide,
3-Methyl-4-{2-oxo-2-[7-(7H-pyrrolo[2,3-d]pyrimidin-4-yl)-4,7-diaza-spiro[2.5]oct-4-yl]-ethoxy}-benzenesulfonamide,
1-{2-Oxo-2-[7-(7H-pyrrolo[2,3-d]pyrimidin-4-yl)-4,7-diaza-spiro[2.5]oct-4-yl]-ethyl}-1H-pyrazole-4-sulfonic acid amide,
Indan-1-yl-[7-(7H-pyrrolo[2,3-d]pyrimidin-4-yl)-4,7-diaza-spiro[2.5]oct-4-yl]-methanone,
(5-Methyl-pyrazin-2-yl)-[7-(7H-pyrrolo[2,3-d]pyrimidin-4-yl)-4,7-diaza-spiro[2.5]oct-4-yl]-methanone,
[7-(7H-Pyrrolo[2,3-d]pyrimidin-4-yl)-4,7-diaza-spiro[2.5]oct-4-yl]-(1,2,3,4-tetrahydro-naphthalen-1-yl)-methanone,
[7-(7H-Pyrrolo[2,3-d]pyrimidin-4-yl)-4,7-diaza-spiro[2.5]oct-4-yl]-(1,2,3,4-tetrahydro-naphthalen-1-yl)-methanone,
(3-Methyl-pyrazin-2-yl)-[7-(7H-pyrrolo[2,3-d]pyrimidin-4-yl)-4,7-diaza-spiro[2.5]oct-4-yl]-methanone,
(6-Methyl-pyrazin-2-yl)-[7-(7H-pyrrolo[2,3-d]pyrimidin-4-yl)-4,7-diaza-spiro[2.5]oct-4-yl]-methanone,
(3-Methyl-quinoxalin-2-yl)-[7-(7H-pyrrolo[2,3-d]pyrimidin-4-yl)-4,7-diaza-spiro[2.5]oct-4-yl]-methanone,
2-(4-Methanesulfonyl-phenyl)-1-[7-(7H-pyrrolo[2,3-d]pyrimidin-4-yl)-4,7-diaza-spiro[2.5]oct-4-yl]-ethanone,
Pyrazin-2-yl-[3-(7H-pyrrolo[2,3-d]pyrimidin-4-yl)-3,8-diaza-bicyclo[3.2.1]oct-8-yl]-methanone,
5-[7-(7H-Pyrrolo[2,3-d]pyrimidin-4-yl)-4,7-diaza-spiro[2.5]octane-4-carbonyl]-thiophene-3-sulfonic acid isobutyl-amide,
5-[7-(7H-Pyrrolo[2,3-d]pyrimidin-4-yl)-4,7-diaza-spiro[2.5]octane-4-carbonyl]-thiophene-3-sulfonic acid isobutyl-amide,
N-(3-{4-[7-(7H-Pyrrolo[2,3-d]pyrimidin-4-yl)-4,7-diaza-spiro[2.5]octane-4-carbonyl]-benzenesulfonylamino}-propyl)-acetamide,
N-(2-{4-[7-(7H-Pyrrolo[2,3-d]pyrimidin-4-yl)-4,7-diaza-spiro[2.5]octane-4-carbonyl]-benzenesulfonylamino}-ethyl)-acetamide,
N-Furan-2-ylmethyl-4-[7-(7H-pyrrolo[2,3-d]pyrimidin-4-yl)-4,7-diaza-spiro[2.5]octane-4-carbonyl]-benzenesulfonamide,
N-(5-Methyl-furan-2-ylmethyl)-4-[7-(7H-pyrrolo[2,3-d]pyrimidin-4-yl)-4,7-diaza-spiro[2.5]octane-4-carbonyl]-benzenesulfonamide,
(2-{4-[7-(7H-Pyrrolo[2,3-d]pyrimidin-4-yl)-4,7-diaza-spiro[2.5]octane-4-carbonyl]-benzenesulfonylamino}-ethyl)-carbamic acid tert-butyl ester,
4-{1-[7-(7H-Pyrrolo[2,3-d]pyrimidin-4-yl)-4,7-diaza-spiro[2.5]octane-4-carbonyl]-cyclopropyl}-benzonitrile,
N-{4-[7-(7H-Pyrrolo[2,3-d]pyrimidin-4-yl)-4,7-diaza-spiro[2.5]octane-4-carbonyl]-phenyl}-methanesulfonamide,
Propane-1-sulfonic acid {4-[7-(7H-pyrrolo[2,3-d]pyrimidin-4-yl)-4,7-diaza-spiro[2.5]octane-4-carbonyl]-phenyl}-amide,
Propane-2-sulfonic acid {4-[7-(7H-pyrrolo[2,3-d]pyrimidin-4-yl)-4,7-diaza-spiro[2.5]octane-4-carbonyl]-phenyl}-amide,
[4-(2-Methoxy-ethanesulfonyl)-phenyl]-[7-(7H-pyrrolo[2,3-d]pyrimidin-4-yl)-4,7-diaza-spiro[2.5]oct-4-yl]-methanone,
3-Fluoro-4-{2-oxo-2-[7-(7H-pyrrolo[2,3-d]pyrimidin-4-yl)-4,7-diaza-spiro[2.5]oct-4-yl]-ethoxy}-benzene sulfonamide,
1-{3-Oxo-3-[7-(7H-pyrrolo[2,3-d]pyrimidin-4-yl)-4,7-diaza-spiro[2.5]oct-4-yl]-propyl}-1H-pyrazole-4-sulfonic acid amide,
7-(7H-Pyrrolo[2,3-d]pyrimidin-4-yl)-4,7-diaza-spiro[2.5]octane-4-carboxylic acid cyclohexylamide,
7-(7H-Pyrrolo[2,3-d]pyrimidin-4-yl)-4,7-diaza-spiro[2.5]octane-4-carbothioic acid cyclohexylamide,
7-(7H-Pyrrolo[2,3-d]pyrimidin-4-yl)-4,7-diaza-spiro[2.5]octane-4-carbothioic acid benzylamide,
(5,6-Dihydro-4H-cyclopenta[b]thiophen-2-yl)-[7-(7H-pyrrolo[2,3-d]pyrimidin-4-yl)-4,7-diaza-spiro[2.5]oct-4-yl]-methanethione,
(5,6-Dihydro-4H-cyclopenta[b]thiophen-2-yl)-[7-(7H-pyrrolo[2,3-d]pyrimidin-4-yl)-4,7-diaza-spiro[2.5]oct-4-yl]-methanethione,
4-{2-[7-(7H-Pyrrolo[2,3-d]pyrimidin-4-yl)-4,7-diaza-spiro[2.5]oct-4-yl]-2-thioxo-ethyl}-benzonitrile,
2-Phenoxy-1-[7-(7H-pyrrolo[2,3-d]pyrimidin-4-yl)-4,7-diaza-spiro[2.5]oct-4-yl]-ethanone,
2-Methoxy-1-[7-(7H-pyrrolo[2,3-d]pyrimidin-4-yl)-4,7-diaza-spiro[2.5]oct-4-yl]-ethanone,
7-(7H-Pyrrolo[2,3-d]pyrimidin-4-yl)-4,7-diaza-spiro[2.5]octane-4-carboxylic acid butylamide,
7-(7H-Pyrrolo[2,3-d]pyrimidin-4-yl)-4,7-diaza-spiro[2.5]octane-4-carboxylic acid phenethyl-amide,
7-(7H-Pyrrolo[2,3-d]pyrimidin-4-yl)-4,7-diaza-spiro[2.5]octane-4-carboxylic acid 4-chloro-phenyl ester,
2-Methoxy-1-[7-(7H-pyrrolo[2,3-d]pyrimidin-4-yl)-4,7-diaza-spiro[2.5]oct-4-yl]-ethanethione,
2-Phenoxy-1-[7-(7H-pyrrolo[2,3-d]pyrimidin-4-yl)-4,7-diaza-spiro[2.5]oct-4-yl]-ethanethione,
4-[4-(2-Methyl-propane-2-sulfinyl)-4,7-diaza-spiro[2.5]oct-7-yl]-7H-pyrrolo[2,3-d]pyrimidine,
7-(7H-Pyrrolo[2,3-d]pyrimidin-4-yl)-4,7-diaza-spiro[2.5]octane-4-carboxylic acid cyclopentyl ester,
2-Phenylamino-1-[7-(7H-pyrrolo[2,3-d]pyrimidin-4-yl)-4,7-diaza-spiro[2.5]oct-4-yl]-ethanone,
4-{3-Oxo-3-[7-(7H-pyrrolo[2,3-d]pyrimidin-4-yl)-4,7-diaza-spiro[2.5]oct-4-yl]-propoxy}-benzenesulfonamide,
4-{3-Oxo-3-[7-(7H-pyrrolo[2,3-d]pyrimidin-4-yl)-4,7-diaza-spiro[2.5]oct-4-yl]-propylamino}-benzenesulfonamide, 4-{2-Oxo-2-[7-(7H-pyrrolo[2,3-d]pyrimidin-4-yl)-4,7-diaza-spiro[2.5]oct-4-yl]-ethylamino}-benzenesulfonamide, 3-Methylsulfanyl-1-[7-(7H-pyrrolo[2,3-d]pyrimidin-4-yl)-4,7-diaza-spiro[2.5]oct-4-yl]-propan-1-one, 3-Methoxy-1-[7-(7H-pyrrolo[2,3-d]pyrimidin-4-yl)-4,7-diaza-spiro[2.5]oct-4-yl]-propan-1-one, 3-Dimethylamino-1-[7-(7H-pyrrolo[2,3-d]pyrimidin-4-yl)-4,7-diaza-spiro[2.5]oct-4-yl]-propan-1-one, 7-(7H-Pyrrolo[2,3-d]pyrimidin-4-yl)-4,7-diaza-spiro[2.5]octane-4-sulfonic acid (2-cyano-ethyl)-methyl-amide, 7-(7H-Pyrrolo[2,3-d]pyrimidin-4-yl)-4,7-diaza-spiro[2.5]octane-4-sulfonic acid diethylamide, and 7-(7H-Pyrrolo[2,3-d]pyrimidin-4-yl)-4,7-diaza-spiro[2.5]octane-4-sulfonic acid cyclohexyl-methyl-amide.

30. A pharmaceutical composition comprising a compound according to claim 1 or a pharmaceutically acceptable salt, hydrate, or solvate thereof together with a pharmaceutically acceptable vehicle or excipient.

31. The composition according to claim 30 further comprising another therapeutically active compound.

* * * * *